United States Patent
Nie et al.

(10) Patent No.: US 9,604,961 B2
(45) Date of Patent: *Mar. 28, 2017

(54) HISTONE DEMETHYLASE INHIBITORS

(71) Applicant: Celgene Quanticel Research, Inc., San Diego, CA (US)

(72) Inventors: Zhe Nie, San Diego, CA (US); Jeffrey Alan Stafford, San Diego, CA (US); James Marvin Veal, Apex, NC (US); Michael Brennan Wallace, San Diego, CA (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,241

(22) PCT Filed: Dec. 5, 2013

(86) PCT No.: PCT/US2013/073424
§ 371 (c)(1),
(2) Date: Jul. 31, 2015

(87) PCT Pub. No.: WO2014/089364
PCT Pub. Date: Jun. 12, 2014

(65) Prior Publication Data
US 2016/0002201 A1    Jan. 7, 2016

Related U.S. Application Data

(60) Provisional application No. 61/734,330, filed on Dec. 6, 2012, provisional application No. 61/784,414, filed on Mar. 14, 2013.

(51) Int. Cl.
| | |
|---|---|
| *C07D 401/04* | (2006.01) |
| *C07D 405/14* | (2006.01) |
| *C07D 401/14* | (2006.01) |
| *A61K 31/44* | (2006.01) |
| *A61K 31/4439* | (2006.01) |
| *A61K 31/444* | (2006.01) |

(52) U.S. Cl.
CPC ............ *C07D 401/04* (2013.01); *A61K 31/44* (2013.01); *A61K 31/444* (2013.01); *A61K 31/4439* (2013.01); *C07D 401/14* (2013.01); *C07D 405/14* (2013.01)

(58) Field of Classification Search
CPC ......................... C07D 401/04; C07D 405/14
USPC ................ 546/276.1; 514/337, 341
See application file for complete search history.

(56) References Cited

U.S. PATENT DOCUMENTS

| | | |
|---|---|---|
| 4,685,957 A | 8/1987 | Gehring et al. |
| 4,695,308 A | 9/1987 | Gehring et al. |
| 4,699,647 A | 10/1987 | Rorer |
| 4,711,658 A | 12/1987 | Gehring et al. |
| 4,734,125 A | 3/1988 | Gehring et al. |
| 4,770,692 A | 9/1988 | Stetter et al. |
| 4,772,309 A | 9/1988 | Stetter et al. |
| 4,799,951 A | 1/1989 | Stetter et al. |
| 4,808,209 A | 2/1989 | Gehring et al. |
| 4,810,283 A | 3/1989 | Gehring et al. |
| 4,812,165 A | 3/1989 | Schallner et al. |
| 4,820,847 A | 4/1989 | Gallenkamp et al. |
| 4,826,867 A | 5/1989 | Jensen-Korte et al. |
| 4,877,439 A | 10/1989 | Gehring et al. |
| 4,881,965 A | 11/1989 | Yamamoto et al. |
| 4,956,378 A | 9/1990 | Burford et al. |
| 4,971,989 A | 11/1990 | Jensen-Korte et al. |
| 5,175,176 A | 12/1992 | Sasse et al. |
| 5,200,309 A | 4/1993 | Merkel et al. |
| 5,250,405 A | 10/1993 | Merkel et al. |
| 5,262,284 A | 11/1993 | Lau et al. |
| 5,292,744 A | 3/1994 | Sasse et al. |
| 5,298,368 A | 3/1994 | Merkel et al. |
| 5,340,707 A | 8/1994 | Ohnishi et al. |
| 5,342,444 A | 8/1994 | Harnisch et al. |
| 5,376,519 A | 12/1994 | Merkel et al. |
| 5,389,504 A | 2/1995 | Ling et al. |
| 5,610,003 A | 3/1997 | Lussier |
| 5,814,631 A | 9/1998 | Fukami et al. |
| 5,821,043 A | 10/1998 | Merkel et al. |
| 5,942,381 A | 8/1999 | Merkel et al. |
| 5,958,662 A | 9/1999 | Merkel et al. |
| 5,965,491 A | 10/1999 | Wu et al. |
| 6,010,839 A | 1/2000 | Crawley et al. |

(Continued)

FOREIGN PATENT DOCUMENTS

| | | |
|---|---|---|
| EP | 2592154 A1 | 5/2013 |
| WO | WO-9422853 A1 | 10/1994 |

(Continued)

OTHER PUBLICATIONS

Berge et al. Pharmaceutical Salts. Journal of Pharmaceutical Sciences 66(1):1-19 (Jan. 1977).
Co-pending U.S. Appl. No. 14/755,791, filed Jun. 30, 2015.
King et al. Quantitative High-Throughput Screening Identifies 8-Hydroxyquinolines as Cell-Active Histone Demethylase Inhibitors. PLoS One 5(11, e15535):1-12 (Nov. 2010).
Klose et al. JmjC-domain-containing proteins and histone demethylation. Nature Reviews Genetics 7:715-727 (Sep. 2006).
Lachner et al. An epigenetic road map for histone lysine methylation. Journal of Cell Science 116:2117-2124 (Jun. 1, 2003).

(Continued)

*Primary Examiner* — Patricia L Morris
(74) *Attorney, Agent, or Firm* — Wiley Rein LLP

(57) ABSTRACT

Provided herein are substituted pyrazolylpyridine, pyrazolylpyridazine, and pyrazolylpyrimidine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like.

2 Claims, No Drawings

(56) References Cited

U.S. PATENT DOCUMENTS

| | | |
|---|---|---|
| 6,121,271 A | 9/2000 | Dollings et al. |
| 6,132,943 A | 10/2000 | Younathan et al. |
| 6,255,489 B1 | 7/2001 | Klintz et al. |
| 6,362,192 B1 | 3/2002 | Ptock et al. |
| 6,403,620 B1 | 6/2002 | Galemmo, Jr. et al. |
| 8,178,538 B2 | 5/2012 | Alberati et al. |
| 8,987,461 B2 | 3/2015 | Nie et al. |
| 2002/0049310 A1 | 4/2002 | Tateishi et al. |
| 2002/0096082 A1 | 7/2002 | Omatsu et al. |
| 2002/0183324 A1 | 12/2002 | Jacobson et al. |
| 2002/0183362 A1 | 12/2002 | Brown et al. |
| 2003/0028017 A1 | 2/2003 | Yee et al. |
| 2003/0032657 A1 | 2/2003 | Brown et al. |
| 2003/0040608 A1 | 2/2003 | Tateishi et al. |
| 2003/0191279 A1 | 10/2003 | Goldstein et al. |
| 2004/0048863 A1 | 3/2004 | Bunker et al. |
| 2004/0171649 A1 | 9/2004 | Annis et al. |
| 2004/0198987 A1 | 10/2004 | Freudenberger et al. |
| 2004/0248850 A1 | 12/2004 | Ernst et al. |
| 2005/0075372 A1 | 4/2005 | Lahm et al. |
| 2005/0096354 A1 | 5/2005 | Gladwell et al. |
| 2005/0215785 A1 | 9/2005 | Taylor et al. |
| 2005/0215798 A1 | 9/2005 | Annis et al. |
| 2005/0282868 A1 | 12/2005 | Finkelstein et al. |
| 2006/0014808 A1 | 1/2006 | Hughes et al. |
| 2006/0014815 A1 | 1/2006 | Mase et al. |
| 2006/0041142 A1 | 2/2006 | Koyakumaru et al. |
| 2006/0142333 A1 | 6/2006 | MacDonald et al. |
| 2006/0241304 A1 | 10/2006 | Taylor et al. |
| 2007/0010526 A1 | 1/2007 | Haeberlein et al. |
| 2007/0066640 A1 | 3/2007 | Castiglioni et al. |
| 2007/0093498 A1 | 4/2007 | Brewster et al. |
| 2007/0129369 A1 | 6/2007 | Sundermann et al. |
| 2007/0142327 A1 | 6/2007 | Funke et al. |
| 2007/0232598 A1 | 10/2007 | Funke et al. |
| 2007/0267959 A1 | 11/2007 | Ragini et al. |
| 2007/0270416 A1 | 11/2007 | Funke et al. |
| 2008/0027114 A1 | 1/2008 | Funke et al. |
| 2008/0070863 A1 | 3/2008 | Funke et al. |
| 2008/0090861 A1 | 4/2008 | Barrett et al. |
| 2008/0119505 A1 | 5/2008 | Kautz et al. |
| 2008/0167316 A1 | 7/2008 | Kautz et al. |
| 2008/0187575 A1 | 8/2008 | Klebl et al. |
| 2008/0194563 A1 | 8/2008 | Hellmuth et al. |
| 2008/0221167 A1 | 9/2008 | Fischer et al. |
| 2008/0221168 A1 | 9/2008 | Schmidt et al. |
| 2008/0269293 A1 | 10/2008 | Chi et al. |
| 2008/0275053 A1 | 11/2008 | Giblin et al. |
| 2008/0280869 A1 | 11/2008 | Almstead et al. |
| 2009/0005410 A1 | 1/2009 | Charvat et al. |
| 2009/0036686 A1 | 2/2009 | Annis |
| 2009/0048269 A1 | 2/2009 | Finlay et al. |
| 2009/0088452 A1 | 4/2009 | Coleman et al. |
| 2009/0131640 A1 | 5/2009 | Berkelman |
| 2009/0149506 A1 | 6/2009 | Funke et al. |
| 2009/0298853 A1 | 12/2009 | Bauer et al. |
| 2009/0306039 A1 | 12/2009 | Pan et al. |
| 2009/0306076 A1 | 12/2009 | Thompson et al. |
| 2010/0016319 A1 | 1/2010 | Ohno et al. |
| 2010/0069367 A1 | 3/2010 | Boren et al. |
| 2010/0120784 A1 | 5/2010 | Lachance et al. |
| 2010/0137312 A1 | 6/2010 | Nardi et al. |
| 2010/0152045 A1 | 6/2010 | Lyga et al. |
| 2010/0152193 A1 | 6/2010 | Alberati et al. |
| 2010/0179141 A1 | 7/2010 | Belanger et al. |
| 2010/0204164 A1 | 8/2010 | Crouse et al. |
| 2010/0216827 A1 | 8/2010 | Ma et al. |
| 2010/0227864 A1 | 9/2010 | Shimizu et al. |
| 2010/0249192 A1 | 9/2010 | Li et al. |
| 2010/0292226 A1 | 11/2010 | Funke et al. |
| 2010/0292233 A1 | 11/2010 | Jones et al. |
| 2011/0028478 A1 | 2/2011 | Behnke et al. |
| 2011/0028482 A1 | 2/2011 | Behnke et al. |
| 2011/0046136 A1 | 2/2011 | Almstead et al. |
| 2011/0059940 A1 | 3/2011 | Gilligan et al. |
| 2011/0059962 A1 | 3/2011 | Alekshun et al. |
| 2011/0136735 A1 | 6/2011 | Barnes et al. |
| 2011/0152265 A1 | 6/2011 | Kling et al. |
| 2011/0152325 A1 | 6/2011 | Kling et al. |
| 2011/0152533 A1 | 6/2011 | Sinha et al. |
| 2011/0172186 A1 | 7/2011 | Behnke et al. |
| 2011/0190365 A1 | 8/2011 | Werner et al. |
| 2011/0306587 A1 | 12/2011 | Allen et al. |
| 2012/0083463 A1 | 4/2012 | Maue et al. |
| 2012/0178733 A1 | 7/2012 | Zhu et al. |
| 2012/0220550 A1 | 8/2012 | Bae et al. |
| 2012/0232117 A1 | 9/2012 | Bae et al. |
| 2015/0164872 A1 | 6/2015 | Nie et al. |

FOREIGN PATENT DOCUMENTS

| | | |
|---|---|---|
| WO | WO-9824785 A1 | 6/1998 |
| WO | WO-2006000336 A2 | 1/2006 |
| WO | WO-2007002313 A2 | 1/2007 |
| WO | WO-2007046809 A1 | 4/2007 |
| WO | WO-2007131538 A1 | 11/2007 |
| WO | WO-2008098798 A1 | 8/2008 |
| WO | WO-2008106202 A1 | 9/2008 |
| WO | WO-2010043866 A2 | 4/2010 |
| WO | WO-2011120026 A1 | 9/2011 |
| WO | WO-2011124930 A1 | 10/2011 |
| WO | WO-2012061169 A1 | 5/2012 |
| WO | WO-2012063207 A1 | 5/2012 |
| WO | WO-2012069175 A1 | 5/2012 |
| WO | WO-2012080376 A1 | 6/2012 |
| WO | WO-2014089364 A1 | 6/2014 |

OTHER PUBLICATIONS

Leurs et al. Inhibitor scaffold for the histone lysine demethylase KDM4C (JMJD2C). Bioorganic & Medicinal Chemistry Letters 22:5811-5813 (available online Aug. 2, 2012).

Lin et al. Loss of the retinoblastoma binding protein 2 (RBP2) histone demethylase suppresses tumorigenesis in mice lacking Rb1 or Men1. PNAS USA 108(33):13379-13386 (Aug. 16, 2011).

Margueron et al. The key to development: interpreting the histone code? Current Opinion in Genetics & Development 15:163-176 (2005).

PCT/US2013/073424 International Preliminary Report on Patentability dated Jun. 18, 2015.

PCT/US2013/073424 International Search Report and Written Opinion dated Mar. 7, 2014.

Stahl et al. Handbook of Pharmaceutical Salts. Verlag Helvetica Chimica Acta, Zurich, 2002.

HISTONE DEMETHYLASE INHIBITORS

CROSS REFERENCE

This application is filed pursuant to 35 U.S.C. 371 as a United States National Phase Application of International Application No. PCT/US2013/073424, filed on Dec. 5, 2013, which claims the benefit of U.S. Provisional Application No. 61/784,414, filed Mar. 14, 2013, and U.S. Provisional Application No. 61/734,330, filed Dec. 6, 2012, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted pyrazolylpyridine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like. The substituted pyrazolylpyridine derivative compounds described herein are based upon a disubstituted pyridine ring bearing at the 4-position a carboxylic acid, carboxylic acid ester or carboxylic acid bioisostere thereof, and at the 2-position a substituted 1-pyrazolyl group.

One embodiment provides a compound of Formula (I) or a tautomer, stereoisomer, geometric isomer, N-oxide, or pharmaceutically acceptable salt thereof,

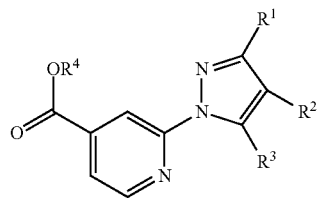

Formula (I)

wherein,
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is hydrogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^4$ is hydrogen or alkyl;
each $R^5$ is independently hydrogen, alkyl, carbocyclyl, heterocyclyl, aryl, heteroaryl, carbocyclylalkyl, heterocyclylalkyl, aralkyl, or heteroarylalkyl;
with the provision:
if $R^2$ and $R^3$ are both hydrogen, then $R^1$ is not hydrogen, methyl, trifluoromethyl, isopropyl or cyclopropyl; or
if $R^1$ and $R^3$ are both hydrogen, then $R^2$ is not methyl, or trifluoromethyl; or
if $R^1$ and $R^3$ are both methyl, then $R^2$ is not hydrogen, methyl or ethyl; or
if $R^1$ and $R^2$ are hydrogen, then $R^3$ is not

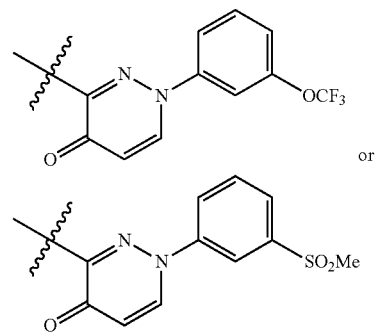

One embodiment provides a compound of Formula (II) or a tautomer, stereoisomer, geometric isomer, N-oxide, or pharmaceutically acceptable salt thereof,

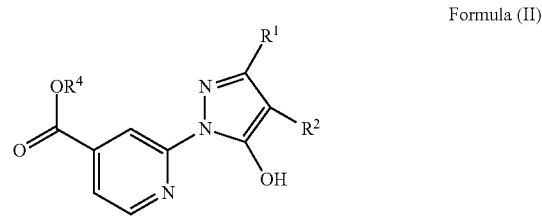

Formula (II)

wherein,
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^4$ is hydrogen or alkyl; and
each $R^5$ is independently hydrogen, alkyl, carbocyclyl, heterocyclyl, aryl, heteroaryl, carbocyclylalkyl, heterocyclylalkyl, aralkyl, or heteroarylalkyl.

One embodiment provides a compound of Formula (III) or a tautomer, stereoisomer, geometric isomer, N-oxide, or pharmaceutically acceptable salt thereof,

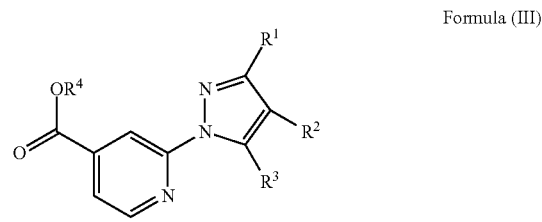

Formula (III)

wherein,
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;

R³ is C₂-C₁₀ alkyl, carbocyclyl, heterocyclyl, aryl, heteroaryl, carbocyclylalkyl, heterocyclylalkyl, aralkyl, or heteroarylalkyl;
R⁴ is hydrogen or alkyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

One embodiment provides a compound of Formula (IV) or a tautomer, stereoisomer, geometric isomer, N-oxide, or pharmaceutically acceptable salt thereof,

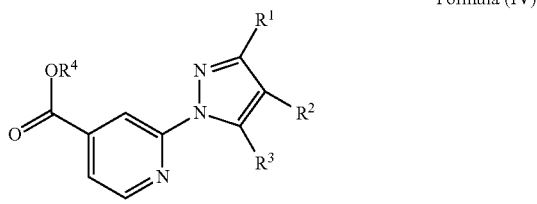

Formula (IV)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R³ is —O—X—Y;
R⁴ is hydrogen or alkyl;
each R⁵ is independently hydrogen, alkyl, carbocyclyl, heterocyclyl, aryl, heteroaryl, carbocyclylalkyl, heterocyclylalkyl, aralkyl, or heteroarylalkyl;
X is C₁-C₈ alkylene or

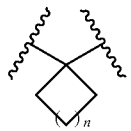

where n is 0 to 4; and
Y is hydrogen, carbocyclyl, aryl, or heteroaryl.

One embodiment provides a compound of Formula (V) or a tautomer, stereoisomer, geometric isomer, N-oxide, or pharmaceutically acceptable salt thereof,

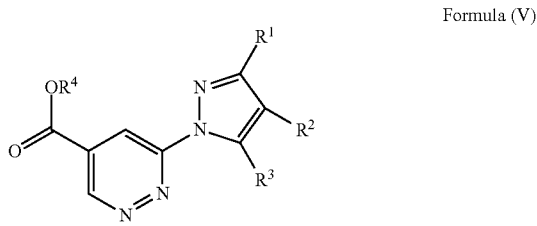

Formula (V)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R³ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R⁴ is hydrogen or alkyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

One embodiment provides a pharmaceutical composition comprising a pharmaceutically acceptable carrier and a compound of Formula (I), Formula (II), Formula (III), Formula (IV), or Formula (V), or a tautomer, stereoisomer, geometric isomer, N-oxide, or pharmaceutically acceptable salt thereof.

One embodiment provides a method for treating cancer in subject comprising administering to the subject in need thereof a composition comprising a compound of Formula (I), Formula (II), Formula (III), Formula (IV), or Formula (V), or a tautomer, stereoisomer, geometric isomer, N-oxide, or pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

DEFINITIONS

As used in the specification and appended claims, unless specified to the contrary, the following terms have the meaning indicated below.

"Amino" refers to the —NH₂ radical.
"Cyano" refers to the —CN radical.
"Nitro" refers to the —NO₂ radical.
"Oxa" refers to the —O— radical.
"Oxo" refers to the =O radical.
"Thioxo" refers to the =S radical.
"Imino" refers to the =N—H radical.

"Oximo" refers to the =N—OH radical.

"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises two to ten carbon atoms (e.g., $C_2$-$C_{10}$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (isobutyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butyryl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —Re-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R carbocyclyl where R$^c$ is an alkylene chain as defined above. The alkylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

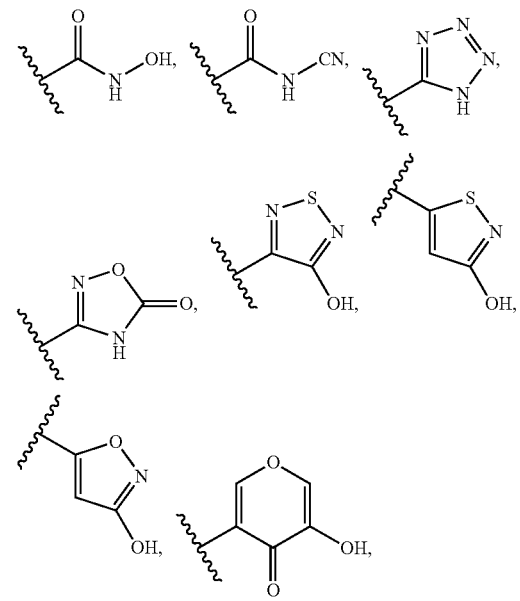

and the like.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecular structures are non-superimposeable mirror images of one another.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

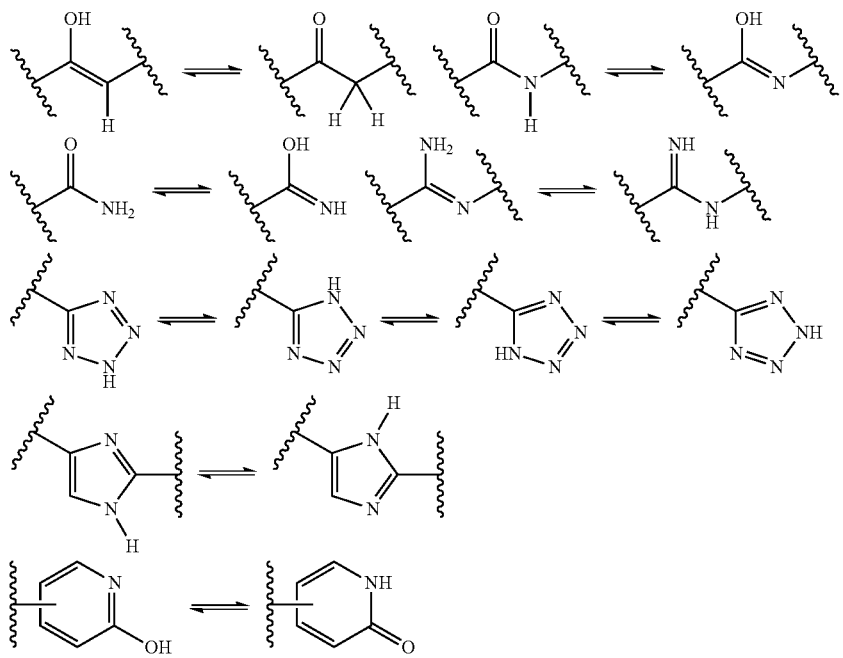

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted pyrazolylpyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Pyrazolylpyridine Derivative Compounds

Substituted pyrazolylpyridine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound of Formula (I) or a tautomer, stereoisomer, geometric isomer, N-oxide, or pharmaceutically acceptable salt thereof,

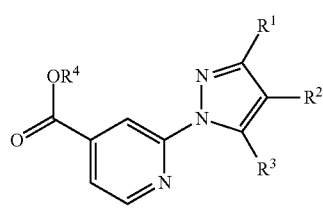

Formula (I)

wherein,
$R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
$R^2$ is hydrogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
$R^4$ is hydrogen or alkyl;
each $R^5$ is independently hydrogen, alkyl, carbocyclyl, heterocyclyl, aryl, heteroaryl, carbocyclylalkyl, heterocyclylalkyl, aralkyl, or heteroarylalkyl;
with the provision:
if $R^2$ and $R^3$ are both hydrogen, then $R^1$ is not hydrogen, methyl, trifluoromethyl, isopropyl or cyclopropyl; or
if $R^1$ and $R^3$ are both hydrogen, then $R^2$ is not methyl, or trifluoromethyl; or
if $R^1$ and $R^3$ are both methyl, then $R^2$ is not hydrogen, methyl or ethyl; or
if $R^1$ and $R^2$ are hydrogen, then $R^3$ is not

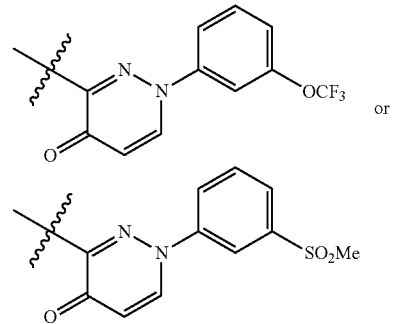

Another embodiment provides a compound of Formula (I), wherein $R^4$ is hydrogen. Another embodiment provides a compound of Formula (I), wherein $R^4$ is alkyl. Another embodiment provides a compound of Formula (I), wherein $R^3$ is hydroxy. Another embodiment provides a compound of Formula (I), wherein $R^3$ is $C_2$-$C_{10}$ alkyl. Another embodiment provides a compound of Formula (I), wherein $R^3$ is aralkyl. Another embodiment provides a compound of Formula (I), wherein $R^3$ is —OR$^5$. Another embodiment provides a compound of Formula (I), wherein —OR$^5$ is carbocyclylalkyl, heterocyclylalkyl, aralkyl, or heteroarylalkyl. Another embodiment provides a compound of Formula (I), wherein —OR$^5$ is aralkyl, or heteroarylalkyl. Another embodiment provides a compound of Formula (I), wherein —OR$^5$ is carbocyclylalkyl, or heterocyclylalkyl. Another embodiment provides a compound of Formula (I), wherein $R^3$ is aryl. Another embodiment provides a compound of Formula (I), wherein $R^1$ and $R^2$ are both hydrogen. Another embodiment provides a compound of Formula (I), wherein $R^1$ is hydrogen. Another embodiment provides a compound of Formula (I), wherein $R^2$ is hydrogen. Another embodiment provides a compound of Formula (I), wherein $R^1$ and $R^2$ are both hydrogen. Another embodiment provides a compound of Formula (I), wherein $R^3$ is phenyl substituted by at least one substituent selected from alkyl, halogen, hydroxy, alkoxy or alkylsulfone. Another embodiment provides a compound of Formula (I), wherein $R^3$ is phenyl substituted at the 4-position.

One embodiment provides a compound of Formula (II) or a tautomer, stereoisomer, geometric isomer, N-oxide, or pharmaceutically acceptable salt thereof,

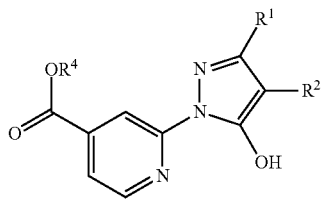

Formula (II)

wherein, $R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;

$R^4$ is hydrogen or alkyl; and each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (II), wherein $R^4$ is hydrogen. Another embodiment provides a compound of Formula (II), wherein $R^4$ is alkyl. Another embodiment provides a compound of Formula (II), wherein $R^1$ or $R^2$ is alkyl. Another embodiment provides a compound of Formula (II), wherein $R^1$ or $R^2$ is carbocyclyl. Another embodiment provides a compound of Formula (II), wherein $R^1$ or $R^2$ is aryl. Another embodiment provides a compound of Formula (II), wherein $R^1$ or $R^2$ is aralkyl.

Another embodiment provides a compound of Formula (II), wherein $R^1$ is hydrogen. Another embodiment provides a compound of Formula (II), wherein $R^2$ is hydrogen. Another embodiment provides a compound of Formula (II), wherein $R^1$ is alkyl. Another embodiment provides a compound of Formula (II), wherein $R^2$ is alkyl. Another embodiment provides a compound of Formula (II), wherein $R^1$ and $R^2$ are alkyl. Another embodiment provides a compound of Formula (II), wherein $R^1$ is carbocyclyl. Another embodiment provides a compound of Formula (II), wherein $R^2$ is carbocyclyl. Another embodiment provides a compound of Formula (II), wherein $R^1$ is aryl. Another embodiment provides a compound of Formula (II), wherein $R^2$ is aryl. Another embodiment provides a compound of Formula (II), wherein $R^1$ is aralkyl. Another embodiment provides a compound of Formula (II), wherein $R^1$ is aralkyl and $R^2$ is hydrogen. Another embodiment provides a compound of Formula (II), wherein $R^1$ is aralkyl and the aralkyl comprises a $C_1$ alkylene group. Another embodiment provides a compound of Formula (II), wherein $R^1$ is aralkyl and the aralkyl comprises a $C_1$-$C_3$ alkylene group. Another embodiment provides a compound of Formula (II), wherein $R^1$ is aralkyl and the aralkyl comprises an optionally substituted phenyl group. Another embodiment provides a compound of Formula (II), wherein $R^1$ is aralkyl and the aralkyl comprises a benzyl group. Another embodiment provides a compound of Formula (II), wherein $R^2$ is aralkyl.

Another embodiment provides a compound of Formula (II), wherein $R^4$ is hydrogen and $R^1$ is carbocyclylalkyl. Another embodiment provides a compound of Formula (II), wherein $R^4$ is hydrogen and $R^2$ is carbocyclylalkyl. Another embodiment provides a compound of Formula (II), wherein $R^4$ is hydrogen and $R^1$ is hydrogen. Another embodiment provides a compound of Formula (II), wherein $R^4$ is hydrogen and $R^2$ is hydrogen. Another embodiment provides a compound of Formula (II), wherein $R^4$ is hydrogen and $R^1$ is alkyl. Another embodiment provides a compound of Formula (II), wherein $R^4$ is hydrogen and $R^2$ is alkyl. Another embodiment provides a compound of Formula (II), wherein $R^4$ is hydrogen and $R^1$ is carbocyclyl. Another embodiment provides a compound of Formula (II), wherein $R^4$ is hydrogen and $R^2$ is carbocyclyl. Another embodiment provides a compound of Formula (II), wherein $R^4$ is hydrogen and $R^1$ is aryl. Another embodiment provides a compound of Formula (II), wherein $R^4$ is hydrogen and $R^2$ is aryl. Another embodiment provides a compound of Formula (II), wherein $R^4$ is hydrogen and $R^1$ is aralkyl. Another embodiment provides a compound of Formula (II), wherein $R^4$ is hydrogen, $R^1$ is aralkyl and $R^2$ is hydrogen. Another embodiment provides a compound of Formula (II), wherein $R^4$ is hydrogen, $R^1$ is aralkyl and the aralkyl comprises a $C_1$ alkylene group. Another embodiment provides a compound of Formula (II), wherein $R^4$ is hydrogen, $R^1$ is aralkyl and the aralkyl comprises a $C_1$-$C_3$ alkylene group. Another embodiment provides a compound of Formula (II), wherein $R^4$ is hydrogen, $R^1$ is aralkyl and the aralkyl comprises an optionally substituted phenyl group. Another embodiment provides a compound of Formula (II), wherein $R^4$ is hydrogen, $R^1$ is aralkyl and the aralkyl comprises a benzyl group. Another embodiment provides a compound of Formula (II), wherein $R^2$ is aralkyl. Another embodiment provides a compound of Formula (II), wherein $R^4$ is hydrogen, $R^1$ is carbocyclylalkyl. Another embodiment provides a compound of Formula (II), wherein $R^4$ is hydrogen and $R^2$ is carbocyclylalkyl.

One embodiment provides a compound of Formula (III) or a tautomer, stereoisomer, geometric isomer, N-oxide, or pharmaceutically acceptable salt thereof,

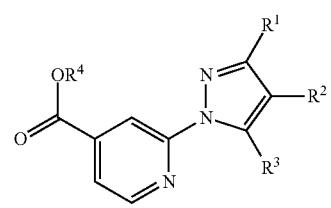

Formula (III)

wherein, $R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;

$R^3$ is $C_2$-$C_{10}$ alkyl, carbocyclyl, heterocyclyl, aryl, heteroaryl, carbocyclylalkyl, heterocyclylalkyl, aralkyl, or heteroarylalkyl;

$R^4$ is hydrogen or alkyl; and each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (III), wherein $R^4$ is hydrogen. Another embodiment provides a compound of Formula (III), wherein $R^4$ is alkyl. Another embodiment provides a compound of Formula (III), wherein $R^3$ is $C_2$-$C_{10}$ alkyl. Another embodiment provides a compound of Formula (III), wherein $R^3$ is aryl. Another embodiment provides a compound of Formula (III), wherein $R^3$ is aralkyl.

One embodiment provides a compound of Formula (IV) or a tautomer, stereoisomer, geometric isomer, N-oxide, or pharmaceutically acceptable salt thereof,

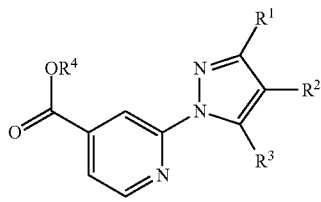

Formula (IV)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is —O—X—Y;

$R^4$ is hydrogen or alkyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl;

X is $C_1$-$C_8$ alkylene or

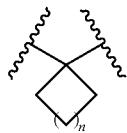

where n is 0 to 4; and

Y is hydrogen, carbocyclyl, aryl, or heteroaryl.

Another embodiment provides a compound of Formula (IV), wherein $R^4$ is hydrogen. Another embodiment provides a compound of Formula (IV), wherein $R^4$ is alkyl. Another embodiment provides a compound of Formula (IV), wherein $R^1$ and $R^2$ are hydrogen. Another embodiment provides a compound of Formula (IV), wherein X is $C_1$-$C_4$ alkylene. Another embodiment provides a compound of Formula (IV), wherein X is $C_1$-$C_2$ alkylene. Another embodiment provides a compound of Formula (IV), wherein X is $C_1$ alkylene. Another embodiment provides a compound of Formula (IV), wherein Y is hydrogen. Another embodiment provides a compound of Formula (IV), wherein Y is carbocyclyl. Another embodiment provides a compound of Formula (IV), wherein Y is aryl. Another embodiment provides a compound of Formula (IV), wherein Y is a phenyl. Another embodiment provides a compound of Formula (IV), wherein Y is heteroaryl.

Another embodiment provides a compound of Formula (IV), wherein $R^1$ is hydrogen. Another embodiment provides a compound of Formula (IV), wherein $R^2$ is hydrogen. Another embodiment provides a compound of Formula (IV), wherein $R^1$ and $R^2$ are hydrogen, and X is $C_1$-$C_2$ alkylene. Another embodiment provides a compound of Formula (IV), wherein $R^1$ and $R^2$ are hydrogen, and X is $C_1$ alkylene. Another embodiment provides a compound of Formula (IV), wherein $R^1$ and $R^2$ are hydrogen, X is $C_1$-$C_2$ alkylene, and Y is a phenyl. Another embodiment provides a compound of Formula (IV), wherein $R^1$ and $R^2$ are hydrogen, X is $C_1$ alkylene, and Y is a phenyl. Another embodiment provides a compound of Formula (IV), wherein $R^4$ is hydrogen, $R^1$ and $R^2$ are hydrogen, X is $C_1$-$C_2$ alkylene, and Y is a phenyl. Another embodiment provides a compound of Formula (IV), wherein $R^4$ is hydrogen, $R^1$ and $R^2$ are hydrogen, X is $C_1$ alkylene, and Y is a phenyl. Another embodiment provides a compound of Formula (IV), wherein Y is a phenyl optionally substituted with an alkoxy, an aralkoxy, or a cycloalkylalkoxy. Another embodiment provides a compound of Formula (IV), wherein Y is a phenyl optionally substituted with an alkenyl or aralkyl. Another embodiment provides a compound of Formula (IV), wherein $R^4$ is hydrogen, $R^1$ and $R^2$ are hydrogen, X is $C_1$-$C_2$ alkylene, and Y is a phenyl optionally substituted with an alkoxy, an aralkoxy, or a cycloalkylalkoxy. Another embodiment provides a compound of Formula (IV), wherein $R^4$ is hydrogen, $R^1$ and $R^2$ are hydrogen, X is $C_1$-$C_2$ alkylene, and Y is a phenyl optionally substituted with an alkenyl or aralkyl.

In some embodiments the carboxylic acid or ester group of the substituted pyrazolylpyridine derivative compound is replaced by a carboxylic acid bioisostere. One embodiment provides a compound of Formula (VII) or a tautomer, stereoisomer, geometric isomer, N-oxide, or pharmaceutically acceptable salt thereof,

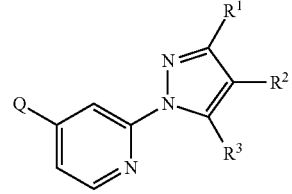

Formula (VII)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

Q is —C(O)N(H)CN, —C(O)N(H)OH, or tetrazolyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides the compound of Formula (VII) wherein:

if $R^2$ and $R^3$ are both hydrogen, then $R^1$ is not hydrogen, methyl, trifluoromethyl, isopropyl or cyclopropyl; or if $R^1$ and $R^3$ are both hydrogen, then $R^2$ is not methyl, trifluoromethyl, bromine or chlorine;

or if $R^1$ and $R^3$ are both methyl, then $R^2$ is not hydrogen, methyl or ethyl.

Another embodiment provides a compound of Formula (VII), wherein $R^4$ is hydrogen. Another embodiment provides a compound of Formula (VII), wherein $R^4$ is alkyl. Another embodiment provides a compound of Formula (VII), wherein $R^3$ is hydroxy. Another embodiment provides a compound of Formula (VII), wherein R³ is C₂-C₁₀ alkyl. Another embodiment provides a compound of Formula (VII), wherein R³ is aralkyl. Another embodiment provides a compound of Formula (VII), wherein R³ is —OR⁵. Another embodiment provides a compound of Formula (VII), wherein —OR⁵ is carbocyclylalkyl, heterocyclylalkyl, aralkyl, or heteroarylalkyl. Another embodiment provides a compound of Formula (VII), wherein —OR⁵ is aralkyl, or heteroarylalkyl. Another embodiment provides a compound of Formula (VII), wherein —OR⁵ is carbocyclylalkyl, or heterocyclylalkyl. Another embodiment provides a compound of Formula (VII), wherein R³ is aryl. Another embodiment provides a compound of Formula (VII), wherein R¹ and R² are both hydrogen. Another embodiment provides a compound of Formula (VII), wherein R¹ is hydrogen. Another embodiment provides a compound of Formula (VII), wherein R² is hydrogen. Another embodiment provides a compound of Formula (VII), wherein R¹ and R² are both hydrogen. Another embodiment provides a compound of Formula (VII), wherein R³ is phenyl substituted by at least one substituent selected from alkyl, halogen, hydroxy, alkoxy or alkylsulfone. Another embodiment provides a compound of Formula (VII), wherein R³ is phenyl substituted at the 4-position.

One embodiment provides a compound of Formula (VIII) or a tautomer, stereoisomer, geometric isomer, N-oxide, or pharmaceutically acceptable salt thereof,

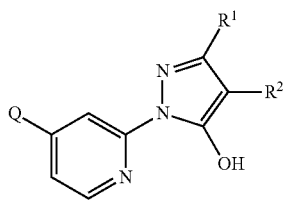

Formula (VIII)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
Q is —C(O)N(H)CN, —C(O)N(H)OH, or tetrazolyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (VIII), wherein R⁴ is hydrogen. Another embodiment provides a compound of Formula (VIII), wherein R⁴ is alkyl. Another embodiment provides a compound of Formula (VIII), wherein R¹ or R² is alkyl. Another embodiment provides a compound of Formula (VIII), wherein R¹ or R² is carbocyclyl. Another embodiment provides a compound of Formula (VIII), wherein R¹ or R² is aryl. Another embodiment provides a compound of Formula (VIII), wherein R¹ or R² is aralkyl.

One embodiment provides a compound of Formula (IX) or a tautomer, stereoisomer, geometric isomer, N-oxide, or pharmaceutically acceptable salt thereof,

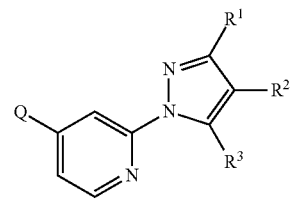

Formula (IX)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R³ is C₂-C₁₀ alkyl, carbocyclyl, heterocyclyl, aryl, heteroaryl, carbocyclylalkyl, heterocyclylalkyl, aralkyl, or heteroarylalkyl;
Q is —C(O)N(H)CN, —C(O)N(H)OH, or tetrazolyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (IX), wherein R⁴ is hydrogen. Another embodiment provides a compound of Formula (IX), wherein R⁴ is alkyl. Another embodiment provides a compound of Formula (IX), wherein R³ is C₂-C₁₀ alkyl. Another embodiment provides a compound of Formula (IX), wherein R³ is aryl. Another embodiment provides a compound of Formula (IX), wherein R³ is aralkyl.

One embodiment provides a compound of Formula (X) or a tautomer, stereoisomer, geometric isomer, N-oxide, or pharmaceutically acceptable salt thereof,

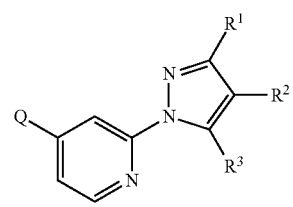

Formula (X)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R³ is —O—X—Y;
Q is —C(O)N(H)CN, —C(O)N(H)OH, or tetrazolyl;
each R⁵ is independently hydrogen, alkyl, carbocyclyl, heterocyclyl, aryl, heteroaryl, carbocyclylalkyl, heterocyclylalkyl, aralkyl, or heteroarylalkyl;

X is $C_1$-$C_8$ alkylene or

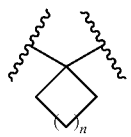

where n is 0 to 4; and
Y is hydrogen, carbocyclyl, aryl, or heteroaryl.

Another embodiment provides a compound of Formula (X), wherein $R^4$ is hydrogen. Another embodiment provides a compound of Formula (X), wherein $R^4$ is alkyl. Another embodiment provides a compound of Formula (X), wherein $R^1$ and $R^2$ are hydrogen. Another embodiment provides a compound of Formula (X), wherein X is $C_1$-$C_4$ alkylene. Another embodiment provides a compound of Formula (X), wherein X is $C_1$-$C_2$ alkylene. Another embodiment provides a compound of Formula (X), wherein X is $C_1$ alkylene. Another embodiment provides a compound of Formula (X), wherein Y is hydrogen. Another embodiment provides a compound of Formula (X), wherein Y is carbocyclyl. Another embodiment provides a compound of Formula (X), wherein Y is aryl. Another embodiment provides a compound of Formula (X), wherein Y is phenyl. Another embodiment provides a compound of Formula (X), wherein Y is heteroaryl.

Substituted Pyrazolylpyridazine Derivative Compounds

Substituted pyrazolylpyridazine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound of Formula (V) or a tautomer, stereoisomer, geometric isomer, N-oxide, or pharmaceutically acceptable salt thereof,

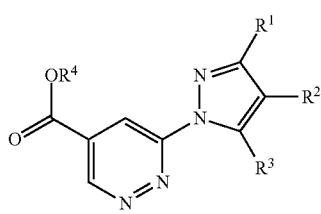

Formula (V)

wherein,
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^4$ is hydrogen or alkyl; and
each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (V), wherein $R^4$ is hydrogen. Another embodiment provides a compound of Formula (V), wherein $R^4$ is alkyl. Another embodiment provides a compound of Formula (V), wherein $R^3$ is hydroxy. Another embodiment provides a compound of Formula (V), wherein $R^3$ is $C_2$-$C_{10}$ alkyl. Another embodiment provides a compound of Formula (V), wherein $R^3$ is aralkyl. Another embodiment provides a compound of Formula (V), wherein $R^3$ is —$OR^5$. Another embodiment provides a compound of Formula (V), wherein —$OR^5$ is carbocyclylalkyl, heterocyclylalkyl, aralkyl, or heteroarylalkyl. Another embodiment provides a compound of Formula (V), wherein —$OR^5$ is aralkyl, or heteroarylalkyl. Another embodiment provides a compound of Formula (V), wherein —$OR^5$ is carbocyclylalkyl, or heterocyclylalkyl. Another embodiment provides a compound of Formula (V), wherein $R^3$ is aryl. Another embodiment provides a compound of Formula (V), wherein $R^1$ and $R^2$ are both hydrogen. Another embodiment provides a compound of Formula (V), wherein $R^1$ is hydrogen. Another embodiment provides a compound of Formula (V), wherein $R^2$ is hydrogen. Another embodiment provides a compound of Formula (V), wherein $R^1$ and $R^2$ are both hydrogen. Another embodiment provides a compound of Formula (V), wherein $R^3$ is phenyl substituted by at least one substituent selected from alkyl, halogen, hydroxy, alkoxy or alkylsulfone. Another embodiment provides a compound of Formula (V), wherein $R^3$ is phenyl substituted at the 4-position.

One embodiment provides a compound of Formula (XI) or a tautomer, stereoisomer, geometric isomer, N-oxide, or pharmaceutically acceptable salt thereof,

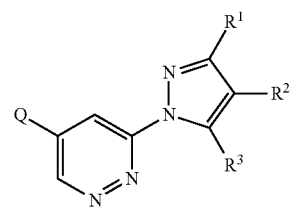

Formula (XI)

wherein,
$R^1$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^2$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
$R^3$ is hydrogen, halogen, —OH, —$OR^5$, —$N(R^5)_2$, alkyl, carbocyclyl, heterocyclyl, aryl, heteroaryl, carbocyclylalkyl, heterocyclylalkyl, aralkyl, or heteroarylalkyl;
Q is —C(O)N(H)CN, —C(O)N(H)OH, or tetrazolyl; and
each $R^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (XI), wherein $R^4$ is hydrogen. Another embodiment provides a compound of Formula (XI), wherein $R^4$ is alkyl. Another embodiment provides a compound of Formula (XI), wherein $R^3$ is hydroxy. Another embodiment provides a compound of Formula (XI), wherein $R^3$ is $C_2$-$C_{10}$ alkyl. Another embodiment provides a compound of Formula (XI), wherein $R^3$ is aralkyl. Another embodiment provides a compound of Formula (XI), wherein $R^3$ is —$OR^5$. Another embodiment provides a compound of Formula (XI), wherein —$OR^5$ is carbocyclylalkyl, heterocyclylalkyl, aralkyl, or heteroarylalkyl. Another embodiment provides a compound of Formula (XI), wherein —OR$^5$ is aralkyl, or heteroarylalkyl. Another embodiment provides a compound of Formula (XI), wherein —OR$^5$ is carbocyclylalkyl, or heterocyclylalkyl. Another embodiment provides a compound of Formula (XI), wherein R$^3$ is aryl. Another embodiment provides a compound of Formula (XI), wherein R$^1$ and R$^2$ are both hydrogen. Another embodiment provides a compound of Formula (XI), wherein R$^1$ is hydrogen. Another embodiment provides a compound of Formula (XI), wherein R$^2$ is hydrogen. Another embodiment provides a compound of Formula (XI), wherein R$^1$ and R$^2$ are both hydrogen. Another embodiment provides a compound of Formula (XI), wherein R$^3$ is phenyl substituted by at least one substituent selected from alkyl, halogen, hydroxy, alkoxy or alkylsulfone. Another embodiment provides a compound of Formula (XI), wherein R$^3$ is phenyl substituted at the 4-position.

Substituted Pyrazolylpyrimidine Derivative Compounds

Substituted pyrazolylpyrimidine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound of Formula (XII) or a tautomer, stereoisomer, geometric isomer, N-oxide, or pharmaceutically acceptable salt thereof,

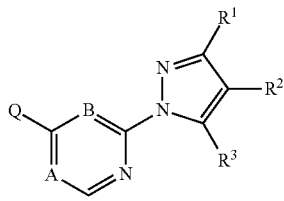

Formula (XII)

wherein,
Q is —CO$_2$R$^4$, —C(O)N(H)CN, —C(O)N(H)OH, or tetrazolyl;
A is N and B is CH; or A is CH and B is N; or A is C—OH and B is CH;
R$^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^3$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^4$ is hydrogen or alkyl;
each R$^5$ is independently hydrogen, alkyl, carbocyclyl, heterocyclyl, aryl, heteroaryl, carbocyclylalkyl, heterocyclylalkyl, aralkyl, or heteroarylalkyl;
with the provision that R$^1$, R$^2$ and R$^3$ are not all hydrogen.

Another embodiment provides a compound of Formula (XII), wherein A is N and B is CH. Another embodiment provides a compound of Formula (XII), wherein A is CH and B is N. Another embodiment provides a compound of Formula (XII), wherein A is C—OH and B is CH. Another embodiment provides a compound of Formula (XII), wherein Q is —CO$_2$R$^4$ and R$^4$ is hydrogen. Another embodiment provides a compound of Formula (XII), wherein wherein Q is —CO$_2$R$^4$ and R$^4$ is alkyl. Another embodiment provides a compound of Formula (XII), wherein Q is —C(O)N(H)CN. Another embodiment provides a compound of Formula (XII), wherein Q is —C(O)N(H)OH. Another embodiment provides a compound of Formula (XII), wherein Q is tetrazolyl. Another embodiment provides a compound of Formula (XII), wherein R$^3$ is hydroxy. Another embodiment provides a compound of Formula (XII), wherein R$^3$ is C$_2$-C$_{10}$ alkyl. Another embodiment provides a compound of Formula (XII), wherein R$^3$ is aralkyl. Another embodiment provides a compound of Formula (XII), wherein R$^3$ is —OR$^5$. Another embodiment provides a compound of Formula (XII), wherein —OR$^5$ is carbocyclylalkyl, heterocyclylalkyl, aralkyl, or heteroarylalkyl. Another embodiment provides a compound of Formula (XII), wherein —OR$^5$ is aralkyl, or heteroarylalkyl. Another embodiment provides a compound of Formula (XII), wherein —OR$^5$ is carbocyclylalkyl, or heterocyclylalkyl. Another embodiment provides a compound of Formula (XII), wherein R$^3$ is aryl. Another embodiment provides a compound of Formula (XII), wherein R$^1$ and R$^2$ are both hydrogen. Another embodiment provides a compound of Formula (XII), wherein R$^1$ is hydrogen. Another embodiment provides a compound of Formula (XII), wherein R$^2$ is hydrogen. Another embodiment provides a compound of Formula (XII), wherein R$^1$ and R$^2$ are both hydrogen. Another embodiment provides a compound of Formula (XII), wherein R$^3$ is phenyl substituted by at least one substituent selected from alkyl, halogen, hydroxy, alkoxy or alkylsulfone. Another embodiment provides a compound of Formula (XII), wherein R$^3$ is phenyl substituted at the 4-position.

One embodiment provides a compound of Formula (XIII) or a tautomer, stereoisomer, geometric isomer, N-oxide, or pharmaceutically acceptable salt thereof,

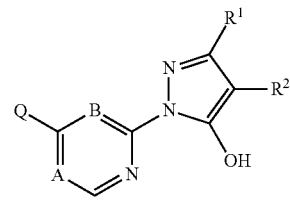

Formula (XIII)

wherein,
Q is —CO$_2$R$^4$, —C(O)N(H)CN, —C(O)N(H)OH, or tetrazolyl;
A is N and B is CH; or A is CH and B is N; or A is C—OH and B is CH;
R$^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^4$ is hydrogen or alkyl; and
each R$^5$ is independently hydrogen, alkyl, carbocyclyl, heterocyclyl, aryl, heteroaryl, carbocyclylalkyl, heterocyclylalkyl, aralkyl, or heteroarylalkyl.

Another embodiment provides a compound of Formula (XIII), wherein A is N and B is CH. Another embodiment provides a compound of Formula (XIII), wherein A is CH and B is N. Another embodiment provides a compound of Formula (XIII), wherein A is C—OH and B is CH. Another embodiment provides a compound of Formula (XIII), wherein Q is —CO$_2$R$^4$ and R$^4$ is hydrogen. Another embodiment provides a compound of Formula (XIII), wherein wherein Q is —CO$_2$R$^4$ and R$^4$ is alkyl. Another embodiment provides a compound of Formula (XIII), wherein Q is —C(O)N(H)CN. Another embodiment provides a compound of Formula (XIII), wherein Q is —C(O)N(H)OH. Another embodiment provides a compound of Formula (XIII), wherein Q is tetrazolyl. Another embodiment provides a compound of Formula (XIII), wherein R$^4$ is hydrogen. Another embodiment provides a compound of Formula (XIII), wherein R$^4$ is alkyl. Another embodiment provides a compound of Formula (XIII), wherein R$^1$ or R$^2$ is alkyl. Another embodiment provides a compound of Formula (XIII), wherein R$^1$ or R$^2$ is carbocyclyl. Another embodiment provides a compound of Formula (XIII), wherein R$^1$ or R$^2$ is aryl. Another embodiment provides a compound of Formula (XIII), wherein R$^1$ or R$^2$ is aralkyl.

One embodiment provides a compound of Formula (XIV) or a tautomer, stereoisomer, geometric isomer, N-oxide, or pharmaceutically acceptable salt thereof, Formula (XIV)

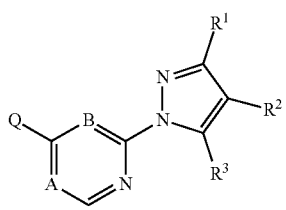

wherein,
Q is —CO$_2$R$^4$, —C(O)N(H)CN, —C(O)N(H)OH, or tetrazolyl;
A is N and B is CH; or A is CH and B is N; or A is C—OH and B is CH;
R$^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;
R$^3$ is —O—X—Y;
R$^4$ is hydrogen or alkyl;
each R$^5$ is independently hydrogen, alkyl, carbocyclyl, heterocyclyl, aryl, heteroaryl, carbocyclylalkyl, heterocyclylalkyl, aralkyl, or heteroarylalkyl;
X is C$_1$-C$_8$ alkylene or

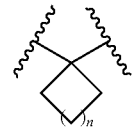

where n is 0 to 4; and
Y is hydrogen, carbocyclyl, aryl, or heteroaryl.

Another embodiment provides a compound of Formula (XIV), wherein A is N and B is CH. Another embodiment provides a compound of Formula (XIV), wherein A is CH and B is N. Another embodiment provides a compound of Formula (XIV), wherein A is C—OH and B is CH. Another embodiment provides a compound of Formula (XIV), wherein Q is —CO$_2$R$^4$ and R$^4$ is hydrogen. Another embodiment provides a compound of Formula (XIV), wherein wherein Q is —CO$_2$R$^4$ and R$^4$ is alkyl. Another embodiment provides a compound of Formula (XIV), wherein Q is —C(O)N(H)CN. Another embodiment provides a compound of Formula (XIV), wherein Q is —C(O)N(H)OH. Another embodiment provides a compound of Formula (XIV), wherein Q is tetrazolyl. Another embodiment provides a compound of Formula (XIV), wherein R$^4$ is hydrogen. Another embodiment provides a compound of Formula (XIV), wherein R$^4$ is alkyl. Another embodiment provides a compound of Formula (XIV), wherein R$^1$ and R$^2$ are hydrogen. Another embodiment provides a compound of Formula (XIV), wherein X is C$_1$-C$_4$ alkylene. Another embodiment provides a compound of Formula (XIV), wherein X is C$_1$-C$_2$ alkylene. Another embodiment provides a compound of Formula (XIV), wherein X is C$_1$ alkylene. Another embodiment provides a compound of Formula (XIV), wherein Y is hydrogen. Another embodiment provides a compound of Formula (XIV), wherein Y is carbocyclyl. Another embodiment provides a compound of Formula (XIV), wherein Y is aryl. Another embodiment provides a compound of Formula (XIV), wherein Y is phenyl. Another embodiment provides a compound of Formula (XIV), wherein Y is heteroaryl.

In some embodiments, the substituted pyrazolylpyridine derivative compound disclosed herein has the structure provided in Table 1.

TABLE 1

| Chemical Synthesis Example | Structure | Name |
|---|---|---|
| 1 | 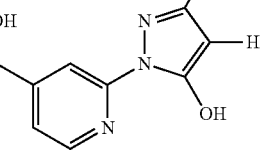 | 2-(5-hydroxy-3-methyl-1H-pyrazol-1-yl)isonicotinic acid |

TABLE 1-continued

| Chemical Synthesis Example | Structure | Name |
|---|---|---|
| 2 | 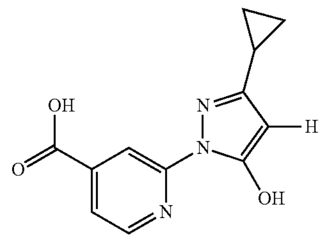 [SMILES: O=C(O)c1ccnc(-n2nc(C3CC3)cc2O)c1] | 2-(3-cyclopropyl-5-hydroxy-1H-pyrazol-1-yl)isonicotinic acid |
| 3 | 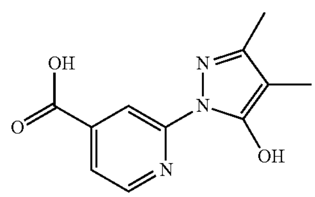 [SMILES: Cc1nn(-c2cc(C(=O)O)ccn2)c(O)c1C] | 2-(5-hydroxy-3,4-dimethyl-1H-pyrazol-1-yl)isonicotinic acid |
| 4 | 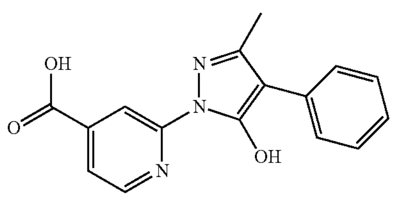 [SMILES: Cc1nn(-c2cc(C(=O)O)ccn2)c(O)c1-c1ccccc1] | 2-(5-hydroxy-3-methyl-4-phenyl-1H-pyrazol-1-yl)isonicotinic acid |
| 5 | 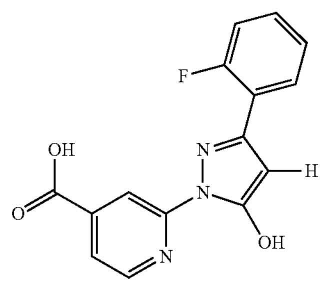 [SMILES: O=C(O)c1ccnc(-n2nc(-c3ccccc3F)cc2O)c1] | 2-(3-(2-fluorophenyl)-5-hydroxy-1H-pyrazol-1-yl)isonicotinic acid |
| 6 | 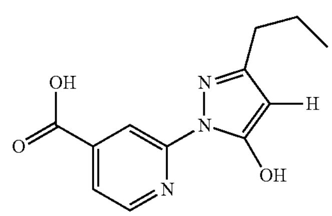 [SMILES: CCCc1cc(O)n(-c2cc(C(=O)O)ccn2)n1] | 2-(5-hydroxy-3-propyl-1H-pyrazol-1-yl)isonicotinic acid |
| 7 | 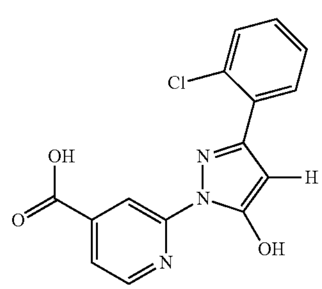 [SMILES: O=C(O)c1ccnc(-n2nc(-c3ccccc3Cl)cc2O)c1] | 2-(3-(2-chlorophenyl)-5-hydroxy-1H-pyrazol-1-yl)isonicotinic acid |

TABLE 1-continued
| Chemical Synthesis Example | Structure | Name |
|---|---|---|
| 8 | 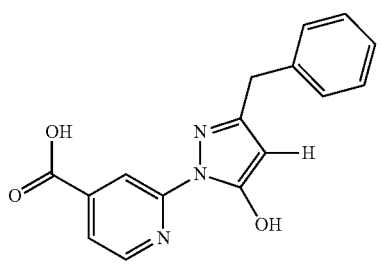 [SMILES: O=C(O)c1ccnc(-n2nc(Cc3ccccc3)cc2O)c1] | 2-(3-benzyl-5-hydroxy-1H-pyrazol-1-yl)isonicotinic acid |
| 9 | 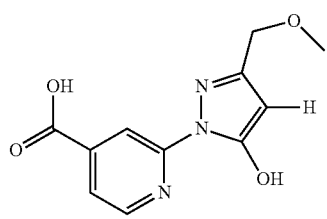 [SMILES: COCc1cc(O)n(-c2cc(C(=O)O)ccn2)n1] | 2-(5-hydroxy-3-(methoxymethyl)-1H-pyrazol-1-yl)isonicotinic acid |
| 10 | 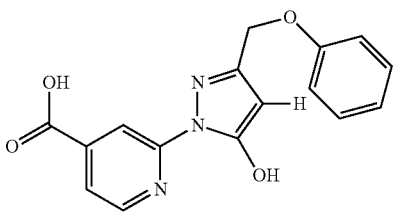 [SMILES: O=C(O)c1ccnc(-n2nc(COc3ccccc3)cc2O)c1] | 2-(5-hydroxy-3-(phenoxymethyl)-1H-pyrazol-1-yl)isonicotinic acid |
| 11 | 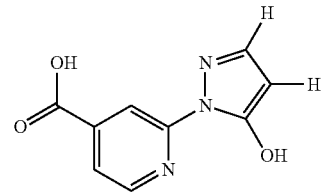 [SMILES: O=C(O)c1ccnc(-n2nccc2O)c1] | 2-(5-hydroxy-1H-pyrazol-1-yl)isonicotinic acid |
| 12 | 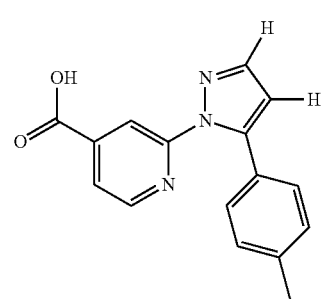 [SMILES: Cc1ccc(-c2ccnn2-c2cc(C(=O)O)ccn2)cc1] | 2-(5-p-tolyl-1H-pyrazol-1-yl)isonicotinic acid |
| 13 | 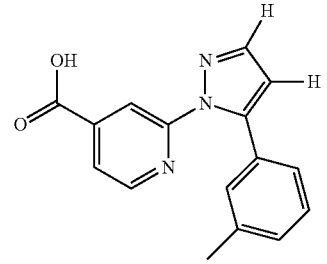 [SMILES: Cc1cccc(-c2ccnn2-c2cc(C(=O)O)ccn2)c1] | 2-(5-m-tolyl-1H-pyrazol-1-yl)isonicotinic acid |

TABLE 1-continued

| Chemical Synthesis Example | Structure | Name |
|---|---|---|
| 14 | 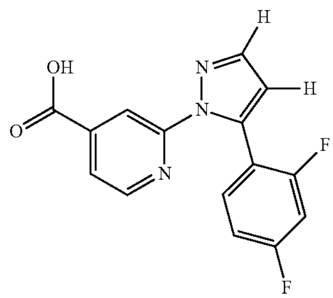 [SMILES: O=C(O)c1ccnc(-n2nccc2-c2ccc(F)cc2F)c1] | 2-(5-(2,4-difluorophenyl)-1H-pyrazol-1-yl)isonicotinic acid |
| 15 | 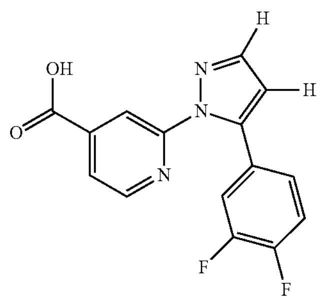 [SMILES: O=C(O)c1ccnc(-n2nccc2-c2ccc(F)c(F)c2)c1] | 2-(5-(3,4-difluorophenyl)-1H-pyrazol-1-yl)isonicotinic acid |
| 16 | 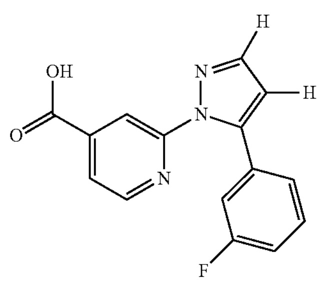 [SMILES: O=C(O)c1ccnc(-n2nccc2-c2cccc(F)c2)c1] | 2-(5-(3-fluorophenyl)-1H-pyrazol-1-yl)isonicotinic acid |
| 17 | 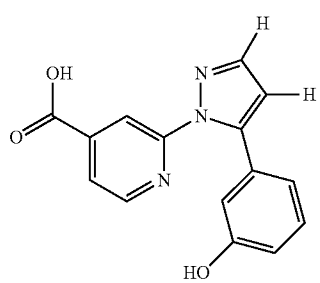 [SMILES: O=C(O)c1ccnc(-n2nccc2-c2cccc(O)c2)c1] | 2-(5-(3-hydroxyphenyl)-1H-pyrazol-1-yl)isonicotinic acid |
| 18 | 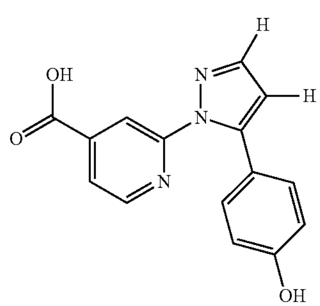 [SMILES: O=C(O)c1ccnc(-n2nccc2-c2ccc(O)cc2)c1] | 2-(5-(4-hydroxyphenyl)-1H-pyrazol-1-yl)isonicotinic acid |

TABLE 1-continued

| Chemical Synthesis Example | Structure | Name |
|---|---|---|
| 19 | 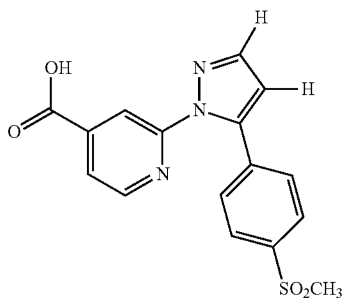 [SMILES: CS(=O)(=O)c1ccc(-c2ccnn2-c2cc(C(=O)O)ccn2)cc1] | 2-(5-(4-(methylsulfonyl)phenyl)-1H-pyrazol-1-yl)isonicotinic acid |
| 20 | 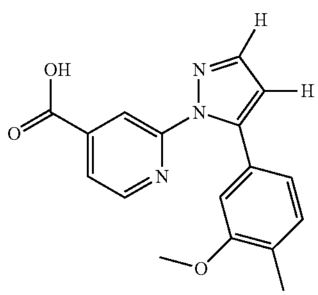 [SMILES: COc1cc(-c2ccnn2-c2cc(C(=O)O)ccn2)ccc1C] | 2-(5-(3-methoxy-4-methylphenyl)-1H-pyrazol-1-yl)isonicotinic acid |
| 21 | 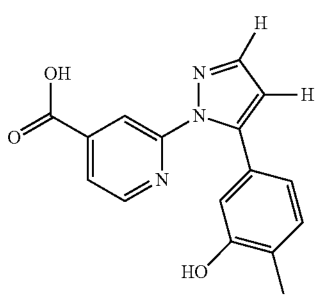 [SMILES: Cc1ccc(-c2ccnn2-c2cc(C(=O)O)ccn2)cc1O] | 2-(5-(3-hydroxy-4-methylphenyl)-1H-pyrazol-1-yl)isonicotinic acid |
| 22 | 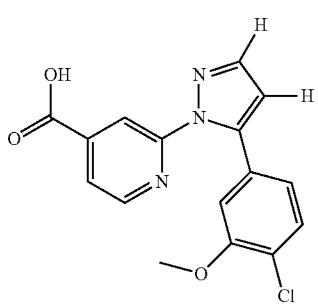 [SMILES: COc1cc(-c2ccnn2-c2cc(C(=O)O)ccn2)ccc1Cl] | 2-(5-(4-chloro-3-methoxyphenyl)-1H-pyrazol-1-yl)isonicotinic acid |
| 23 | 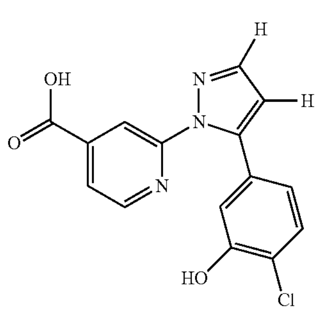 [SMILES: O=C(O)c1ccnc(-n2nccc2-c2ccc(Cl)c(O)c2)c1] | 2-(5-(4-chloro-3-hydroxyphenyl)-1H-pyrazol-1-yl)isonicotinic acid |

TABLE 1-continued

| Chemical Synthesis Example | Structure | Name |
|---|---|---|
| 24 | 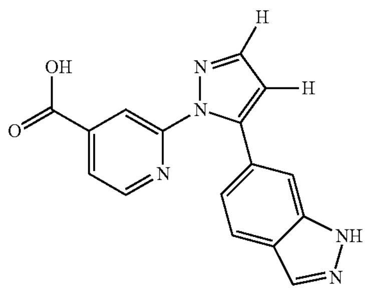 [SMILES: O=C(O)c1ccnc(-n2nccc2-c2ccc3cn[nH]c3c2)c1] | 2-[5-(1H-indazol-6-yl)-1H-pyrazol-1-yl]pyridine-4-carboxylic acid |
| 25 | 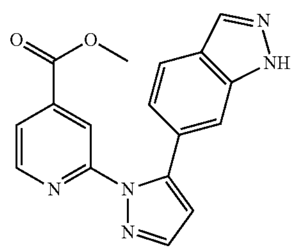 [SMILES: COC(=O)c1ccnc(-n2nccc2-c2ccc3cn[nH]c3c2)c1] | methyl 2-[5-(1H-indazol-6-yl)-1H-pyrazol-1-yl]pyridine-4-carboxylate |
| 26 | 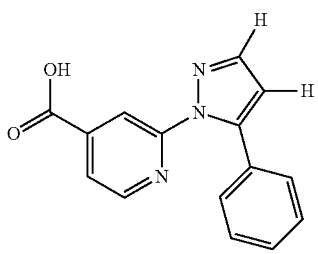 [SMILES: O=C(O)c1ccnc(-n2nccc2-c2ccccc2)c1] | 2-(5-phenyl-1H-pyrazol-1-yl)isonicotinic acid |
| 27 | 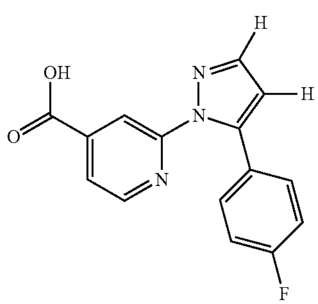 [SMILES: O=C(O)c1ccnc(-n2nccc2-c2ccc(F)cc2)c1] | 2-(5-(4-fluorophenyl)-1H-pyrazol-1-yl)isonicotinic acid |
| 28 | 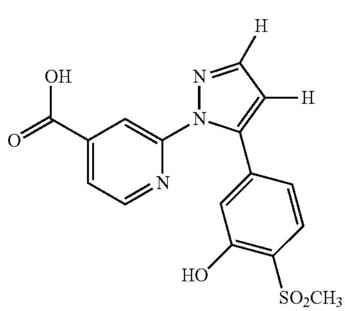 [SMILES: CS(=O)(=O)c1ccc(-c2ccnn2-c2cc(C(=O)O)ccn2)cc1O] | 2-(5-(3-hydroxy-4-(methylsulfonyl)phenyl)-1H-pyrazol-1-yl)isonicotinic acid |

TABLE 1-continued

| Chemical Synthesis Example | Structure | Name |
|---|---|---|
| 29 | 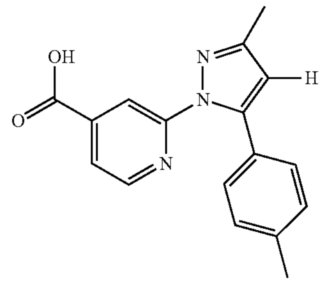 [SMILES: Cc1ccc(-c2cc(C)nn2-c2cc(C(=O)O)ccn2)cc1] | 2-(3-methyl-5-p-tolyl-1H-pyrazol-1-yl)isonicotinic acid |
| 30 | 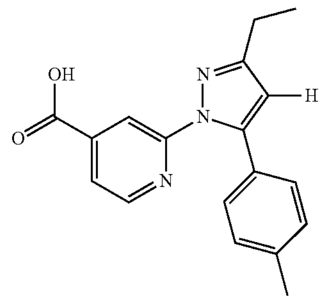 [SMILES: CCc1cc(-c2ccc(C)cc2)n(-c2cc(C(=O)O)ccn2)n1] | 2-(3-ethyl-5-p-tolyl-1H-pyrazol-1-yl)isonicotinic acid |
| 31 | 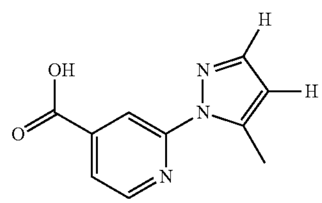 | 2-(5-methyl-1H-pyrazol-1-yl)isonicotinic acid |
| 32 | 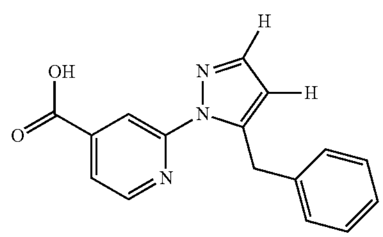 [SMILES: O=C(O)c1ccnc(-n2nccc2Cc2ccccc2)c1] | 2-(5-benzyl-1H-pyrazol-1-yl)isonicotinic acid |
| 33 | 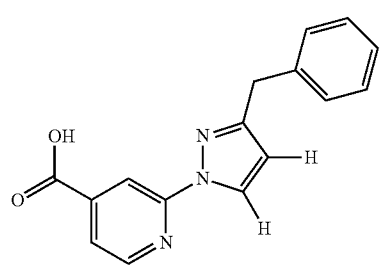 [SMILES: O=C(O)c1ccnc(-n2ccc(Cc3ccccc3)n2)c1] | 2-(3-benzyl-1H-pyrazol-1-yl)isonicotinic acid |
| 34 | 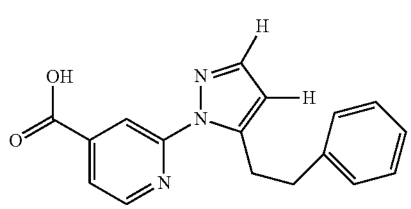 [SMILES: O=C(O)c1ccnc(-n2nccc2CCc2ccccc2)c1] | 2-(5-phenethyl-1H-pyrazol-1-yl)isonicotinic acid |

TABLE 1-continued

| Chemical Synthesis Example | Structure | Name |
|---|---|---|
| 35 | 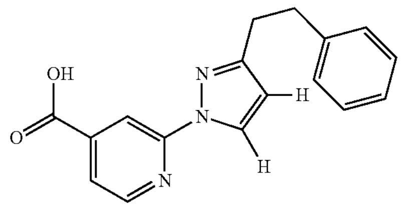 [SMILES: O=C(O)c1ccnc(-n2ccc(CCc3ccccc3)n2)c1] | 2-(3-phenethyl-1H-pyrazol-1-yl)isonicotinic acid |
| 36 | 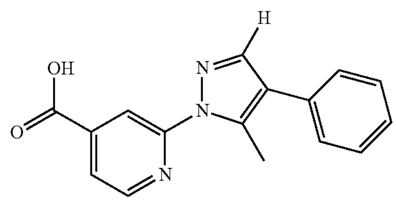 [SMILES: Cc1c(-c2ccccc2)cnn1-c1cc(C(=O)O)ccn1] | 2-(5-methyl-4-phenyl-1H-pyrazol-1-yl)isonicotinic acid |
| 37 | 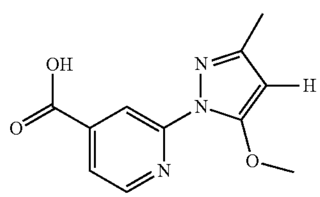 [SMILES: COc1cc(C)nn1-c1cc(C(=O)O)ccn1] | 2-(5-methoxy-3-methyl-1H-pyrazol-1-yl)isonicotinic acid |
| 38 | 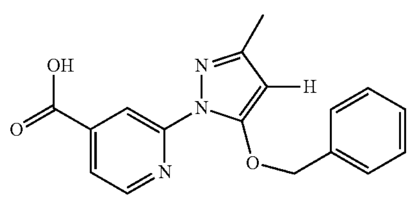 [SMILES: Cc1cc(OCc2ccccc2)n(-c2cc(C(=O)O)ccn2)n1] | 2-(5-(benzyloxy)-3-methyl-1H-pyrazol-1-yl)isonicotinic acid |
| 39 | 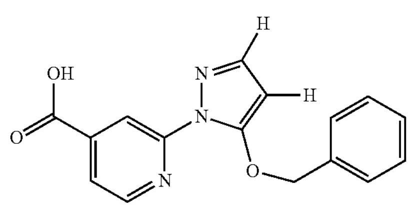 [SMILES: O=C(O)c1ccnc(-n2nccc2OCc2ccccc2)c1] | 2-(5-(benzyloxy)-1H-pyrazol-1-yl)isonicotinic acid |
| 40 | 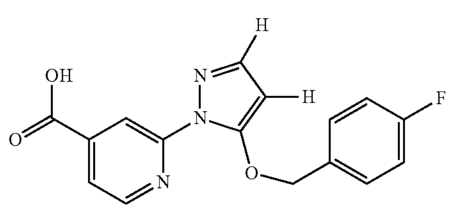 [SMILES: O=C(O)c1ccnc(-n2nccc2OCc2ccc(F)cc2)c1] | 2-{5-[(4-fluorobenzyl)oxy]-1H-pyrazol-1-yl}pyridine-4-carboxylic acid |
| 41 | 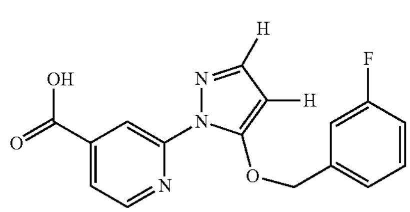 [SMILES: O=C(O)c1ccnc(-n2nccc2OCc2cccc(F)c2)c1] | 2-{5-[(3-fluorobenzyl)oxy]-1H-pyrazol-1-yl}pyridine-4-carboxylic acid |

TABLE 1-continued

| Chemical Synthesis Example | Structure | Name |
|---|---|---|
| 42 | 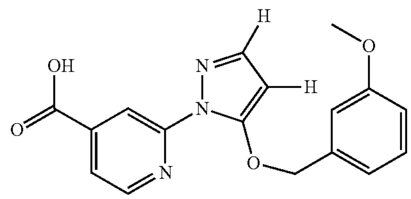 [SMILES: COc1cccc(COc2ccnn2-c2cc(C(=O)O)ccn2)c1] | 2-{5-[(3-methoxybenzyl)oxy]-1H-pyrazol-1-yl}pyridine-4-carboxylic acid |
| 43 | 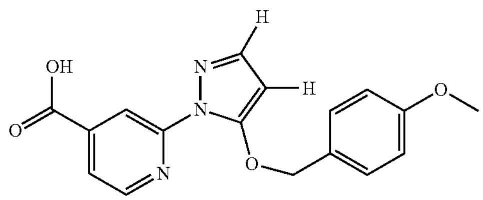 [SMILES: COc1ccc(COc2ccnn2-c2cc(C(=O)O)ccn2)cc1] | 2-{5-[(4-methoxybenzyl)oxy]-1H-pyrazol-1-yl}pyridine-4-carboxylic acid |
| 44 | 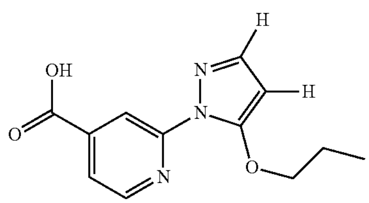 [SMILES: CCCOc1ccnn1-c1cc(C(=O)O)ccn1] | 2-(5-butyl-1H-pyrazol-1-yl)isonicotinic acid |
| 45 | 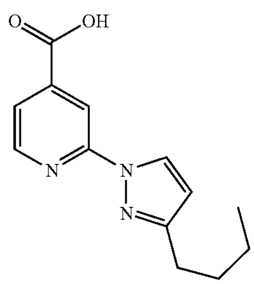 [SMILES: CCCCc1ccn(-c2cc(C(=O)O)ccn2)n1] | 2-(3-butyl-1H-pyrazol-1-yl)pyridine-4-carboxylic acid |
| 46 | 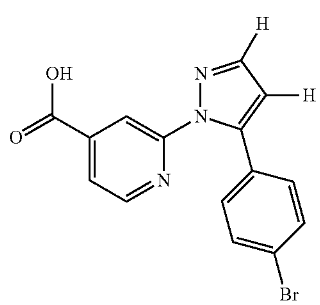 [SMILES: O=C(O)c1ccnc(-n2nccc2-c2ccc(Br)cc2)c1] | 2-(5-(4-bromophenyl)-1H-pyrazol-1-yl)isonicotinic acid |
| 47 | 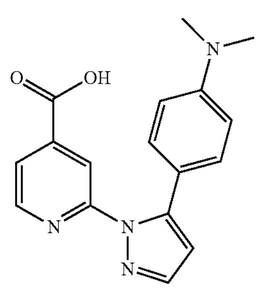 [SMILES: CN(C)c1ccc(-c2ccnn2-c2cc(C(=O)O)ccn2)cc1] | 2-{5-[4-(dimethylamino)phenyl]-1H-pyrazol-1-yl}pyridine-4-carboxylic acid |

TABLE 1-continued

| Chemical Synthesis Example | Structure | Name |
|---|---|---|
| 48 | 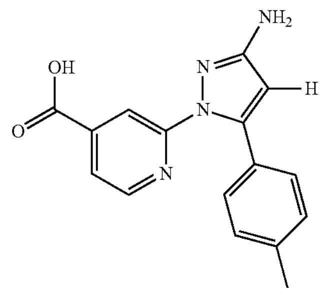 [SMILES: Cc1ccc(-c2cc(N)nn2-c2cc(C(=O)O)ccn2)cc1] | 2-[3-amino-5-(4-methylphenyl)-1H-pyrazol-1-yl]pyridine-4-carboxylic acid |
| 49 | 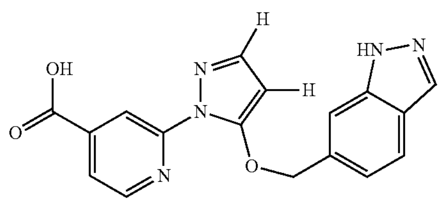 [SMILES: O=C(O)c1ccnc(-n2nccc2OCc2ccc3cn[nH]c3c2)c1] | 2-[5-(1H-indazol-6-ylmethoxy)-1H-pyrazol-1-yl]pyridine-4-carboxylic acid |
| 50 | 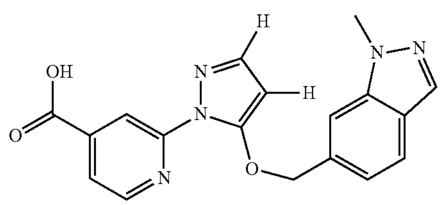 [SMILES: Cn1ncc2ccc(COc3ccnn3-c3cc(C(=O)O)ccn3)cc21] | 2-{5-[(1-methyl-1H-indazol-6-yl)methoxy]-1H-pyrazol-1-yl}pyridine-4-carboxylic acid |
| 51 | 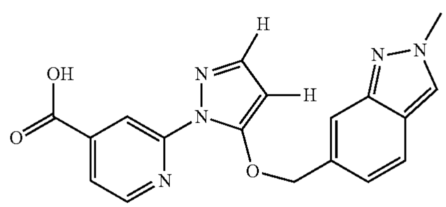 [SMILES: Cn1cc2ccc(COc3ccnn3-c3cc(C(=O)O)ccn3)cc2n1] | 2-{5-[(1-methyl-1H-indazol-6-yl)methoxy]-1H-pyrazol-1-yl}pyridine-4-carboxylic acid |
| 52 | 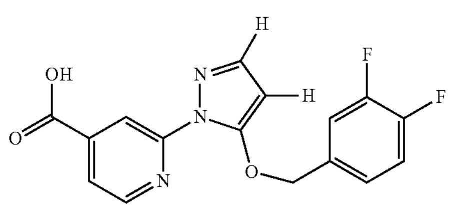 [SMILES: O=C(O)c1ccnc(-n2nccc2OCc2ccc(F)c(F)c2)c1] | 2-{5-[(3,4-difluorobenzyl)oxy]-1H-pyrazol-1-yl}pyridine-4-carboxylic acid |
| 53 | 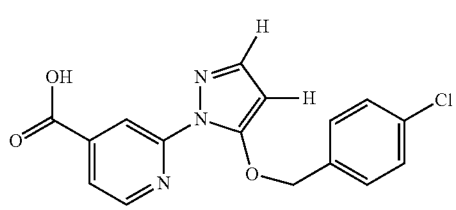 [SMILES: O=C(O)c1ccnc(-n2nccc2OCc2ccc(Cl)cc2)c1] | 2-{5-[(4-chlorobenzyl)oxy]-1H-pyrazol-1-yl}pyridine-4-carboxylic acid |
| 54 | 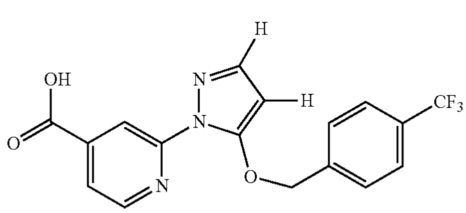 [SMILES: O=C(O)c1ccnc(-n2nccc2OCc2ccc(C(F)(F)F)cc2)c1] | 2-(5-{[4-(trifluoromethyl)benzyl]oxy}-1H-pyrazol-1-yl)pyridine-4-carboxylic acid |

TABLE 1-continued

| Chemical Synthesis Example | Structure | Name |
|---|---|---|
| 55 | 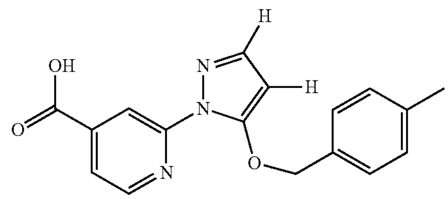 [SMILES: Cc1ccc(COc2ccnn2-c2cc(C(=O)O)ccn2)cc1] | 2-{5-[(4-methylbenzyl)oxy]-1H-pyrazol-1-yl}pyridine-4-carboxylic acid |
| 56 | 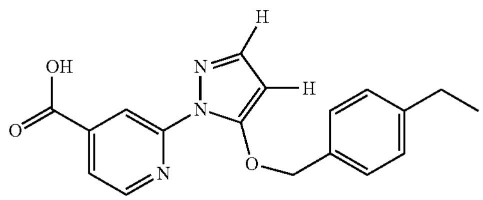 [SMILES: CCc1ccc(COc2ccnn2-c2cc(C(=O)O)ccn2)cc1] | 2-{5-[(4-ethylbenzyl)oxy]-1H-pyrazol-1-yl}pyridine-4-carboxylic acid |
| 57 | 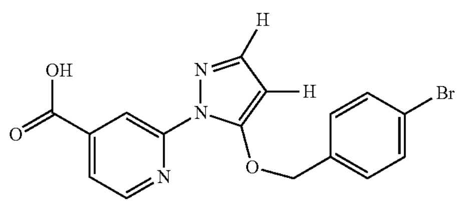 [SMILES: O=C(O)c1ccnc(-n2nccc2OCc2ccc(Br)cc2)c1] | 2-{5-[(4-bromobenzyl)oxy]-1H-pyrazol-1-yl}pyridine-4-carboxylic acid |
| 58 | 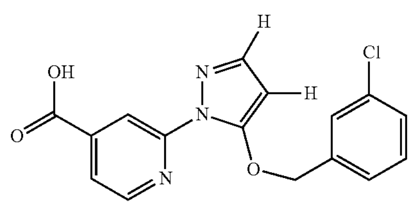 [SMILES: O=C(O)c1ccnc(-n2nccc2OCc2cccc(Cl)c2)c1] | 2-{5-[(3-chlorobenzyl)oxy]-1H-pyrazol-1-yl}pyridine-4-carboxylic acid |
| 59 | 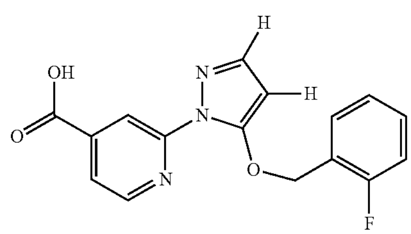 [SMILES: O=C(O)c1ccnc(-n2nccc2OCc2ccccc2F)c1] | 2-{5-[(2-fluorobenzyl)oxy]-1H-pyrazol-1-yl}pyridine-4-carboxylic acid |
| 60 | 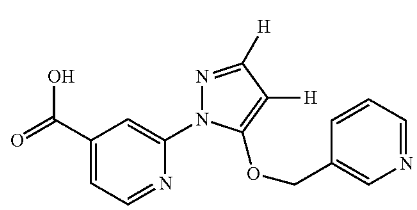 [SMILES: O=C(O)c1ccnc(-n2nccc2OCc2cccnc2)c1] | 2-[5-(pyridin-3-ylmethoxy)-1H-pyrazol-1-yl]pyridine-4-carboxylic acid |
| 61 | 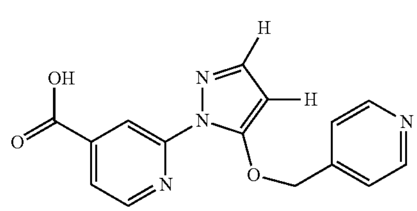 [SMILES: O=C(O)c1ccnc(-n2nccc2OCc2ccncc2)c1] | 2-[5-(pyridin-4-ylmethoxy)-1H-pyrazol-1-yl]pyridine-4-carboxylic acid |

TABLE 1-continued

| Chemical Synthesis Example | Structure | Name |
|---|---|---|
| 62 | 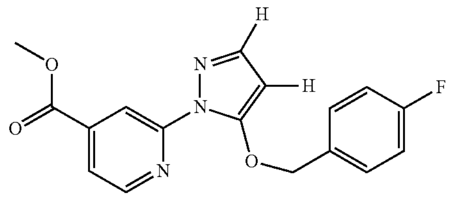 [SMILES: COC(=O)c1ccnc(-n2nccc2OCc2ccc(F)cc2)c1] | methyl 2-{5-[(4-fluorobenzyl)oxy]-1H-pyrazol-1-yl}pyridine-4-carboxylate |
| 63 | 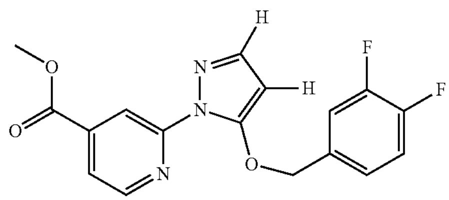 [SMILES: COC(=O)c1ccnc(-n2nccc2OCc2ccc(F)c(F)c2)c1] | methyl 2-{5-[(3,4-difluorobenzyl)oxy]-1H-pyrazol-1-yl}pyridine-4-carboxylate |
| 64 | 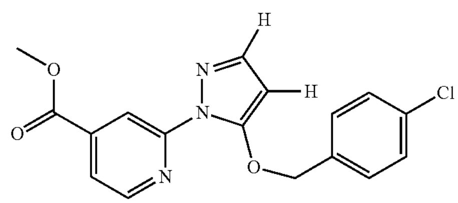 [SMILES: COC(=O)c1ccnc(-n2nccc2OCc2ccc(Cl)cc2)c1] | methyl 2-{5-[(4-chlorobenzyl)oxy]-1H-pyrazol-1-yl}pyridine-4-carboxylate |
| 65 | 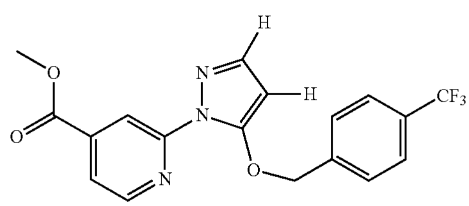 [SMILES: COC(=O)c1ccnc(-n2nccc2OCc2ccc(C(F)(F)F)cc2)c1] | methyl 2-(5-{[4-(trifluoromethyl)benzyl]oxy}-1H-pyrazol-1-yl)pyridine-4-carboxylate |
| 66 | 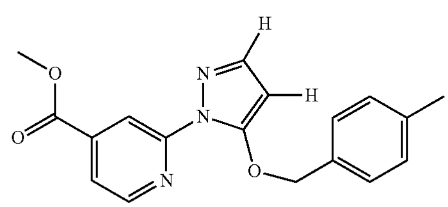 [SMILES: COC(=O)c1ccnc(-n2nccc2OCc2ccc(C)cc2)c1] | methyl 2-{5-[(4-methylbenzyl)oxy]-1H-pyrazol-1-yl}pyridine-4-carboxylate |
| 67 | 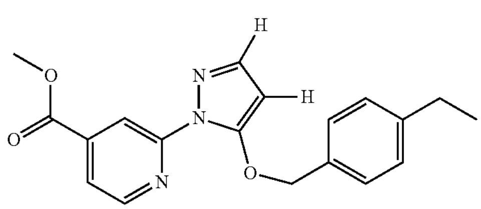 [SMILES: CCc1ccc(COc2ccnn2-c2cc(C(=O)OC)ccn2)cc1] | methyl 2-{5-[(4-ethylbenzyl)oxy]-1H-pyrazol-1-yl}pyridine-4-carboxylate |
| 68 | 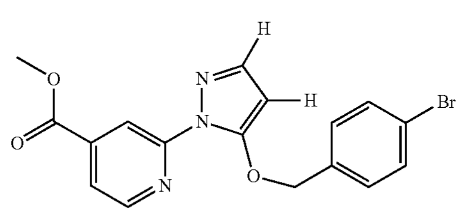 [SMILES: COC(=O)c1ccnc(-n2nccc2OCc2ccc(Br)cc2)c1] | methyl 2-{5-[(4-bromobenzyl)oxy]-1H-pyrazol-1-yl}pyridine-4-carboxylate |

TABLE 1-continued

| Chemical Synthesis Example | Structure | Name |
|---|---|---|
| 69 | 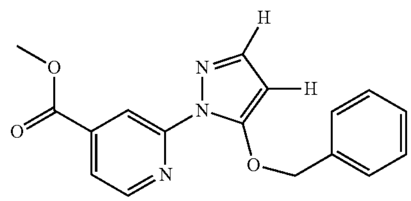 [SMILES: COC(=O)c1ccnc(-n2nccc2OCc2ccccc2)c1] | methyl 2-[5-(benzyloxy)-1H-pyrazol-1-yl]pyridine-4-carboxylate |
| 70 | 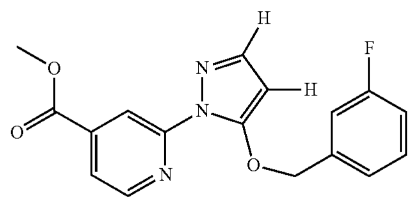 [SMILES: COC(=O)c1ccnc(-n2nccc2OCc2cccc(F)c2)c1] | methyl 2-{5-[(3-fluorobenzyl)oxy]-1H-pyrazol-1-yl}pyridine-4-carboxylate |
| 71 | 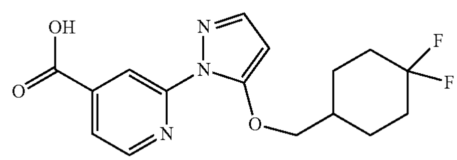 [SMILES: O=C(O)c1ccnc(-n2nccc2OCC2CCC(F)(F)CC2)c1] | 2-{5-[(4,4-difluorocyclohexyl)methoxy]-1H-pyrazol-1-yl}pyridine-4-carboxylic acid |
| 72 | 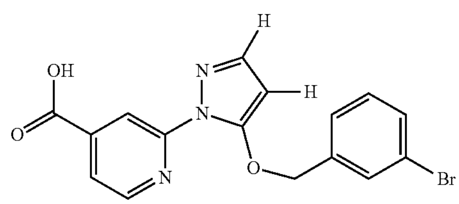 [SMILES: O=C(O)c1ccnc(-n2nccc2OCc2cccc(Br)c2)c1] | 2-{5-[(3-bromobenzyl)oxy]-1H-pyrazol-1-yl}pyridine-4-carboxylic acid |
| 73 | 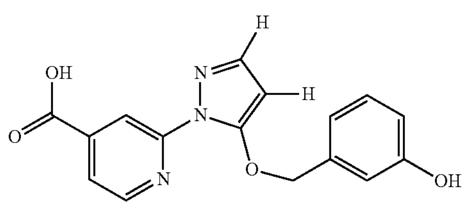 | 2-{5-[(3-hydroxybenzyl)oxy]-1H-pyrazol-1-yl}pyridine-4-carboxylic acid |
| 74 | 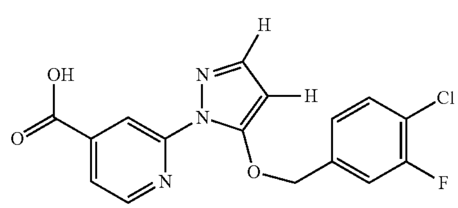 [SMILES: O=C(O)c1ccnc(-n2nccc2OCc2ccc(Cl)c(F)c2)c1] | 2-{5-[(4-chloro-3-fluorobenzyl)oxy]-1H-pyrazol-1-yl}pyridine-4-carboxylic acid |
| 75 | 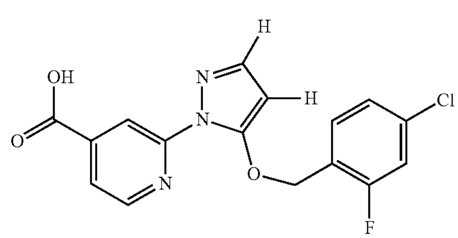 [SMILES: O=C(O)c1ccnc(-n2nccc2OCc2ccc(Cl)cc2F)c1] | 2-{5-[(4-chloro-2-fluorobenzyl)oxy]-1H-pyrazol-1-yl}pyridine-4-carboxylic acid |

TABLE 1-continued

| Chemical Synthesis Example | Structure | Name |
|---|---|---|
| 76 | 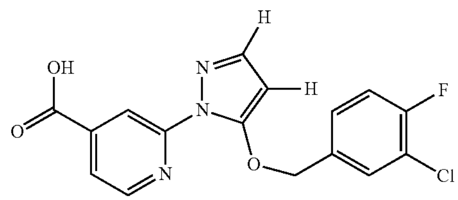 [SMILES: O=C(O)c1ccnc(-n2nccc2OCc2ccc(F)c(Cl)c2)c1] | 2-{5-[(3-chloro-4-fluorobenzyl)oxy]-1H-pyrazol-1-yl}pyridine-4-carboxylic acid |
| 77 | 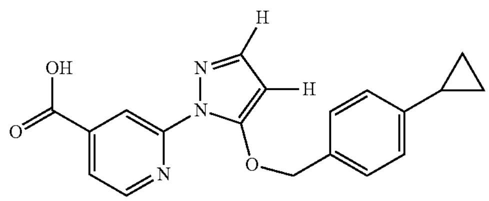 [SMILES: O=C(O)c1ccnc(-n2nccc2OCc2ccc(C3CC3)cc2)c1] | 2-{5-[(4-cyclopropylbenzyl)oxy]-1H-pyrazol-1-yl}pyridine-4-carboxylic acid |
| 78 | 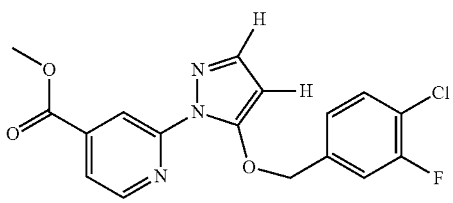 [SMILES: COC(=O)c1ccnc(-n2nccc2OCc2ccc(Cl)c(F)c2)c1] | methyl 2-{5-[(4-chloro-3-fluorobenzyl)oxy]-1H-pyrazol-1-yl}pyridine-4-carboxylate |
| 79 | 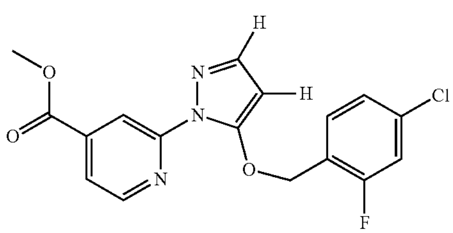 [SMILES: COC(=O)c1ccnc(-n2nccc2OCc2ccc(Cl)cc2F)c1] | methyl 2-{5-[(4-chloro-2-fluorobenzyl)oxy]-1H-pyrazol-1-yl}pyridine-4-carboxylate |
| 80 | 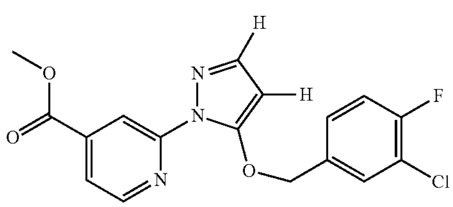 [SMILES: COC(=O)c1ccnc(-n2nccc2OCc2ccc(F)c(Cl)c2)c1] | methyl 2-{5-[(3-chloro-4-fluorobenzyl)oxy]-1H-pyrazol-1-yl}pyridine-4-carboxylate |
| 81 | 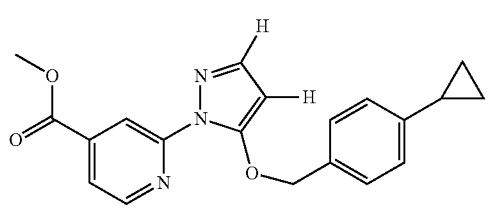 [SMILES: COC(=O)c1ccnc(-n2nccc2OCc2ccc(C3CC3)cc2)c1] | methyl 2-{5-[(4-cyclopropylbenzyl)oxy]-1H-pyrazol-1-yl}pyridine-4-carboxylate |
| 82 | 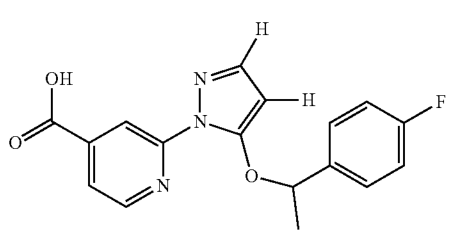 [SMILES: CC(Oc1ccnn1-c1cc(C(=O)O)ccn1)c1ccc(F)cc1] | 2-[5-[1-(4-fluorophenyl)ethoxy]pyrazol-1-yl]pyridine-4-carboxylic acid |

TABLE 1-continued

| Chemical Synthesis Example | Structure | Name |
|---|---|---|
| 83 | 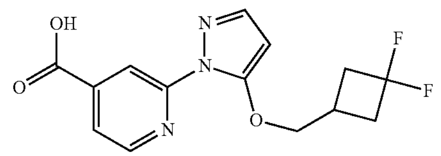 [SMILES: O=C(O)c1ccnc(-n2nccc2OCC2CC(F)(F)C2)c1] | 2-[5-[(3,3-difluorocyclobutyl)methoxy]pyrazol-1-yl]pyridine-4-carboxylic acid |
| 84 | 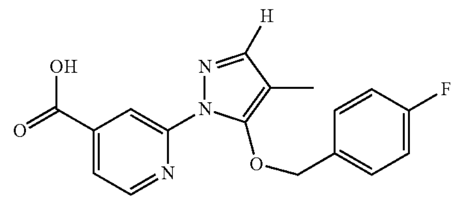 [SMILES: Cc1cnn(-c2cc(C(=O)O)ccn2)c1OCc1ccc(F)cc1] | 2-[5-[(4-fluorophenyl)methoxy]-4-methylpyrazol-1-yl]pyridine-4-carboxylic acid |
| 85 | 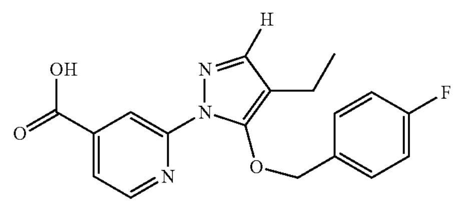 [SMILES: CCc1cnn(-c2cc(C(=O)O)ccn2)c1OCc1ccc(F)cc1] | 2-[4-ethyl-5-[(4-fluorophenyl)methoxy]pyrazol-1-yl]pyridine-4-carboxylic acid |
| 86 | 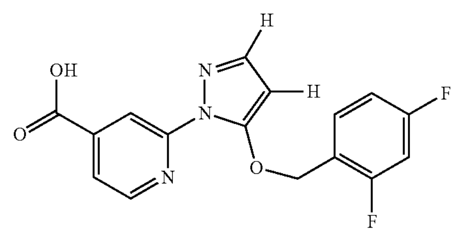 [SMILES: O=C(O)c1ccnc(-n2nccc2OCc2ccc(F)cc2F)c1] | 2-[5-[(2,4-difluorophenyl)methoxy]pyrazol-1-yl]pyridine-4-carboxylic acid |
| 87 | 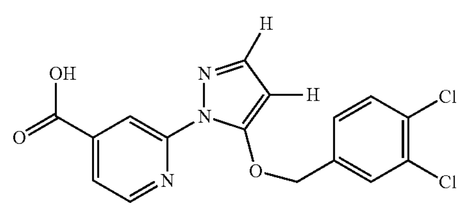 [SMILES: O=C(O)c1ccnc(-n2nccc2OCc2ccc(Cl)c(Cl)c2)c1] | 2-[5-[(3,4-dichlorophenyl)methoxy]pyrazol-1-yl]pyridine-4-carboxylic acid |
| 88 | 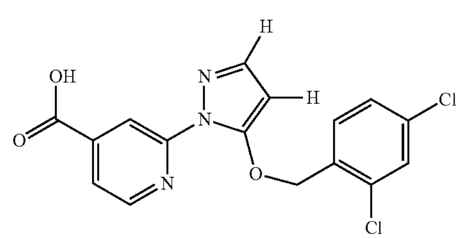 [SMILES: O=C(O)c1ccnc(-n2nccc2OCc2ccc(Cl)cc2Cl)c1] | 2-[5-[(2,4-dichlorophenyl)methoxy]pyrazol-1-yl]pyridine-4-carboxylic acid |
| 89 | 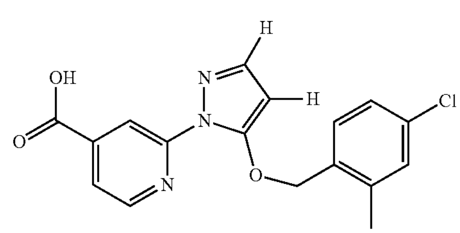 [SMILES: Cc1cc(Cl)ccc1COc1ccnn1-c1cc(C(=O)O)ccn1] | 2-[5-[(4-chloro-2-methylphenyl)methoxy]pyrazol-1-yl]pyridine-4-carboxylic acid |

TABLE 1-continued

| Chemical Synthesis Example | Structure | Name |
|---|---|---|
| 90 | 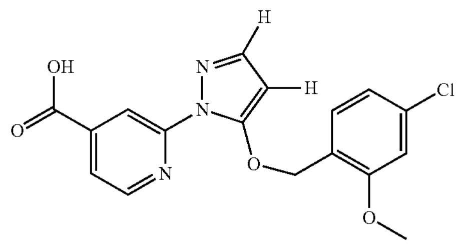 [SMILES: COc1cc(Cl)ccc1COc1ccnn1-c1cc(C(=O)O)ccn1] | 2-[5-[(4-chloro-2-methoxyphenyl)methoxy]pyrazol-1-yl]pyridine-4-carboxylic acid |
| 91 | 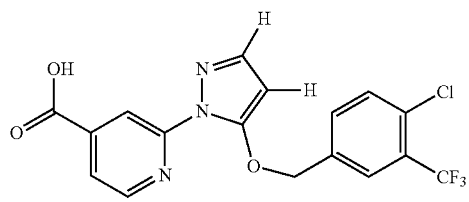 [SMILES: O=C(O)c1ccnc(-n2nccc2OCc2ccc(Cl)c(C(F)(F)F)c2)c1] | 2-[5-[[4-chloro-3-(trifluoromethyl)phenyl]methoxy]pyrazol-1-yl]pyridine-4-carboxylic acid |
| 92 | 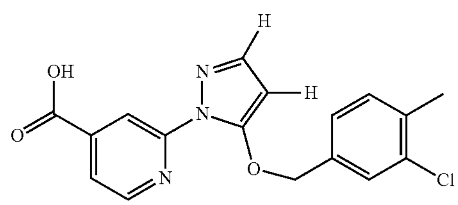 [SMILES: Cc1ccc(COc2ccnn2-c2cc(C(=O)O)ccn2)cc1Cl] | 2-[5-[(3-chloro-4-methylphenyl)methoxy]pyrazol-1-yl]pyridine-4-carboxylic acid |
| 93 | 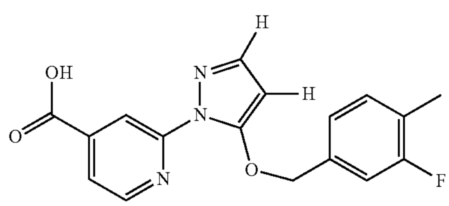 [SMILES: Cc1ccc(COc2ccnn2-c2cc(C(=O)O)ccn2)cc1F] | 2-[5-[(3-fluoro-4-methylphenyl)methoxy]pyrazol-1-yl]pyridine-4-carboxylic acid |
| 94 | 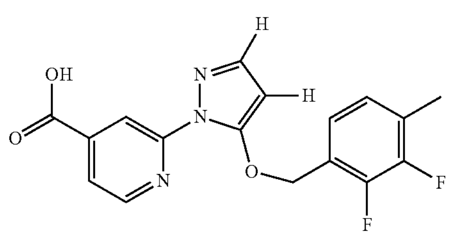 [SMILES: Cc1ccc(COc2ccnn2-c2cc(C(=O)O)ccn2)c(F)c1F] | 2-[5-[(2,3-difluoro-4-methylphenyl)methoxy]pyrazol-1-yl]pyridine-4-carboxylic acid |
| 95 | 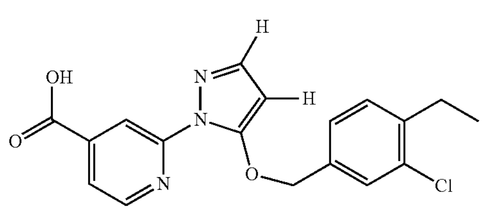 [SMILES: CCc1ccc(COc2ccnn2-c2cc(C(=O)O)ccn2)cc1Cl] | 2-[5-[(3-chloro-4-ethylphenyl)methoxy]pyrazol-1-yl]pyridine-4-carboxylic acid |
| 96 | 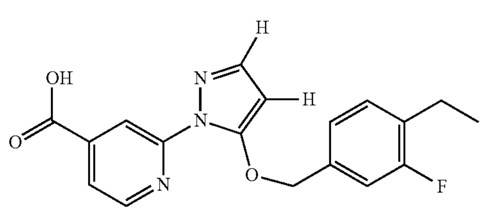 [SMILES: CCc1ccc(COc2ccnn2-c2cc(C(=O)O)ccn2)cc1F] | 2-[5-[(4-ethyl-3-fluorophenyl)methoxy]pyrazol-1-yl]pyridine-4-carboxylic acid |

TABLE 1-continued

| Chemical Synthesis Example | Structure | Name |
|---|---|---|
| 97 | 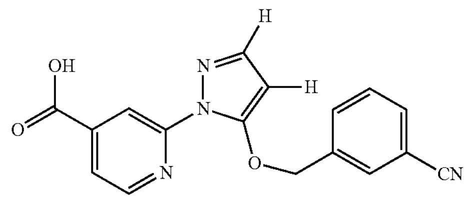 [SMILES: N#Cc1cccc(COc2ccnn2-c2cc(C(=O)O)ccn2)c1] | 2-[5-[(3-cyanophenyl)methoxy]pyrazol-1-yl]pyridine-4-carboxylic acid |
| 98 | 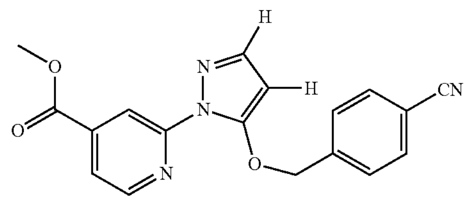 [SMILES: COC(=O)c1ccnc(-n2nccc2OCc2ccc(C#N)cc2)c1] | methyl 2-[5-[(4-cyanophenyl)methoxy]pyrazol-1-yl]pyridine-4-carboxylate |
| 99 | 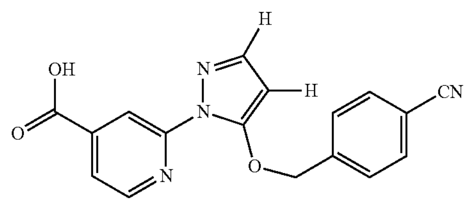 [SMILES: N#Cc1ccc(COc2ccnn2-c2cc(C(=O)O)ccn2)cc1] | 2-[5-[(4-cyanophenyl)methoxy]pyrazol-1-yl]pyridine-4-carboxylic acid |
| 100 | 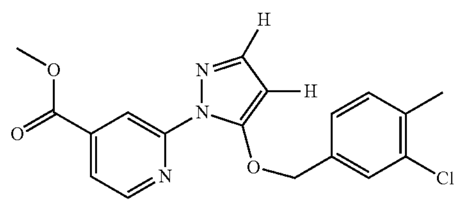 [SMILES: COC(=O)c1ccnc(-n2nccc2OCc2ccc(C)c(Cl)c2)c1] | methyl 2-[5-[(3-chloro-4-methylphenyl)methoxy]pyrazol-1-yl]pyridine-4-carboxylate |
| 101 | 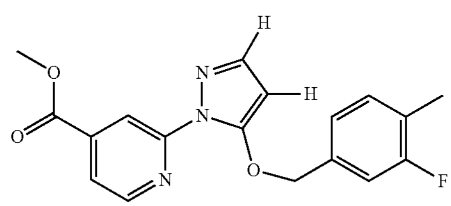 [SMILES: COC(=O)c1ccnc(-n2nccc2OCc2ccc(C)c(F)c2)c1] | methyl 2-[5-[(3-fluoro-4-methylphenyl)methoxy]pyrazol-1-yl]pyridine-4-carboxylate |
| 102 | 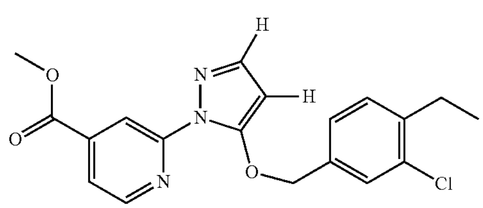 [SMILES: CCc1ccc(COc2ccnn2-c2cc(C(=O)OC)ccn2)cc1Cl] | methyl 2-[5-[(3-chloro-4-ethylphenyl)methoxy]pyrazol-1-yl]pyridine-4-carboxylate |
| 103 | 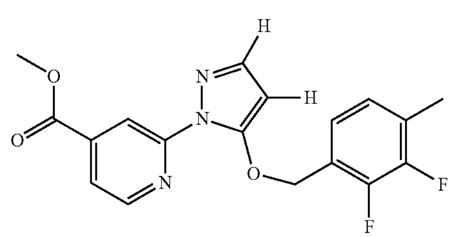 [SMILES: COC(=O)c1ccnc(-n2nccc2OCc2ccc(C)c(F)c2F)c1] | methyl 2-[5-[(2,3-difluoro-4-methylphenyl)methoxy]pyrazol-1-yl]pyridine-4-carboxylate |

TABLE 1-continued

| Chemical Synthesis Example | Structure | Name |
|---|---|---|
| 104 | 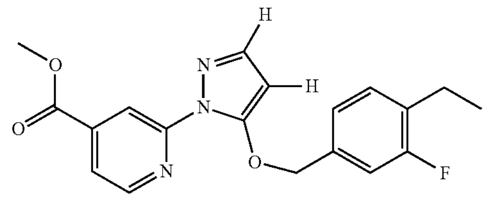 [SMILES: CCc1ccc(COc2ccnn2-c2cc(C(=O)OC)ccn2)cc1F] | methyl 2-[5-[(4-ethyl-3-fluorophenyl)methoxy]pyrazol-1-yl]pyridine-4-carboxylate |
| 105 | 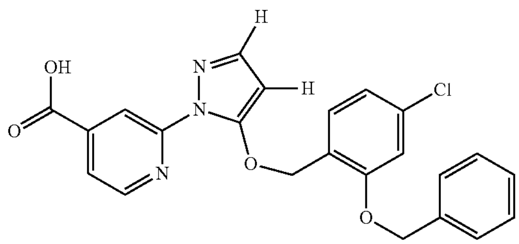 [SMILES: O=C(O)c1ccnc(-n2nccc2OCc2ccc(Cl)cc2OCc2ccccc2)c1] | 2-[5-[(4-chloro-2-phenylmethoxyphenyl)methoxy]pyrazol-1-yl]pyridine-4-carboxylic acid |
| 106 | 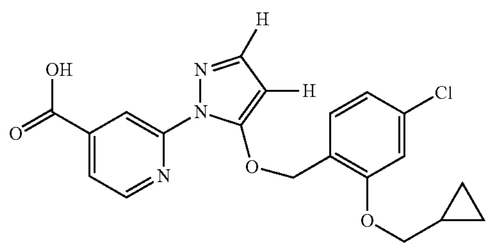 [SMILES: O=C(O)c1ccnc(-n2nccc2OCc2ccc(Cl)cc2OCC2CC2)c1] | 2-[5-[[4-chloro-2-(cyclopropylmethoxy)phenyl]methoxy]pyrazol-1-yl]pyridine-4-carboxylic acid |
| 107 | 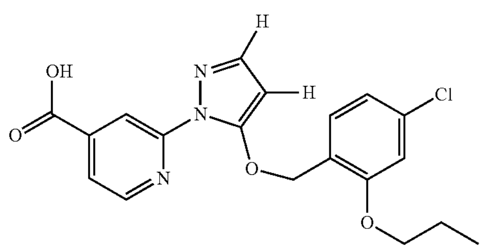 [SMILES: CCCOc1cc(Cl)ccc1COc1ccnn1-c1cc(C(=O)O)ccn1] | 2-[5-[(4-chloro-2-propoxyphenyl)methoxy]pyrazol-1-yl]pyridine-4-carboxylic acid |
| 108 | 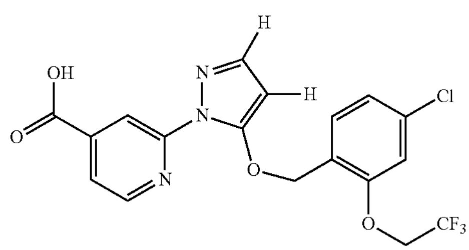 [SMILES: O=C(O)c1ccnc(-n2nccc2OCc2ccc(Cl)cc2OCC(F)(F)F)c1] | 2-[5-[[4-chloro-2-(2,2,2-trifluoroethoxy)phenyl]methoxy]pyrazol-1-yl]pyridine-4-carboxylic acid |
| 109 | 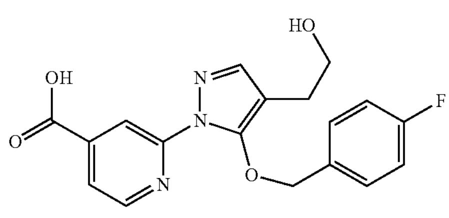 [SMILES: O=C(O)c1ccnc(-n2ncc(CCO)c2OCc2ccc(F)cc2)c1] | 2-[5-[(4-fluorophenyl)methoxy]-4-(2-hydroxyethyl)pyrazol-1-yl]pyridine-4-carboxylic acid |

TABLE 1-continued

| Chemical Synthesis Example | Structure | Name |
|---|---|---|
| 110 | 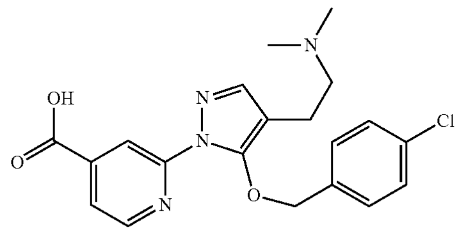 [SMILES: CN(C)CCc1cnn(-c2cc(C(=O)O)ccn2)c1OCc1ccc(Cl)cc1] | 2-[4-[2-(dimethylamino)ethyl]-5-[(4-fluorophenyl)methoxy]pyrazol-1-yl]pyridine-4-carboxylic acid |
| 111 | 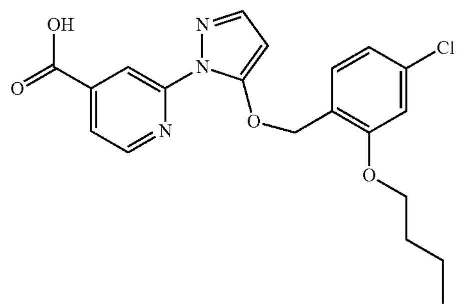 [SMILES: CCCCOc1cc(Cl)ccc1COc1ccnn1-c1cc(C(=O)O)ccn1] | 2-[5-[(2-butoxy-4-chlorophenyl)methoxy]pyrazol-1-yl]pyridine-4-carboxylic acid |
| 112 | 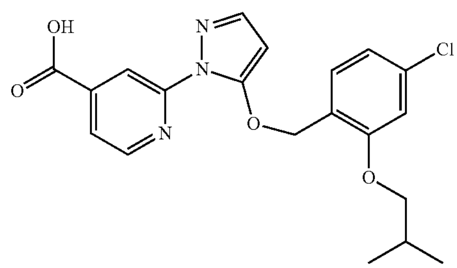 [SMILES: CC(C)COc1cc(Cl)ccc1COc1ccnn1-c1cc(C(=O)O)ccn1] | 2-[5-[[4-chloro-2-(2-methylpropoxy)phenyl]methoxy]pyrazol-1-yl]pyridine-4-carboxylic acid |
| 113 | 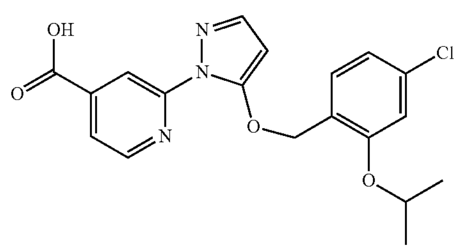 [SMILES: CC(C)Oc1cc(Cl)ccc1COc1ccnn1-c1cc(C(=O)O)ccn1] | 2-[5-[(4-chloro-2-propan-2-yloxyphenyl)methoxy]pyrazol-1-yl]pyridine-4-carboxylic acid |
| 114 | 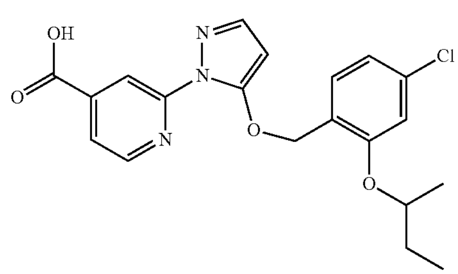 [SMILES: CCC(C)Oc1cc(Cl)ccc1COc1ccnn1-c1cc(C(=O)O)ccn1] | 2-[5-[(2-butan-2-yloxy-4-chlorophenyl)methoxy]pyrazol-1-yl]pyridine-4-carboxylic acid |

TABLE 1-continued

| Chemical Synthesis Example | Structure | Name |
|---|---|---|
| 115 | 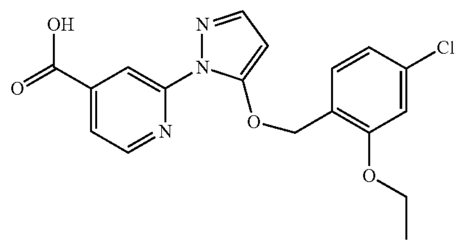 [SMILES: CCOc1cc(Cl)ccc1COc1ccnn1-c1cc(C(=O)O)ccn1] | 2-[5-[(4-chloro-2-ethoxyphenyl)methoxy]pyrazol-1-yl]pyridine-4-carboxylic acid |
| 116 | 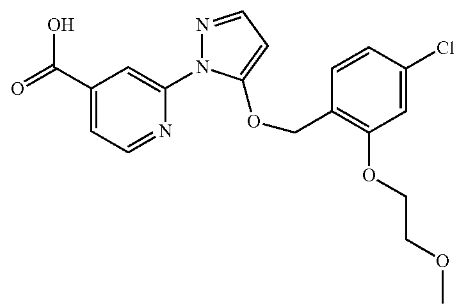 [SMILES: COCCOc1cc(Cl)ccc1COc1ccnn1-c1cc(C(=O)O)ccn1] | 2-[5-[[4-chloro-2-(2-methoxyethoxy)phenyl]methoxy]pyrazol-1-yl]pyridine-4-carboxylic acid |
| 117 | 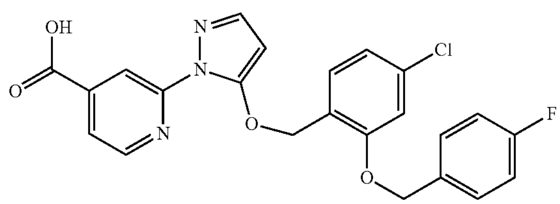 [SMILES: O=C(O)c1ccnc(-n2nccc2OCc2ccc(Cl)cc2OCc2ccc(F)cc2)c1] | 2-[5-[[4-chloro-2-[(4-fluorophenyl)methoxy]phenyl]methoxy]pyrazol-1-yl]pyridine-4-carboxylic acid |
| 118 | 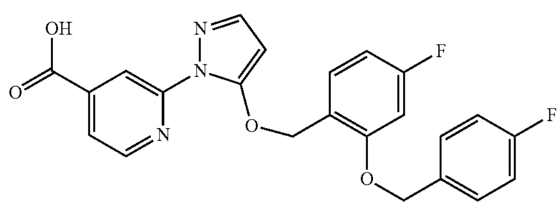 [SMILES: O=C(O)c1ccnc(-n2nccc2OCc2ccc(F)cc2OCc2ccc(F)cc2)c1] | 2-[5-[[4-fluoro-2-[(4-fluorophenyl)methoxy]phenyl]methoxy]pyrazol-1-yl]pyridine-4-carboxylic acid |
| 119 | 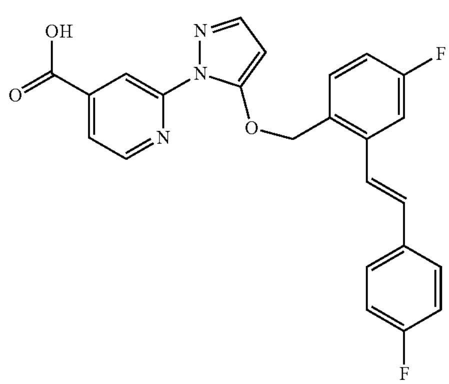 [SMILES: O=C(O)c1ccnc(-n2nccc2OCc2ccc(F)cc2/C=C/c2ccc(F)cc2)c1] | 2-[5-[[4-fluoro-2-[(E)-2-(4-fluorophenyl)ethenyl]phenyl]methoxy]pyrazol-1-yl]pyridine-4-carboxylic acid |

TABLE 1-continued

| Chemical Synthesis Example | Structure | Name |
|---|---|---|
| 120 | 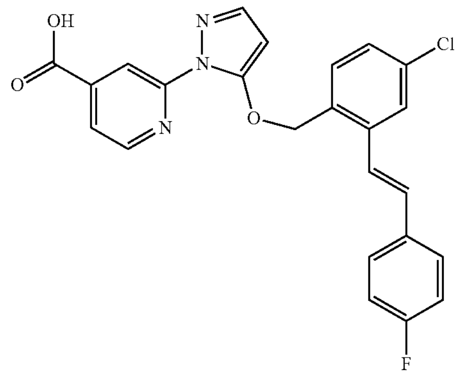 [SMILES: O=C(O)c1ccnc(-n2nccc2OCc2ccc(Cl)cc2/C=C/c2ccc(F)cc2)c1] | 2-[5-[[4-chloro-2-[(E)-2-(4-fluorophenyl)ethenyl]phenyl]methoxy]pyrazol-1-yl]pyridine-4-carboxylic acid |
| 121 | 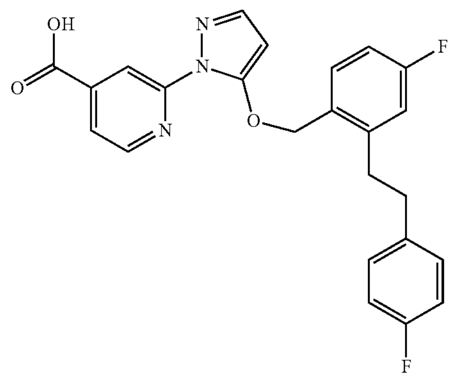 [SMILES: O=C(O)c1ccnc(-n2nccc2OCc2ccc(F)cc2CCc2ccc(F)cc2)c1] | 2-[5-[[4-fluoro-2-[2-(4-fluorophenyl)ethyl]phenyl]methoxy]pyrazol-1-yl]pyridine-4-carboxylic acid |
| 122 | 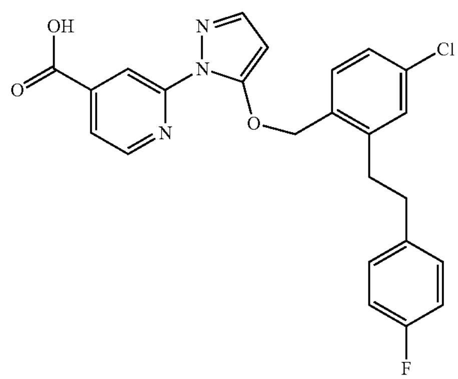 [SMILES: O=C(O)c1ccnc(-n2nccc2OCc2ccc(Cl)cc2CCc2ccc(F)cc2)c1] | 2-[5-[[4-chloro-2-[2-(4-fluorophenyl)ethyl]phenyl]methoxy]pyrazol-1-yl]pyridine-4-carboxylic acid |
| 123 | 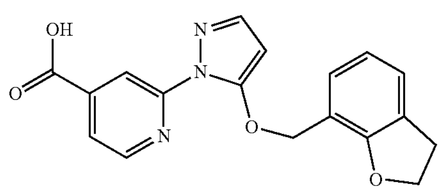 [SMILES: O=C(O)c1ccnc(-n2nccc2OCc2cccc3c2OCC3)c1] | 2-[5-(2,3-dihydro-1-benzofuran-7-ylmethoxy)pyrazol-1-yl]pyridine-4-carboxylic acid |
| 124 | 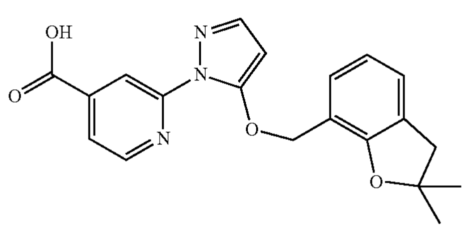 [SMILES: CC1(C)Cc2cccc(COc3ccnn3-c3cc(C(=O)O)ccn3)c2O1] | 2-[5-[(2,2-dimethyl-3H-1-benzofuran-7-yl)methoxy]pyrazol-1-yl]pyridine-4-carboxylic acid |

TABLE 1-continued

| Chemical Synthesis Example | Structure | Name |
|---|---|---|
| 125 | 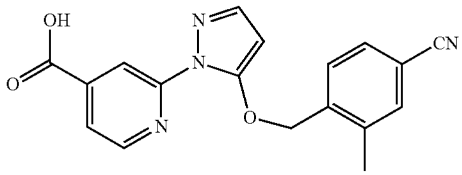 [SMILES: Cc1cc(C#N)ccc1COc1ccnn1-c1cc(C(=O)O)ccn1] | 2-[5-[(4-cyano-2-methylphenyl)methoxy]pyrazol-1-yl]pyridine-4-carboxylic acid |
| 126 | 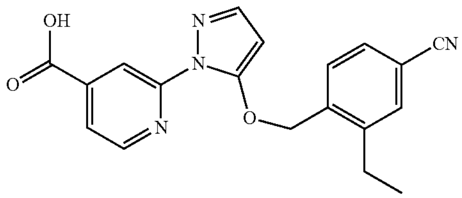 [SMILES: CCc1cc(C#N)ccc1COc1ccnn1-c1cc(C(=O)O)ccn1] | 2-[5-[(4-cyano-2-ethylphenyl)methoxy]pyrazol-1-yl]pyridine-4-carboxylic acid |
| 127 | 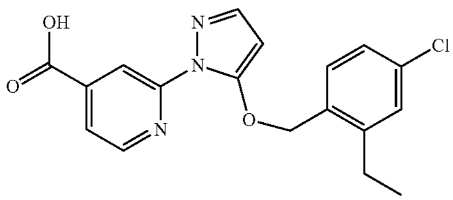 [SMILES: CCc1cc(Cl)ccc1COc1ccnn1-c1cc(C(=O)O)ccn1] | 2-[5-[(4-chloro-2-ethylphenyl)methoxy]pyrazol-1-yl]pyridine-4-carboxylic acid |
| 128 | 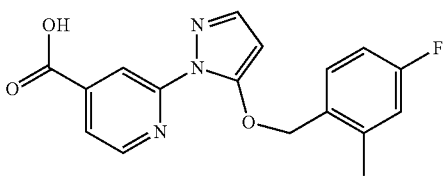 [SMILES: Cc1cc(F)ccc1COc1ccnn1-c1cc(C(=O)O)ccn1] | 2-[5-[(4-fluoro-2-methylphenyl)methoxy]pyrazol-1-yl]pyridine-4-carboxylic acid |
| 129 | 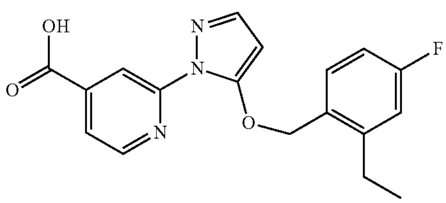 [SMILES: CCc1cc(F)ccc1COc1ccnn1-c1cc(C(=O)O)ccn1] | 2-[5-[(2-ethyl-4-fluorophenyl)methoxy]pyrazol-1-yl]pyridine-4-carboxylic acid |
| 130 | 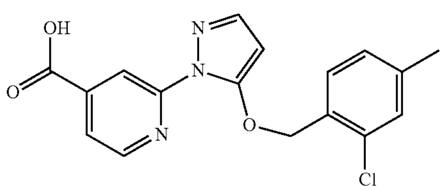 [SMILES: Cc1ccc(COc2ccnn2-c2cc(C(=O)O)ccn2)c(Cl)c1] | 2-[5-[(2-chloro-4-methylphenyl)methoxy]pyrazol-1-yl]pyridine-4-carboxylic acid |
| 131 | 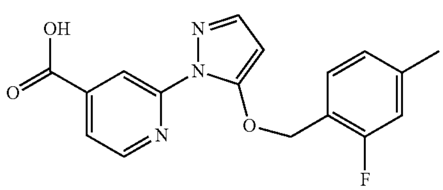 | 2-[5-[(2-fluoro-4-methylphenyl)methoxy]pyrazol-1-yl]pyridine-4-carboxylic acid |
| 132 | 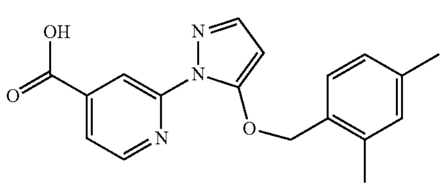 [SMILES: Cc1ccc(COc2ccnn2-c2cc(C(=O)O)ccn2)c(C)c1] | 2-[5-[(2,4-dimethylphenyl)methoxy]pyrazol-1-yl]pyridine-4-carboxylic acid |

TABLE 1-continued

| Chemical Synthesis Example | Structure | Name |
|---|---|---|
| 133 | 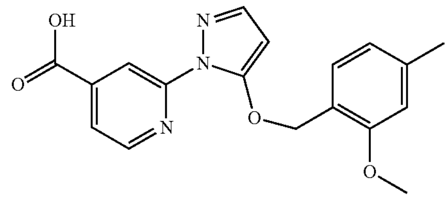 [SMILES: COc1cc(C)ccc1COc1ccnn1-c1cc(C(=O)O)ccn1] | 2-[5-[(2-methoxy-4-methylphenyl)methoxy]pyrazol-1-yl]pyridine-4-carboxylic acid |
| 134 | 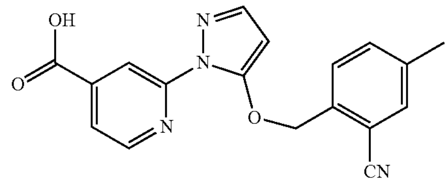 [SMILES: Cc1ccc(COc2ccnn2-c2cc(C(=O)O)ccn2)c(C#N)c1] | 2-[5-[(2-cyano-4-methylphenyl)methoxy]pyrazol-1-yl]pyridine-4-carboxylic acid |
| 135 | 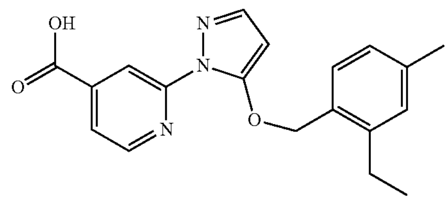 [SMILES: CCc1cc(C)ccc1COc1ccnn1-c1cc(C(=O)O)ccn1] | 2-[5-[(2-ethyl-4-methylphenyl)methoxy]pyrazol-1-yl]pyridine-4-carboxylic acid |
| 136 | 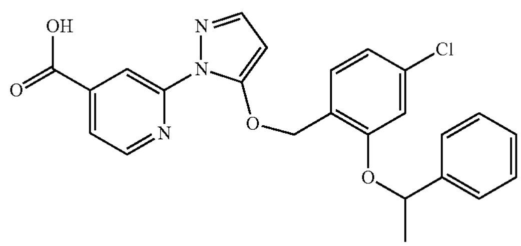 [SMILES: CC(Oc1cc(Cl)ccc1COc1ccnn1-c1cc(C(=O)O)ccn1)c1ccccc1] | 2-[5-[[4-chloro-2-(1-phenylethoxy)phenyl]methoxy]pyrazol-1-yl]pyridine-4-carboxylic acid |
| 137 | 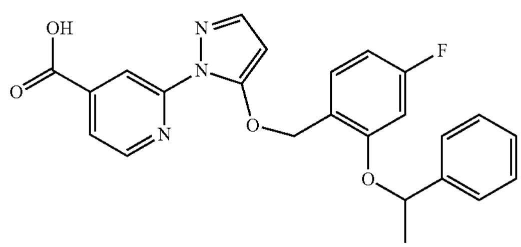 [SMILES: CC(Oc1cc(F)ccc1COc1ccnn1-c1cc(C(=O)O)ccn1)c1ccccc1] | 2-[5-[[4-fluoro-2-(1-phenylethoxy)phenyl]methoxy]pyrazol-1-yl]pyridine-4-carboxylic acid |
| 138 | 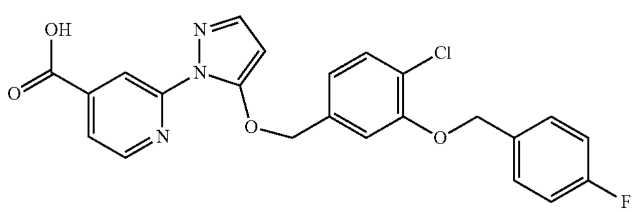 [SMILES: O=C(O)c1ccnc(-n2nccc2OCc2ccc(Cl)c(OCc3ccc(F)cc3)c2)c1] | 2-[5-[[4-chloro-3-[(4-fluorophenyl)methoxy]phenyl]methoxy]pyrazol-1-yl]pyridine-4-carboxylic acid |
| 139 | 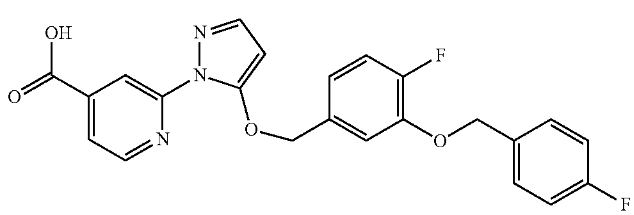 [SMILES: O=C(O)c1ccnc(-n2nccc2OCc2ccc(F)c(OCc3ccc(F)cc3)c2)c1] | 2-[5-[[4-fluoro-3-[(4-fluorophenyl)methoxy]phenyl]methoxy]pyrazol-1-yl]pyridine-4-carboxylic acid |

TABLE 1-continued

| Chemical Synthesis Example | Structure | Name |
|---|---|---|
| 140 | 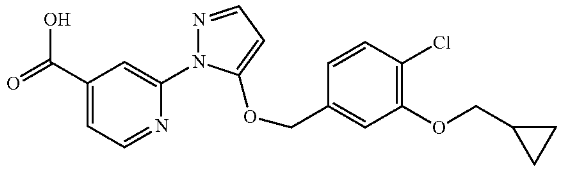 [SMILES: O=C(O)c1ccnc(-n2nccc2OCc2ccc(Cl)c(OCC3CC3)c2)c1] | 2-[5-[[4-chloro-3-(cyclopropylmethoxy)phenyl]methoxy]pyrazol-1-yl]pyridine-4-carboxylic acid |
| 141 | 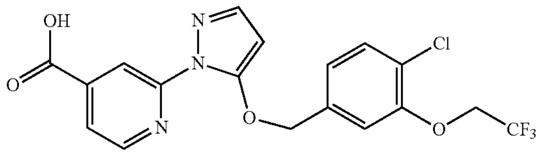 [SMILES: O=C(O)c1ccnc(-n2nccc2OCc2ccc(Cl)c(OCC(F)(F)F)c2)c1] | 2-[5-[[4-chloro-3-(2,2,2-trifluoroethoxy)phenyl]methoxy]pyrazol-1-yl]pyridine-4-carboxylic acid |
| 142 | 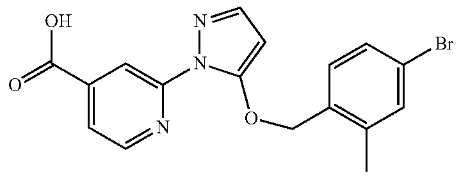 [SMILES: Cc1cc(Br)ccc1COc1ccnn1-c1cc(C(=O)O)ccn1] | 2-[5-[(4-bromo-2-methylphenyl)methoxy]pyrazol-1-yl]pyridine-4-carboxylic acid |
| 143 | 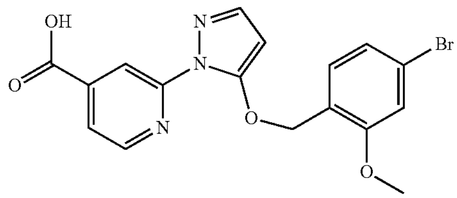 [SMILES: COc1cc(Br)ccc1COc1ccnn1-c1cc(C(=O)O)ccn1] | 2-[5-[(4-bromo-2-methoxyphenyl)methoxy]pyrazol-1-yl]pyridine-4-carboxylic acid |
| 144 | 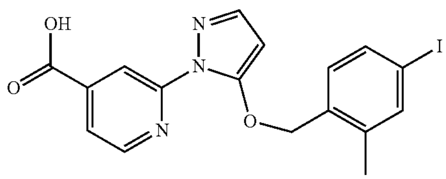 [SMILES: Cc1cc(I)ccc1COc1ccnn1-c1cc(C(=O)O)ccn1] | 2-[5-[(4-iodo-2-methylphenyl)methoxy]pyrazol-1-yl]pyridine-4-carboxylic acid |
| 145 | 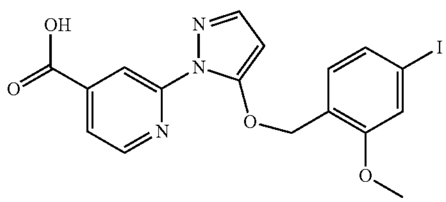 [SMILES: COc1cc(I)ccc1COc1ccnn1-c1cc(C(=O)O)ccn1] | 2-[5-[(4-iodo-2-methoxyphenyl)methoxy]pyrazol-1-yl]pyridine-4-carboxylic acid |
| 146 | 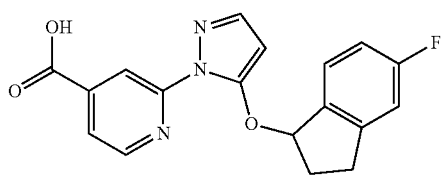 [SMILES: O=C(O)c1ccnc(-n2nccc2OC2CCc3cc(F)ccc32)c1] | 2-[5-[(5-fluoro-2,3-dihydro-1H-inden-1-yl)oxy]pyrazol-1-yl]pyridine-4-carboxylic acid |
| 147 | 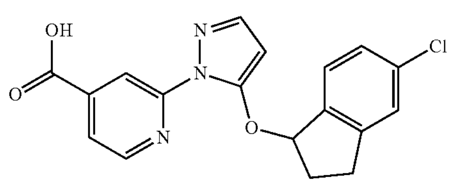 [SMILES: O=C(O)c1ccnc(-n2nccc2OC2CCc3cc(Cl)ccc32)c1] | 2-[5-[(5-chloro-2,3-dihydro-1H-inden-1-yl)oxy]pyrazol-1-yl]pyridine-4-carboxylic acid |

TABLE 1-continued

| Chemical Synthesis Example | Structure | Name |
|---|---|---|
| 148 | 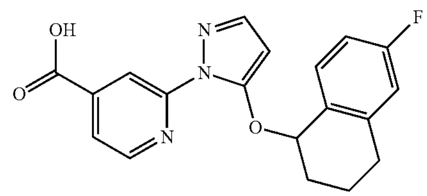 [SMILES: O=C(O)c1ccnc(-n2nccc2OC2CCCc3cc(F)ccc32)c1] | 2-[5-[(6-fluoro-1,2,3,4-tetrahydronaphthalen-1-yl)oxy]pyrazol-1-yl]pyridine-4-carboxylic acid |
| 149 | 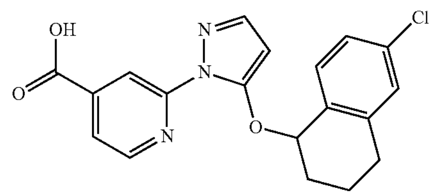 [SMILES: O=C(O)c1ccnc(-n2nccc2OC2CCCc3cc(Cl)ccc32)c1] | 2-[5-[(6-chloro-1,2,3,4-tetrahydronaphthalen-1-yl)oxy]pyrazol-1-yl]pyridine-4-carboxylic acid |
| 150 | 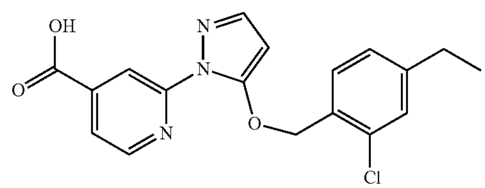 | 2-[5-[(2-chloro-4-ethylphenyl)methoxy]pyrazol-1-yl]pyridine-4-carboxylic acid |
| 151 | 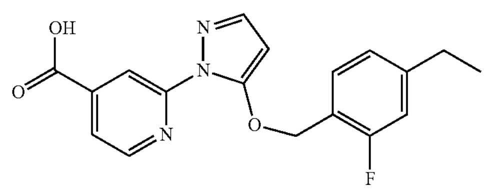 [SMILES: CCc1ccc(COc2ccnn2-c2cc(C(=O)O)ccn2)c(F)c1] | 2-[5-[(4-ethyl-2-fluorophenyl)methoxy]pyrazol-1-yl]pyridine-4-carboxylic acid |
| 152 | 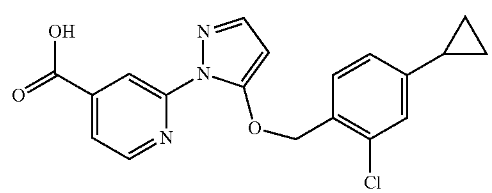 [SMILES: O=C(O)c1ccnc(-n2nccc2OCc2ccc(C3CC3)cc2Cl)c1] | 2-[5-[(2-chloro-4-cyclopropylphenyl)methoxy]pyrazol-1-yl]pyridine-4-carboxylic acid |
| 153 | 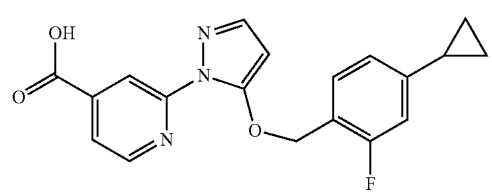 [SMILES: O=C(O)c1ccnc(-n2nccc2OCc2ccc(C3CC3)cc2F)c1] | 2-[5-[(4-cyclopropyl-2-fluorophenyl)methoxy]pyrazol-1-yl]pyridine-4-carboxylic acid |
| 154 | 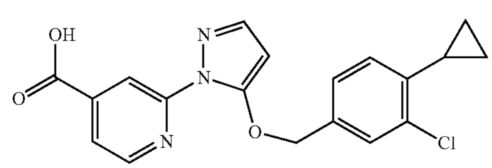 [SMILES: O=C(O)c1ccnc(-n2nccc2OCc2ccc(C3CC3)c(Cl)c2)c1] | 2-[5-[(3-chloro-4-cyclopropylphenyl)methoxy]pyrazol-1-yl]pyridine-4-carboxylic acid |
| 155 | 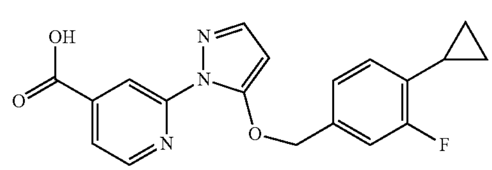 [SMILES: O=C(O)c1ccnc(-n2nccc2OCc2ccc(C3CC3)c(F)c2)c1] | 2-[5-[(4-cyclopropyl-3-fluorophenyl)methoxy]pyrazol-1-yl]pyridine-4-carboxylic acid |

TABLE 1-continued

| Chemical Synthesis Example | Structure | Name |
|---|---|---|
| 156 | 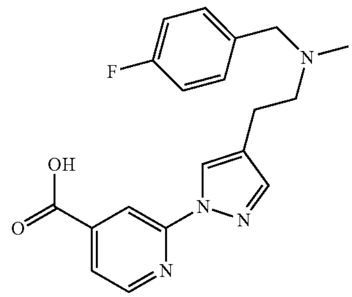 [SMILES: CN(CCc1cnn(-c2cc(C(=O)O)ccn2)c1)Cc1ccc(F)cc1] | 2-[4-[2-[(4-fluorophenyl)methyl-methylamino]ethyl]pyrazol-1-yl]pyridine-4-carboxylic acid |
| 157 | 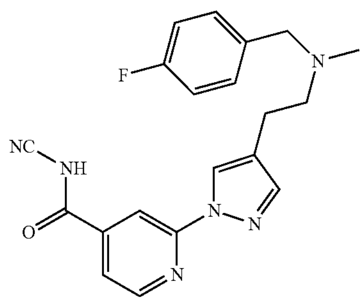 [SMILES: CN(CCc1cnn(-c2cc(C(=O)NC#N)ccn2)c1)Cc1ccc(F)cc1] | N-cyano-2-[4-[2-[(4-fluorophenyl)methyl-methylamino]ethyl]pyrazol-1-yl]pyridine-4-carboxamide |
| 158 | 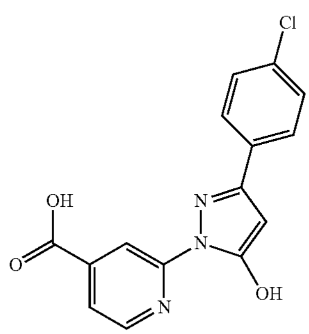 [SMILES: O=C(O)c1ccnc(-n2nc(-c3ccc(Cl)cc3)cc2O)c1] | 2-[3-(4-chlorophenyl)-5-hydroxypyrazol-1-yl]pyridine-4-carboxylic acid |
| 159 | 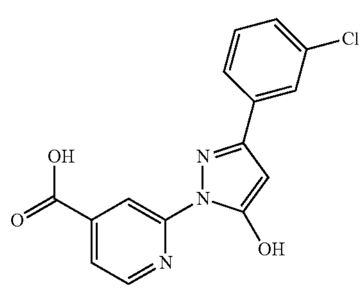 [SMILES: O=C(O)c1ccnc(-n2nc(-c3cccc(Cl)c3)cc2O)c1] | 2-[3-(3-chlorophenyl)-5-hydroxypyrazol-1-yl]pyridine-4-carboxylic acid |
| 160 | 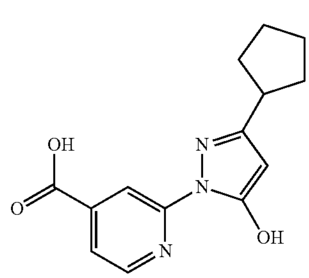 [SMILES: O=C(O)c1ccnc(-n2nc(C3CCCC3)cc2O)c1] | 2-(3-cyclopentyl-5-hydroxypyrazol-1-yl)pyridine-4-carboxylic acid |

TABLE 1-continued

| Chemical Synthesis Example | Structure | Name |
|---|---|---|
| 161 | 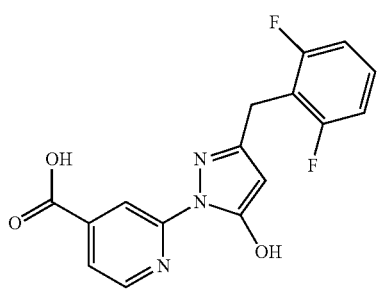 [SMILES: O=C(O)c1ccnc(-n2nc(Cc3c(F)cccc3F)cc2O)c1] | 2-[3-[(2,6-difluorophenyl)methyl]-5-hydroxypyrazol-1-yl]pyridine-4-carboxylic acid |
| 162 | 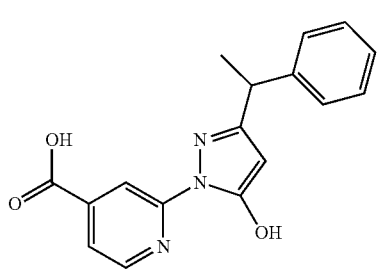 [SMILES: CC(c1ccccc1)c1cc(O)n(-c2cc(C(=O)O)ccn2)n1] | 2-[5-hydroxy-3-(1-phenylethyl)pyrazol-1-yl]pyridine-4-carboxylic acid |
| 163 | 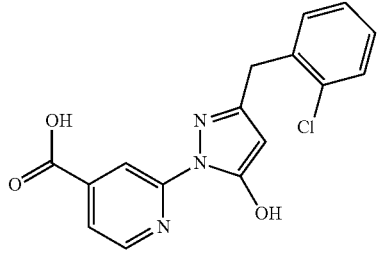 [SMILES: O=C(O)c1ccnc(-n2nc(Cc3ccccc3Cl)cc2O)c1] | 2-[3-[(2-chlorophenyl)methyl]-5-hydroxypyrazol-1-yl]pyridine-4-carboxylic acid |
| 164 | 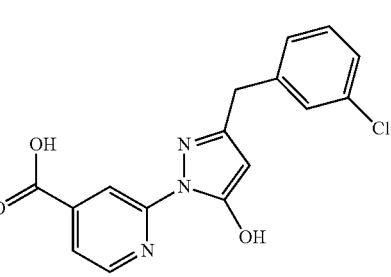 | 2-[3-[(3-chlorophenyl)methyl]-5-hydroxypyrazol-1-yl]pyridine-4-carboxylic acid |
| 165 | 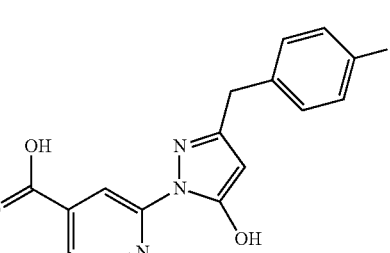 | 2-[3-[(4-chlorophenyl)methyl]-5-hydroxypyrazol-1-yl]pyridine-4-carboxylic acid |

TABLE 1-continued

| Chemical Synthesis Example | Structure | Name |
|---|---|---|
| 166 | 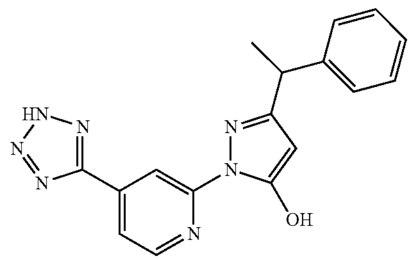 [SMILES: CC(c1ccccc1)c1cc(O)n(-c2cc(-c3nn[nH]n3)ccn2)n1] | 5-(1-phenylethyl)-2-[4-(1H-tetrazol-5-yl)pyridin-2-yl]pyrazol-3-ol |
| 167 | 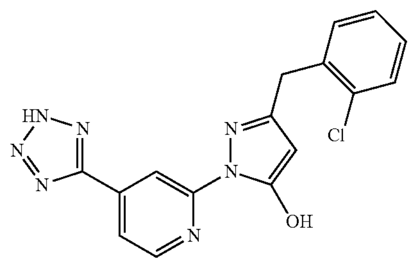 [SMILES: Oc1cc(Cc2ccccc2Cl)nn1-c1cc(-c2nn[nH]n2)ccn1] | 5-[(2-chlorophenyl)methyl]-2-[4-(1H-tetrazol-5-yl)pyridin-2-yl]pyrazol-3-ol |
| 168 | 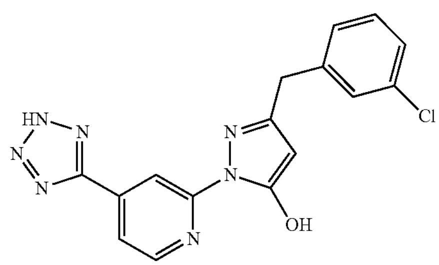 [SMILES: Oc1cc(Cc2cccc(Cl)c2)nn1-c1cc(-c2nn[nH]n2)ccn1] | 5-[(3-chlorophenyl)methyl]-2-[4-(1H-tetrazol-5-yl)pyridin-2-yl]pyrazol-3-ol |
| 169 | 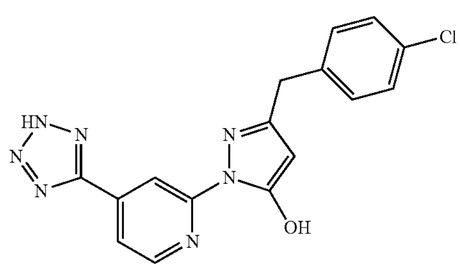 [SMILES: Oc1cc(Cc2ccc(Cl)cc2)nn1-c1cc(-c2nn[nH]n2)ccn1] | 5-[(4-chlorophenyl)methyl]-2-[4-(1H-tetrazol-5-yl)pyridin-2-yl]pyrazol-3-ol |
| 170 | 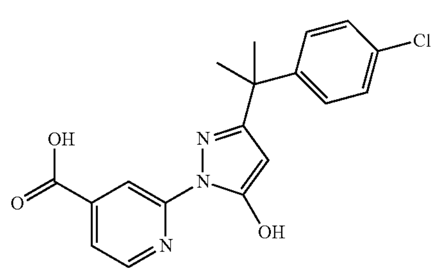 [SMILES: CC(C)(c1ccc(Cl)cc1)c1cc(O)n(-c2cc(C(=O)O)ccn2)n1] | 2-[3-[2-(4-chlorophenyl)propan-2-yl]-5-hydroxypyrazol-1-yl]pyridine-4-carboxylic acid |

TABLE 1-continued

| Chemical Synthesis Example | Structure | Name |
|---|---|---|
| 171 | 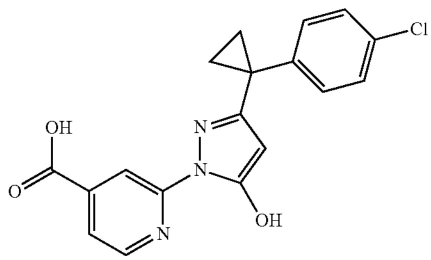 [SMILES: O=C(O)c1ccnc(-n2nc(C3(c4ccc(Cl)cc4)CC3)cc2O)c1] | 2-[3-[1-(4-chlorophenyl)cyclopropyl]-5-hydroxypyrazol-1-yl]pyridine-4-carboxylic acid |
| 172 | 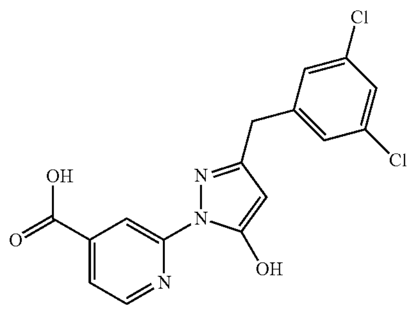 [SMILES: O=C(O)c1ccnc(-n2nc(Cc3cc(Cl)cc(Cl)c3)cc2O)c1] | 2-[3-[(3,5-dichlorophenyl)methyl]-5-hydroxypyrazol-1-yl]pyridine-4-carboxylic acid |
| 173 | 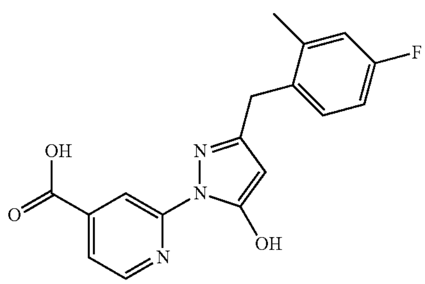 [SMILES: Cc1cc(F)ccc1Cc1cc(O)n(-c2cc(C(=O)O)ccn2)n1] | 2-[3-[(4-fluoro-2-methylphenyl)methyl]-5-hydroxypyrazol-1-yl]pyridine-4-carboxylic acid |
| 174 | 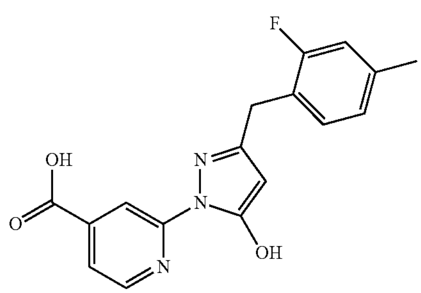 [SMILES: Cc1ccc(Cc2cc(O)n(-c3cc(C(=O)O)ccn3)n2)c(F)c1] | 2-[3-[(2-fluoro-4-methylphenyl)methyl]-5-hydroxypyrazol-1-yl]pyridine-4-carboxylic acid |
| 175 | 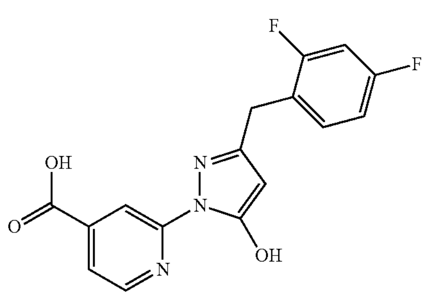 [SMILES: O=C(O)c1ccnc(-n2nc(Cc3ccc(F)cc3F)cc2O)c1] | 2-[3-[(2,4-difluorophenyl)methyl]-5-hydroxypyrazol-1-yl]pyridine-4-carboxylic acid |

In additional embodiments, the substituted pyrazolylpyridine derivative compound disclosed herein is selected from a compound of Table 2.

TABLE 2

2-(5-{[1-(4-fluorophenyl)cyclopropyl]oxy}-1H-pyrazol-1-yl)pyridine-4-carboxylic acid 2-(5-{[1-(4-chlorophenyl)cyclopropyl]oxy}-1H-pyrazol-1-yl)pyridine-4-carboxylic acid 2-{5-[(1R)-1-(4-fluorophenyl)ethoxy]-1H-pyrazol-1-yl}pyridine-4-carboxylic acid 2-{5-[(1R)-1-(4-chlorophenyl)ethoxy]-1H-pyrazol-1-yl}pyridine-4-carboxylic acid TABLE 2-continued 2-{5-[(1S)-1-(4-fluorophenyl)ethoxy]-1H-pyrazol-1-yl}pyridine-4-carboxylic acid 2-{5-[(1S)-1-(4-chlorophenyl)ethoxy]-1H-pyrazol-1-yl}pyridine-4-carboxylic acid 2-(5-{[2-(4-fluorophenyl)propan-2-yl]oxy}-1H-pyrazol-1-yl)pyridine-4-carboxylic acid 2-(5-{[2-(4-chlorophenyl)propan-2-yl]oxy}-1H-pyrazol-1-yl)pyridine-4-carboxylic acid TABLE 2-continued

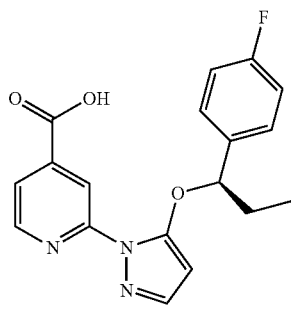 [SMILES: CC[C@@H](Oc1ccnn1-c1cc(C(=O)O)ccn1)c1ccc(F)cc1]

2-{5-[(1R)-1-(4-fluorophenyl)propoxy]-
1H-pyrazol-1-yl}pyridine-4-carboxylic
acid

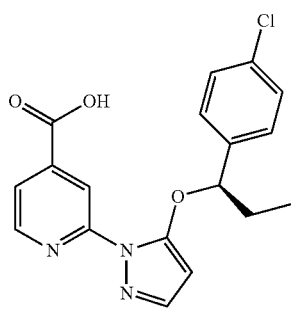 [SMILES: CC[C@@H](Oc1ccnn1-c1cc(C(=O)O)ccn1)c1ccc(Cl)cc1]

2-{5-[(1R)-1-(4-chlorophenyl)propoxy]-1H-
pyrazol-1-yl}pyridine-4-carboxylic acid

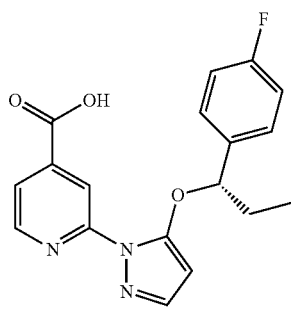

2-{5-[(1S)-1-(4-fluorophenyl)propoxy]-
1H-pyrazol-1-yl}pyridine-4-carboxylic
acid

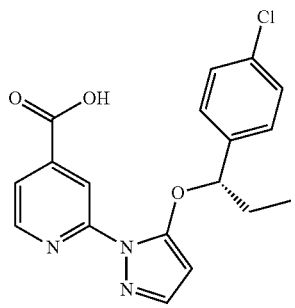 [SMILES: CC[C@H](Oc1ccnn1-c1cc(C(=O)O)ccn1)c1ccc(Cl)cc1]

2-{5-[(1S)-1-(4-chlorophenyl)propoxy]-1H-
pyrazol-1-yl}pyridine-4-carboxylic acid TABLE 2-continued

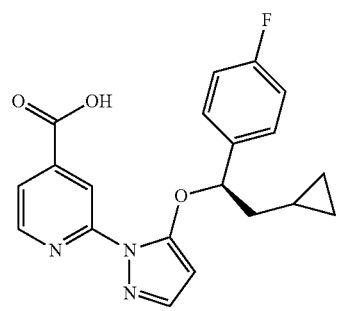

2-{5-[(1R)-2-cyclopropyl-1-(4-
fluorophenyl)ethoxy]-1H-pyrazol-1-
yl}pyridine-4-carboxylic acid

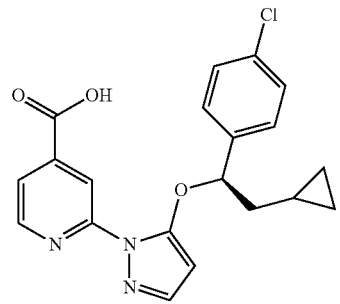 [SMILES: O=C(O)c1ccnc(-n2nccc2O[C@H](CC2CC2)c2ccc(Cl)cc2)c1]

2-{5-[(1R)-2-cyclopropyl-1-(4-
chlorophenyl)ethoxy]-1H-pyrazol-1-
yl}pyridine-4-carboxylic acid

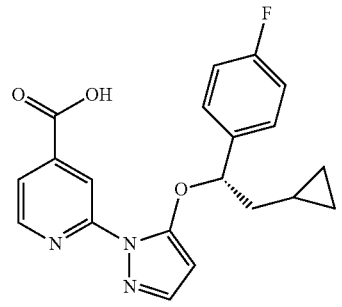

2-{5-[(1S)-2-cyclopropyl-1-(4-
fluorophenyl)ethoxy]-1H-pyrazol-1-
yl}pyridine-4-carboxylic acid

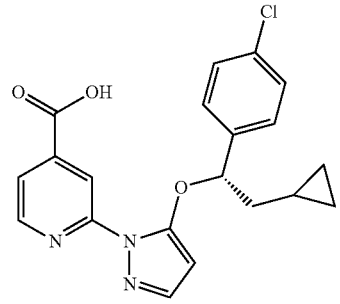 [SMILES: O=C(O)c1ccnc(-n2nccc2O[C@@H](CC2CC2)c2ccc(Cl)cc2)c1]

2-{5-[(1S)-2-cyclopropyl-1-(4-
chlorophenyl)ethoxy]-1H-pyrazol-1-
yl}pyridine-4-carboxylic acid TABLE 2-continued

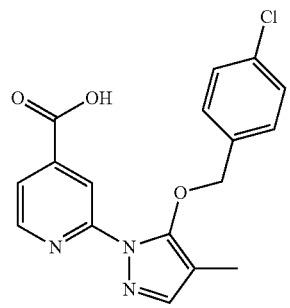 [SMILES: Cc1cnn(-c2cc(C(=O)O)ccn2)c1OCc1ccc(Cl)cc1]

2-{5-[(4-chlorobenzyl)oxy]-4-methyl-1H-
pyrazol-1-yl}pyridine-4-carboxylic acid

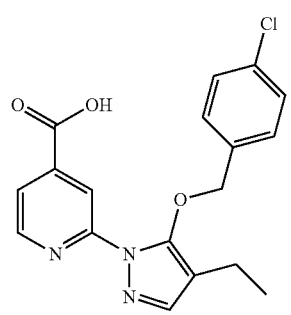 [SMILES: CCc1cnn(-c2cc(C(=O)O)ccn2)c1OCc1ccc(Cl)cc1]

2-{4-ethyl-5-[(4-chlorobenzyl)oxy]-1H-
pyrazol-1-yl}pyridine-4-carboxylic acid

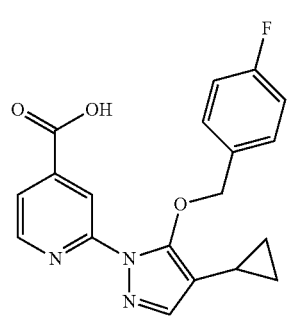 [SMILES: O=C(O)c1ccnc(-n2ncc(C3CC3)c2OCc2ccc(F)cc2)c1]

2-{4-cyclopropyl-5-[(4-
fluorobenzyl)oxy]-1H-pyrazol-1-
yl}pyridine-4-carboxylic acid

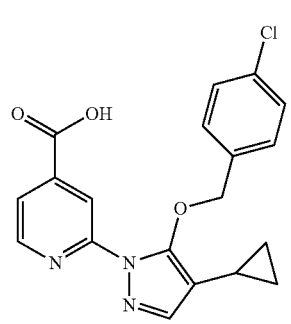 [SMILES: O=C(O)c1ccnc(-n2ncc(C3CC3)c2OCc2ccc(Cl)cc2)c1]

2-{5-[(4-chlorobenzyl)oxy]-4-cyclopropyl-
1H-pyrazol-1-yl}pyridine-4-carboxylic acid TABLE 2-continued

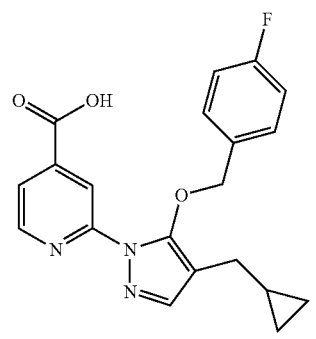 [SMILES: O=C(O)c1ccnc(-n2ncc(CC3CC3)c2OCc2ccc(F)cc2)c1]

2-{4-(cyclopropylmethyl)-5-[(4-
fluorobenzyl)oxy]-1H-pyrazol-1-
yl}pyridine-4-carboxylic acid

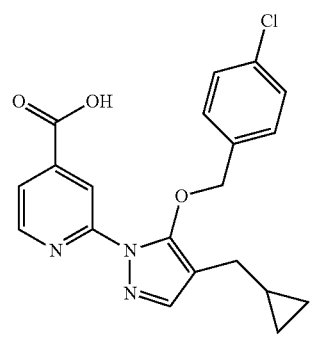

2-{4-(cyclopropylmethyl)-5-[(4-
chlorobenzyl)oxy]-1H-pyrazol-1-
yl}pyridine-4-carboxylic acid

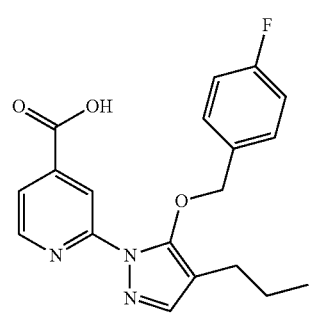 [SMILES: CCCc1cnn(-c2cc(C(=O)O)ccn2)c1OCc1ccc(F)cc1]

2-{5-[(4-fluorobenzyl)oxy]-4-propyl-1H-
pyrazol-1-yl}pyridine-4-carboxylic acid

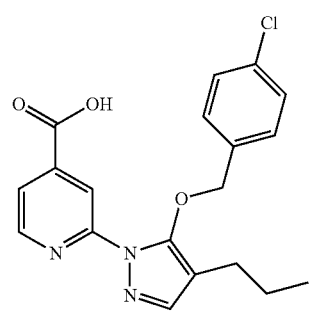 [SMILES: CCCc1cnn(-c2cc(C(=O)O)ccn2)c1OCc1ccc(Cl)cc1]

2-{5-[(4-chlorobenzyl)oxy]-4-propyl-1H-
pyrazol-1-yl}pyridine-4-carboxylic acid

TABLE 2-continued

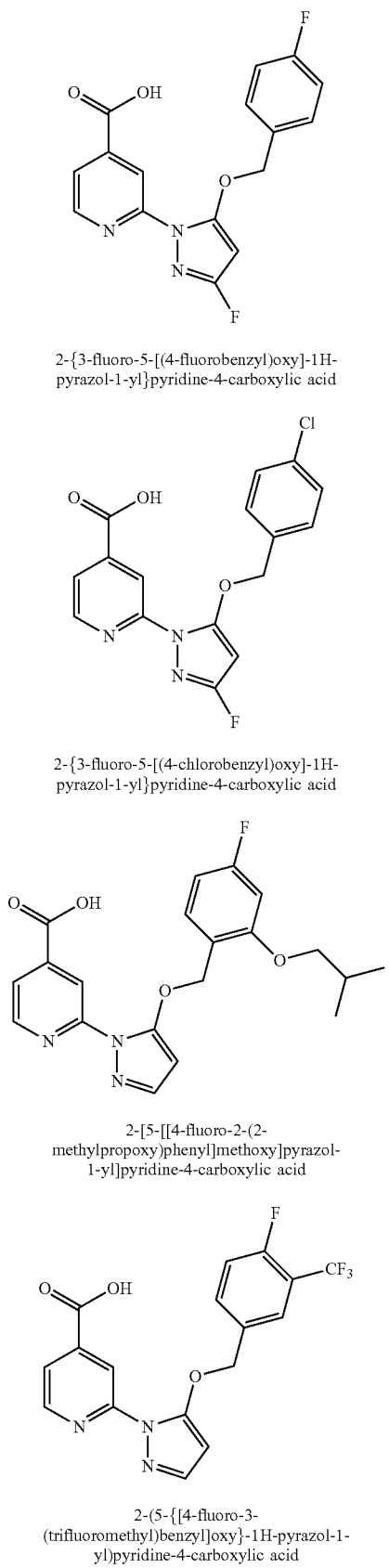

2-{3-fluoro-5-[(4-fluorobenzyl)oxy]-1H-pyrazol-1-yl}pyridine-4-carboxylic acid

2-{3-fluoro-5-[(4-chlorobenzyl)oxy]-1H-pyrazol-1-yl}pyridine-4-carboxylic acid

2-[5-[[4-fluoro-2-(2-methylpropoxy)phenyl]methoxy]pyrazol-1-yl]pyridine-4-carboxylic acid 2-(5-{[4-fluoro-3-(trifluoromethyl)benzyl]oxy}-1H-pyrazol-1-yl)pyridine-4-carboxylic acid TABLE 2-continued

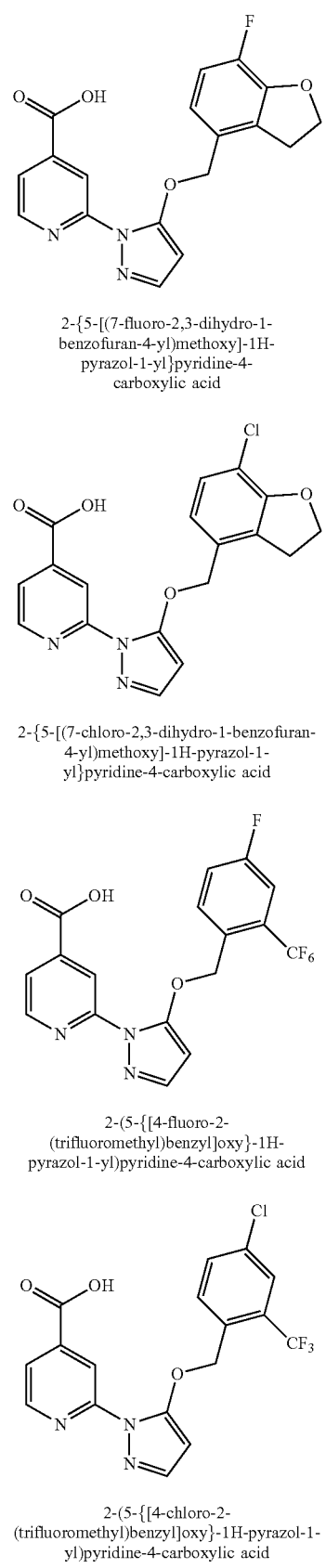

2-{5-[(7-fluoro-2,3-dihydro-1-benzofuran-4-yl)methoxy]-1H-pyrazol-1-yl}pyridine-4-carboxylic acid 2-{5-[(7-chloro-2,3-dihydro-1-benzofuran-4-yl)methoxy]-1H-pyrazol-1-yl}pyridine-4-carboxylic acid 2-(5-{[4-fluoro-2-(trifluoromethyl)benzyl]oxy}-1H-pyrazol-1-yl)pyridine-4-carboxylic acid 2-(5-{[4-chloro-2-(trifluoromethyl)benzyl]oxy}-1H-pyrazol-1-yl)pyridine-4-carboxylic acid TABLE 2-continued

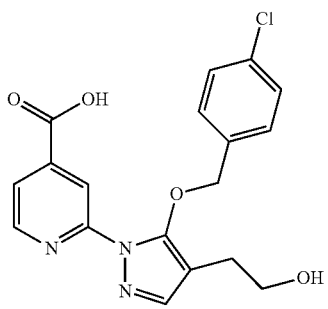 [SMILES: O=C(O)c1ccnc(-n2ncc(CCO)c2OCc2ccc(Cl)cc2)c1]

2-{5-[(4-chlorobenzyl)oxy]-4-(2-hydroxyethyl)-1H-pyrazol-1-yl}pyridine-4-carboxylic acid

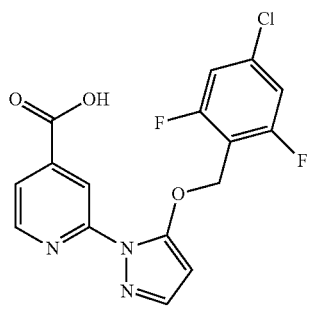 [SMILES: O=C(O)c1ccnc(-n2nccc2OCc2c(F)cc(Cl)cc2F)c1]

2-{5-[(4-chloro-2,6-difluorobenzyl)oxy]-1H-pyrazol-1-yl}pyridine-4-carboxylic acid

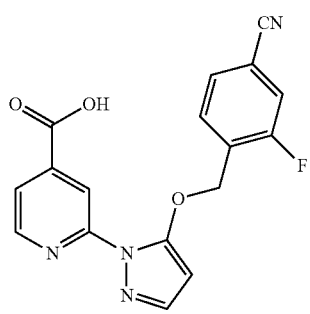 [SMILES: N#Cc1ccc(COc2ccnn2-c2cc(C(=O)O)ccn2)c(F)c1]

2-{5-[(4-cyano-2-fluorobenzyl)oxy]-1H-pyrazol-1-yl}pyridine-4-carboxylic acid

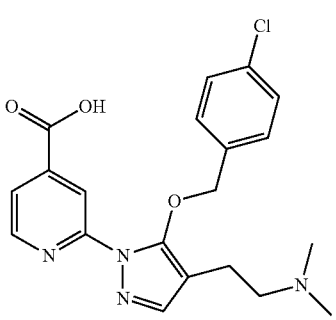 [SMILES: CN(C)CCc1cnn(-c2cc(C(=O)O)ccn2)c1OCc1ccc(Cl)cc1]

2-{5-[(4-chlorobenzyl)oxy]-4-[2-(dimethylamino)ethyl]-1H-pyrazol-1-yl}pyridine-4-carboxylic acid TABLE 2-continued

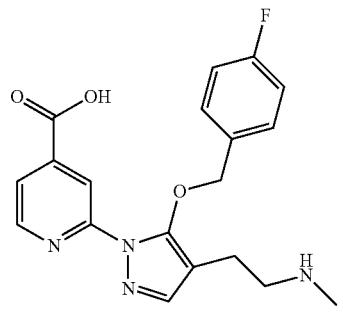 [SMILES: CNCCc1cnn(-c2cc(C(=O)O)ccn2)c1OCc1ccc(F)cc1]

2-{5-[(4-fluorobenzyl)oxy]-4-[2-(methylamino)ethyl]-1H-pyrazol-1-yl}pyridine-4-carboxylic acid

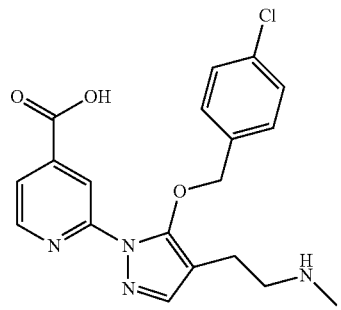 [SMILES: CNCCc1cnn(-c2cc(C(=O)O)ccn2)c1OCc1ccc(Cl)cc1]

2-{5-[(4-chlorobenzyl)oxy]-4-[2-(methylamino)ethyl]-1H-pyrazol-1-yl}pyridine-4-carboxylic acid

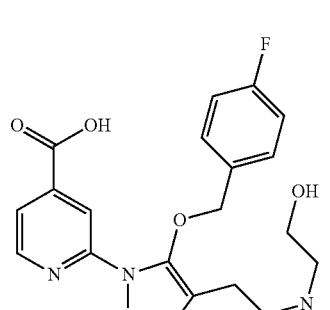

2-(5-(4-fluorobenzyloxy)-4-(2-((2-hydroxyethyl)(methyl)amino)ethyl)-1H-pyrazol-1-yl)isonicotinic acid

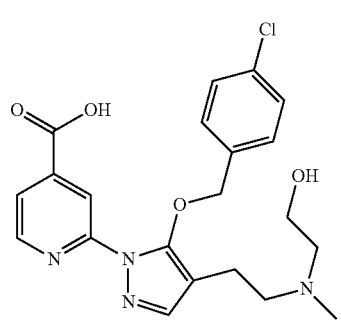 [SMILES: CN(CCO)CCc1cnn(-c2cc(C(=O)O)ccn2)c1OCc1ccc(F)cc1]

2-(5-(4-chlorobenzyloxy)-4-(2-((2-hydroxyethyl)(methyl)amino)ethyl)-1H-pyrazol-1-yl)isonicotinic acid TABLE 2-continued

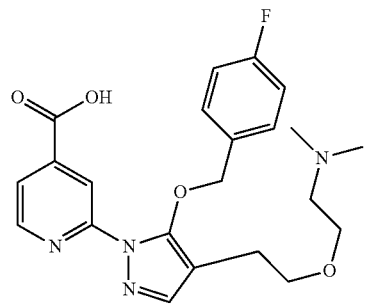

2-(4-(2-(2-(dimethylamino)ethoxy)ethyl)-
5-(4-fluorobenzyloxy)-1H-
pyrazol-1-yl)isonicotinic acid

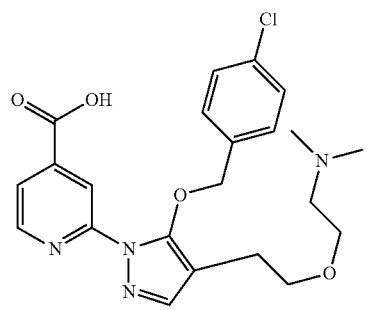 [SMILES: CN(C)CCOCCc1cnn(-c2cc(C(=O)O)ccn2)c1OCc1ccc(Cl)cc1]

2-(5-(4-chlorobenzyloxy)-4-(2-(2-
(dimethylamino)ethoxy)ethyl)-1H-
pyrazol-1-yl)isonicotinic acid

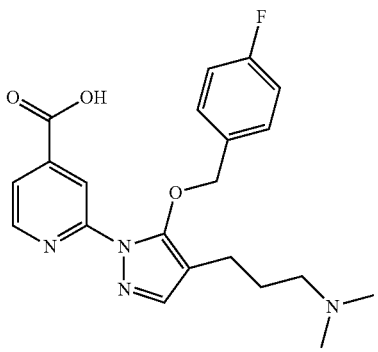 [SMILES: CN(C)CCCc1cnn(-c2cc(C(=O)O)ccn2)c1OCc1ccc(F)cc1]

2-(4-(3-(dimethylamino)propyl)-5-(4-
fluorobenzyloxy)-1H-pyrazol-1-
yl)isonicotinic acid

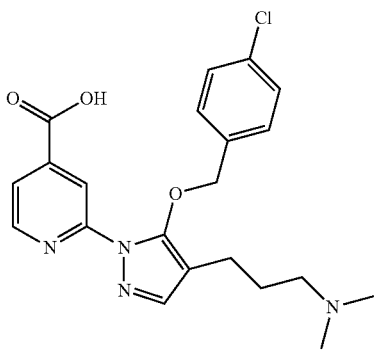 [SMILES: CN(C)CCCc1cnn(-c2cc(C(=O)O)ccn2)c1OCc1ccc(Cl)cc1]

2-(5-(4-chlorobenzyloxy)-4-(3-
(dimethylamino)propyl)-1H-
pyrazol-1-yl)isonicotinic acid TABLE 2-continued

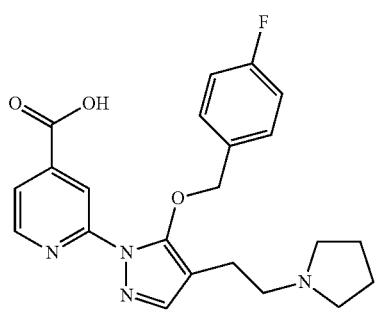

2-[5-[(4-fluorophenyl)methoxy]-4-(2-
pyrrolidin-1-ylethyl)pyrazol-1-
yl]pyridine-4-carboxylic acid

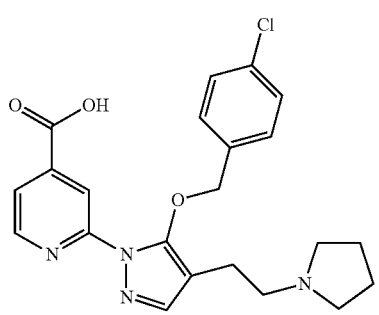 [SMILES: O=C(O)c1ccnc(-n2ncc(CCN3CCCC3)c2OCc2ccc(Cl)cc2)c1]

2-[5-[(4-chlorophenyl)methoxy]-4-(2-
pyrrolidin-1-ylethyl)pyrazol-1-yl]pyridine-
4-carboxylic acid

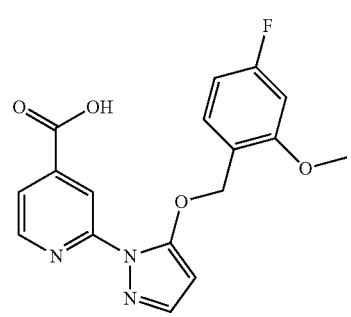 [SMILES: COc1cc(F)ccc1COc1ccnn1-c1cc(C(=O)O)ccn1]

2-[5-[(4-fluoro-2-
methoxyphenyl)methoxy]pyrazol-
1-yl]pyridine-4-carboxylic acid

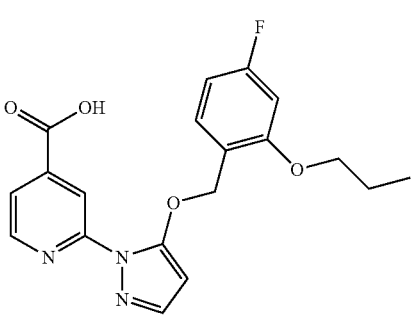 [SMILES: CCCOc1cc(F)ccc1COc1ccnn1-c1cc(C(=O)O)ccn1]

2-[5-[(4-fluoro-2-
propoxyphenyl)methoxy]pyrazol-
1-yl]pyridine-4-carboxylic acid

TABLE 2-continued

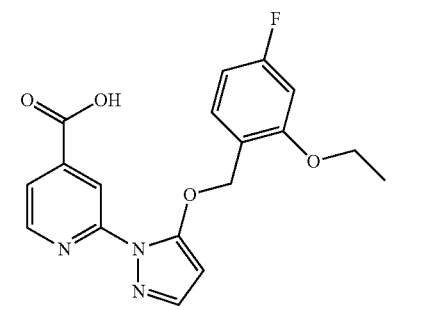 [SMILES: CCOc1cc(F)ccc1COc1ccnn1-c1cc(C(=O)O)ccn1]

2-[5-[(2-ethoxy-4-fluorophenyl)methoxy]pyrazol-1-yl]pyridine-4-carboxylic acid

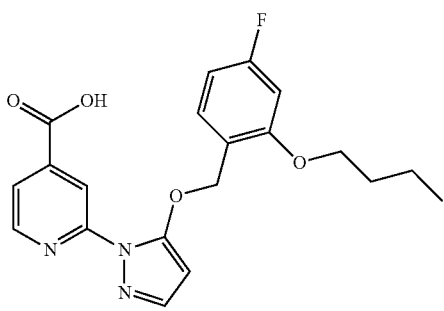 [SMILES: CCCCOc1cc(F)ccc1COc1ccnn1-c1cc(C(=O)O)ccn1]

2-[5-[(2-butoxy-4-fluorophenyl)methoxy]pyrazol-1-yl]pyridine-4-carboxylic acid

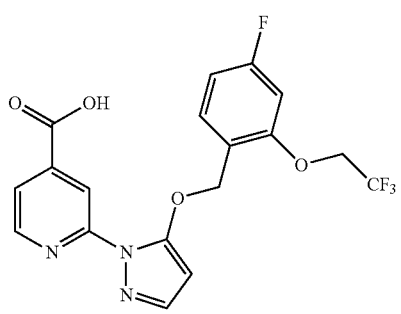 [SMILES: O=C(O)c1ccnc(-n2nccc2OCc2ccc(F)cc2OCC(F)(F)F)c1]

2-[5-[[4-fluoro-2-(2,2,2-trifluoroethoxy)phenyl]methoxy]pyrazol-1-yl]pyridine-4-carboxylic acid

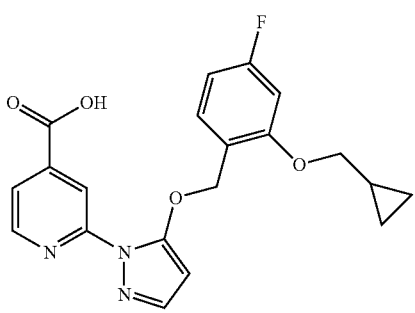 [SMILES: O=C(O)c1ccnc(-n2nccc2OCc2ccc(F)cc2OCC2CC2)c1]

2-[5-[[2-(cyclopropylmethoxy)-4-fluorophenyl]methoxy]pyrazol-1-yl]pyridine-4-carboxylic acid

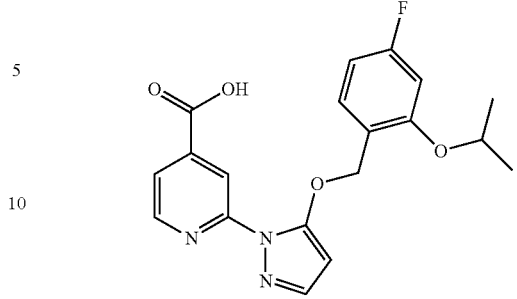

2-[5-[(4-fluoro-2-propan-2-yloxyphenyl)methoxy]pyrazol-1-yl]pyridine-4-carboxylic acid

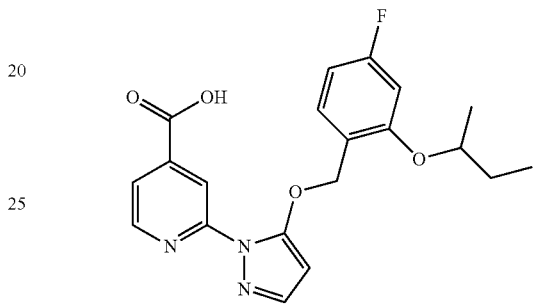

2-[5-[(2-butan-2-yloxy-4-fluorophenyl)methoxy]pyrazol-1-yl]pyridine-4-carboxylic acid Preparation of the Substituted Pyrazolylpyridine, Pyrazolylpyridazine, and Pyrazolylpyrimidine Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted pyrazolylpyridine derivative compounds described herein is P. H. Stahl & C. G. Wermuth "Handbook of Pharmaceutical Salts", Verlag Helvetica Chimica Acta, Zurich, 2002.

The substituted pyrazolylpyridine and pyrazolylpyridazine derivative compounds are prepared by the general synthetic routes described below in Schemes 1-8.

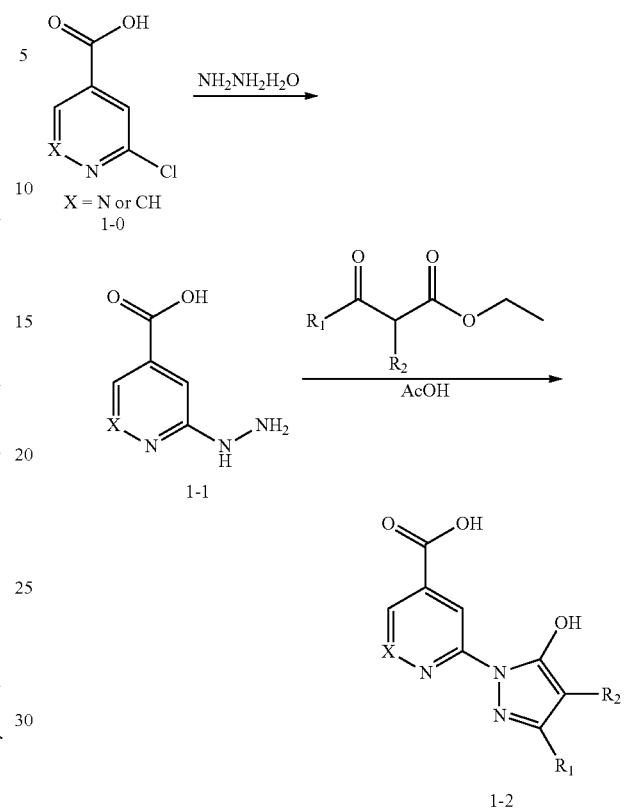

One method for preparing compounds such as compound 1-2 is provided in Scheme 1. 2-Chloroisonicotinic acid or 6-chloropyridazine-4-carboxylic acid are treated with hydrazine hydrate in an organic solvent, such as 1,4-dioxane, under reflux conditions (e.g., about 100° C.) to give intermediates 1-1. Subsequent reaction with substituted acetoacetyl ester in AcOH under heating conditions affords compound s1-2.

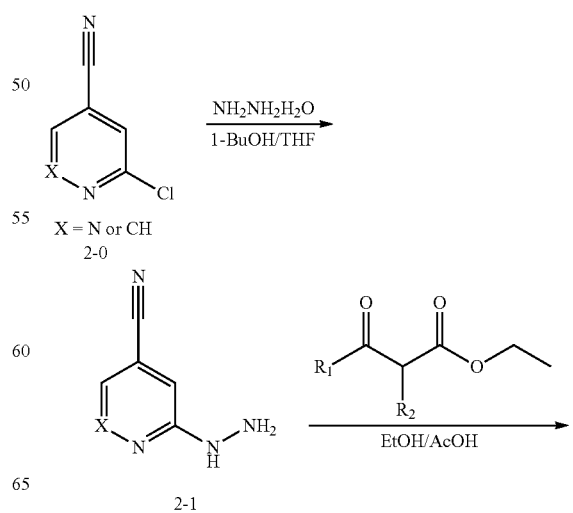

-continued

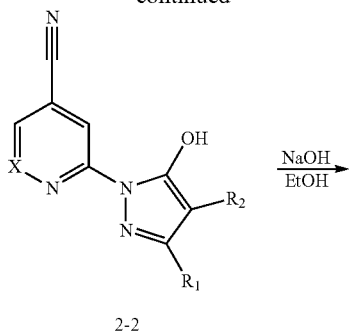

2-2

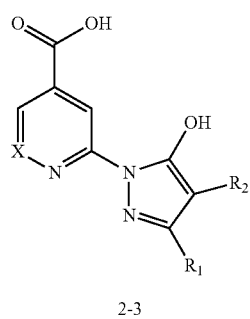

2-3

A method for preparing compounds such as compounds 2-3 is provided in Scheme 2. 2-Chloroisonicotinonitrile or 6-chloropyridazine-4-carbonitrile are treated with hydrazine hydrate in a mixture of an alcoholic solvent (such as 1-butanol) and an organic solvent (such as THF) at elevated temperature (e.g. about 60-100° C.) to give intermediates 2-1. Subsequent reaction with an acetoacetyl ester in a mixture of an alcoholic solvent (such as ethanol) heated to reflux in presence of acetic acid provides cyclized hydroxypyrazole pyridine intermediates 2-2. Hydrolysis using concentrated sodium hydroxide solution (such as 5-10 N) in ethanol provides the acids 2-3.

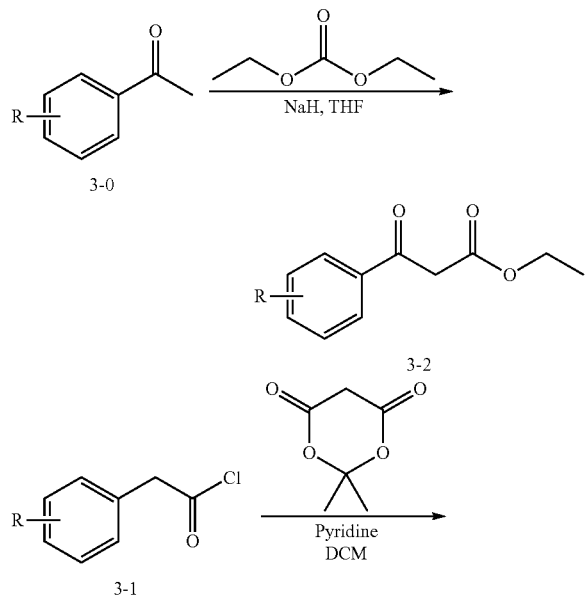

-continued

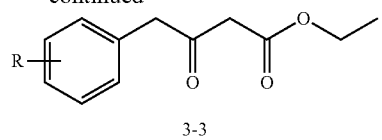

3-3

Two methods of preparing acetoacetyl esters are provided in Scheme 3. In the first method, a substituted acetophenone is treated with diethyl carbonate and sodium hydride in an organic solvent such as THF to give ketoester 3-2. In the second method, an acetyl chloride can is reacted with 2,2-dimethyl-1,3-dioxane-4,6-dione in presence of a base, such as pyridine, in an organic solvent, such as DCM, to give intermediate 3-3. Ketoesters such as 3-2 and 3-3 are condensed with 2-hydrazinylisonicotinonitrile, 6-hydrazinylpyridazine-4-carbonitrile, 2-hydrazinylpyrimidine-4-carbonitrile or 6-hydrazinylpyrimidine-4-carbonitrile to generate hydroxypyrazole pyridine, hydroxypyrazole pyridazine, and hydroxypyrazole pyrimidine analogs.

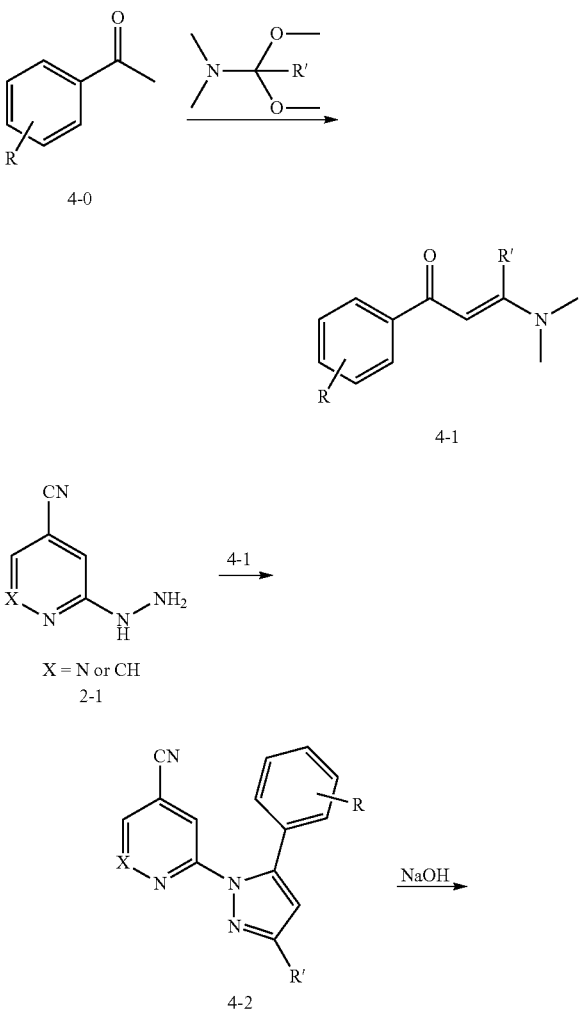

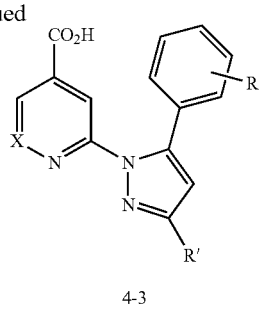

4-3

A method for preparing compounds such as compounds 4-3 is provided in Scheme 4. Substituted acetophenones are reacted with either DMF-DMA or (1,1-dimethoxy-ethyl)-dimethylamine under heating conditions (e.g. about 100-120° C.) to give intermediate 4-1. Subsequent cyclization with 2-hydrazylisonicotinonitrile or 6-hydrazinylpyridazine-4-carbonitrile, either as free bases or hydrochloride salts, in an alcohol solvent such as 2-methoxyethanol (if hydrochloride salt is used), or ethanol in the presence of acetic acid (if the free bases of compounds 2-1 are used) under heating conditions provides intermediates 4-2. Hydrolysis of the nitrile group using concentrated sodium hydroxide solution (5-10 M) in ethanol with heat affords the acid products 4-3.

A method for preparing compounds such as compounds 5-3 is provided in Scheme 5. Cyclization of 2-hydrazinylisoniconinonitrile or 6-hydrazinylpyridazine-4-carbonitrile with ethyl 3-oxobutanoate in an alcoholic solvent, such as ethanol, in presence of acetic acid provides intermediates 5-1. Alkylation of the hydroxyl group using an alkyl halide, such as alkyl bromide or alkyl iodide, in an organic solvent, such as DMF, in the presence of a base, e.g. K$_2$CO$_3$, gives products 5-2. Subsequent hydrolysis using concentrated NaOH in alcohol provides the acid products 5-3.

Scheme 5

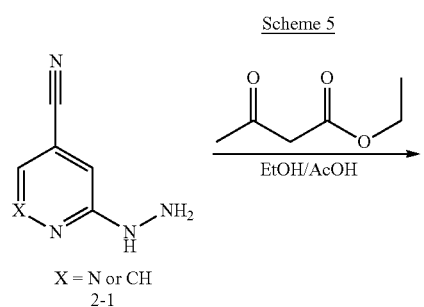

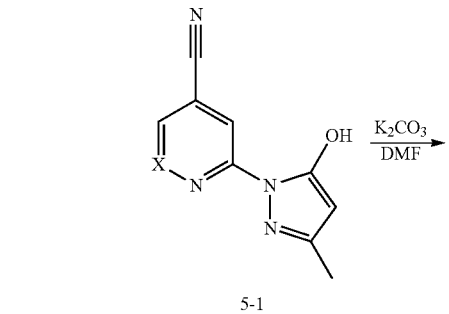

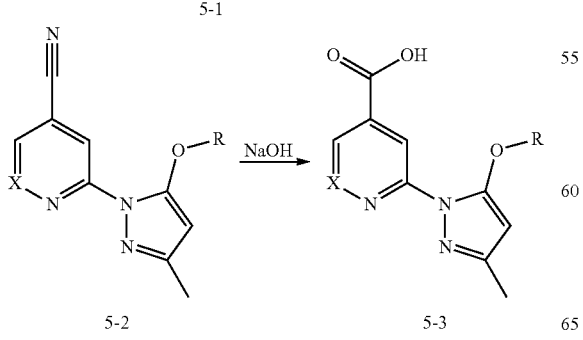

Scheme 6

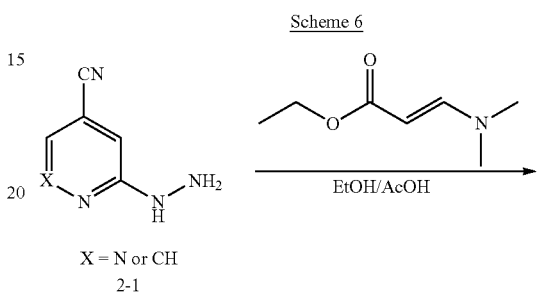

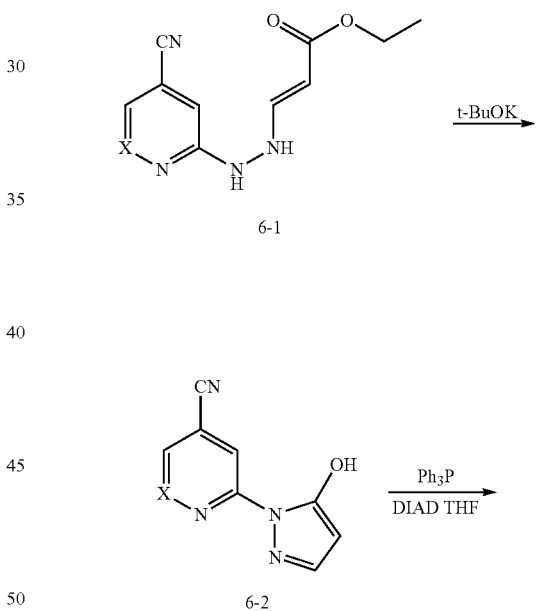

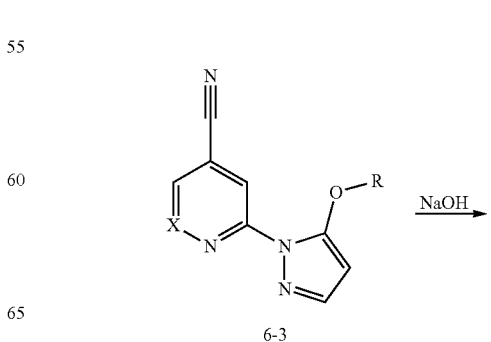

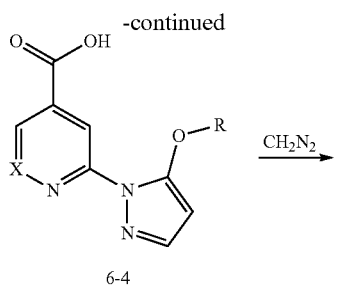

Methods for preparing compounds of formula 7-2 and 7-3 are provided in Scheme 7. Treatment of acids 7-1 with hydroxylamine hydrochloride in the presence of a coupling reagent, such as HATU, in a solvent, such as DMF, at room temperature for 1 to 24 hours provides compounds 7-2. Compounds 7-1 can also be used to prepare N-acylcyanamides such as compound 7-3. Treatment of 7-1 with cyanamide in the presence of an acid coupling reagent, such as HATU, in a solvent, such as DMF, at room temperature for 1 to 24 hours provides compounds 7-3.

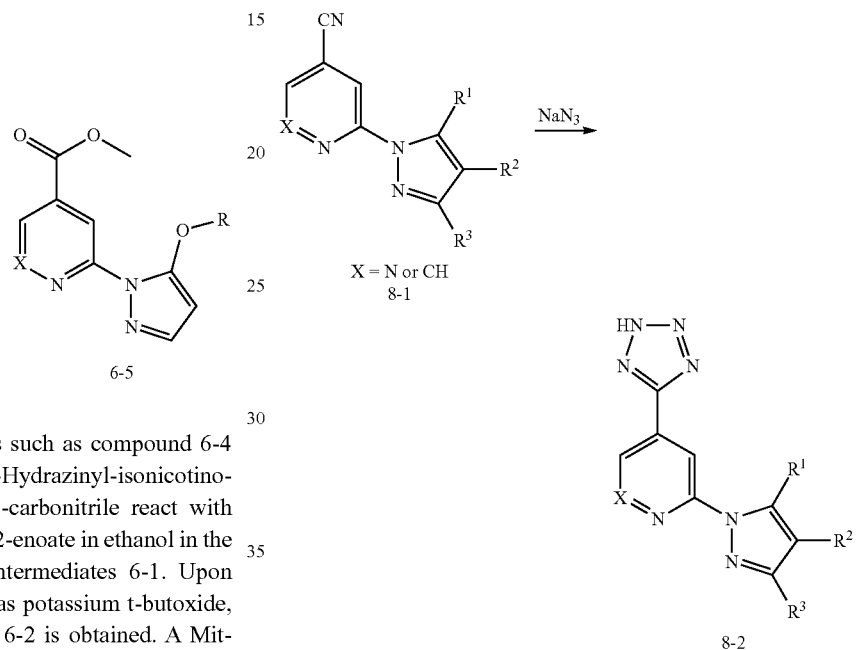

A method to prepare compounds such as compound 6-4 and 6-5 is provided in Scheme 6. 2-Hydrazinyl-isonicotinonitrile or 6-hydrazinylpyridazine-4-carbonitrile react with ethyl (2E)-3-(dimethylamino)prop-2-enoate in ethanol in the presence of acetic acid to give intermediates 6-1. Upon treatment with a strong base, such as potassium t-butoxide, the hydroxypyrazole intermediates 6-2 is obtained. A Mitsunobu reaction, wherein intermediates 6-2 are treated with an alcohol, an azadicarboxylate, such as DIAD, a ligand, such as triphenylphosphine, in an organic solvent, such as THF, gives a mixture of O-alkylation and N-alkylation products. Separation via flash column chromatography provides the desired O-alkylation products 6-3, which are then hydrolyzed to the acids 6-4. The acids are then treated with excess diazomethane (e.g. 10 equiv.) in an organic solvent such as THF to give the methyl esters, compounds 6-5.

A method for preparing compounds of formula 8-2 is provided in Scheme 8. Treatment of the nitrile intermediates 8-1 with sodium azide and ammonium chloride in DMF followed by heating to 90° C. for 2 to 24 hours provides the desired tetrazole derivatives 8-2.

The substituted pyrazolylpyrimidine derivative compounds are prepared by the general synthetic routes described below in Schemes 9-15.

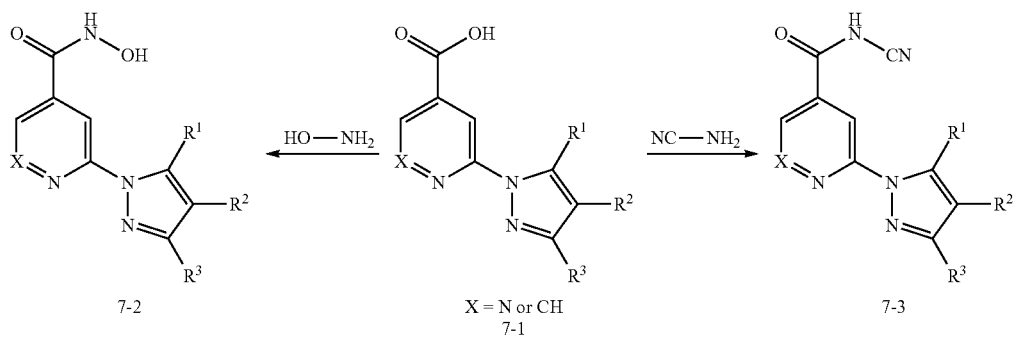

Scheme 9

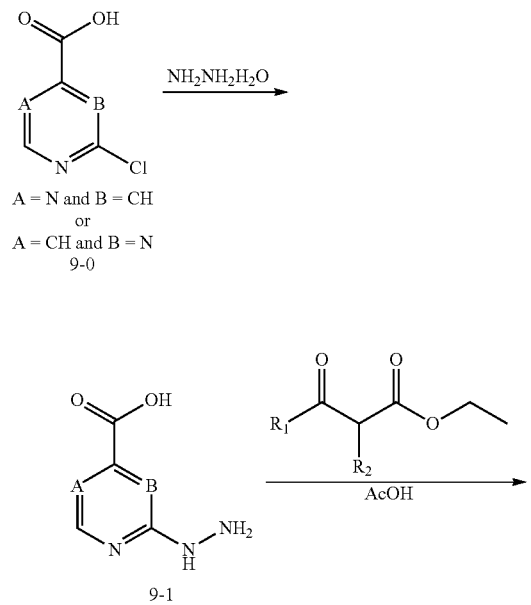

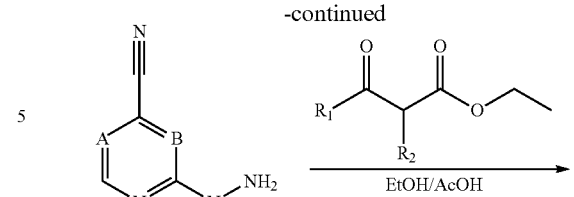

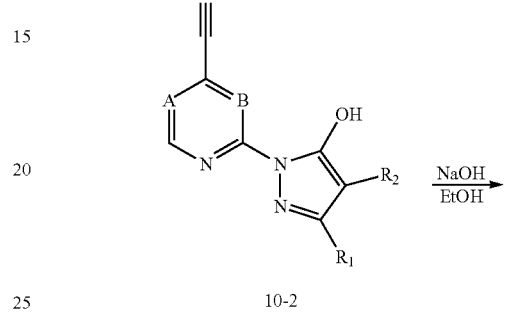

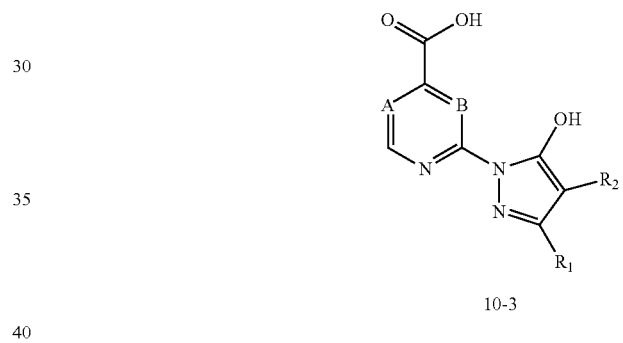

One method for preparing compounds such as compounds 9-2 is provided in Scheme 9. 6-Chloropyrimidine-4-carboxylic acid or 2-chloropyrimidine-4-carboxylic acid are treated with hydrazine hydrate in an organic solvent, such as 1,4-dioxane, under reflux conditions (e.g., about 100° C.) to give intermediates 9-1. Subsequent reaction with substituted acetoacetyl ester in AcOH under heating conditions affords compounds 9-2.

Scheme 10

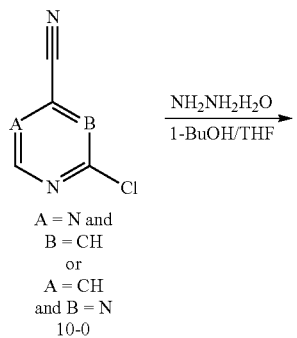

A method for preparing compounds such as compounds 10-3 is provided in Scheme 10. 2-Chloropyrimidine-4-carbonitrile or 6-chloropyrimidine-4-carbonitrile are treated with hydrazine hydrate in a mixture of an alcoholic solvent (such as 1-butanol) and an organic solvent (such as THF) at elevated temperature (e.g. about 60-100° C.) to give intermediates 10-1. Subsequent reaction with an acetoacetyl ester in a mixture of an alcoholic solvent (such as ethanol) heated to reflux in presence of acetic acid provides cyclized hydroxypyrazole pyridine intermediates 10-2. Hydrolysis using concentrated sodium hydroxide solution (such as 5-10 N) in ethanol provides the acids 10-3.

Scheme 11

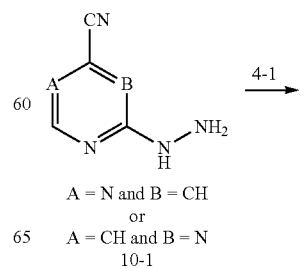

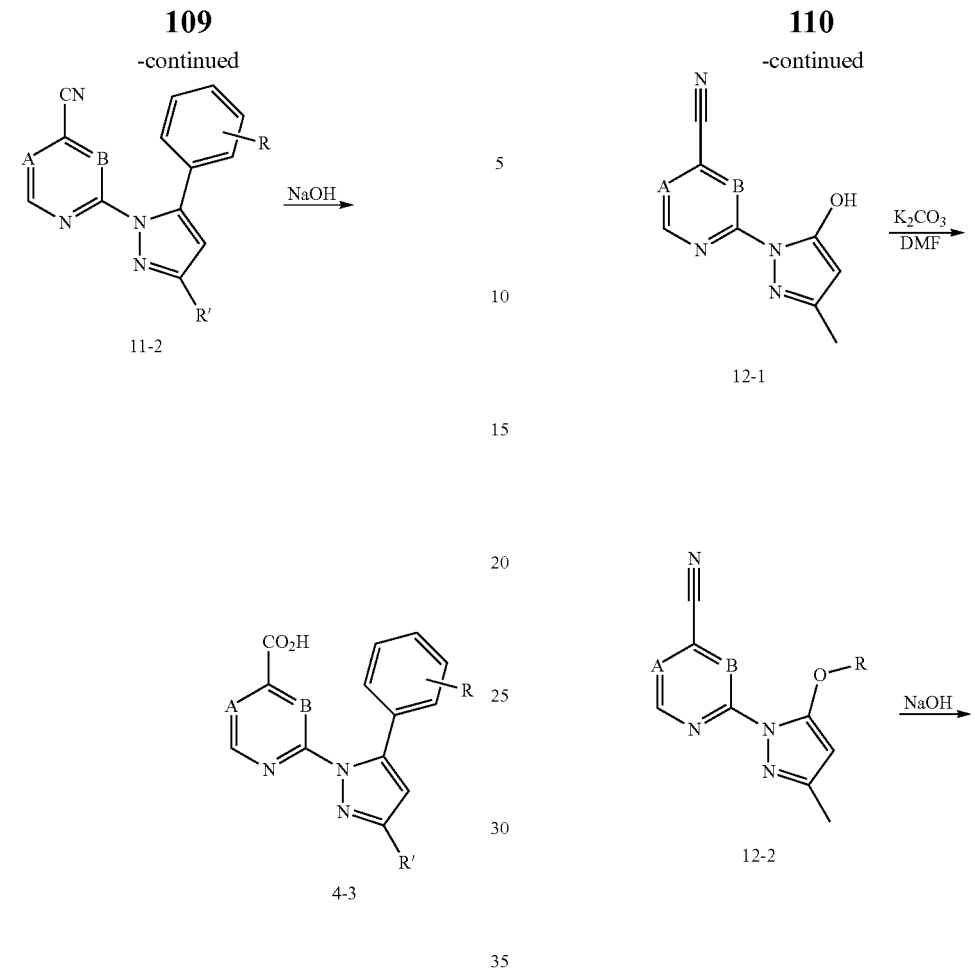

A method for preparing compounds such as compounds 11-3 is provided in Scheme 11. Cyclization of 2-hydrazinylpyrimidine-4-carbonitrile or 6-hydrazinylpyrimidine-4-carbonitrile either as free base or hydrochloride salts with intermediate 4-1, in an alcohol solvent such as 2-methoxyethanol (if hydrochloride salts are used), or ethanol in the presence of acetic acid (if the free base of compounds 10-1 are used) under heating conditions provides intermediates 11-2. Hydrolysis of the nitrile group using concentrated sodium hydroxide solution (5-10 M) in ethanol with heat affords the acid products 11-3.

Scheme 12

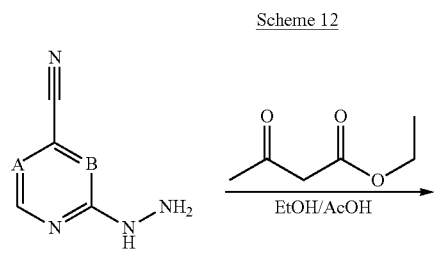

A method for preparing compounds such as compounds 12-3 is provided in Scheme 12. Cyclization of 2-hydrazinylpyrimidine-4-carbonitrile or 6-hydrazinylpyrimidine-4-carbonitrile with ethyl 3-oxobutanoate in an alcoholic solvent, such as ethanol, in presence of acetic acid provides intermediates 12-1. Alkylation of the hydroxyl group using an alkyl halide, such as alkyl bromide or alkyl iodide, in an organic solvent, such as DMF, in the presence of a base, e.g. $K_2CO_3$, gives products 12-2. Subsequent hydrolysis using concentrated NaOH in alcohol provides the acid products 12-3.

Scheme 13

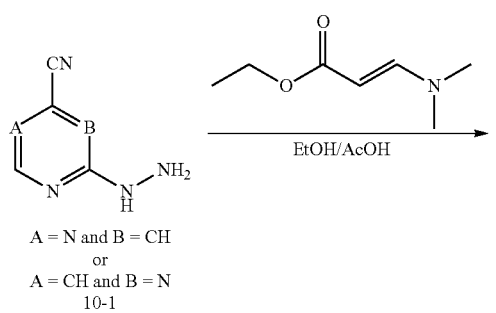

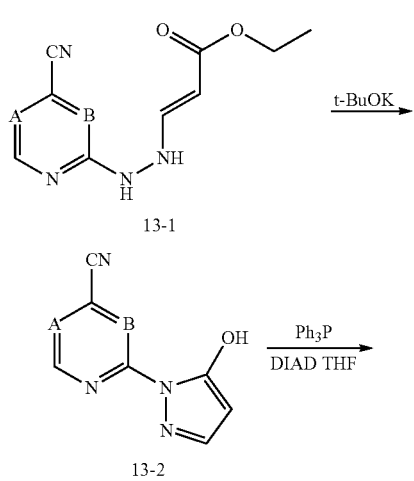

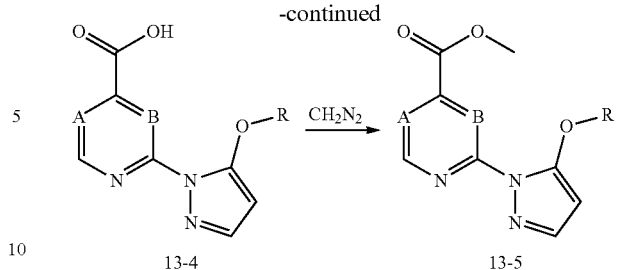

A method to prepare compounds such as compounds 13-4 or 13-5 is provided in Scheme 13. 2-Hydrazinylpyrimidine-4-carbonitrile or 6-hydrazinylpyrimidine-4-carbonitrile react with ethyl (2E)-3-(dimethylamino)prop-2-enoate in ethanol in the presence of acetic acid to give intermediates 13-1. Upon treatment with a strong base, such as potassium t-butoxide, the hydroxypyrazole intermediates 13-2 are obtained. A Mitsunobu reaction, wherein intermediates 13-2 are treated with an alcohol, an azadicarboxylate, such as DIAD, a ligand, such as triphenylphosphine, in an organic solvent, such as THF, gives a mixture of O-alkylation and N-alkylation products. Separation via flash column chromatography provides the desired O-alkylation products 13-3, which is then hydrolyzed to the acids 13-4. The acids are then treated with excess diazomethane (e.g. 10 equiv.) in an organic solvent such as THF to give the methyl esters, compounds 13-5.

Scheme 14

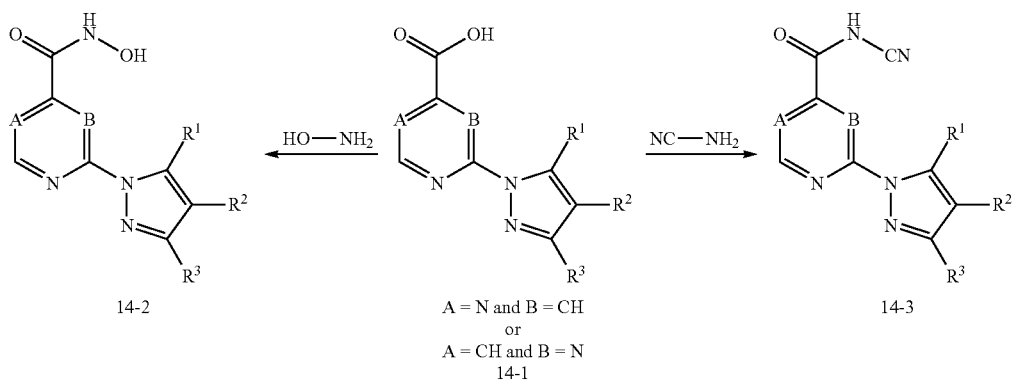

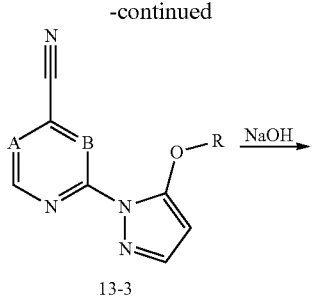

Methods for preparing compounds of formula 14-2 and 14-3 are provided in Scheme 14. Treatment of acids 14-1 with hydroxylamine hydrochloride in the presence of a coupling reagent, such as HATU, in a solvent, such as DMF, at room temperature for 1 to 24 hours provides compounds 14-2. Compounds 14-1 can also be used to prepare N-acyl-cyanamides such as compounds 14-3. Treatment of 14-1 with cyanamide in the presence of an acid coupling reagent, such as HATU, in a solvent, such as DMF, at room temperature for 1 to 24 hours provides compounds 14-3.

Scheme 15

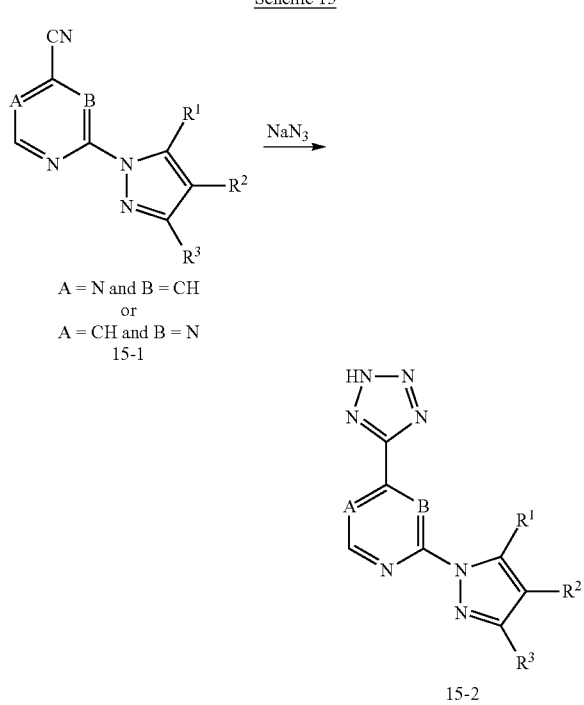

A = N and B = CH
or
A = CH and B = N
15-1

15-2

A method for preparing compounds of formula 15-2 is provided in Scheme 15. Treatment of the nitrile intermediates 15-1 with sodium azide and ammonium chloride in DMF followed by heating to 90° C. for 2 to 24 hours provides the desired tetrazole derivatives 15-2.

In each of the above reaction procedures or schemes, the various substituents may be selected from among the various substituents otherwise taught herein.

In each of the above reaction procedures or schemes, the various substituents may be selected from among the various substituents otherwise taught herein.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenyosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known to demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33),13379-86; doi: 10.1073/pnas.1110104108) and the authors of the study concluded that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3σ, and knockdown of JARID1B was found to increase the levels of tri-methylated H3K4 at these genes.

FBXL10 and FBXL11

F-box and leucine-rich repeat protein 10 (FBXL10) and F-box and leucine-rich repeat protein 11 (FBXL11) are multifunctional F-box family proteins that demethylate histone H3 through a hydroxylation based mechanism. FBXL10, also known as lysine (K)-specific demethylase 2B (KDM2B) or Jumonji C domain-containing histone demethylase 1B (JHDM1B), preferentially demethylates trimethylated K4 and dimethylated K36 of histone H3, but contains weak or no activity for mono- and tri-methylated H3-K36. FBXL10 contains three domains, a catalytic JMJC domain, an F-box domain and a CXXC DNA-binding domain. The N-terminal JMJC domain coordinates iron and α-ketoglutarate to catalyze demethylation through the hydroxylation based mechanism. The CXXC DNA-binding domain allows FBXL10 to preferentially bind to transcribed region of the ribosomal RNA, leading to repression of the ribosomal RNA gene transcription and ultimately leading to inhibition of cell growth and proliferation. FBXL10 has been found to be overexpressed in acute myeloid leukemia, bladder carcinoma and pancreatic ductal adenocarcinoma. Recently, it has been demonstrated that FBXL10 regulates the expression of Polycomb target genes, those proteins are epigenetic regulators essential for stem cell differentiation. This regulation implicates FBXL10's involvement in tumorigenesis through the regulation of these Polycomb target genes.

FBXL11, also known as KDM2A or JHDM1A, demethylates mono- and di-methylated K36 of histone H3. The COX DNA-binding domain recognizes non-methylated DNA and targets CpG island regions where it specifically removes H3K3 methylation. Further, FBXL11 is required to maintain a heterochromatic state, sustain centromeric integrity and genomic stability during mitosis. In addition, FBXL11 is a key negative regulator of NF-KB. Overexpression of FBXL11 has been observed in non-small cell lung cancer (NSCLC) where FBXL11 upregulates phosphor-ERK1/2 by repressing DUSP3 expression in NSCLC cell lines. Negative regulation of gluconeogenic gene expression by FBXL11 results in suppression of two rate-limiting gluconeogenic enzymes, critical for maintaining blood glucose homeostasis.

In an additional embodiment is a method for inhibiting a histone-demethylase enzyme comprising contacting a histone demethylase enzyme with a compound of Formula (I) or a tautomer, stereoisomer, geometric isomer, N-oxide, or pharmaceutically acceptable salt thereof,

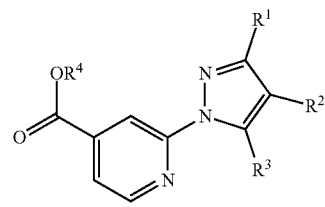

Formula (I)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^4$ is hydrogen or alkyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl;

with the provision:

if $R^2$ and $R^3$ are both hydrogen, then $R^1$ is not hydrogen, methyl, trifluoromethyl, isopropyl or cyclopropyl; or if $R^1$ and $R^3$ are both hydrogen, then $R^2$ is not methyl, or trifluoromethyl; or if $R^1$ and $R^3$ are both methyl, then $R^2$ is not hydrogen, methyl or ethyl; or if $R^1$ and $R^2$ are hydrogen, then $R^3$ is not

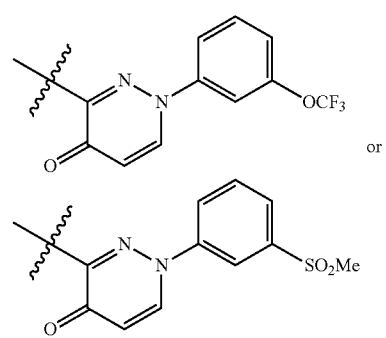

In an additional embodiment is a method for inhibiting a histone-demethylase enzyme comprising contacting a histone demethylase enzyme with a compound of Formula (II)

or a tautomer, stereoisomer, geometric isomer, N-oxide, or pharmaceutically acceptable salt thereof,

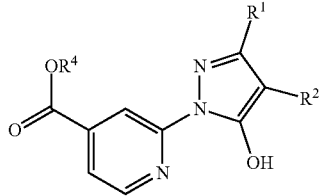

Formula (II)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^4$ is hydrogen or alkyl; and each $R^5$ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for inhibiting a histone-demethylase enzyme comprising contacting a histone demethylase enzyme with a compound of Formula (III) or a tautomer, stereoisomer, geometric isomer, N-oxide, or pharmaceutically acceptable salt thereof,

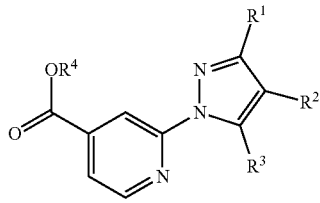

Formula (III)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is $C_2$-$C_{10}$ alkyl, carbocyclyl, heterocyclyl, aryl, heteroaryl, carbocyclylalkyl, heterocyclylalkyl, aralkyl, or heteroarylalkyl;

$R^4$ is hydrogen or alkyl; and each $R^5$ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for inhibiting a histone-demethylase enzyme comprising contacting a histone demethylase enzyme with a compound of Formula (IV) or a tautomer, stereoisomer, geometric isomer, N-oxide, or pharmaceutically acceptable salt thereof,

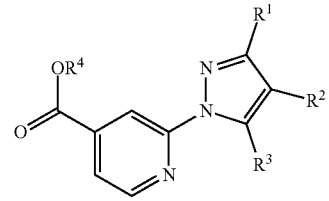

Formula (IV)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is —O—X—Y;

$R^4$ is hydrogen or alkyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl;

X is $C_1$-$C_8$ alkylene or

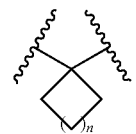

where n is 0 to 4; and

Y is hydrogen, carbocyclyl, aryl, or heteroaryl.

In an additional embodiment is a method for inhibiting a histone-demethylase enzyme comprising contacting a histone demethylase enzyme with a compound of Formula (V) or a tautomer, stereoisomer, geometric isomer, N-oxide, or pharmaceutically acceptable salt thereof,

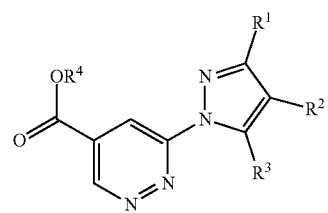

Formula (V)

wherein, $R^1$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^4$ is hydrogen or alkyl; and each $R^5$ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for inhibiting a histone-demethylase enzyme comprising contacting a histone demethylase enzyme with a compound of Formula (VI) or a tautomer, stereoisomer, geometric isomer, N-oxide, or pharmaceutically acceptable salt thereof,

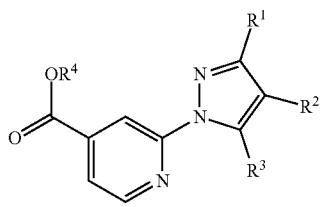

Formula (VI)

wherein,

R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R³ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R⁴ is hydrogen or alkyl;

each R⁵ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for inhibiting a histone-demethylase enzyme comprising contacting a histone demethylase enzyme with a compound of Formula (VII)-(XIV) or a tautomer, stereoisomer, geometric isomer, N-oxide, or pharmaceutically acceptable salt thereof In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is selected from JARID1A, JARID1B, JMJD2C, JMJD2A, or FBXL10.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JHDM protein(s)).

In an additional embodiment is a method for treating cancer in subject comprising administering to the subject in need thereof a composition comprising a compound of Formula (I) or a tautomer, stereoisomer, geometric isomer, N-oxide, or pharmaceutically acceptable salt thereof,

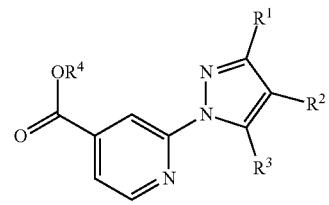

Formula (I)

wherein,

R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R² is hydrogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R³ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

R⁴ is hydrogen or alkyl;

each R⁵ is independently hydrogen, alkyl, carbocyclyl, heterocyclyl, aryl, heteroaryl, carbocyclylalkyl, heterocyclylalkyl, aralkyl, or heteroarylalkyl;

with the provision:

if R² and R³ are both hydrogen, then R¹ is not hydrogen, methyl, trifluoromethyl, isopropyl or cyclopropyl; or if R¹ and R³ are both hydrogen, then R² is not methyl, or trifluoromethyl; or if R¹ and R³ are both methyl, then R² is not hydrogen, methyl or ethyl; or if R¹ and R² are hydrogen, then R³ is not

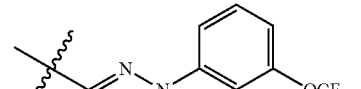

or

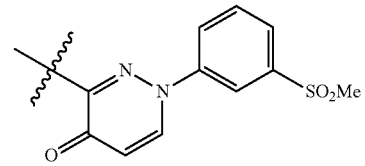

In an additional embodiment is a method for treating cancer in subject comprising administering to the subject in need thereof a composition comprising a compound of Formula (II) or a tautomer, stereoisomer, geometric isomer, N-oxide, or pharmaceutically acceptable salt thereof,

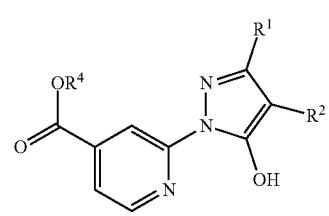

Formula (II)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R⁴ is hydrogen or alkyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for treating cancer in subject comprising administering to the subject in need thereof a composition comprising a compound of Formula (III) or a tautomer, stereoisomer, geometric isomer, N-oxide, or pharmaceutically acceptable salt thereof, Formula (III)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R³ is C₂-C₁₀ alkyl, carbocyclyl, heterocyclyl, aryl, heteroaryl, carbocyclylalkyl, heterocyclylalkyl, aralkyl, or heteroarylalkyl;
R⁴ is hydrogen or alkyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for treating cancer in subject comprising administering to the subject in need thereof a composition comprising a compound of Formula (IV) or a tautomer, stereoisomer, geometric isomer, N-oxide, or pharmaceutically acceptable salt thereof, Formula (IV)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R³ is —O—X—Y;
R⁴ is hydrogen or alkyl;

each R⁵ is independently hydrogen, alkyl, carbocyclyl, heterocyclyl, aryl, heteroaryl, carbocyclylalkyl, heterocyclylalkyl, aralkyl, or heteroarylalkyl;
X is C₁-C₈ alkylene or where n is 0 to 4; and
Y is hydrogen, carbocyclyl, aryl, or heteroaryl.

In an additional embodiment is a method for treating cancer in subject comprising administering to the subject in need thereof a composition comprising a compound of Formula (V) or a tautomer, stereoisomer, geometric isomer, N-oxide, or pharmaceutically acceptable salt thereof, Formula (V)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R² is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R³ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;
R⁴ is hydrogen or alkyl; and
each R⁵ is independently hydrogen, alkyl, carbocyclyl, heterocyclyl, aryl, heteroaryl, carbocyclylalkyl, heterocyclylalkyl, aralkyl, or heteroarylalkyl.

In an additional embodiment is a method for treating cancer in subject comprising administering to the subject in need thereof a composition comprising a compound of Formula (VI) or a tautomer, stereoisomer, geometric isomer, N-oxide, or pharmaceutically acceptable salt thereof, Formula (VI)

wherein,
R¹ is hydrogen, halogen, —OH, —OR⁵, —N(R⁵)₂, alkyl, carbocyclyl, heterocyclyl, aryl, heteroaryl, carbocyclylalkyl, heterocyclylalkyl, aralkyl, or heteroarylalkyl;

$R^2$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^3$ is hydrogen, halogen, —OH, —OR$^5$, —N(R$^5$)$_2$, alkyl, carbocyclyl, heterocyclyl, aryl, heteroaryl, carbocyclylalkyl, heterocyclylalkyl, aralkyl, or heteroarylalkyl;

$R^4$ is hydrogen or alkyl;

each $R^5$ is independently hydrogen, alkyl, carbocyclyl, heterocyclyl, aryl, heteroaryl, carbocyclylalkyl, heterocyclylalkyl, aralkyl, or heteroarylalkyl.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I), (II), (III), (IV), (V), or (VI) or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (I), (II), (III), (IV), (V), or (VI), or a pharmaceutically acceptable salt thereof, wherein the tumor is characterized by a loss of multiple endocrine neoplasia type 1 gene (Men1) function.

In an additional embodiment is a method for inhibiting the growth of a tumor comprising administering a composition comprising a compound of Formula (VII)-(XIV) or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (VII)-(XIV), or a pharmaceutically acceptable salt thereof, wherein the tumor is characterized by a loss of multiple endocrine neoplasia type 1 gene (Men1) function.

In an additional embodiment is a method for treating cancer in subject comprising administering to the subject in need thereof a composition comprising a compound of Formula (VII)-(XIV) or a tautomer, stereoisomer, geometric isomer, N-oxide, or pharmaceutically acceptable salt thereof. In a further embodiment is the method for treating cancer in a subject wherein the cancer is selected from prostate cancer, breast cancer, bladder cancer, lung cancer or melanoma.

Pharmaceutical Compositions

In certain embodiments, a substituted pyrazolylpyridine, pyrazolylpyridazine, or pyrazolylpyrimidine derivative compound as described herein is administered as a pure chemical. In other embodiments, the substituted pyrazolylpyridine, pyrazolylpyridazine, or pyrazolylpyrimidine derivative compound as described is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising at least one substituted pyrazolylpyridine derivative compound, or a stereoisomer, prodrug, pharmaceutically acceptable salt, hydrate, solvate, or N-oxide thereof, together with one or more pharmaceutically acceptable carriers and, optionally, other therapeutic and/or prophylactic ingredients. Also provided herein is a pharmaceutical composition comprising at least one substituted pyrazolylpyridazine derivative compound, or a stereoisomer, prodrug, pharmaceutically acceptable salt, hydrate, solvate, or N-oxide thereof, together with one or more pharmaceutically acceptable carriers and, optionally, other therapeutic and/or prophylactic ingredients. Further provided herein is a pharmaceutical composition comprising at least one substituted pyrazolylpyrimidine derivative compound, or a stereoisomer, prodrug, pharmaceutically acceptable salt, hydrate, solvate, or N-oxide thereof, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formulas (I)-(V) or a tautomer, stereoisomer, geometric isomer, N-oxide, or pharmaceutically acceptable salt thereof.

One embodiment provides a pharmaceutical composition comprising a pharmaceutically acceptable carrier and a compound of Formulas (VII)-(XIV) or a tautomer, stereoisomer, geometric isomer, N-oxide, or pharmaceutically acceptable salt thereof.

In certain embodiments, the substituted pyrazolylpyridine derivative compound as described by Formulas (I)-(V) is substantially pure, in that it contains less than about 5%, or less than about 1%, or less than about 0.1%, of other organic small molecules, such as contaminating intermediates or by-products that are created, for example, in one or more of the steps of a synthesis method. In certain embodiments, the compound as described by Formulas (VII)-(XIV) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted pyrazolylpyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1: 2-Hydrazinylpyridine-4-carboxylic acid

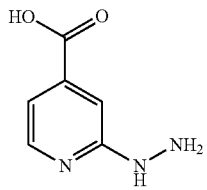

To a solution of 2-chloropyridine-4-carboxylic acid (1.57 g, 100 mmol) in 1,4-dioxane (30 mL) was added hydrazine hydrate (1.0 g, 200 mmol) dropwise at rt. The reaction mixture was heated at 100° C. overnight. The mixture was concentrated, and the residue was purified by flash column chromatography (CH$_2$Cl$_2$/MeOH=20/1) to afford the title compound (650 mg, 42%) as a white solid. [M+H] Calc'd for C$_6$H$_7$N$_3$O$_2$, 154. Found, 154.

Example 1

2-(5-hydroxy-3-methyl-1H-pyrazol-1-yl)isonicotinic acid

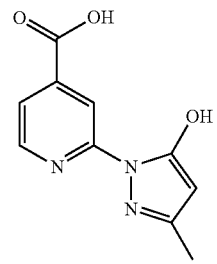 [SMILES: Cc1cc(O)n(-c2cc(C(=O)O)ccn2)n1]

A mixture of 2-hydrazinylpyridine-4-carboxylic acid (306 mg, 2 mmol, PREPARATION 1) and ethyl 3-oxobutanoate (390 mg, 3 mmol) in AcOH (5 mL) was stirred at 100° C. overnight. The reaction mixture was cooled, concentrated, and purified by prep-HPLC to afford the title compound (72 mg, 16%) as yellow solid. $^1$H NMR (400 MHz, CD$_3$OD): δ 2.72 (3H, s), 4.86 (1H, s), 7.71 (1H, d, J=4.8 Hz), 8.55 (1H, d J=4.8 Hz), 8.81 (1H, s). [M+H] Calc'd for C$_{10}$H$_9$N$_3$O$_3$, 220. Found, 220.

Example 2

2-(3-cyclopropyl-5-hydroxy-1H-pyrazol-1-yl)isonicotinic acid

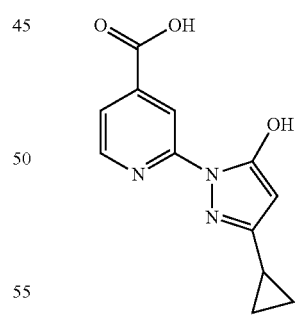

The title compound was prepared in 24% yield from 2-hydrazinylpyridine-4-carboxylic acid and ethyl 3-cyclopropyl-3-oxopropanoate according to the procedure for the preparation of Example 1. $^1$H NMR (400 MHz, CD$_3$OD): δ 0.83-0.88 (2H, m), 1.05-1.09 (2H, m), 1.88-1.91 (1H, m), 4.86 (1H, s), 7.70 (1H, dd, J=5.2, 1.2 Hz), 8.54 (1H, d, J=5.2 Hz), 8.75 (1H, s). [M+H] Calc'd for C$_{12}$H$_{11}$N$_3$O$_3$, 246. Found, 246.

Preparation 2: 2-Hydrazinylpyridine-4-carbonitrile

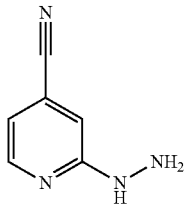

To a solution of 2-chloropyridine-4-carbonitrile (20.0 g, 144 mmol) in 1-butanol (150 mL) was added 1 M solution of hydrazine hydrate in THF (303 mL, 303 mmol) dropwise at rt. It was then heated at 60° C. overnight. The mixture was concentrated, and the residue was purified by flash column chromatography (CH$_2$Cl$_2$/MeOH=20/1) to afford the title compound (3.5 g, 18%) as a white solid. [M+H] Calc'd for C$_6$H$_6$N$_4$, 135. Found, 135.

Example 3

2-(5-Hydroxy-3,4-dimethyl-1H-pyrazol-1-yl)isonicotinic acid

A. 2-(5-Hydroxy-3,4-dimethyl-1H-pyrazol-1-yl)pyridine-4-carbonitrile

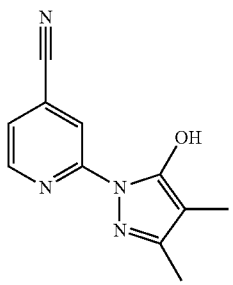 [SMILES: Cc1nn(-c2cc(C#N)ccn2)c(O)c1C]

A mixture of 2-hydrazinylpyridine-4-carbonitrile (134 mg, 1 mmol, PREPARATION 2) and 2-methyl-3-oxo-butyric acid ethyl ester (158 mg, 1.1 mmol) in EtOH (5 mL) and AcOH (1 mL) was stirred at 90° C. overnight. The reaction mixture was cooled, concentrated, and purified by flash column chromatography (CH$_2$Cl$_2$) to afford the title compound (100 mg, 47%) as an orange solid. [M+H] Calc'd for C$_{11}$H$_{10}$N$_4$O, 215. Found, 215.

B. 2-(5-hydroxy-3,4-dimethyl-1H-pyrazol-1-yl)isonicotinic acid

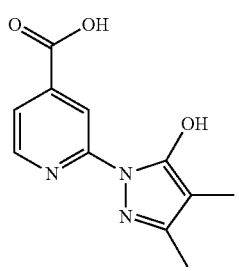 [SMILES: Cc1nn(-c2cc(C(=O)O)ccn2)c(O)c1C]

To a solution of 2-(5-hydroxy-3,4-dimethyl-1H-pyrazol-1-yl)pyridine-4-carbonitrile (100 mg, 0.47 mmol) in EtOH (5 mL) was added 5 M NaOH (2 mL) at rt, then stirred at 90° C. for 1 h. The reaction mixture was cooled, acidified with 1 N HCl to pH=3, filtered to give a yellow solid, then recrystallized from EtOH to afford the title compound (22 mg, 21%) as a white solid. $^1$H NMR (400 MHz, CD$_3$OD): δ 1.84 (3H, s), 2.23 (3H, s), 7.71 (1H, dd, J=4.8, 1.2 Hz), 8.52 (1H, d, J=5.2 Hz), 8.65 (1H, s). [M+H] Calc'd for C$_{11}$H$_{11}$N$_3$O$_3$, 234. Found, 234.

Example 4

2-(5-Hydroxy-3-methyl-4-phenyl-1H-pyrazol-1-yl)isonicotinic acid

A. 2-(5-Hydroxy-3-methyl-4-phenyl-1H-pyrazol-1-yl)pyridine-4-carbonitrile

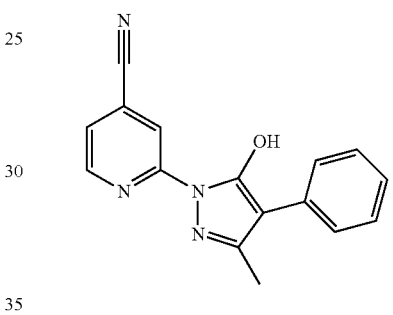

The title compound was prepared in 29% yield from 2-hydrazinylpyridine-4-carbonitrile (PREPARATION 2) and 3-oxo-2-phenyl-butyric acid ethyl ester according to the procedure for the preparation of Example 3, part A. [M+H] Calc'd for C$_{16}$H$_{12}$N$_4$O, 277. Found, 277.

B. 2-(5-Hydroxy-3-methyl-4-phenyl-1H-pyrazol-1-yl)isonicotinic acid

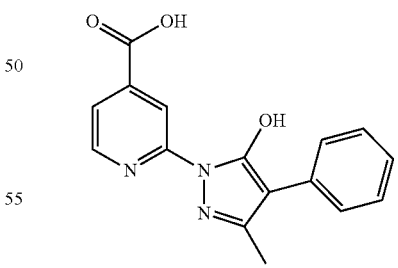

The title compound was prepared in 59% yield from 2-(5-hydroxy-3-methyl-4-phenyl-1H-pyrazol-1-yl)pyridine-4-carbonitrile according to the procedure for the preparation of Example 3, part B. $^1$H NMR (400 MHz, CD$_3$OD): δ 2.31 (3H, s), 7.15 (1H, t, J=7.6 Hz), 7.30 (2H, t, J=7.6 Hz), 7.44 (2H, d, J=7.2 Hz), 7.64 (1H, d, J=4.8 Hz), 8.48 (1H, d, J=5.2 Hz), 8.81-8.82 (1H, m). [M+H] Calc'd for C$_{16}$H$_{13}$N$_3$O$_3$, 296. Found, 296.

Example 5

2-(3-(2-Fluorophenyl)-5-hydroxy-1H-pyrazol-1-yl)isonicotinic acid

A. 2-[3-(2-Fluorophenyl)-5-hydroxy-1H-pyrazol-1-yl]pyridine-4-carbonitrile

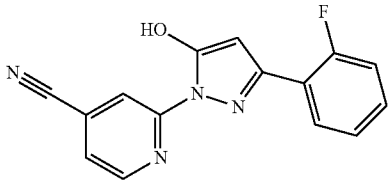 [SMILES: N#Cc1ccnc(-n2nc(-c3ccccc3F)cc2O)c1]

The title compound was prepared in 48% yield from 2-hydrazinylpyridine-4-carbonitrile (PREPARATION 2) and ethyl 3-(2-fluorophenyl)-3-oxopropanoate according to the procedure for the preparation of Example 3, part A. $^1$H NMR (300 MHz, DMSO-$d_6$): δ 6.15-6.17 (1H, m), 7.13-7.41 (4H, m), 8.07-8.12 (1H, m), 8.34 (1H, s), 8.48-8.50 (1H, m), 11.64 (1H, s). [M+H] Calc'd for $C_{15}H_9FN_4O$, 281. Found, 281.

B. 2-(3-(2-fluorophenyl)-5-hydroxy-1H-pyrazol-1-yl)isonicotinic acid

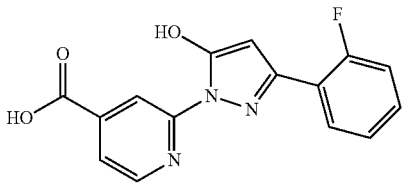 [SMILES: O=C(O)c1ccnc(-n2nc(-c3ccccc3F)cc2O)c1]

The title compound was prepared in 75% yield from 2-[3-(2-fluorophenyl)-5-hydroxy-1H-pyrazol-1-yl]pyridine-4-carbonitrile according to the procedure for the preparation of Example 3, part B. $^1$H NMR (400 MHz, DMSO-$d_6$): δ 6.06 (1H, s), 7.29-7.34 (2H, m), 7.44-7.45 (1H, m), 7.78-7.79 (1H, m), 8.01-8.05 (1H, m), 8.26 (1H, s), 8.68 (1H, d, J=5.2 Hz). [M+H] Calc'd for $C_{15}H_{10}FN_3O_3$, 300. Found, 300.

Example 6

2-(5-Hydroxy-3-propyl-1H-pyrazol-1-yl)isonicotinic acid

A. 2-(5-Hydroxy-3-propyl-1H-pyrazol-1-yl)pyridine-4-carbonitrile

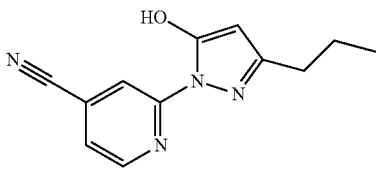 [SMILES: CCCc1cc(O)n(-c2cc(C#N)ccn2)n1]

The title compound was prepared in 44% yield from 2-hydrazinylpyridine-4-carbonitrile (PREPARATION 2) and ethyl 3-oxohexanoate according to the procedure for the preparation of Example 3, part A. [M+H] Calc'd for $C_{12}H_{12}N_4O$, 229. Found, 229.

B. 2-(5-Hydroxy-3-propyl-1H-pyrazol-1-yl)isonicotinic acid

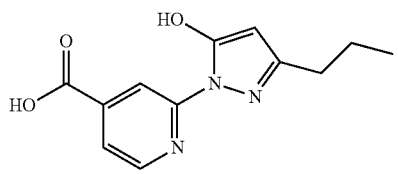 [SMILES: CCCc1cc(O)n(-c2cc(C(=O)O)ccn2)n1]

The title compound was prepared in 78% yield from 2-(5-hydroxy-3-propyl-1H-pyrazol-1-yl)pyridine-4-carbonitrile according to the procedure for the preparation of Example 3, part B. $^1$H NMR (400 MHz, CD$_3$OD): δ 1.05 (3H, t, J=6.8 Hz), 1.71-1.80 (2H, m), 2.61 (3H, t, J=7.2 Hz), 4.87 (1H, s), 7.75 (1H, d, J=4.8 Hz), 8.58 (1H, d, J=5.2 Hz), 8.83-8.85 (1H, m). [M+H] Calc'd for $C_{12}H_{13}N_3O_3$, 248. Found, 248.

Example 7

2-(3-(2-Chlorophenyl)-5-hydroxy-1H-pyrazol-1-yl)isonicotinic acid

A. Ethyl 3-(2-chlorophenyl)-3-oxopropanoate

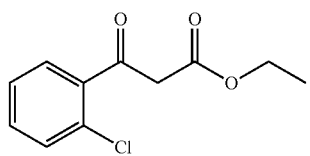

Sodium hydride (1.45 g, 36 mmol) and diethyl carbonate (2.14 g, 18 mmol) were suspended in 10 ml of THF. 1-(2-Chlorophenyl)ethanone (1.4 g, 9 mmol) was gradually added into the reaction flask, maintaining the reaction mixture temperature at 40° C. for 2 h. Then 1 mL of ethanol was added thereto and heated under reflux conditions for 4 h. After cooling, 1 mL of ethanol was added and the mixture was poured onto ice water, and extracted with ether. Ether extracts are combined, washed with water, dried with anhydrous magnesium sulfate, and evaporated. The resulting oil is purified by flash column chromatography (PE/EA=50/1) to afford the title compound (680 mg, 34%) as a yellow oil. $^1$H NMR (400 MHz, CDCl$_3$): δ 1.24 (3H, t, J=6.8 Hz), 4.03 (2H, s), 4.19 (2H, q, J=6.8 Hz), 7.31-7.36 (2H, m), 7.42-7.45 (2H, m). [M+H] Calc'd for $C_{11}H_{11}ClO_3$, 227. Found, 227.

B. 2-[3-(2-Chlorophenyl)-5-hydroxy-1H-pyrazol-1-yl]pyridine-4-carbonitrile

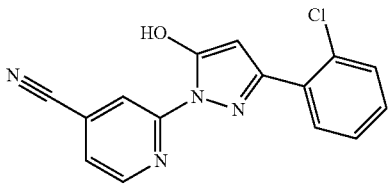 [SMILES: N#Cc1ccnc(-n2nc(-c3ccccc3Cl)cc2O)c1]

The title compound was prepared in 75% yield from 2-hydrazinylpyridine-4-carbonitrile (PREPARATION 2) and ethyl 3-(2-chlorophenyl)-3-oxopropanoate according to the procedure for the preparation of Example 3, part A. [M+H] Calc'd for $C_{15}H_9ClN_4O$, 297. Found, 297.

C. 2-(3-(2-Chlorophenyl)-5-hydroxy-1H-pyrazol-1-yl)isonicotinic acid

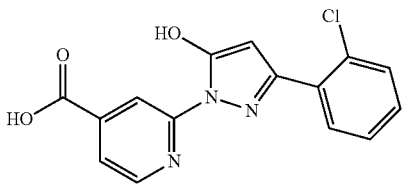 [SMILES: O=C(O)c1ccnc(-n2nc(-c3ccccc3Cl)cc2O)c1]

The title compound was prepared in 72% yield from 2-[3-(2-chlorophenyl)-5-hydroxy-1H-pyrazol-1-yl]pyridine-4-carbonitrile according to the procedure for the preparation of Example 3, part B. $^1$H NMR (400 MHz, CD$_3$OD): δ 4.81 (1H, s), 7.35-7.37 (2H, m), 7.48-7.49 (1H, m), 7.78-7.79 (2H, m), 8.54-8.55 (2H, m). [M+H] Calc'd for $C_{15}H_{10}ClN_3O_3$, 316. Found, 316.

Example 8

2-(3-Benzyl-5-hydroxy-1H-pyrazol-1-yl)isonicotinic acid

A. Ethyl 3-oxo-4-phenylbutanoate

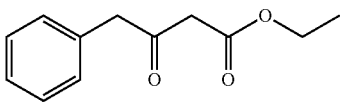

To a solution of phenylacetyl chloride (1 mL, 7.56 mmol) was added dropwise a solution of 2,2-dimethyl-1,3-dioxane-4,6-dione (1.09 g, 7.56 mmol) and pyridine (1.3 mL) in CH$_2$Cl$_2$ (20 mL) at 0° C. The solution was stirred for 30 min at 0° C., then allowed to warm slowly to rt and stirred overnight. The reaction mixture was then washed with 10% aqueous HCl (2×10 mL). The organic layer was dried (MgSO$_4$), filtered, and concentrated under reduced pressure. The crude residue was dissolved in EtOH (20 mL) and heated under reflux conditions for 4 h. The mixture was cooled to rt and then concentrated under reduced pressure. The resulting oil was purified by flash column chromatography (PE/EA=1/4) to afford the title compound (600 mg, 38%) as a yellow oil. [M+H] Calc'd for $C_{12}H_{14}O_3$, 207. Found, 207.

B. 2-(3-Benzyl-5-hydroxy-1H-pyrazol-1-yl)pyridine-4-carbonitrile

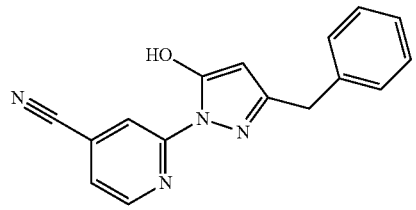 [SMILES: N#Cc1ccnc(-n2nc(Cc3ccccc3)cc2O)c1]

The title compound was prepared in 53% yield from 2-hydrazinylpyridine-4-carbonitrile (PREPARATION 2) and ethyl 3-oxo-4-phenylbutanoate according to the procedure for the preparation of Example 3, part A. [M+H] Calc'd for $C_{16}H_{12}N_4O$, 277. Found, 277.

C. 2-(3-Benzyl-5-hydroxy-1H-pyrazol-1-yl)isonicotinic acid

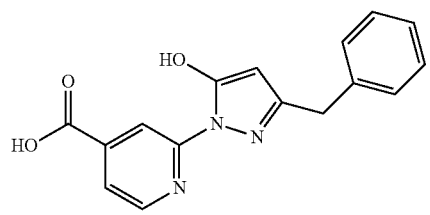 [SMILES: O=C(O)c1ccnc(-n2nc(Cc3ccccc3)cc2O)c1]

The title compound was prepared in 78% yield from 2-(3-benzyl-5-hydroxy-1H-pyrazol-1-yl)pyridine-4-carbonitrile according to the procedure for the preparation of Example 3, part B. $^1$H NMR (400 MHz, CD$_3$OD): δ 3.96 (2H, s), 4.88 (1H, s), 7.24-7.27 (1H, m), 7.34-7.37 (4H, m), 7.75-7.77 (1H, m), 8.58 (1H, d, J=5.2 Hz), 8.76 (1H, s). [M+H] Calc'd for $C_{16}H_{13}N_3O_3$, 296. Found, 296.

Example 9

2-(5-hydroxy-3-(methoxymethyl)-1H-pyrazol-1-yl)isonicotinic acid

A. 2-[5-Hydroxy-3-(methoxymethyl)-1H-pyrazol-1-yl]pyridine-4-carbonitrile

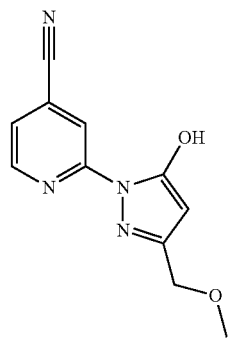 [SMILES: COCc1cc(O)n(-c2cc(C#N)ccn2)n1]

The title compound was prepared in 39% yield from 2-hydrazinylpyridine-4-carbonitrile (PREPARATION 2) and methyl 4-methoxy-3-oxobutanoate according to the procedure for the preparation of Example 3, part A. [M+H] Calc'd for $C_{11}H_{10}N_4O_2$, 231. Found, 231.

B: 2-(5-Hydroxy-3-(methoxymethyl)-1H-pyrazol-1-yl)isonicotinic acid

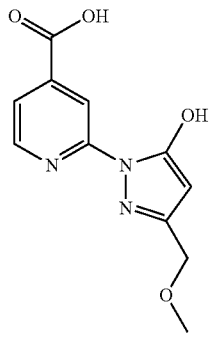 [SMILES: COCc1cc(O)n(-c2cc(C(=O)O)ccn2)n1]

The title compound was prepared in 19% yield from 2-[5-hydroxy-3-(methoxymethyl)-1H-pyrazol-1-yl]pyridine-4-carbonitrile according to the procedure for the preparation of Example 3, part B. $^1$H NMR (400 MHz, CD$_3$OD): δ 3.33 (3H, s), 4.44 (2H, s), 4.78 (1H, s), 7.69 (1H, d, J=5.2, 0.8 Hz), 8.46-7.48 (2H, m). [M+H] Calc'd for $C_{11}H_nN_3O_4$, 250. Found, 250.

Example 10

2-(5-Hydroxy-3-(phenoxymethyl)-1H-pyrazol-1-yl)isonicotinic acid

A. 2-[5-Hydroxy-3-(phenoxymethyl)-1H-pyrazol-1-yl]pyridine-4-carbonitrile

The title compound was prepared in 58% yield from 2-hydrazinylpyridine-4-carbonitrile (PREPARATION 2) and methyl 3-oxo-4-phenoxybutanoate according to the procedure for the preparation of Example 3, part A. [M+H] Calc'd for $C_{16}H_{12}N_4O_2$, 293. Found, 293.

B. 2-(5-Hydroxy-3-(phenoxymethyl)-1H-pyrazol-1-yl)isonicotinic acid

The title compound was prepared in 49% yield from 2-[5-hydroxy-3-(phenoxymethyl)-1H-pyrazol-1-yl]pyridine-4-carbonitrile according to the procedure for the preparation of Example 3, part B. $^1$H NMR (400 MHz, CD$_3$OD): δ 4.75 (1H, s), 4.95 (2H, s), 6.85 (1H, t, J=7.6 Hz), 6.92 (2H, d, J=8.0 Hz), 7.18 (2H, t, J=7.2 Hz), 7.68 (1H, dd, J=4.8, 1.2 Hz), 8.41-8.46 (2H, m). [M+H] Calc'd for $C_{16}H_{13}N_3O_4$, 312. Found, 312.

Example 11

2-(5-Hydroxy-1H-pyrazol-1-yl)isonicotinic acid

A. Ethyl 1-(4-cyanopyridin-2-yl)-5-hydroxy-1H-pyrazole-4-carboxylate

A mixture of 2-hydrazinylpyridine-4-carbonitrile (5.36 g, 40 mmol, PREPARATION 2), diethyl (ethoxymethylidene)propanedioate (8.64 g, 40 mmol) and K$_2$CO$_3$ (10.76 g, 80 mmol) in H$_2$O (100 mL) was stirred at 100° C. for 4 h. The reaction mixture was cooled to rt and filtered to afford the title compound (2.5 g, 24%) as a yellow solid. $^1$H NMR (400 MHz, CDCl$_3$): δ 1.19 (3H, t, J=7.2 Hz), 4.02 (2H, q, J=7.2 Hz), 7.38 (1H, dd, J=4.8, 1.6 Hz), 7.53 (1H, s), 8.53 (1H, d, J=5.2 Hz), 8.79 (1H, s). [M+H] Calc'd for $C_{12}H_{10}N_4O_3$, 259. Found, 259.

B. 2-(4-carboxy-5-hydroxy-1H-pyrazol-1-yl)pyridine-4-carboxylic acid

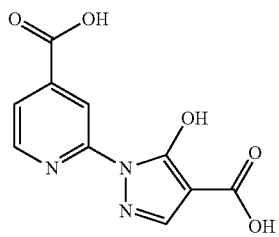 [SMILES: O=C(O)c1ccnc(-n2ncc(C(=O)O)c2O)c1]

To a solution of ethyl 1-(4-cyanopyridin-2-yl)-5-hydroxy-1H-pyrazole-4-carboxylate (2.0 g, 7.7 mmol) in EtOH (50 mL) was added 5 M NaOH (20 mL) at rt, then stirred at 90° C. overnight. The reaction mixture was cooled, acidified with 1 N HCl to pH=3, filtered to give a yellow solid, then crystallized from EtOH to afford the title compound (1.7 g, 88%) as a yellow solid. [M+H] Calc'd for $C_{10}H_7N_3O_5$, 250. Found, 250.

C. 2-(5-hydroxy-1H-pyrazol-1-yl)isonicotinic acid

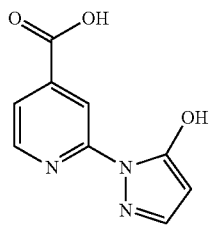 [SMILES: O=C(O)c1ccnc(-n2nccc2O)c1]

A solution of 2-(4-carboxy-5-hydroxy-1H-pyrazol-1-yl)pyridine-4-carboxylic acid (1.7 g, 6.8 mmol) in conc. HCl (50 mL) was heated at 90° C. for 2 h. The reaction mixture was cooled, extracted with EtOAc (200 mL), and washed with water and brine. The organic phase was dried, concentrated, and recrystallized from EtOH to afford the title compound (230 mg, 47%) as a yellow solid. $^1$H NMR (400 MHz, $CD_3OD$): δ 4.86 (1H, s), 7.68 (1H, s), 7.80 (1H, d, J=5.2 Hz), 8.60 (1H, d, J=1.6 Hz), 8.73 (1H, br). [M+H] Calc'd for $C_9H_7N_3O_3$, 206. Found, 206.

Preparation 3: 2-Hydrazinylpyridine-4-carbonitrile hydrochloride salt

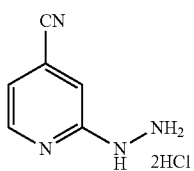

To a solution of 2-hydrazinylpyridine-4-carbonitrile (2.13 g, 16 mmol, PREPARATION 2) in EtOAc (10 mL) was added HCl (4 M in EtOAc, 15 mL) at rt. It was then stirred at rt for 30 min. The reaction mixture was filtered and washed with EtOAc and dried to give the title compound (3.13 g, 95%) as a yellow solid.

Example 12

2-(5-p-tolyl-1H-pyrazol-1-yl)isonicotinic acid

A. (2E)-3-(dimethylamino)-1-(4-methylphenyl)prop-2-en-1-one

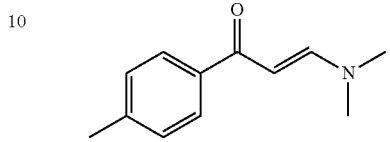

A solution of 1-(4-methylphenyl)ethanone (1.34 g, 10 mmol) in DMF-DMA (10 mL) was stirred at 100° C. overnight. The reaction mixture was cooled, concentrated, and purified by flash column chromatography (PE/EA=4:1~2:1) to give the title compound (1.40 g, 74%) as a yellow solid. $^1$H NMR (400 MHz, $CDCl_3$): δ 2.37 (3H, s), 2.95-3.11 (6H, m), 6.72 (1H, d, J=12.0 Hz), 7.21 (2H, d, J=8.0 Hz), 7.78-7.82 (m, 3H).

B. 2-[5-(4-Methylphenyl)-1H-pyrazol-1-yl]pyridine-4-carbonitrile

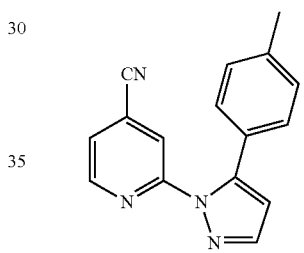

A mixture of 2-hydrazinylpyridine-4-carbonitrile hydrochloride salt (124 mg, 0.6 mmol, PREPARATION 3) and (2E)-3-(dimethylamino)-1-(4-methylphenyl)prop-2-en-1-one (95 mg, 0.5 mmol) in 2-methoxyethanol (3 mL) was stirred at 100° C. for 2 h. The reaction mixture was cooled, concentrated, and dissolved in EtOAc and then washed with water and brine. The organic phase was dried, concentrated, triturated with EA/PE (1:10, 5 mL), filtered, and dried to give the title compound (120 mg, 92%) as a yellow solid. $^1$H NMR (400 MHz, $CDCl_3$): δ 2.38 (3H, s), 6.49 (1H, d, J=1.6 Hz), 7.16 (4H, s), 7.38 (1H, dd, J=5.2, 1.2 Hz), 7.76 (1H, d, J=1.2 Hz), 7.90 (1H, s), 8.44 (1H, d, J=5.2 Hz).

C. 2-(5-p-tolyl-1H-pyrazol-1-yl)isonicotinic acid

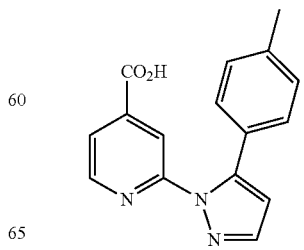

To a solution of 2-[5-(4-methylphenyl)-1H-pyrazol-1-yl]pyridine-4-carbonitrile (120 mg, 0.46 mmol) in EtOH (1 mL) was added 10 M NaOH (1 mL) at rt, then stirred at 90° C. for 1 h. The reaction mixture was cooled, acidified with 1 N HCl to pH=3, extracted with EtOAc (20 mL), and washed with water and brine. The organic phase was dried, concentrated, triturated with EA/PE (1:1, 5 mL), filtered, and dried to give the title compound (60 mg, 47%) as a brown solid. $^1$H NMR (400 MHz, DMSO-d$_6$): δ 2.30 (3H, s), 6.65 (1H, d, J=2.0 Hz), 7.13 (4H, s), 7.77 (1H, dd, J=4.8, 1.2 Hz), 7.82 (1H, d, J=1.2 Hz), 8.44 (1H, d, J=4.8 Hz), 13.97 (1H, br s). [M+H] Calc'd for $C_{16}H_{13}N_3O_2$, 280. Found, 280.

Example 13

2-(5-m-tolyl-1H-pyrazol-1-yl)isonicotinic acid

A. (2E)-3-(Dimethylamino)-1-(3-methylphenyl)prop-2-en-1-one

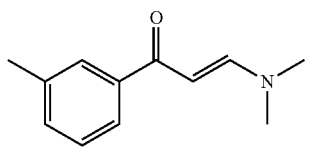

The title compound was prepared in 35% yield from 1-(3-methylphenyl)ethanone and DMF-DMA according to the procedure for the preparation of Example 12, part A. $^1$H NMR (400 MHz, CDCl$_3$): δ 2.39 (3H, s), 2.79-3.11 (6H, m), 5.70 (1H, d, J=12.4 Hz), 7.24-7.31 (2H, m), 7.66-7.71 (2H, m), 7.78 (1H, d, J=12.4 Hz).

B. 2-[5-(3-Methylphenyl)-1H-pyrazol-1-yl]pyridine-4-carbonitrile

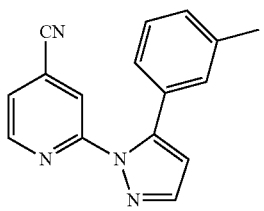 [SMILES: Cc1cccc(-c2ccnn2-c2cc(C#N)ccn2)c1]

The title compound was prepared in quantitative yield from 2-hydrazinylpyridine-4-carbonitrile hydrochloride salt (PREPARATION 3) and (2E)-3-(dimethylamino)-1-(3-methylphenyl)prop-2-en-1-one according to the procedure for the preparation of Example 12, part B. $^1$H NMR (400 MHz, CDCl$_3$): δ 2.35 (3H, s), 6.51 (1H, d, J=1.6 Hz), 7.00 (1H, d, J=3.2 Hz), 7.22 (3H, m), 7.38 (1H, dd, J=5.2, 1.2 Hz), 7.77 (1H, d, J=1.6 Hz), 7.92 (1H, s), 8.42 (1H, d, J=4.8 Hz).

C. 2-(5-m-Tolyl-1H-pyrazol-1-yl)isonicotinic acid

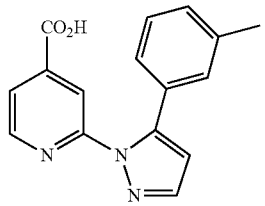

The title compound was prepared in 44% yield from 2-[5-(3-methylphenyl)-1H-pyrazol-1-yl]pyridine-4-carbonitrile according to the procedure for the preparation of Example 12, part C. $^1$H NMR (400 MHz, DMSO-d$_6$): δ 2.27 (3H, s), 6.67 (1H, d, J=1.6 Hz), 6.97 (1H, d, J=7.6 Hz), 7.13-7.21 (3H, m), 7.78 (1H, d, J=4.4 Hz), 7.83 (1H, d, J=1.6 Hz), 8.09 (1H, s), 8.43 (1H, d, J=5.2 Hz), 13.90 (1H, br s). [M+H] Calc'd for $C_{16}H_{13}N_3O_2$, 280. Found, 280.

Example 14

2-(5-(2,4-difluorophenyl)-1H-pyrazol-1-yl)isonicotinic acid

A. (2E)-1-(2,4-Difluorophenyl)-3-(dimethylamino)prop-2-en-1-one

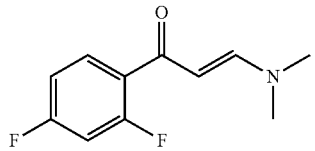

The title compound was prepared in 82% yield from 1-(2,4-difluorophenyl)ethanone and DMF-DMA according to the procedure for the preparation of Example 12, part A. $^1$H NMR (400 MHz, CDCl$_3$): δ 2.90 (3H, s), 3.11 (3H, s), 5.59-5.62 (1H, m), 6.77-6.83 (1H, m), 6.88-6.93 (m, 1H), 7.75-7.83 (2H, m).

B. 2-[5-(2,4-Difluorophenyl)-1H-pyrazol-1-yl]pyridine-4-carbonitrile

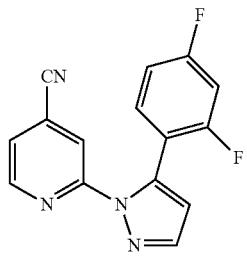 [SMILES: N#Cc1ccnc(-n2nccc2-c2ccc(F)cc2F)c1]

The title compound was prepared in 83% yield from 2-hydrazinylpyridine-4-carbonitrile hydrochloride salt (PREPARATION 3) and (2E)-1-(2,4-difluorophenyl)-3-(dimethylamino)prop-2-en-1-one according to the procedure for the preparation of Example 12, part B. $^1$H NMR (400

MHz, CDCl$_3$): δ 6.51 (1H, d, J=1.6 Hz), 6.77-6.82 (1H, m), 6.92-6.97 (1H, m), 7.34-7.40 (2H, m), 7.80 (1H, d, J=2.0 Hz), 8.20 (1H, s), 8.27 (1H, dd, J=5.2, 1.2 Hz).

C. 2-(5-(2,4-difluorophenyl)-1H-pyrazol-1-yl)isonicotinic acid

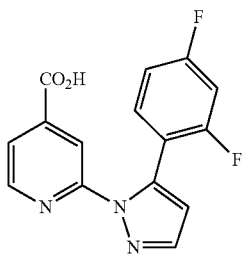 [SMILES: O=C(O)c1ccnc(-n2nccc2-c2ccc(F)cc2F)c1]

The title compound was prepared in 50% yield from 2-[5-(2,4-difluorophenyl)-1H-pyrazol-1-yl]pyridine-4-carbonitrile according to the procedure for the preparation of Example 12, part C. $^1$H NMR (400 MHz, DMSO-d$_6$): δ 6.72 (1H, d, J=2.0 Hz), 7.13-7.18 (1H, m), 7.23-7.28 (1H, m), 7.48-7.53 (1H, m), 7.72 (1H, dd, J=5.2, 1.2 Hz), 7.93 (1H, d, J=1.6 Hz), 8.22 (1H, s), 8.33 (1H, d, J=5.2 Hz), 13.92 (1H, br s). [M+H] Calc'd for C$_{15}$H$_9$F$_2$N$_3$O$_2$, 302. Found, 302.

Example 15

2-(5-(3,4-difluorophenyl)-1H-pyrazol-1-yl)isonicotinic acid

A. (2E)-1-(3,4-Difluorophenyl)-3-(dimethylamino)prop-2-en-1-one

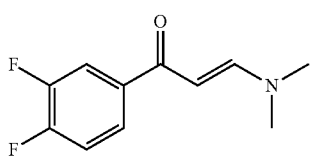

The title compound was prepared in 84% yield from 1-(3,4-difluorophenyl)ethanone and DMF-DMA according to the procedure for the preparation of Example 12, part A. $^1$H NMR (400 MHz, CDCl$_3$): δ 2.93 (3H, s), 3.16 (3H, s), 5.62 (1H, d, J=12.0 Hz), 7.13-7.20 (1H, m), 7.63-7.76 (2H, m), 7.83 (1H, d, J=12.0 Hz).

B. 2-[5-(3,4-difluorophenyl)-1H-pyrazol-1-yl]pyridine-4-carbonitrile

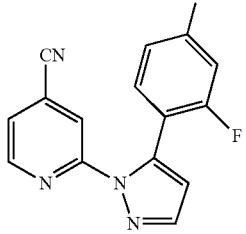

The title compound was prepared in 83% yield from 2-hydrazinylpyridine-4-carbonitrile hydrochloride salt (PREPARATION 3) and (2E)-1-(3,4-difluorophenyl)-3-(dimethylamino)prop-2-en-1-one according to the procedure for the preparation of Example 12, part B. $^1$H NMR (400 MHz, CDCl$_3$): δ 6.50 (1H, d, J=1.6 Hz), 7.01-7.04 (1H, m), 7.11-7.18 (2H, m), 7.38-7.40 (1H, m), 7.77 (1H, d, J=2.0 Hz), 8.12 (1H, s), 8.36 (1H, d, J=4.8 Hz).

C. 2-(5-(3,4-difluorophenyl)-1H-pyrazol-1-yl)isonicotinic acid

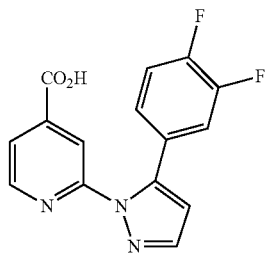 [SMILES: O=C(O)c1ccnc(-n2nccc2-c2ccc(F)c(F)c2)c1]

The title compound was prepared in 48% yield from 2-[5-(3,4-difluorophenyl)-1H-pyrazol-1-yl]pyridine-4-carbonitrile according to the procedure for the preparation of Example 12, part C. $^1$H NMR (400 MHz, DMSO-d6): δ 6.74 (1H, d, J=1.2 Hz), 7.11-7.13 (1H, m), 7.37-7.46 (2H, m), 7.76-7.78 (1H, m), 7.87 (1H, d, J=1.6 Hz), 8.17 (1H, s), 8.41 (1H, d, J=5.2 Hz), 13.97 (1H, br s). [M+H] Calc'd for C$_{15}$H$_9$F$_2$N$_3$O$_2$, 302. Found, 302.

Example 16

2-(5-(3-fluorophenyl)-1H-pyrazol-1-yl)isonicotinic acid

A. (2E)-3-(dimethylamino)-1-(3-fluorophenyl)prop-2-en-1-one

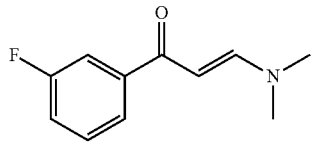

The title compound was prepared in 92% yield from 1-(3-fluorophenyl)ethanone and DMF-DMA according to the procedure for the preparation of Example 12, part A. $^1$H NMR (400 MHz, CDCl$_3$): δ 2.93 (3H, s), 3.15 (3H, s), 5.65 (1H, d, J=12.4 Hz), 7.11-7.16 (1H, m), 7.34-7.39 (1H, m), 7.57-7.67 (2H, m), 7.81 (1H, d, J=12.4 Hz).

B. 2-[5-(3-fluorophenyl)-1H-pyrazol-1-yl]pyridine-4-carbonitrile

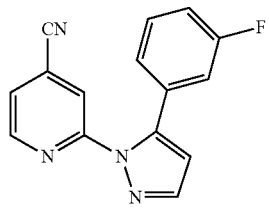 [SMILES: N#Cc1ccnc(-n2nccc2-c2cccc(F)c2)c1]

The title compound was prepared in 98% yield from 2-hydrazinylpyridine-4-carbonitrile hydrochloride salt (PREPARATION 3) and (2E)-3-(dimethylamino)-1-(3-fluorophenyl)prop-2-en-1-one according to the procedure for the preparation of Example 12, part B. $^1$H NMR (400 MHz, CDCl$_3$): δ 6.53 (1H, d, J=1.6 Hz), 6.99-7.10 (3H, m), 7.29-7.35 (1H, m), 7.38-7.40 (1H, m), 7.78 (1H, d, J=2.0 Hz), 8.05 (1H, s), 8.38 (1H, d, J=4.8 Hz).

C. 2-(5-(3-fluorophenyl)-1H-pyrazol-1-yl)isonicotinic acid

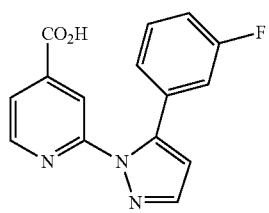 [SMILES: O=C(O)c1ccnc(-n2nccc2-c2cccc(F)c2)c1]

The title compound was prepared in 57% yield from 2-[5-(3-fluorophenyl)-1H-pyrazol-1-yl]pyridine-4-carbonitrile according to the procedure for the preparation of Example 12, part C. $^1$H NMR (400 MHz, DMSO-d$_6$): δ 6.76 (1H, d, J=1.2 Hz), 6.77-7.19 (3H, m), 7.36-7.39 (1H, m), 7.78 (1H, dd, J=5.2, 1.2 Hz), 7.87 (1H, d, J=1.2 Hz), 8.15 (1H, s), 8.42 (1H, d, J=4.8 Hz), 13.86 (1H, br s). [M+H] Calc'd for C$_{15}$H$_{10}$FN$_3$O$_2$, 284. Found, 284.

Example 17

2-(5-(3-hydroxyphenyl)-1H-pyrazol-1-yl)isonicotinic acid

A. (2E)-3-(dimethylamino)-1-(3-methoxyphenyl)prop-2-en-1-one

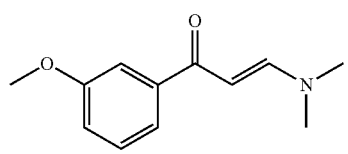

The title compound was prepared in 89% yield from 1-(3-methoxyphenyl)ethanone and DMF-DMA according to the procedure for the preparation of Example 12, part A. $^1$H NMR (400 MHz, CDCl$_3$): δ 2.94 (3H, s), 3.13 (3H, s), 3.85 (3H, s), 7.69 (1H, d, J=12.4 Hz), 6.98-7.01 (1H, m), 7.29-7.46 (3H, m), 7.79 (1H, d, J=12.4 Hz).

B. 2-[5-(3-methoxyphenyl)-1H-pyrazol-1-yl]pyridine-4-carbonitrile

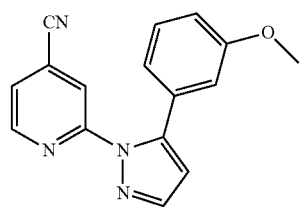 [SMILES: COc1cccc(-c2ccnn2-c2cc(C#N)ccn2)c1]

The title compound was prepared in 98% yield from 2-hydrazinylpyridine-4-carbonitrile hydrochloride salt (PREPARATION 3) and (2E)-3-(dimethylamino)-1-(3-methoxyphenyl)prop-2-en-1-one according to the procedure for the preparation of Example 12, part B. $^1$H NMR (400 MHz, CDCl$_3$): δ 3.78 (3H, s), 6.53 (1H, s), 6.81-6.85 (2H, m), 6.90-6.93 (1H, m), 7.24-7.28 (1H, m), 7.38 (1H, dd, J=5.6, 1.2 Hz), 7.77 (1H, d, J=2.0 Hz), 7.93 (1H, s), 8.44 (1H, dd, J=5.2, 0.8 Hz).

C. 2-[5-(3-methoxyphenyl)-1H-pyrazol-1-yl]pyridine-4-carboxylic acid

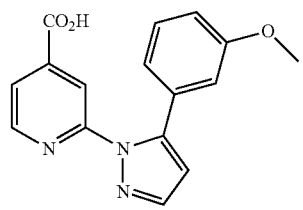 [SMILES: COc1cccc(-c2ccnn2-c2cc(C(=O)O)ccn2)c1]

The title compound was prepared in 93% yield from 2-[5-(3-methoxyphenyl)-1H-pyrazol-1-yl]pyridine-4-carbonitrile according to the procedure for the preparation of Example 12, part C. $^1$H NMR (300 MHz, DMSO-d$_6$): δ 3.67 (3H, s), 6.71-6.92 (4H, m), 7.21-7.26 (1H, m), 7.78-7.84 (2H, m), 8.09 (1H, s), 8.45 (1H, d, J=5.1 Hz).

D. 2-(5-(3-hydroxyphenyl)-1H-pyrazol-1-yl)isonicotinic acid

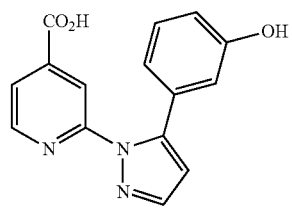 [SMILES: O=C(O)c1ccnc(-n2nccc2-c2cccc(O)c2)c1]

To a solution of 2-[5-(3-methoxyphenyl)-1H-pyrazol-1-yl]pyridine-4-carboxylic acid (160 mg, 0.54 mmol) in CH$_2$Cl$_2$ (5 mL) was added 1 M BBr$_3$ in CH$_2$Cl$_2$ (5 mL) at 0° C., then stirred at 45° C. overnight. The reaction mixture was cooled, concentrated and dissolved with EtOAc, then washed with water and brine. The organic phase was dried, concentrated and purified by prep-HPLC to give the title compound (54 mg, 35%) as a yellow solid. $^1$H NMR (400 MHz, DMSO-d$_6$): δ 6.60-6.65 (3H, m), 6.71 (1H, dd, J=8.4, 2.0 Hz), 7.11 (1H, t, J=8.0 Hz), 7.78-7.82 (2H, m), 8.04 (1H, s), 8.48 (1H, d, J=5.2 Hz), 9.46 (1H, s), 13.93 (1H, br s). [M+H] Calc'd for C$_{15}$H$_{11}$N$_3$O$_3$, 282. Found, 282.

Example 18

2-(5-(4-hydroxyphenyl)-1H-pyrazol-1-yl)isonicotinic acid

A. (2E)-3-(dimethylamino)-1-(4-methoxyphenyl)prop-2-en-1-one

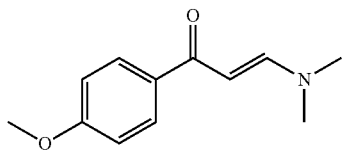

The title compound was prepared in 88% yield from 1-(4-methoxyphenyl)ethanone and DMF-DMA according to the procedure for the preparation of Example 12, part A. $^1$H NMR (400 MHz, CDCl$_3$): δ 2.88-3.06 (6H, br s), 3.85 (3H, s), 5.71 (1H, d, J=12.0 Hz), 6.91 (2H, d, J=8.8 Hz), 7.84 (1H, d, J=12.0 Hz), 7.91 (2H, d, J=8.8 Hz).

B. 2-[5-(4-methoxyphenyl)-1H-pyrazol-1-yl]pyridine-4-carbonitrile

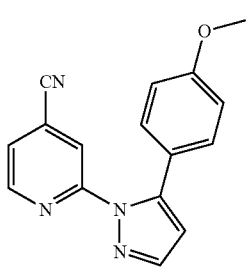 [SMILES: COc1ccc(-c2ccnn2-c2cc(C#N)ccn2)cc1]

The title compound was prepared in 100% yield from 2-hydrazinylpyridine-4-carbonitrile hydrochloride salt (PREPARATION 3) and (2E)-3-(dimethylamino)-1-(4-methoxyphenyl)prop-2-en-1-one according to the procedure for the preparation of Example 12, part B. $^1$H NMR (400 MHz, CDCl$_3$): δ 3.84 (3H, s), 6.46 (1H, d, J=5.6 Hz), 6.88 (2H, dd, J=6.8, 2.0 Hz), 7.20 (2H, dd, J=6.4, 2.0 Hz), 7.37 (1H, dd, J=5.2, 1.6 Hz), 7.75 (1H, d, J=1.6 Hz), 7.91 (1H, s), 8.44 (1H, dd, J=4.8, 0.8 Hz).

C. 2-[5-(4-methoxyphenyl)-1H-pyrazol-1-yl]pyridine-4-carboxylic acid

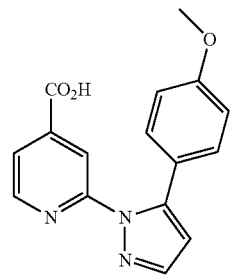 [SMILES: COc1ccc(-c2ccnn2-c2cc(C(=O)O)ccn2)cc1]

The title compound was prepared in 79% yield from 2-[5-(4-methoxyphenyl)-1H-pyrazol-1-yl]pyridine-4-carbonitrile according to the procedure for the preparation of Example 12, part C. $^1$H NMR (300 MHz, DMSO-d$_6$): δ 3.76 (3H, s), 6.61 (1H, s), 6.88-6.91 (2H, m), 7.16-7.19 (2H, m), 7.76-7.80 (2H, m), 8.06 (1H, s), 8.45 (1H, d, J=5.1 Hz).

D. 2-(5-(4-hydroxyphenyl)-1H-pyrazol-1-yl)isonicotinic acid

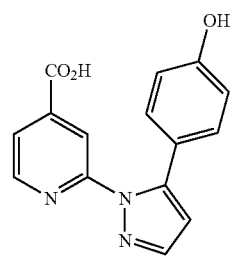 [SMILES: O=C(O)c1ccnc(-n2nccc2-c2ccc(O)cc2)c1]

The title compound was prepared in 32% yield from 2-[5-(4-methoxyphenyl)-1H-pyrazol-1-yl]pyridine-4-carbonitrile according to the procedure for the preparation of Example 17, part D. $^1$H NMR (400 MHz, DMSO-d$_6$): δ 6.56 (1H, d, J=2.0 Hz), 6.71 (2H, d, J=8.4 Hz), 7.05 (2H, d, J=8.4 Hz), 7.76-7.78 (2H, m), 8.02 (1H, s), 8.48 (1H, d, J=4.8 Hz), 9.63 (1H, s), 13.89 (1H, br s). [M+H] Calc'd for C$_{15}$H$_{11}$N$_3$O$_3$, 282. Found, 282.

Example 19

2-(5-(4-(methylsulfonyl)phenyl)-1H-pyrazol-1-yl)isonicotinic acid

A. (2E)-3-(dimethylamino)-1-[4-(methylsulfonyl)phenyl]prop-2-en-1-one

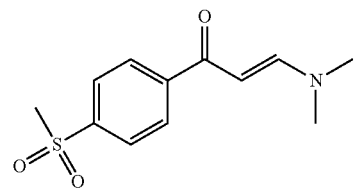 [SMILES: CN(C)/C=C/C(=O)c1ccc(S(C)(=O)=O)cc1]

The title compound was prepared in 87% yield from 1-[4-(methylsulfonyl)phenyl]ethanone and DMF-DMA according to the procedure for the preparation of Example 12, part A. ¹H NMR (400 MHz, CDCl₃): δ 2.96 (3H, s), 3.06 (3H, s), 3.19 (3H, s), 5.66 (1H, d, J=12 Hz), 7.83 (1H, d, J=12 Hz), 7.96-8.04 (4H, m).

B. 2-{5-[4-(methylsulfonyl)phenyl]-1H-pyrazol-1-yl}pyridine-4-carbonitrile

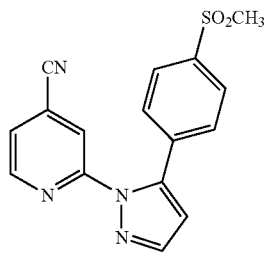 [SMILES: CS(=O)(=O)c1ccc(-c2ccnn2-c2cc(C#N)ccn2)cc1]

The title compound was prepared in 100% yield from 2-hydrazinylpyridine-4-carbonitrile hydrochloride salt (PREPARATION 3) and (2E)-3-(dimethylamino)-1-[4-(methylsulfonyl)phenyl]prop-2-en-1-one according to the procedure for the preparation of Example 12, part B. ¹H NMR (400 MHz, CDCl₃): δ 3.10 (3H, s), 6.58 (1H, d, J=1.6 Hz), 7.39 (1H, dd, J=5.2, 1.2 Hz), 7.51 (2H, d, J=8.4 Hz), 7.81 (1H, d, J=1.6 Hz), 7.93 (2H, d, J=8.4 Hz), 8.20 (1H, s), 8.29 (1H, d, J=5.2 Hz).

C. 2-(5-(4-(methylsulfonyl)phenyl)-1H-pyrazol-1-yl)isonicotinic acid

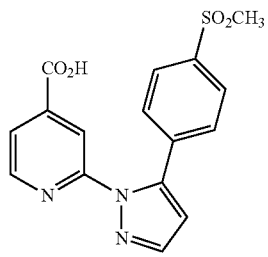 [SMILES: CS(=O)(=O)c1ccc(-c2ccnn2-c2cc(C(=O)O)ccn2)cc1]

The title compound was prepared in 44% yield from 2-{5-[4-(methylsulfonyl)phenyl]-1H-pyrazol-1-yl}pyridine-4-carbonitrile according to the procedure for the preparation of Example 12, part C. ¹H NMR (400 MHz, DMSO-d₆): δ 3.25 (3H, s), 6.84 (1H, d, J=1.6 Hz), 7.57 (2H, d, J=8.4 Hz), 7.05 (1H, dd, J=4.8, 1.2 Hz), 7.87-7.93 (3H, m), 8.22 (1H, s), 8.40 (1H, d, J=4.8 Hz), 13.98 (1H, br s). [M+H] Calc'd for $C_{16}H_{13}N_3O_4S$, 344. Found, 344.

Example 20

2-(5-(3-methoxy-4-methylphenyl)-1H-pyrazol-1-yl)isonicotinic acid

A. (2E)-3-(dimethylamino)-1-(3-methoxy-4-methylphenyl)prop-2-en-1-one

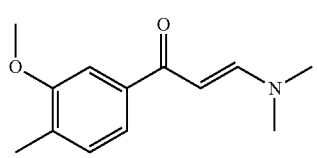 [SMILES: COc1cc(C(=O)/C=C/N(C)C)ccc1C]

The title compound was prepared in 49% yield from 1-(3-hydroxy-4-methylphenyl)ethanone and DMF-DMA according to the procedure for the preparation of Example 12, part A. ¹H NMR (400 MHz, CDCl₃): δ 2.25 (3H, s), 2.95-3.10 (6H, m), 3.89 (3H, s), 5.72 (1H, d, J=12.0 Hz), 7.14 (1H, d, J=7.6 Hz), 7.37 (1H, dd, J=7.6, 1.2 Hz), 7.45 (1H, d, J=1.2 Hz) 7.80 (1H, d, J=12.4 Hz). [M+H] Calc'd for $C_{12}H_{15}NO_2$, 220. Found, 220.

B. 2-[5-(3-methoxy-4-methylphenyl)-1H-pyrazol-1-yl]pyridine-4-carbonitrile

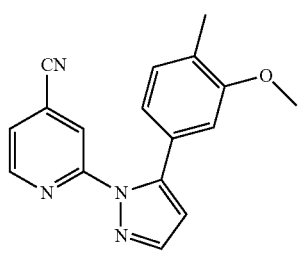 [SMILES: COc1cc(-c2ccnn2-c2cc(C#N)ccn2)ccc1C]

The title compound was prepared in 100% yield from 2-hydrazinylpyridine-4-carbonitrile hydrochloride salt (PREPARATION 3) and (2E)-3-(dimethylamino)-1-(3-methoxy-4-methylphenyl)prop-2-en-1-one according to the procedure for the preparation of Example 12, part B. ¹H NMR (400 MHz, CDCl₃): δ 2.24 (3H, s), 3.73 (3H, s), 6.51 (1H, d, J=1.6 Hz), 6.71-6.75 (2H, m), 7.08 (1H, d, J=8.0 Hz), 7.39 (1H, dd, J=5.2, 1.2 Hz), 7.77 (1H, d, J=1.2 Hz), 7.90 (1H, s), 8.47 (1H, d, J=5.2 Hz). [M+H] Calc'd for $C_{17}H_{14}N_4O$, 291. Found, 291.

C. 2-(5-(3-methoxy-4-methylphenyl)-1H-pyrazol-1-yl)isonicotinic acid

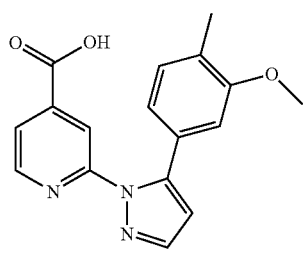 [SMILES: COc1cc(-c2ccnn2-c2cc(C(=O)O)ccn2)ccc1C]

The title compound was prepared in 53% yield from 2-[5-(3-methoxy-4-methylphenyl)-1H-pyrazol-1-yl]pyridine-4-carbonitrile according to the procedure for the preparation of Example 12, part C. $^1$H NMR (400 MHz, DMSO-d$_6$): δ 2.13 (3H, s), 3.63 (3H, s), 6.69-6.71 (2H, m), 6.79 (1H, d, J=1.6 Hz), 7.07 (1H, d, J=7.6 Hz), 7.78-7.83 (2H, m), 8.08 (1H, s), 8.48 (1H, d, J=4.8 Hz), 13.92 (1H, br s). [M+H] Calc'd for $C_{17}H_{15}N_3O_3$, 310. Found, 310.

Example 21

2-(5-(3-hydroxy-4-methylphenyl)-1H-pyrazol-1-yl)isonicotinic acid

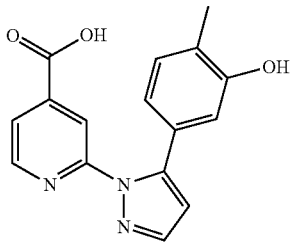 [SMILES: Cc1ccc(-c2ccnn2-c2cc(C(=O)O)ccn2)cc1O]

The title compound was prepared in 24% yield from 2-(5-(3-methoxy-4-methylphenyl)-1H-pyrazol-1-yl)isonicotinic acid according to the procedure for the preparation of Example 17, part D. $^1$H NMR (400 MHz, DMSO-d$_6$): δ 2.09 (3H, s), 6.57-6.61 (3H, m), 7.00 (1H, d, J=7.2 Hz), 7.79 (2H, dd, J=4.0, 2.0 Hz), 8.02 (1H, s), 8.50 (1H, d, J=4.8 Hz), 9.30 (1H, s), 13.92 (1H, br s). [M+H] Calc'd for $C_{16}H_{13}N_3O_3$, 296. Found, 296.

Example 22

2-(5-(4-chloro-3-methoxyphenyl)-1H-pyrazol-1-yl)isonicotinic acid

A. (2E)-1-(4-chloro-3-methoxyphenyl)-3-(dimethylamino)prop-2-en-1-one

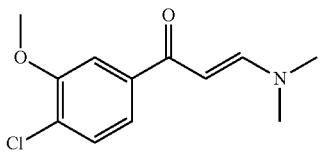 [SMILES: COc1cc(C(=O)/C=C/N(C)C)ccc1Cl]

The title compound was prepared in 43% yield from 1-(4-chloro-3-hydroxyphenyl)ethanone and DMF-DMA according to the procedure for the preparation of Example 12, part A. $^1$H NMR (400 MHz, CDCl$_3$): δ 2.94 (3H, br s), δ 3.16 (3H, br s), 3.97 (3H, s), 5.67 (1H, d, J=12.4 Hz), 7.38 (2H, s), 7.56 (1H, s), 7.81 (1H, d, J=12.4 Hz). [M+H] Calc'd for $C_{11}H_{12}ClNO_2$, 240. Found, 240.

B. 2-[5-(4-chloro-3-methoxyphenyl)-1H-pyrazol-1-yl]pyridine-4-carbonitrile

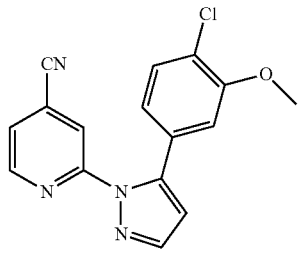 [SMILES: COc1cc(-c2ccnn2-c2cc(C#N)ccn2)ccc1Cl]

The title compound was prepared in 74% yield from 2-hydrazinylpyridine-4-carbonitrile hydrochloride salt (PREPARATION 3) and (2E)-1-(4-chloro-3-methoxyphenyl)-3-(dimethylamino)prop-2-en-1-one according to the procedure for the preparation of Example 12, part B. $^1$H NMR (400 MHz, CDCl$_3$): δ 3.82 (3H, s), 6.53 (1H, d, J=2.0 Hz), 6.78 (1H, d, J=2.4 Hz), 6.89 (1H, d, J=1.6 Hz), 7.32 (1H, d, J=8.0 Hz), 7.39 (1H, dd, J=5.2, 1.2 Hz), 7.78 (1H, d, J=1.2 Hz), 8.07 (1H, s), 8.39 (1H, dd, J=5.2, 0.8 Hz). [M+H] Calc'd for $C_{16}H_{11}ClN_4O$, 311. Found, 311.

C. 2-(5-(4-chloro-3-methoxyphenyl)-1H-pyrazol-1-yl)isonicotinic acid

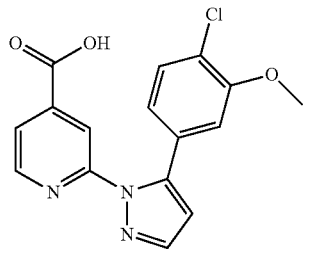 [SMILES: COc1cc(-c2ccnn2-c2cc(C(=O)O)ccn2)ccc1Cl]

The title compound was prepared in 71% yield from 2-[5-(4-chloro-3-methoxyphenyl)-1H-pyrazol-1-yl]pyridine-4-carbonitrile according to the procedure for the preparation of Example 12, part C. $^1$H NMR (400 MHz, CDCl$_3$): δ 3.79 (3H, s), 6.55 (1H, d, J=1.2 Hz), 6.79 (1H, s), 6.87 (1H, d, J=2.0 Hz), 7.30 (1H, d, J=8.4 Hz), 7.82 (2H, s), 8.15 (1H, s), 8.32 (1H, s), 8.46 (1H, d, J=4.8 Hz). [M+H] Calc'd for $C_{16}H_{12}ClN_3O_3$, 330. Found, 330.

Example 23

2-(5-(4-chloro-3-hydroxyphenyl)-1H-pyrazol-1-yl)isonicotinic acid

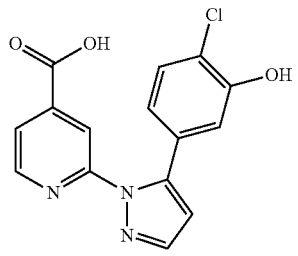 [SMILES: O=C(O)c1ccnc(-n2nccc2-c2ccc(Cl)c(O)c2)c1]

The title compound was prepared in 19% yield from 2-(5-(4-chloro-3-methoxyphenyl)-1H-pyrazol-1-yl)isonicotinic acid according to the procedure for the preparation of Example 17, part D. $^1$H NMR (400 MHz, CD$_3$OD): δ 6.51 (1H, s), 6.60 (1H, dd, J=8.4, 2.0 Hz), 6.66 (1H, d, J=2.0 Hz), 7.14 (1H, d, J=8.4 Hz), 7.68 (1H, s), 7.77 (1H, d, J=4.4 Hz), 7.93 (1H, s), 8.39 (1H, s). [M+H] Calc'd for C$_{15}$H$_{10}$ClN$_3$O$_3$, 316. Found, 316.

Example 24

2-[5-(1H-indazol-6-yl)-1H-pyrazol-1-yl]pyridine-4-carboxylic acid

A. 1-(1H-indazol-6-yl)ethanone (24-a)

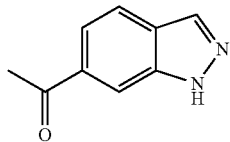

24-a

To a solution of 6-bromo-1H-indazole (5.0 g, 25.4 mmol) in 40 mL THF was added dropwise n-BuLi (2.5M, 30 mL, 76.2 mmol) at −65° C., and the mixture was stirred for 2 h. Then, N-methoxy-N-methylacetamide (2.9 g, 27.9 mmol) was added. The reaction mixture was stirred for another 2 h at −65° C., then quenched with 40 mL H$_2$O. The mixture was extracted with EtOAc (3×50 mL). The combined organic layers were washed with 100 mL brine, dried, and concentrated to dryness. The residue was purified by flash column chromatography (PE/EA=40/1) to give the title compound 24-a (370 mg, 9%) as a yellow solid. [M+H] Calc'd for C$_9$H$_8$N$_2$O, 161. Found, 161.

B. 1-(1-((2-(trimethylsilyl)ethoxy)methyl)-1H-indazol-6-yl)ethanone (24-b1) and 1-(2-((2-(trimethylsilyl)ethoxy)methyl)-2H-indazol-6-yl)ethanone (24-b2)

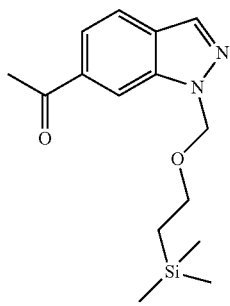

24b-b1

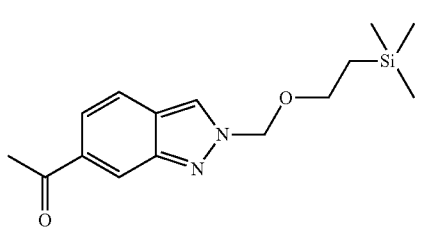

24b-b2

To a solution of 1-(1H-indazol-6-yl)ethanone 24-a (200 mg, 1.25 mmol) in 4 mL DMF was added NaH (77 mg, 1.9 mmol) at 0-5° C., and the mixture was stirred for 1 h at 0-5° C. 2-(Trimethylsilyl)ethoxymethyl chloride (215 mg, 1.29 mmol) was then added. The mixture was stirred for 2 h prior to the addition of 5 mL H$_2$O. The reaction mixture was extracted (3×10 mL EtOAc), dried, and concentrated to dryness to give a mixture of the products 24-b1 and 24-b2 (280 mg, 77%) as a yellow oil, which was used without further purification for the next synthetic step. [M+H] Calc'd for C$_{15}$H$_{22}$N$_2$O$_2$Si, 291. Found, 291.

C. 3-(dimethylamino)-1-(1-((2-(trimethylsilyl)ethoxy)methyl)-1H-indazol-6-yl)prop-2-en-1-one (24-c1) and 3-(dimethylamino)-1-(2-((2-(trimethylsilyl)ethoxy)methyl)-2H-indazol-6-yl)prop-2-en-1-one (24-c2)

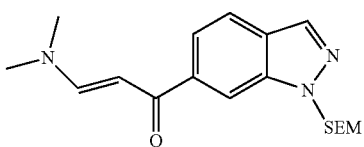

24-c1

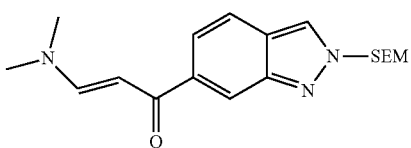

24-c2

To a regioisomeric mixture of compound 3 (700 mg, 2.4 mmol) in 10 mL DMF was added 2 mL DMF-DMA, and the mixture was heated to 115° C. and stirred for 4 h. The reaction mixture was cooled and concentrated to dryness to give the crude product 24-c1 and 24-c2 (900 mg, 100%) as a yellow oil, and was used without further purification for the next synthetic step. [M+H] Calc'd for C$_{18}$H$_{27}$N$_3$O$_2$Si, 346. Found, 346.

D. 2-(5-(1-((2-(trimethylsilyl)ethoxy)methyl)-1H-indazol-6-yl)-1H-pyrazol-1-yl)isonicotinonitrile (24-d1) and 2-(5-(2-((2-(trimethylsilyl)ethoxy)methyl)-2H-indazol-6-yl)-1H-pyrazol-1-yl)isonicotinonitrile (24-d2)

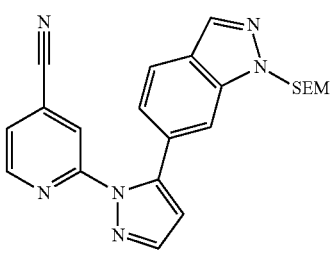

24-d1

24-d2

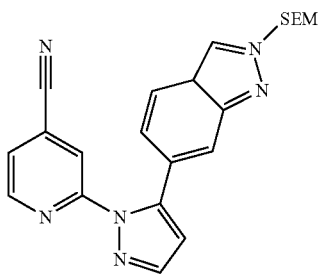

A mixture of compounds 24-c1 and 24-c2 (900 mg, 2.6 mmol) and 2-hydrazinylpyridine-4-carbonitrile (350 mg, 2.6 mmol) in EtOH (10 mL) and AcOH (2 mL) was stirred at 90° C. overnight. The reaction mixture was cooled, concentrated, and purified by prep-HPLC to afford compounds 24-d1 and 24-d2 (390 mg, 36%), and was used without further purification for the next synthetic step. [M+H] Calc'd for $C_{22}H_{24}N_6OSi$, 417. Found, 417.

E. 2-(5-(1-((2-(trimethylsilyl)ethoxy)methyl)-1H-indazol-6-yl)-1H-pyrazol-1-yl)isonicotinic acid (24-e1) and 2-(5-(2-((2-(trimethylsilyl)ethoxy)methyl)-2H-indazol-6-yl)-1H-pyrazol-1-yl)isonicotinic acid (24-e2)

24-e1

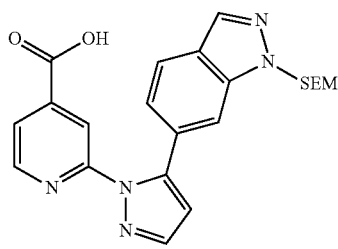

24-e2

To a solution of compounds 24-d1 and 24-d2 (390 mg, 0.94 mmol) in EtOH (10 mL) was added 5 M NaOH (2 mL) at rt, then stirred at 90° C. for 1 h. The reaction mixture was cooled, acidified with 1 N HCl to pH=3, filtered to give a yellow solid, and recrystallized from EtOH to afford compounds 24-e1 and 24-e2 (230 mg, 56%) as a white solid, which was used without further purification for the next synthetic step. [M+H] Calc'd for $C_{22}H_{25}N_5O_3Si$, 436. Found, 436.

F. 2-[5-(1H-indazol-6-yl)-1H-pyrazol-1-yl]pyridine-4-carboxylic acid

The solution of compounds 24-e1 and 24-e2 (50 mg, 0.12 mmol) in HCl/EtOAc (6 M, 10 mmol) was stirred overnight at rt. The reaction mixture was filtered, and the solids were stirred with EtOAc/PE (0.5 mL/5 mL) for 1 h. After filtration, the solids were washed with hexane to give the title compound (13 mg, 37%) as a yellow solid. $^1$H NMR (400 MHz, MeOD-d$_4$): δ 6.75 (1H, s), 7.06 (1H, dd, J=6.8, 1.6 Hz), 7.51 (1H, s), 7.77 (1H, d, J=8.4 Hz), 7.88 (2H, s), 8.14 (2H, d, J=1.2 Hz), 8.45 (1H, d, J=2.0 Hz). [M+H] Calc'd for $C_{16}H_{11}N_5O_2$, 306. Found, 306.

Example 25

Methyl 2-[5-(1H-indazol-6-yl)-1H-pyrazol-1-yl]pyridine-4-carboxylate

A. Methyl 2-(5-(1-((2-(trimethylsilyl)ethoxy)methyl)-1H-indazol-6-yl)-1H-pyrazol-1-yl)isonicotinate (25-a1) and methyl 2-(5-(2-((2-(trimethylsilyl)ethoxy)methyl)-2H-indazol-6-yl)-1H-pyrazol-1-yl)isonicotinate (25-a2)

25-a1

25-a2

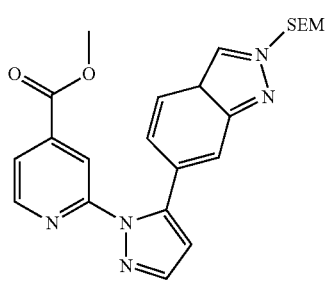

To a solution of compound 24-e1 and 24-e2 (50 mg, 0.12 mmol) in CH$_2$Cl$_2$/DMF (2 mL/1 drop) was added oxalyl chloride (0.5 mL), and the mixture was stirred for 1 h at rt. Then the reaction mixture was added dropwise to MeOH (1 mL), and the resultant mixture was stirred for 30 min at rt. Removal of volatiles provided compounds 25-a1 and 25-a2 (60 mg, 100%) as a yellow solid, which was used without further purification for the next synthetic step. [M+H] Calc'd for $C_{23}H_{27}N_5O_3Si$, 450. Found, 450.

B. Methyl 2-[5-(1H-indazol-6-yl)-1H-pyrazol-1-yl]pyridine-4-carboxylate

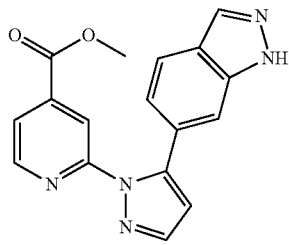

The solution of compounds 25-a1 and 25-a2 (60 mg, 0.12 mmol) in TFA/CH$_2$Cl$_2$ (0.5 mL/2 mL) was stirred overnight at rt. The mixture was concentrated, and the residue was adjusted to pH=8 with saturated aq. NaHCO$_3$. The mixture was extracted with CH$_2$Cl$_2$. The combined organic layers were washed with brine, dried over Na$_2$SO$_4$, filtered, concentrated, and purified by prep-HPLC to afford the title compound (10 mg, 28%) as a yellow solid. $^1$H NMR (400 MHz, MeOD-d$_4$): δ 3.96 (3H, s), 6.74 (1H, d, J=1.6 Hz), 7.00 (1H, dd, J=8.4, 1.2 Hz), 7.50 (1H, s), 7.74 (1H, d, J=8.4 Hz), 7.87 (2H, m), 8.07 (1H, s), 8.13 (1H, s), 8.46 (1H, d, J=7.2 Hz). [M+H] Calc'd for $C_{17}H_{13}N_5O_2$, 320. Found, 320.

Example 26

2-(5-phenyl-1H-pyrazol-1-yl)isonicotinic acid

A. (E)-3-(dimethylamino)-1-phenylprop-2-en-1-one

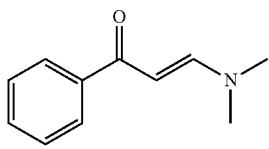

A mixture of acetophenone (8.0 g, 66.58 mmol, 1.0 eq) and DMF (5.8 g, 79.90 mmol, 1.2 eq.) in 10.0 mL of DMA in a 25-mL microwave vial was irradiated at 115° C. for 0.5-1 h. The crude reaction mixture was triturated with n-hexane, and the resultant solid was filtered to afford the title compound as a pale yellow solid (3.4 g. 29.3% yield). [M+H] Calc'd for $C_{11}H_{13}NO$, 176. Found, 176.

B. 2-(5-phenyl-1H-pyrazol-1-yl)isonicotinonitrile

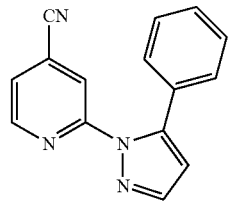 [SMILES: N#Cc1ccnc(-n2nccc2-c2ccccc2)c1]

To a solution of 2-hydrazinylisonicotinonitrile (100 mg, 0.75 mmol, 1.0 eq., PREPARATION 2) and (E)-3-(dimethylamino)-1-phenylprop-2-en-1-one (132 mg, 0.75 mmol, 1.0 eq.) in ethanol (10 mL) was added 2-5 drops of AcOH. The reaction mixture was under reflux conditions for 12 h. After reaction completion, volatiles were removed under reduced pressure, and the resultant crude material was purified by flash column chromatography (20% EtOAc/hexane) to obtain the title compound as a yellow oil (150 mg, 81% yield). [M+H] Calc'd for $C_{15}H_{10}N_4$, 247.09. Found 247.

C. 2-(5-phenyl-1H-pyrazol-1-yl)isonicotinic acid

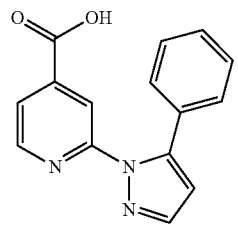 [SMILES: O=C(O)c1ccnc(-n2nccc2-c2ccccc2)c1]

To a stirred solution of 2-(5-phenyl-1H-pyrazol-1-yl)isonicotinonitrile (100 mg, 0.41 mmol) in EtOH (10 mL) was added a solution of 25% NaOH in water (1.0 mL). The reaction mixture was heated under reflux conditions at 80° C. for 1 h. After reaction completion, the solvent was removed, and the resultant mixture was diluted with water, and the pH was adjusted to pH=4-5 with 2.0 N HCl. The mixture was extracted with EtOAc (3×15 mL), the combined organic layers were dried over Na$_2$SO$_4$, and the solvent was removed to obtain pale yellow solid, which was washed with hexane and dried under reduced pressure to afford the title compound (60 mg, 55% yield). $^1$H NMR (300 MHz, DMSO-d$_6$) δ 8.5 (S, 1H), 8.2 (d, 1H, J=2.1 Hz), 7.9 (s, 1H), 7.78 (s, 1H), 7.7 (d, 1H, J=2.7 Hz), 7.3 (m, 2H), 7.2 (m, 1H), 6.65 (s, 2H). [M+H] Calc'd for $C_{15}H_{11}N_3O_2$, 266. Found, 266.

Example 27

2-(5-(4-fluorophenyl)-1H-pyrazol-1-yl)isonicotinic acid

A. (E)-3-(dimethylamino)-1-(4-fluorophenyl)prop-2-en-1-one

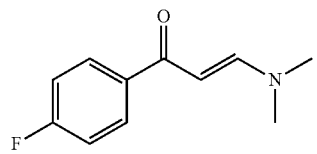

The title compound was prepared in 39% yield from 1-(4-fluorophenyl)ethanone according to the procedure for the preparation of Example 26, part A. $^1$H NMR (500 MHz, CDCl$_3$) δ 7.91 (dd, 2H, J=5.8, 7.7 Hz), 7.79 (d, 1H, J=12.6 Hz), 7.0 (t, 2H, J=8.7, 7.7 Hz), 5.6 (d, 1H, J=12.6 Hz), 3.14 (s, 3H), 2.92 (s, 3H). [M+H] Calc'd for C$_{11}$H$_{12}$FNO, 193. Found, 193.

B. 2-(5-(4-fluorophenyl)-1H-pyrazol-1-yl)isonicotinonitrile

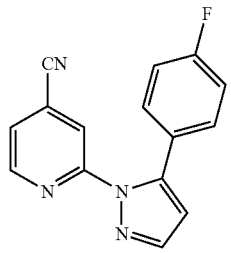 [SMILES: N#Cc1ccnc(-n2nccc2-c2ccc(F)cc2)c1]

The title compound was prepared in 32% yield from 2-hydrazinylisonicotinonitrile (PREPARATION 2) and (E)-3-(dimethylamino)-1-(4-fluorophenyl)prop-2-en-1-one according to the procedure for the preparation of Example 26, part B. $^1$H NMR (500 MHz, CDCl$_3$) δ 8.36 (d, 1H, J=4.8 Hz), 8.0 (s, 1H), 7.7 (s, 1H), 7.37 (d, 1H, J=3.8 Hz), 7.25 (d, 2H, J=5.8), 7.0 (t, 2H, J=8.7 Hz, 1H), 6.45 (s, 1H). [M+H] Calc'd for C$_{15}$H$_9$FN$_4$, 265. Found, 265.

C. 2-(5-(4-fluorophenyl)-1H-pyrazol-1-yl)isonicotinic acid

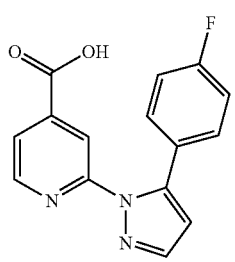 [SMILES: O=C(O)c1ccnc(-n2nccc2-c2ccc(F)cc2)c1]

The title compound was prepared in 35% yield from 2-(5-(4-fluorophenyl)-1H-pyrazol-1-yl)isonicotinonitrile according to the procedure for the preparation of Example 26, part C. $^1$H NMR (500 MHz, DMSO-d$_6$): δ 8.8 (d, 1H, J=4.4 Hz), 8.5 (s, 1H), 8.26 (s, 1H), 8.2 (d, 1H, J=4.4 Hz), 7.74 (t, 2H, J=7.7 Hz), 7.54 (t, 2H, J=7.7 Hz), 7.1 (s, 1H). [M+H] Calc'd for C$_{15}$H$_{10}$FN$_3$O$_2$, 283. Found, 283.

Example 28

2-(5-(3-hydroxy-4-(methylsulfonyl)phenyl)-1H-pyrazol-1-yl)isonicotinic acid

A. 5-acetyl-2-(methylsulfanyl)phenyl acetate

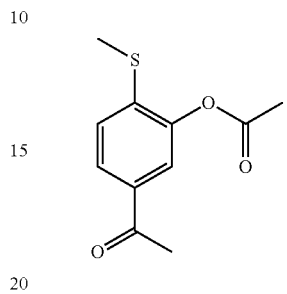

To a solution of 2-(methylsulfanyl)phenol (4.2 g, 30 mmol) in CS$_2$ (50 mL) was added dropwise acetyl chloride (5.2 g, 66 mmol) at 0° C. for 10 min. The resulting mixture was stirred for 20 min at rt. Then AlCl$_3$ (10.8 g, 81 mmol) was added, and the reaction mixture was heated under reflux conditions for 3 h. The reaction mixture was poured into ice water, conc. HCl (5 mL) was added, and the reaction mixture was extracted with CH$_2$Cl$_2$. The combined organic layers were washed with brine, dried over Na$_2$SO$_4$ and concentrated. The residue was dissolved in CH$_2$Cl$_2$ (50 mL), cooled to 0° C. and treated successively with acetyl chloride (1.2 g, 15 mmol) and triethylamine (1.5 g, 15 mmol). The mixture was stirred at rt for 2 h and poured into water. After separation of the layers, the organic phase was washed successively with water, 3 N HCl and 10% aq. KHCO$_3$, dried over Na$_2$SO$_4$, and evaporated to dryness. Recrystallization of the resulting solid from benzene-hexane afforded the title compound (2.5 g, 37%). $^1$H NMR (400 MHz, CDCl$_3$): δ 2.08 (3H, s), 2.47 (3H, s), 2.55 (3H, s), 7.26 (1H, d, J=4.8 Hz), 7.57 (1H, d, J=4.8 Hz), 7.60 (1H, s).

B. 5-acetyl-2-(methylsulfonyl)phenyl acetate

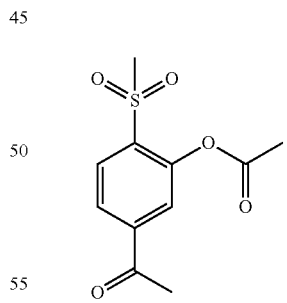

To a solution of 5-acetyl-2-(methylsulfanyl)phenyl acetate (2.24 g, 10 mmol) in CH$_2$Cl$_2$ (20 mL) was added mCPBA (8.62 g, 50 mmol) at 0° C. and the mixture was stirred at rt for 3 h. A solution of NaHCO$_3$ was added and extracted with CH$_2$Cl$_2$. The organic phase was washed successively with water, 3 N HCl and 10% aq. KHCO$_3$, dried over Na$_2$SO$_4$, and evaporated to afford the crude product (2.1 g, 82%). $^1$H NMR (400 MHz, CDCl$_3$): δ 2.10 (3H, s), 2.57 (3H, s), 2.84 (3H, s), 7.86 (1H, d, J=4.8 Hz), 7.93 (1H, s), 8.05 (1H, d, J=4.8 Hz).

C. 5-[(2E)-3-(dimethylamino)prop-2-enoyl]-2-(methylsulfonyl)phenyl acetate

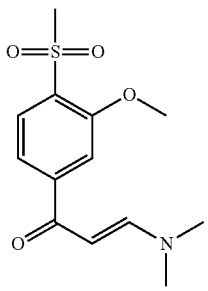 [SMILES: COc1cc(C(=O)/C=C/N(C)C)ccc1S(C)(=O)=O]

A solution of 5-acetyl-2-(methylsulfonyl)phenyl acetate (1.5 g, 5.8 mmol) and DMF-DMA (1.2 g, 10 mmol) in DMF (20 mL) was stirred at 100° C. overnight. The reaction mixture was cooled, concentrated, and purified by flash column chromatography (PE/EtOAc=4:1~2:1) to give the title compound (0.5 g, 30%). [M+H] Calc'd for $C_{13}H_{17}NO_4S$, 284. Found, 284.

D. 2-{5-[3-methoxy-4-(methylsulfonyl)phenyl]-1H-pyrazol-1-yl}pyridine-4-carbonitrile

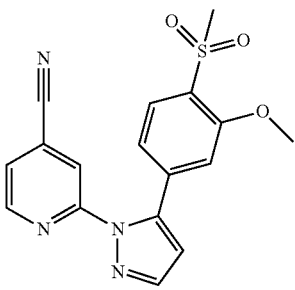 [SMILES: COc1cc(-c2ccnn2-c2cc(C#N)ccn2)ccc1S(C)(=O)=O]

A mixture of 5-[(2E)-3-(dimethylamino)prop-2-enoyl]-2-(methylsulfonyl)phenyl acetate (1.5 g, 5.3 mmol) and 2-hydrazinylisonicotinonitrile (0.8 g, 6 mmol, PREPARATION 2) in EtOH (15 mL) and AcOH (3 mL) was stirred at 90° C. overnight. The reaction mixture was cooled, concentrated, and purified by prep-HPLC to afford the title compound (270 mg, 14%). $^1$H NMR (400 MHz, CDCl$_3$): δ 3.26 (3H, s), 3.96 (3H, s), 6.58 (1H, d, J=1.6 Hz), 6.96 (1H, dd, J=8.4, 1.2 Hz), 7.05 (1H, d, J=1.2 Hz), 7.41 (1H, dd, J=4.8, 1.2 Hz), 7.81 (1H, d, J=2.0 Hz), 7.93 (1H, d, J=8.4 Hz), 8.18 (1H, s), 8.35 (1H, d, J=4.8 Hz). [M+H] Calc'd for $C_{17}H_{14}N_4O_3S$, 355. Found, 355.

E. 2-{5-[3-methoxy-4-(methylsulfonyl)phenyl]-1H-pyrazol-1-yl}pyridine-4-carboxylic acid

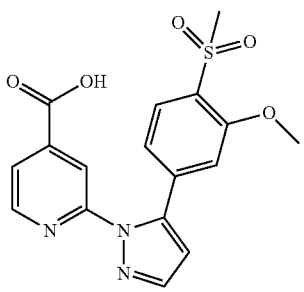 [SMILES: COc1cc(-c2ccnn2-c2cc(C(=O)O)ccn2)ccc1S(C)(=O)=O]

To a solution of 2-{5-[3-methoxy-4-(methylsulfonyl)phenyl]-1H-pyrazol-1-yl}pyridine-4-carbonitrile (270 mg, 0.76 mmol) in EtOH (5 mL) was added 5 M NaOH (2 mL) at rt, then stirred at 90° C. for 1 h. The reaction mixture was cooled, acidified with 1 N HCl to pH=3, filtered to give a yellow solid, then recrystallized from EtOH to afford the title compound (230 mg, 80%) as a white solid. [M+H] Calc'd for $C_{17}H_{15}N_3O_5S$, 374. Found, 374.

F. 2-(5-(3-hydroxy-4-(methylsulfonyl)phenyl)-1H-pyrazol-1-yl)isonicotinic acid

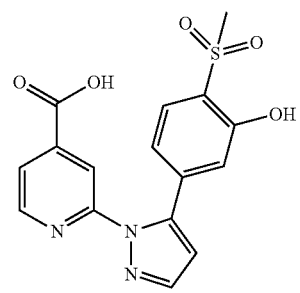 [SMILES: CS(=O)(=O)c1ccc(-c2ccnn2-c2cc(C(=O)O)ccn2)cc1O]

The title compound was prepared in 6% yield from 2-{5-[3-methoxy-4-(methylsulfonyl)phenyl]-1H-pyrazol-1-yl}pyridine-4-carboxylic acid according to the procedure for the preparation of Example 17, part D. $^1$H NMR (400 MHz, DMSO-d$_6$): δ 3.21 (3H, s), 6.78 (1H, d, J=1.6 Hz), 6.89-6.92 (2H, m), 7.65 (1H, d, J=8.0 Hz), 7.81-7.82 (1H, m), 7.90 (1H, d, J=2.0 Hz), 8.16 (1H, s), 8.48 (1H, d, J=4.8 Hz), 11.12 (1H, br). [M+H] Calc'd for $C_{16}H_{13}N_3O_5S$, 360. Found, 360.

Example 29

2-(3-methyl-5-p-tolyl-1H-pyrazol-1-yl)isonicotinic acid

A. (2E)-3-(dimethylamino)-1-(4-methylphenyl)but-2-en-1-one

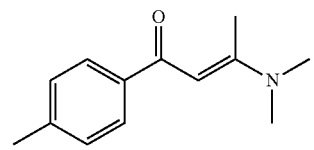

A solution of 1-(4-methylphenyl)ethanone (2.0 g, 15 mmol) in (1,1-dimethoxy-ethyl)-dimethyl-amine was heated to 120° C. and stirred overnight. The reaction mixture was cooled and concentrated to dryness. The residue was stirred with 25 mL hexane for 1 h and filtered. The solids were washed with hexane and then dried to give the title compound (1.8 g, 60%) as a yellow solid. $^1$H NMR (400 MHz, CDCl$_3$): δ 2.37 (3H, s), 2.65 (3H, s), 3.07 (6H, s), 5.68 (1H, s), 7.19 (2H, d, J=7.6 Hz), 7.77 (2H, d, J=8.0 Hz). [M+H] Calc'd for $C_{13}H_{17}NO$, 204. Found, 204.

B. 2-[3-methyl-5-(4-methylphenyl)-1H-pyrazol-1-yl]pyridine-4-carbonitrile

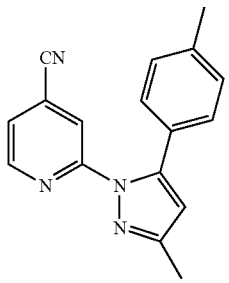 [SMILES: Cc1ccc(-c2cc(C)nn2-c2cc(C#N)ccn2)cc1]

To a solution of (2E)-3-(dimethylamino)-1-(4-methylphenyl)but-2-en-1-one (227 mg, 1.1 mmol) and 2-hydrazinylisonicotinonitrile (150 mg, 1.1 mmol, PREPARATION 2) in 10 mL EtOH was added 2 mL AcOH. The reaction mixture was heated under reflux conditions overnight before being cooled and concentrated to dryness. The residue was adjusted to pH>8 with saturated aq. $K_2CO_3$ and then extracted with EtOAc (3×10 mL). The combined organic layers were washed with 20 mL brine, dried, and concentrated to dryness to give the title compound (170 mg, 55.6%) as a yellow solid. $^1$H NMR (400 MHz, CDCl$_3$): δ 2.38 (6H, s), 6.30 (1H, s), 7.15 (4H, s), 7.33 (1H, d, J=4.0 Hz), 7.78 (1H, s), 8.44 (1H, d, J=4.8 Hz). [M+H] Calc'd for $C_{17}H_{14}N_4$, 275. Found, 275.

C. 2-(3-methyl-5-p-tolyl-1H-pyrazol-1-yl)isonicotinic acid

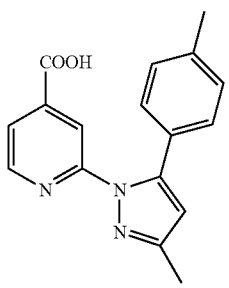 [SMILES: Cc1ccc(-c2cc(C)nn2-c2cc(C(=O)O)ccn2)cc1]

The title compound was prepared in 22% yield from 2-[3-methyl-5-(4-methylphenyl)-1H-pyrazol-1-yl]pyridine-4-carbonitrile according to the procedure for the preparation of Example 28, part E. $^1$H NMR (300 MHz, DMSO-d$_6$): δ 2.28 (3H, s), 2.30 (3H, s), 6.44 (1H, s), 7.15 (4H, s), 7.72 (1H, d, J=4.5 Hz), 8.06 (1H, s), 8.70 (1H, d, J=4.5 Hz). [M+H] Calc'd for $C_{17}H_{15}N_3O_2$, 294. Found, 294.

Example 30

2-(3-ethyl-5-p-tolyl-1H-pyrazol-1-yl)isonicotinic acid

A. 1-(4-methylphenyl)pentane-1,3-dione

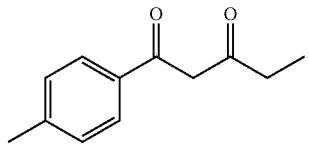

To a suspension of NaH (60%, 106 mg, 4.44 mmol) in 2 mL propionic acid ethyl ester was added 1-(4-methylphenyl)ethanone (500 mg, 3.7 mmol) at 0-5° C. The reaction mixture was stirred overnight at rt. Water was added, and the mixture was extracted with EtOAc (3×50 mL). The organic layers were washed with brine, dried over Na$_2$SO$_4$, and concentrated to dryness. The residue was purified by flash column chromatography (PE/EtOAc=10/1) to give the title compound (370 mg, 52%) as a yellow oil. $^1$H NMR (400 MHz, CDCl$_3$): δ 1.22 (3H, m), 2.45 (5H, m), 6.17 (2H, s), 7.27 (2H, d, J=10 Hz), 7.81 (2H, d, J=11.2 Hz). [M+H] Calc'd for $C_{12}H_{14}O_2$, 191. Found, 191.

B. 2-[3-ethyl-5-(4-methylphenyl)-1H-pyrazol-1-yl]pyridine-4-carbonitrile

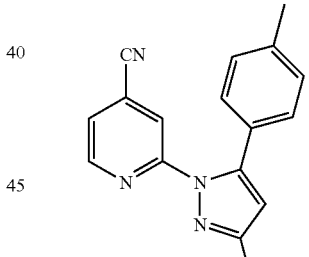

To a solution of 1-(4-methylphenyl)pentane-1,3-dione (370 mg, 1.9 mmol) and 2-hydrazinylisonicotinonitrile (150 mg, 1.1 mmol, PREPARATION 2) in 10 mL EtOH was added 2 mL AcOH. The reaction mixture was heated under reflux conditions overnight before being cooled and concentrated to dryness. The residue was adjusted to pH>8 with saturated aq. $K_2CO_3$, then extracted by EtOAc (10 mL×3). The combined organic layers were washed with 20 mL brine, dried over Na$_2$SO$_4$, concentrated, and purified by flash column chromatography (PE/EtOAc=10/1) to give the title compound (560 mg, 77%) as a yellow solid. $^1$H NMR (400 MHz, CDCl$_3$): δ 1.33 (3H, m), 2.38 (3H, s), 2.76 (2H, m), 6.33 (1H, s), 7.15 (4H, m), 7.31 (1H, m), 7.82 (1H, s), 8.42 (1H, m). [M+H] Calc'd for $C_{18}H_{16}N_4$, 289. Found, 289.

C. 2-(3-ethyl-5-p-tolyl-1H-pyrazol-1-yl)isonicotinic acid

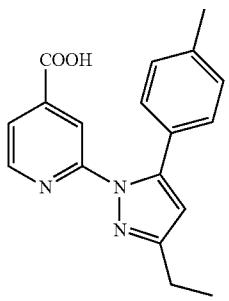 [SMILES: CCc1cc(-c2ccc(C)cc2)n(-c2cc(C(=O)O)ccn2)n1]

The title compound was prepared in 69% yield from 2-[3-ethyl-5-(4-methylphenyl)-1H-pyrazol-1-yl]pyridine-4-carbonitrile according to the procedure for the preparation of Example 28, part E. $^1$H NMR (400 MHz, DMSO-d$_6$): δ 1.26 (3H, m), 2.30 (3H, s), 2.66 (2H, m), 6.33 (1H, s), 7.12 (4H, m), 7.72 (1H, m), 8.07 (1H, s), 8.39 (1H, d, J=4.8 Hz), 13.88 (1H, s). [M+H] Calc'd for $C_{18}H_{17}N_3O_2$, 308. Found, 308.

Example 31

2-(5-methyl-1H-pyrazol-1-yl)isonicotinic acid

A. 2-(5-methyl-1H-pyrazol-1-yl)pyridine-4-carbonitrile (31-a1) and 2-(3-methyl-1H-pyrazol-1-yl)pyridine-4-carbonitrile (31-a2)

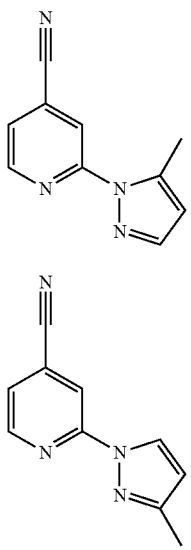

A mixture of 2-hydrazinylisonicotinonitrile (268 mg, 2 mmol, PREPARATION 2) and (3E)-4-(dimethylamino)but-3-en-2-one (339 mg, 3 mmol) in EtOH (5 mL) and AcOH (1 mL) was stirred at 90° C. overnight. The reaction mixture was cooled, concentrated, and purified by prep-HPLC to afford compound 31-a1 (90 mg) and compound 31-a2 (150 mg). 31-a1: $^1$H NMR (400 MHz, CDCl3): δ 2.38 (3H, s), 6.29 (1H, d, J=2.8 Hz), 7.32 (1H, dd J=5.2, 1.2 Hz), 8.18 (1H, s), 8.42 (1H, d, J=2.8 Hz), 8.52-8.53 (1H, m). [M+H] Calc'd for $C_{10}H_8N_4$, 185. Found, 185.

31-a2: $^1$H NMR (400 MHz, CDCl$_3$): δ 2.71 (3H, s), 6.22 (1H, d, J=0.8 Hz), 7.36 (1H, dd, J=4.8, 1.2 Hz), 7.61 (1H, d, J=1.2 Hz), 8.26 (1H, d, J=2.8 Hz), 8.57 (1H, dd, J=5.2, 0.8 Hz). [M+H] Calc'd for $C_{10}H_8N_4$, 185. Found, 185.

B. 2-(5-methyl-1H-pyrazol-1-yl)isonicotinic acid

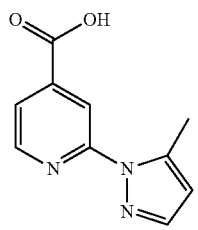

The title compound was prepared in 53% yield from 2-(5-methyl-1H-pyrazol-1-yl)pyridine-4-carbonitrile (31-a1) according to the procedure for the preparation of Example 28, part E. $^1$H NMR (400 MHz, DMSO-d$_6$): δ 2.31 (3H, s), 6.42 (1H, d, J=2.8 Hz), 7.70 (1H, dd J=5.2, 1.2 Hz), 8.25 (1H, s), 8.53 (1H, d, J=2.8 Hz), 8.61 (1H, d, J=5.2 Hz), 13.86 (1H, s). [M+H] Calc'd for $C_{10}H_9N_3O_2$, 204. Found, 204.

Example 32

2-(5-benzyl-1H-pyrazol-1-yl)isonicotinic acid

A. 1-phenylpropan-2-one

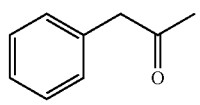

A solution of 1-phenylpropan-2-ol (2.72 g, 20 mmol) in CH$_2$Cl$_2$ (20 mL) was added pyridinium chlorochromate (PCC, 5.4 g, 25 mmol) at 0° C. and the mixture was stirred for 3 h. The mixture was concentrated and purified by flash column chromatography (PE/EtOAc=20:1) to give the title compound (2.3 g, 84%) as a yellow oil.

B. (3E)-4-hydroxy-1-phenylbut-3-en-2-one

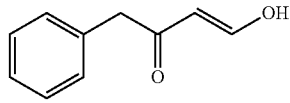 [SMILES: O=C(/C=C/O)Cc1ccccc1]

To a solution of 1-phenylpropan-2-one (1.78 g, 13 mmol) in anhydrous diethyl ether (50 ml) containing sodium cut in small pieces (299 mg, 13 mmol), ethyl formate (1.4 g, 20 mmol) was added slowly with stirring and ice-cooling. After standing overnight at rt, water was added, and the ether layer was washed with water. The organic phase was dried, concentrated, and purified by flash column chromatography (PE/EtOAc=10:1) to give the title compound (1.2 g, 57%) as a yellow oil.

C. (3E)-4-(dimethylamino)-1-phenylbut-3-en-2-one

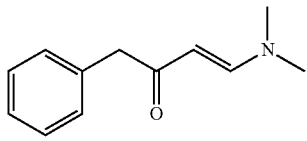

A solution of (3E)-4-hydroxy-1-phenylbut-3-en-2-one (1.2 g, 7.4 mmol) in THF (20 mL) was added dimethylamine hydrochloride (1.8 g, 22.2 mmol), $K_2CO_3$ (6.1 g, 44.4 mmol) and the mixture was stirred at rt overnight. The mixture was concentrated and purified by flash column chromatography (PE/EtOAc=10:1) to give the title compound (0.6 g, 43%) as a yellow oil. [M+H] Calc'd for $C_{12}H_{15}NO$, 190. Found, 190.

D. 2-(5-benzyl-1H-pyrazol-1-yl)pyridine-4-carbonitrile (32-d1) and 2-(3-benzyl-1H-pyrazol-1-yl)pyridine-4-carbonitrile (32-d2)

32-d1

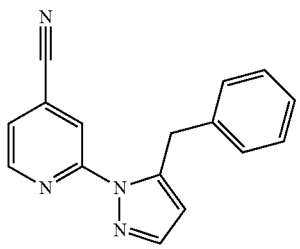

32-d2

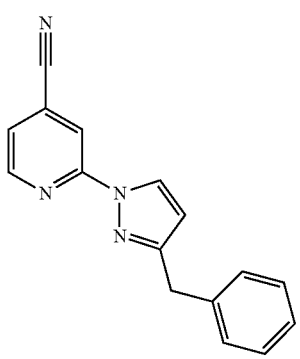

A mixture of 2-hydrazinylisonicotinonitrile (268 mg, 2 mmol, PREPARATION 2) and (3E)-4-(dimethylamino)-1-phenylbut-3-en-2-one (567 mg, 3 mmol) in EtOH (5 mL) and AcOH (1 mL) was stirred at 90° C. overnight. The reaction mixture was cooled, concentrated, and purified by prep-HPLC to afford compound 32-d1 (100 mg) and compound 32-d2 (110 mg).

32-d1: [M+H] Calc'd for $C_{16}H_{12}N_4$, 261. Found, 261.

32-d2: [M+H] Calc'd for $C_{16}H_{12}N_4$, 261. Found, 261.

E. 2-(5-benzyl-1H-pyrazol-1-yl)isonicotinic acid

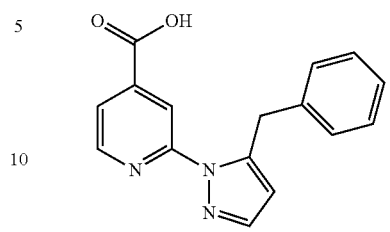

The title compound was prepared in 57% yield from 2-(5-benzyl-1H-pyrazol-1-yl)pyridine-4-carbonitrile (32-d1) according to the procedure for the preparation of Example 28, part E. $^1$H NMR (300 MHz, DMSO-$d_6$): δ 4.03 (2H, s), 6.40 (1H, d, J=2.4 Hz), 7.21-7.25 (1H, m), 7.27-7.32 (4H, m), 7.70 (1H, dd, J=4.8, 1.2 Hz), 8.27 (1H, s), 8.54 (1H, d, J=2.4 Hz), 8.60 (1H, d, J=5.4 Hz). [M+H] Calc'd for $C_{16}H_{13}N_3O_2$, 280. Found, 280.

Example 33

2-(3-benzyl-1H-pyrazol-1-yl)isonicotinic acid

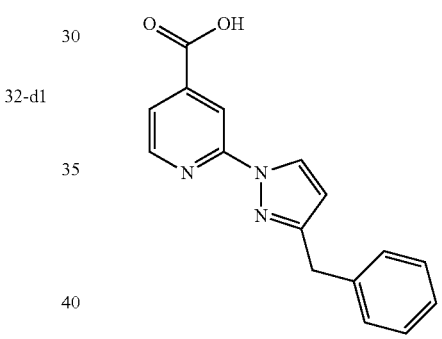

The title compound was prepared in 30% yield from 2-(3-benzyl-1H-pyrazol-1-yl)pyridine-4-carbonitrile (32-d2) according to the procedure for the preparation of Example 28, part E. $^1$H NMR (300 MHz, DMSO-$d_6$): δ 4.53 (2H, s), 6.19 (1H, s), 7.17-7.27 (5H, m), 7.69-7.72 (2H, m), 8.20 (1H, s), 8.60 (1H, d, J=4.8 Hz). [M+H] Calc'd for $C_{16}H_{13}N_3O_2$, 280. Found, 280.

Example 34

2-(5-phenethyl-1H-pyrazol-1-yl)isonicotinic acid

A. (1E)-1-(dimethylamino)-5-phenylpent-1-en-3-one

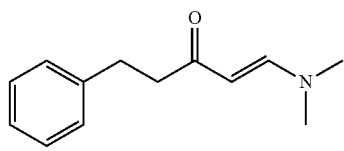

A solution of 4-phenylbutan-2-one (3.96 g, 20 mmol) and DMF-DMA (2.4 g, 20 mmol) in DMF (10 mL) was stirred at 100° C. overnight. The reaction mixture was cooled, concentrated, and purified by silica gel column (PE/EA=4: 1~2:1) to give the title compound (1.5 g, 37%) as a yellow oil.

B. 2-[5-(2-phenylethyl)-1H-pyrazol-1-yl]pyridine-4-carbonitrile (34-b1) and 2-[3-(2-phenylethyl)-1H-pyrazol-1-yl]pyridine-4-carbonitrile (34-b2)

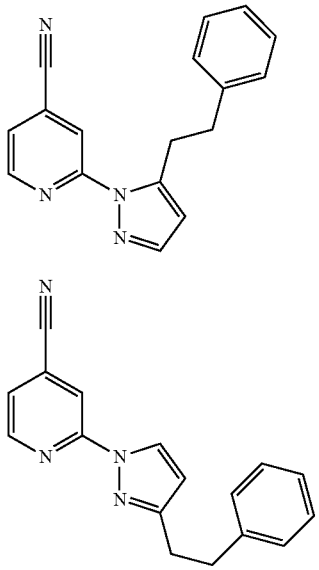

A mixture of 2-hydrazinylisonicotinonitrile (268 mg, 2 mmol, PREPARATION 2) and (1E)-1-(dimethylamino)-5-phenylpent-1-en-3-one (406 mg, 2 mmol) in EtOH (5 mL) and AcOH (1 mL) was stirred at 90° C. overnight. The reaction mixture was cooled, concentrated, and purified by prep-HPLC to afford compound 34-b1 (92 mg) and compound 34-b2 (180 mg).

34-b1: [M+H] Calc'd for $C_{17}H_{14}N_4$, 275. Found, 275.
34-b2: [M+H] Calc'd for $C_{17}H_{14}N_4$, 275. Found, 275.

C. 2-(5-phenethyl-1H-pyrazol-1-yl)isonicotinic acid

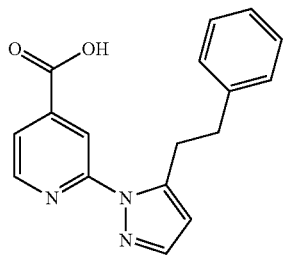 [SMILES: O=C(O)c1ccnc(-n2nccc2CCc2ccccc2)c1]

The title compound was prepared in 46% yield from 2-[5-(2-phenylethyl)-1H-pyrazol-1-yl]pyridine-4-carbonitrile (34-b1) according to the procedure for the preparation of Example 28, part E. $^1$H NMR (400 MHz, DMSO-$d_6$): δ 2.95-3.03 (4H, m), 6.46 (1H, d, J=2.4 Hz), 7.16-7.21 (1H, m), 7.26-7.29 (4H, m), 7.70 (1H, dd, J=4.2, 1.2 Hz), 8.26 (1H, s), 8.53 (1H, d, J=2.4 Hz), 8.61 (1H, d, J=5.2 Hz). [M+H] Calc'd for $C_{17}H_{15}N_3O_2$, 294. Found, 294.

Example 35

2-(3-phenethyl-1H-pyrazol-1-yl)isonicotinic acid

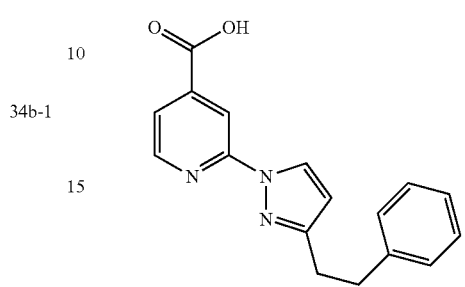

The title compound was prepared in 61% yield from 2-[3-(2-phenylethyl)-1H-pyrazol-1-yl]pyridine-4-carbonitrile (34-b2) according to the procedure for the preparation of Example 28, part E. $^1$H NMR (400 MHz, DMSO-$d_6$): δ 2.93 (2H, t, J=7.6 Hz), 3.41 (2H, t, J=7.6 Hz), 6.41 (1H, s), 7.15-7.29 (5H, m), 7.70 (1H, d, J=1.6 Hz), 7.75 (1H, dd, J=4.2, 1.6 Hz) 8.23 (s, 1H), 8.69 (1H, d, J=4.2 Hz), 13.86 (1H, br). [M+H] Calc'd for $C_{17}H_{15}N_3O_2$, 294. Found, 294.

Example 36

2-(5-methyl-4-phenyl-1H-pyrazol-1-yl)isonicotinic acid

A. (3E)-4-(dimethylamino)-3-phenylbut-3-en-2-one

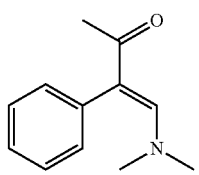

A solution of 1-phenylpropan-2-one (2.3 g, 20 mmol) and DMF-DMA (2.4 g, 20 mmol) in DMF (10 mL) was stirred at 100° C. overnight. The reaction mixture was cooled, concentrated, and purified by silica gel column (PE/EtOAc=4:1~2:1) to give the title compound (0.7 g, 18%) as a yellow oil.

B. 2-(5-methyl-4-phenyl-1H-pyrazol-1-yl)pyridine-4-carbonitrile

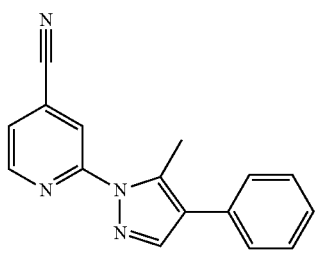 [SMILES: Cc1c(-c2ccccc2)cnn1-c1cc(C#N)ccn1]

The title compound was prepared in 34% yield from (3E)-4-(dimethylamino)-3-phenylbut-3-en-2-one and 2-hydrazinylisonicotinonitrile (PREPARATION 2) according to the procedure for the preparation of Example 28, part D. [M+H] Calc'd for $C_{16}H_{12}N_4$, 261. Found, 261.

C. 2-(5-methyl-4-phenyl-1H-pyrazol-1-yl)isonicotinic acid

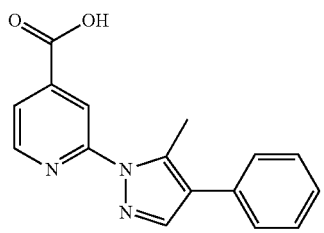 [SMILES: Cc1c(-c2ccccc2)cnn1-c1cc(C(=O)O)ccn1]

The title compound was prepared in 41% yield from 2-(5-methyl-4-phenyl-1H-pyrazol-1-yl)pyridine-4-carbonitrile according to the procedure for the preparation of Example 28, part E. $^1$H NMR (400 MHz, DMSO-$d_6$): δ 2.72 (3H, s), 7.32-7.36 (1H, m), 7.45-7.51 (4H, m), 7.79 (1H, dd, J=4.8, 1.2 Hz), 7.98 (1H, s), 8.29 (1H, s), 8.71 (1H, d, J=4.8 Hz), 13.90-13.91 (1H, broad). [M+H] Calc'd for $C_{16}H_{13}N_3O_2$, 280. Found, 280.

Example 37

2-(5-methoxy-3-methyl-1H-pyrazol-1-yl)isonicotinic acid

A. 2-(5-hydroxy-3-methyl-1H-pyrazol-1-yl)pyridine-4-carbonitrile

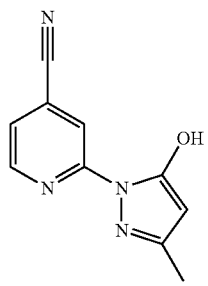

A mixture of 2-hydrazinylisonicotinonitrile (536 mg, 4 mmol, PREPARATION 2) and ethyl 3-oxobutanoate (780 mg, 6 mmol) in EtOH (10 mL) and AcOH (2 mL) was stirred at 90° C. overnight. The reaction mixture was cooled, concentrated, and purified by flash column chromatography (CH$_2$Cl$_2$) to afford the title compound (500 mg, 67%) as a yellow solid.

[M+H] Calc'd for $C_{10}H_8N_4O$, 201. Found, 201.

B. 2-(5-methoxy-3-methyl-1H-pyrazol-1-yl)pyridine-4-carbonitrile

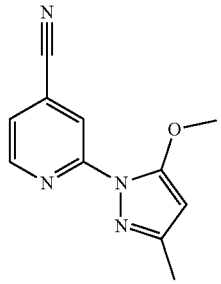 [SMILES: COc1cc(C)nn1-c1cc(C#N)ccn1]

To a solution of 2-(5-hydroxy-3-methyl-1H-pyrazol-1-yl)pyridine-4-carbonitrile (200 mg, 1 mmol) and K$_2$CO$_3$ (276 mg, 2 mmol) in DMF was added MeI (213 mg, 1.5 mmol) dropwise at −20° C. The mixture was warmed to 0° C. and stirred for 3 h. Water was added, and the reaction mixture was extracted with EtOAc, then washed with water and brine. The organic phase was dried, concentrated, and purified by prep-HPLC to afford the title compound (50 mg). [M+H] Calc'd for $C_{11}H_{10}N_4O$, 215. Found, 215.

C. 2-(5-methoxy-3-methyl-1H-pyrazol-1-yl)isonicotinic acid

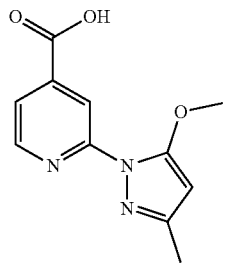 [SMILES: COc1cc(C)nn1-c1cc(C(=O)O)ccn1]

The title compound was prepared in 81% yield from 2-(5-methoxy-3-methyl-1H-pyrazol-1-yl)pyridine-4-carbonitrile according to the procedure for the preparation of Example 28, part E. $^1$H NMR (400 MHz, DMSO-$d_6$): δ 2.19 (3H, s), 4.33 (3H, s), 5.78 (1H, s), 7.69 (1H, d, J=4.4 Hz), 8.04 (1H, s), 8.63 (1H, d, J=5.2 Hz). [M+H] Calc'd for $C_{11}H_{11}N_3O_3$, 234. Found, 234.

Example 38

2-(5-(benzyloxy)-3-methyl-1H-pyrazol-1-yl)isonicotinic acid

A. 2-[5-(benzyloxy)-3-methyl-1H-pyrazol-1-yl]pyridine-4-carbonitrile

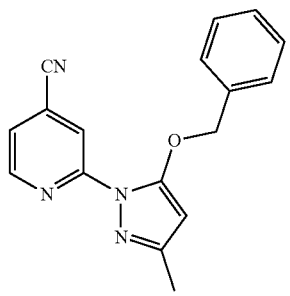 [SMILES: Cc1cc(OCc2ccccc2)n(-c2cc(C#N)ccn2)n1]

To a solution of 2-(5-hydroxy-3-methyl-1H-pyrazol-1-yl)pyridine-4-carbonitrile (300 mg, 1.5 mmol) and K₂CO₃ (518 mg, 3.75 mmol) in DMF was added benzyl bromide (308 mg, 1.8 mmol) dropwise at −20° C., then the mixture was warmed to 0° C. and stirred for 3 h. Water was added, and the reaction mixture was extracted with EtOAc, then washed with water and brine. The organic phase was dried, concentrated, and purified by prep-HPLC to afford the title compound (20 mg). [M+H] calc'd for C₁₇H₁₄N₄O, 291. Found, 291.

B. 2-(5-(benzyloxy)-3-methyl-1H-pyrazol-1-yl)isonicotinic acid

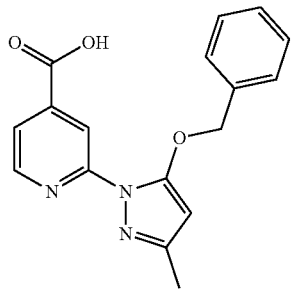 [SMILES: Cc1cc(OCc2ccccc2)n(-c2cc(C(=O)O)ccn2)n1]

The title compound was prepared in 29% yield from 2-[5-(benzyloxy)-3-methyl-1H-pyrazol-1-yl]pyridine-4-carbonitrile according to the procedure for the preparation of Example 28, part E. ¹H NMR (400 MHz, CD₃OD): δ 2.23 (3H, s), 5.26 (2H, s), 5.73 (1H, s), 7.30-7.38 (3H, s), 7.44-7.46 (2H, m), 7.74 (1H, d, J=4.8 Hz), 8.18 (1H, s), 8.49 (1H, d, J=4.4 Hz). [M+H] Calc'd for C₁₇H₁₅N₃O₃, 310. Found, 310.

Example 39

2-(5-(benzyloxy)-1H-pyrazol-1-yl)isonicotinic acid

A. ethyl (2E)-3-[2-(4-cyanopyridin-2-yl)hydrazinyl]prop-2-enoate

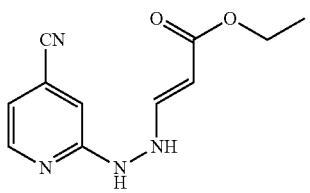 [SMILES: CCOC(=O)/C=C/NNc1cc(C#N)ccn1]

To a solution of 2-hydrazinylisonicotinonitrile (500 mg, 3.73 mmol, PREPARATION 2) and ethyl (2E)-3-(dimethylamino)prop-2-enoate (534 mg, 3.73 mmol) in 20 mL EtOH was added 4 mL AcOH, before the mixture was heated under reflux conditions overnight. The reaction mixture was cooled and concentrated to dryness. The residue was adjusted to pH>8 with sat'd. aq. NaHCO₃ and extracted with EtOAc. The combined organic layers were washed with brine, dried, and concentrated to dryness. The residue was purified by flash column chromatography (PE/EtOAc=5/1) to give the title compound (300 mg, 35%) as a yellow solid. [M+H] Calc'd for C₁₁H₁₂N₄O₂, 233. Found, 233.

B. 2-(5-hydroxy-1H-pyrazol-1-yl)pyridine-4-carbonitrile

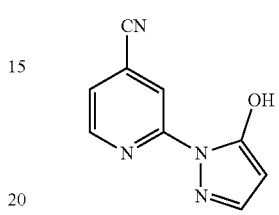

To a solution of ethyl (2E)-3-[2-(4-cyanopyridin-2-yl)hydrazinyl]prop-2-enoate (2.0 g, 8.62 mmol) in 30 mL EtOH was added t-BuOK (1.93 g, 17.24 mmol) at 0-5° C. The mixture was stirred for 3 days at rt. The mixture was adjusted to pH=6 with 1 N HCl with cooling. The mixture was extracted with EtOAc (3×100 mL). The organic layers were washed with 200 ml brine, dried over Na₂SO₄, and concentrated to dryness. The resultant residue was stirred with PE/EtOAc (10/10 mL) for 30 min and filtered to give the title compound (500 mg, 31%) as a red solid. ¹H NMR (400 MHz, CDCl₃): δ 4.63 (1H, s), 7.12 (1H, dd, J=4.8, 1.2 Hz), 7.16 (1H, s), 8.35 (1H, d, J=4.4 Hz), 8.43 (1H, s). [M+H] Calc'd for C₉H₆N₄O, 187. Found, 187.

C. 2-[5-(benzyloxy)-1H-pyrazol-1-yl]pyridine-4-carbonitrile

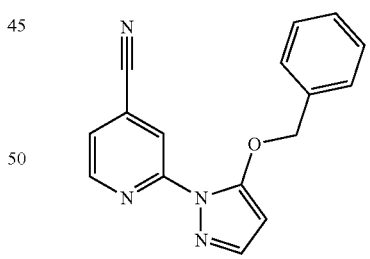

To a solution of 2-(5-hydroxy-1H-pyrazol-1-yl)pyridine-4-carbonitrile (186 mg, 1 mmol), phenylmethan-1-ol (216 mg, 2 mmol), and PPh₃ (523 mg, 2 mmol) in THF (10 mL) was added dropwise DIAD (402 mg, 2 mmoL) at 0° C. under N₂. Then the mixture was stirred at rt overnight. Water was added, and the reaction mixture was extracted with EtOAc, then washed with water and brine. The organic phase was dried, concentrated, and purified by prep-HPLC to afford the title compound (60 mg). ¹H NMR (400 MHz, CDCl₃): δ 5.25 (2H, s), 5.75 (1H, d, J=2.0 Hz), 7.36-7.44 (5H, m), 7.57 (1H, d, J=2.0 Hz), 8.04 (1H, s), 8.71 (1H, d, J=5.2 Hz). [M+H] Calc'd for C₁₆H₁₂N₄O, 277. Found, 277.

D. 2-(5-(benzyloxy)-1H-pyrazol-1-yl)isonicotinic acid

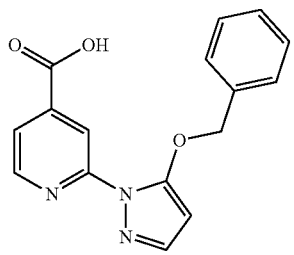 [SMILES: O=C(O)c1ccnc(-n2nccc2OCc2ccccc2)c1]

The title compound was prepared in 31% yield from 2-[5-(benzyloxy)-1H-pyrazol-1-yl]pyridine-4-carbonitrile according to the procedure for the preparation of Example 28, part E. $^1$H NMR (400 MHz, DMSO-$d_6$): δ 5.28 (2H, s), 5.92 (1H, br), 7.24-7.29 (3H, m), 7.30-7.32 (2H, m), 7.39-7.42 (1H, m), 7.56 (1H, br), 8.24 (1H, s), 8.60 (1H, s). [M+H] Calc'd for $C_{16}H_{13}N_3O_3$, 296. Found, 296.

Example 40

2-{5-[(4-fluorobenzyl)oxy]-1H-pyrazol-1-yl}pyridine-4-carboxylic acid

A. 2-{5-[(4-fluorobenzyl)oxy]-1H-pyrazol-1-yl}pyridine-4-carbonitrile

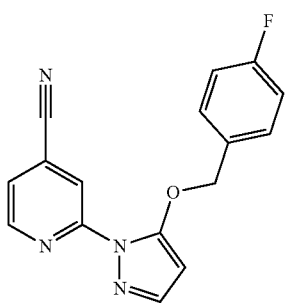 [SMILES: N#Cc1ccnc(-n2nccc2OCc2ccc(F)cc2)c1]

To a mixture of 2-(5-hydroxy-1H-pyrazol-1-yl)pyridine-4-carbonitrile (185 mg, 0.99 mmol), 4-fluorobenzyl alcohol (188 mg, 1.49 mol), PPh$_3$ (391 mg, 1.49 mmol) and THF (4 mL) cooled in an ice-water bath, TMAD (257 mg, 1.49 mmol) was added. The reaction mixture was stirred overnight at rt, filtered, and concentrated before purification by prep-HPLC to give the title compound (40 mg, 13%). $^1$H NMR (400 MHz, CDCl$_3$): δ 5.14 (2H, s), 5.68 (1H, s), 7.00-7.05 (2H, m), 7.33-7.36 (3H, m), 7.52 (1H, s), 7.96 (1H, s), 8.64 (1H, s). [M+H] Calc'd for $C_{16}H_{11}FN_4O$, 295. Found, 295.

B. 2-{5-[(4-fluorobenzyl)oxy]-1H-pyrazol-1-yl}pyridine-4-carboxylic acid

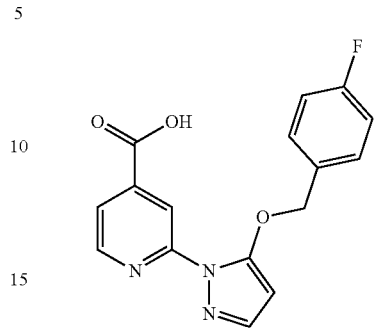

The title compound was prepared in 47% yield from 2-{5-[(4-fluorobenzyl)oxy]-1H-pyrazol-1-yl}pyridine-4-carbonitrile according to the procedure for the preparation of Example 28, part E. $^1$H NMR (400 MHz, DMSO-$d_6$): δ 5.27 (2H, s), 6.01 (1H, d, J=2.0 Hz), 7.19-7.24 (2H, m), 7.52-7.60 (3H, m), 7.76 (1H, d, J=4.8 Hz), 8.08 (1H, s), 8.68 (1H, d, J=4.8 Hz). [M+H] Calc'd for $C_{16}H_{12}FN_3O_3$, 313. Found, 313.

Example 41

2-{5-[(3-fluorobenzyl)oxy]-1H-pyrazol-1-yl}pyridine-4-carboxylic acid

A. 2-{5-[(3-fluorobenzyl)oxy]-1H-pyrazol-1-yl}pyridine-4-carbonitrile

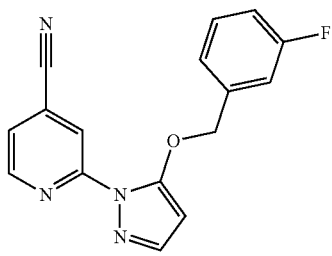 [SMILES: N#Cc1ccnc(-n2nccc2OCc2cccc(F)c2)c1]

The title compound was prepared in 27% yield from 2-(5-hydroxy-1H-pyrazol-1-yl)pyridine-4-carbonitrile and 3-fluorobenzyl alcohol according to the procedure for the preparation of Example 39, part C. $^1$H NMR (400 MHz, CDCl$_3$): δ 5.24 (2H, s), 5.73 (1H, d, J=2.0 Hz), 7.03-7.05 (1H, m), 7.07-7.21 (2H, m), 7.36-7.38 (1H, m), 7.40-7.42 (1H, m), 7.57 (1H, d, J=2.0 Hz), 8.04 (1H, s), 8.71 (1H, d, J=4.2 Hz). [M+H] Calc'd for $C_{16}H_{11}FN_4O$, 295. Found, 295.

B. 2-{5-[(3-fluorobenzyl)oxy]-1H-pyrazol-1-yl}pyridine-4-carboxylic acid

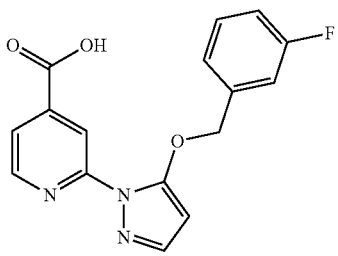 [SMILES: O=C(O)c1ccnc(-n2nccc2OCc2cccc(F)c2)c1]

The title compound was prepared in 50% yield from 2-{5-[(3-fluorobenzyl)oxy]-1H-pyrazol-1-yl}pyridine-4-carbonitrile according to the procedure for the preparation of Example 28, part E. $^1$H NMR (400 MHz, DMSO-$d_6$): δ 5.20 (2H, s), 5.86 (1H, s), 6.93-6.98 (1H, m), 7.13-7.19 (2H, m), 7.26-7.31 (1H, m), 7.49 (1H, d, J=1.2 Hz), 7.75 (1H, d, J=4.8 Hz), 8.18 (1H, s), 8.56 (1H, d, J=4.8 Hz). [M+H] Calc'd for $C_{16}H_{12}FN_3O_3$, 313. Found, 313.

Example 42

2-{5-[(3-methoxybenzyl)oxy]-1H-pyrazol-1-yl}pyridine-4-carboxylic acid

A. 2-{5-[(3-methoxybenzyl)oxy]-1H-pyrazol-1-yl}pyridine-4-carbonitrile

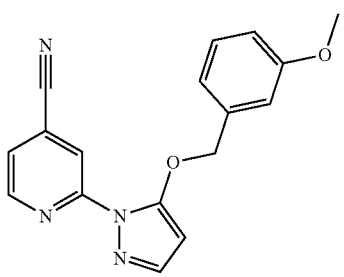 [SMILES: COc1cccc(COc2ccnn2-c2cc(C#N)ccn2)c1]

The title compound was prepared in 13% yield from 2-(5-hydroxy-1H-pyrazol-1-yl)pyridine-4-carbonitrile and 3-methoxybenzyl alcohol according to the procedure for the preparation of Example 39, part C. [M+H] Calc'd for $C_{17}H_{14}N_4O_2$, 307. Found, 307.

B. 2-{5-[(3-methoxybenzyl)oxy]-1H-pyrazol-1-yl}pyridine-4-carboxylic acid

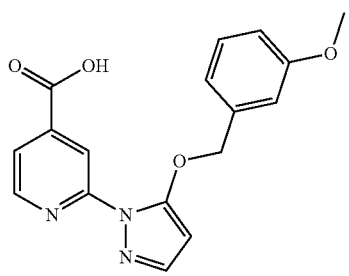 [SMILES: COc1cccc(COc2ccnn2-c2cc(C(=O)O)ccn2)c1]

The title compound was prepared in 22% yield from 2-{5-[(3-methoxybenzyl)oxy]-1H-pyrazol-1-yl}pyridine-4-carbonitrile according to the procedure for the preparation of Example 28, part E. $^1$H NMR (400 MHz, DMSO-$d_6$): δ 3.75 (3H, s), 5.26 (2H, s), 6.01 (1H, d, J=2.0 Hz), 6.85-6.87 (1H, m), 7.04-7.07 (2H, m), 7.27-7.29 (1H, m), 7.60 (1H, d, J=2.0 Hz), 7.77 (1H, d, J=4.8 Hz), 8.09 (1H, s), 8.70 (1H, d, J=5.2 Hz). [M+H] Calc'd for $C_{17}H_{15}N_3O_4$, 326. Found, 326.

Example 43

2-{5-[(4-methoxybenzyl)oxy]-1H-pyrazol-1-yl}pyridine-4-carboxylic acid

A. 2-{5-[(4-methoxybenzyl)oxy]-1H-pyrazol-1-yl}pyridine-4-carbonitrile

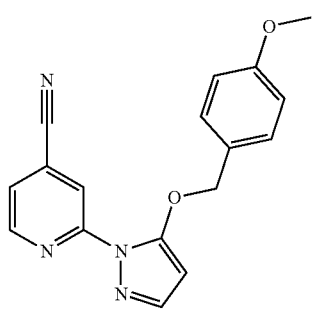 [SMILES: COc1ccc(COc2ccnn2-c2cc(C#N)ccn2)cc1]

The title compound was prepared in 14% yield from 2-(5-hydroxy-1H-pyrazol-1-yl)pyridine-4-carbonitrile and 4-methoxybenzyl alcohol according to the procedure for the preparation of Example 39, part C. $^1$H NMR (400 MHz, CDCl$_3$): δ 3.81 (3H, s), 5.17 (2H, s), 5.75 (1H, d, J=2.0 Hz), 6.91-6.93 (2H, m), 7.34-7.39 (3H, m), 7.57 (1H, d, J=2.0 Hz), 8.01 (1H, s), 8.69 (1H, d, J=4.8 Hz). [M+H] Calc'd for $C_{17}H_{14}N_4O_2$, 307. Found, 307.

B. 2-{5-[(4-methoxybenzyl)oxy]-1H-pyrazol-1-yl}pyridine-4-carboxylic acid

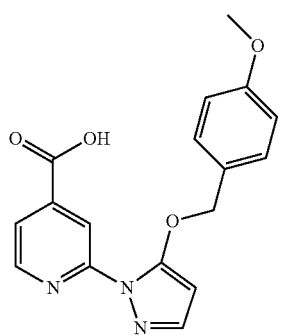 [SMILES: COc1ccc(COc2ccnn2-c2cc(C(=O)O)ccn2)cc1]

The title compound was prepared in 62% yield from 2-{5-[(4-methoxybenzyl)oxy]-1H-pyrazol-1-yl}pyridine-4-carbonitrile according to the procedure for the preparation of Example 28, part E. $^1$H NMR (400 MHz, CD$_3$OD): δ 3.82 (3H, s), 5.24 (2H, s), 5.99 (1H, d, J=2.0 Hz), 6.93-6.95 (2H, m), 7.41-7.43 (2H, m), 7.61 (1H, d, J=2.0 Hz), 7.86 (1H, d, J=5.2 Hz), 8.28 (1H, s), 8.67 (1H, d, J=4.8 Hz). [M+H] Calc'd for $C_{17}H_{15}N_3O_4$, 326. Found, 326.

Example 44

2-(5-butyl-1H-pyrazol-1-yl)pyridine-4-carboxylic acid

A. (1E)-1-(dimethylamino)hept-1-en-3-one

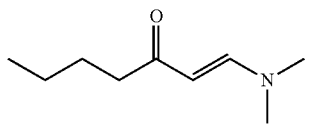

A solution of 2-hexanone (2.0 g, 20 mmol) and DMF-DMA (2.4 g, 20 mmol) in DMF (10 mL) was stirred at 100° C. overnight. The reaction mixture was cooled, concentrated, and purified by flash column chromatography (PE/EtOAc=4:1~2:1) to give the title compound (0.6 g, 19%) as yellow oil.

B. 2-(5-butyl-1H-pyrazol-1-yl)pyridine-4-carbonitrile (44-b1) and 2-(3-butyl-1H-pyrazol-1-yl)pyridine-4-carbonitrile (44-b2)

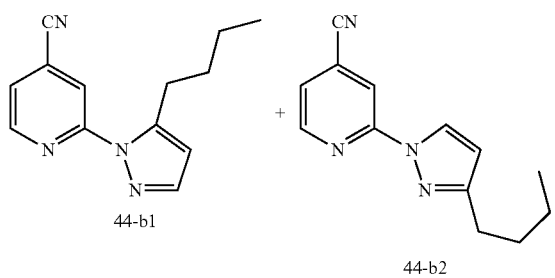 [SMILES: CCCCc1ccnn1-c1cc(C#N)ccn1 ; CCCCc1ccn(-c2cc(C#N)ccn2)n1]

A mixture of 2-hydrazinylisonicotinonitrile (268 mg, 2 mmol, PREPARATION 2) and (1E)-1-(dimethylamino)hept-1-en-3-one (310 mg, 2 mmol) in EtOH (5 mL) and AcOH (1 mL) was stirred at 90° C. overnight. The reaction mixture was cooled, concentrated, and purified by prep-HPLC to afford compound 44-b1 (60 mg) and compound 44-b2 (100 mg).

44-b1: [M+H] Calc'd for $C_{13}H_{14}N_4$, 227. Found, 227.
44-b2: [M+H] Calc'd for $C_{13}H_{14}N_4$, 227. Found, 227.

C. 2-(5-butyl-1H-pyrazol-1-yl)pyridine-4-carboxylic acid

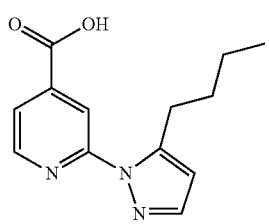 [SMILES: CCCCc1ccnn1-c1cc(C(=O)O)ccn1]

The title compound was prepared in 34% yield from 2-(5-butyl-1H-pyrazol-1-yl)pyridine-4-carbonitrile (44-b1) according to the procedure for the preparation of Example 28, part E. $^1$H NMR (400 MHz, DMSO-$d_6$): δ 0.92 (3H, t, J=7.6 Hz), 1.34-1.40 (2H, m), 1.61-1.67 (2H, m), 2.66 (2H, t, J=7.6 Hz), 6.45 (1H, d, J=2.4 Hz), 7.69-7.71 (1H, m), 8.25 (1H, s), 8.52 (1H, d, J=2.8 Hz), 8.61 (1H, d, J=5.2 Hz). [M+H] Calc'd for $C_{13}H_{15}N_3O_2$, 246. Found, 246.

Example 45

2-(3-butyl-1H-pyrazol-1-yl)pyridine-4-carboxylic acid

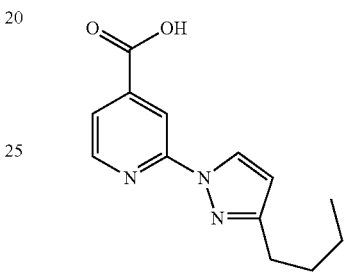

The title compound was prepared in 55% yield from 2-(3-butyl-1H-pyrazol-1-yl)pyridine-4-carbonitrile (44-b2) according to the procedure for the preparation of Example 28, part E. $^1$H NMR (400 MHz, DMSO-$d_6$): δ 0.89 (3H, t, J=7.6 Hz), 1.32-1.38 (2H, m), 1.57-1.61 (2H, m), 3.11 (2H, t, J=7.6 Hz), 6.36 (1H, d, J=0.8 Hz), 7.68 (1H, d, J=1.6 Hz), 7.74-7.76 (1H, m), 8.25 (1H, s), 8.66 (1H, d, J=5.2 Hz). [M+H] Calc'd for $C_{13}H_{15}N_3O_2$, 246. Found, 246.

Example 46

2-[5-(4-bromophenyl)-1H-pyrazol-1-yl]pyridine-4-carboxylic acid

A. (2E)-1-(4-bromophenyl)-3-(dimethylamino)prop-2-en-1-one

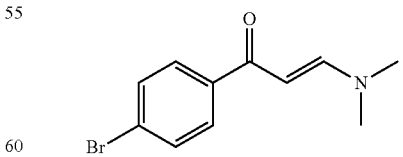

A solution of 1-(4-bromophenyl)ethanone (2.0 g, 10 mmol) in DMF-DMA (25 mL) was stirred at 100° C. for 16 h. The solution was concentrated and purified by flash column chromatography (hexanes:EtOAc=4:1~2:1) to give the title compound (1.57 g, 61%) as an orange-brown solid.

B. 2-[5-(4-bromophenyl)-1H-pyrazol-1-yl]pyridine-4-carbonitrile

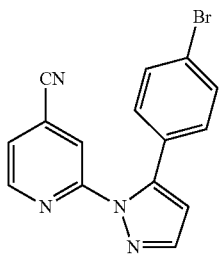 [SMILES: N#Cc1ccnc(-n2nccc2-c2ccc(Br)cc2)c1]

A solution of (2E)-1-(4-bromophenyl)-3-(dimethylamino)prop-2-en-1-one (100 mg, 0.39 mmol) and 2-hydrazinylpyridine-4-carbonitrile hydrochloride salt (90 mg, 0.43 mmol, PREPARATION 3) in MeOH (10 mL) was heated under reflux conditions for 30 min and then cooled to rt. The solution was concentrated, and the residue was purified by flash column chromatography (hexanes:EtOAc=1:1) to give the title compound (108 mg, 85%) as an orange-yellow solid.

C. 2-[5-(4-bromophenyl)-1H-pyrazol-1-yl]pyridine-4-carboxylic acid

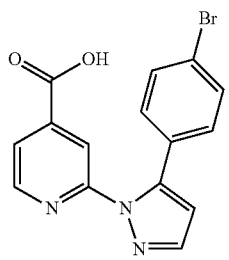 [SMILES: O=C(O)c1ccnc(-n2nccc2-c2ccc(Br)cc2)c1]

To a solution of 2-[5-(4-bromophenyl)-1H-pyrazol-1-yl]pyridine-4-carbonitrile (100 mg, 0.31 mmol) in MeOH (4 mL) was added 10 N NaOH (4 mL), and the solution was heated under reflux conditions for 1 h. The solution was then cooled to 0° C. and the pH was adjusted to pH=2 by dropwise addition of 12 N HCl. The resulting precipitate was filtered to give the title compound (92 mg, 87%) as an off-white solid. $^1$H NMR (400 MHz, CD$_3$OD): δ 6.64 (1H, s), 7.16 (2H, d, J=8.8 Hz), 7.48 (2H, d, J=8.8 Hz), 7.79 (1H, s), 7.84 (1H, d, J=8.4 Hz), 8.13 (1H, s), 8.42 (1H, d, J=8.4 Hz). [M+H] Calc'd for C$_{15}$H$_{10}$BrN$_3$O$_2$, 344. Found, 344.

Example 47

2-{5-[4-(dimethylamino)phenyl]-1H-pyrazol-1-yl}pyridine-4-carboxylic acid

A. (2E)-3-(dimethylamino)-1-[4-(dimethylamino)phenyl]prop-2-en-1-one

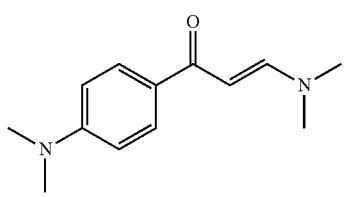

A solution of 1-[4-(dimethylamino)phenyl]ethanone (500 mg, 3.1 mmol) in DMF-DMA (10 mL), toluene (10 mL), and AcOH (2 drops), was heated under reflux conditions for 48 h. The solution was concentrated and purified by flash column chromatography (hexanes:EtOAc=8:2~1:1) to give the title compound (121 mg, 18%) as a yellow solid.

B. 2-{5-[4-(dimethylamino)phenyl]-1H-pyrazol-1-yl}pyridine-4-carbonitrile

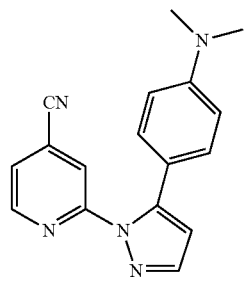 [SMILES: CN(C)c1ccc(-c2ccnn2-c2cc(C#N)ccn2)cc1]

The title compound was prepared in 69% yield from 2-hydrazinylpyridine-4-carbonitrile hydrochloride salt (PREPARATION 3) and (2E)-3-(dimethylamino)-1-[4-(dimethylamino)phenyl]prop-2-en-1-one according to the procedure for the preparation of Example 46, part B.

C. 2-{5-[4-(dimethylamino)phenyl]-1H-pyrazol-1-yl}pyridine-4-carboxylic acid

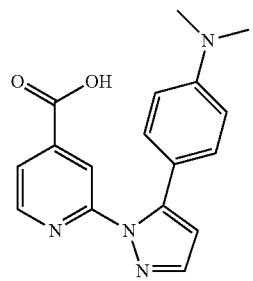 [SMILES: CN(C)c1ccc(-c2ccnn2-c2cc(C(=O)O)ccn2)cc1]

The title compound was prepared in 47% yield from 2-{5-[4-(dimethylamino)phenyl]-1H-pyrazol-1-yl}pyridine-4-carbonitrile according to the procedure for the preparation of Example 46, part B. $^1$H NMR (400 MHz, DMSO-d$_6$): δ 2.88 (6H, s), 6.53 (1H, s), 6.63 (2H, d, J=16 Hz), 7.06 (2H, d, J=16 Hz), 7.73 (1H, s), 7.77 (1H, d, J=8 Hz), 8.00 (1H, s), 8.48 (1H, d, J=8 Hz). [M+H] Calc'd for C$_{17}$H$_{16}$N$_4$O$_2$, 309. Found, 309.

Example 48

2-[3-amino-5-(4-methylphenyl)-1H-pyrazol-1-yl]pyridine-4-carboxylic acid

A. methyl 4-(4-methylphenyl)-2,4-dioxobutanoate

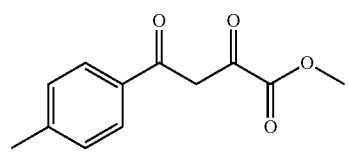

Sodium (1.0 g, 43 mmol) was dissolved in MeOH (50 mL) and then evaporated to a dry white powder. To the powder was added MTBE (100 mL) and diethyloxalate (5.14 g, 35.2 mmol). To the resulting solution was added a solution of 1-(4-methylphenyl)ethanone (5.0 g, 37.3 mmol) in MTBE (50 mL) dropwise over 45 min. The resulting suspension was allowed to stir for 1 h, and the precipitate was filtered and washed with MTBE/hexanes (1:1, 50 mL). The solid was suspended in 1 N HCl (100 mL) and extracted with EtOAc (2×100 mL). The combined extracts were dried (MgSO$_4$), filtered, and concentrated to an oily residue which crystallized on standing at rt. The yellow solid was triturated with MTBE/hexanes (1:1) and filtered to give the title compound (3.76 g, 46%) as a white solid.

B. methyl 1-(4-cyanopyridin-2-yl)-5-(4-methylphenyl)-1H-pyrazole-3-carboxylate

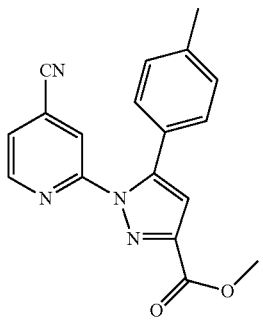 [SMILES: COC(=O)c1cc(-c2ccc(C)cc2)n(-c2cc(C#N)ccn2)n1]

A solution of methyl 4-(4-methylphenyl)-2,4-dioxobutanoate (500 mg, 22.7 mmol) and 2-hydrazinylpyridine-4-carbonitrile hydrochloride salt (500 mg, 24.2 mmol, PREPARATION 3) in AcOH (10 mL) was heated at 100° C. for 30 min and cooled to rt. The solution was concentrated to an oily residue which was partitioned between EtOAc (50 mL) and water (50 mL). The pH was adjusted to pH=8 using a saturated aq. Na$_2$CO$_3$ solution. The organics were dried (MgSO$_4$), filtered, and concentrated to give a solid which was triturated with MTBE/hexanes (1:1) and filtered to give the title compound (613 mg, 85%) as a yellow solid. $^1$H NMR (400 MHz, CD$_3$OD): δ 2.48 (3H, s), 3.92 (3H, s), 7.01 (1H, s), 7.08-7.21 (4H, m), 7.71 (1H, d, J=4.8 Hz), 8.12 (1H, s), 8.48 (1H, d, J=4.8 Hz), 8.00 (1H, s), 8.48 (1H, d, J=8 Hz).

C. 1-(4-cyanopyridin-2-yl)-5-(4-methylphenyl)-1H-pyrazole-3-carboxylic acid

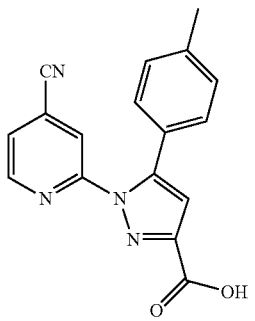 [SMILES: Cc1ccc(-c2cc(C(=O)O)nn2-c2cc(C#N)ccn2)cc1]

A solution of methyl 1-(4-cyanopyridin-2-yl)-5-(4-methylphenyl)-1H-pyrazole-3-carboxylate (500 mg, 1.57 mmol) in DMF/THF (1:1, 15 mL) was heated to 65° C. and NaOH (628 mg, 15.7 mmol) in water (1 mL) was added. The resulting solution was stirred at 65° C. and monitored by TLC. The reaction was cooled to rt at the point where a second more polar eluting product (relative to the product spot) began to form. The pH of the solution was adjusted to pH=4 with 6 N HCl, and the reaction mixture was extracted with EtOAc (2×50 mL). The organic layers were combined, washed with water (2×50 mL), dried (MgSO$_4$), filtered, concentrated, and purified by flash column chromatography (EtOAc:hexanes=40:60) to give the title compound (196 mg, 41%).

D. tert-Butyl[1-(4-cyanopyridin-2-yl)-5-(4-methylphenyl)-1H-pyrazol-3-yl]carbamate

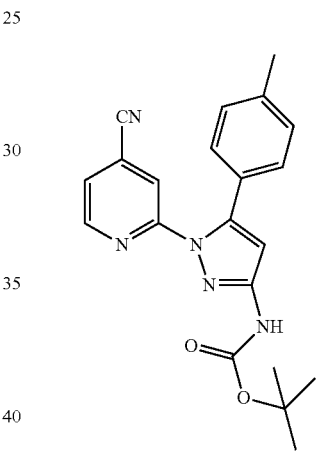

To a solution of 1-(4-cyanopyridin-2-yl)-5-(4-methylphenyl)-1H-pyrazole-3-carboxylic acid (190 mg, 0.63 mmol) in THF (5 mL) at 0° C. was added isobutyl chloroformate (93.8 mg, 0.69 mmol) followed by dropwise addition of a solution of TEA (76.4 mg, 0.76 mmol) in THF (0.5 mL). The resulting suspension was allowed to stir at rt for 1 h before NaN$_3$ (203 mg, 3.12 mmol) in water (1 mL) was added. The solution was stirred an additional hour. The solution was diluted with water (20 mL) and extracted with EtOAc (2×20 mL). The organic layers were dried (MgSO$_4$), filtered, and concentrated, and the residue dissolved in tert-butyl alcohol (20 mL). The solution was heated at 75° C. for 4 h until TLC indicated the rearrangement reaction to be complete. The solution was diluted with water (10 mL) and extracted with EtOAc (2×20 mL). The organic layers were dried (MgSO$_4$), filtered, concentrated, and purified by flash column chromatography (EtOAc/hexanes=30:70) to give the title compound (152 mg, 65%) as a white solid.

E. 2-[3-amino-5-(4-methylphenyl)-1H-pyrazol-1-yl]pyridine-4-carboxylic acid

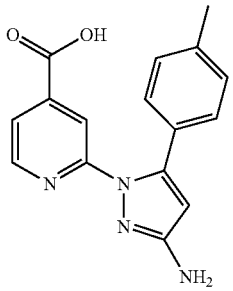 [SMILES: Cc1ccc(-c2cc(N)nn2-c2cc(C(=O)O)ccn2)cc1]

A solution of tert-butyl [1-(4-cyanopyridin-2-yl)-5-(4-methylphenyl)-1H-pyrazol-3-yl]carbamate (150 mg, 0.4 mmol) in TFA (2 mL) was heated to 50° C. for 30 min and evaporated to an oily residue. To the residue was added 10 N NaOH (2 mL) followed by MeOH (2 mL). The solution was stirred at 70° C. for 4 h and then cooled to rt. Solvent was evaporated, and the pH of the resulting aqueous phase was carefully adjusted to pH=5.5 using conc. HCl and then 1 N HCl. The resulting mixture was extracted with EtOAc (2×20 mL). The organic layers were dried (MgSO$_4$), filtered, concentrated to an oil, and purified by flash column chromatography (MeOH/EtOAc=5:95) to give the title compound (56 mg, 48%) as a beige solid. $^1$H NMR (400 MHz, DMSO-d$_6$): δ 2.28 (3H, s), 5.73 (1H, s), 5.82 (1H, s), 7.05-7.18 (4H, m), 7.51 (1H, d, J=5.2 Hz), 8.02 (1H, s), 8.22 (1H, d, J=5.2 Hz). [M+H] Calc'd for C$_{16}$H$_{14}$N$_4$O$_2$, 295. Found, 295.

Example 49

2-[5-(1H-indazol-6-ylmethoxy)-1H-pyrazol-1-yl]pyridine-4-carboxylic acid

A. 1-tert-Butyl, 6-methyl 1H-indazole-1,6-dicarboxylate

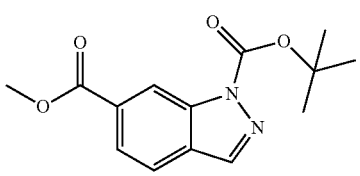 [SMILES: COC(=O)c1ccc2cnn(C(=O)OC(C)(C)C)c2c1]

To an ice-cooled solution of methyl 1H-indazole-6-carboxylate (502 mg, 2.84 mmol), DMAP (69 mg, 0.57 mmol) and Et$_3$N (431 mg, 4.26 mmol) in THF (10 mL) was added Boc$_2$O (743 mg, 3.41 mmol) slowly. The reaction mixture was stirred overnight at room temperature. It was then concentrated, the residue was extracted with ethyl acetate, collected the organic phase, concentrated for gel chromatograph to provide 797 mg of the title compound (100%). $^1$H NMR (400 MHz, CDCl$_3$): δ 1.74 (9H, s), 3.97 (3H, s), 7.77 (1H, dd, J=0.4 Hz, J=8.4 Hz), 7.95 (1H, dd, J=1.2 Hz, J=8.4 Hz), 8.21 (1H, d, J=0.8 Hz), 8.90 (1H, s). [M+H] Calc'd for C$_{14}$H$_{16}$N$_2$O$_4$, 277, 221, 177. Found, 221.

B. tert-butyl 6-(hydroxymethyl)-1H-indazole-1-carboxylate

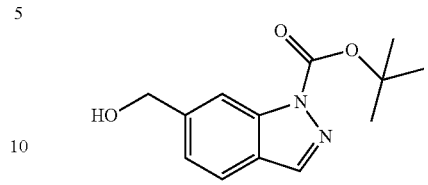

A solution of 1-tert-butyl 6-methyl 1H-indazole-1,6-dicarboxylate (766 mg, 2.76 mmol) in anhydrous THF (11 mL) was cooled to −30° C., LiAlH$_4$ (210 mg, 5.53 mmol) was added in portions below −30° C., and the mixture was stirred at this temperature for 1.5 h, added water:10% NaOH:water=0.8 mL:2.4 mL:0.8 mL carefully, filtered, and the filtrate was concentrated and purified by silica gel chromatograph to afford 100 mg of the title compound (14%). $^1$H NMR (400 MHz, CDCl$_3$): δ 1.72 (9H, s), 4.86 (2H, s), 7.33 (1H, d, J=8.0 Hz), 7.69 (1H, d, J=8.4 Hz), 8.13 (1H, s), 8.21 (1H, s). [M+H] Calc'd for C$_{13}$H$_{16}$N$_2$O$_3$, 249. Found, 249.

C. tert-butyl 5-((1-(4-cyanopyridin-2-yl)-1H-pyrazol-5-yloxy)methyl)-1H-indazole-1-carboxylate

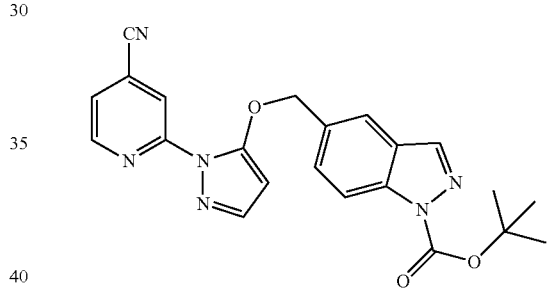

The title compound was prepared in 17% yield from 2-(5-hydroxy-1H-pyrazol-1-yl)pyridine-4-carbonitrile and tert-butyl 6-(hydroxymethyl)-1H-indazole-1-carboxylate according to the procedure for the preparation of Example 39, part C. $^1$H NMR (400 MHz, CDCl3): δ 1.71 (9H, s), 5.41 (2H, s), 5.78 (1H, d, J=1.6 Hz), 7.37-7.42 (2H, m), 7.57 (1H, d, J=1.6 Hz), 7.76 (1H, d, J=8.0 Hz), 8.07 (1H, s), 8.17 (1H, s), 8.41 (1H, s), 8.78 (1H, d, J=8.4 Hz). [M+H] Calc'd for C$_{22}$H$_{20}$N$_6$O$_3$, 417. Found, 417.

D. 2-[5-(1H-indazol-6-ylmethoxy)-1H-pyrazol-1-yl]pyridine-4-carboxylic acid

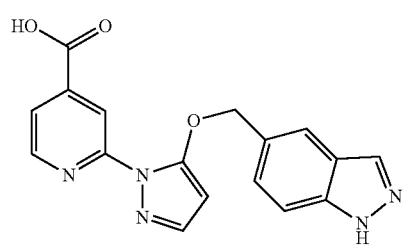 [SMILES: O=C(O)c1ccnc(-n2nccc2OCc2ccc3[nH]ncc3c2)c1]

To a solution of tert-butyl 5-((1-(4-cyanopyridin-2-yl)-1H-pyrazol-5-yloxy)methyl)-1H-indazole-1-carboxylate (65 mg, 0.15 mmol) in ethyl acetate (2 mL) was added HCl in EtOAc (5 mL) and the mixture was stirred for 2 h. Solvent was removed and the residue was dissolved with ethanol (2 mL), NaOH (2.5 mL, 5M) was added, the mixture was then stirred for 6 h at 90° C. Cooled to 0° C., and the solution was acidified with HCl (2N) (pH=4), filtered, the solid was purified by HPLC to afford 8 mg of the title compound (15%). $^1$H NMR (400 MHz, CD$_3$OD): δ 3.86 (2H, s), 4.91 (1H, s), 7.15 (1H, d, J=8.0 Hz), 7.45 (1H, s), 7.55 (1H, s), 7.71 (1H, d, J=8.0 Hz), 7.78 (1H, d, J=4.8 Hz), 7.99 (1H, s), 8.59 (1H, d, J=4.8 Hz), 8.83 (1H, s). [M+H] Calc'd for C$_{17}$H$_{13}$N$_5$O$_3$, 336. Found, 336.

Preparation 4: Methyl 1-methyl-1H-indazole-6-carboxylate and methyl 2-methyl-2H-indazole-6-carboxylate

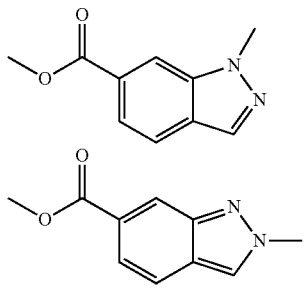

To an ice-cooled solution of methyl 1H-indazole-6-carboxylate (566 mg, 3.21 mmol) was added NaH (154 mg, 3.85 mmol), the mixture was then stirred at room temperature for 30 min. Methyl iodide (547 mg, 3.85 mmol) was added drop wise, and the reaction mixture was stirred overnight. Cooled to 0° C., added water and extracted with ethyl acetate. The organic phase was concentrated and purified by gel chromatograph to provide 130 mg of methyl 1-methyl-1H-indazole-6-carboxylate and 230 mg of methyl 2-methyl-2H-indazole-6-carboxylate, 59%. $^1$H NMR for methyl 1-methyl-1H-indazole-6-carboxylate: $^1$H NMR (400 MHz, CDCl$_3$): δ 3.97 (3H, s), 4.14 (3H, s), 7.74-7.82 (2H, m), 8.02 (1H, s), 8.17 (1H, d, J=0.8 Hz). $^1$H NMR for methyl 2-methyl-2H-indazole-6-carboxylate: $^1$H NMR (400 MHz, CDCl3): δ 3.94 (3H, s), 4.25 (3H, s), 7.65-7.72 (2H, m), 7.92 (1H, s), 8.47 (1H, d, J=1.2 Hz). [M+H] Calc'd for C$_{10}$H$_{10}$N$_2$O$_2$, 191. Found, 191.

Example 50

2-{5-[(1-methyl-1H-indazol-6-yl)methoxy]-1H-pyrazol-1-yl}pyridine-4-carboxylic acid A. (1-methyl-1H-indazol-6-yl)methanol

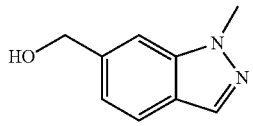

A solution of methyl 1-methyl-1H-indazole-6-carboxylate (230 mg, 1.21 mmol, PREPARATION 4) in anhydrous THF (4 mL) was cooled to 0° C., LiAlH$_4$ (92 mg, 2.42 mmol) was added in portions below 0° C., and the mixture was then stirred at 0° C. for 1.5 h, added water:10% NaOH:water=0.2 mL:0.2 mL:0.6 mL carefully, filtered, and the filtrate was concentrated and purified by silica gel flash column to give 192 mg of crude product which was used directly for next step (98%). [M+H] Calc'd for C$_9$H$_{10}$N$_2$O, 163. Found, 163.

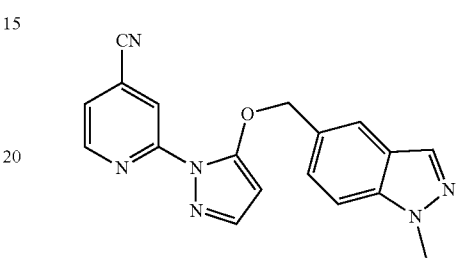

B. 2-{5-[(1-methyl-1H-indazol-6-yl)methoxy]-1H-pyrazol-1-yl}pyridine-4-carbonitrile The title compound was prepared in 11% yield from 2-(5-hydroxy-1H-pyrazol-1-yl)pyridine-4-carbonitrile and (1-methyl-1H-indazol-6-yl)methanol according to the procedure for the preparation of Example 39, part C. $^1$H NMR (400 MHz, CDCl$_3$): δ 4.09 (3H, s), 5.40 (2H, s), 5.78 (1H, d, J=1.6 Hz), 7.19-7.17 (1H, m), 7.40 (1H, dd, J=1.2 Hz, J=5.2 Hz), 7.51 (1H, s), 7.58 (1H, d, J=2.0 Hz), 7.75 (1H, s, J=8.4 Hz), 7.99 (1H, d, J=0.4 Hz), 8.07 (1H, s), 8.71 (1H, d, J=8.4 Hz). [M+H] Calc'd for C$_{18}$H$_{14}$N$_6$O, 331. Found, 331.

C. 2-{5-[(1-methyl-1H-indazol-6-yl)methoxy]-1H-pyrazol-1-yl}pyridine-4-carboxylic acid

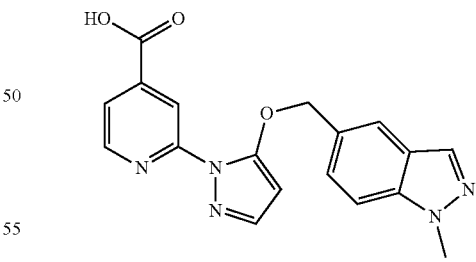

The title compound was prepared in 45% yield from 2-{5-[(1-methyl-1H-indazol-6-yl)methoxy]-1H-pyrazol-1-yl}pyridine-4-carbonitrile according to the procedure for the preparation of Example 28, part E. $^1$H NMR (400 MHz, DMSO-d$_6$): δ 4.03 (3H, s), 5.42 (2H, s), 6.07 (1H, d, J=1.6 Hz), 7.22 (1H, dd, J=0.8 Hz, J=8.4 Hz), 7.60 (1H, d, J=1.6 Hz), 7.75-7.78 (3H, m), 8.04 (1H, s), 8.11 (1H, s), 8.71 (1H, d, J=4.8 Hz), 13.86 (1H, d, J=4.0 Hz). [M+H] Calc'd for C$_{18}$H$_{15}$N$_5$O$_3$, 350. Found, 350.

Example 51

2-{5-[(2-methyl-2H-indazol-5-yl)methoxy]-1H-pyrazol-1-yl}pyridine-4-carboxylic acid

A. (2-methyl-2H-indazol-6-yl)methanol

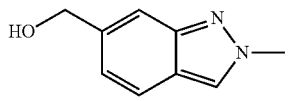

The title compound was prepared in 71% yield from methyl 2-methyl-2H-indazole-6-carboxylate according to the procedure for the preparation of Example 50, part A. [M+H] Calc'd for $C_9H_{10}N_2O$, 163. Found, 163.

B. 2-{5-[(2-methyl-2H-indazol-5-yl)methoxy]-1H-pyrazol-1-yl}pyridine-4-carbonitrile

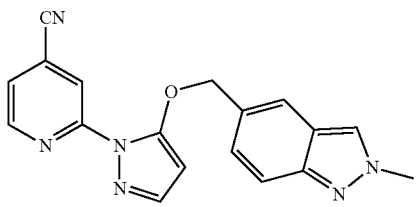 [SMILES: Cn1cc2cc(COc3ccnn3-c3cc(C#N)ccn3)ccc2n1]

The title compound was prepared in 23% yield from 2-(5-hydroxy-1H-pyrazol-1-yl)pyridine-4-carbonitrile and (2-methyl-2H-indazol-6-yl)methanol according to the procedure for the preparation of Example 39, part C. $^1$H NMR (400 MHz, DMSO-d$_6$): δ 4.16 (3H, s), 5.35 (2H, s), 6.05 (1H, d, J=2.0 Hz), 7.11 (1H, dd, J=2.0 Hz, J=8.4 Hz), 7.61 (1H, d, J=2.4 Hz), 7.68-7.71 (2H, m), 7.81 (1H, dd, J=1.2 Hz, J=5.2 Hz), 8.07 (1H, s), 8.32 (1H, s), 8.75 (1H, dd, J=0.4 Hz, J=3.2 Hz). [M+H] Calc'd for $C_{18}H_{14}N_6O$, 331. Found, 331.

C. 2-{5-[(2-methyl-2H-indazol-5-yl)methoxy]-1H-pyrazol-1-yl}pyridine-4-carboxylic acid

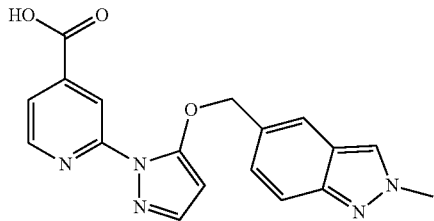 [SMILES: Cn1cc2cc(COc3ccnn3-c3cc(C(=O)O)ccn3)ccc2n1]

The title compound was prepared in 45% yield from 2-{5-[(2-methyl-2H-indazol-5-yl)methoxy]-1H-pyrazol-1-yl}pyridine-4-carbonitrile according to the procedure for the preparation of Example 28, part E. $^1$H NMR (400 MHz, DMSO-d$_6$): δ 4.15 (3H, s), 5.34 (2H, s), 6.04 (1H, d, J=1.6 Hz), 7.11 (1H, dd, J=1.2 Hz, J=8.8 Hz), 7.58 (1H, d, J=1.6 Hz), 7.68 (1H, d, J=8.8 Hz), 7.71 (1H, s), 7.75 (1H, dd, J=1.2 Hz, J=4.8 Hz), 8.08 (1H, s), 8.32 (1H, s), 8.68 (1H, d, J=4.8 Hz), 13.84 (1H, s). [M+H] Calc'd for $C_{15}H_{15}N_5O_3$, 350. Found, 350.

Example 52

2-{5-[(3,4-difluorobenzyl)oxy]-1H-pyrazol-1-yl}pyridine-4-carboxylic acid

A. 2-{5-[(3,4-difluorobenzyl)oxy]-1H-pyrazol-1-yl}pyridine-4-carbonitrile

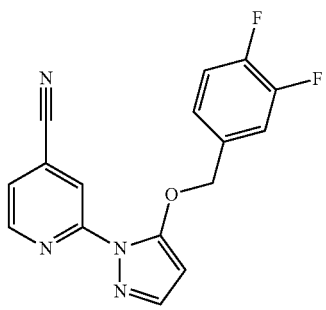 [SMILES: N#Cc1ccnc(-n2nccc2OCc2ccc(F)c(F)c2)c1]

The title compound was prepared from 2-(5-hydroxy-1H-pyrazol-1-yl)pyridine-4-carbonitrile and (3,4-difluorophenyl)methanol according to the procedure for the preparation of Example 39, part C. $^1$H NMR (400 MHz, CDCl$_3$): δ 5.19 (2H, s), 5.73 (1H, d, J=2.0 Hz), 7.16-7.34 (3H, m), 7.41-7.42 (1H, m), 7.57 (1H, s, J=2.0 Hz), 8.04 (1H, s), 8.70 (1H, s, J=4.4 Hz).

[M+H] Calc'd for $C_{16}H_{10}F_2N_4O$, 313. Found, 313.

B. 2-{5-[(3,4-difluorobenzyl)oxy]-1H-pyrazol-1-yl}pyridine-4-carboxylic acid

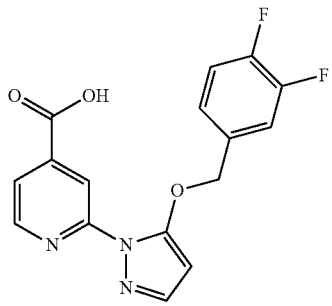 [SMILES: O=C(O)c1ccnc(-n2nccc2OCc2ccc(F)c(F)c2)c1]

The title compound was prepared from 2-{5-[(3,4-difluorobenzyl)oxy]-1H-pyrazol-1-yl}pyridine-4-carbonitrile according to the procedure for the preparation of Example 28, part E. $^1$H NMR (400 MHz, DMSO-d$_6$): δ 5.28 (2H, s), 6.02 (1H, d, J=2.0 Hz), 7.35-7.37 (1H, m), 7.43-7.50 (1H, m), 7.55-7.61 (2H, m), 7.76 (1H, dd, J=1.2 Hz, J=5.2 Hz), 8.08 (1H, s), 8.69 (1H, d, J=5.2 Hz), 13.90 (1H, d, J=1.6 Hz). [M+H] Calc'd for $C_{16}H_{11}F_2N_3O_3$, 332. Found, 332.

Example 53

2-{5-[(4-chlorobenzyl)oxy]-1H-pyrazol-1-yl}pyridine-4-carboxylic acid

A. 2-{5-[(4-chlorobenzyl)oxy]-1H-pyrazol-1-yl}pyridine-4-carbonitrile

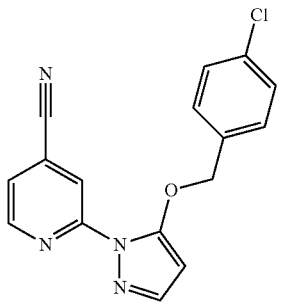 [SMILES: N#Cc1ccnc(-n2nccc2OCc2ccc(Cl)cc2)c1]

The title compound was prepared from 2-(5-hydroxy-1H-pyrazol-1-yl)pyridine-4-carbonitrile and (4-chlorophenyl)methanol according to the procedure for the preparation of Example 39, part C. $^1$H NMR (400 MHz, CDCl$_3$): δ 5.21 (2H, s), 6.72 (1H, d, J=2.0 Hz), 7.26 (1H, s), 7.37-7.47 (4H, m), 7.56 (1H, d, J=2.0 Hz), 8.03 (1H, s), 8.69 (1H, d, J=4.8 Hz) [M+H] Calc'd for C$_{16}$H$_{11}$ClN$_4$O, 311. Found, 311.

B. 2-{5-[(4-chlorobenzyl)oxy]-1H-pyrazol-1-yl}pyridine-4-carboxylic acid

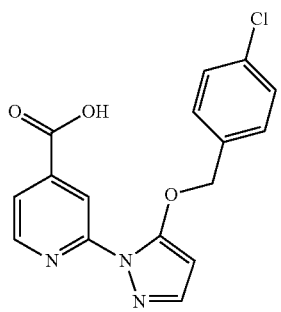 [SMILES: O=C(O)c1ccnc(-n2nccc2OCc2ccc(Cl)cc2)c1]

The title compound was prepared from 2-{5-[(4-chlorobenzyl)oxy]-1H-pyrazol-1-yl}pyridine-4-carbonitrile according to the procedure for the preparation of Example 28, part E. $^1$H NMR (300 MHz, DMSO-d$_6$): δ 5.28 (2H, s), 6.00 (1H, d, J=1.8 Hz), 7.42-7.57 (4H, m), 7.60 (1H, d, J=1.8 Hz), 7.75-7.76 (1H, m), 8.08 (1H, s), 8.68 (1H, t, J=4.8 Hz), 13.89 (1H, d, J=3.6 Hz). [M+H] Calc'd for C$_{16}$H$_{12}$ClN$_3$O$_3$, 330. Found, 330.

Example 54

2-(5-{[4-(trifluoromethyl)benzyl]oxy}-1H-pyrazol-1-yl)pyridine-4-carboxylic acid

A. 2-(5-{[4-(trifluoromethyl)benzyl]oxy}-1H-pyrazol-1-yl)pyridine-4-carbonitrile

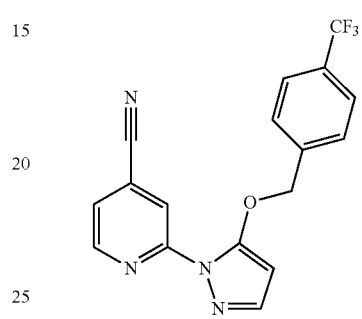

The title compound was prepared from 2-(5-hydroxy-1H-pyrazol-1-yl)pyridine-4-carbonitrile and [4-(trifluoromethyl)phenyl]methanol according to the procedure for the preparation of Example 39, part C. $^1$H NMR (400 MHz, CDCl$_3$): δ 5.31 (2H, s), 5.73 (1H, d, J=1.6 Hz), 7.42 (1H, dd, J=1.2 Hz, J=4.8 Hz), 7.55-7.57 (3H, m), 7.66-7.68 (2H, m), 8.05 (1H, s), 8.70 (1H, d, J=4.8 Hz). [M+H] Calc'd for C$_{17}$H$_{11}$F$_3$N$_4$O, 345. Found, 345.

B. 2-(5-{[4-(trifluoromethyl)benzyl]oxy}-1H-pyrazol-1-yl)pyridine-4-carboxylic acid

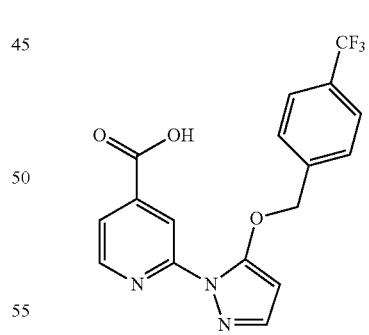

The title compound was prepared from 2-(5-{[4-(trifluoromethyl)benzyl]oxy}-1H-pyrazol-1-yl)pyridine-4-carbonitrile according to the procedure for the preparation of Example 28, part E. $^1$H NMR (400 MHz, DMSO-d$_6$): δ 5.41 (2H, s), 6.01 (1H, d, J=1.6 Hz), 7.61 (1H, d, J=1.6 Hz), 7.70-7.78 (5H, m), 8.11 (1H, s), 8.71 (1H, d, J=5.2 Hz), 13.90-13.92 (1H, m). [M+H] Calc'd for C$_{17}$H$_{12}$F$_3$N$_3$O$_3$, 364. Found, 364.

Example 55

2-{5-[(4-methylbenzyl)oxy]-1H-pyrazol-1-yl}pyridine-4-carboxylic acid

A. 2-{5-[(4-methylbenzyl)oxy]-1H-pyrazol-1-yl}pyridine-4-carbonitrile

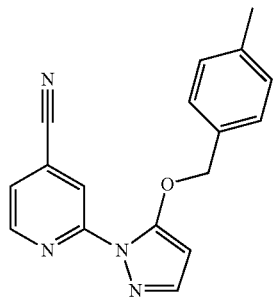 [SMILES: Cc1ccc(COc2ccnn2-c2cc(C#N)ccn2)cc1]

The title compound was prepared from 2-(5-hydroxy-1H-pyrazol-1-yl)pyridine-4-carbonitrile and (4-methylphenyl)methanol according to the procedure for the preparation of Example 39, part C. $^1$H NMR (400 MHz, CDCl$_3$): δ 2.36 (3H, s), 5.20 (2H, s), 5.74 (1H, s, J=1.6 Hz), 7.19-7.32 (4H, m), 7.38 (1H, dd, J=1.2 Hz, J=4.8 Hz), 7.56 (1H, s, J=1.2 Hz), 8.02 (1H, s), 8.70 (1H, s, J=4.8 Hz). [M+H] Calc'd for C$_{17}$H$_{14}$N$_4$O, 291. Found, 291.

B. 2-{5-[(4-methylbenzyl)oxy]-1H-pyrazol-1-yl}pyridine-4-carboxylic acid

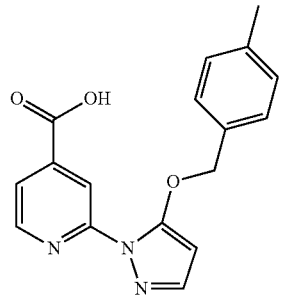 [SMILES: Cc1ccc(COc2ccnn2-c2cc(C(=O)O)ccn2)cc1]

The title compound was prepared from 2-{5-[(4-methylbenzyl)oxy]-1H-pyrazol-1-yl}pyridine-4-carbonitrile according to the procedure for the preparation of Example 28, part E. $^1$H NMR (400 MHz, DMSO-d$_6$): δ 2.97 (s, 3H), 5.22 (2H, s), 6.00 (1H, d, J=1.6 Hz), 7.18-7.37 (4H, m), 7.58 (1H, d, J=2.0 Hz), 7.75 (1H, dd, J=1.6 Hz, J=5.2 Hz), 8.07 (1H, s), 8.68 (1H, d, J=4.8 Hz), 13.87 (1H, s). [M+H] Calc'd for C$_{17}$H$_{15}$N$_3$O$_3$, 310. Found, 310.

Example 56

2-{5-[(4-ethylbenzyl)oxy]-1H-pyrazol-1-yl}pyridine-4-carboxylic acid

A. 2-{5-[(4-ethylbenzyl)oxy]-1H-pyrazol-1-yl}pyridine-4-carbonitrile

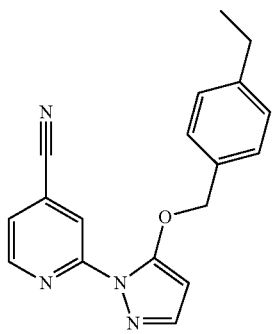 [SMILES: CCc1ccc(COc2ccnn2-c2cc(C#N)ccn2)cc1]

The title compound was prepared from 2-(5-hydroxy-1H-pyrazol-1-yl)pyridine-4-carbonitrile and (4-ethylphenyl)methanol according to the procedure for the preparation of Example 39, part C. $^1$H NMR (400 MHz, CDCl$_3$): δ 1.26 (3H, t, J=6.0 Hz)), 2.66 (2H, q, J=6.0 Hz), 5.01 (2H, s), 5.75 (1H, d, J=2.0 Hz), 7.22-7.35 (4H, m), 7.39 (1H, dd, J=0.8 Hz, J=4.8 Hz), 7.57 (1H, d, J=2.0 Hz), 8.02 (1H, s), 8.71 (1H, d, J=4.8 Hz). [M+H] Calc'd for C$_{18}$H$_{16}$N$_4$O, 305. Found, 305.

B. 2-{5-[(4-ethylbenzyl)oxy]-1H-pyrazol-1-yl}pyridine-4-carboxylic acid

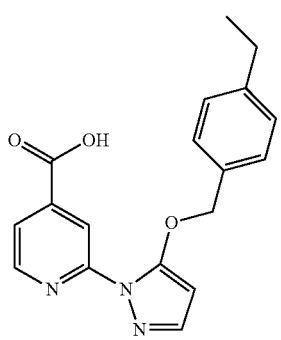 [SMILES: CCc1ccc(COc2ccnn2-c2cc(C(=O)O)ccn2)cc1]

The title compound was prepared from 2-{5-[(4-ethylbenzyl)oxy]-1H-pyrazol-1-yl}pyridine-4-carbonitrile according to the procedure for the preparation of Example 28, part E. $^1$H NMR (400 MHz, DMSO-d$_6$): δ 1.16 (3H, t, J=8.0 Hz), 2.59 (2H, q, J=8.0 Hz), 5.23 (2H, s), 6.00 (1H, d, J=1.6 Hz), 7.21-7.39 (4H, m), 7.58 (1H, d, J=2.0 Hz), 7.74 (1H, dd, J=0.8 Hz, J=4.8 Hz), 8.07 (1H, s), 8.68 (1H, d, J=4.8 Hz), 13.88 (1H, s). [M+H] Calc'd for C$_{18}$H$_{17}$N$_3$O$_3$, 324. Found, 324.

Example 57

2-{5-[(4-bromobenzyl)oxy]-1H-pyrazol-1-yl}pyridine-4-carboxylic acid

A. 2-{5-[(4-bromobenzyl)oxy]-1H-pyrazol-1-yl}pyridine-4-carbonitrile

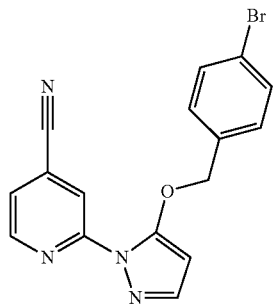 [SMILES: N#Cc1ccnc(-n2nccc2OCc2ccc(Br)cc2)c1]

The title compound was prepared from 2-(5-hydroxy-1H-pyrazol-1-yl)pyridine-4-carbonitrile and (4-bromophenyl)methanol according to the procedure for the preparation of Example 39, part C. $^1$H NMR (400 MHz, CDCl$_3$): δ 5.19 (2H, s), 5.72 (1H, s), 7.30-7.32 (2H, m), 7.41 (1H, d, J=0.8 Hz, J=5.2 Hz), 7.52-7.54 (2H, m), 7.56 (1H, d, J=0.8 Hz), 8.03 (1H, s), 8.69 (1H, d, J=4.0 Hz). [M+H] Calc'd for C$_{16}$H$_{11}$BrN$_4$O, 355. Found, 355.

B. 2-{5-[(4-bromobenzyl)oxy]-1H-pyrazol-1-yl}pyridine-4-carboxylic acid

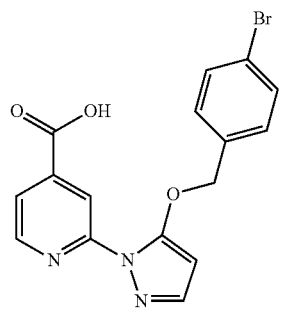

The title compound was prepared from 2-{5-[(4-bromobenzyl)oxy]-1H-pyrazol-1-yl}pyridine-4-carbonitrile according to the procedure for the preparation of Example 28, part E. $^1$H NMR (400 MHz, DMSO-d$_6$): δ 5.27 (2H, s), 6.00 (1H, d, J=2.0 Hz), 7.44-7.46 (2H, m), 7.58-7.60 (3H, m), 7.76 (1H, d, J=1.2 Hz, J=4.8 Hz), 8.09 (1H, s), 8.69 (1H, d, J=5.2 Hz), 13.90 (1H, s). [M+H] Calc'd for C$_{16}$H$_{12}$BrN$_3$O$_3$, 374. Found, 374.

Example 58

2-{5-[(3-chlorobenzyl)oxy]-1H-pyrazol-1-yl}pyridine-4-carboxylic acid

A. 2-{5-[(3-chlorobenzyl)oxy]-1H-pyrazol-1-yl}pyridine-4-carbonitrile

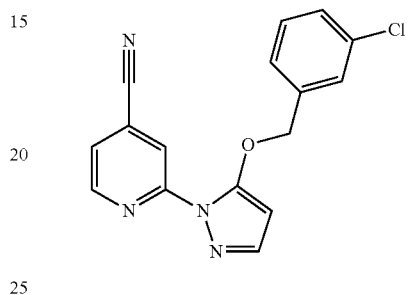

The title compound was prepared from 2-(5-hydroxy-1H-pyrazol-1-yl)pyridine-4-carbonitrile and (3-chlorophenyl)methanol according to the procedure for the preparation of Example 39, part C. $^1$H NMR (400 MHz, CDCl$_3$): δ 5.22 (2H, s), 5.73 (1H, d, J=1.6 Hz), 7.30-7.35 (3H, m) 7.41-7.43 (1H, m), 7.47 (1H, s), 7.57 (1H, d, J=2.0 Hz), 8.05 (1H, s), 8.72 (1H, d, J=5.2 Hz). [M+H] Calc'd for C$_{16}$H$_{11}$ClN$_4$O, 311. Found, 311.

B. 2-{5-[(3-chlorobenzyl)oxy]-1H-pyrazol-1-yl}pyridine-4-carboxylic acid

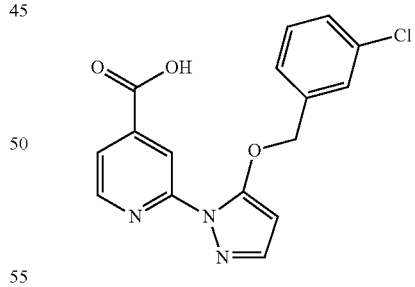

The title compound was prepared from 2-{5-[(3-chlorobenzyl)oxy]-1H-pyrazol-1-yl}pyridine-4-carbonitrile according to the procedure for the preparation of Example 28, part E. $^1$H NMR (400 MHz, DMSO-d$_6$): δ 5.31 (2H, s), 6.01 (1H, d, J=1.2 Hz), 7.41-7.44 (3H, m), 7.59-7.61 (2H, m), 7.77 (1H, d, J=4.8 Hz), 8.09 (1H, s), 8.70 (1H, d, J=4.8 Hz), 13.90 (1H, s). [M+H] Calc'd for C$_{16}$H$_{12}$ClN$_3$O$_3$, 330. Found, 330.

Example 59

2-{5-[(2-fluorobenzyl)oxy]-1H-pyrazol-1-yl}pyridine-4-carboxylic acid

A. 2-{5-[(2-fluorobenzyl)oxy]-1H-pyrazol-1-yl}pyridine-4-carbonitrile

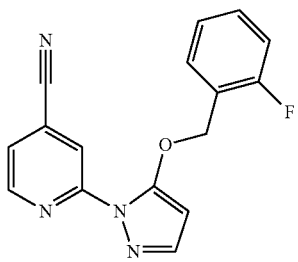 [SMILES: N#Cc1ccnc(-n2nccc2OCc2ccccc2F)c1]

The title compound was prepared from 2-(5-hydroxy-1H-pyrazol-1-yl)pyridine-4-carbonitrile and (2-fluorophenyl)methanol according to the procedure for the preparation of Example 39, part C. $^1$H NMR (400 MHz, CDCl$_3$): δ 5.31 (2H, s), 5.81 (1H, d, J=1.6 Hz), 7.09-7.20 (2H, m), 7.36-7.41 (2H, m), 7.48-7.51 (1H, m), 7.58 (1H, d, J=2.0 Hz), 8.03 (1H, s), 8.70 (1H, d, J=5.2 Hz). [M+H] Calc'd for C$_{16}$H$_{11}$FN$_4$O, 295. Found, 295.

B. 2-{5-[(2-fluorobenzyl)oxy]-1H-pyrazol-1-yl}pyridine-4-carboxylic acid

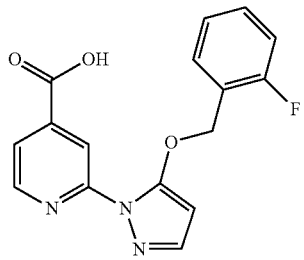 [SMILES: O=C(O)c1ccnc(-n2nccc2OCc2ccccc2F)c1]

The title compound was prepared from 2-{5-[(2-fluorobenzyl)oxy]-1H-pyrazol-1-yl}pyridine-4-carbonitrile according to the procedure for the preparation of Example 28, part E. $^1$H NMR (300 MHz, DMSO-d$_6$): δ 5.33 (2H, s), 6.07 (1H, d, J=1.8 Hz), 7.21-7.27 (2H, m), 7.39-7.47 (1H, m), 7.60-7.64 (2H, m), 7.74 (1H, dd, J=1.2 Hz, J=4.8 Hz), 8.08 (1H, s), 8.67 (1H, d, J=2.4 Hz), 13.84 (1H, s). [M+H] Calc'd for C$_{16}$H$_{12}$FN$_3$O$_3$, 314. Found, 314.

Example 60

2-[5-(pyridin-3-ylmethoxy)-1H-pyrazol-1-yl]pyridine-4-carboxylic acid

A. 2-[5-(pyridin-3-ylmethoxy)-1H-pyrazol-1-yl]pyridine-4-carbonitrile

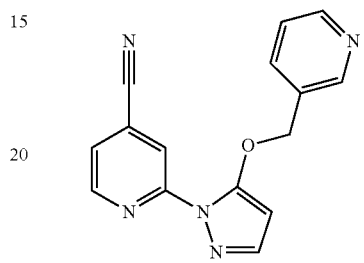

The title compound was prepared from 2-(5-hydroxy-1H-pyrazol-1-yl)pyridine-4-carbonitrile and pyridin-3-ylmethanol according to the procedure for the preparation of Example 39, part C. $^1$H NMR (400 MHz, CDCl$_3$): δ 5.27 (2H, s), 5.78 (1H, d, J=2.0 Hz), 7.41 (1H, dd, J=1.2 Hz, J=5.2 Hz), 7.36 (1H, dd, J=4.8 Hz, J=7.6 Hz), 7.58 (1H, d, J=2.0 Hz), 7.80 (1H, d, J=8.0 Hz), 8.03 (1H, s), 8.63 (1H, dd, J=1.2 Hz, J=4.8 Hz), 8.69-8.72 (2H, m). [M+H] Calc'd for C$_{15}$H$_{11}$N$_5$O, 278. Found, 278.

B. 2-[5-(pyridin-3-ylmethoxy)-1H-pyrazol-1-yl]pyridine-4-carboxylic acid

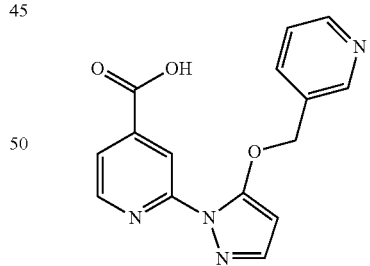

The title compound was prepared from 2-[5-(pyridin-3-ylmethoxy)-1H-pyrazol-1-yl]pyridine-4-carbonitrile according to the procedure for the preparation of Example 28, part E. $^1$H NMR (400 MHz, DMSO-d$_6$): δ 5.47 (2H, s), 6.09 (1H, d, J=2.0 Hz), 7.64 (1H, d, J=1.6 Hz), 7.78 (1H, dd, J=1.2 Hz, J=5.2 Hz), 7.75-7.88 (1H, m), 8.11 (1H, s), 8.40 (1H, d, J=8.0 Hz), 8.72 (1H, d, J=5.2 Hz), 8.80 (1H, d, J=5.2 Hz), 8.95 (1H, s), 13.98 (1H, s). [M+H] Calc'd for C$_{15}$H$_{12}$N$_4$O$_3$, 297. Found, 297.

Example 61

2-[5-(pyridin-4-ylmethoxy)-1H-pyrazol-1-yl]pyridine-4-carboxylic acid

A. 2-[5-(pyridin-4-ylmethoxy)-1H-pyrazol-1-yl]pyridine-4-carbonitrile

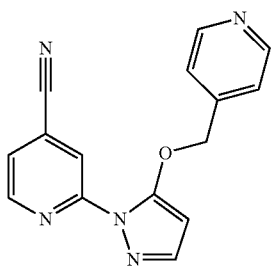 [SMILES: N#Cc1ccnc(-n2nccc2OCc2ccncc2)c1]

The title compound was prepared from 2-(5-hydroxy-1H-pyrazol-1-yl)pyridine-4-carbonitrile and pyridin-4-ylmethanol according to the procedure for the preparation of Example 39, part C. $^1$H NMR (400 MHz, CDCl$_3$): δ 5.29 (2H, d, J=9.2 Hz), 5.72 (1H, d, J=2.0 Hz), 7.38 (2H, d, J=6.4 Hz), 7.44 (1H, dd, J=1.6 Hz, J=5.2 Hz), 7.57 (1H, d, J=2.0 Hz), 8.09 (1H, s), 8.65 (2H, d, J=5.2 Hz), 8.72 (1H, d, J=5.2 Hz). [M+H] Calc'd for C$_{15}$H$_{11}$N$_5$O, 278. Found, 278.

B. 2-[5-(pyridin-4-ylmethoxy)-1H-pyrazol-1-yl]pyridine-4-carboxylic acid

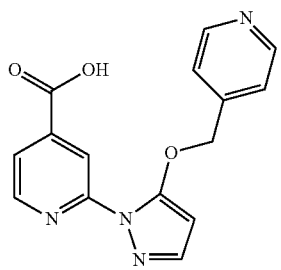 [SMILES: O=C(O)c1ccnc(-n2nccc2OCc2ccncc2)c1]

The title compound was prepared from 2-[5-(pyridin-4-ylmethoxy)-1H-pyrazol-1-yl]pyridine-4-carbonitrile according to the procedure for the preparation of Example 28, part E. $^1$H NMR (400 MHz, DMSO-d$_6$): δ 5.50 (2H, s), 6.01 (1H, d, J=1.6 Hz), 7.63 (1H, d, J=2.0 Hz), 7.75 (2H, d, J=6.4 Hz), 7.80 (1H, dd, J=1.2 Hz, J=5.2 Hz), 8.15 (1H, s), 8.74-8.75 (3H, m), 13.98 (1H, s). [M+H] Calc'd for C$_{15}$H$_{12}$N$_4$O$_3$, 297. Found, 297.

Example 62 methyl 2-[5-(benzyloxy)-1H-pyrazol-1-yl]pyridine-4-carboxylate

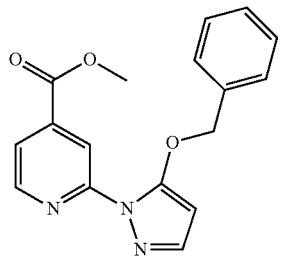 [SMILES: COC(=O)c1ccnc(-n2nccc2OCc2ccccc2)c1]

A solution of compound 2-(5-(benzyloxy)-1H-pyrazol-1-yl)isonicotinic acid (32 mg, 011 mmol, 1.0 eq.) in THF was added CH$_2$N$_2$ (~10 eq.), the mixture was stirred for 30 min; the solvent was removed to obtain the desired product (25 mg). $^1$H NMR (400 MHz, CDCl$_3$): δ 3.88 (3H, s), 5.18 (2H, s), 5.69 (1H, s), 7.28-7.39 (5H, m), 7.51 (1H, s), 7.69 (1H, d, J=4.4 Hz), 8.28 (1H, s), 8.65 (1H, s). [M+H] Calc'd for C$_{17}$H$_{15}$N$_3$O$_3$, 310. Found, 310.

Example 63 methyl 2-{5-[(3,4-difluorobenzyl)oxy]-1H-pyrazol-1-yl}pyridine-4-carboxylate

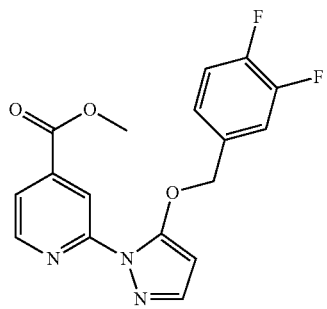 [SMILES: COC(=O)c1ccnc(-n2nccc2OCc2ccc(F)c(F)c2)c1]

The title compound was prepared from 2-{5-[(3,4-difluorobenzyl)oxy]-1H-pyrazol-1-yl}pyridine-4-carboxylic acid according to the procedure for the preparation of Example 62. $^1$H NMR (400 MHz, CDCl$_3$): δ 3.90 (3H, s), 5.12 (2H, s), 5.68 (1H, s), 7.09-7.13 (2H, m), 7.24-7.29 (1H, m), 7.52 (1H, s), 7.72 (1H, d, J=4.8 Hz), 8.26 (1H, s), 8.65 (1H, s). [M+H] Calc'd for C$_{17}$H$_{13}$F$_2$N$_3$O$_3$, 346. Found, 346.

Example 64

Methyl 2-{5-[(4-chlorobenzyl)oxy]-1H-pyrazol-1-yl}pyridine-4-carboxylate

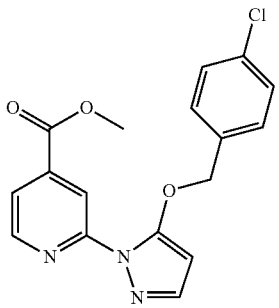 [SMILES: COC(=O)c1ccnc(-n2nccc2OCc2ccc(Cl)cc2)c1]

The title compound was prepared from 2-{5-[(4-chlorobenzyl)oxy]-1H-pyrazol-1-yl}pyridine-4-carboxylic acid according to the procedure for the preparation of Example 62. $^1$H NMR (400 MHz, CDCl$_3$): δ 3.89 (3H, s), 5.14 (2H, s), 5.67 (1H, s), 7.28-7.33 (4H, m), 7.50 (1H, s), 7.70 (1H, d, J=4.8 Hz), 8.25 (1H, s), 8.63 (1H, s). [M+H] Calc'd for C$_{17}$H$_{14}$ClN$_3$O$_3$, 344. Found, 344.

Example 65

Methyl 2-(5-(4-(trifluoromethyl)benzyloxy)-1H-pyrazol-1-yl)isonicotinate

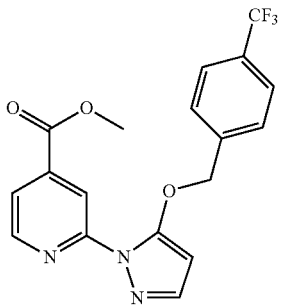 [SMILES: COC(=O)c1ccnc(-n2nccc2OCc2ccc(C(F)(F)F)cc2)c1]

The title compound was prepared from 2-(5-{[4-(trifluoromethyl)benzyl]oxy}-1H-pyrazol-1-yl)pyridine-4-carboxylic acid according to the procedure for the preparation of Example 62. $^1$H NMR (400 MHz, CDCl$_3$): δ 3.96 (3H, s), 5.30 (2H, s), 5.75 (1H, s), 7.57-7.59 (3H, m), 7.65-7.67 (2H, m), 7.78 (1H, d, J=4.8 Hz), 8.34 (1H, s), 8.71 (1H, s). [M+H] Calc'd for C$_{15}$H$_{14}$F$_3$N$_3$O$_3$, 378. Found, 378.

Example 66

Methyl 2-{5-[(4-methylbenzyl)oxy]-1H-pyrazol-1-yl}pyridine-4-carboxylate

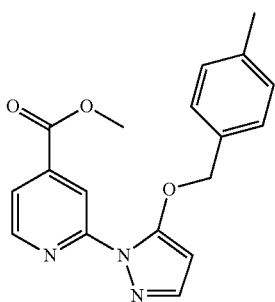 [SMILES: COC(=O)c1ccnc(-n2nccc2OCc2ccc(C)cc2)c1]

The title compound was prepared from 2-{5-[(4-methylbenzyl)oxy]-1H-pyrazol-1-yl}pyridine-4-carboxylic acid according to the procedure for the preparation of Example 62. $^1$H NMR (400 MHz, CDCl$_3$): δ 2.29 (3H, s), 3.88 (3H, s), 5.13 (2H, s), 5.67 (1H, s), 7.11-7.27 (4H, m), 7.50 (1H, d, J=1.2 Hz), 8.67 (1H, dd, J=0.8 Hz, J=4.8 Hz), 8.26 (1H, s), 8.63 (1H, d, J=4.4 Hz). [M+H] Calc'd for C$_{18}$H$_{17}$N$_3$O$_3$, 324. Found, 324.

Example 67

Methyl 2-{5-[(4-ethylbenzyl)oxy]-1H-pyrazol-1-yl}pyridine-4-carboxylate

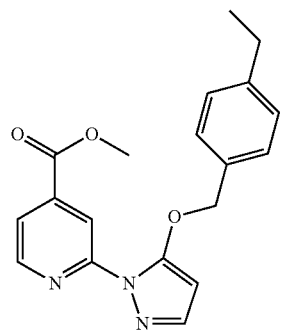 [SMILES: CCc1ccc(COc2ccnn2-c2cc(C(=O)OC)ccn2)cc1]

The title compound was prepared from 2-{5-[(4-ethylbenzyl)oxy]-1H-pyrazol-1-yl}pyridine-4-carboxylic acid according to the procedure for the preparation of Example 62. $^1$H NMR (400 MHz, CDCl$_3$): δ 1.17 (3H, t, J=7.6 Hz), 2.59 (2H, q, J=7.6 Hz), 3.88 (3H, s), 5.14 (2H, s), 5.68 (1H, d, J=1.2 Hz), 7.14-7.30 (4H, m), 7.50 (1H, d, J=1.2 Hz), 7.68 (1H, d, J=5.2 Hz), 8.27 (1H, s), 8.63 (1H, d, J=4.8 Hz). [M+H] Calc'd for C$_{19}$H$_{19}$N$_3$O$_3$, 338. Found, 338.

Example 68

Methyl 2-{5-[(4-bromobenzyl)oxy]-1H-pyrazol-1-yl}pyridine-4-carboxylate

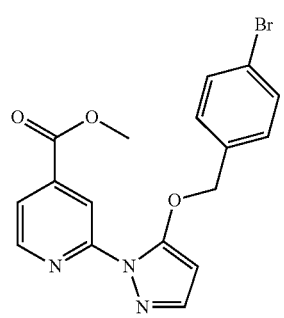

The title compound was prepared from 2-{5-[(4-bromobenzyl)oxy]-1H-pyrazol-1-yl}pyridine-4-carboxylic acid according to the procedure for the preparation of Example 62. $^1$H NMR (400 MHz, CDCl$_3$): δ 3.89 (3H, s), 5.13 (2H, s), 5.67 (1H, s), 7.25-7.46 (4H, m), 7.52 (1H, s), 7.71 (1H, d, J=4.8 Hz), 8.26 (1H, s), 8.64 (1H, s). [M+H] Calc'd for C$_{17}$H$_{14}$BrN$_3$O$_3$, 388. Found, 388.

Example 69

Methyl 2-{5-[(4-fluorobenzyl)oxy]-1H-pyrazol-1-yl}pyridine-4-carboxylate

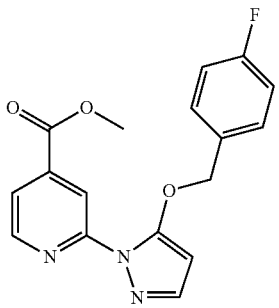

The title compound was prepared from 2-{5-[(4-fluorobenzyl)oxy]-1H-pyrazol-1-yl}pyridine-4-carboxylic acid according to the procedure for the preparation of Example 62. $^1$H NMR (400 MHz, CDCl$_3$): δ 3.88 (3H, s), 5.14 (2H, s), 5.68 (1H, s), 6.99-7.03 (2H, m), 7.34-7.38 (2H, m), 7.51 (1H, s), 7.69 (1H, d, J=4.8 Hz), 8.25 (1H, s), 8.63 (1H, s). [M+H] Calc'd for C$_{17}$H$_{14}$FN$_3$O$_3$, 328. Found, 328.

Example 70

Methyl 2-{5-[(3-fluorobenzyl)oxy]-1H-pyrazol-1-yl}pyridine-4-carboxylate

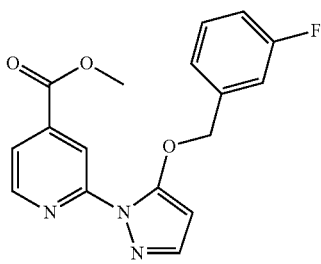 [SMILES: COC(=O)c1ccnc(-n2nccc2OCc2cccc(F)c2)c1]

The title compound was prepared from 2-{5-[(3-fluorobenzyl)oxy]-1H-pyrazol-1-yl}pyridine-4-carboxylic acid according to the procedure for the preparation of Example 62. $^1$H NMR (400 MHz, CDCl$_3$): δ 3.90 (3H, s), 5.17 (2H, s), 5.68 (1H, s), 6.95-7.00 (1H, m), 7.14 (2H, d, J=8.0 Hz), 7.26-7.32 (1H, m), 7.52 (1H, s), 7.72 (1H, d, J=5.2 Hz), 8.28 (1H, s), 8.65 (1H, d, J=3.6 Hz). [M+H] Calc'd for C$_{17}$H$_{14}$FN$_3$O$_3$, 328. Found, 328.

Example 71

2-{5-[(4,4-difluorocyclohexyl)methoxy]-1H-pyrazol-1-yl}pyridine-4-carboxylic acid A. 2-{5-[(4,4-difluorocyclohexyl)methoxy]-1H-pyrazol-1-yl}pyridine-4-carbonitrile

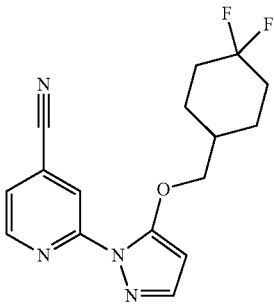 [SMILES: N#Cc1ccnc(-n2nccc2OCC2CCC(F)(F)CC2)c1]

The title compound was prepared from 2-(5-hydroxy-1H-pyrazol-1-yl)pyridine-4-carbonitrile and (4,4-difluorocyclohexyl)methanol according to the procedure for the preparation of Example 39, part C. $^1$H NMR (400 MHz, CDCl$_3$): δ 1.40-1.43 (2H, m), 1.66-1.74 (2H, m), 1.84-1.88 (3H, m), 2.08-2.11 (2H, m), 3.97 (2H, d, J=6.0 Hz), 5.62 (1H, d, J=1.6 Hz), 7.33 (1H, d, J=4.8 Hz), 7.50 (1H, d, J=1.6 Hz), 7.94 (1H, s), 8.61 (1H, d, J=5.2 Hz). [M+H] Calc'd for C$_{16}$H$_{16}$F$_2$N$_4$O, 319. Found, 319.

B. 2-{5-[(4,4-difluorocyclohexyl)methoxy]-1H-pyrazol-1-yl}pyridine-4-carboxylic acid

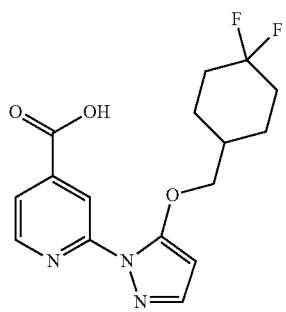 [SMILES: O=C(O)c1ccnc(-n2nccc2OCC2CCC(F)(F)CC2)c1]

The title compound was prepared from 2-{5-[(4,4-difluorocyclohexyl)methoxy]-1H-pyrazol-1-yl}pyridine-4-carbonitrile according to the procedure for the preparation of Example 28, part E. $^1$H NMR (400 MHz, DMSO-d$_6$): δ 1.34-1.37 (2H, m), 1.78-2.04 (7H, m), 4.06 (2H, d, J=8.4 Hz), 5.94 (1H, d, J=1.6 Hz), 7.58 (1H, d, J=1.6 Hz), 7.75 (1H, dd, J=1.2 Hz, J=4.8 Hz), 8.07 (1H, s), 8.66 (1H, d, J=5.2 Hz), 13.89 (1H, s). [M+H] Calc'd for C$_{16}$H$_{17}$F$_2$N$_3$O$_3$, 338. Found, 338.

Example 72

2-{5-[(3-bromobenzyl)oxy]-1H-pyrazol-1-yl}pyridine-4-carboxylic acid

A. 2-{5-[(3-bromobenzyl)oxy]-1H-pyrazol-1-yl}pyridine-4-carbonitrile

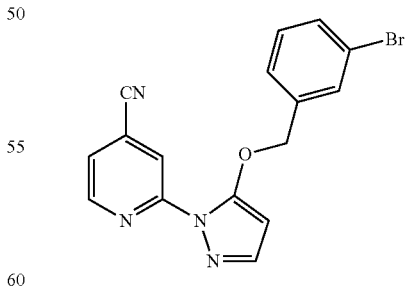

The title compound was prepared from 2-(5-hydroxy-1H-pyrazol-1-yl)pyridine-4-carbonitrile and (3-bromophenyl)methanol according to the procedure for the preparation of Example 39, part C. $^1$H NMR (400 MHz, CDCl$_3$): δ 5.22 (2H, s), 5.74 (1H, s), 7.28 (1H, d, J=7.6 Hz), 7.35 (1H, d, J=7.6 Hz), 7.42 (1H, d, J=4.4 Hz), 7.49 (1H, d, J=8.0 Hz), 7.57 (1H, d, J=1.2 Hz), 7.64 (1H, s), 8.05 (1H, s), 8.72 (1H, d, J=4.8 Hz). [M+H] Calc'd for $C_{16}H_{11}BrN_4O$, 355. Found, 355.

B. 2-{5-[(3-bromobenzyl)oxy]-1H-pyrazol-1-yl}pyridine-4-carboxylic acid

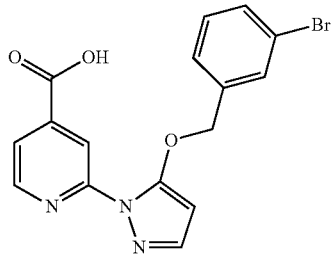 [SMILES: O=C(O)c1ccnc(-n2nccc2OCc2cccc(Br)c2)c1]

The title compound was prepared from 2-{5-[(3-bromobenzyl)oxy]-1H-pyrazol-1-yl}pyridine-4-carbonitrile according to the procedure for the preparation of Example 28, part E. $^1$H NMR (400 MHz, DMSO-$d_6$): δ 5.30 (2H, s), 6.01 (1H, d, J=1.6 Hz), 7.36 (1H, t, J=8.0 Hz), 7.47-7.55 (2H, m), 7.61 (1H, d, J=2.0 Hz), 7.73 (1H, s), 8.77 (1H, dd, J=0.8 Hz, J=4.8 Hz), 8.09 (1H, s), 8.70 (1H, d, J=5.2 Hz), 13.89 (1H, s). [M+H] Calc'd for $C_{16}H_{12}BrN_3O_3$, 374. Found, 374.

Example 73

2-{5-[(3-hydroxybenzyl)oxy]-1H-pyrazol-1-yl}pyridine-4-carboxylic acid

A. 3-({[1-(4-cyanopyridin-2-yl)-1H-pyrazol-5-yl]oxy}methyl)phenyl acetate

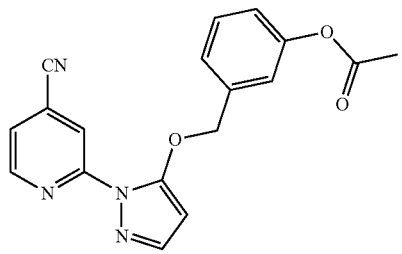 [SMILES: CC(=O)Oc1cccc(COc2ccnn2-c2cc(C#N)ccn2)c1]

The title compound was prepared from 2-(5-hydroxy-1H-pyrazol-1-yl)pyridine-4-carbonitrile and 3-(hydroxymethyl)phenyl acetate according to the procedure for the preparation of Example 39, part C. $^1$H NMR (400 MHz, CDCl$_3$): δ 2.24 (3H, s), 5.17 (2H, s), 5.66 (1H, d, J=1.6 Hz), 7.01-7.03 (1H, m), 7.14 (1H, s), 7.20-7.22 (1H, m), 7.32-7.36 (2H, m), 7.49 (1H, d, J=1.6 Hz), 7.97 (1H, s), 8.63 (1H, d, J=4.8 Hz). [M+H] Calc'd for $C_{18}H_{14}N_4O_3$, 335. Found, 335.

B. 2-{5-[(3-hydroxybenzyl)oxy]-1H-pyrazol-1-yl}pyridine-4-carboxylic acid

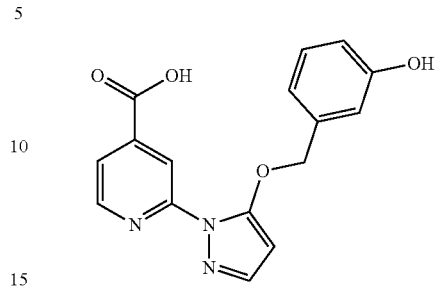

The title compound was prepared from 3-({[1-(4-cyanopyridin-2-yl)-1H-pyrazol-5-yl]oxy}methyl)phenyl acetate according to the procedure for the preparation of Example 28, part E. $^1$H NMR (400 MHz, DMSO-$d_6$): δ 5.20 (2H, s), 5.97 (1H, d, J=1.6 Hz), 6.70-6.72 (1H, m), 6.85-6.89 (2H, m), 7.15-7.18 (1H, m), 7.58 (1H, d, J=1.2 Hz), 7.76-7.77 (1H, m), 8.08 (1H, s), 8.70 (1H, d, J=5.2 Hz), 9.48 (1H, s), 13.89 (1H, s). [M+H] Calc'd for $C_{16}H_{13}N_3O_4$, 312. Found, 312.

Example 74

2-{5-[(4-chloro-3-fluorobenzyl)oxy]-1H-pyrazol-1-yl}pyridine-4-carboxylic acid

A. 2-{5-[(4-chloro-3-fluorobenzyl)oxy]-1H-pyrazol-1-yl}pyridine-4-carbonitrile

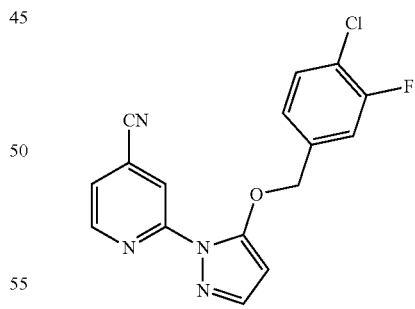

The title compound was prepared from 2-(5-hydroxy-1H-pyrazol-1-yl)pyridine-4-carbonitrile and (4-chloro-3-fluorophenyl)methanol according to the procedure for the preparation of Example 39, part C. $^1$H NMR (400 MHz, CDCl$_3$): δ 5.21 (2H, s), 5.72 (1H, d, J=1.6 Hz), 7.15 (1H, d, J=8.0 Hz), 7.28 (1H, dd, J=1.6 Hz, J=9.6 Hz), 7.40-7.44 (2H, m), 7.57 (1H, d, J=2.08 Hz), 8.04 (1H, s), 8.70 (1H, d, J=4.8 Hz). [M+H] Calc'd for $C_{16}H_{10}ClFN_4O$, 329. Found, 329.

B. 2-{5-[(4-chloro-3-fluorobenzyl)oxy]-1H-pyrazol-1-yl}pyridine-4-carboxylic acid

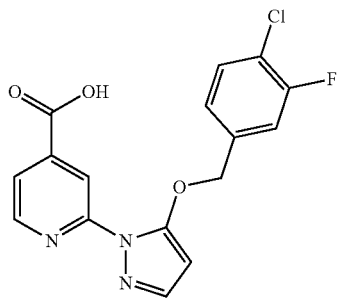 [SMILES: O=C(O)c1ccnc(-n2nccc2OCc2ccc(Cl)c(F)c2)c1]

The title compound was prepared from 2-{5-[(4-chloro-3-fluorobenzyl)oxy]-1H-pyrazol-1-yl}pyridine-4-carbonitrile according to the procedure for the preparation of Example 28, part E. $^1$H NMR (400 MHz, DMSO-d$_6$): δ 5.31 (2H, s), 6.01 (1H, d, J=2.0 Hz), 7.36 (1H, d, J=8.4 Hz), 7.55 (1H, dd, J=2.0 Hz, J=10.4 Hz), 7.60-7.64 (2H, m), 8.77 (1H, dd, J=0.8 Hz, J=4.8 Hz), 8.10 (1H, s), 8.70 (1H, d, J=4.8 Hz), 13.88 (1H, d, J=3.2 Hz). [M+H] Calc'd for C$_{16}$H$_{11}$ClFN$_3$O$_3$, 348. Found, 348.

B. 2-{5-[(4-chloro-2-fluorobenzyl)oxy]-1H-pyrazol-1-yl}pyridine-4-carboxylic acid

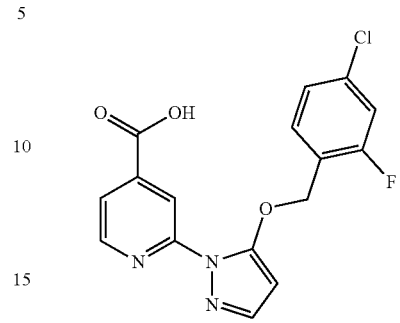

The title compound was prepared from 2-{5-[(4-chloro-2-fluorobenzyl)oxy]-1H-pyrazol-1-yl}pyridine-4-carbonitrile according to the procedure for the preparation of Example 28, part E. $^1$H NMR (400 MHz, DMSO-d$_6$): δ 5.32 (2H, s), 6.08 (1H, d, J=1.6 Hz), 7.34 (1H, dd, J=1.6 Hz, J=8.0 Hz), 7.49 (1H, dd, J=2.0 Hz, J=9.6 Hz), 7.61-7.68 (2H, m), 7.75 (1H, dd, J=1.6 Hz, J=5.2 Hz), 8.05 (1H, s), 8.67 (1H, d, J=5.2 Hz), 13.89 (1H, s). [M+H] Calc'd for C$_{16}$H$_{11}$ClFN$_3$O$_3$, 348. Found, 348.

Example 75

2-{5-[(4-chloro-2-fluorobenzyl)oxy]-1H-pyrazol-1-yl}pyridine-4-carboxylic acid

A. 2-{5-[(4-chloro-2-fluorobenzyl)oxy]-1H-pyrazol-1-yl}pyridine-4-carbonitrile

Example 76

2-{5-[(3-chloro-4-fluorobenzyl)oxy]-1H-pyrazol-1-yl}pyridine-4-carboxylic acid

A. 2-{5-[(3-chloro-4-fluorobenzyl)oxy]-1H-pyrazol-1-yl}pyridine-4-carbonitrile

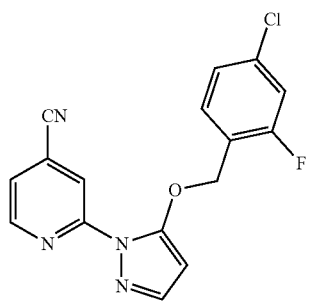 [SMILES: N#Cc1ccnc(-n2nccc2OCc2ccc(Cl)cc2F)c1]

The title compound was prepared from 2-(5-hydroxy-1H-pyrazol-1-yl)pyridine-4-carbonitrile and (4-chloro-2-fluorophenyl)methanol according to the procedure for the preparation of Example 39, part C. $^1$H NMR (400 MHz, CDCl$_3$): δ 5.19 (2H, s), 5.72 (1H, d, J=1.6 Hz), 7.07-7.13 (2H, m), 7.33-7.41 (2H, m), 7.51 (1H, d, J=2.0 Hz), 7.95 (1H, s), 8.62 (1H, d, J=5.2 Hz). [M+H] Calc'd for C$_{16}$H$_{10}$ClFN$_4$O, 329. Found, 329.

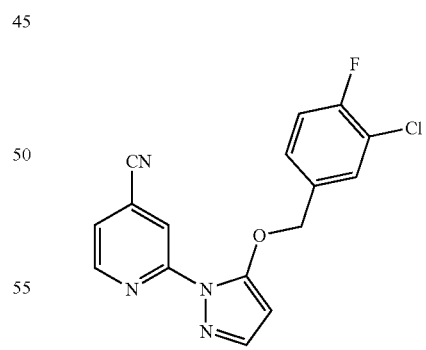

The title compound was prepared from 2-(5-hydroxy-1H-pyrazol-1-yl)pyridine-4-carbonitrile and (3-chloro-4-fluorophenyl)methanol according to the procedure for the preparation of Example 39, part C. [M+H] Calc'd for C$_{16}$H$_{10}$ClFN$_4$O, 329. Found, 329.

B. 2-{5-[(3-chloro-4-fluorobenzyl)oxy]-1H-pyrazol-1-yl}pyridine-4-carboxylic acid

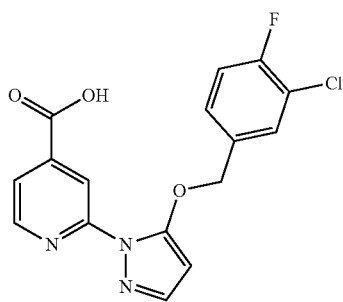 [SMILES: O=C(O)c1ccnc(-n2nccc2OCc2ccc(F)c(Cl)c2)c1]

The title compound was prepared from 2-{5-[(3-chloro-4-fluorobenzyl)oxy]-1H-pyrazol-1-yl}pyridine-4-carbonitrile according to the procedure for the preparation of Example 28, part E. $^1$H NMR (400 MHz, DMSO-$d_6$): δ 5.28 (2H, s), 6.02 (1H, d, J=2.0 Hz), 7.42-7.52 (2H, m), 7.61 (1H, d, J=1.6 Hz), 7.74-7.78 (2H, m), 8.08 (1H, s), 8.68 (1H, d, J=5.2 Hz), 13.90 (1H, s). [M+H] Calc'd for $C_{16}H_{11}ClFN_3O_3$, 348. Found, 348.

Example 77

2-{5-[(4-cyclopropylbenzyl)oxy]-1H-pyrazol-1-yl}pyridine-4-carboxylic acid

A. 2-{5-[(4-cyclopropylbenzyl)oxy]-1H-pyrazol-1-yl}pyridine-4-carbonitrile

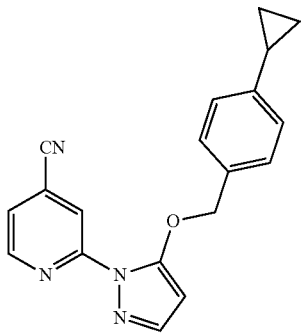 [SMILES: N#Cc1ccnc(-n2nccc2OCc2ccc(C3CC3)cc2)c1]

The title compound was prepared from 2-(5-hydroxy-1H-pyrazol-1-yl)pyridine-4-carbonitrile and (4-cyclopropylphenyl)methanol according to the procedure for the preparation of Example 39, part C. $^1$H NMR (400 MHz, CDCl$_3$): δ 0.61-0.65 (2H, m), 0.89-0.94 (2H, m), 1.91-1.84 (1H, m), 5.12 (2H, s), 5.67 (1H, d, J=1.6 Hz), 7.01-7.24 (4H, m), 7.32-7.33 (1H, m), 7.50 (1H, d, J=1.2 Hz), 7.95 (1H, s), 8.63 (1H, d, J=4.8 Hz). [M+H] Calc'd for $C_{19}H_{16}N_4O$, 317. Found, 317.

B. 2-{5-[(4-cyclopropylbenzyl)oxy]-1H-pyrazol-1-yl}pyridine-4-carboxylic acid

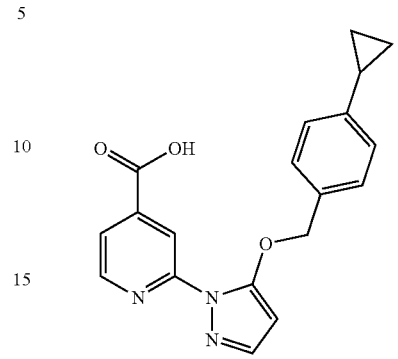

The title compound was prepared from 2-{5-[(4-cyclopropylbenzyl)oxy]-1H-pyrazol-1-yl}pyridine-4-carbonitrile according to the procedure for the preparation of Example 28, part E. $^1$H NMR (400 MHz, DMSO-$d_6$): δ 0.64-0.67 (2H, m), 0.91-1.96 (2H, m), 1.87-1.93 (1H, m), 5.21 (2H, s), 6.00 (1H, d, J=1.6 Hz), 7.06-7.08 (2H, m), 7.33-7.35 (2H, m), 7.58 (1H, d, J=2.0 Hz), 7.74 (1H, dd, J=1.2 Hz, J=5.2 Hz), 8.06 (1H, s), 8.67 (1H, d, J=4.8 Hz), 13.91 (1H, s). [M+H] Calc'd for $C_{19}H_{17}N_3O_3$, 336. Found, 336.

Example 78

Methyl 2-{5-[(4-chloro-3-fluorobenzyl)oxy]-1H-pyrazol-1-yl}pyridine-4-carboxylate

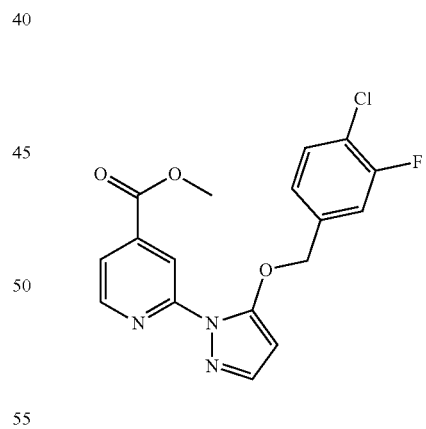

The title compound was prepared from 2-{5-[(4-chloro-3-fluorobenzyl)oxy]-1H-pyrazol-1-yl}pyridine-4-carboxylic acid according to the procedure for the preparation of Example 62. $^1$H NMR (400 MHz, CDCl$_3$): δ 3.90 (3H, s), 5.14 (2H, s), 5.67 (1H, s), 7.09 (1H, d, J=8.4 Hz), 7.23 (1H, d, J=9.6 Hz), 7.35 (1H, t, J=8.0 Hz), 7.52 (1H, s), 7.72 (1H, d, J=4.4 Hz), 8.26 (1H, s), 8.64 (1H, d, J=3.6 Hz). [M+H] Calc'd for $C_{17}H_{13}ClFN_3O_3$, 362. Found, 362.

Example 79

Methyl 2-{5-[(4-chloro-2-fluorobenzyl)oxy]-1H-pyrazol-1-yl}pyridine-4-carboxylate

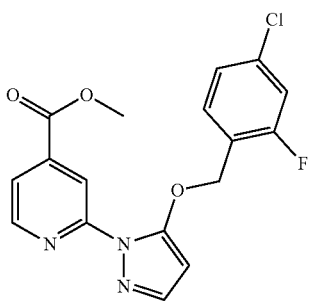 [SMILES: COC(=O)c1ccnc(-n2nccc2OCc2ccc(Cl)cc2F)c1]

The title compound was prepared from 2-{5-[(4-chloro-2-fluorobenzyl)oxy]-1H-pyrazol-1-yl}pyridine-4-carboxylic acid according to the procedure for the preparation of Example 62. $^1$H NMR (400 MHz, CDCl$_3$): δ 3.90 (3H, s), 5.20 (2H, s), 5.73 (1H, s), 7.07 (1H, dd, J=2.0 Hz, J=9.6 Hz), 7.11 (1H, dd, J=2.0 Hz, J=9.6 Hz), 7.43 (1H, t, J=8.0 Hz), 7.52 (1H, s), 7.70 (1H, d, J=4.4 Hz), 8.24 (1H, s), 8.63 (1H, s). [M+H] Calc'd for C$_{17}$H$_{13}$ClFN$_3$O$_3$, 362. Found, 362.

Example 80

Methyl 2-{5-[(3-chloro-4-fluorobenzyl)oxy]-1H-pyrazol-1-yl}pyridine-4-carboxylate

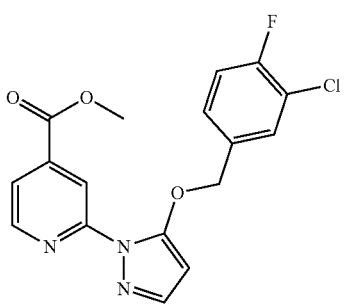 [SMILES: COC(=O)c1ccnc(-n2nccc2OCc2ccc(F)c(Cl)c2)c1]

The title compound was prepared from 2-{5-[(3-chloro-4-fluorobenzyl)oxy]-1H-pyrazol-1-yl}pyridine-4-carboxylic acid according to the procedure for the preparation of Example 62. $^1$H NMR (400 MHz, CDCl$_3$): δ 3.90 (3H, s), 5.11 (2H, s), 5.68 (1H, s), 7.09 (1H, t, J=8.4 Hz), 7.23-7.27 (1H, m), 7.48 (1H, dd, J=1.6 Hz, J=7.2 Hz), 7.51 (1H, d, J=1.2 Hz), 7.71 (1H, dd, J=1.6 Hz, J=5.2 Hz), 8.25 (1H, s), 8.64 (1H, d, J=4.4 Hz). [M+H] Calc'd for C$_{17}$H$_{13}$ClFN$_3$O$_3$, 362. Found, 362.

Example 81

Methyl 2-{5-[(4-cyclopropylbenzyl)oxy]-1H-pyrazol-1-yl}pyridine-4-carboxylate

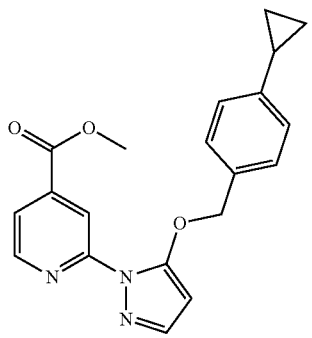 [SMILES: COC(=O)c1ccnc(-n2nccc2OCc2ccc(C3CC3)cc2)c1]

The title compound was prepared from 2-{5-[(4-cyclopropylbenzyl)oxy]-1H-pyrazol-1-yl}pyridine-4-carboxylic acid according to the procedure for the preparation of Example 62. $^1$H NMR (400 MHz, CDCl$_3$): δ 0.60-0.64 (2H, m), 0.88-0.93 (2H, m), 1.81-1.85 (1H, m), 3.89 (3H, d, J=6.4 Hz), 5.12 (2H, s), 5.67 (1H, s), 7.00-7.26 (4H, m), 7.50 (1H, s), 7.68 (1H, d, J=4.8 Hz), 8.26 (1H, s), 8.62 (1H, s). [M+H] Calc'd for C$_{20}$H$_{19}$N$_3$O$_3$, 350. Found, 350.

Example 82

2-[5-[1-(4-fluorophenyl)ethoxy]pyrazol-1-yl]pyridine-4-carboxylic acid

A. 2-[5-[1-(4-fluorophenyl)ethoxy]pyrazol-1-yl]pyridine-4-carbonitrile

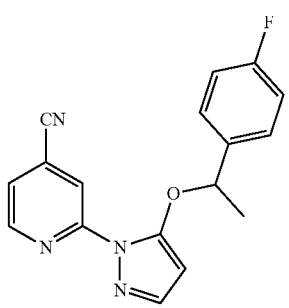 [SMILES: CC(Oc1ccnn1-c1cc(C#N)ccn1)c1ccc(F)cc1]

The title compound was prepared from 2-(5-hydroxy-1H-pyrazol-1-yl)pyridine-4-carbonitrile and 1-(4-fluorophenyl)ethanol according to the procedure for the preparation of Example 39, part C. $^1$H NMR (400 MHz, CDCl$_3$): δ 1.65 (3H, d, J=6.4 Hz), 5.24 (1H, q, J=6.4 Hz), 5.44 (1H, d, J=2.0 Hz), 6.95-7.00 (2H, m), 7.27-7.30 (2H, m), 7.35 (1H, dd, J=0.8 Hz, J=5.2 Hz), 7.41 (1H, d, J=2.0 Hz), 7.97 (1H, s), 8.66 (1H, d, J=4.8 Hz). [M+H] Calc'd for C$_{17}$H$_{13}$FN$_4$O, 309. Found, 309.

B. 2-[5-[1-(4-fluorophenyl)ethoxy]pyrazol-1-yl]pyridine-4-carboxylic acid

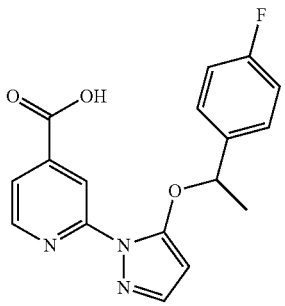 [SMILES: CC(Oc1ccnn1-c1cc(C(=O)O)ccn1)c1ccc(F)cc1]

The title compound was prepared from 2-[5-[1-(4-fluorophenyl)ethoxy]pyrazol-1-yl]pyridine-4-carbonitrile according to the procedure for the preparation of Example 28, part E. $^1$H NMR (400 MHz, DMSO-$d_6$) δ: 1.58 (3H, d, J=6.4 Hz), 5.53 (1H, q, J=6.4 Hz), 5.81 (1H, d, J=1.6 Hz), 7.16-7.20 (2H, m), 7.49-7.52 (3H, m), 7.76 (1H, dd, J=1.2 Hz, J=5.2 Hz), 8.05 (1H, s), 8.70 (1H, d, J=4.8 Hz), 13.97 (1H, s). LCMS (mobile phase: 5%-95% Acetonitrile-Water-0.02% NH$_4$Ac): purity is >95%, Rt=2.587 min. [M+H] Calc'd for $C_{17}H_{14}FN_3O_3$, 328. Found, 328.

Example 83

2-[5-[(3,3-difluorocyclobutyl)methoxy]pyrazol-1-yl]pyridine-4-carboxylic acid

A. 2-[5-[(3,3-difluorocyclobutyl)methoxy]pyrazol-1-yl]pyridine-4-carbonitrile

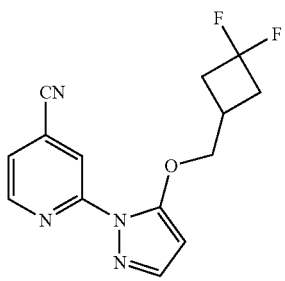 [SMILES: N#Cc1ccnc(-n2nccc2OCC2CC(F)(F)C2)c1]

The title compound was prepared from 2-(5-hydroxy-1H-pyrazol-1-yl)pyridine-4-carbonitrile and (3,3-difluorocyclobutyl)methanol according to the procedure for the preparation of Example 39, part C. $^1$H NMR (400 MHz, CDCl$_3$): δ 2.48-2.71 (5H, m), 5.14 (2H, d, J=4.4 Hz), 5.64 (1H, d, J=1.6 Hz), 7.34 (1H, dd, J=0.4 Hz, J=4.8 Hz), 7.51 (1H, d, J=2.0 Hz), 7.93 (1H, s), 8.61 (1H, d, J=4.8 Hz). [M+H] Calc'd for $C_{14}H_{12}F_2N_4O$, 291. Found, 291.

B. 2-[5-[(3,3-difluorocyclobutyl)methoxy]pyrazol-1-yl]pyridine-4-carboxylic acid

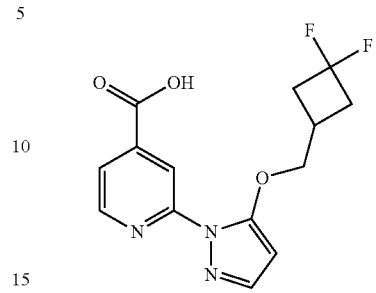

The title compound was prepared from 2-[5-[(3,3-difluorocyclobutyl)methoxy]pyrazol-1-yl]pyridine-4-carbonitrile according to the procedure for the preparation of Example 28, part E. $^1$H NMR (400 MHz, DMSO-$d_6$): δ 2.50-2.69 (5H, m), 4.23 (2H, d, J=4.4 Hz), 5.96 (1H, d, J=2.0 Hz), 7.60 (1H, d, J=1.6 Hz), 7.76 (1H, dd, J=1.2 Hz, J=4.8 Hz), 8.07 (1H, s), 8.66 (1H, d, J=5.2 Hz), 13.87 (1H, s). LCMS (mobile phase: 5%-95% Acetonitrile-Water-0.02% NH$_4$Ac): purity is >95%, Rt=2.273 min. [M+H] Calc'd for $C_{14}H_{13}F_2N_3O_3$, 310. Found, 310.

Example 84

2-[5-[(4-fluorophenyl)methoxy]-4-methylpyrazol-1-yl]pyridine-4-carboxylic acid

A. ethyl (E)-3-(dimethylamino)-2-methylprop-2-enoate

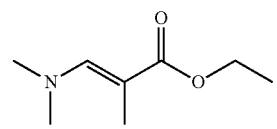

A solution of N,N,N',N'-tetramethyl-1-[(2-methylpropan-2-yl)oxy]methanediamine (2.47 g, 14.19 mmol), ethyl propionate (2.17 g, 21.27 mmol) and DMF (2 mL) in a sealed tube was heated to 90° C. for 24 h. Then extracted with ethyl acetate, collected the organic phase and washed with water, brine and dried with anhydrous sodium sulfate. Organic phase was concentrated and purified by silica gel chromatograph to give 0.68 g of the title compound (30%). $^1$H NMR (400 MHz, CDCl$_3$): δ 1.24 (3H, t, J=7.2 Hz), 1.95 (3H, s), 3.00 (6H, s), 4.11 (2H, q, J=7.2 Hz), 7.28 (1H, s). [M+H] Calc'd for $C_8H_{15}NO_2$, 158. Found, 158.

B. ethyl (E)-3-[2-(4-cyanopyridin-2-yl)hydrazinyl]-2-methylprop-2-enoate

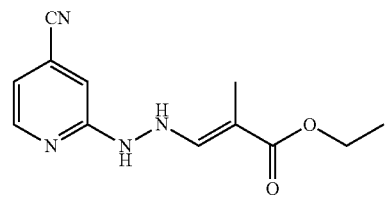 [SMILES: CCOC(=O)/C(C)=C/NNc1cc(C#N)ccn1]

A solution of ethyl (E)-3-(dimethylamino)-2-methylprop-2-enoate (668 mg, 4.25 mmol) and 2-hydrazinylpyridine-4-carbonitrile (570 mg, 4.25 mmol, PREPARATION 2) in 2 mL HOAc and 10 mL EtOH was charged to a flask and the mixture was heated to 90° C. for 30 min. Cooled to room temperature and removed the solvent. The residue was dissolved in ethylacetate and water, aqueous basified with NaHCO$_3$ sat (pH=8), extracted with ethylacetate. The organic phase was washed with brine and dried with anhydrous sodium sulfate and then purified by silica gel chromatograph to give 0.65 g of the title compound (62%). [M+H] Calc'd for $C_{12}H_{14}N_4O_2$, 247. Found, 247.

C. 2-(5-hydroxy-4-methylpyrazol-1-yl)pyridine-4-carbonitrile

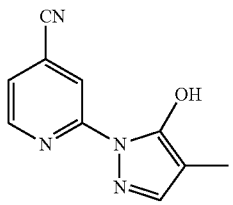

To a cooled mixture of ethyl (E)-3-[2-(4-cyanopyridin-2-yl)hydrazinyl]-2-methylprop-2-enoate (415 mg, 1.69 mmol) in ethanol (18 mL) was added t-BuOK (568 mg, 5.06 mmol) slowly. After that, the mixture was stirred overnight, filtered, the solid was acidified with HCl (1N), filtered, collected the solid and dried to give 250 mg of the title compound (74%). $^1$H NMR (400 MHz, CDCl$_3$): δ 1.93 (3H, s), 7.55 (1H, dd, J=1.2 Hz, J=4.8 Hz), 7.64 (1H, s), 8.64 (1H, d, J=4.8 Hz), 8.72 (1H, s). [M+H] Calc'd for $C_{10}H_8N_4O$, 201. Found, 201.

D. 2-[5-[(4-fluorophenyl)methoxy]-4-methylpyrazol-1-yl]pyridine-4-carbonitrile

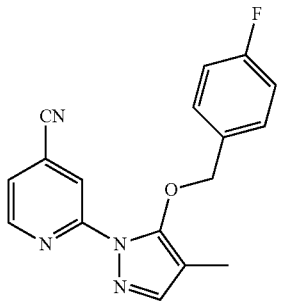 [SMILES: Cc1cnn(-c2cc(C#N)ccn2)c1OCc1ccc(F)cc1]

The title compound was prepared from 2-(5-hydroxy-4-methylpyrazol-1-yl)pyridine-4-carbonitrile and 4-fluorobenzyl alcohol according to the procedure for the preparation of Example 39, part C. $^1$H NMR (300 MHz, CDCl$_3$): δ 1.91 (3H, s), 5.14 (2H, s), 7.26 (2H, s), 7.33-7.37 (3H, m), 7.46 (1H, s), 7.99 (1H, s), 8.62 (1H, d, J=5.1 Hz). [M+H] Calc'd for $C_{17}H_{13}FN_4O$, 309. Found, 309.

E. 2-[5-[(4-fluorophenyl)methoxy]-4-methylpyrazol-1-yl]pyridine-4-carboxylic acid

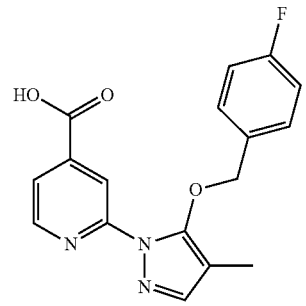 [SMILES: Cc1cnn(-c2cc(C(=O)O)ccn2)c1OCc1ccc(F)cc1]

The title compound was prepared from 2-[5-[(4-fluorophenyl)methoxy]-4-methylpyrazol-1-yl]pyridine-4-carbonitrile according to the procedure for the preparation of Example 28, part E. $^1$H NMR (400 MHz, DMSO-d$_6$): δ 1.89 (3H, s), 5.16 (2H, s), 7.14-7.19 (2H, m), 7.44-7.47 (2H, m), 7.53 (1H, s), 7.75 (1H, dd, J=1.6 Hz, J=4.8 Hz), 8.03 (1H, s), 8.69 (1H, d, J=5.2 Hz). LCMS (mobile phase: 5%-95% Acetonitrile-Water-0.1% TFA): purity is >95%, Rt=3.614 min. [M+H] Calc'd for $C_{17}H_{14}FN_3O_3$, 328. Found, 328.

Example 85

2-[4-ethyl-5-[(4-fluorophenyl)methoxy]pyrazol-1-yl]pyridine-4-carboxylic acid

A. ethyl (2E)-2-(dimethylaminomethylidene)butanoate

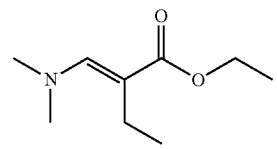

The title compound was prepared from N,N,N',N'-tetramethyl-1-[(2-methylpropan-2-yl)oxy]methanediamine and ethyl butanoate according to the procedure for the preparation of Example 84, part A. [M+H] Calc'd for $C_9H_{17}NO_2$, 172. Found, 172.

B. ethyl (2E)-2-[[2-(4-cyanopyridin-2-yl)hydrazinyl]methylidene]butanoate

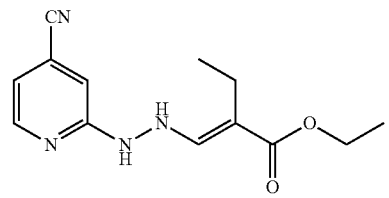 [SMILES: CCOC(=O)/C(=C/NNc1cc(C#N)ccn1)CC]

The title compound was prepared from ethyl (2E)-2-(dimethylaminomethylidene)butanoate and 2-hydrazinylpyridine-4-carbonitrile (PREPARATION 2) according to the procedure for the preparation of Example 84, part B. [M+H] Calc'd for $C_{13}H_{16}N_4O_2$, 261. Found, 261.

C. 2-(4-ethyl-5-hydroxypyrazol-1-yl)pyridine-4-carbonitrile

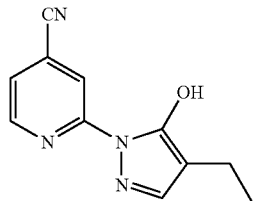 [SMILES: CCc1cnn(-c2cc(C#N)ccn2)c1O]

The title compound was prepared from ethyl (2E)-2-[[2-(4-cyanopyridin-2-yl)hydrazinyl]methylidene]butanoate according to the procedure for the preparation of Example 84, part C. [M+H] Calc'd for $C_{11}H_{10}N_4O$, 215. Found, 215.

D. 2-[4-ethyl-5-[(4-fluorophenyl)methoxy]pyrazol-1-yl]pyridine-4-carbonitrile

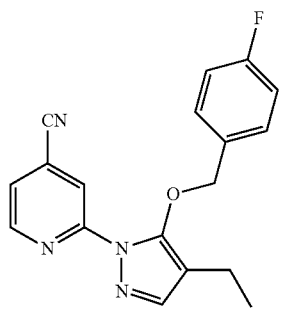 [SMILES: CCc1cnn(-c2cc(C#N)ccn2)c1OCc1ccc(F)cc1]

The title compound was prepared from 2-(4-ethyl-5-hydroxypyrazol-1-yl)pyridine-4-carbonitrile and 4-fluorobenzyl alcohol according to the procedure for the preparation of Example 39, part C. [M+H] Calc'd for $C_{15}H_{18}FN_4O$, 323. Found, 323.

E. 2-[4-ethyl-5-[(4-fluorophenyl)methoxy]pyrazol-1-yl]pyridine-4-carboxylic acid

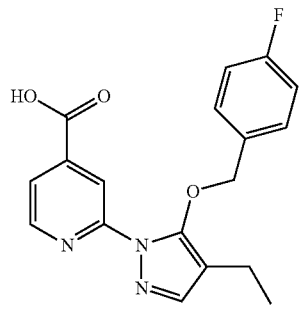 [SMILES: CCc1cnn(-c2cc(C(=O)O)ccn2)c1OCc1ccc(F)cc1]

The title compound was prepared from 2-[4-ethyl-5-[(4-fluorophenyl)methoxy]pyrazol-1-yl]pyridine-4-carbonitrile according to the procedure for the preparation of Example 28, part E. $^1$H NMR (400 MHz, DMSO-$d_6$): δ 1.11 (3H, t, J=7.6 Hz), 2.32 (2H, q, J=7.6 Hz), 5.14 (2H, s), 7.15-7.20 (2H, m), 7.44-7.47 (2H, m), 7.61 (1H, s), 7.75 (1H, dd, J=1.6 Hz, J=4.8 Hz), 8.04 (1H, s), 8.69 (1H, d, J=5.2 Hz), 13.89 (1H, s). LCMS (mobile phase: 10%-95% Acetonitrile-Water-0.02% NH$_4$Ac): purity is >95%, Rt=2.633 min. [M+H] Calc'd for $C_{15}H_{16}FN_3O_3$, 342. Found, 342.

Example 86

2-[5-[(2,4-difluorophenyl)methoxy]pyrazol-1-yl]pyridine-4-carboxylic acid

A. 2-[5-[(2,4-difluorophenyl)methoxy]pyrazol-1-yl]pyridine-4-carbonitrile

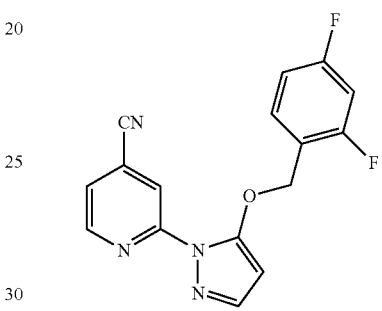

The title compound was prepared from 2-(5-hydroxy-1H-pyrazol-1-yl)pyridine-4-carbonitrile and (2,4-difluorophenyl)methanol according to the procedure for the preparation of Example 39, part C. $^1$H NMR (400 MHz, CDCl$_3$): δ 5.19 (2H, s), 5.74 (1H, d, J=2.0 Hz), 6.78-6.86 (2H, m), 7.33 (1H, dd, J=1.2 Hz, J=4.8 Hz), 7.39-7.45 (1H, m), 7.51 (1H, d, J=1.6 Hz), 7.94 (1H, s), 8.62 (1H, d, J=4.8 Hz). [M+H] Calc'd for $C_{16}H_{10}F_2N_4O$, 313. Found, 313.

B. 2-[5-[(2,4-difluorophenyl)methoxy]pyrazol-1-yl]pyridine-4-carboxylic acid

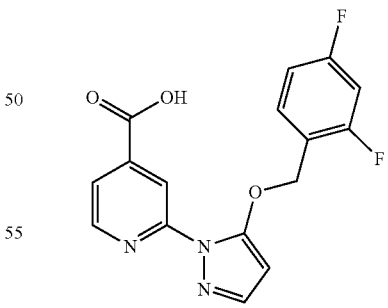

The title compound was prepared from 2-[5-[(2,4-difluorophenyl)methoxy]pyrazol-1-yl]pyridine-4-carbonitrile according to the procedure for the preparation of Example 28, part E. $^1$H NMR (400 MHz, DMSO-$d_6$): δ 5.29 (2H, s), 6.08 (1H, d, J=2.0 Hz), 7.11-7.15 (1H, m), 7.27-7.33 (1H, m), 7.61 (1H, d, J=2.0 Hz), 7.68 (1H, dd, J=8.0, 15.6 Hz), 7.72-7.75 (1H, m), 8.04 (1H, s), 8.65 (1H, d, J=5.2 Hz). LCMS (mobile phase: 5%-95% Acetonitrile-Water-0.1%

TFA): purity is >95%, Rt=3.349 min. [M+H] Calc'd for $C_{16}H_{11}F_2N_3O_3$, 332. Found, 332.

Example 87

2-[5-[(3,4-dichlorophenyl)methoxy]pyrazol-1-yl]pyridine-4-carboxylic acid

A. 2-[5-[(3,4-dichlorophenyl)methoxy]pyrazol-1-yl]pyridine-4-carbonitrile

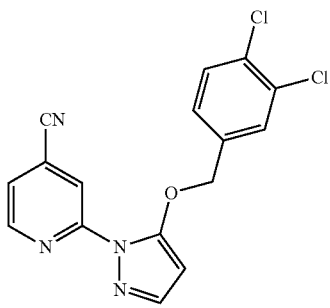 [SMILES: N#Cc1ccnc(-n2nccc2OCc2ccc(Cl)c(Cl)c2)c1]

The title compound was prepared from 2-(5-hydroxy-1H-pyrazol-1-yl)pyridine-4-carbonitrile and (3,4-dichlorophenyl)methanol according to the procedure for the preparation of Example 39, part C. $^1$H NMR (400 MHz, CDCl$_3$): δ 5.12 (2H, s), 5.66 (1H, d, J=1.6 Hz), 7.20 (1H, d, J=2.0 Hz), 7.35 (1H, dd, J=1.2, 5.2 Hz), 7.40 (1H, d, J=8.0 Hz), 7.52 (2H, m), 7.98 (1H, s), 8.64 (1H, d, J=4.8 Hz). [M+H] Calc'd for $C_{16}H_{10}Cl_2N_4O$, 345. Found, 345.

B. 2-[5-[(3,4-dichlorophenyl)methoxy]pyrazol-1-yl]pyridine-4-carboxylic acid

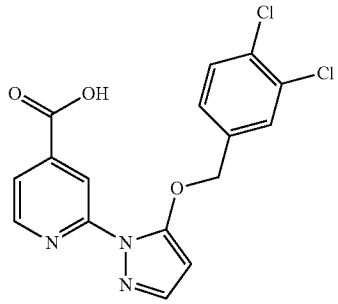 [SMILES: O=C(O)c1ccnc(-n2nccc2OCc2ccc(Cl)c(Cl)c2)c1]

The title compound was prepared from 2-[5-[(3,4-dichlorophenyl)methoxy]pyrazol-1-yl]pyridine-4-carbonitrile according to the procedure for the preparation of Example 28, part E. $^1$H NMR (400 MHz, DMSO-d$_6$): δ 5.30 (2H, s), 6.01 (1H, d, J=2.0 Hz), 7.46-7.48 (1H, m), 7.60-7.67 (2H, m), 7.76-7.80 (2H, m), 8.09 (1H, s), 8.69 (1H, d, J=5.2 Hz). LCMS (mobile phase: 5%-95% Acetonitrile-Water-0.1% TFA): purity is >95%, Rt=3.773 min. [M+H] Calc'd for $C_{16}H_{11}Cl_2N_3O_3$, 364. Found, 364.

Example 88

2-[5-[(2,4-dichlorophenyl)methoxy]pyrazol-1-yl]pyridine-4-carboxylic acid

A. 2-[5-[(2,4-dichlorophenyl)methoxy]pyrazol-1-yl]pyridine-4-carbonitrile

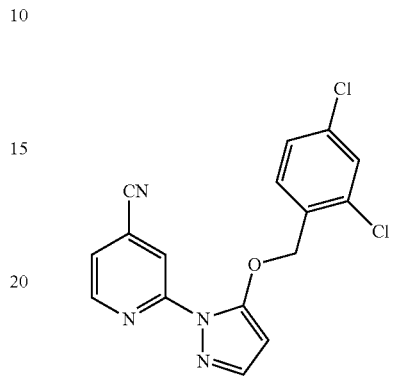

The title compound was prepared from 2-(5-hydroxy-1H-pyrazol-1-yl)pyridine-4-carbonitrile and (2,4-dichlorophenyl)methanol according to the procedure for the preparation of Example 39, part C. $^1$H NMR (400 MHz, CDCl$_3$): δ 5.29 (2H, s), 5.79 (1H, d, J=1.6 Hz), 7.29-7.32 (1H, m), 7.42 (1H, dd, J=1.2, 5.2 Hz), 7.45 (1H, d, J=2.4 Hz), 7.53 (1H, d, J=8.4 Hz), 7.59 (1H, d, J=1.6 Hz), 8.06 (1H, s), 8.71 (1H, d, J=4.8 Hz). [M+H] Calc'd for $C_{16}H_{10}Cl_2N_4O$, 345. Found, 345.

B. 2-[5-[(2,4-dichlorophenyl)methoxy]pyrazol-1-yl]pyridine-4-carboxylic acid

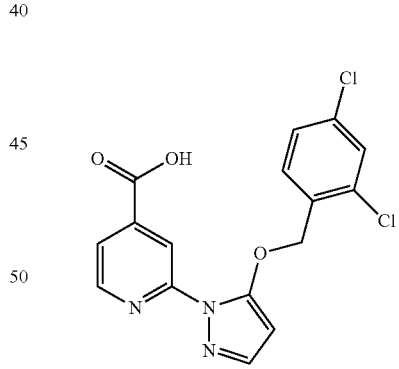

The title compound was prepared from 2-[5-[(2,4-dichlorophenyl)methoxy]pyrazol-1-yl]pyridine-4-carbonitrile according to the procedure for the preparation of Example 28, part E. $^1$H NMR (400 MHz, DMSO-d$_6$): δ 5.33 (2H, s), 6.08 (1H, d, J=2.4 Hz), 7.50 (1H, dd, J=2.4, 8.4 Hz), 7.62 (1H, d, J=1.6 Hz), 7.69 (1H, d, J=1.6 Hz), 7.72 (1H, d, J=8.4 Hz), 7.76 (1H, dd, J=1.6, 4.8 Hz), 8.09 (1H, s), 8.69 (1H, d, J=4.8 Hz), 13.88 (1H, s). LCMS (mobile phase: 5%-95% Acetonitrile-Water-0.1% TFA): purity is >95%, Rt=3.773 min. [M+H] Calc'd for $C_{16}H_{11}Cl_2N_3O_3$, 364. Found, 364.

Example 89

2-[5-[(4-chloro-2-methylphenyl)methoxy]pyrazol-1-yl]pyridine-4-carboxylic acid

A. 2-[5-[(4-chloro-2-methylphenyl)methoxy]pyrazol-1-yl]pyridine-4-carbonitrile

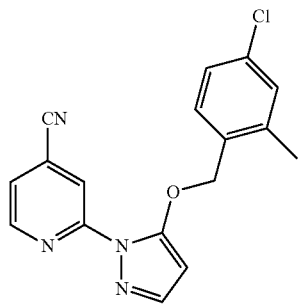 [SMILES: Cc1cc(Cl)ccc1COc1ccnn1-c1cc(C#N)ccn1]

The title compound was prepared from 2-(5-hydroxy-1H-pyrazol-1-yl)pyridine-4-carbonitrile and (4-chloro-2-methylphenyl)methanol according to the procedure for the preparation of Example 39, part C. $^1$H NMR (400 MHz, CDCl$_3$): δ 2.36 (3H, s), 5.18 (2H, s), 5.77 (1H, d, J=2.0 Hz), 7.18-7.22 (2H, m), 7.34 (1H, d, J=8.0 Hz), 7.39 (1H, dd, J=1.2 Hz J=5.2 Hz), 7.58 (1H, d, J=2.0 Hz), 8.00 (1H, s), 8.67 (1H, d, J=5.2 Hz). [M+H] Calc'd for C$_{17}$H$_{13}$ClN$_4$O, 325. Found, 325.

B. 2-[5-[(4-chloro-2-methylphenyl)methoxy]pyrazol-1-yl]pyridine-4-carboxylic acid

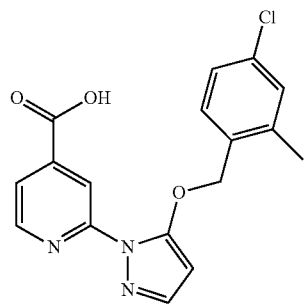 [SMILES: Cc1cc(Cl)ccc1COc1ccnn1-c1cc(C(=O)O)ccn1]

The title compound was prepared from 2-[5-[(4-chloro-2-methylphenyl)methoxy]pyrazol-1-yl]pyridine-4-carbonitrile according to the procedure for the preparation of Example 28, part E. $^1$H NMR (400 MHz, DMSO-d$_6$): δ 2.34 (3H, s), 5.26 (2H, s), 6.09 (1H, d, J=2.0 Hz), 7.27 (1H, dd, J=2.4, 8.0 Hz), 7.31 (1H, s), 7.51 (1H, d, J=8.0 Hz), 7.61 (1H, d, J=2.0 Hz), 7.74 (1H, dd, J=1.6, 4.8 Hz), 8.05 (1H, s), 8.66 (1H, d, J=4.8 Hz), 13.92 (1H, s). LCMS (mobile phase: 5%-95% Acetonitrile-Water-0.1% TFA): purity is >95%, Rt=3.773 min. [M+H] Calc'd for C$_{17}$H$_{14}$ClN$_3$O$_3$, 344. Found, 344.

Example 90

2-[5-[(4-chloro-2-methoxyphenyl)methoxy]pyrazol-1-yl]pyridine-4-carboxylic acid

A. 2-[5-[(4-chloro-2-methoxyphenyl)methoxy]pyrazol-1-yl]pyridine-4-carbonitrile

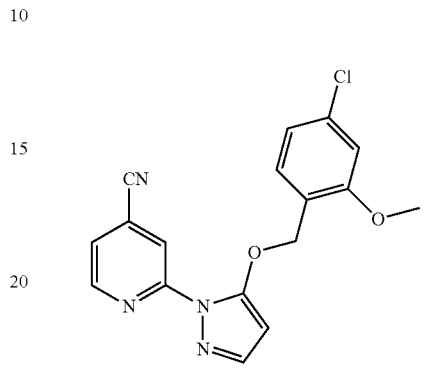

The title compound was prepared from 2-(5-hydroxy-1H-pyrazol-1-yl)pyridine-4-carbonitrile and (4-chloro-2-methoxyphenyl)methanol according to the procedure for the preparation of Example 39, part C. $^1$H NMR (400 MHz, CDCl$_3$): δ 3.89 (3H, s), 5.22 (2H, s), 5.78 (1H, d, J=2.0 Hz), 6.92 (1H, d, J=2.0 Hz), 6.95-6.98 (1H, m), 7.33-7.35 (1H, m), 7.39 (1H, dd, J=1.2, 5.2 Hz), 7.57-7.58 (1H, m), 8.06 (1H, s), 8.70 (1H, d, J=5.2 Hz). [M+H] Calc'd for C$_{17}$H$_{13}$ClN$_4$O$_2$, 341. Found, 341.

B. 2-[5-[(4-chloro-2-methoxyphenyl)methoxy]pyrazol-1-yl]pyridine-4-carboxylic acid

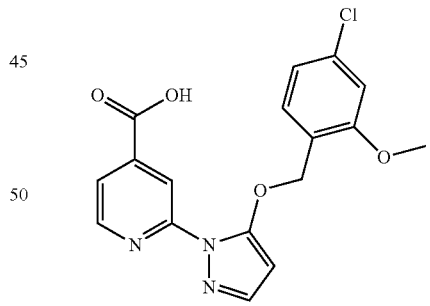

The title compound was prepared from 2-[5-[(4-chloro-2-methoxyphenyl)methoxy]pyrazol-1-yl]pyridine-4-carbonitrile according to the procedure for the preparation of Example 28, part E. $^1$H NMR (400 MHz, DMSO-d$_6$): δ 3.84 (3H, s), 5.22 (2H, s), 6.00 (1H, d, J=2.0 Hz), 7.03 (1H, dd, J=2.0, 8.4 Hz), 7.13 (1H, d, J=1.6 Hz), 7.49-7.51 (1H, m), 7.58 (1H, d, J=2.0 Hz), 7.74 (1H, dd, J=0.8 Hz, J=4.8 Hz), 8.05 (1H, s), 8.65 (1H, d, J=5.2 Hz). LCMS (mobile phase: 5%-95% Acetonitrile-Water-0.02% NH$_4$Ac): purity is >95%, Rt=2.706 min. [M+H] Calc'd for C$_{17}$H$_{14}$ClN$_3$O$_4$, 360. Found, 360.

Example 91

2-[5-[[4-chloro-3-(trifluoromethyl)phenyl]methoxy]pyrazol-1-yl]pyridine-4-carboxylic acid A. 2-[5-[[4-chloro-3-(trifluoromethyl)phenyl]methoxy]pyrazol-1-yl]pyridine-4-carbonitrile

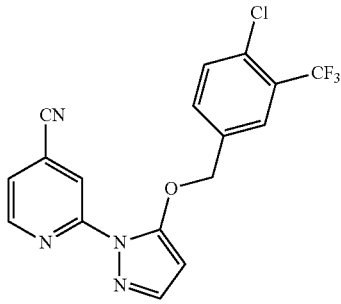 [SMILES: N#Cc1ccnc(-n2nccc2OCc2ccc(Cl)c(C(F)(F)F)c2)c1]

The title compound was prepared from 2-(5-hydroxy-1H-pyrazol-1-yl)pyridine-4-carbonitrile and [4-chloro-3-(trifluoromethyl)phenyl]methanol according to the procedure for the preparation of Example 39, part C. $^1$H NMR (400 MHz, CDCl$_3$): δ 5.25 (2H, s), 5.76 (1H, d, J=1.6 Hz), 7.42 (1H, dd, J=1.6, 5.2 Hz), 7.54 (2H, s), 7.58 (1H, d, J=2.0 Hz), 7.89 (1H, s), 8.00 (1H, s), 8.06 (1H, s), 8.69 (1H, d, J=4.8 Hz). [M+H] Calc'd for C$_{17}$H$_{10}$ClF$_3$N$_4$O, 379. Found, 379.

B. 2-[5-[[4-chloro-3-(trifluoromethyl)phenyl]methoxy]pyrazol-1-yl]pyridine-4-carboxylic acid

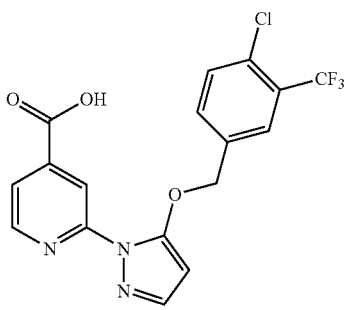

The title compound was prepared from 2-[5-[[4-chloro-3-(trifluoromethyl)phenyl]methoxy]pyrazol-1-yl]pyridine-4-carbonitrile according to the procedure for the preparation of Example 28, part E. $^1$H NMR (400 MHz, DMSO-d$_6$): δ 5.39 (2H, s), 6.03 (1H, d, J=2.4 Hz), 7.62 (1H, d, J=1.6 Hz), 7.75-7.80 (3H, m), 8.05 (1H, s), 8.09 (1H, s), 8.67 (1H, d, J=5.2 Hz), 13.93 (1H, s). LCMS (mobile phase: 5%-95% Acetonitrile-Water-0.1% TFA): purity is >95%, Rt=3.773 min. [M+H] Calc'd for C$_{17}$H$_{11}$ClF$_3$N$_3$O$_3$, 398. Found, 398.

Example 92

2-[5-[(3-chloro-4-methylphenyl)methoxy]pyrazol-1-yl]pyridine-4-carboxylic acid

A. (3-chloro-4-methylphenyl)methanol

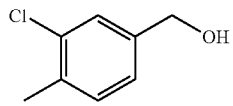

To a solution of 4-chloro-2-methylbenzoic acid (800 mg, 4.69 mmol) in THF (8 mL) that was cooled at 0° C., BH$_3$THF (14 mL, 1M in THF) was added into the solution drop wise. The mixture was then stirred at r.t. overnight. Add methanol to the system at 0° C. slowly until no gas released. Remove the solvent and the residue was extracted with ethylacetate, concentrated the organic phase to give 894 mg of the title compound (85%). $^1$H NMR (400 MHz, CDCl$_3$): δ 2.36 (3H, s), 4.63 (2H, s), 7.13-7.22 (2H, m), 7.35 (1H, s).

B. 2-[5-[(3-chloro-4-methylphenyl)methoxy]pyrazol-1-yl]pyridine-4-carbonitrile

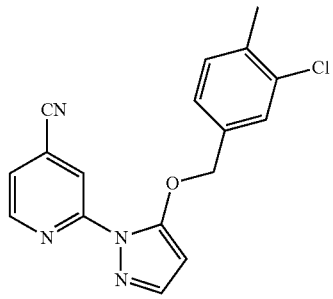 [SMILES: Cc1ccc(COc2ccnn2-c2cc(C#N)ccn2)cc1Cl]

The title compound was prepared from 2-(5-hydroxy-1H-pyrazol-1-yl)pyridine-4-carbonitrile and (3-chloro-4-methylphenyl)methanol according to the procedure for the preparation of Example 39, part C. $^1$H NMR (400 MHz, CDCl$_3$): δ 2.38 (3H, s), 5.18 (2H, s), 5.73 (1H, d, J=1.6 Hz), 7.19-7.25 (2H, m), 7.41 (1H, dd, J=1.2, 4.8 Hz), 7.44 (1H, s), 7.57 (1H, d, J=1.6 Hz), 8.03 (1H, s), 8.71 (1H, d, J=5.2 Hz). [M+H] Calc'd for C$_{17}$H$_{13}$ClN$_4$O, 325. Found, 325.

C. 2-[5-[(3-chloro-4-methylphenyl)methoxy]pyrazol-1-yl]pyridine-4-carboxylic acid

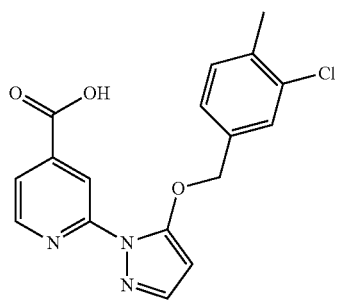 [SMILES: Cc1ccc(COc2ccnn2-c2cc(C(=O)O)ccn2)cc1Cl]

The title compound was prepared from 2-[5-[(3-chloro-4-methylphenyl)methoxy]pyrazol-1-yl]pyridine-4-carbonitrile according to the procedure for the preparation of Example 28, part E. $^1$H NMR (400 MHz, DMSO-d$_6$): δ 2.31 (3H, s), 5.23 (2H, s), 5.94 (1H, d, J=2.0 Hz), 7.31-7.37 (2H, m), 7.52-7.54 (2H, m), 7.65 (1H, d, J=4.8 Hz), 7.94 (1H, s), 8.45 (1H, d, J=4.8 Hz). LCMS (mobile phase: 5%-95% Acetonitrile-Water-0.02% NH$_4$Ac): purity is >95%, Rt=2.787 min. [M+H] Calc'd for C$_{17}$H$_{14}$ClN$_3$O$_3$, 344. Found, 344.

Example 93

2-[5-[(3-fluoro-4-methylphenyl)methoxy]pyrazol-1-yl]pyridine-4-carboxylic acid

A. 2-[5-[(3-fluoro-4-methylphenyl)methoxy]pyrazol-1-yl]pyridine-4-carbonitrile

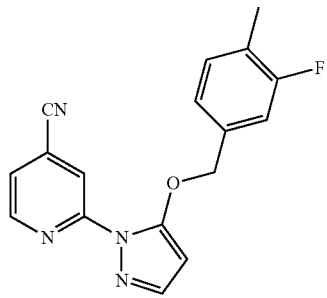 [SMILES: Cc1ccc(COc2ccnn2-c2cc(C#N)ccn2)cc1F]

The title compound was prepared from 2-(5-hydroxy-1H-pyrazol-1-yl)pyridine-4-carbonitrile and (3-fluoro-4-methylphenyl)methanol according to the procedure for the preparation of Example 39, part C. $^1$H NMR (400 MHz, CDCl$_3$): δ 2.28 (3H, s), 5.19 (2H, s), 5.72 (1H, d, J=2.0 Hz), 7.18-7.20 (1H, m), 7.07-7.11 (2H, m), 7.41 (1H, dd, J=1.2, 4.8 Hz), 7.56 (1H, d, J=1.6 Hz), 8.03 (1H, s), 8.71 (1H, d, J=4.8 Hz). [M+H] Calc'd for C$_{17}$H$_{13}$FN$_4$O, 309. Found, 309.

B. 2-[5-[(3-fluoro-4-methylphenyl)methoxy]pyrazol-1-yl]pyridine-4-carboxylic acid

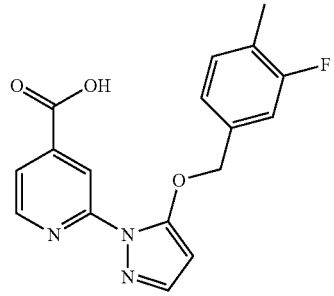 [SMILES: Cc1ccc(COc2ccnn2-c2cc(C(=O)O)ccn2)cc1F]

The title compound was prepared from 2-[5-[(3-fluoro-4-methylphenyl)methoxy]pyrazol-1-yl]pyridine-4-carbonitrile according to the procedure for the preparation of Example 28, part E. $^1$H NMR (400 MHz, DMSO-d$_6$): δ 2.22 (3H, s), 5.25 (2H, s), 6.00 (1H, d, J=2.0 Hz), 7.19-7.31 (3H, m), 7.59 (1H, d, J=1.6 Hz), 7.76-7.77 (1H, m), 8.07 (1H, s), 8.68 (1H, d, J=5.2 Hz), 13.91 (1H, s). LCMS (mobile phase: 5%-95% Acetonitrile-Water-0.1% TFA): purity is >95%, Rt=3.337 min. [M+H] Calc'd for C$_{17}$H$_{14}$FN$_3$O$_3$, 328. Found, 328.

Example 94

2-[5-[(2,3-difluoro-4-methylphenyl)methoxy]pyrazol-1-yl]pyridine-4-carboxylic acid A. (2,3-difluoro-4-methylphenyl)methanol

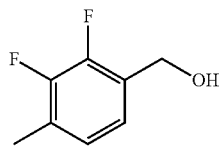

The title compound was prepared from 2,3-difluoro-4-methyl-benzoic acid according to the procedure for the preparation of Example 92, part A. $^1$H NMR (400 MHz, CDCl$_3$): δ 2.36 (3H, s), 4.63 (2H, s), 7.13-7.22 (2H, m), 7.35 (1H, s).

B. 2-[5-[(2,3-difluoro-4-methylphenyl)methoxy]pyrazol-1-yl]pyridine-4-carbonitrile

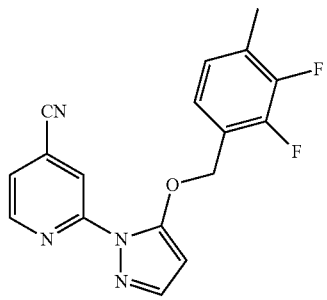 [SMILES: Cc1ccc(COc2ccnn2-c2cc(C#N)ccn2)c(F)c1F]

The title compound was prepared from 2-(5-hydroxy-1H-pyrazol-1-yl)pyridine-4-carbonitrile and (2,3-difluoro-4-methylphenyl)methanol according to the procedure for the preparation of Example 39, part C. $^1$H NMR (400 MHz, CDCl$_3$): δ 2.32 (3H, s), 5.28 (2H, s), 5.80 (1H, s), 6.98 (1H, d, J=6.8 Hz), 7.11 (1H, d, J=7.2 Hz), 7.40 (1H, d, J=5.2 Hz), 7.58 (1H, s), 8.01 (1H, s), 8.70 (1H, d, J=4.8 Hz). [M+H] Calc'd for C$_{17}$H$_{12}$F$_2$N$_4$O, 327. Found, 327.

C. 2-[5-[(2,3-difluoro-4-methylphenyl)methoxy]pyrazol-1-yl]pyridine-4-carboxylic acid

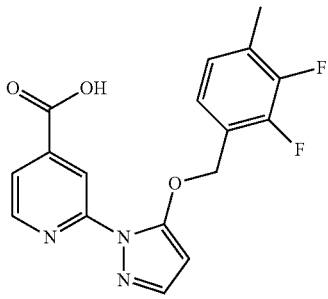 [SMILES: Cc1ccc(COc2ccnn2-c2cc(C(=O)O)ccn2)c(F)c1F]

The title compound was prepared from 2-[5-[(2,3-difluoro-4-methylphenyl)methoxy]pyrazol-1-yl]pyridine-4-carbonitrile according to the procedure for the preparation of Example 28, part E. $^1$H NMR (400 MHz, DMSO-d$_6$): δ 2.27 (3H, s), 5.32 (2H, s), 6.08 (1H, s), 7.10-7.14 (1H, m), 7.28-7.31 (1H, m), 7.61 (1H, s), 7.75 (1H, d, J=4.8 Hz), 8.03 (1H, s), 8.66 (1H, d, J=4.8 Hz), 13.90 (1H, s). LCMS (mobile phase: 5%-95% Acetonitrile-Water-0.02% NH$_4$Ac): purity is >95%, Rt=2.269 min. [M+H] Calc'd for C$_{17}$H$_{13}$F$_2$N$_3$O$_3$, 346. Found, 346.

Preparation 5: methyl 3-amino-4-ethylbenzoate

A. 4-ethyl-3-nitrobenzoic acid

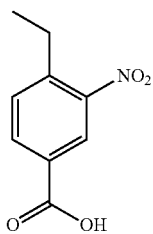

To a suspension of 4-ethyl benzoic acid (4.53 g, 30.16 mmol) in concentrated sulfuric acid (24 mL) at 0° C. was added nitric acid (12 mL). The mixture was stirred for 1.5 h at 0° C. Poured into ice water, filtered and dried the solid to give 5.79 g of the title compound (98%). $^1$H NMR (400 MHz, DMSO-d$_6$): δ 1.23 (3H, t, J=7.2 Hz), 2.88 (2H, q, J=7.2 Hz), 7.67 (1H, d, J=8.0 Hz), 8.15 (1H, dd, J=1.6, 8.0 Hz), 8.36 (1H, d, J=1.6 Hz).

B. methyl 4-ethyl-3-nitrobenzoate

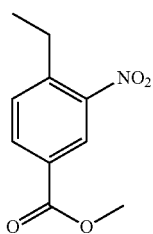

To a suspension of 4-ethyl-3-nitrobenzoic acid (5.76 g, 29.53 mmol) in methanol (30 mL) at 0° C., was added SOCl$_2$ (10.54 g, 88.61 mmol) slowly, stirred at this temperature for 1 h, then heated to 50° C. and stirred at this temperature for 3 h. Cooled to room temperature and removed the solvent, the residue was extracted with ethyl acetate, and concentrated to give 6.05 g of the title compound (98%). $^1$H NMR (400 MHz, CDCl$_3$): δ 1.31 (3H, t, J=7.2 Hz), 2.97 (2H, q, J=7.2 Hz), 3.96 (3H, s), 7.47 (1H, d, J=8.4 Hz), 8.17 (1H, dd, J=1.6, 8.4 Hz), 8.52 (1H, d, J=1.6 Hz).

C. methyl 3-amino-4-ethylbenzoate

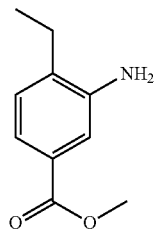

Charged methyl 4-ethyl-3-nitrobenzoate (5.0 g, 23.92 mmol), Pd/C (500 mg) and methanol (50 mL) to a flask, purged with hydrogen and stirred at r.t. overnight. It was then filtered and concentrated to give 4.0 g of the title compound (94%). $^1$H NMR (400 MHz, CDCl$_3$): δ 1.26 (3H, t, J=7.6 Hz), 2.54 (2H, q, J=7.6 Hz), 3.73 (2H, s), 3.87 (3H, s), 7.12 (1H, d, J=8.0 Hz), 7.35 (1H, s), 7.41 (1H, d, J=7.6 Hz). [M+H] Calc'd for C$_{10}$H$_{13}$NO$_2$, 180. Found, 180.

Example 95

2-[5-[(3-chloro-4-ethylphenyl)methoxy]pyrazol-1-yl]pyridine-4-carboxylic acid

A. methyl 3-chloro-4-ethylbenzoate

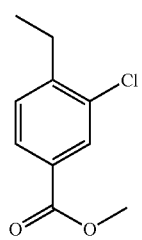

Charge NaNO$_2$ (579 mg, 8.37 mmol) and concentrated sulfuric acid (6 mL) to a flask. As methyl 3-amino-4-ethylbenzoate (1.37 g, 7.62 mmol, PREPARATION 5) in acetic acid (18 mL) was added at 0° C., color of the mixture turned to yellow, and then stirred at 5° C. for 1.5 h. The solution above was added to a dark mixture of CuCl (1.65 g, 16.65 mmol) in concentrated HCl (18 mL) slowly at 0° C., stirred for 2 h, and poured into ice water, extracted with DCM, the organic phase was concentrated to give 582 mg of the title compound (38%). $^1$H NMR (400 MHz, CDCl$_3$): δ 1.25 (3H, t, J=8.0 Hz), 2.80 (2H, q, J=7.6 Hz), 3.91 (3H, s), 7.30 (1H, d, J=7.6 Hz), 7.85 (1H, dd, J=1.2, 7.6 Hz), 8.01 (1H, d, J=1.6 Hz).

B. (3-chloro-4-ethylphenyl)methanol

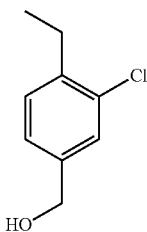

To a solution of methyl 3-chloro-4-ethylbenzoate (367 mg, 1.85 mmol) in THF (5 mL) that cooled to −50° C., LiAlH₄ (141 mg, 2.70 mmol) was added in portions. After which, the mixture was stirred at this temperature for 1 h. Added water (0.2 mL) slowly, followed by NaOH (aq, 10%, 0.2 mL) and water (0.6 mL), the resulted mixture was filtered and washed with THF, concentrated the filtrate to give 308 mg of the title compound (98%). $^1$H NMR (400 MHz, CDCl$_3$): δ 1.22 (3H, t, J=7.6 Hz), 2.74 (2H, q, J=7.6 Hz), 4.63 (2H, d, J=5.2 Hz), 7.17-7.23 (2H, m), 7.35 (1H, s).

C. 2-[5-[(3-chloro-4-ethylphenyl)methoxy]pyrazol-1-yl]pyridine-4-carbonitrile

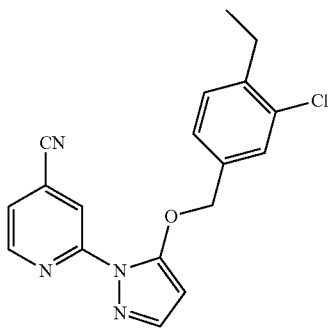 [SMILES: CCc1ccc(COc2ccnn2-c2cc(C#N)ccn2)cc1Cl]

The title compound was prepared from 2-(5-hydroxy-1H-pyrazol-1-yl)pyridine-4-carbonitrile and (3-chloro-4-ethylphenyl)methanol according to the procedure for the preparation of Example 39, part C. $^1$H NMR (400 MHz, CDCl$_3$): δ 1.23 (3H, t, J=8.0 Hz), 2.76 (2H, t, J=8.0 Hz), 5.18 (2H, s), 5.74 (1H, d, J=0.8 Hz), 7.26 (2H, s), 7.40-7.44 (2H, m), 7.57 (1H, s), 8.03 (1H, s), 8.72 (1H, d, J=4.8 Hz). [M+H] Calc'd for C$_{18}$H$_{15}$ClN$_4$O, 339. Found, 339.

C. 2-[5-[(3-chloro-4-ethylphenyl)methoxy]pyrazol-1-yl]pyridine-4-carboxylic acid

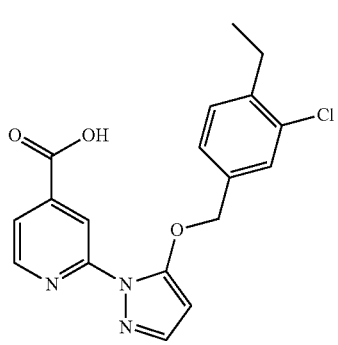 [SMILES: CCc1ccc(COc2ccnn2-c2cc(C(=O)O)ccn2)cc1Cl]

The title compound was prepared from 2-[5-[(3-chloro-4-ethylphenyl)methoxy]pyrazol-1-yl]pyridine-4-carbonitrile according to the procedure for the preparation of Example 28, part E. $^1$H NMR (400 MHz, DMSO-d$_6$): δ 1.15 (3H, t, J=10.0 Hz), 2.68 (2H, q, J=10.0 Hz), 5.23 (2H, s), 5.95 (1H, d, J=2.4 Hz), 7.36 (2H, s), 7.53 (2H, d, J=2.8 Hz), 7.67 (1H, d, J=6.4 Hz), 7.96 (1H, s), 8.47 (1H, d, J=6.4 Hz). LCMS (mobile phase: 5%-95% Acetonitrile-Water-0.1% TFA): purity is >95%, Rt=3.773 min. [M+H] Calc'd for C$_{18}$H$_{16}$ClN$_3$O$_3$, 358. Found, 358.

Example 96

2-[5-[(4-ethyl-3-fluorophenyl)methoxy]pyrazol-1-yl]pyridine-4-carboxylic acid

A. methyl 4-ethyl-3-fluorobenzoate

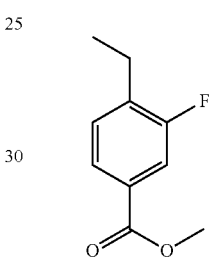

At 0° C., NaNO$_2$ (667 mg, 9.66 mmol) was added to a solution of methyl 3-amino-4-ethylbenzoate (1.57 g, 8.78 mmol, PREPARATION 5) in Py-HF (20 mL) in portions. The mixture was then heated to 25° C. for 5 h, pour into ice water, and extracted with DCM, concentrated the organic phase for silica gel chromatograph (PE/EA=10/1) to give 650 mg of the title compound (40%). $^1$H NMR (400 MHz, CDCl$_3$): δ 1.24 (3H, t, J=7.6 Hz), 2.72 (2H, q, J=7.6 Hz), 3.91 (3H, s), 7.25-7.29 (1H, m), 7.65 (1H, dd, J=1.2, 10.4 Hz), 7.75 (1H, dd, J=1.6, 8.0 Hz).

B. (4-ethyl-3-fluorophenyl)methanol

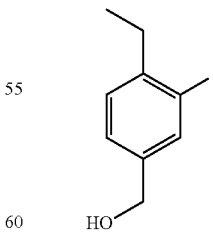

The title compound was prepared from methyl 4-ethyl-3-fluorobenzoate according to the procedure for the preparation of Example 95, part B. $^1$H NMR (400 MHz, CDCl$_3$): δ 1.22 (3H, t, J=8.0 Hz), 2.66 (2H, q, J=8.0 Hz), 4.64 (2H, s), 7.01-7.05 (2H, m), 7.18 (1H, t, J=8.0 Hz).

C. 2-[5-[(4-ethyl-3-fluorophenyl)methoxy]pyrazol-1-yl]pyridine-4-carbonitrile

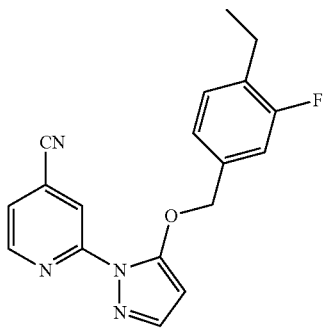 [SMILES: CCc1ccc(COc2ccnn2-c2cc(C#N)ccn2)cc1F]

The title compound was prepared from 2-(5-hydroxy-1H-pyrazol-1-yl)pyridine-4-carbonitrile and (4-ethyl-3-fluorophenyl)methanol according to the procedure for the preparation of Example 39, part C. $^1$H NMR (400 MHz, CDCl$_3$): δ 1.16 (3H, t, J=7.6 Hz), 2.60 (2H, t, J=7.6 Hz), 5.13 (2H, s), 5.66 (1H, d, J=1.2 Hz), 7.02-7.05 (2H, m), 7.14-7.18 (1H, m), 7.34 (1H, d, J=5.2 Hz), 7.50 (1H, d, J=1.2 Hz), 7.96 (1H, s), 8.64 (1H, d, J=4.8 Hz). [M+H] Calc'd for C$_{18}$H$_{15}$FN$_4$O, 323. Found, 323.

D. 2-[5-[(4-ethyl-3-fluorophenyl)methoxy]pyrazol-1-yl]pyridine-4-carboxylic acid

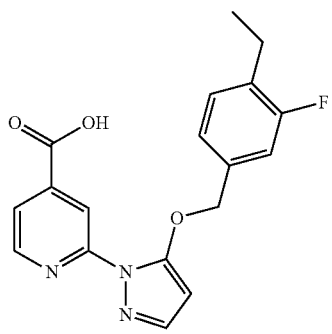 [SMILES: CCc1ccc(COc2ccnn2-c2cc(C(=O)O)ccn2)cc1F]

The title compound was prepared from 2-[5-[(4-ethyl-3-fluorophenyl)methoxy]pyrazol-1-yl]pyridine-4-carbonitrile according to the procedure for the preparation of Example 28, part E. $^1$H NMR (400 MHz, DMSO-d$_6$): δ 1.15 (3H, t, J=7.6 Hz), 2.61 (2H, q, J=7.6 Hz), 5.26 (2H, s), 6.01 (1H, d, J=1.6 Hz), 7.20-7.33 (3H, m), 7.60 (1H, d, J=1.6 Hz), 7.76 (1H, dd, J=1.2, 4.8 Hz), 8.08 (1H, s), 8.69 (1H, d, J=4.8 Hz) LCMS (mobile phase: 5%-95% Acetonitrile-Water-0.1% TFA): purity is >95%, Rt=3.634 min. [M+H] Calc'd for C$_{18}$H$_{16}$FN$_3$O$_3$, 342. Found, 342.

Preparation 6: methyl 2-(5-hydroxypyrazol-1-yl)pyridine-4-carboxylate

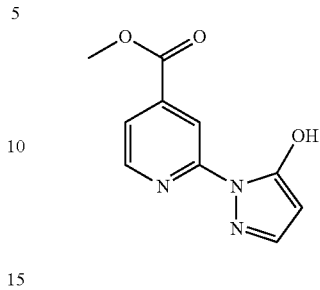

A solution of methyl 2-{5-[(4-bromobenzyl)oxy]-1H-pyrazol-1-yl}pyridine-4-carboxylate (765 mg, 1.97 mmol, EXAMPLE 68) in DCM (8 mL) was purged with nitrogen and cooled to −78° C. BBr$_3$ (6 mL, 5.93 mmol, 1M in DCM) was added at this temperature. Thereto, the mixture was stirred at the same temperature for an hour, methanol was added until no gas released, and then the above mixture was basified with NaHCO$_3$ aq (pH=3). Extracted with ethylacetate three times, and the organic phase was washed with brine and dried with Na$_2$SO$_4$, concentrated and the residue was washed with ethylacetate to give 260 mg of the title compound (60%). $^1$H NMR (400 MHz, CD$_3$OD): δ 4.02 (3H, s), 7.91-7.97 (2H, m), 8.69-8.70 (2H, m). [M+H] Calc'd for C$_{10}$H$_9$N$_3$O$_3$, 220. Found, 220.

Example 97

2-[5-[(3-cyanophenyl)methoxy]pyrazol-1-yl]pyridine-4-carboxylic acid

A. methyl 2-[5-[(3-cyanophenyl)methoxy]pyrazol-1-yl]pyridine-4-carboxylate

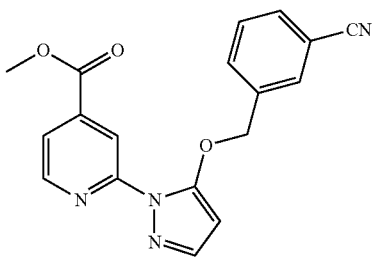 [SMILES: COC(=O)c1ccnc(-n2nccc2OCc2cccc(C#N)c2)c1]

The title compound was prepared from methyl 2-(5-hydroxypyrazol-1-yl)pyridine-4-carboxylate (PREPARATION 6) and (3-cyanophenyl)methanol according to the procedure for the preparation of Example 39, part C. [M+H] Calc'd for C$_{18}$H$_{14}$N$_4$O$_3$, 335. Found, 335.

B. 2-[5-[(3-cyanophenyl)methoxy]pyrazol-1-yl]pyridine-4-carboxylic acid

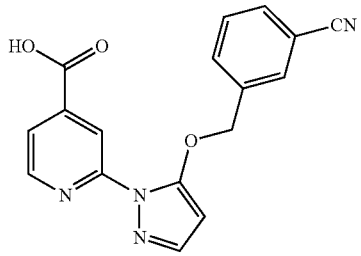 [SMILES: N#Cc1cccc(COc2ccnn2-c2cc(C(=O)O)ccn2)c1]

A solution of methyl 2-[5-[(3-cyanophenyl)methoxy]pyrazol-1-yl]pyridine-4-carboxylate (1.0 eq) and LiOH.H₂O (3.0 eq) in a mixture of water (2 mL) and THF (2 mL) was stirred at room temperature for 30 min. Diluted with another 2 mL water, and the mixture was washed with ethyl acetate twice (6 mL×2). The water phase was acidified with 1N HCl (pH=3), filtered and dried the solid to give the title compound. ¹H NMR (400 MHz, DMSO-d₆): δ 5.36 (2H, s), 6.03 (1H, s), 7.61-7.64 (2H, m), 7.77-7.78 (1H, m), 7.82-7.84 (2H, m), 7.96 (1H, s), 8.09 (1H, s), 8.69 (1H, d, J=4.4 Hz), 13.92 (1H, s). LCMS (mobile phase: 10%-95% Acetonitrile-Water-0.02% NH₄Ac): purity is >95%, Rt=2.106 min. [M+H] Calc'd for C₁₇H₁₂N₄O₃, 321. Found, 321.

Example 98 methyl 2-[5-[(4-cyanophenyl)methoxy]pyrazol-1-yl]pyridine-4-carboxylate

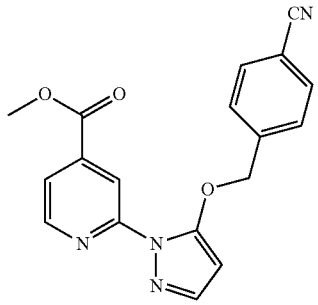 [SMILES: COC(=O)c1ccnc(-n2nccc2OCc2ccc(C#N)cc2)c1]

The title compound was prepared from methyl 2-(5-hydroxypyrazol-1-yl)pyridine-4-carboxylate (PREPARATION 6) and (4-cyanophenyl)methanol according to the procedure for the preparation of Example 39, part C. [M+H] Calc'd for C₁₈H₁₄N₄O₃, 335. Found, 335.

Example 99

2-[5-[(4-cyanophenyl)methoxy]pyrazol-1-yl]pyridine-4-carboxylic acid

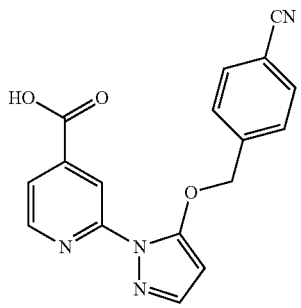 [SMILES: N#Cc1ccc(COc2ccnn2-c2cc(C(=O)O)ccn2)cc1]

The title compound was prepared from methyl 2-[5-[(4-cyanophenyl)methoxy]pyrazol-1-yl]pyridine-4-carboxylate (EXAMPLE 98) according to the procedure for the preparation of Example 97, part B. ¹H NMR (400 MHz, DMSO-d₆): δ 5.41 (2H, s), 6.00 (1H, d, J=2.0 Hz), 7.61 (1H, d, J=1.6 Hz), 7.67-7.69 (2H, m), 7.77 (1H, dd, J=0.8 Hz, J=4.8 Hz), 7.87-7.89 (2H, m), 8.10 (1H, s), 8.70 (1H, d, J=5.2 Hz), 13.92 (1H, s). LCMS (mobile phase: 10%-95% Acetonitrile-Water-0.02% NH₄Ac): purity is >95%, Rt=2.104 min. [M+H] Calc'd for C₁₇H₁₂N₄O₃, 321. Found, 321.

Example 100 methyl 2-[5-[(3-chloro-4-methylphenyl)methoxy]pyrazol-1-yl]pyridine-4-carboxylate

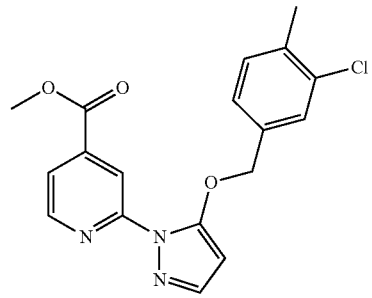 [SMILES: COC(=O)c1ccnc(-n2nccc2OCc2ccc(C)c(Cl)c2)c1]

The title compound was prepared from 2-[5-[(3-chloro-4-methylphenyl)methoxy]pyrazol-1-yl]pyridine-4-carboxylic acid (EXAMPLE 92) according to the procedure for the preparation of Example 62. ¹H NMR (400 MHz, CDCl₃): δ 2.38 (3H, s), 3.96 (3H, s), 5.18 (2H, s), 5.74 (1H, d, J=1.6 Hz), 7.21-7.26 (2H, m), 7.45 (1H, s), 7.58 (1H, d, J=2.0 Hz), 7.77-7.78 (1H, m), 8.33 (1H, s), 8.71 (1H, d, J=5.2 Hz). LCMS (mobile phase: 30%-95% Acetonitrile-Water-0.02% NH₄Ac): purity is >95%, Rt=3.628 min. [M+H] Calc'd for C₁₈H₁₆ClN₃O₃, 358. Found, 358.

Example 101 methyl 2-[5-[(3-fluoro-4-methylphenyl)methoxy]pyrazol-1-yl]pyridine-4-carboxylate

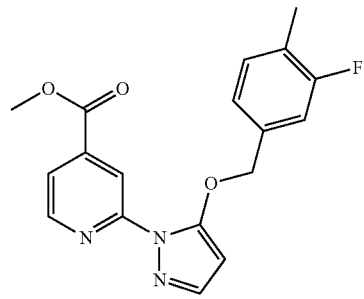 [SMILES: COC(=O)c1ccnc(-n2nccc2OCc2ccc(C)c(F)c2)c1]

The title compound was prepared from 2-[5-[(3-fluoro-4-methylphenyl)methoxy]pyrazol-1-yl]pyridine-4-carboxylic acid (EXAMPLE 93) according to the procedure for the preparation of Example 62. ¹H NMR (400 MHz, CDCl₃): δ 2.28 (3H, s), 3.97 (3H, s), 5.21 (2H, s), 5.75 (1H, s), 7.09-7.21 (3H, m), 7.60 (1H, s), 7.79 (1H, d, J=4.8 Hz), 8.35

(1H, s), 8.73 (1H, s). LCMS (mobile phase: 20%-95% Acetonitrile-Water-0.1% NH₄OH): purity is >95%, Rt=3.936 min. [M+H] Calc'd for C₁₅H₁₆FN₃O₃, 342. Found, 342.

Example 102 methyl 2-[5-[(3-chloro-4-ethylphenyl)methoxy]pyrazol-1-yl]pyridine-4-carboxylate

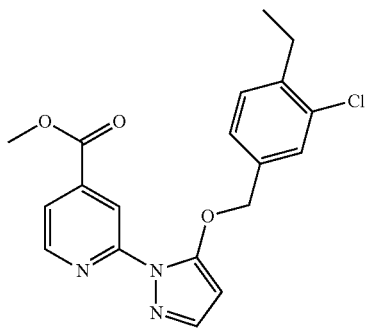 [SMILES: CCc1ccc(COc2ccnn2-c2cc(C(=O)OC)ccn2)cc1Cl]

The title compound was prepared from 2-[5-[(3-chloro-4-ethylphenyl)methoxy]pyrazol-1-yl]pyridine-4-carboxylic acid (EXAMPLE 95) according to the procedure for the preparation of Example 62. ¹H NMR (400 MHz, CDCl₃): δ 1.23 (3H, t, J=7.6 Hz), 2.76 (2H, q, J=7.6 Hz), 3.97 (3H, s), 5.18 (2H, s), 5.75 (1H, s), 7.26 (2H, s), 7.45 (1H, s), 7.58 (1H,$), 7.78 (1H, d, J=8.0 Hz), 8.33 (1H, s), 8.72 (1H, d, J=0.8 Hz). LCMS (mobile phase: 20%-95% Acetonitrile-Water-0.02% NH₄OH): purity is >95%, Rt=4.602 min. [M+H] Calc'd for C₁₉H₁₈ClN₃O₃, 372. Found, 372.

Example 103 methyl 2-[5-[(2,3-difluoro-4-methylphenyl)methoxy]pyrazol-1-yl]pyridine-4-carboxylate

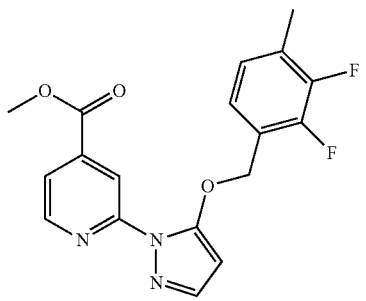 [SMILES: COC(=O)c1ccnc(-n2nccc2OCc2ccc(C)c(F)c2F)c1]

The title compound was prepared from 2-[5-[(2,3-difluoro-4-methylphenyl)methoxy]pyrazol-1-yl]pyridine-4-carboxylic acid (EXAMPLE 94) according to the procedure for the preparation of Example 62. ¹H NMR (400 MHz, CDCl₃): δ 2.31 (3H, s), 3.96 (3H, s), 5.27 (2H, s), 5.80 (1H, d, J=6.4 Hz), 6.94-6.97 (1H, m), 7.13-7.17 (1H, m), 7.58 (1H, s), 7.76 (1H, d, J=4.0 Hz), 8.30 (1H, s), 8.69 (1H, d, J=2.4 Hz). LCMS (mobile phase: 30%-95% Acetonitrile-Water-0.02% NH₄Ac): purity is >95%, Rt=3.485 min. [M+H] Calc'd for C₁₈H₁₅F₂N₃O₃, 360. Found, 360.

Example 104 methyl 2-[5-[(4-ethyl-3-fluorophenyl)methoxy]pyrazol-1-yl]pyridine-4-carboxylate

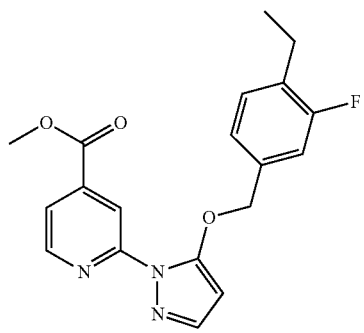 [SMILES: CCc1ccc(COc2ccnn2-c2cc(C(=O)OC)ccn2)cc1F]

The title compound was prepared from 2-[5-[(4-ethyl-3-fluorophenyl)methoxy]pyrazol-1-yl]pyridine-4-carboxylic acid (EXAMPLE 96) according to the procedure for the preparation of Example 62. ¹H NMR (400 MHz, CDCl₃): δ 1.23 (3H, t, J=7.6 Hz), 2.67 (2H, q, J=7.6 Hz), 3.97 (3H, s), 5.20 (2H, s), 5.75 (1H, d, J=1.6 Hz), 7.12-7.23 (3H, m), 7.58 (1H, d, J=2.0 Hz), 7.78 (1H, dd, J=1.6, 5.2 Hz), 8.34 (1H, s), 8.71 (1H, d, J=5.2 Hz). LCMS (mobile phase: 30%-95% Acetonitrile-Water-0.02% NH₄Ac): purity is >95%, Rt=3.783 min. [M+H] Calc'd for C₁₉H₁₈FN₃O₃, 356. Found, 356.

Preparation 7: 5-chloro-2-(hydroxymethyl)phenol

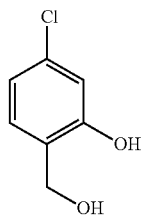

BH₃ (1M in THF, 359 mL) was added into a solution of 4-chloro-2-hydroxybenzoic acid (20.63 g, 0.12 mmol) in THF (40 mL) drop wise at 0° C. After which, the mixture was stirred at r.t. overnight. Extracted with EA twice, and washed the organic phase with brine and dried with anhydrous Na₂SO₄, concentrated to give the title compound (12 g, 63%). ¹H NMR (400 MHz, DMSO-d₆): δ 4.42 (2H, s), 4.97-5.06 (1H, m), 6.77 (1H, d, J=2.0 Hz), 6.82 (1H, dd, J=2.0 Hz, 8.0 Hz), 7.27 (1H, d, J=8.4 Hz), 9.85 (1H, s).

Example 105

2-[5-[(4-chloro-2-phenylmethoxyphenyl)methoxy]pyrazol-1-yl]pyridine-4-carboxylic acid

A. (4-chloro-2-phenylmethoxyphenyl)methanol

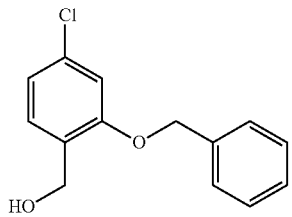 [SMILES: OCc1ccc(Cl)cc1OCc1ccccc1]

(Bromomethyl)benzene (323 mg, 1.89 mmol) was added to a mixture of 5-chloro-2-(hydroxymethyl)phenol (300 mg, 1.89 mmol, PREPARATION 7) and NaOH (1.1 mL, 2M in water) in ethanol (5 mL) at r.t. slowly. The reaction mixture was stirred overnight. Poured into ice water, and extracted with ethyl acetate twice, and washed the organic phase with water twice, brine and dried with anhydrous $Na_2SO_4$. The solvents were removed and the residue purified by silica gel chromatograph to give 120 mg of the title compound (28%).

B. 2-[5-[(4-chloro-2-phenylmethoxyphenyl)methoxy]pyrazol-1-yl]pyridine-4-carbonitrile

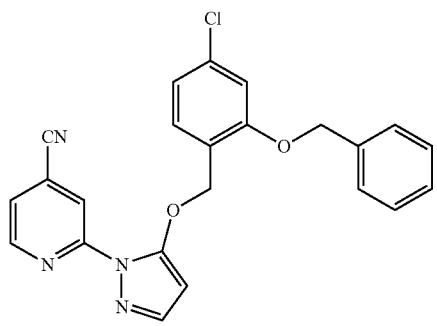 [SMILES: N#Cc1ccnc(-n2nccc2OCc2ccc(Cl)cc2OCc2ccccc2)c1]

The title compound was prepared from 2-(5-hydroxy-1H-pyrazol-1-yl)pyridine-4-carbonitrile and (4-chloro-2-phenylmethoxyphenyl)methanol according to the procedure for the preparation of Example 39, part C. $^1$H NMR (400 MHz, CDCl$_3$): δ 5.11 (2H, s), 5.27 (2H, s), 5.74 (1H, d, J=2.0 Hz), 6.98-7.00 (2H, m), 7.33-7.39 (7H, m), 7.55 (1H, d, J=2.0 Hz), 7.99 (1H, s), 8.67 (1H, d, J=5.2 Hz). [M+H] Calc'd for $C_{23}H_{17}ClN_4O_2$, 417. Found, 417.

C. 2-[5-[(4-chloro-2-phenylmethoxyphenyl)methoxy]pyrazol-1-yl]pyridine-4-carboxylic acid

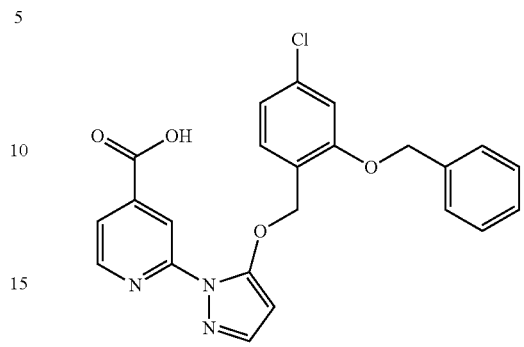

The title compound was prepared from 2-[5-[(4-chloro-2-phenylmethoxyphenyl)methoxy]pyrazol-1-yl]pyridine-4-carbonitrile according to the procedure for the preparation of Example 28, part E. $^1$H NMR (400 MHz, DMSO-d$_6$): δ 5.21 (2H, s) 5.22 (2H, s), 5.92 (1H, d, J=1.6 Hz), 7.03 (1H, dd, J=1.6 Hz, J=8.0 Hz), 7.19 (1H, d, J=1.2 Hz), 7.28-7.39 (5H, m), 7.50-7.52 (2H, m), 7.65 (1H, d, J=4.8 Hz), 7.95 (1H, s), 8.44 (1H, d, J=4.8 Hz). LCMS (mobile phase: 5%-95% Acetonitrile-Water-0.1% TFA): purity is >95%, Rt=4.032 min. [M+H] Calc'd for $C_{23}H_{18}ClN_3O_4$, 436. Found, 436.

Example 106

2-[5-[[4-chloro-2-(cyclopropylmethoxy)phenyl]methoxy]pyrazol-1-yl]pyridine-4-carboxylic acid

A. [4-chloro-2-(cyclopropylmethoxy)phenyl]methanol

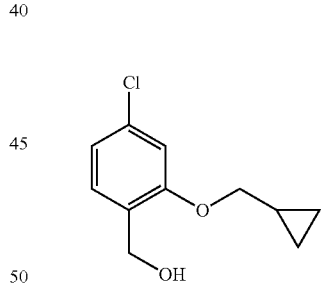

Charged 5-chloro-2-(hydroxymethyl)phenol (616 mg, 3.88 mmol, PREPARATION 7), bromocyclopropylmethanol (525 mg, 3.88 mmol), $K_2CO_3$ (1.07 g, 7.77 mmol) and DMF (6 mL) to a flask, purged with nitrogen and heated to 80° C. overnight. Poured into ice water, and extracted with ethyl acetate twice, and washed the organic phase with water twice, brine and dried with anhydrous $Na_2SO_4$, removed the solvent for silica gel chromatograph to give 108 mg of the title compound (13%). $^1$H NMR (400 MHz, CDCl$_3$): δ 0.33-0.37 (2H, m), 0.63-0.68 (2H, m), 1.26-1.28 (1H, m), 3.84 (2H, d, J=7.2 Hz), 4.67 (2H, s), 4.86 (1H, s), 6.84 (1H, d, J=1.2 Hz), 6.91 (1H, dd, J=2.0 Hz, 8.0 Hz), 7.19 (1H, d, J=7.6 Hz).

B. 2-[5-[[4-chloro-2-(cyclopropylmethoxy)phenyl]methoxy]pyrazol-1-yl]pyridine-4-carbonitrile

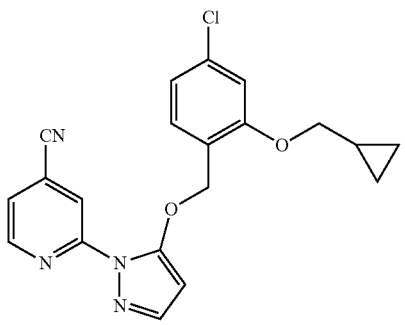 [SMILES: N#Cc1ccnc(-n2nccc2OCc2ccc(Cl)cc2OCC2CC2)c1]

The title compound was prepared from 2-(5-hydroxy-1H-pyrazol-1-yl)pyridine-4-carbonitrile and [4-chloro-2-(cyclopropylmethoxy)phenyl]methanol according to the procedure for the preparation of Example 39, part C. [M+H] Calc'd for $C_{20}H_{17}ClN_4O_2$, 381. Found, 381.

C. 2-[5-[[4-chloro-2-(cyclopropylmethoxy)phenyl]methoxy]pyrazol-1-yl]pyridine-4-carboxylic acid

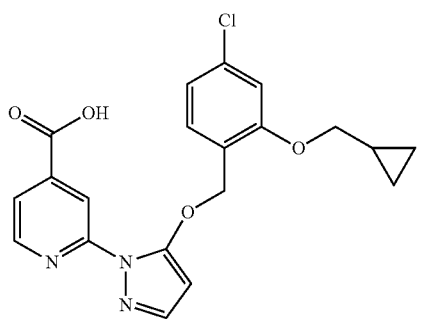 [SMILES: O=C(O)c1ccnc(-n2nccc2OCc2ccc(Cl)cc2OCC2CC2)c1]

The title compound was prepared from 2-[5-[[4-chloro-2-(cyclopropylmethoxy)phenyl]methoxy]pyrazol-1-yl]pyridine-4-carbonitrile according to the procedure for the preparation of Example 28, part E. $^1$H NMR (400 MHz, DMSO-$d_6$): δ 0.28-0.29 (2H, m), 0.50-0.54 (2H, m), 1.15-1.19 (1H, m), 3.87 (2H, d, J=6.8 Hz), 5.28 (2H, s), 6.99 (1H, d, J=6.4 Hz), 6.92-6.98 (2H, m), 7.41 (1H, d, J=8.0 Hz), 7.60 (1H, s), 7.82 (1H, d, J=2.8 Hz), 8.26 (1H, s), 8.63 (1H, d, J=3.2). LCMS (mobile phase: 10%-95% Acetonitrile-Water-0.1% TFA): purity is >95%, Rt=3.611 min. [M+H] Calc'd for $C_{20}H_{18}ClN_3O_4$, 400. Found, 400.

Example 107

2-[5-[(4-chloro-2-propoxyphenyl)methoxy]pyrazol-1-yl]pyridine-4-carboxylic acid

A. (4-chloro-2-propoxyphenyl)methanol

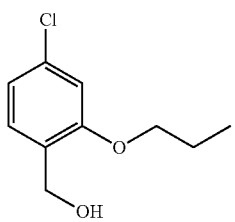

Charge 5-chloro-2-(hydroxymethyl)phenol (997 mg, 6.29 mmol, PREPARATION 7), iodopropane (1.17 g, 6.92 mmol), $K_2CO_3$ (1.74 g, 12.58 mmol) and DMF (6 mL) to a sealed tube. The reaction mixture was heated to 100° C. overnight. It was then poured into ice-water and extracted with ethyl acetate twice, washed the organic phase with water twice, brine and dried with $Na_2SO_4$, concentrated and purified by silica gel chromatograph to give the title compound (729 mg, 58%). $^1$H NMR (400 MHz, CDCl$_3$): δ 1.05 (3H, t, J=7.2 Hz), 1.79-1.88 (2H, m), 3.96 (2H, t, J=6.4 Hz), 4.64 (2H, s), 6.85 (1H, d, J=1.2 Hz), 6.91 (1H, dd, J=1.6 Hz, 8.4 Hz), 7.20 (1H, d, J=8.0 Hz).

B. 2-[5-[(4-chloro-2-propoxyphenyl)methoxy]pyrazol-1-yl]pyridine-4-carbonitrile

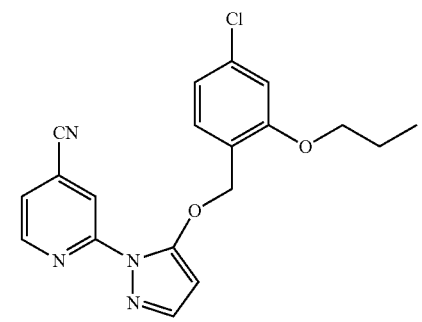 [SMILES: CCCOc1cc(Cl)ccc1COc1ccnn1-c1cc(C#N)ccn1]

The title compound was prepared from 2-(5-hydroxy-1H-pyrazol-1-yl)pyridine-4-carbonitrile and (4-chloro-2-propoxyphenyl)methanol according to the procedure for the preparation of Example 39, part C. $^1$H NMR (400 MHz, CDCl$_3$): δ 1.01 (3H, t, J=7.2 Hz), 1.77-1.86 (2H, m), 3.98 (2H, t, J=2.4 Hz), 5.24 (2H, s), 5.78 (1H, d, J=1.6 Hz), 6.90 (1H, d, J=1.6 Hz), 6.95 (1H, dd, J=2.0 Hz, 8.4 Hz), 7.34 (1H, d, J=8.4 Hz), 7.39 (1H, dd, J=0.8 Hz, 4.8 Hz), 7.58 (1H, d, J=1.6 Hz), 8.05 (1H, d, s), 8.70 (1H, d, J=4.8 Hz). [M+H] Calc'd for $C_{19}H_{17}ClN_4O_2$, 369. Found, 369.

C. 2-[5-[(4-chloro-2-propoxyphenyl)methoxy]pyrazol-1-yl]pyridine-4-carboxylic acid

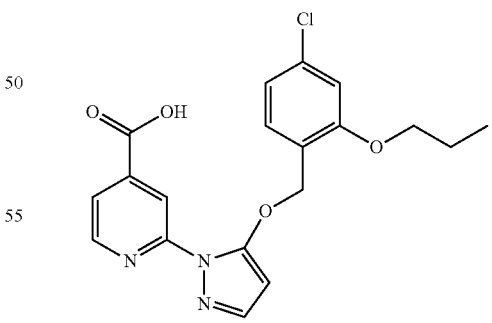

The title compound was prepared from 2-[5-[(4-chloro-2-propoxyphenyl)methoxy]pyrazol-1-yl]pyridine-4-carbonitrile according to the procedure for the preparation of Example 28, part E. $^1$H NMR (400 MHz, DMSO-$d_6$): δ 0.88 (3H, t, J=7.2 Hz), 1.61-1.70 (2H, m), 3.98 (2H, t, J=6.4 Hz), 5.20 (2H, s), 6.01 (1H, d, J=2.0 Hz), 7.01 (1H, dd, J=2.0 Hz, 8.4 Hz), 7.10 (1H, d, J=1.6 Hz), 7.49 (1H, d, J=8.4 Hz), 7.59

(1H, d, J=2.0 Hz), 7.74 (1H, dd, J=0.8 Hz, 5.2 Hz), 8.04 (1H, s), 8.66 (1H, d, J=4.8 Hz), 13.86 (1H, s). LCMS (mobile phase: 5%-95% Acetonitrile-Water-0.02% NH₄Ac): purity is >95%, Rt=2.889 min. [M+H] Calc'd for $C_{19}H_{18}ClN_3O_4$, 388. Found, 388.

Example 108

2-[5-[[4-chloro-2-(2,2,2-trifluoroethoxy)phenyl]methoxy]pyrazol-1-yl]pyridine-4-carboxylic acid A. 2,2,2-trifluoroethyl 4-methylbenzenesulfonate

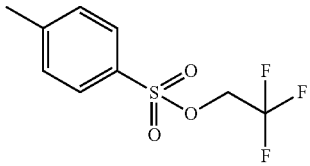 [SMILES: Cc1ccc(S(=O)(=O)OCC(F)(F)F)cc1]

To a solution of 4-methylbenzenesulfonyl chloride (3.4 g, 17.83 mmol) and Et₃N (3.61 g, 35.66 mmol) in DCM (80 mL) was added 2,2,2-trifluoroethan-1-ol (2.32 g, 23.18 mmol) slowly, the mixture was then stirred at r.t. until TLC showed no starting material. Water was added to the reaction mixture, and extracted with DCM, collected the organic phase and washed with brine, dried with anhydrous Na₂SO₄, removed the solvent to give 4.2 g of the title compound (93%). ¹H NMR (400 MHz, CDCl₃): δ 2.47 (3H, s), 4.34 (2H, q, J=8.0 Hz), 7.38 (2H, d, J=8.0 Hz), 7.81 (2H, d, J=8.0 Hz).

B. [4-chloro-2-(2,2,2-trifluoroethoxy)phenyl]methanol

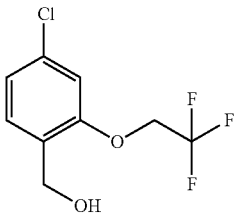 [SMILES: OCc1ccc(Cl)cc1OCC(F)(F)F]

Charged 2,2,2-trifluoroethyl 4-methylbenzenesulfonate (1.62 g, 6.37 mmol), 5-chloro-2-(hydroxymethyl)phenol (1.01 g, 6.37 mmol, PREPARATION 7), K₂CO₃ (1.76 g, 12.74 mmol) and DMF (7 mL) to a flask; heated to 100° C. overnight. The reaction mixture was then poured into ice-water and extracted with EA twice, washed the organic phase with water twice, brine and dried with Na₂SO₄, concentrated for gel chromatograph to give the title compound (200 mg, 13%). ¹H NMR (400 MHz, CDCl₃): δ 4.39 (2H, q, J=8.0 Hz), 4.70 (2H, d, J=5.2 Hz), 6.83 (1H, d, J=1.6 Hz), 7.05 (1H, dd, J=1.6 Hz, 8.0 Hz), 7.33 (1H, d, J=7.6 Hz).

C. 2-[5-[[4-chloro-2-(2,2,2-trifluoroethoxy)phenyl]methoxy]pyrazol-1-yl]pyridine-4-carbonitrile

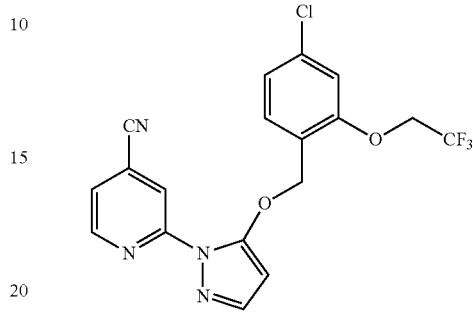

The title compound was prepared in 81% yield from 2-(5-hydroxy-1H-pyrazol-1-yl)pyridine-4-carbonitrile and [4-chloro-2-(2,2,2-trifluoroethoxy)phenyl]methanol according to the procedure for the preparation of Example 39, part C. ¹H NMR (400 MHz, CDCl₃): δ 4.43 (2H, q, J=8.0 Hz), 5.26 (2H, s), 5.79 (1H, d, J=1.6 Hz), 6.91 (1H, d, J=1.6 Hz), 7.10 (1H, dd, J=2.0 Hz, 8.4 Hz), 7.40 (1H, dd, J=1.2 Hz, 5.2 Hz), 7.44 (1H, d, J=8.0 Hz), 7.58 (1H, d, J=2.0 Hz), 8.04 (1H, s), 8.69 (1H, d, J=5.2 Hz). [M+H] Calc'd for $C_{18}H_{12}ClF_3N_4O_2$, 409. Found, 409.

D. 2-[5-[[4-chloro-2-(2,2,2-trifluoro ethoxy)phenyl]methoxy]pyrazol-1-yl]pyridine-4-carboxylic acid

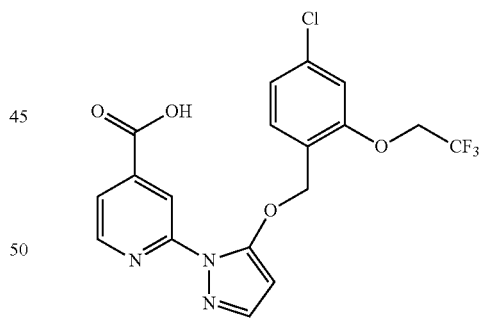

The title compound was prepared from 2-[5-[[4-chloro-2-(2,2,2-trifluoroethoxy)phenyl]methoxy]pyrazol-1-yl]pyridine-4-carbonitrile according to the procedure for the preparation of Example 28, part E. 1H NMR (400 MHz, DMSO-d₆): δ 4.87 (2H, q, J=8.0H), 5.22 (2H, s), 5.99 (1H, d, J=1.6 Hz), 7.16 (1H, dd, J=1.6 Hz, J=8.0 Hz), 7.34 (1H, d, J=1.2 Hz), 7.56-7.60 (2H, m), 7.74 (1H, dd, J=0.4 Hz, J=4.8 Hz), 8.05 (1H, s), 8.66 (1H, d, J=5.2 Hz), 13.88 (1H, s). LCMS (mobile phase: 5%-95% Acetonitrile-Water-0.1% TFA): purity is >95%, Rt=3.505 min. [M+H] Calc'd for $C_{18}H_{13}ClF_3N_3O_4$, 428. Found, 428.

Preparation 8: 2-[4-[2-[tert-butyl(dimethyl)silyl]oxyethyl]-5-[(4-fluorophenyl)methoxy]pyrazol-1-yl]pyridine-4-carbonitrile A. 4-hydroxybutanoyloxylithium

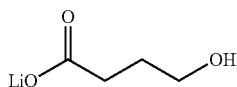

Charge oxolan-2-one (9.64 g, 0.11 mmol), lithium hydroxide (4.7 g, 0.11 mmol), methanol (10 mL) and water (4 mL) to a flask. The reaction mixture was stirred at r.t. for 16 h. The solvent was removed to give the title compound (14.1 g, 100%) which was used for the next step without further purification.

B. 4-[tert-butyl(dimethyl)silyl]oxybutanoyloxylithium

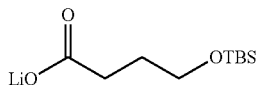 [SMILES: CC(C)(C)[Si](C)(C)OCCCC(=O)O]

To a suspension of 4-hydroxybutanoyloxylithium (5.17 g, 41.03 mmol) and 1H-imidazole (4.19 g, 61.55 mmol) in DMF (20 mL) was added TBSCl (7.42 g, 49.04 mmol) in portions at r.t. The reaction mixture was then stirred overnight. The reaction solution was poured into water and extracted with ethyl acetate three times. The organic phase separated and washed with water twice, brine and dried with anhydrous $Na_2SO_4$. It was then concentrated to give the title compound as colorless oil (8.0 g, 89%). [M+H] Calc'd for $C_{10}H_{21}LiO_3Si$, 225. Found, 225.

C. 4-[tert-butyl(dimethyl)silyl]oxybutanoic acid

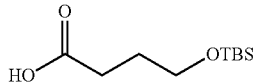

To a solution of 4-[tert-butyl(dimethyl)silyl]oxybutanoyloxylithium (8.0 g, 35.71 mmol) in ethyl acetate (10 mL), was carefully added $KHSO_4$ (5%) to adjust pH to about 1. It was then extracted with ethyl acetate three times and organic extracts washed with brine and dried with anhydrous $NaSO_4$. The organic extracts were concentrated to give the title compound (7.4 g, 95%). [M+H] Calc'd for $C_{10}H_{22}O_3Si$, 219. Found, 219.

D. methyl 4-[tert-butyl(dimethyl)silyl]oxybutanoate

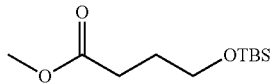

$CH_2N_2$ (1.04 g, 248.1 mmol) in ether (10 mL) was added to 4-[tert-butyl(dimethyl)silyl]oxybutanoic acid (5.41 g, 24.81 mmol) in a flask. The mixture was stirred overnight, concentrated to give the title compound (5.44 g, 95%). $^1$H NMR (400 MHz, $CDCl_3$): δ 0.03 (6H, s), 0.88 (9H, s), 1.81-184 (2H, m), 2.39 (2H, t, J=7.2 Hz), 3.63 (2H, d, J=6.4 Hz), 3.66 (3H, s). [M+H] Calc'd for $C_{11}H_{24}O_3Si$, 233. Found, 233.

E. methyl (2E)-4-[tert-butyl(dimethyl)silyl]oxy-2-(dimethylaminomethylidene)butanoate

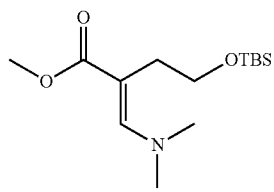 [SMILES: COC(=O)/C(=C/N(C)C)CCO[Si](C)(C)C(C)(C)C]

A mixture of methyl 4-[tert-butyl(dimethyl)silyl]oxybutanoate (6.8 g, 29.31 mmol) and N,N,N',N'-tetramethyl-1-[(2-methylpropan-2-yl)oxy]methanediamine (5.1 g, 29.31 mmol) in DMF (14 mL) in sealed tube was heated to 100° C. overnight. Added water to the mixture at 0° C. and extracted with ethyl acetate twice. The organic phase was separated and washed with water (2×) and brine and dried with anhydrous $Na_2SO_4$. The organic phase was concentrated to give the title compound (7.33 g, 91%). [M+H] Calc'd for $C_{14}H_{29}NO_3Si$, 288. Found, 288.

F. methyl (2E)-4-[tert-butyl(dimethyl)silyl]oxy-2-[[2-(4-cyanopyridin-2-yl)hydrazinyl]methylidene]butanoate

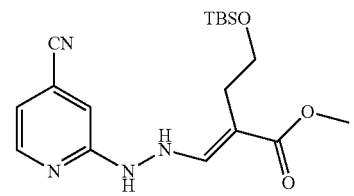 [SMILES: COC(=O)/C(=C/NNc1cc(C#N)ccn1)CCO[Si](C)(C)C(C)(C)C]

Charged methyl (2E)-4-[tert-butyl(dimethyl)silyl]oxy-2-(dimethylaminomethylidene)butanoate (7.33 g, 50%, 12.72 mmol), 2-hydrazinopyridine-4-carbonaitrile (1.70 g, 12.72 mmol), acetic acid (10 mL) and ethanol (50 mL) to a flask, the mixture was heated to 90° C. for 30 min, cooled to r.t. and basified with $NaHCO_3$ at 0° C. to pH=8. It was then extracted with ethyl acetate twice, concentrated and purified by silica gel chromatograph (PE/EA=10/1) to give the title compound (3.3 g, 34%). $^1$H NMR (400 MHz, $CDCl_3$): δ 0.04 (6H, d, J=1.6 Hz), 0.89 (9H, s), 1.96-2.17 (2H, m), 3.59 (1H, q, J=6.4 Hz), 3.69 (2H, d, J=6.0 Hz), 3.74 (3H, s), 6.91-6.92 (1H, m), 7.19 (1H, d, J=6.0 Hz), 7.38 (1H, s), 8.22 (1H, d, J=5.2 Hz), 8.33 (1H, s). [M+H] Calc'd for $C_{18}H_{28}N_4O_3Si$, 377. Found, 377.

G. 2-[4-[2-[tert-butyl(dimethyl)silyl]oxyethyl]-5-hydroxypyrazol-1-yl]pyridine-4-carbonitrile

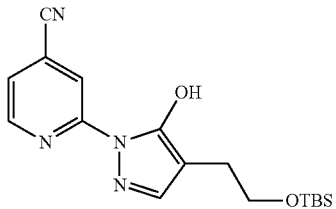 [SMILES: CC(C)(C)[Si](C)(C)OCCc1cnn(-c2cc(C#N)ccn2)c1O]

To a mixture of methyl (2E)-4-[tert-butyl(dimethyl)silyl]oxy-2-[[2-(4-cyanopyridin-2-yl)hydrazinyl]methylidene]butanoate (3.3 g, 8.77 mmol) in ethanol (50 mL) at 0° C. was added t-BuOK (2.95 g, 26.33 mmol). The reaction mixture was stirred overnight at r.t. It was then cooled to 0° C., diluted with ethyl acetate, and acidified with NaHSO₄ (5%) to pH=3. The organic phase was separated and concentrated to a residue which was washed with PE/EA to give 300 mg of the title compound (10%). $^1$H NMR (400 MHz, CD$_3$OD): δ 0.00 (6H, s), 0.85 (9H, s), 2.49 (2H, d, J=6.4 Hz), 3.74 (2H, d, J=6.4 Hz), 7.48 (1H, dd, J=1.2 Hz, 4.8 Hz), 7.60 (1H, s), 8.57 (1H, d, J=4.8 Hz), 8.61-8.63 (1H, m). [M+H] Calc'd for C$_{17}$H$_{24}$N$_4$O$_2$Si, 345. Found, 345.

H. 2-[4-[2-[tert-butyl(dimethyl)silyl]oxyethyl]-5-[(4-fluorophenyl)methoxy]pyrazol-1-yl]pyridine-4-carbonitrile

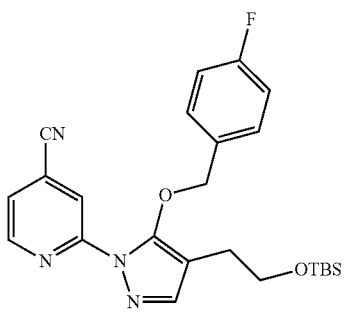 [SMILES: CC(C)(C)[Si](C)(C)OCCc1cnn(-c2cc(C#N)ccn2)c1OCc1ccc(F)cc1]

The title compound was prepared in 43% yield from 2-[4-[2-[tert-butyl(dimethyl)silyl]oxyethyl]-5-hydroxypyrazol-1-yl]pyridine-4-carbonitrile and (4-fluorophenyl)methanol according to the procedure for the preparation of Example 39, part C. $^1$H NMR (400 MHz, CDCl$_3$): δ 0.00 (6H, s), 0.85 (9H, s), 2.50 (2H, t, J=6.4 Hz), 3.68 (2H, d, J=6.4 Hz), 5.12 (2H, s), 6.98-7.02 (2H, m), 7.30-7.34 (3H, m), 7.54 (1H, s), 7.98 (1H, s), 8.58 (1H, d, J=5.2 Hz). [M+H] Calc'd for C$_{24}$H$_{29}$FN$_4$O$_2$Si, 453. Found, 453.

Example 109

2-[5-[(4-fluorophenyl)methoxy]-4-(2-hydroxyethyl)pyrazol-1-yl]pyridine-4-carboxylic acid

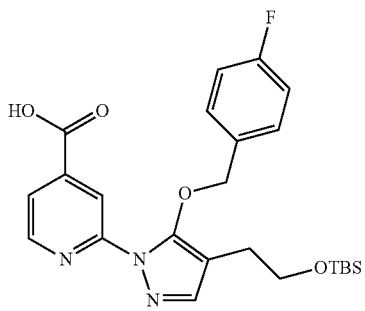 [SMILES: CC(C)(C)[Si](C)(C)OCCc1cnn(-c2cc(C(=O)O)ccn2)c1OCc1ccc(F)cc1]

The title compound was prepared in 50% yield from 2-[4-[2-[tert-butyl(dimethyl)silyl]oxyethyl]-5-[(4-fluorophenyl)methoxy]pyrazol-1-yl]pyridine-4-carbonitrile (PREPARATION 8) according to the procedure for the preparation of Example 28, part E. $^1$H NMR (400 MHz, DMSO-d$_6$): δ 2.47 (2H, t, J=6.4 Hz), 3.52-3.57 (2H, m), 4.73 (1H, t, J=4.8 Hz), 5.16 (2H, s), 7.17 (2H, t, J=8.8 Hz), 7.46 (2H, dd, J=6.4 Hz, 8.4 Hz), 7.61 (1H, s), 7.75 (1H, dd, J=1.6 Hz, 4.8 Hz), 8.03 (1H, s), 8.69 (1H, d, J=5.2 Hz). LCMS (mobile phase: 5%-95% Acetonitrile-Water-0.02% NH4Ac): purity is >95%, Rt=2.154 min. [M+H] Calc'd for C$_{18}$H$_{16}$FN$_3$O$_4$, 358. Found, 358.

Example 110

2-[4-[2-(dimethylamino)ethyl]-5-[(4-fluorophenyl)methoxy]pyrazol-1-yl]pyridine-4-carboxylic acid

A. 2-[5-[(4-fluorophenyl)methoxy]-4-(2-hydroxyethyl)pyrazol-1-yl]pyridine-4-carbonitrile

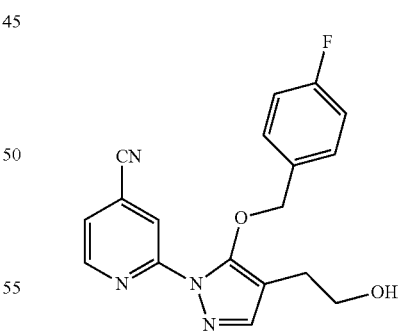

To a mixture of 2-[4-[2-[tert-butyl(dimethyl)silyl]oxyethyl]-5-[(4-fluorophenyl)methoxy]pyrazol-1-yl]pyridine-4-carbonitrile (60 mg, 0.13 mmol, PREPARATION 8) in THF (5 mL) was added 3N HCl (1 mL) at 0° C. The reaction mixture was stirred for 2 h at r.t. Cooled to 0° C., added ethyl acetate, water and acidified with NaHCO$_3$ to pH=8, and the mixture was then extracted with ethyl acetate and concentrated to afford the title compound (40 mg, 91%). [M+H] Calc'd for C$_{15}$H$_{15}$FN$_4$O$_2$, 339. Found, 339.

B. 2-[1-(4-cyanopyridin-2-yl)-5-[(4-fluorophenyl)methoxy]pyrazol-4-yl]ethyl methanesulfonate

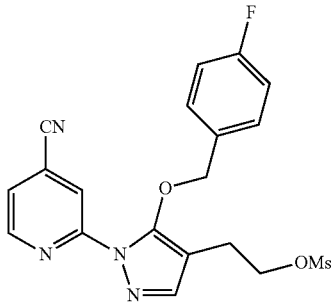 [SMILES: CS(=O)(=O)OCCc1cnn(-c2cc(C#N)ccn2)c1OCc1ccc(F)cc1]

To a mixture of 2-[5-[(4-fluorophenyl)methoxy]-4-(2-hydroxyethyl)pyrazol-1-yl]pyridine-4-carbonitrile (40 mg, 0.12 mmol), Et$_3$N (26 mg, 0.26 mmol) in DCM (5 mL) was added MeSO$_2$Cl (17 mg, 0.15 mmoL) at 0° C. The reaction mixture was then stirred for 2 h at r.t. Water was added and extracted with DCM and concentrated to afford the title compound (42 mg, 87%). [M+H] Calc'd for C$_{19}$H$_{17}$FN$_4$O$_4$S, 417. Found, 417.

C. 2-[4-[2-(dimethylamino)ethyl]-5-[(4-fluorophenyl)methoxy]pyrazol-1-yl]pyridine-4-carbonitrile

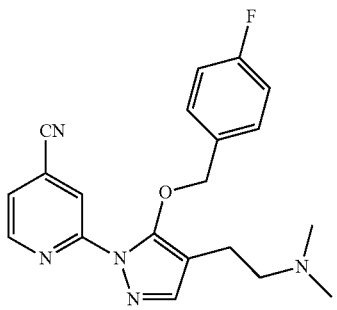 [SMILES: CN(C)CCc1cnn(-c2cc(C#N)ccn2)c1OCc1ccc(F)cc1]

To a solution of 2-[1-(4-cyanopyridin-2-yl)-5-[(4-fluorophenyl)methoxy]pyrazol-4-yl]ethyl methanesulfonate (42 mg, 0.1 mmol) and dimethylamine hydrochloride (41 mg, 0.5 mmol) in ACN (3 mL) was added K$_2$CO$_3$ (276 mg, 2 mmol) and KI (62 mg, 0.4 mmol) at rt. The reaction mixture was heated to 80° C. and stirred overnight. Filtered, solvent removed and purified by prep-HPLC to give the title compound (16 mg, 44%). $^1$H NMR (400 MHz, CDCl$_3$): δ 2.45 (6H, s), 2.56-2.61 (2H, m), 2.69-2.73 (2H, m), 5.16 (2H, s), 7.03-7.07 (2H, m), 7.35-7.41 (3H, m), 7.53 (1H, s), 8.03 (1H, s), 8.64 (1H, d, J=4.8 Hz). [M+H] Calc'd for C$_{20}$H$_{20}$FN$_5$O, 366. Found, 366.

D. 2-[4-[2-(dimethylamino)ethyl]-5-[(4-fluorophenyl)methoxy]pyrazol-1-yl]pyridine-4-carboxylic acid

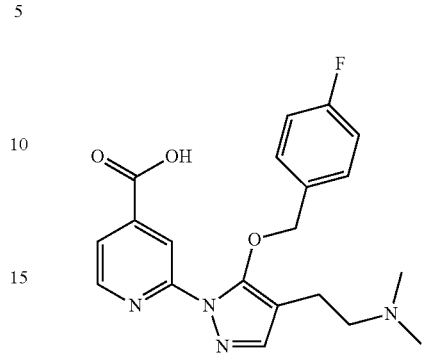

A mixture of 2-[4-[2-(dimethylamino)ethyl]-5-[(4-fluorophenyl)methoxy]pyrazol-1-yl]pyridine-4-carbonitrile (16 mg, 0.04 mmol) in NaOH aqueous (5M, 0.1 mL) and ethanol (2 mL) was heated to reflux for half an hour. It was then cooled in an ice-water bath, adjusted pH to 3-4, filtered, collected the solid and dried to give the title compound (11 mg, 50%). $^1$H NMR (400 MHz, CD$_3$OD): δ 2.68-2.71 (2H, m), 2.81 (6H, s), 3.21-3.24 (2H, m), 5.08 (2H, s), 6.91-6.96 (2H, m), 7.24-7.27 (2H, m), 7.56 (1H, s), 7.77 (1H, d, J=4.4 Hz), 8.04 (1H, s), 8.56 (1H, br). LCMS (mobile phase: 5%-95% Acetonitrile-Water-0.02% NH$_4$Ac): purity is >95%, Rt=2.153 min. [M+H] Calc'd for C$_{20}$H$_{21}$FN$_4$O$_3$, 385. Found, 385.

Example 111

2-[5-[(2-butoxy-4-chlorophenyl)methoxy]pyrazol-1-yl]pyridine-4-carboxylic acid

A. (4-chloro-2-butoxyphenyl)methanol

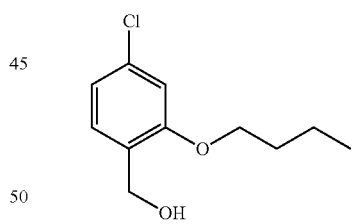

Charged 5-chloro-2-(hydroxymethyl)phenol (965 mg, 6.09 mmol, PREPARATION 7), bromobutane (918 mmol, 6.70 mmol), K$_2$CO$_3$ (1.68 g, 12.19 mmol) and DMF (6 mL) to a sealed tube, and the mixture was heated to 100° C. overnight. After cooling to room temperature, the reaction mixture was poured into ice water, extracted with ethyl acetate twice, and the organic extract was washed with water, brine and dried with anhydrous Na$_2$SO$_4$. Solvent removed and the residue was purified by flash column chromatograph to give 600 mg of the title compound (46%). $^1$H NMR (300 MHz, CDCl$_3$): δ 0.98 (3H, t, J=7.2 Hz), 1.46-1.56 (2H, m), 1.75-1.84 (2H, m), 2.23 (1H, t, J=6.0 Hz), 4.00 (2H, t, J=6.3 Hz), 4.64 (2H, d, J=6.3 Hz), 6.85 (1H, d, J=1.8 Hz), 6.91 (1H, dd, J=1.8 Hz, 8.1 Hz), 7.19 (1H, d, J=7.8 Hz).

B. 2-[5-[(2-butoxy-4-chlorophenyl)methoxy]pyrazol-1-yl]pyridine-4-carbonitrile

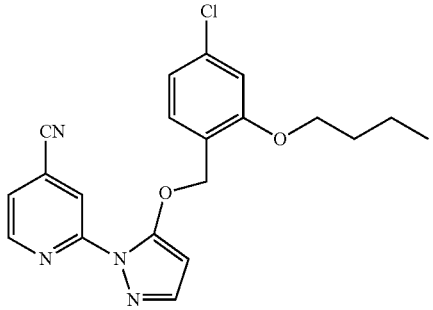 [SMILES: CCCCOc1cc(Cl)ccc1COc1ccnn1-c1cc(C#N)ccn1]

The title compound was prepared from 2-(5-hydroxy-1H-pyrazol-1-yl)pyridine-4-carbonitrile and (4-chloro-2-butoxyphenyl)methanol according to the procedure for the preparation of Example 39, part C. $^1$H NMR (400 MHz, CDCl$_3$): δ 0.95 (3H, t, J=7.2 Hz), 1.41-1.48 (2H, m), 1.74-1.79 (2H, m), 4.01 (2H, t, J=6.4 Hz), 5.23 (2H, s), 5.77 (1H, d, J=1.6 Hz), 6.90 (1H, d, J=2.0 Hz), 6.95 (1H, dd, J=1.6 Hz, 7.6 Hz), 7.34 (1H, d, J=8.0 Hz), 7.39 (1H, dd, J=0.8 Hz, 4.8 Hz), 7.57 (1H, d, J=1.6 Hz), 8.04 (1H, s), 8.70 (1H, d, J=4.8 Hz). [M+H] Calc'd for C$_{20}$H$_{19}$ClN$_4$O$_2$, 383. Found, 383.

C. 2-[5-[(2-butoxy-4-chlorophenyl)methoxy]pyrazol-1-yl]pyridine-4-carboxylic acid

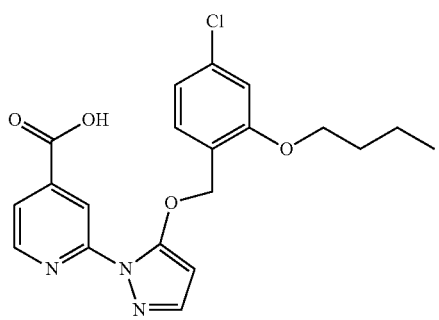 [SMILES: CCCCOc1cc(Cl)ccc1COc1ccnn1-c1cc(C(=O)O)ccn1]

The title compound was prepared from 2-[5-[(2-butoxy-4-chlorophenyl)methoxy]pyrazol-1-yl]pyridine-4-carbonitrile according to the procedure for the preparation of Example 28, part E. $^1$H NMR (400 MHz, DMSO-d6): δ 0.82 (3H, t, J=7.2 Hz), 1.27-1.36 (2H, m), 1.57-1.64 (2H, m), 4.00 (2H, t, J=6.4 Hz), 5.19 (2H, s), 5.99 (1H, d, J=2.0 Hz), 7.01 (1H, dd, J=1.6 Hz, 8.0 Hz), 7.10 (1H, d, J=1.6 Hz), 7.48 (1H, d, J=8.4 Hz), 7.59 (1H, d, J=1.6 Hz), 7.74 (1H, d, J=5.2 Hz), 8.04 (1H, s), 8.66 (1H, d, J=5.2 Hz), 13.86 (1H, s). [M+H] Calc'd for C$_{20}$H$_{20}$ClN$_3$O$_4$, 402. Found, 402.

Example 112

2-[5-[[4-chloro-2-(2-methylpropoxy)phenyl]methoxy]pyrazol-1-yl]pyridine-4-carboxylic acid

A. [4-chloro-2-(2-methylpropoxy)phenyl]methanol

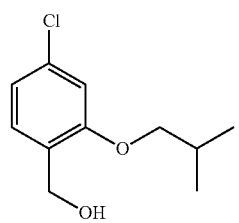

The title compound was prepared from 5-chloro-2-(hydroxymethyl)phenol (PREPARATION 7) and 1-bromo-2-methylpropane according to the procedure for the preparation of Example 111, part A. $^1$H NMR (400 MHz, CDCl$_3$): δ 1.04 (6H, d, J=6.8 Hz), 2.07-2.17 (1H, m), 2.29 (1H, s), 3.75 (2H, d, J=6.4 Hz), 4.65 (2H, d, J=4.8 Hz), 6.83 (1H, d, J=2.0 Hz), 6.90 (1H, dd, J=2.0 Hz, 8.0 Hz), 7.20 (1H, d, J=8.0 Hz).

B. 2-[5-[[4-chloro-2-(2-methylpropoxy)phenyl]methoxy]pyrazol-1-yl]pyridine-4-carbonitrile The title compound was prepared from 2-(5-hydroxy-1H-pyrazol-1-yl)pyridine-4-carbonitrile and [4-chloro-2-(2-methylpropoxy)phenyl]methanol according to the procedure for the preparation of Example 39, part C. $^1$H NMR (400 MHz, CDCl$_3$): δ 1.00 (6H, d, J=6.8 Hz), 2.06-2.12 (1H, m), 3.77 (2H, d, J=6.0 Hz), 5.24 (2H, s), 5.77 (1H, d, J=2.0 Hz), 6.89 (1H, d, J=1.6 Hz), 6.95 (1H, dd, J=2.0 Hz, 8.0 Hz), 7.34 (1H, d, J=8.0 Hz), 7.39 (1H, dd, J=0.8 Hz, 4.8 Hz), 7.57 (1H, d, J=2.0 Hz), 8.03 (1H, s), 8.70 (1H, d, J=4.8 Hz). [M+H] Calc'd for C$_{20}$H$_{19}$ClN$_4$O$_2$, 383. Found, 383.

C. 2-[5-[[4-chloro-2-(2-methylpropoxy)phenyl]methoxy]pyrazol-1-yl]pyridine-4-carboxylic acid

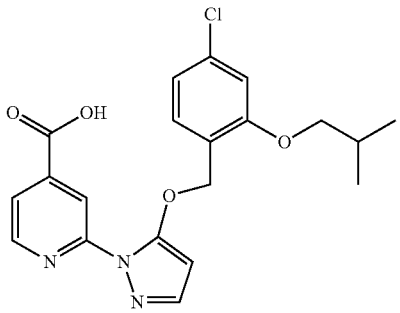 [SMILES: CC(C)COc1cc(Cl)ccc1COc1ccnn1-c1cc(C(=O)O)ccn1]

The title compound was prepared from 2-[5-[[4-chloro-2-(2-methylpropoxy)phenyl]methoxy]pyrazol-1-yl]pyridine-4-carbonitrile according to the procedure for the preparation of Example 28, part E. $^1$H NMR (400 MHz, DMSO-d$_6$): δ 0.88 (6H, d, J=6.4 Hz), 1.91-1.97 (1H, m), 3.79 (2H, d, J=6.0 Hz), 5.19 (2H, s), 5.96 (1H, d, J=2.0 Hz), 7.01 (1H, dd, J=2.0 Hz, 8.4 Hz), 7.09 (1H, d, J=2.0 Hz), 7.48 (1H, d, J=8.0 Hz), 7.55 (1H, d, J=1.6 Hz), 7.68 (1H, d, J=8.4 Hz), 7.96 (1H, s), 8.52 (1H, d, J=4.4 Hz). [M+H] Calc'd for C$_{20}$H$_{20}$ClN$_3$O$_4$, 402. Found, 402.

Example 113

2-[5-[(4-chloro-2-propan-2-yloxyphenyl)methoxy]pyrazol-1-yl]pyridine-4-carboxylic acid

A. (4-chloro-2-propan-2-yloxyphenyl)methanol

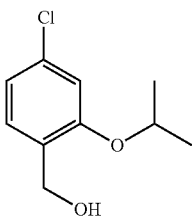

The title compound was prepared from 5-chloro-2-(hydroxymethyl)phenol (PREPARATION 7) and isopropylbromide according to the procedure for the preparation of Example 111, part A. $^1$H NMR (400 MHz, CDCl$_3$): δ 1.36 (6H, d, J=6.4 Hz), 2.40 (1H, s), 4.55-4.59 (1H, m), 4.61 (2H, s), 6.86 (1H, d, J=2.0 Hz), 6.89 (1H, dd, J=1.6 Hz, 7.6 Hz), 7.18 (1H, d, J=7.6 Hz).

B. 2-[5-[(4-chloro-2-propan-2-yloxyphenyl)methoxy]pyrazol-1-yl]pyridine-4-carbonitrile

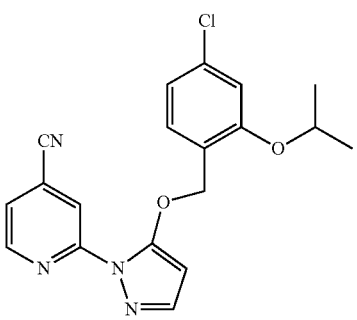 [SMILES: CC(C)Oc1cc(Cl)ccc1COc1ccnn1-c1cc(C#N)ccn1]

The title compound was prepared from 2-(5-hydroxy-1H-pyrazol-1-yl)pyridine-4-carbonitrile and (4-chloro-2-propan-2-yloxyphenyl)methanol according to the procedure for the preparation of Example 39, part C. $^1$H NMR (400 MHz, DMSO-d$_6$): δ 1.34 (6H, d, J=6.0 Hz), 4.56-4.62 (1H, m), 5.21 (2H, s), 5.77 (1H, d, J=1.6 Hz), 6.90 (1H, d, J=1.2 Hz), 6.93 (1H, dd, J=1.6 Hz, 8.0 Hz), 7.34 (1H, d, J=8.0 Hz), 7.39 (1H, dd, J=1.2 Hz, 5.2 Hz), 7.57 (1H, d, J=1.6 Hz), 8.04 (1H, s), 8.70 (1H, d, J=4.8 Hz). [M+H] Calc'd for C$_{19}$H$_{17}$ClN$_4$O$_2$, 369. Found, 369.

C. 2-[5-[(4-chloro-2-propan-2-yloxyphenyl)methoxy]pyrazol-1-yl]pyridine-4-carboxylic acid

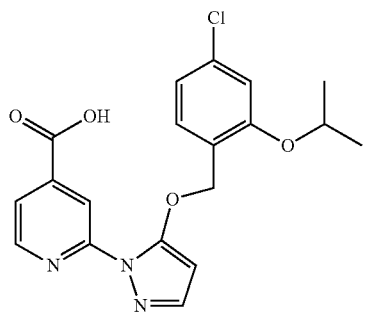 [SMILES: CC(C)Oc1cc(Cl)ccc1COc1ccnn1-c1cc(C(=O)O)ccn1]

The title compound was prepared from 2-[5-[(4-chloro-2-propan-2-yloxyphenyl)methoxy]pyrazol-1-yl]pyridine-4-carbonitrile according to the procedure for the preparation of Example 28, part E. $^1$H NMR (400 MHz, DMSO-d$_6$): δ 1.19 (6H, d, J=6.0 Hz), 4.66-4.72 (1H, m), 5.17 (2H, s), 5.99 (1H, d, J=2.0 Hz), 6.99 (1H, dd, J=2.0 Hz, 8.0 Hz), 7.13 (1H, d, J=2.0 Hz), 7.48 (1H, d, J=8.0 Hz), 7.58 (1H, d, J=2.0 Hz), 7.74 (1H, dd, J=1.6 Hz, 5.2 Hz), 8.05 (1H, s), 8.66 (1H, d, J=4.8 Hz), 13.87 (1H, s). [M+H] Calc'd for C$_{19}$H$_{18}$ClN$_3$O$_4$, 388. Found, 388.

Example 114

2-[5-[(2-butan-2-yloxy-4-chlorophenyl)methoxy]pyrazol-1-yl]pyridine-4-carboxylic acid

A. (2-butan-2-yloxy-4-chlorophenyl)methanol

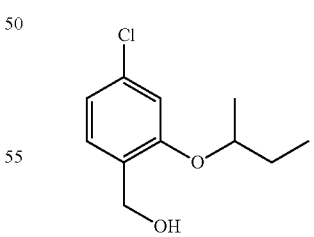

The title compound was prepared from 5-chloro-2-(hydroxymethyl)phenol (PREPARATION 7) and 2-bromobutane according to the procedure for the preparation of Example 111, part A. $^1$H NMR (400 MHz, CDCl$_3$): δ 0.98 (3H, t, J=7.6 Hz), 1.32 (3H, d, J=6.0 Hz), 1.65-1.79 (2H, m), 2.30 (1H, t, J=6.8 Hz), 4.32-4.40 (1H, m), 4.62 (2H, d, J=6.4 Hz), 6.85 (1H, d, J=1.6 Hz), 6.89 (1H, dd, J=1.6 Hz, 7.6 Hz), 7.19 (1H, d, J=8.4 Hz).

B. 2-[5-[(2-butan-2-yloxy-4-chlorophenyl)methoxy]pyrazol-1-yl]pyridine-4-carbonitrile

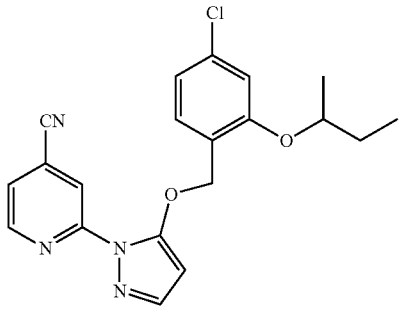 [SMILES: CCC(C)Oc1cc(Cl)ccc1COc1ccnn1-c1cc(C#N)ccn1]

The title compound was prepared from 2-(5-hydroxy-1H-pyrazol-1-yl)pyridine-4-carbonitrile and (2-butan-2-yloxy-4-chlorophenyl)methanol according to the procedure for the preparation of Example 39, part C. [M+H] Calc'd for $C_{20}H_{19}ClN_4O_2$, 383. Found, 383.

C. 2-[5-[(2-butan-2-yloxy-4-chlorophenyl)methoxy]pyrazol-1-yl]pyridine-4-carboxylic acid

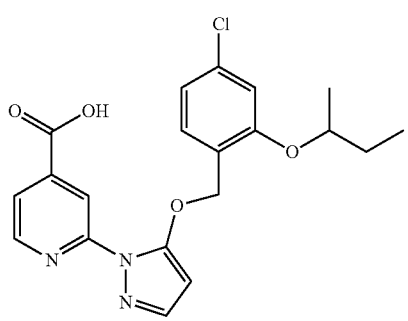 [SMILES: CCC(C)Oc1cc(Cl)ccc1COc1ccnn1-c1cc(C(=O)O)ccn1]

The title compound was prepared from 2-[5-[(2-butan-2-yloxy-4-chlorophenyl)methoxy]pyrazol-1-yl]pyridine-4-carbonitrile according to the procedure for the preparation of Example 28, part E. $^1$H NMR (400 MHz, DMSO-d$_6$): δ 0.82 (3H, t, J=7.6 Hz), 1.14 (3H, d, J=6.0 Hz), 1.50-1.59 (2H, m), 4.46-4.51 (1H, m), 5.15 (2H, s), 5.92 (1H, d, J=2.0 Hz), 6.98 (1H, dd, J=1.6 Hz, 8.0 Hz), 7.11 (1H, d, J=1.6 Hz), 7.47 (1H, d, J=7.6 Hz), 7.52 (1H, d, J=1.6 Hz), 7.64 (1H, d, J=4.8 Hz), 7.93 (1H, s), 8.45 (1H, d, J=4.4 Hz). [M+H] Calc'd for $C_{20}H_{20}ClN_3O_4$, 402. Found, 402.

Example 115

2-[5-[(4-chloro-2-ethoxyphenyl)methoxy]pyrazol-1-yl]pyridine-4-carboxylic acid

A. (4-chloro-2-ethoxyphenyl)methanol

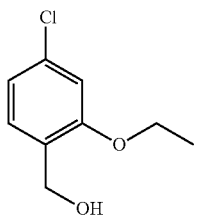

The title compound was prepared from 5-chloro-2-(hydroxymethyl)phenol (PREPARATION 7) and ethylbromide according to the procedure for the preparation of Example 111, part A. $^1$H NMR (400 MHz, CDCl$_3$): δ 1.44 (3H, t, J=6.8 Hz), 2.24 (1H, s), 4.07 (2H, q, J=6.8 Hz), 4.64 (2H, s), 6.85 (1H, d, J=1.6 Hz), 6.91 (1H, dd, J=1.6 Hz, 7.6 Hz), 7.20 (1H, d, J=8.0 Hz).

B. 2-[5-[(4-chloro-2-ethoxyphenyl)methoxy]pyrazol-1-yl]pyridine-4-carbonitrile

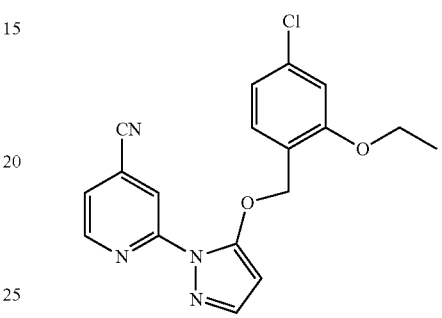

The title compound was prepared from 2-(5-hydroxy-1H-pyrazol-1-yl)pyridine-4-carbonitrile and (4-chloro-2-ethoxyphenyl)methanol according to the procedure for the preparation of Example 39, part C. $^1$H NMR (400 MHz, DMSO-d$_6$): δ 1.42 (3H, t, J=6.8 Hz), 4.09 (2H, q, J=6.8 Hz), 5.23 (2H, s), 5.79 (1H, d, J=1.6 Hz), 6.90 (1H, dd, J=2.0 Hz, 8.0 Hz), 6.95 (1H, dd, J=2.0 Hz, 8.0 Hz), 7.34 (1H, d, J=8.0 Hz), 7.39 (1H, m), 7.57 (1H, d, J=2.0 Hz), 8.05 (1H, s), 8.70 (1H, d, J=5.2 Hz). [M+H] Calc'd for $C_{18}H_{15}ClN_4O_2$, 355. Found, 355.

C. 2-[5-[(4-chloro-2-ethoxyphenyl)methoxy]pyrazol-1-yl]pyridine-4-carboxylic acid

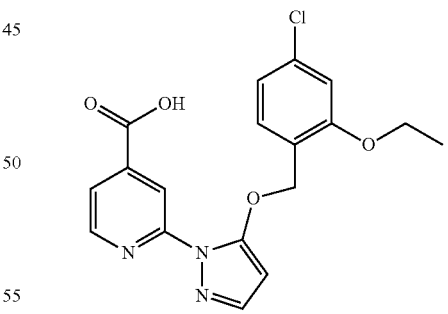

The title compound was prepared from 2-[5-[(4-chloro-2-ethoxyphenyl)methoxy]pyrazol-1-yl]pyridine-4-carbonitrile according to the procedure for the preparation of Example 28, part E. $^1$H NMR (400 MHz, DMSO-d$_6$): δ 1.26 (3H, t, J=6.8 Hz), 4.08 (2H, q, J=6.8 Hz), 5.20 (2H, s), 6.01 (1H, d, J=2.0 Hz), 7.01 (1H, dd, J=2.0 Hz, 8.0 Hz), 7.10 (1H, d, J=2.0 Hz), 7.48 (1H, d, J=8.0 Hz), 7.59 (1H, d, J=2.0 Hz), 7.74 (1H, dd, J=1.2 Hz, 5.2 Hz), 8.05 (1H, s), 8.67 (1H, d, J=4.8 Hz), 13.87 (1H, s). [M+H] Calc'd for $C_{18}H_{16}ClN_3O_4$, 374. Found, 374.

Example 116

2-[5-[[4-chloro-2-(2-methoxyethoxy)phenyl]methoxy]pyrazol-1-yl]pyridine-4-carboxylic acid A. [4-chloro-2-(2-methoxyethoxy)phenyl]methanol

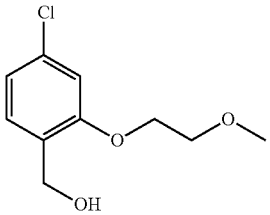

The title compound was prepared from 5-chloro-2-(hydroxymethyl)phenol (PREPARATION 7) and 2-methoxyethylbromide according to the procedure for the preparation of Example 111, part A. $^1$H NMR (400 MHz, CDCl$_3$): δ 3.24 (3H, s), 3.73-3.75 (2H, m), 4.16-4.18 (2H, m), 4.62 (2H, s), 6.87 (1H, d, J=1.6 Hz), 6.93 (1H, dd, J=2.0 Hz, 8.0 Hz), 7.18 (1H, d, J=8.0 Hz).

B. 2-[5-[[4-chloro-2-(2-methoxyethoxy)phenyl]methoxy]pyrazol-1-yl]pyridine-4-carbonitrile

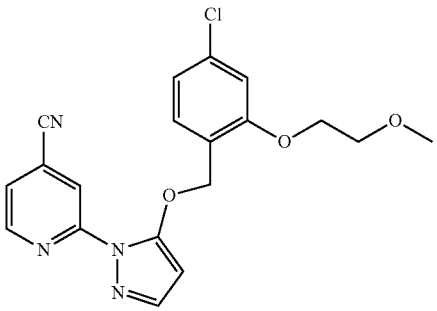 [SMILES: COCCOc1cc(Cl)ccc1COc1ccnn1-c1cc(C#N)ccn1]

The title compound was prepared from 2-(5-hydroxy-1H-pyrazol-1-yl)pyridine-4-carbonitrile and (4-chloro-2-(2-methoxyethoxy)phenyl)methanol according to the procedure for the preparation of Example 39, part C. $^1$H NMR (400 MHz, CDCl$_3$): δ 3.39 (3H, s), 3.74 (2H, t, J=4.8 Hz), 4.18 (2H, t, J=4.8 Hz), 5.26 (2H, s), 5.81 (1H, s), 6.92 (1H, d, J=1.6 Hz), 6.98 (1H, dd, J=2.0 Hz, 8.0 Hz), 7.35 (1H, d, J=8.0 Hz), 7.39 (1H, d, J=5.2 Hz), 7.57 (1H, d, J=1.2 Hz), 8.06 (1H, s), 8.70 (1H, d, J=5.2 Hz). [M+H] Calc'd for C$_{19}$H$_{17}$ClN$_4$O$_3$, 385. Found, 385.

C. 2-[5-[[4-chloro-2-(2-methoxyethoxy)phenyl]methoxy]pyrazol-1-yl]pyridine-4-carboxylic acid

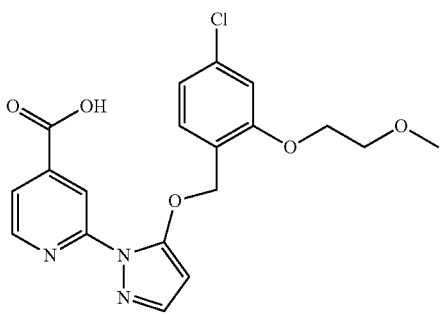 [SMILES: COCCOc1cc(Cl)ccc1COc1ccnn1-c1cc(C(=O)O)ccn1]

The title compound was prepared from 2-[5-[[4-chloro-2-(2-methoxyethoxy)phenyl]methoxy]pyrazol-1-yl]pyridine-4-carbonitrile according to the procedure for the preparation of Example 28, part E. $^1$H NMR (400 MHz, DMSO-d$_6$): δ 3.25 (3H, s), 3.61 (2H, t, J=4.4 Hz), 4.17 (2H, t, J=4.4 Hz), 5.20 (2H, s), 6.00 (1H, d, J=2.0 Hz), 7.03 (1H, dd, J=2.0 Hz, 8.4 Hz), 7.16 (1H, d, J=1.6 Hz), 7.49 (1H, d, J=8.0 Hz), 7.59 (1H, d, J=1.6 Hz), 7.74 (1H, dd, J=1.2 Hz, 5.2 Hz), 8.06 (1H, s), 8.67 (1H, d, J=5.2 Hz), 13.85 (1H, s). [M+H] Calc'd for C$_{19}$H$_{18}$ClN$_3$O$_5$, 404. Found, 404.

Example 117

2-[5-[[4-chloro-2-[(4-fluorophenyl)methoxy]phenyl]methoxy]pyrazol-1-yl]pyridine-4-carboxylic acid A. [4-chloro-2-[(4-fluorophenyl)methoxy]phenyl]methanol

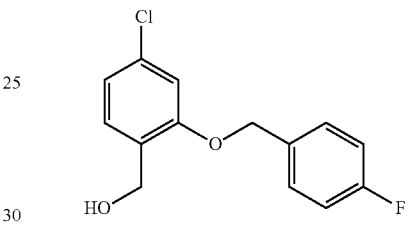

To a solution of 5-chloro-2-(hydroxymethyl)phenol (943 mg, 5.95 mmol) and NaOH (3.5 mL, 6.54 mmol, 2M in water) in ethanol (10 mL) was added 4-(bromomethyl)-1-fluorobenzene (1.13 g, 5.95 mmol) slowly, the mixture was then stirred at room temperature overnight. Water was added to the reaction mixture, and extracted with ethyl acetate. The organic phase was collected and washed with water, brine, and dried with anhydrous Na$_2$SO$_4$. The solvent was removed to give 900 mg of the title compound (57%). $^1$H NMR (400 MHz, CDCl$_3$): δ 2.08 (1H, t, J=6.4 Hz), 4.67 (2H, d, J=6.4 Hz), 5.05 (2H, s), 6.93 (1H, d, J=1.2 Hz), 6.96 (1H, dd, J=1.6 Hz, 8.0 Hz), 7.07-7.11 (2H, m), 7.25 (1H, d, J=6.0 Hz), 7.37-7.40 (2H, m).

B. 2-[5-[[4-chloro-2-[(4-fluorophenyl)methoxy]phenyl]methoxy]pyrazol-1-yl]pyridine-4-carbonitrile

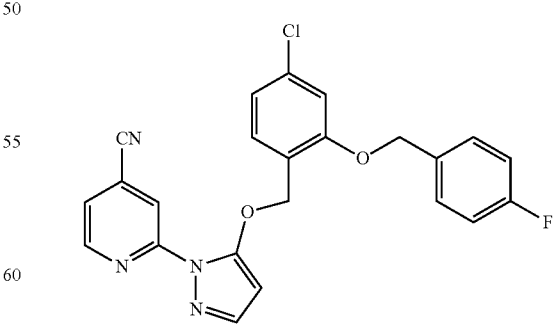

The title compound was prepared from 2-(5-hydroxy-1H-pyrazol-1-yl)pyridine-4-carbonitrile and [4-chloro-2-[(4-fluorophenyl)methoxy]phenyl]methanol according to the procedure for the preparation of Example 39, part C. $^1$H NMR (400 MHz, CDCl$_3$): δ 5.07 (2H, s), 5.25 (2H, s), 5.73 (1H, d, J=1.6 Hz), 6.98-7.07 (4H, m), 7.32-7.39 (4H, m), 7.55 (1H, d, J=1.6 Hz), 8.00 (1H, s), 8.67 (1H, d, J=5.2 Hz). [M+H] Calc'd for C$_{23}$H$_{16}$ClFN$_4$O$_2$, 435. Found, 435.

C. 2-[5-[[4-chloro-2-[(4-fluorophenyl)methoxy]phenyl]methoxy]pyrazol-1-yl]pyridine-4-carboxylic acid

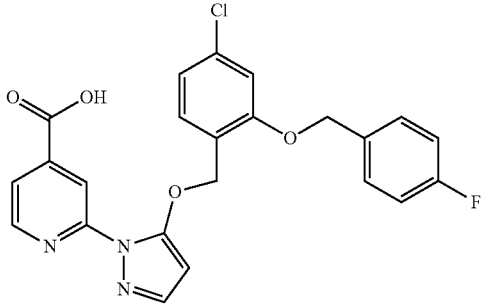 [SMILES: O=C(O)c1ccnc(-n2nccc2OCc2ccc(Cl)cc2OCc2ccc(F)cc2)c1]

The title compound was prepared from 2-[5-[[4-chloro-2-[(4-fluorophenyl)methoxy]phenyl]methoxy]pyrazol-1-yl]pyridine-4-carbonitrile according to the procedure for the preparation of Example 28, part E. $^1$H NMR (400 MHz, DMSO-d$_6$): δ 5.17 (2H, s), 5.24 (2H, s), 5.99 (1H, s), 7.05 (1H, d, J=8.0 Hz), 7.14 (2H, t, J=8.8 Hz), 7.21 (1H, s), 7.43 (2H, dd, J=5.6 Hz, 8.0 Hz), 7.52 (1H, d, J=8.0 Hz), 7.58 (1H, s), 7.73 (1H, d, J=5.2 Hz), 8.04 (1H, s), 8.65 (1H, d, J=5.6 Hz), 13.86 (1H, s). [M+H] Calc'd for C$_{23}$H$_{17}$ClFN$_3$O$_4$, 454. Found, 454.

Example 118

2-[5-[[4-fluoro-2-[(4-fluorophenyl)methoxy]phenyl]methoxy]pyrazol-1-yl]pyridine-4-carboxylic acid A. [4-fluoro-2-[(4-fluorophenyl)methoxy]phenyl]methanol

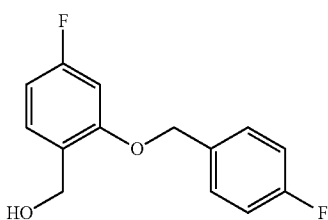 [SMILES: OCc1ccc(F)cc1OCc1ccc(F)cc1]

The title compound was prepared from 5-fluoro-2-(hydroxymethyl)phenol and 4-(bromomethyl)-1-fluorobenzene according to the procedure for the preparation of Example 117, part A. $^1$H NMR (400 MHz, CDCl$_3$): δ 2.07 (1H, t, J=6.8 Hz), 4.67 (2H, d, J=6.0 Hz), 5.05 (2H, s), 6.65-6.68 (2H, m), 7.07-7.11 (2H, m), 7.24-7.28 (1H, m), 7.37-7.41 (2H, m).

B. 2-[5-[[4-fluoro-2-[(4-fluorophenyl)methoxy]phenyl]methoxy]pyrazol-1-yl]pyridine-4-carbonitrile

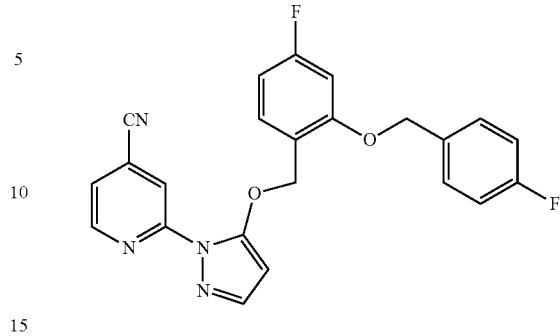

The title compound was prepared from 2-(5-hydroxy-1H-pyrazol-1-yl)pyridine-4-carbonitrile and [4-fluoro-2-[(4-fluorophenyl)methoxy]phenyl]methanol according to the procedure for the preparation of Example 39, part C. [M+H] Calc'd for C$_{23}$H$_{16}$F$_2$N$_4$O$_2$, 419. Found, 419.

C. 2-[5-[[4-fluoro-2-[(4-fluorophenyl)methoxy]phenyl]methoxy]pyrazol-1-yl]pyridine-4-carboxylic acid

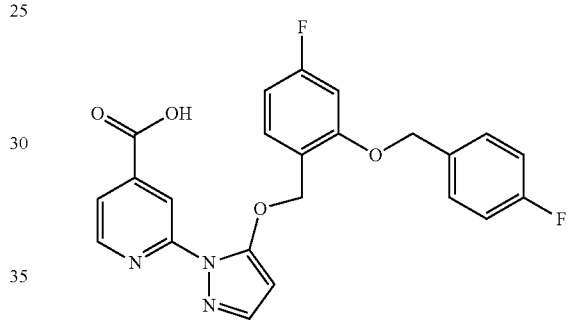

The title compound was prepared from 2-[5-[[4-fluoro-2-[(4-fluorophenyl)methoxy]phenyl]methoxy]pyrazol-1-yl]pyridine-4-carbonitrile according to the procedure for the preparation of Example 28, part E. $^1$H NMR (400 MHz, DMSO-d$_6$): δ 5.15 (2H, s), 5.22 (2H, s), 6.00 (1H, d, J=2.0 Hz), 6.78-6.83 (1H, m), 7.03 (1H, t, J=2.4 Hz, 11.6 Hz), 7.12 (2H, t, J=8.8 Hz), 7.42 (2H, dd, J=5.2 Hz, 8.4 Hz), 7.53 (1H, t, J=8.0 Hz), 7.57 (1H, d, J=2.0 Hz), 7.72 (1H, d, J=0.8 Hz, 4.8 Hz), 8.02 (1H, s), 8.62 (1H, d, J=5.2 Hz). [M+H] Calc'd for C$_{23}$H$_{17}$F$_2$N$_3$O$_4$, 438. Found, 438.

Example 119

2-[5-[[4-fluoro-2-[(E)-2-(4-fluorophenyl)ethenyl]phenyl]methoxy]pyrazol-1-yl]pyridine-4-carboxylic acid A. [4-fluoro-2-[(E)-2-(4-fluorophenyl)ethenyl]phenyl]methanol

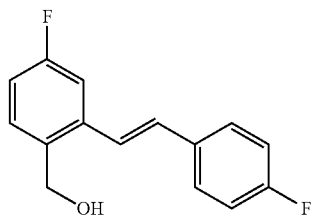 [SMILES: OCc1ccc(F)cc1/C=C/c1ccc(F)cc1]

Charged (2-bromo-4-fluorophenyl)methanol (954 mg, 4.65 mmol), 4-fluoro-1-vinylbenzene (1.14 g, 9.31 mmol), Pd(PPh$_3$)$_2$Cl$_2$ (49 mg, 0.07 mmol), Et$_3$N (942 mg, 9.31 mmol) and DMF (5 mL) to a sealed tube, the mixture was then purged with nitrogen, heated to 150° C. for 3 h in microwave oven. The reaction mixture was filtered, the filtrate was then extracted with ethyl acetate, concentrated and purified by flash column chromatograph to give 569 mg of the title compound (50%). $^1$H NMR (400 MHz, CDCl$_3$): δ 1.60 (1H, t, J=6.4 Hz), 4.78 (2H, d, J=6.4 Hz), 6.93-7.08 (4H, m), 7.31-7.35 (3H, m), 7.48-7.52 (2H, m).

B. 2-[5-[[4-fluoro-2-[(E)-2-(4-fluorophenyl)ethenyl] phenyl]methoxy]pyrazol-1-yl]pyridine-4-carbonitrile

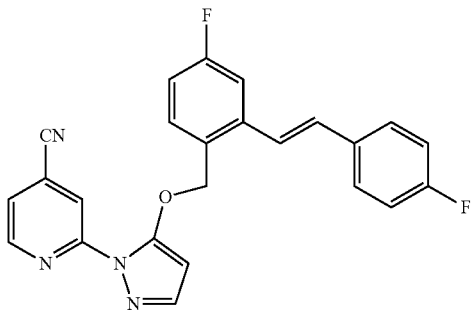

The title compound was prepared from 2-(5-hydroxy-1H-pyrazol-1-yl)pyridine-4-carbonitrile and [4-fluoro-2-[(E)-2-(4-fluorophenyl)ethenyl]phenyl]methanol according to the procedure for the preparation of Example 39, part C. $^1$H NMR (400 MHz, CDCl$_3$): δ 5.31 (2H, s), 5.82 (1H, d, J=1.6 Hz), 6.96-7.04 (4H, m), 7.22-7.23 (1H, m), 7.34-7.41 (5H, m), 7.59 (1H, d, J=1.6 Hz), 7.90 (1H, s), 8.51 (1H, d, J=4.8 Hz). [M+H] Calc'd for C$_{24}$H$_{16}$F$_2$N$_4$O, 415. Found, 415.

C. 2-[5-[[4-fluoro-2-[(E)-2-(4-fluorophenyl)ethenyl] phenyl]methoxy]pyrazol-1-yl]pyridine-4-carboxylic acid

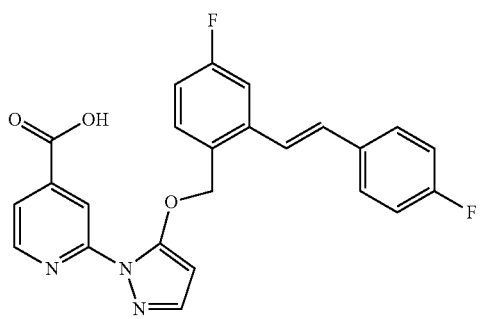

The title compound was prepared from 2-[5-[[4-fluoro-2-[(E)-2-(4-fluorophenyl)ethenyl]phenyl]methoxy]pyrazol-1-yl]pyridine-4-carbonitrile according to the procedure for the preparation of Example 28, part E. $^1$H NMR (400 MHz, DMSO-d$_6$): δ 5.45 (2H, s), 6.13 (1H, d, J=1.6 Hz), 7.09-7.25 (4H, m), 7.38 (1H, d, J=16.0 Hz), 7.51-7.65 (6H, m), 7.25 (1H, s), 8.50 (1H, d, J=5.6 Hz), 13.83 (1H, s). [M+H] Calc'd for C$_{24}$H$_{17}$F$_2$N$_3$O$_3$, 434. Found, 434.

Example 120

2-[5-[[4-chloro-2-[(E)-2-(4-fluorophenyl)ethenyl] phenyl]methoxy]pyrazol-1-yl]pyridine-4-carboxylic acid A. (2-bromo-4-chlorophenyl)methanol

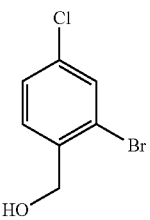

Added BH$_3$ (1M in THF, 40 mL) to a solution of 2-bromo-4-chlorobenzoic acid (3.14 g, 13.33 mmol) in THF (3 mL) drop wise at 0° C. The reaction mixture was stirred at room temperature overnight. Extracted with ethyl acetate twice, and washed the organic phase with brine and dried with anhydrous Na$_2$SO$_4$, concentrated to give the title compound (2.5 g, 85%). $^1$H NMR (300 MHz, CDCl$_3$): δ 4.72 (2H, s), 7.32 (1H, dd, J=1.8 Hz, 8.1 Hz), 7.43 (1H, d, J=8.1 Hz), 7.56 (1H, d, J=2.1 Hz).

B. [4-chloro-2-[(E)-2-(4-fluorophenyl)ethenyl]phenyl]methanol

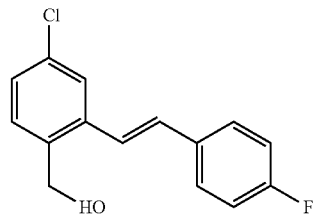 [SMILES: OCc1ccc(Cl)cc1/C=C/c1ccc(F)cc1]

The title compound was prepared from (2-bromo-4-chlorophenyl)methanol and 4-fluoro-1-vinylbenzene according to the procedure for the preparation of Example 119, part B. $^1$H NMR (400 MHz, CDCl$_3$): δ 1.72 (1H, t, J=5.6 Hz), 4.77 (2H, d, J=5.2 Hz), 6.98-7.08 (3H, m), 7.22-7.34 (3H, m), 7.47-7.50 (2H, m), 7.60 (1H, d, J=1.6 Hz).

C. 2-[5-[[4-chloro-2-[(E)-2-(4-fluorophenyl)ethenyl] phenyl]methoxy]pyrazol-1-yl]pyridine-4-carbonitrile

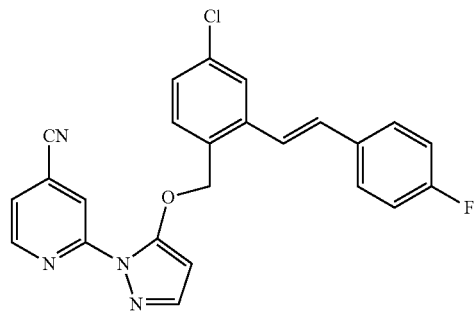 [SMILES: N#Cc1ccnc(-n2nccc2OCc2ccc(Cl)cc2/C=C/c2ccc(F)cc2)c1]

The title compound was prepared from 2-(5-hydroxy-1H-pyrazol-1-yl)pyridine-4-carbonitrile and [4-chloro-2-[(E)-2-(4-fluorophenyl)ethenyl]phenyl]methanol according to the procedure for the preparation of Example 39, part C. $^1$H NMR (400 MHz, CDCl$_3$): δ 5.31 (2H, s), 5.81 (1H, d, J=2.0 Hz), 6.96-7.04 (3H, m), 7.18-7.28 (3H, m), 7.35-7.39 (3H, m), 7.59 (1H, d, J=1.6 Hz), 7.63 (1H, d, J=2.4 Hz), 7.90 (1H, s), 8.51 (1H, d, J=4.8 Hz). [M+H] Calc'd for C$_{24}$H$_{16}$ClFN$_4$O, 431. Found, 431.

D. 2-[5-[[4-chloro-2-[(E)-2-(4-fluorophenyl)ethenyl]phenyl]methoxy]pyrazol-1-yl]pyridine-4-carboxylic acid

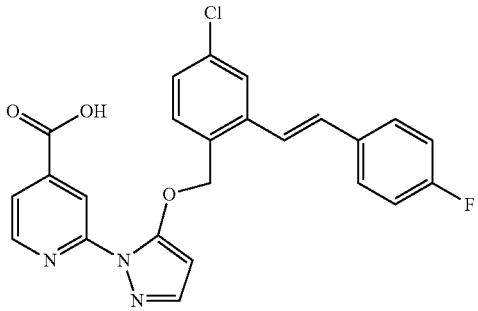 [SMILES: O=C(O)c1ccnc(-n2nccc2OCc2ccc(Cl)cc2/C=C/c2ccc(F)cc2)c1]

The title compound was prepared from 2-[5-[[4-chloro-2-[(E)-2-(4-fluorophenyl)ethenyl]phenyl]methoxy]pyrazol-1-yl]pyridine-4-carbonitrile according to the procedure for the preparation of Example 28, part E. $^1$H NMR (400 MHz, DMSO-d$_6$): δ 5.45 (2H, s), 6.11 (1H, d, J=2.0 Hz), 7.16-7.27 (3H, m), 7.34-7.38 (2H, m), 7.53-7.63 (5H, m), 7.80 (1H, d, J=2.0 Hz), 7.98 (1H, s), 8.48 (1H, d, J=4.8 Hz). [M+H] Calc'd for C$_{24}$H$_{17}$ClFN$_3$O$_3$, 450. Found, 450.

Example 121

2-[5-[[4-fluoro-2-[2-(4-fluorophenyl)ethyl]phenyl]methoxy]pyrazol-1-yl]pyridine-4-carboxylic acid A. [4-fluoro-2-[2-(4-fluorophenyl)ethyl]phenyl]methanol

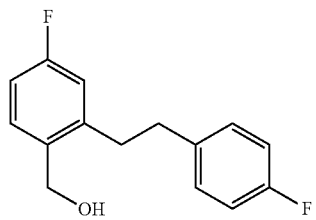 [SMILES: OCc1ccc(F)cc1CCc1ccc(F)cc1]

Charged [4-fluoro-2-[(E)-2-(4-fluorophenyl)ethenyl]phenyl]methanol (568 mg, 2.31 mmol, EXAMPLE 119, part A), Pd/C (65 mg) and methanol (6 mL) to a flask, the mixture was then purged with hydrogen, stirred at room temperature overnight. It was then filtered, filtrate concentrated to give a residue which was purified by flash column chromatograph to give 214 mg of the title compound (37%). $^1$H NMR (400 MHz, CDCl$_3$): δ 1.42 (1H, t, J=5.2 Hz), 2.83-2.98 (4H, m), 4.59 (2H, d, J=5.6 Hz), 6.88-6.98 (4H, m), 7.08-7.11 (2H, m), 7.29-7.33 (1H, m).

B. 2-[5-[[4-fluoro-2-[2-(4-fluorophenyl)ethyl]phenyl]methoxy]pyrazol-1-yl]pyridine-4-carbonitrile

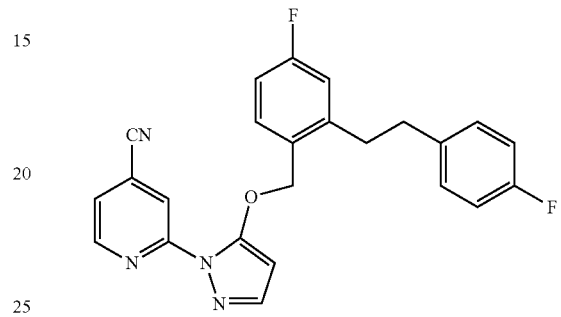

The title compound was prepared from 2-(5-hydroxy-1H-pyrazol-1-yl)pyridine-4-carbonitrile and [4-fluoro-2-[2-(4-fluorophenyl)ethyl]phenyl]methanol according to the procedure for the preparation of Example 39, part C. $^1$H NMR (400 MHz, CDCl$_3$): δ 2.86-2.98 (4H, m), 5.05 (2H, s), 5.73 (1H, d, J=2.0 Hz), 6.90-78.01 (6H, m), 7.33-7.39 (2H, m), 7.59 (1H, d, J=1.6 Hz), 7.95 (1H, s), 8.56 (1H, d, J=4.4 Hz). [M+H] Calc'd for C$_{24}$H$_{18}$F$_2$N$_4$O, 417. Found, 417.

C. 2-[5-[[4-fluoro-2-[2-(4-fluorophenyl)ethyl]phenyl]methoxy]pyrazol-1-yl]pyridine-4-carboxylic acid

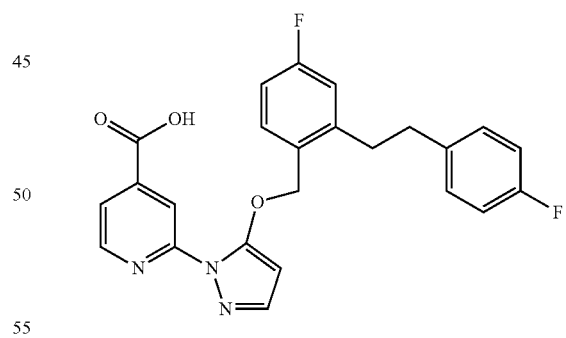

The title compound was prepared from 2-[5-[[4-fluoro-2-[2-(4-fluorophenyl)ethyl]phenyl]methoxy]pyrazol-1-yl]pyridine-4-carbonitrile according to the procedure for the preparation of Example 28, part E. $^1$H NMR (400 MHz, DMSO-d$_6$): δ 2.80-2.93 (4H, m), 5.25 (2H, s), 6.09 (1H, d, J=1.6 Hz), 7.00-7.12 (6H, m), 7.56 (1H, dd, J=6.4 Hz, 8.4 Hz), 7.62 (1H, d, J=1.6 Hz), 7.68 (1H, dd, J=1.6 Hz, 5.2 Hz), 8.01 (1H, s), 8.55 (1H, d, J=4.8 Hz). [M+H] Calc'd for C$_{24}$H$_{19}$F$_2$N$_3$O$_3$, 436. Found, 436.

Example 122

2-[5-[[4-chloro-2-[2-(4-fluorophenyl)ethyl]phenyl]methoxy]pyrazol-1-yl]pyridine-4-carboxylic acid

A. [4-chloro-2-[2-(4-fluorophenyl)ethyl]phenyl]methanol

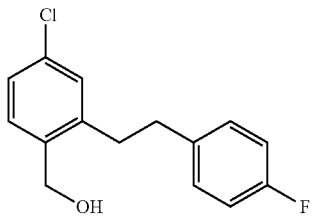

The title compound was prepared from [4-chloro-2-[(E)-2-(4-fluorophenyl)ethenyl]phenyl]methanol (EXAMPLE 120, part B) according to the procedure for the preparation of Example 121, part A. $^1$H NMR (400 MHz, CDCl$_3$): δ 1.46 (1H, s), 2.84-2.94 (4H, m), 4.54 (2H, d, J=4.0 Hz), 6.84-6.98 (2H, m), 7.08-7.11 (2H, m), 7.18-7.20 (2H, m), 7.29 (1H, d, J=8.0 Hz).

B. 2-[5-[[4-chloro-2-[2-(4-fluorophenyl)ethyl]phenyl]methoxy]pyrazol-1-yl]pyridine-4-carbonitrile

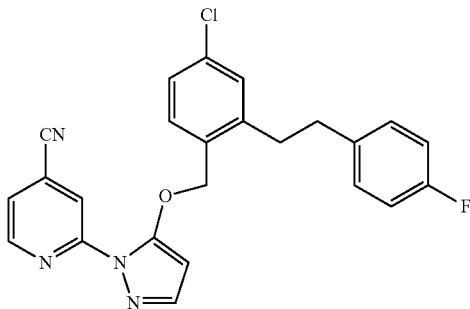 [SMILES: N#Cc1ccnc(-n2nccc2OCc2ccc(Cl)cc2CCc2ccc(F)cc2)c1]

The title compound was prepared from 2-(5-hydroxy-1H-pyrazol-1-yl)pyridine-4-carbonitrile and [4-chloro-2-[2-(4-fluorophenyl)ethyl]phenyl]methanol according to the procedure for the preparation of Example 39, part C. $^1$H NMR (400 MHz, CDCl$_3$): δ 2.86-2.95 (4H, m), 5.03 (2H, s), 5.70 (1H, d, J=2.0 Hz), 6.91-7.01 (4H, m), 7.21-7.24 (2H, m), 7.33-7.36 (2H, m), 7.58 (1H, d, J=1.6 Hz), 7.96 (1H, s), 8.57 (1H, dd, J=0.8 Hz, 5.2 Hz). [M+H] Calc'd for C$_{24}$H$_{18}$ClFN$_4$O, 433. Found, 433.

C. 2-[5-[[4-chloro-2-[2-(4-fluorophenyl)ethyl]phenyl]methoxy]pyrazol-1-yl]pyridine-4-carboxylic acid

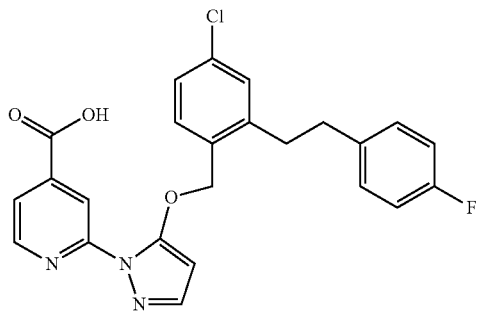 [SMILES: O=C(O)c1ccnc(-n2nccc2OCc2ccc(Cl)cc2CCc2ccc(F)cc2)c1]

The title compound was prepared from 2-[5-[[4-chloro-2-[2-(4-fluorophenyl)ethyl]phenyl]methoxy]pyrazol-1-yl]pyridine-4-carbonitrile according to the procedure for the preparation of Example 28, part E. $^1$H NMR (400 MHz, DMSO-d$_6$): δ 2.80-2.93 (4H, m), 5.27 (2H, s), 6.08 (1H, d, J=2.0 Hz), 7.03 (2H, t, J=9.1 Hz), 7.12 (2H, dd, J=6.0 Hz, 8.4 Hz), 7.29 (1H, dd, J=2.4 Hz, 8.4 Hz), 7.33 (1H, d, J=2.0 Hz), 7.55 (1H, d, J=8.4 Hz), 7.62 (1H, d, J=2.0 Hz), 7.69 (1H, dd, J=1.2 Hz, 5.2 Hz), 8.02 (1H, s), 8.56 (1H, d, J=5.2 Hz). [M+H] Calc'd for C$_{24}$H$_{19}$ClFN$_3$O$_3$, 452. Found, 452.

Example 123

2-[5-(2,3-dihydro-1-benzofuran-7-ylmethoxy)pyrazol-1-yl]pyridine-4-carboxylic acid

A. 2,3-dihydro-1-benzofuran-7-ylmethanol

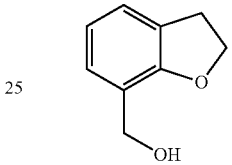

Added BH$_3$ (1M in THF, 9 mL) to a solution of 2,3-dihydro-1-benzofuran-7-carboxylic acid (481 mg, 2.93 mmol) in THF (7 mL) drop wise at 0° C., thereto, the mixture was stirred at room temperature overnight. Extracted with ethyl acetate twice, and washed the organic phase with brine and dried with anhydrous Na$_2$SO$_4$, concentrated to give the title compound (340 mg, 77%). $^1$H NMR (400 MHz, CDCl$_3$): δ 2.09 (1H, s), 3.22 (2H, t, J=8.8 Hz), 4.61 (2H, t, J=8.8 Hz), 4.67 (2H, s), 6.83 (1H, t, J=7.6 Hz), 7.08 (1H, d, J=7.2 Hz), 7.14 (1H, d, J=7.2 Hz).

B. 2-[5-(2,3-dihydro-1-benzofuran-7-ylmethoxy)pyrazol-1-yl]pyridine-4-carbonitrile

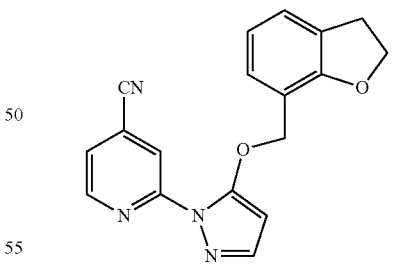

The title compound was prepared from 2-(5-hydroxy-1H-pyrazol-1-yl)pyridine-4-carbonitrile and 2,3-dihydro-1-benzofuran-7-ylmethanol according to the procedure for the preparation of Example 39, part C. $^1$H NMR (400 MHz, CDCl$_3$): δ 3.27 (2H, q, J=8.8 Hz), 4.68 (2H, q, J=8.8 Hz), 5.21 (2H, s), 5.83 (1H, d, J=2.0 Hz), 6.86 (1H, q, J=7.6 Hz), 7.17 (1H, d, J=7.6 Hz), 7.22 (1H, d, J=7.2 Hz), 7.37 (1H, dd, J=1.2 Hz, 4.8 Hz), 7.58 (1H, d, J=2.0 Hz), 8.14 (1H, s), 8.70 (1H, d, J=4.8 Hz). [M+H] Calc'd for C$_{15}$H$_{14}$N$_4$O$_2$, 319. Found, 319.

C. 2-[5-(2,3-dihydro-1-benzofuran-7-ylmethoxy)pyrazol-1-yl]pyridine-4-carboxylic acid

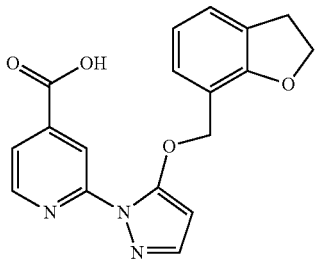 [SMILES: O=C(O)c1ccnc(-n2nccc2OCc2cccc3c2OCC3)c1]

The title compound was prepared from 2-[5-(2,3-dihydro-1-benzofuran-7-ylmethoxy)pyrazol-1-yl]pyridine-4-carbonitrile according to the procedure for the preparation of Example 28, part E. $^1$H NMR (400 MHz, DMSO-$d_6$): δ 3.17 (2H, q, J=8.4 Hz), 4.55 (2H, q, J=8.4 Hz), 5.11 (2H, s), 5.93 (1H, s), 6.81 (1H, t, J=7.2 Hz), 7.18-7.20 (2H, m), 7.48 (1H, s), 7.62 (1H, d, J=4.8 Hz), 7.86 (1H, s), 8.39 (1H, d, J=5.2 Hz). [M+H] Calc'd for $C_{18}H_{15}N_3O_4$, 338. Found, 338.

Example 124

2-[5-[(2,2-dimethyl-3H-1-benzofuran-7-yl)methoxy]pyrazol-1-yl]pyridine-4-carboxylic acid A. 2-[5-[(2,2-dimethyl-3H-1-benzofuran-7-yl)methoxy]pyrazol-1-yl]pyridine-4-carbonitrile

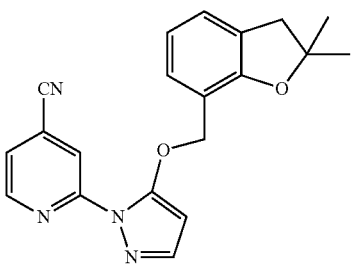 [SMILES: CC1(C)Cc2cccc(COc3ccnn3-c3cc(C#N)ccn3)c2O1]

The title compound was prepared from 2-(5-hydroxy-1H-pyrazol-1-yl)pyridine-4-carbonitrile and (2,2-dimethyl-3H-1-benzofuran-7-yl)methanol according to the procedure for the preparation of Example 39, part C. $^1$H NMR (400 MHz, CDCl$_3$): δ 1.48 (6H, s), 3.03 (2H, s), 5.21 (2H, s), 5.83 (1H, d, J=2.0 Hz), 6.83 (1H, q, J=8.0 Hz), 7.13 (1H, d, J=7.2 Hz), 7.18 (1H, d, J=8.0 Hz), 7.37 (1H, dd, J=0.8 Hz, 4.8 Hz), 7.56 (1H, d, J=1.6 Hz), 8.07 (1H, s), 8.70 (1H, d, J=4.8 Hz). [M+H] Calc'd for $C_{20}H_{18}N_4O_2$, 347. Found, 347.

B. 2-[5-[(2,2-dimethyl-3H-1-benzofuran-7-yl)methoxy]pyrazol-1-yl]pyridine-4-carboxylic acid

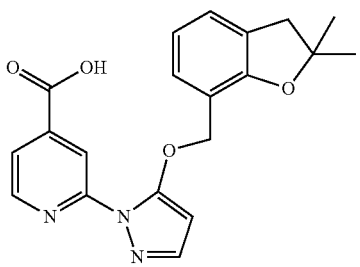 [SMILES: CC1(C)Cc2cccc(COc3ccnn3-c3cc(C(=O)O)ccn3)c2O1]

The title compound was prepared from 2-[5-[(2,2-dimethyl-3H-1-benzofuran-7-yl)methoxy]pyrazol-1-yl]pyridine-4-carbonitrile according to the procedure for the preparation of Example 28, part E. $^1$H NMR (400 MHz, DMSO-$d_6$): δ 1.38 (6H, s), 3.00 (2H, s), 5.14 (2H, s), 6.00 (1H, d, J=2.0 Hz), 6.70-6.81 (1H, m), 7.15-7.22 (2H, m), 7.56 (1H, d, J=2.0 Hz), 7.74 (1H, dd, J=1.2 Hz, 5.2 Hz), 8.05 (1H, s), 8.66 (1H, d, J=5.2 Hz). [M+H] Calc'd for $C_{20}H_{19}N_3O_4$, 366. Found, 366.

Example 125

2-[5-[(4-cyano-2-methylphenyl)methoxy]pyrazol-1-yl]pyridine-4-carboxylic acid

A. 4-(hydroxymethyl)-3-methylbenzonitrile

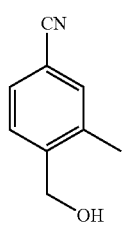

Charge methyl 4-cyano-2-methylbenzoate (627 mg, 3.57 mmol), THF (12 mL) and ethanol (12 mL) to a flask, followed by CaCl$_2$ (418 mg, 3.57 mmol) and NaBH$_4$ (265 mg, 7.16 mmol). The mixture was then stirred at room temperature overnight. Water was added, and the mixture was extracted with ethyl acetate. The organic extract was concentrated and purified by flash column chromatograph to give 325 mg of the title compound (62%). $^1$H NMR (300 MHz, CDCl$_3$): δ 1.83 (1H, t, J=5.4 Hz), 2.33 (3H, s), 4.75 (2H, d, J=5.4 Hz), 7.43 (1H, s), 7.52-7.56 (2H, m).

B. methyl 2-[5-[(4-cyano-2-methylphenyl)methoxy]pyrazol-1-yl]pyridine-4-carboxylate

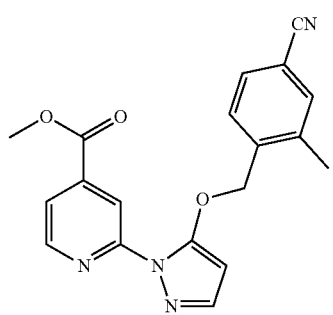

To a mixture of methyl 2-(5-hydroxypyrazol-1-yl)pyridine-4-carboxylate (PREPARATION 6, 112 mg, 0.51 mmol), 4-(hydroxymethyl)-3-methylbenzonitrile (83 mg, 0.56 mmol), PPh$_3$ (268 mg, 1.02 mmol) and THF (6 mL) cooled in ice-water bath, DIAD (207 mg, 1.02 mmol) was added. The mixture was stirred overnight at room temperature. It was then concentrated and purified by flash column chromatograph to give 112 mg of the title compound (63%). [M+H] Calc'd for $C_{19}H_{16}N_4O_3$, 349. Found, 349.

C. 2-[5-[(4-cyano-2-methylphenyl)methoxy]pyrazol-1-yl]pyridine-4-carboxylic acid

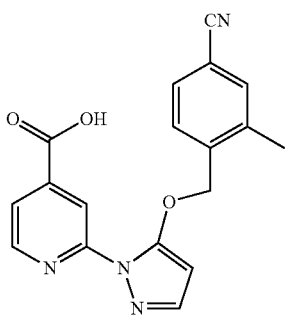 [SMILES: Cc1cc(C#N)ccc1COc1ccnn1-c1cc(C(=O)O)ccn1]

Charged methyl 2-[5-[(4-cyano-2-methylphenyl)methoxy]pyrazol-1-yl]pyridine-4-carboxylate (112 mg, 0.32 mmol), LiOH.H$_2$O (14 mg, 0.32 mmol), water (2 mL) and THF (2 mL) to a flask, then the mixture was stirred at room temperature for 30 min, added another 2 mL water, and the mixture was washed with ethyl acetate twice (6 mL×2). The aqueous phase was acidified with 1N HCl (pH=3), filtered and dried the solid to give the title compound. $^1$H NMR (300 MHz, DMSO-d$_6$): δ 2.37 (3H, s), 5.37 (2H, s), 6.10 (1H, d, J=1.8 Hz), 7.62 (1H, d, J=1.5 Hz), 7.70-7.77 (4H, m), 8.08 (1H, s), 8.68 (1H, d, J=5.4 Hz). [M+H] Calc'd for C$_{18}$H$_{14}$N$_4$O$_3$, 335. Found, 335.

Example 126

2-[5-[(4-cyano-2-ethylphenyl)methoxy]pyrazol-1-yl]pyridine-4-carboxylic acid

A. 4-bromo-2-ethylbenzoic acid

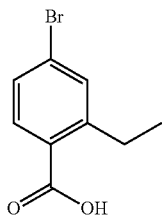

To a yellow solution of 2,2,6,6-TMPH (8.30 g, 58.88 mmol) in THF (9 mL) was added n-BuLi (25 mL) slowly at −78° C. under protection of nitrogen. Thereto, the mixture was warmed up to room temperature, stirred at this temperature for an hour, and then cooled to −78° C. again. A solution of 4-bromo-2-methylbenzoic acid (6.0 g, 28.04 mmol) in THF (60 mL) was added slowly, kept stirring at this temperature for an hour, added MeI (7.96 g, 56.07 mmol) solution (in 35 mL THF), the mixture above was then stirred overnight at room temperature. LCMS showed the reaction was completed. Water was added, the mixture was then washed with ethyl acetate. The aqueous phase was acidified to pH=1, extracted with ethyl acetate twice, and concentrated the organic phase to a residue which was trituated with PE/EA=1/1 to give 4.28 g of the title compound (67%).

B. methyl 4-bromo-2-ethylbenzoate

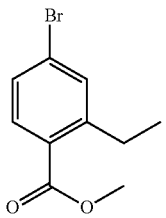

Charged compound 4-bromo-2-ethylbenzoic acid (2.05 g, 9.58 mmol) and methanol (20 mL) to a flask, SOCl$_2$ (3.42 g, 28.74 mmol) was added slowly at 0° C. The reaction mixture was heated to 70° C. for three hour. Solvent was removed and the residue was dissolved in CH$_2$Cl$_2$, filtered, the filtrate was concentrated to a residue which was purified by flash column chromatograph to give 1.9 g of the title compound (87%).

C. methyl 4-cyano-2-ethylbenzoate

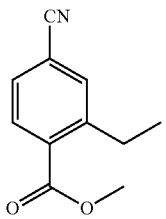

Charged methyl 4-bromo-2-ethylbenzoate (1.9 g, 7.85 mmol), Zn(CN)$_2$ (1.48 g, 12.56 mmol), Pd (PPh$_3$)$_4$ (1.0 g, 0.94 mmol) and DMF (30 mL) to a flask, the system was then purged with nitrogen and heated at 100° C. for 6 h. The reaction mixture was then filtered. The filtrate was extracted with ethyl acetate and concentrated the organic phase for flash column chromatograph to give 0.6 g of the title compound (40%). $^1$H NMR (400 MHz, CDCl$_3$): δ 1.24 (3H, t, J=7.6 Hz), 2.99 (2H, q, J=7.6 Hz), 3.92 (3H, s), 7.52-7.54 (1H, m), 7.57 (1H, s), 7.90 (1H, d, J=8.0 Hz).

D. 3-ethyl-4-(hydroxymethyl)benzonitrile

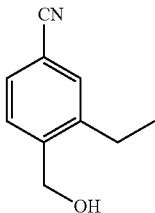

The title compound was prepared from methyl 4-cyano-2-ethylbenzoate according to the procedure for the preparation of Example 125, part A. $^1$H NMR (300 MHz, CDCl$_3$): δ 1.23 (3H, t, J=5.7 Hz), 1.63 (1H, s), 2.67 (2H, q, J=5.7 Hz), 4.68 (2H, s), 7.16-7.19 (2H, m), 7.30 (1H, d, J=6.0 Hz)

E. methyl 2-[5-[(4-cyano-2-ethylphenyl)methoxy]pyrazol-1-yl]pyridine-4-carboxylate

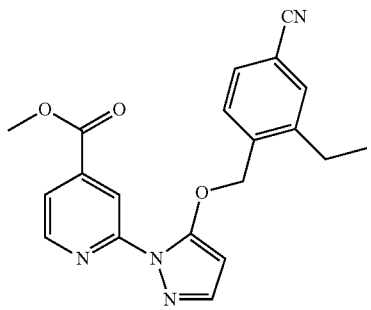 [SMILES: CCc1cc(C#N)ccc1COc1ccnn1-c1cc(C(=O)OC)ccn1]

The title compound was prepared from methyl 2-(5-hydroxypyrazol-1-yl)pyridine-4-carboxylate (PREPARATION 6) and 3-ethyl-4-(hydroxymethyl)benzonitrile according to the procedure for the preparation of Example 125, part B. $^1$H NMR (400 MHz, CDCl$_3$): δ 1.26 (3H, t, J=7.6 Hz), 2.73 (2H, q, J=7.6 Hz), 3.96 (3H, s), 5.28 (2H, s), 5.77 (1H, d, J=1.2 Hz), 7.53-7.67 (4H, m), 7.77 (1H, d, J=4.8 Hz), 8.31 (1H, s), 8.67 (1H, d, J=4.8 Hz). [M+H] Calc'd for C$_{20}$H$_{18}$N$_4$O$_3$, 363. Found, 363.

F. 2-[5-[(4-cyano-2-ethylphenyl)methoxy]pyrazol-1-yl]pyridine-4-carboxylic acid

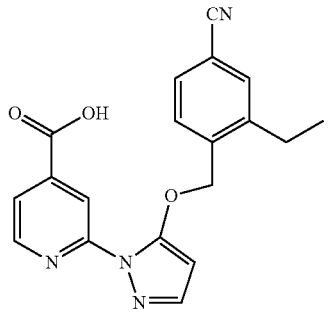 [SMILES: CCc1cc(C#N)ccc1COc1ccnn1-c1cc(C(=O)O)ccn1]

The title compound was prepared from methyl 2-[5-[(4-cyano-2-ethylphenyl)methoxy]pyrazol-1-yl]pyridine-4-carboxylate according to the procedure for the preparation of Example 125, part C. $^1$H NMR (400 MHz, DMSO-d$_6$): δ 1.16 (3H, t, J=7.6 Hz), 2.73 (2H, q, J=7.6 Hz), 5.39 (2H, s), 6.10 (1H, s), 7.62 (1H, s), 7.69-7.76 (4H, m), 8.08 (1H, s), 8.67 (1H, d, J=5.2 Hz). [M+H] Calc'd for C$_{19}$H$_{16}$N$_4$O$_3$, 349. Found, 349.

Example 127

2-[5-[(4-chloro-2-ethylphenyl)methoxy]pyrazol-1-yl]pyridine-4-carboxylic acid

A. 4-chloro-2-ethylbenzoic acid

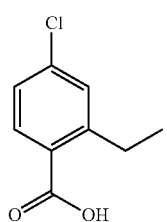

To a yellow solution of 2,2,6,6-TMPH (5.45 g, 38.69 mmol) in THF (6 mL) was added n-BuLi (16 mL) slowly at −78° C. under protection of nitrogen, thereto, the mixture was warmed up to room temperature, stirred at this temperature for an hour, and then cooled to −78° C. again, a solution of 4-chloro-2-methylbenzoic acid (3.0 g, 17.58 mmol) in THF (30 mL) was added slowly, kept stirring at this temperature for an hour, added MeI (5.49 g, 38.69 mmol) solution (in 20 mL THF), the mixture above was then stirred overnight at room temperature. LCMS showed the completion of the reaction, added water, the mixture was then washed with ethyl acetate, the aqueous phase was acidified to pH=1, extracted with ethyl acetate twice, and concentrated the organic phase, washed the residue with PE/EA=1/1 to give 1.5 g of the title compound (46%).

B. (4-chloro-2-ethylphenyl)methanol

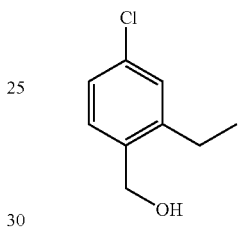

The title compound was prepared from 4-chloro-2-ethylbenzoic acid according to the procedure for the preparation of Example 123, part A. $^1$H NMR (300 MHz, CDCl$_3$): δ 1.23 (3H, t, J=5.7 Hz), 1.63 (1H, s), 2.67 (2H, q, J=5.7 Hz), 4.68 (2H, s), 7.16-7.19 (2H, m), 7.30 (1H, d, J=6.0 Hz).

C. 2-[5-[(4-chloro-2-ethylphenyl)methoxy]pyrazol-1-yl]pyridine-4-carbonitrile

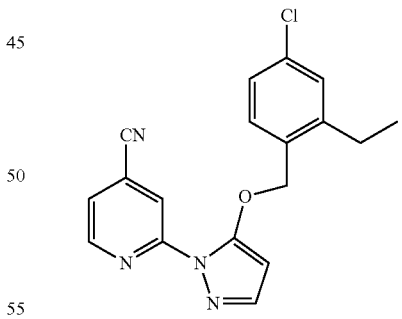

The title compound was prepared from 2-(5-hydroxy-1H-pyrazol-1-yl)pyridine-4-carbonitrile and (4-chloro-2-ethylphenyl)methanol according to the procedure for the preparation of Example 39, part C. $^1$H NMR (400 MHz, CDCl$_3$): δ 1.23 (3H, t, J=7.6 Hz), 2.70 (2H, q, J=7.6 Hz), 5.20 (2H, s), 5.78 (1H, d, J=2.0 Hz), 7.20 (1H, dd, J=2.4 Hz, 8.4 Hz), 7.25 (1H, d, J=1.6 Hz), 7.36 (1H, d, J=8.4 Hz), 7.39 (1H, dd, J=1.6 Hz, 5.2 Hz), 7.59 (1H, d, J=2.0 Hz), 7.99 (1H, s), 8.67 (1H, d, J=4.8 Hz). [M+H] Calc'd for C$_{18}$H$_{15}$ClN$_4$O, 339. Found, 339.

D. 2-[5-[(4-chloro-2-ethylphenyl)methoxy]pyrazol-1-yl]pyridine-4-carboxylic acid

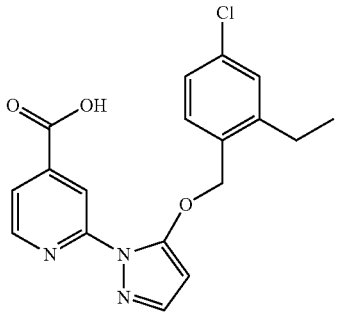 [SMILES: CCc1cc(Cl)ccc1COc1ccnn1-c1cc(C(=O)O)ccn1]

The title compound was prepared from 2-[5-[(4-chloro-2-ethylphenyl)methoxy]pyrazol-1-yl]pyridine-4-carbonitrile according to the procedure for the preparation of Example 28, part E. $^1$H NMR (400 MHz, DMSO-d$_6$): δ 1.12 (3H, t, J=7.6 Hz), 2.69 (2H, q, J=7.6 Hz), 5.28 (2H, s), 6.10 (1H, d, J=2.0 Hz), 6.27 (1H, dd, J=2.4 Hz, 8.4 Hz), 7.31 (1H, d, J=2.0 Hz), 7.53 (1H, d, J=8.0 Hz), 7.61 (1H, d, J=2.0 Hz), 7.74 (1H, dd, J=1.2 Hz, 4.8 Hz), 8.05 (1H, s), 8.64 (1H, d, J=4.8 Hz). [M+H] Calc'd for C$_{18}$H$_{16}$ClN$_3$O$_3$, 358. Found, 358.

Example 128

2-[5-[(4-fluoro-2-methylphenyl)methoxy]pyrazol-1-yl]pyridine-4-carboxylic acid

A. (4-fluoro-2-methylphenyl)methanol

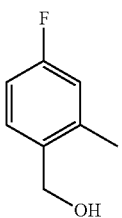

The title compound was prepared from 4-fluoro-2-methylbenzoic acid according to the procedure for the preparation of Example 123, part A.

B. 2-[5-[(4-fluoro-2-methylphenyl)methoxy]pyrazol-1-yl]pyridine-4-carbonitrile

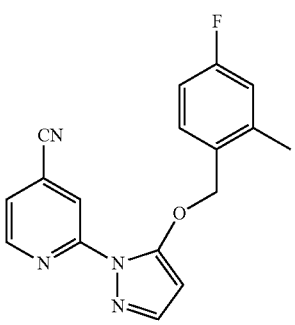 [SMILES: Cc1cc(F)ccc1COc1ccnn1-c1cc(C#N)ccn1]

The title compound was prepared from 2-(5-hydroxy-1H-pyrazol-1-yl)pyridine-4-carbonitrile and (4-fluoro-2-methylphenyl)methanol according to the procedure for the preparation of Example 39, part C. $^1$H NMR (400 MHz, CDCl$_3$): δ 2.38 (3H, s), 5.17 (2H, s), 5.78 (1H, d, J=1.6 Hz), 6.89-6.95 (2H, m), 7.34-7.39 (2H, m), 7.58 (1H, d, J=2.4 Hz), 7.98 (1H, s), 8.67 (1H, d, J=5.2 Hz). [M+H] Calc'd for C$_{17}$H$_{13}$FN$_4$O, 309. Found, 309.

C. 2-[5-[(4-fluoro-2-methylphenyl)methoxy]pyrazol-1-yl]pyridine-4-carboxylic acid

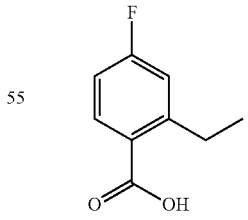

The title compound was prepared from 2-[5-[(4-fluoro-2-methylphenyl)methoxy]pyrazol-1-yl]pyridine-4-carbonitrile according to the procedure for the preparation of Example 28, part E. $^1$H NMR (400 MHz, DMSO-d$_6$): δ 2.35 (3H, s), 5.26 (2H, s), 6.10 (1H, d, J=1.2 Hz), 7.00-7.10 (2H, m), 7.51-7.54 (1H, m), 7.61 (1H, d, J=1.2 Hz), 7.74 (1H, d, J=4.4 Hz), 8.04 (1H, s), 8.65 (1H, d, J=5.2 Hz). [M+H] Calc'd for C$_{17}$H$_{14}$FN$_3$O$_3$, 328. Found, 328.

Example 129

2-[5-[(2-ethyl-4-fluorophenyl)methoxy]pyrazol-1-yl]pyridine-4-carboxylic acid

A. 2-ethyl-4-fluorobenzoic acid

The title compound was prepared from 4-fluoro-2-methylbenzoic acid according to the procedure for the preparation of Example 126, part A. $^1$H NMR (300 MHz, DMSO-d$_6$): δ 1.15 (3H, t, J=7.5 Hz), 2.94 (2H, q, J=7.5 Hz), 7.07-7.20 (2H, m), 7.86 (1H, dd, J=6.3 Hz, 8.7 Hz), 12.91 (1H, s).

B. (2-ethyl-4-fluorophenyl)methanol

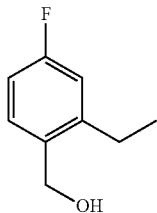

The title compound was prepared from 2-ethyl-4-fluorobenzoic acid according to the procedure for the preparation of Example 123, part A. $^1$H NMR (300 MHz, CDCl$_3$): δ 1.24 (3H, t, J=7.5 Hz), 2.71 (2H, q, J=7.5 Hz), 4.67 (2H, s), 6.84-6.95 (2H, m), 7.31 (1H, dd, J=6.3 Hz, 8.4 Hz).

C. 2-[5-[(2-ethyl-4-fluorophenyl)methoxy]pyrazol-1-yl]pyridine-4-carbonitrile

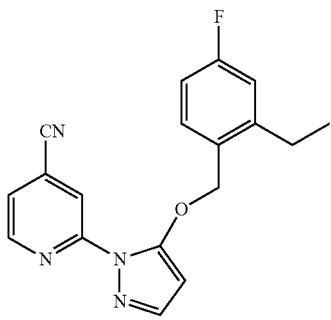 [SMILES: CCc1cc(F)ccc1COc1ccnn1-c1cc(C#N)ccn1]

The title compound was prepared from 2-(5-hydroxy-1H-pyrazol-1-yl)pyridine-4-carbonitrile and (2-ethyl-4-fluorophenyl)methanol according to the procedure for the preparation of Example 39, part C. $^1$H NMR (400 MHz, CDCl$_3$): δ 1.23 (3H, t, J=7.6 Hz), 2.72 (2H, q, J=7.6 Hz), 5.20 (2H, s), 5.79 (1H, d, J=2.0 Hz), 6.89-7.00 (2H, m), 7.36-7.40 (2H, m), 7.59 (1H, d, J=2.0 Hz), 7.98 (1H, s), 8.67 (1H, d, J=5.2 Hz). [M+H] Calc'd for C$_{18}$H$_{18}$FN$_4$O, 323. Found, 323.

D. 2-[5-[(2-ethyl-4-fluorophenyl)methoxy]pyrazol-1-yl]pyridine-4-carboxylic acid

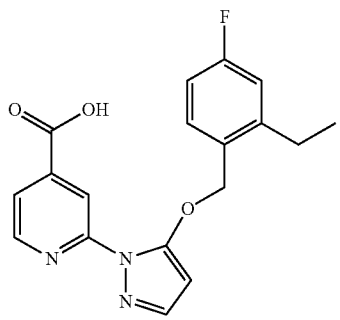 [SMILES: CCc1cc(F)ccc1COc1ccnn1-c1cc(C(=O)O)ccn1]

The title compound was prepared from 2-[5-[(2-ethyl-4-fluorophenyl)methoxy]pyrazol-1-yl]pyridine-4-carbonitrile according to the procedure for the preparation of Example 28, part E. $^1$H NMR (400 MHz, DMSO-d$_6$): δ 1.12 (3H, t, J=7.6 Hz), 2.70 (2H, q, J=7.6 Hz), 5.26 (2H, s), 6.10 (1H, d, J=2.0 Hz), 7.00-7.11 (2H, m), 7.54 (1H, dd, J=6.4 Hz, 8.4 Hz), 7.61 (1H, d, J=2.0 Hz), 7.73-7.74 (1H, m), 8.03 (1H, s), 8.63 (1H, d, J=4.8 Hz). [M+H] Calc'd for C$_{18}$H$_{16}$FN$_3$O$_3$, 342. Found, 342.

Example 130

2-[5-[(2-chloro-4-methylphenyl)methoxy]pyrazol-1-yl]pyridine-4-carboxylic acid

A. (2-chloro-4-methylphenyl)methanol

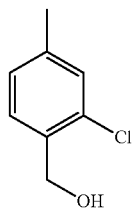

The title compound was prepared from 2-chloro-4-methylbenzoic acid according to the procedure for the preparation of Example 123, part A. $^1$H NMR (400 MHz, CDCl$_3$): δ 1.90 (1H, s), 2.33 (3H, s), 4.74 (2H, s), 7.07 (1H, d, J=7.6 Hz), 7.19 (1H, s), 7.33 (1H, d, J=7.6 Hz).

B. 2-[5-[(2-chloro-4-methylphenyl)methoxy]pyrazol-1-yl]pyridine-4-carbonitrile

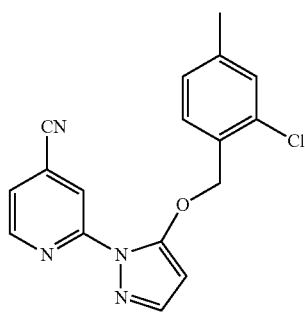 [SMILES: Cc1ccc(COc2ccnn2-c2cc(C#N)ccn2)c(Cl)c1]

The title compound was prepared from 2-(5-hydroxy-1H-pyrazol-1-yl)pyridine-4-carbonitrile and (2-chloro-4-methylphenyl)methanol according to the procedure for the preparation of Example 39, part C. $^1$H NMR (400 MHz, CDCl$_3$): δ 2.35 (3H, s), 5.30 (2H, s), 5.80 (1H, d, J=1.6 Hz), 7.10 (1H, d, J=8.4 Hz), 7.25 (1H, d, J=3.2 Hz), 7.40 (2H, dd, J=1.2 Hz 5.2 Hz), 7.58 (1H, d, J=2.4 Hz), 8.06 (1H, s), 8.71 (1H, d, J=5.2 Hz). [M+H] Calc'd for C$_{17}$H$_{13}$ClN$_4$O, 325. Found, 325.

C. 2-[5-[(2-chloro-4-methylphenyl)methoxy]pyrazol-1-yl]pyridine-4-carboxylic acid

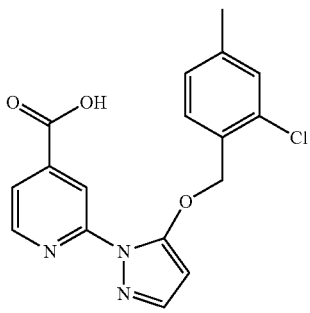 [SMILES: Cc1ccc(COc2ccnn2-c2cc(C(=O)O)ccn2)c(Cl)c1]

The title compound was prepared from 2-[5-[(2-chloro-4-methylphenyl)methoxy]pyrazol-1-yl]pyridine-4-carbonitrile according to the procedure for the preparation of Example 28, part E. $^1$H NMR (400 MHz, DMSO-$d_6$): δ 2.31 (3H, s), 5.28 (2H, s), 6.05 (1H, d, J=2.0 Hz), 7.19 (1H, d, J=7.6 Hz), 7.33 (1H, s), 7.55 (1H, d, J=7.6 Hz), 7.60 (1H, d, J=2.0 Hz), 7.75 (1H, dd, J=1.6 Hz, 5.2 Hz), 8.07 (1H, s), 8.67 (1H, d, J=4.8 Hz). [M+H] Calc'd for $C_{17}H_{14}ClN_3O_3$, 344. Found, 344.

Example 131

2-[5-[(2-fluoro-4-methylphenyl)methoxy]pyrazol-1-yl]pyridine-4-carboxylic acid

A. (2-fluoro-4-methylphenyl)methanol

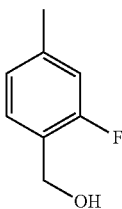

The title compound was prepared from 2-fluoro-4-methylbenzoic acid according to the procedure for the preparation of Example 123, part A. $^1$H NMR (300 MHz, CDCl$_3$): δ 1.71 (1H, t, J=6.0 Hz), 2.34 (3H, s), 4.71 (2H, d, J=6.0 Hz), 6.85-6.96 (2H, m), 7.24-7.30 (1H, m).

B. 2-[5-[(2-fluoro-4-methylphenyl)methoxy]pyrazol-1-yl]pyridine-4-carbonitrile

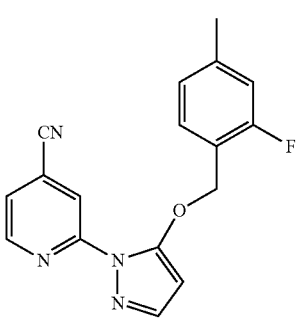 [SMILES: Cc1ccc(COc2ccnn2-c2cc(C#N)ccn2)c(F)c1]

The title compound was prepared from 2-(5-hydroxy-1H-pyrazol-1-yl)pyridine-4-carbonitrile and (2-fluoro-4-methylphenyl)methanol according to the procedure for the preparation of Example 39, part C. $^1$H NMR (400 MHz, CDCl$_3$): δ 2.36 (3H, s), 5.26 (2H, s), 5.80 (1H, d, J=2.0 Hz), 6.93 (1H, d, J=11.2 Hz), 6.98 (1H, d, J=8.0 Hz), 7.31-7.35 (1H, m), 7.38 (1H, dd, J=1.2 Hz, 4.8 Hz), 7.57 (1H, d, J=1.6 Hz), 8.01 (1H, s), 8.69 (1H, d, J=4.8 Hz). [M+H] Calc'd for $C_{17}H_{13}FN_4O$, 309. Found, 309.

C. 2-[5-[(2-fluoro-4-methylphenyl)methoxy]pyrazol-1-yl]pyridine-4-carboxylic acid

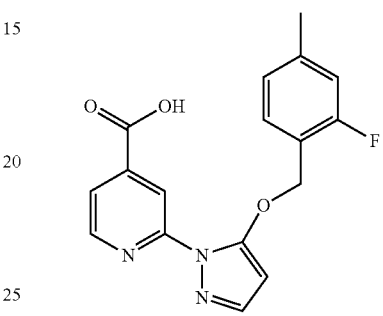

The title compound was prepared from 2-[5-[(2-fluoro-4-methylphenyl)methoxy]pyrazol-1-yl]pyridine-4-carbonitrile according to the procedure for the preparation of Example 28, part E. $^1$H NMR (400 MHz, DMSO-$d_6$): δ 2.31 (3H, s), 5.26 (2H, s), 6.05 (1H, d, J=2.0 Hz), 7.02-7.07 (2H, m), 7.47 (1H, t, J=7.6 Hz), 7.60 (1H, d, J=1.6 Hz), 7.74 (1H, dd, J=1.2 Hz, 5.2 Hz), 8.04 (1H, s), 8.65 (1H, d, J=5.2 Hz). [M+H] Calc'd for $C_{17}H_{14}FN_3O_3$, 328. Found, 328.

Example 132

2-[5-[(2,4-dimethylphenyl)methoxy]pyrazol-1-yl]pyridine-4-carboxylic acid

A. 2-[5-[(2,4-dimethylphenyl)methoxy]pyrazol-1-yl]pyridine-4-carbonitrile

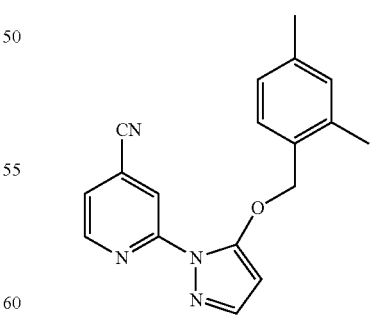

The title compound was prepared from 2-(5-hydroxy-1H-pyrazol-1-yl)pyridine-4-carbonitrile and (2,4-dimethylphenyl)methanol according to the procedure for the preparation of Example 39, part C. [M+H] Calc'd for $C_{18}H_{16}N_4O$, 305. Found, 305.

B. 2-[5-[(2,4-dimethylphenyl)methoxy]pyrazol-1-yl]pyridine-4-carboxylic acid

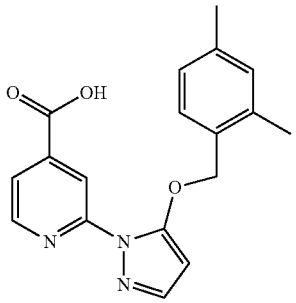 [SMILES: Cc1ccc(COc2ccnn2-c2cc(C(=O)O)ccn2)c(C)c1]

The title compound was prepared from 2-[5-[(2,4-dimethylphenyl)methoxy]pyrazol-1-yl]pyridine-4-carbonitrile according to the procedure for the preparation of Example 28, part E. $^1$H NMR (400 MHz, DMSO-$d_6$): δ 2.25 (3H, s), 2.29 (3H, s), 5.21 (2H, s), 6.06 (1H, d, J=2.0 Hz), 6.99 (1H, d, J=8.0 Hz), 7.02 (1H, s), 7.33 (1H, d, J=7.2 Hz), 7.59 (1H, d, J=1.6 Hz), 7.73-7.74 (1H, m), 8.03 (1H, s), 8.65 (1H, d, J=4.8 Hz), 13.83 (1H, s). [M+H] Calc'd for $C_{18}H_{17}N_3O_3$, 324. Found, 324.

Example 133

2-[5-[(2-methoxy-4-methylphenyl)methoxy]pyrazol-1-yl]pyridine-4-carboxylic acid

A. (2-methoxy-4-methylphenyl)methanol

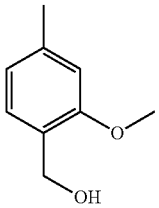

The title compound was prepared from 2-methoxy-4-methylbenzoic acid according to the procedure for the preparation of Example 123, part A. $^1$H NMR (300 MHz, CDCl$_3$): δ 2.35 (3H, s), 3.85 (3H, s), 4.64 (2H, s), 6.70 (1H, s), 6.74 (1H, d, J=5.7 Hz), 7.13 (1H, d, J=5.7 Hz).

B. 2-[5-[(2-methoxy-4-methylphenyl)methoxy]pyrazol-1-yl]pyridine-4-carbonitrile

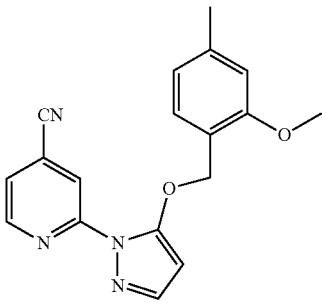 [SMILES: COc1cc(C)ccc1COc1ccnn1-c1cc(C#N)ccn1]

The title compound was prepared from 2-(5-hydroxy-1H-pyrazol-1-yl)pyridine-4-carbonitrile and (2-methoxy-4-methylphenyl)methanol according to the procedure for the preparation of Example 39, part C. $^1$H NMR (400 MHz, CDCl$_3$): δ 3.37 (3H, s), 3.89 (3H, s), 5.23 (2H, s), 5.80 (1H, d, J=2.0 Hz), 6.76-6.79 (2H, m), 7.24-7.26 (1H, m), 7.37 (1H, dd, J=1.2 Hz, 4.8 Hz), 7.58 (1H, d, J=1.6 Hz), 8.08 (1H, s), 8.70 (1H, d, J=4.4 Hz). [M+H] Calc'd for $C_{18}H_{16}N_4O_2$, 321. Found, 321.

C. 2-[5-[(2-methoxy-4-methylphenyl)methoxy]pyrazol-1-yl]pyridine-4-carboxylic acid

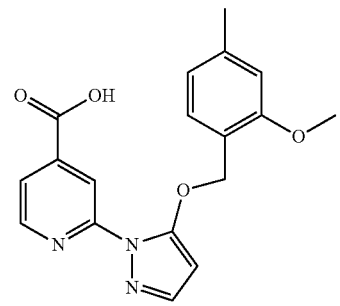 [SMILES: COc1cc(C)ccc1COc1ccnn1-c1cc(C(=O)O)ccn1]

The title compound was prepared from 2-[5-[(2-methoxy-4-methylphenyl)methoxy]pyrazol-1-yl]pyridine-4-carbonitrile according to the procedure for the preparation of Example 28, part E. $^1$H NMR (400 MHz, DMSO-$d_6$): δ 2.30 (3H, s), 3.78 (3H, s), 5.17 (2H, s), 5.99 (1H, d, J=1.6 Hz), 6.76 (1H, d, J=7.6 Hz), 6.86 (1H, s), 7.32 (1H, d, J=7.6 Hz), 7.58 (1H, d, J=1.6 Hz), 7.74 (1H, dd, J=0.8 Hz, 4.8 Hz), 8.06 (1H, s), 8.66 (1H, d, J=4.8 Hz). [M+H] Calc'd for $C_{18}H_{17}N_3O_4$, 340. Found, 340.

Example 134

2-[5-[(2-cyano-4-methylphenyl)methoxy]pyrazol-1-yl]pyridine-4-carboxylic acid

A. methyl 2-cyano-4-methylbenzoate

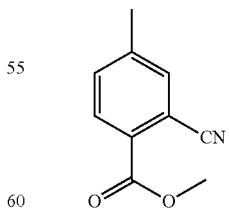

The title compound was prepared from methyl 2-bromo-4-methylbenzoate according to the procedure for the preparation of Example 126, part C. $^1$H NMR (400 MHz, CDCl$_3$): δ 2.45 (3H, s), 3.98 (3H, s), 7.46 (1H, d, J=6.0 Hz), 7.60 (1H, s), 8.03 (1H, d, J=6.0 Hz).

B. 2-(hydroxymethyl)-5-methylbenzonitrile

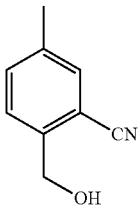

The title compound was prepared from methyl 2-cyano-4-methylbenzoate according to the procedure for the preparation of Example 125, part A. ¹H NMR (300 MHz, CDCl₃): δ 2.44 (3H, s), 5.26 (2H, s), 7.27 (1H, d, J=7.5 Hz), 7.37 (1H, d, J=8.1 Hz), 7.67 (1H, s).

C. methyl 2-[5-[(2-cyano-4-methylphenyl)methoxy]pyrazol-1-yl]pyridine-4-carboxylate

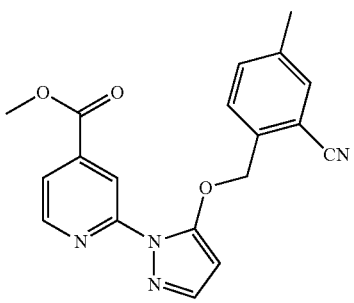 [SMILES: COC(=O)c1ccnc(-n2nccc2OCc2ccc(C)cc2C#N)c1]

The title compound was prepared from methyl 2-(5-hydroxypyrazol-1-yl)pyridine-4-carboxylate (PREPARATION 6) and 2-(hydroxymethyl)-5-methylbenzonitrile according to the procedure for the preparation of Example 125, part B. ¹H NMR (400 MHz, CDCl₃): δ 3.40 (3H, s), 3.97 (3H, s), 5.40 (2H, s), 5.83 (1H, d, J=1.2 Hz), 7.43 (1H, d, J=8.8 Hz), 7.50 (1H, s), 7.58-7.62 (2H, m), 7.76 (1H, d, J=5.2 Hz), 8.33 (1H, s), 8.68 (1H, d, J=5.2 Hz). [M+H] Calc'd for C₁₉H₁₆N₄O₃, 349. Found, 349.

D. 2-[5-[(2-cyano-4-methylphenyl)methoxy]pyrazol-1-yl]pyridine-4-carboxylic acid

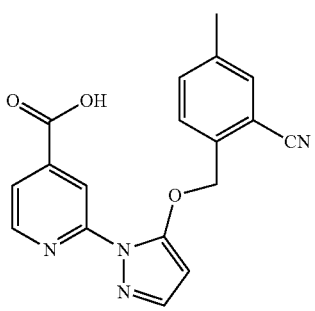 [SMILES: Cc1ccc(COc2ccnn2-c2cc(C(=O)O)ccn2)c(C#N)c1]

The title compound was prepared from methyl 2-[5-[(2-cyano-4-methylphenyl)methoxy]pyrazol-1-yl]pyridine-4-carboxylate according to the procedure for the preparation of Example 125, part C. ¹H NMR (400 MHz, DMSO-d₆): δ 2.35 (3H, s), 5.38 (2H, s), 6.08 (1H, d, J=1.2 Hz), 7.55 (1H, d, J=8.4 Hz), 6.62 (1H, d, J=1.6 Hz), 7.66 (1H, d, J=7.6 Hz), 7.71 (1H, s), 7.74 (1H, d, J=5.2 Hz), 8.04 (1H, s), 8.65 (1H, d, J=5.2 Hz). [M+H] Calc'd for C₁₅H₁₄N₄O₃, 335. Found, 335.

Example 135

2-[5-[(2-ethyl-4-methylphenyl)methoxy]pyrazol-1-yl]pyridine-4-carboxylic acid

A. methyl 2-ethenyl-4-methylbenzoate

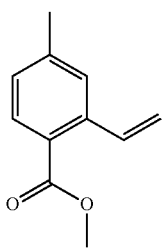

A mixture of methyl 2-bromo-4-methylbenzoate (1.06 g, 4.63 mmol), vinyltrifluoroborate potassium salt (621 mg, 4.63 mmol), Pd(dppf)Cl₂ (203 mg, 0.28 mmol) and TEA (1.40 g, 13.89 mmol) in n-PrOH (11 mL) was purged with nitrogen, and heated to 100° C. for 2 h. It was then cooled to room temperature and filtered, the filtrate was extracted with ethyl acetate twice. Organic extract was concentrated and purified by flash column chromatograph to give 500 mg of the title compound (60%). ¹H NMR (400 MHz, CDCl₃): δ 2.40 (3H, s), 3.88 (3H, s), 5.33 (1H, dd, J=1.2 Hz, 10.8 Hz), 5.62 (1H, dd, J=1.2 Hz, 17.6 Hz), 7.12 (1H, d, J=8.0 Hz), 7.37 (1H, s), 7.48 (1H, dd, J=10.8 Hz, 17.6 Hz), 7.80 (1H, d, J=8.0 Hz).

B. methyl 2-ethyl-4-methylbenzoate

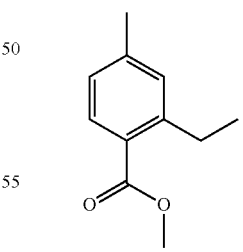

Charged compound methyl 2-ethenyl-4-methylbenzoate (773 mg, 4.42 mmol), Pd/C (100 mg) and methanol (14 mL) to a flask, the mixture was then purged with H₂, and stirred at room temperature overnight. It was then filtered, filtrated concentrated to give the title compound (646 mg, 83%). ¹H NMR (300 MHz, CDCl₃): δ 1.22 (3H, t, J=7.5 Hz), 2.36 (3H, s), 2.95 (2H, q, J=7.5 Hz), 3.87 (3H, s), 7.04 (1H, d, J=8.1 Hz), 7.07 (1H, s), 7.78 (1H, d, J=8.1 Hz).

C. (2-ethyl-4-methylphenyl)methanol

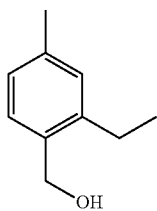

To a solution of compound methyl 2-ethyl-4-methylbenzoate (646 mg, 3.65 mmol) in THF (6 mL) cooled to −50° C., was added LiAlH$_4$ (277 mg, 7.30 mmol) in portions. The mixture was stirred at this temperature for 1 h. Added water (0.3 mL) slowly, followed by NaOH (aq, 10%, 0.3 mL) and water (0.9 mL), the resulting mixture was filtered and washed with THF, concentrated the filtrate to give 518 mg of the title compound (95%). $^1$H NMR (400 MHz, CDCl$_3$): δ 1.23 (3H, t, J=7.2 Hz), 1.54 (1H, s), 2.33 (3H, s), 2.68 (2H, q, J=7.6 Hz), 4.67 (2H, s), 7.01 (1H, d, J=8.0 Hz), 7.03 (1H, s), 7.23 (1H, d, J=7.6 Hz).

D. 2-[5-[(2-ethyl-4-methylphenyl)methoxy]pyrazol-1-yl]pyridine-4-carbonitrile

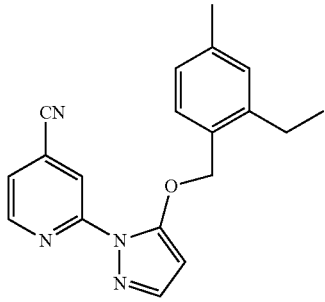 [SMILES: CCc1cc(C)ccc1COc1ccnn1-c1cc(C#N)ccn1]

The title compound was prepared from 2-(5-hydroxy-1H-pyrazol-1-yl)pyridine-4-carbonitrile and (2-ethyl-4-methylphenyl)methanol according to the procedure for the preparation of Example 39, part C. $^1$H NMR (400 MHz, CDCl$_3$): δ 1.20 (3H, t, J=7.6 Hz), 2.35 (3H, s), 2.68 (2H, q, J=7.6 Hz), 5.21 (2H, s), 5.79 (1H, d, J=1.6 Hz), 7.03 (1H, d, J=7.6 Hz), 7.07 (1H, s), 7.27 (1H, d, J=8.4 Hz), 7.36 (1H, dd, J=1.2 Hz, 4.8 Hz), 7.58 (1H, d, J=1.6 Hz), 7.96-7.97 (1H, s), 8.66 (1H, dd, J=0.8 Hz, 5.2 Hz). [M+H] Calc'd for C$_{19}$H$_{18}$N$_4$O, 319. Found, 319.

E. 2-[5-[(2-ethyl-4-methylphenyl)methoxy]pyrazol-1-yl]pyridine-4-carboxylic acid

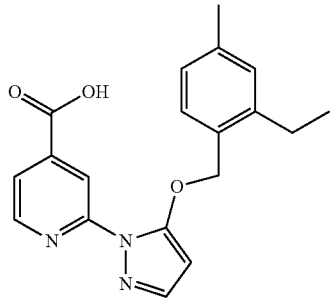 [SMILES: CCc1cc(C)ccc1COc1ccnn1-c1cc(C(=O)O)ccn1]

The title compound was prepared from 2-[5-[(2-ethyl-4-methylphenyl)methoxy]pyrazol-1-yl]pyridine-4-carbonitrile according to the procedure for the preparation of Example 28, part E. $^1$H NMR (400 MHz, DMSO-d$_6$): δ 1.10 (3H, t, J=7.6 Hz), 2.27 (3H, s), 2.64 (2H, q, J=7.6 Hz), 5.22 (2H, s), 6.07 (1H, d, J=2.0 Hz), 7.00 (1H, d, J=7.6 Hz), 7.05 (1H, s), 7.34 (1H, d, J=7.6 Hz), 7.59 (1H, d, J=2.0 Hz), 7.72 (1H, dd, J=1.6 Hz, 5.2 Hz), 8.02 (1H, s), 8.62 (1H, d, J=5.2 Hz). [M+H] Calc'd for C$_{19}$H$_{19}$N$_3$O$_3$, 338. Found, 338.

Example 136

2-[5-[[4-chloro-2-(1-phenylethoxy)phenyl]methoxy]pyrazol-1-yl]pyridine-4-carboxylic acid

A. [4-chloro-2-(1-phenylethoxy)phenyl]methanol

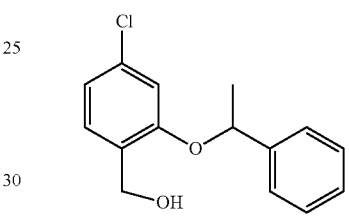

Charged 5-chloro-2-(hydroxymethyl)phenol (787 mg, 4.96 mmol), (bromoethyl)benzene (1.01 g, 5.46 mmol), K$_2$CO$_3$ (1.37 g, 9.93 mmol) and DMF (8 mL) to a flask, heated to 100° C. overnight. Poured into ice water, and extracted with ethyl acetate twice, and washed the organic phase with water twice, brine and dried with anhydrous Na$_2$SO$_4$. Solvent was then removed and purified by flash column chromatograph to give 1.0 g of the title compound (77%).

B. 2-[5-[[4-chloro-2-(1-phenylethoxy)phenyl]methoxy]pyrazol-1-yl]pyridine-4-carbonitrile

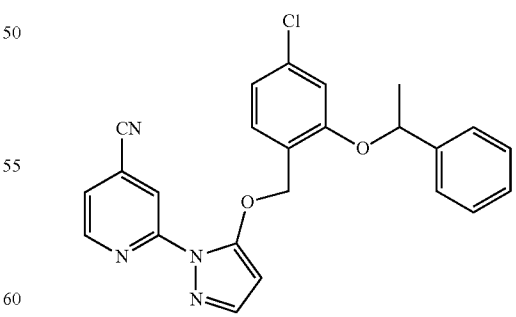

The title compound was prepared from 2-(5-hydroxy-1H-pyrazol-1-yl)pyridine-4-carbonitrile and [4-chloro-2-(1-phenylethoxy)phenyl]methanol according to the procedure for the preparation of Example 39, part C. [M+H] Calc'd for C$_{24}$H$_{19}$ClN$_4$O$_2$, 431. Found, 431.

C. 2-[5-[[4-chloro-2-(1-phenylethoxy)phenyl]methoxy]pyrazol-1-yl]pyridine-4-carboxylic acid

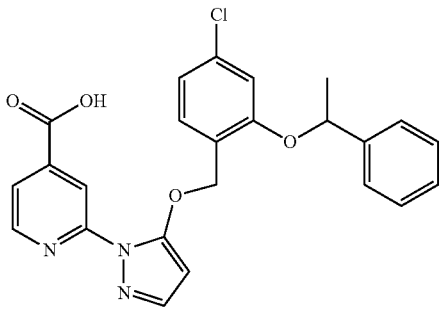

The title compound was prepared from 2-[5-[[4-chloro-2-(1-phenylethoxy)phenyl]methoxy]pyrazol-1-yl]pyridine-4-carbonitrile according to the procedure for the preparation of Example 28, part E. $^1$H NMR (300 MHz, DMSO-$d_6$): δ 1.45 (3H, d, J=6.6 Hz), 5.25-5.33 (2H, m), 5.57-5.63 (1H, m), 6.05 (1H, d, J=1.8 Hz), 6.93-6.95 (2H, m), 7.21-7.35 (5H, m), 7.48 (1H, d, J=8.1 Hz), 7.61 (1H, d, J=1.2 Hz), 7.74-7.56 (1H, m), 8.08 (1H, s), 8.43 (1H, d, J=1.8 Hz). [M+H] Calc'd for $C_{24}H_{20}ClN_3O_4$, 450. Found, 450.

Example 137

2-[5-[[4-fluoro-2-(1-phenylethoxy)phenyl]methoxy]pyrazol-1-yl]pyridine-4-carboxylic acid A. [4-fluoro-2-(1-phenylethoxy)phenyl]methanol

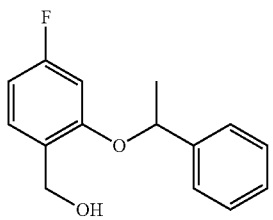 [SMILES: CC(Oc1cc(F)ccc1CO)c1ccccc1]

The title compound was prepared from 5-fluoro-2-(hydroxymethyl)phenol and (bromoethyl)benzene according to the procedure for the preparation of Example 136, part A.

B. 2-[5-[[4-fluoro-2-(1-phenylethoxy)phenyl]methoxy]pyrazol-1-yl]pyridine-4-carbonitrile

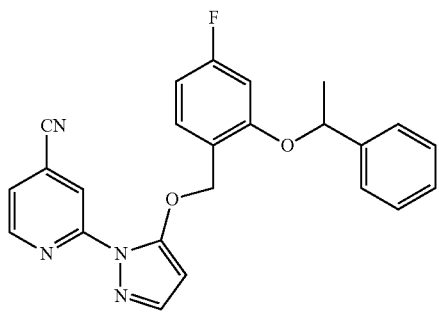 [SMILES: CC(Oc1cc(F)ccc1COc1ccnn1-c1cc(C#N)ccn1)c1ccccc1]

The title compound was prepared from 2-(5-hydroxy-1H-pyrazol-1-yl)pyridine-4-carbonitrile and [4-fluoro-2-(1-phenylethoxy)phenyl]methanol according to the procedure for the preparation of Example 39, part C. [M+H] Calc'd for $C_{24}H_{19}FN_4O_2$, 415. Found, 415.

C. 2-[5-[[4-fluoro-2-(1-phenylethoxy)phenyl]methoxy]pyrazol-1-yl]pyridine-4-carboxylic acid

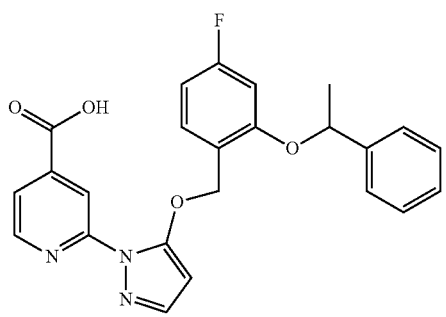

The title compound was prepared from 2-[5-[[4-fluoro-2-(1-phenylethoxy)phenyl]methoxy]pyrazol-1-yl]pyridine-4-carbonitrile according to the procedure for the preparation of Example 28, part E. $^1$H NMR (300 MHz, DMSO-$d_6$): δ 1.45 (3H, d, J=6.6 Hz), 5.24-5.32 (2H, m), 5.53-5.60 (1H, m), 6.07 (1H, d, J=2.1 Hz), 6.67-6.78 (2H, m), 7.21-7.34 (5H, m), 7.50 (1H, t, J=7.8 Hz), 7.60-7.62 (1H, m), 7.74-7.75 (1H, m), 8.07 (1H, s), 8.67 (1H, d, J=5.1 Hz). [M+H] Calc'd for $C_{24}H_{20}FN_3O_4$, 434. Found, 434.

Example 138

2-[5-[[4-chloro-3-[(4-fluorophenyl)methoxy]phenyl]methoxy]pyrazol-1-yl]pyridine-4-carboxylic acid A. 2-chloro-5-(hydroxymethyl)phenol

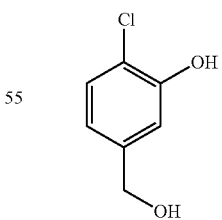

The title compound was prepared from 4-chloro-3-hydroxybenzoic acid according to the procedure for the preparation of Example 123, part A. $^1$H NMR (300 MHz, CDCl$_3$): δ 4.39 (2H, d, J=5.7 Hz), 5.18 (1H, t, J=5.7 Hz), 6.70-6.73 (1H, m), 6.94 (1H, s), 7.23 (1H, d, J=7.8 Hz), 10.03 (1H, s).

B. [4-chloro-3-[(4-fluorophenyl)methoxy]phenyl]
methanol

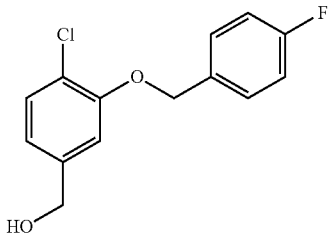 [SMILES: OCc1ccc(Cl)c(OCc2ccc(F)cc2)c1]

The title compound was prepared from 2-chloro-5-(hydroxymethyl)phenol and 4-(bromomethyl)-1-fluorobenzene according to the procedure for the preparation of Example 117, part A. $^1$H NMR (400 MHz, CDCl$_3$): δ 1.71 (1H, t, J=6.0 Hz), 4.65 (2H, d, J=6.4 Hz), 5.12 (2H, s), 6.88-6.90 (1H, m), 7.02 (1H, d, J=2.0 Hz), 7.05-7.10 (2H, m), 7.35 (1H, d, J=8.0 Hz), 7.43-7.46 (2H, m).

C. 2-[5-[[4-chloro-3-[(4-fluorophenyl)methoxy]phenyl]methoxy]pyrazol-1-yl]pyridine-4-carbonitrile

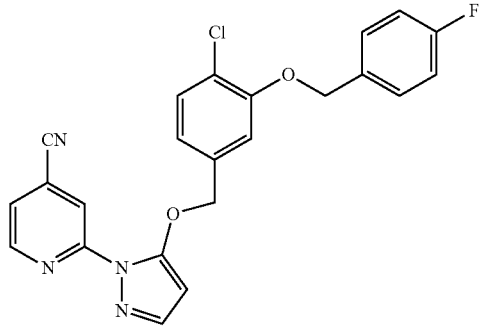 [SMILES: N#Cc1ccnc(-n2nccc2OCc2ccc(Cl)c(OCc3ccc(F)cc3)c2)c1]

The title compound was prepared from 2-(5-hydroxy-1H-pyrazol-1-yl)pyridine-4-carbonitrile and [4-chloro-3-[(4-fluorophenyl)methoxy]phenyl]methanol according to the procedure for the preparation of Example 39, part C. $^1$H NMR (400 MHz, CDCl$_3$): δ 5.10 (2H, s), 5.18 (2H, s), 5.68 (1H, d, J=1.6 Hz), 6.97 (1H, dd, J=1.2 Hz, 8.0 Hz), 7.03-7.07 (3H, m), 7.39-7.43 (4H, m), 7.55 (1H, d, J=1.6 Hz), 8.04 (1H, s), 8.67 (1H, d, J=5.2 Hz). [M+H] Calc'd for C$_{23}$H$_{16}$ClFN$_4$O$_2$, 435. Found, 435.

D. 2-[5-[[4-chloro-3-[(4-fluorophenyl)methoxy]phenyl]methoxy]pyrazol-1-yl]pyridine-4-carboxylic acid

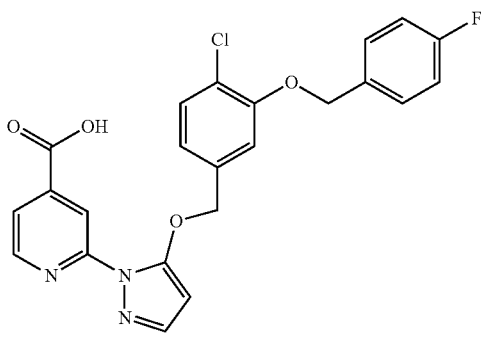 [SMILES: O=C(O)c1ccnc(-n2nccc2OCc2ccc(Cl)c(OCc3ccc(F)cc3)c2)c1]

The title compound was prepared from 2-[5-[[4-chloro-3-[(4-fluorophenyl)methoxy]phenyl]methoxy]pyrazol-1-yl]pyridine-4-carbonitrile according to the procedure for the preparation of Example 28, part E. $^1$H NMR (400 MHz, DMSO-d$_6$): δ 5.18 (2H, s), 5.24 (2H, s), 5.92 (1H, s), 7.04-7.07 (1H, m), 7.19-7.23 (2H, m), 7.39 (1H, s), 7.44 (1H, d, J=8.4 Hz), 7.51-7.54 (3H, m), 7.65 (1H, d, J=6.4 Hz), 7.96 (1H, s), 8.43 (1H, d, J=4.8 Hz). [M+H] Calc'd for C$_{23}$H$_{17}$ClFN$_3$O$_4$, 454. Found, 454.

Example 139

2-[5-[[4-fluoro-3-[(4-fluorophenyl)methoxy]phenyl]methoxy]pyrazol-1-yl]pyridine-4-carboxylic acid A. methyl 4-fluoro-3-[(4-fluorophenyl)methoxy]benzoate

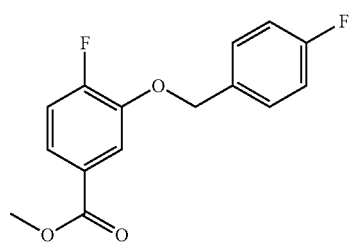 [SMILES: COC(=O)c1ccc(F)c(OCc2ccc(F)cc2)c1]

Charge methyl 4-fluoro-3-hydroxybenzoate (519 mg, 3.05 mmol), 4-(bromomethyl)-1-fluorobenzene (577 mg, 3.05 mmol), K$_2$CO$_3$ (843 mg, 6.10 mmol) and ethanol (10 mL) to a flask. The mixture was then stirred at room temperature overnight. Water was added to the reaction mixture at 0° C., filtered, and the solid dried and purified by flash column chromatograph to give 571 mg of the title compound (67%). $^1$H NMR (400 MHz, CDCl$_3$): δ 3.90 (3H, s), 5.13 (2H, s), 7.06-7.15 (3H, m), 7.41-7.45 (2H, m), 7.63-7.67 (1H, m), 7.71 (1H, dd, J=2.0 Hz, 8.4 Hz).

B. [4-fluoro-3-[(4-fluorophenyl)methoxy]phenyl]methanol

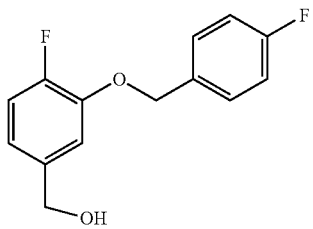 [SMILES: OCc1ccc(F)c(OCc2ccc(F)cc2)c1]

To a solution of methyl 4-fluoro-3-[(4-fluorophenyl)methoxy]benzoate (571 mg, 2.05 mmol) in THF (6 mL) cooled to −50° C., was added LiAlH$_4$ solution (4.6 mL, 4.11 mmol, 1.0 M in THF) drop wise. Thereto, the mixture was stirred at this temperature for 1 h. Added water (0.2 mL) slowly, followed by NaOH (aq, 10%, 0.2 mL) and water (0.6 mL), the resulting mixture was filtered and washed with THF, the filtrate was concentrated to give 444 mg of the title compound (86%). $^1$H NMR (400 MHz, CDCl$_3$): δ 1.67 (1H, t, J=6.0 Hz), 4.62 (2H, d, J=6.0 Hz), 5.10 2H, s), 6.87-6.91 (1H, m), 7.04-7.09 (4H, m), 7.40-7.43 (2H, m).

C. 2-[5-[[4-fluoro-3-[(4-fluorophenyl)methoxy]phenyl]methoxy]pyrazol-1-yl]pyridine-4-carbonitrile

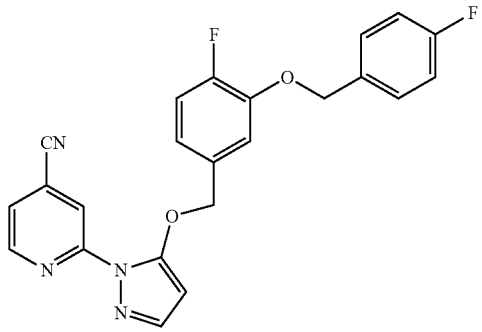 [SMILES: N#Cc1ccnc(-n2nccc2OCc2ccc(F)c(OCc3ccc(F)cc3)c2)c1]

The title compound was prepared from 2-(5-hydroxy-1H-pyrazol-1-yl)pyridine-4-carbonitrile and [4-fluoro-3-[(4-fluorophenyl)methoxy]phenyl]methanol according to the procedure for the preparation of Example 39, part C. $^1$H NMR (400 MHz, CDCl$_3$): δ 5.09 (2H, s), 5.16 (2H, s), 5.69 (1H, s), 6.98-7.13 (5H, m), 7.37-7.40 (3H, m), 7.56 (1H, s), 8.03 (1H, s), 8.67 (1H, d, J=4.8 Hz). [M+H] Calc'd for C$_{23}$H$_{16}$F$_2$N$_4$O$_2$, 419. Found, 419.

D. 2-[5-[[4-fluoro-3-[(4-fluorophenyl)methoxy]phenyl]methoxy]pyrazol-1-yl]pyridine-4-carboxylic acid

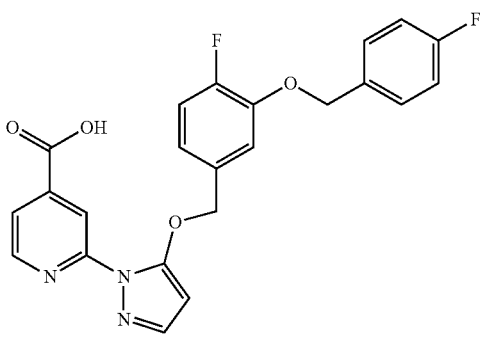 [SMILES: O=C(O)c1ccnc(-n2nccc2OCc2ccc(F)c(OCc3ccc(F)cc3)c2)c1]

The title compound was prepared from 2-[5-[[4-fluoro-3-[(4-fluorophenyl)methoxy]phenyl]methoxy]pyrazol-1-yl]pyridine-4-carbonitrile according to the procedure for the preparation of Example 28, part E. $^1$H NMR (400 MHz, DMSO-d$_6$): δ 5.13 (2H, s), 5.23 (2H, s), 5.98 (1H, s), 7.07 (1H, d, J=0.8 Hz), 7.18-7.25 (3H, m), 7.41 (1H, d, J=8.4 Hz), 7.48-7.51 (2H, m), 7.57 (1H, s), 7.76 (1H, d, J=3.2 Hz), 8.06 (1H, s), 8.60 (1H, s).

Example 140

2-[5-[[4-chloro-3-(cyclopropylmethoxy)phenyl]methoxy]pyrazol-1-yl]pyridine-4-carboxylic acid A.
[4-chloro-3-(cyclopropylmethoxy)phenyl]methanol

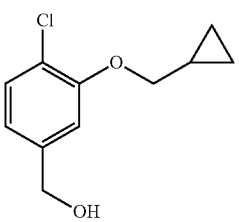 [SMILES: OCc1ccc(Cl)c(OCC2CC2)c1]

The title compound was prepared from 2-chloro-5-(hydroxymethyl)phenol and bromocyclopropylmethanol according to the procedure for the preparation of Example 111, part A. $^1$H NMR (400 MHz, CDCl$_3$): δ 0.36-0.40 (2H, m), 0.62-0.67 (2H, m), 1.29-1.33 (1H, m), 1.76 (1H, s), 3.89 (2H, d, J=6.8 Hz), 4.64 (2H, s), 6.84-6.86 (1H, m), 6.94 (1H, d, J=2.0 Hz), 7.32 (1H, d, J=8.0 Hz).

B. 2-[5-[[4-chloro-3-(cyclopropylmethoxy)phenyl]methoxy]pyrazol-1-yl]pyridine-4-carbonitrile

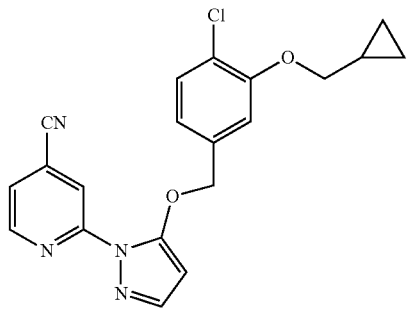 [SMILES: N#Cc1ccnc(-n2nccc2OCc2ccc(Cl)c(OCC3CC3)c2)c1]

The title compound was prepared from 2-(5-hydroxy-1H-pyrazol-1-yl)pyridine-4-carbonitrile and [4-chloro-3-(cyclopropylmethoxy)phenyl]methanol according to the procedure for the preparation of Example 39, part C. $^1$H NMR (400 MHz, CDCl$_3$): δ 0.36-0.40 (2H, m), 0.62-0.67 (2H, m), 1.25-1.32 (1H, m), 3.88 (2H, d, J=6.8 Hz), 5.18 (2H, s), 5.72 (1H, d, J=1.6 Hz), 6.92 (1H, dd, J=4.0 Hz, 8.0 Hz), 7.01 (1H, d, J=1.6 Hz), 7.37 (1H, d, J=8.0 Hz), 7.40 (1H, dd, J=1.2 Hz, 5.2 Hz), 7.56 (1H, d, J=2.0 Hz), 8.04 (1H, s), 8.68 (1H, d, J=5.2 Hz). [M+H] Calc'd for C$_{20}$H$_{17}$ClN$_4$O$_2$, 381. Found, 381.

C. 2-[5-[[4-chloro-3-(cyclopropylmethoxy)phenyl]methoxy]pyrazol-1-yl]pyridine-4-carboxylic acid

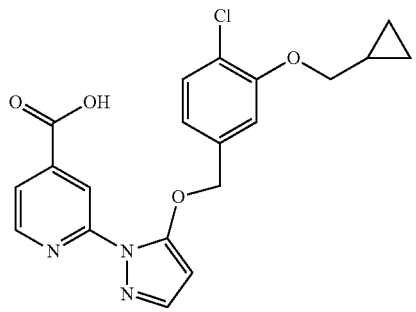 [SMILES: O=C(O)c1ccnc(-n2nccc2OCc2ccc(Cl)c(OCC3CC3)c2)c1]

The title compound was prepared from 2-[5-[[4-chloro-3-(cyclopropylmethoxy)phenyl]methoxy]pyrazol-1-yl]pyridine-4-carbonitrile according to the procedure for the preparation of Example 28, part E. $^1$H NMR (400 MHz, DMSO-d$_6$): δ 0.30-0.34 (2H, m), 0.54-0.58 (2H, m), 1.19-1.25 (1H, m), 3.87 (2H, d, J=6.4 Hz), 5.26 (2H, s), 6.01 (1H, d, J=1.6 Hz), 7.03 (1H, dd, J=1.6 Hz, 8.0 Hz), 7.25 (1H, d, J=1.6 Hz), 7.41 (1H, d, J=8.0 Hz), 7.59 (1H, d, J=2.0 Hz), 7.77 (1H, dd, J=1.6 Hz, 4.8 Hz), 8.08 (1H, s), 8.67 (1H, d, J=4.8 Hz). [M+H] Calc'd for C$_{20}$H$_{18}$ClN$_3$O$_4$, 400. Found, 400.

Example 141

2-[5-[[4-chloro-3-(2,2,2-trifluoroethoxy)phenyl]methoxy]pyrazol-1-yl]pyridine-4-carboxylic acid

A. [4-chloro-3-(2,2,2-trifluoroethoxy)phenyl]methanol

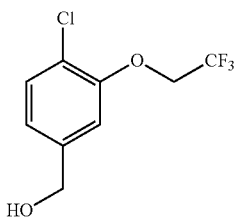

A mixture of 2,2,2-trifluoroethyl 4-methylbenzenesulfonate (1.34 g, 5.28 mmol), 2-chloro-5-(hydroxymethyl)phenol (837 mg, 5.28 mmol), $K_2CO_3$ (1.46 g, 10.56 mmol) and DMF (9 mL) was heated to 100° C. overnight. It was then poured into ice-water and extracted with ethyl acetate twice. Organic phase washed with water twice, brine and dried with $Na_2SO_4$, concentrated to a residue which was purified by flash column chromatograph to give the title compound (903 mg, 75%). $^1$H NMR (400 MHz, $CDCl_3$): δ 1.77 (1H, t, J=5.6 Hz), 4.42 (2H, q, J=8.0 Hz), 4.68 (2H, d, J=5.2 Hz), 6.99 (1H, dd, J=1.6 Hz, 8.0 Hz), 7.02 (1H, s), 7.37 (1H, d, J=8.0 Hz).

B. 2-[5-[[4-chloro-3-(2,2,2-trifluoroethoxy)phenyl]methoxy]pyrazol-1-yl]pyridine-4-carbonitrile

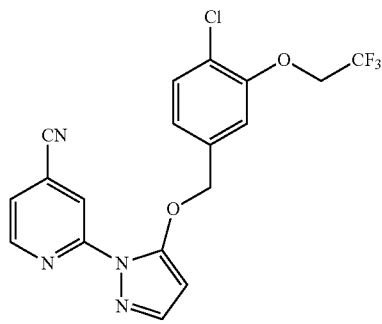 [SMILES: N#Cc1ccnc(-n2nccc2OCc2ccc(Cl)c(OCC(F)(F)F)c2)c1]

The title compound was prepared from 2-(5-hydroxy-1H-pyrazol-1-yl)pyridine-4-carbonitrile and [4-chloro-3-(2,2,2-trifluoroethoxy)phenyl]methanol according to the procedure for the preparation of Example 39, part C. $^1$H NMR (400 MHz, $CDCl_3$): δ 4.41 (2H, d, J=7.6 Hz), 5.20 (2H, s), 5.73 (1H, d, J=2.0 Hz), 7.08 (1H, dd, J=2.0 Hz, 8.0 Hz), 7.14 (1H, d, J=2.0 Hz), 7.41-7.44 (2H, m), 7.57 (1H, d, J=1.6 Hz), 8.05 (1H, s), 8.67 (1H, d, J=4.8 Hz). [M+H] Calc'd for $C_{18}H_{12}ClF_3N_4O_2$, 409. Found, 409.

C. 2-[5-[[4-chloro-3-(2,2,2-trifluoroethoxy)phenyl]methoxy]pyrazol-1-yl]pyridine-4-carboxylic acid

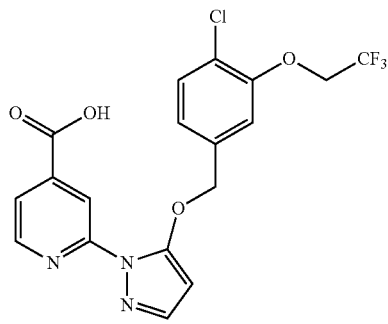 [SMILES: O=C(O)c1ccnc(-n2nccc2OCc2ccc(Cl)c(OCC(F)(F)F)c2)c1]

The title compound was prepared from 2-[5-[[4-chloro-3-(2,2,2-trifluoroethoxy)phenyl]methoxy]pyrazol-1-yl]pyridine-4-carbonitrile according to the procedure for the preparation of Example 28, part E. $^1$H NMR (400 MHz, DMSO-$d_6$): δ 4.81-4.87 (2H, m), 5.26 (2H, s), 6.01 (1H, d, J=1.6 Hz), 7.17-7.20 (1H, m), 7.44 (1H, s), 7.50 (1H, d, J=8.0 Hz), 7.60 (1H, d, J=2.0 Hz), 7.76 (1H, dd, J=1.6 Hz, 5.2 Hz), 8.10 (1H, s), 8.68 (1H, d, J=5.2 Hz). [M+H] Calc'd for $C_{18}H_{13}ClF_3N_3O_4$, 428. Found, 428.

Example 142

2-[5-[(4-bromo-2-methylphenyl)methoxy]pyrazol-1-yl]pyridine-4-carboxylic acid

2-[5-[(4-bromo-2-methylphenyl)methoxy]pyrazol-1-yl]pyridine-4-carbonitrile

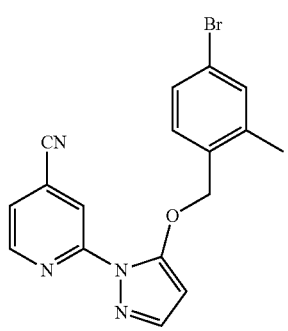 [SMILES: Cc1cc(Br)ccc1COc1ccnn1-c1cc(C#N)ccn1]

The title compound was prepared from 2-(5-hydroxy-1H-pyrazol-1-yl)pyridine-4-carbonitrile and (4-bromo-3-methylphenyl)methanol according to the procedure for the preparation of Example 39, part C. [M+H] Calc'd for $C_{17}H_{13}BrN_4O$, 369. Found, 369.

B. 2-[5-[(4-bromo-2-methylphenyl)methoxy]pyrazol-1-yl]pyridine-4-carboxylic acid

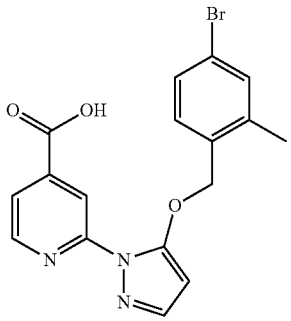 [SMILES: Cc1cc(Br)ccc1COc1ccnn1-c1cc(C(=O)O)ccn1]

The title compound was prepared from 2-[5-[(4-bromo-2-methylphenyl)methoxy]pyrazol-1-yl]pyridine-4-carbonitrile according to the procedure for the preparation of Example 28, part E. $^1$H NMR (400 MHz, DMSO-$d_6$): δ 2.33 (3H, s), 5.24 (2H, s), 6.08 (1H, s), 7.39-7.45 (3H, m), 7.61 (1H, s), 7.74 (1H, d, J=4.4 Hz), 8.06 (1H, s), 8.66 (1H, d, J=4.8 Hz). [M+H] Calc'd for $C_{17}H_{14}BrN_3O_3$, 388. Found, 388.

Example 143

2-[5-[(4-bromo-2-methoxyphenyl)methoxy]pyrazol-1-yl]pyridine-4-carboxylic acid

A. 2-[5-[(4-bromo-2-methoxyphenyl)methoxy]pyrazol-1-yl]pyridine-4-carbonitrile

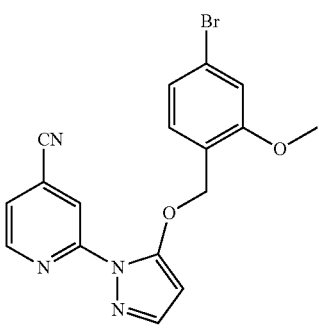 [SMILES: COc1cc(Br)ccc1COc1ccnn1-c1cc(C#N)ccn1]

The title compound was prepared from 2-(5-hydroxy-1H-pyrazol-1-yl)pyridine-4-carbonitrile and (4-bromo-3-methoxyphenyl)methanol according to the procedure for the preparation of Example 39, part C. $^1$H NMR (400 MHz, CDCl$_3$): δ 3.89 (3H, s), 5.20 (2H, s), 5.77 (1H, d, J=1.6 Hz), 7.06 (1H, d, J=1.2 Hz), 7.12 (1H, dd, J=1.6 Hz, 8.0 Hz), 7.28 (1H, d, J=8.0 Hz), 7.39 (1H, dd, J=1.2 Hz, 4.8 Hz), 7.57 (1H, d, J=2.0 Hz), 8.05 (1H, t, J=0.8 Hz), 8.70 (1H, d, J=0.8 Hz, 4.8 Hz). [M+H] Calc'd for $C_{17}H_{13}BrN_4O_2$, 385. Found, 385.

B. 2-[5-[(4-bromo-2-methoxyphenyl)methoxy]pyrazol-1-yl]pyridine-4-carboxylic acid

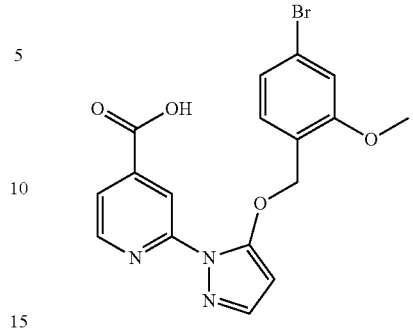

The title compound was prepared from 2-[5-[(4-bromo-2-methoxyphenyl)methoxy]pyrazol-1-yl]pyridine-4-carbonitrile according to the procedure for the preparation of Example 28, part E. $^1$H NMR (400 MHz, DMSO-$d_6$): δ 3.83 (3H, s), 5.18 (2H, s), 6.01 (1H, s), 7.17 (1H, d, J=8.0 Hz), 7.24 (1H, s), 7.43 (1H, d, J=8.4 Hz), 7.59 (1H, s), 7.74 (1H, d, J=4.8 Hz), 8.07 (1H, s), 8.67 (1H, d, J=5.2 Hz). [M+H] Calc'd for $C_{17}H_{14}IN_3O_4$, 404. Found, 404.

Example 144

2-[5-[(4-iodo-2-methylphenyl)methoxy]pyrazol-1-yl]pyridine-4-carboxylic acid

A. (4-iodo-2-methylphenyl)methanol

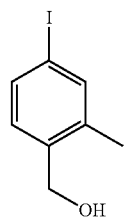

The title compound was prepared from 4-iodo-2-methylbenzoic acid according to the procedure for the preparation of Example 123, part A. $^1$H NMR (400 MHz, CDCl$_3$): δ 2.29 (3H, s), 4.64 (2H, s), 7.09-7.11 (1H, m), 7.53-7.54 (2H, m).

B. 2-[5-[(4-iodo-2-methylphenyl)methoxy]pyrazol-1-yl]pyridine-4-carbonitrile

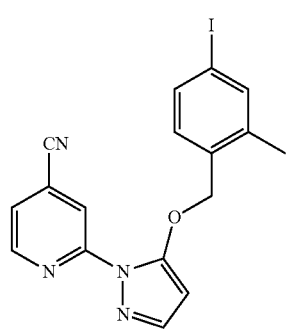 [SMILES: Cc1cc(I)ccc1COc1ccnn1-c1cc(C#N)ccn1]

The title compound was prepared from 2-(5-hydroxy-1H-pyrazol-1-yl)pyridine-4-carbonitrile and (4-iodo-2-methylphenyl)methanol according to the procedure for the preparation of Example 39, part C. $^1$H NMR (400 MHz, CDCl$_3$): δ 2.33 (3H, s), 5.15 (2H, s), 5.76 (1H, d, J=1.6 Hz), 7.14 (1H, d, J=8.0 Hz), 7.39 (1H, dd, J=1.6 Hz, 5.2 Hz), 7.55-7.59 (3H, m), 8.00 (1H, s), 8.66 (1H, d, J=5.2 Hz). [M+H] Calc'd for C$_{17}$H$_{13}$IN$_4$O, 417. Found, 417.

C. 2-[5-[(4-iodo-2-methylphenyl)methoxy]pyrazol-1-yl]pyridine-4-carboxylic acid

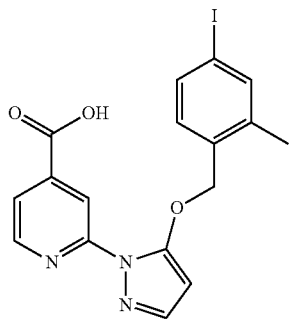 [SMILES: Cc1cc(I)ccc1COc1ccnn1-c1cc(C(=O)O)ccn1]

The title compound was prepared from 2-[5-[(4-iodo-2-methylphenyl)methoxy]pyrazol-1-yl]pyridine-4-carbonitrile according to the procedure for the preparation of Example 28, part E. $^1$H NMR (400 MHz, DMSO-d$_6$): δ 2.30 (3H, s), 5.22 (2H, s), 6.06 (1H, s), 7.28 (1H, d, J=8.0 Hz), 7.56-7.61 (3H, m), 7.74 (1H, d, J=4.8 Hz), 8.05 (1H, s), 8.65 (1H, d, J=4.8 Hz). [M+H] Calc'd for C$_{17}$H$_{14}$IN$_3$O$_3$, 436. Found, 436.

Example 145

2-[5-[(4-iodo-2-methoxyphenyl)methoxy]pyrazol-1-yl]pyridine-4-carboxylic acid

A. (4-iodo-2-methoxyphenyl)methanol

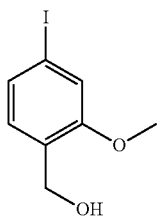

A solution of methyl 4-iodo-2-methoxybenzoate (840 mg, 2.88 mmol) in THF was purged with nitrogen and cooled to −78° C. DIBALH (6 mL, 5.75 mmol, 1M in toluene) was added slowly. The mixture was then stirred at the same temperature for an hour. Saturated aqueous NH$_4$Cl solution was added, followed by extraction with ethyl acetate twice. The organic phase was then washed with brine and dried with anhydrous Na$_2$SO$_4$. Solvent was removed and the resulting residue purified by flash column chromatograph to give 237 mg of the title compound (31%). $^1$H NMR (400 MHz, CDCl$_3$): δ 2.17 (1H, s), 3.84 (3H, s), 4.62 (2H, d, J=4.0 Hz), 7.01 (1H, d, J=7.6 Hz), 7.18 (1H, s), 7.29 (1H, d, J=8.0 Hz).

B. 2-[5-[(4-iodo-2-methoxyphenyl)methoxy]pyrazol-1-yl]pyridine-4-carbonitrile

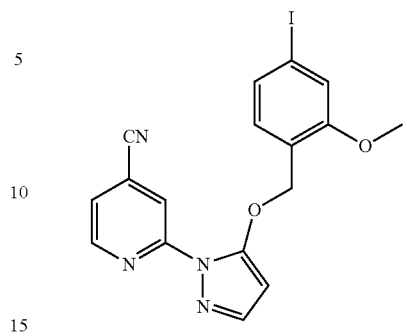

The title compound was prepared from 2-(5-hydroxy-1H-pyrazol-1-yl)pyridine-4-carbonitrile and (4-iodo-2-methoxyphenyl)methanol according to the procedure for the preparation of Example 39, part C. $^1$H NMR (400 MHz, CDCl$_3$): δ 3.88 (3H, s), 5.20 (2H, s), 5.77 (1H, d, J=2.0 Hz), 7.13 (1H, d, J=8.0 Hz), 7.23 (1H, d, J=1.6 Hz), 7.33 (1H, dd, J=1.6 Hz, 8.0 Hz), 7.39 (1H, dd, J=1.2 Hz, 4.8 Hz), 7.57 (1H, d, J=2.0 Hz), 8.05 (1H, t, J=1.2 Hz), 8.70 (1H, d, J=0.8 Hz, 5.2 Hz). [M+H] Calc'd for C$_{17}$H$_{13}$1 N$_4$O$_2$, 433. Found, 433.

C. 2-[5-[(4-iodo-2-methoxyphenyl)methoxy]pyrazol-1-yl]pyridine-4-carboxylic acid

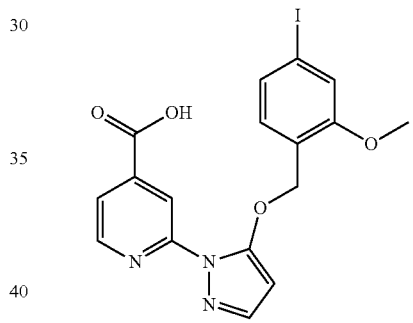

The title compound was prepared from 2-[5-[(4-iodo-2-methoxyphenyl)methoxy]pyrazol-1-yl]pyridine-4-carbonitrile according to the procedure for the preparation of Example 28, part E. $^1$H NMR (400 MHz, DMSO-d$_6$): δ 3.82 (3H, s), 5.15 (2H, s), 5.93 (1H, d, J=1.6 Hz), 7.25 (1H, d, J=8.0 Hz), 7.33-7.35 (2H, m), 7.52 (1H, d, J=2.0 Hz), 7.67 (1H, d, J=4.8 Hz), 7.97 (1H, s), 8.50 (1H, d, J=4.8 Hz). [M+H] Calc'd for C$_{17}$H$_{14}$1 N$_3$O$_4$, 451. Found, 451.

Example 146

2-[5-[(5-fluoro-2,3-dihydro-1H-inden-1-yl)oxy]pyrazol-1-yl]pyridine-4-carboxylic acid A. 5-fluoro-2,3-dihydro-1H-inden-1-ol

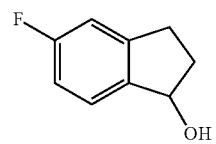

Charged 5-fluoro-2,3-dihydroinden-1-one (486 mg, 3.22 mmol), methanol (8 mL) and dichloromethane (4 mL) to a flask, the mixture was cooled to 0° C. and NaBH$_4$ (119 mg, 3.22 mmol) was added in portions. The reaction mixture was stirred at 0° C. for 15 min, warmed up to room temperature and stirred for 30 min. Added water, extracted with ethyl acetate twice, and washed the organic phase with brine and dried with anhydrous Na$_2$SO$_4$, concentrated to give the title compound (488 mg, 100%). $^1$H NMR (400 MHz, CDCl$_3$): δ 1.94-2.02 (1H, m), 2.46-2.55 (1H, m), 2.76-7.84 (1H, m), 3.01-3.08 (1H, m), 5.20 (2H, t, J=5.6 Hz), 6.89-6.93 (2H, m), 7.32-7.36 (1H, m).

B. 2-[5-[(5-fluoro-2,3-dihydro-1H-inden-1-yl)oxy]pyrazol-1-yl]pyridine-4-carbonitrile

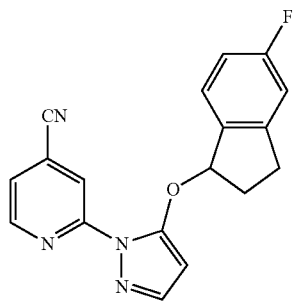 [SMILES: N#Cc1ccnc(-n2nccc2OC2CCc3cc(F)ccc32)c1]

The title compound was prepared from 2-(5-hydroxy-1H-pyrazol-1-yl)pyridine-4-carbonitrile and 5-fluoro-2,3-dihydro-1H-inden-1-ol according to the procedure for the preparation of Example 39, part C. $^1$H NMR (400 MHz, CDCl$_3$): δ 2.39-2.46 (1H, m), 2.59-2.64 (1H, m), 2.90-2.98 (1H, m), 3.13-3.20 (1H, m), 5.72-5.75 (1H, m), 5.84 (1H, d, J=1.6 Hz), 6.89-6.94 (1H, m), 6.98 (1H, d, J=8.8 Hz), 7.34-7.37 (2H, m), 7.62 (1H, d, J=1.6 Hz), 7.86 (1H, s), 8.64 (1H, d, J=4.8 Hz). [M+H] Calc'd for C$_{15}$H$_{13}$FN$_4$O, 321. Found, 321.

C. 2-[5-[(5-fluoro-2,3-dihydro-1H-inden-1-yl)oxy]pyrazol-1-yl]pyridine-4-carboxylic acid

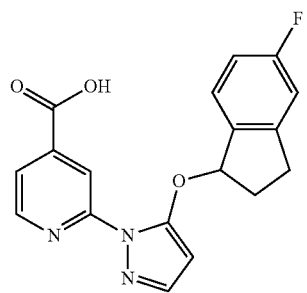 [SMILES: O=C(O)c1ccnc(-n2nccc2OC2CCc3cc(F)ccc32)c1]

The title compound was prepared from 2-[5-[(5-fluoro-2,3-dihydro-1H-inden-1-yl)oxy]pyrazol-1-yl]pyridine-4-carbonitrile according to the procedure for the preparation of Example 28, part E. $^1$H NMR (800 MHz, CD$_3$OD-d$_4$): δ 2.38-2.45 (1H, m), 2.59-2.68 (1H, m), 2.92-2.99 (1H, m), 3.16-3.24 (1H, m), 5.85-5.87 (1H, m), 6.12 (1H, d, J=3.2 Hz), 6.90-6.95 (1H, m), 7.02 (1H, dd, J=4.0 Hz, 18.4 Hz), 7.43 (1H, dd, J=10.4 Hz, 17.6 Hz), 7.66 (1H, d, J=3.2 Hz), 7.81 (1H, dd, J=2.4 Hz, 9.6 Hz), 8.10 (1H, s), 8.61 (1H, d, J=9.6 Hz). [M+H] Calc'd for C$_{18}$H$_{14}$FN$_3$O$_3$, 340. Found, 340.

Example 147

2-[5-[(5-chloro-2,3-dihydro-1H-inden-1-yl)oxy]pyrazol-1-yl]pyridine-4-carboxylic acid A. 5-chloro-2,3-dihydro-1H-inden-1-ol

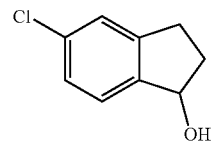 [SMILES: OC1CCc2cc(Cl)ccc21]

The title compound was prepared from 5-chloro-2,3-dihydroinden-1-one according to the procedure for the preparation of Example 146, part A.

B. 2-[5-[(5-chloro-2,3-dihydro-1H-inden-1-yl)oxy]pyrazol-1-yl]pyridine-4-carbonitrile

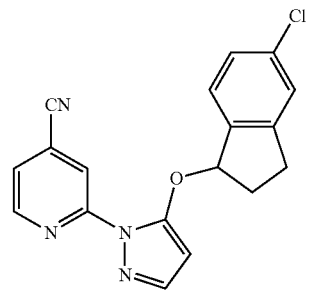 [SMILES: N#Cc1ccnc(-n2nccc2OC2CCc3cc(Cl)ccc32)c1]

The title compound was prepared from 2-(5-hydroxy-1H-pyrazol-1-yl)pyridine-4-carbonitrile and 5-chloro-2,3-dihydro-1H-inden-1-ol according to the procedure for the preparation of Example 39, part C. $^1$H NMR (400 MHz, CDCl$_3$): δ 2.36-2.44 (1H, m), 2.57-2.66 (1H, m), 2.90-2.98 (1H, m), 3.12-3.20 (1H, m), 5.73-5.75 (1H, m), 5.85 (1H, d, J=2.0 Hz), 7.20 (1H, d, J=8.0 Hz), 7.29 (1H, s), 7.32 (1H, d, J=8.0 Hz), 7.36 (1H, dd, J=1.8 Hz, 4.8 Hz), 7.63 (1H, d, J=2.0 Hz), 7.87 (1H, s), 8.65 (1H, d, J=4.8 Hz). [M+H] Calc'd for C$_{18}$H$_{13}$ClN$_4$O, 337. Found, 337.

C. 2-[5-[(5-chloro-2,3-dihydro-1H-inden-1-yl)oxy]pyrazol-1-yl]pyridine-4-carboxylic acid

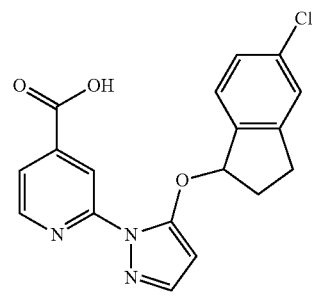 [SMILES: O=C(O)c1ccnc(-n2nccc2OC2CCc3cc(Cl)ccc32)c1]

The title compound was prepared from 2-[5-[(5-chloro-2,3-dihydro-1H-inden-1-yl)oxy]pyrazol-1-yl]pyridine-4-carbonitrile according to the procedure for the preparation of Example 28, part E. ¹H NMR (400 MHz, CD₃OD-d₄): δ 2.35-2.43 (1H, m), 2.59-2.68 (1H, m), 2.92-2.99 (1H, m), 3.14-3.22 (1H, m), 5.85-5.87 (1H, m), 6.13 (1H, d, J=1.6 Hz), 7.02 (1H, dd, J=1.6 Hz, 8.0 Hz), 7.30 (1H, s), 7.39 (1H, d, J=8.0 Hz), 7.66 (1H, d, J=1.6 Hz), 7.81 (1H, dd, J=1.6 Hz, 5.2 Hz), 8.11 (1H, s), 8.61 (1H, d, J=4.8 Hz). [M+H] Calc'd for $C_{18}H_{14}ClN_3O_3$, 356. Found, 356.

Example 148

2-[5-[(6-fluoro-1,2,3,4-tetrahydronaphthalen-1-yl)oxy]pyrazol-1-yl]pyridine-4-carboxylic acid A. 6-fluoro-1,2,3,4-tetrahydronaphthalen-1-ol

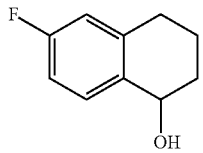

The title compound was prepared from 6-fluoro-3,4-dihydro-2H-naphthalen-1-one according to the procedure for the preparation of Example 146, part A. ¹H NMR (400 MHz, CDCl₃): δ 1.69-2.01 (4H, m), 2.66-2.84 (2H, m), 4.85 (1H, t, J=4.4 Hz), 6.78 (1H, dd, J=2.4 Hz, 9.6 Hz), 6.86-6.91 (1H, m), 7.38 (1H, dd, J=6.0 Hz, 8.4 Hz).

B. 2-[5-[(6-fluoro-1,2,3,4-tetrahydronaphthalen-1-yl)oxy]pyrazol-1-yl]pyridine-4-carbonitrile

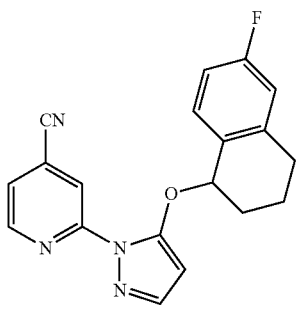 [SMILES: N#Cc1ccnc(-n2nccc2OC2CCCc3cc(F)ccc32)c1]

The title compound was prepared from 2-(5-hydroxy-1H-pyrazol-1-yl)pyridine-4-carbonitrile and 6-fluoro-1,2,3,4-tetrahydronaphthalen-1-ol according to the procedure for the preparation of Example 39, part C. ¹H NMR (400 MHz, CDCl₃): δ 1.82-1.88 (1H, m), 1.99-2.10 (2H, m), 2.28-2.34 (1H, m), 2.74-2.94 (2H, m), 5.35 (1H, t, J=4.0 Hz), 5.85 (1H, d, J=1.6 Hz), 6.84-6.89 (2H, m), 7.29 (1H, dd, J=5.6 Hz, 8.4 Hz), 7.36 (1H, dd, J=0.8 Hz, 4.8 Hz), 7.63 (1H, d, J=2.0 Hz), 7.86 (1H, s), 8.65 (1H, d, J=4.8 Hz). [M+H] Calc'd for $C_{19}H_{15}FN_4O$, 335. Found, 335.

C. 2-[5-[(6-fluoro-1,2,3,4-tetrahydronaphthalen-1-yl)oxy]pyrazol-1-yl]pyridine-4-carboxylic acid

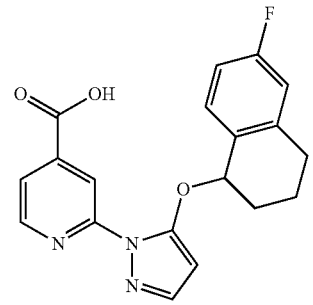 [SMILES: O=C(O)c1ccnc(-n2nccc2OC2CCCc3cc(F)ccc32)c1]

The title compound was prepared from 2-[5-[(6-fluoro-1,2,3,4-tetrahydronaphthalen-1-yl)oxy]pyrazol-1-yl]pyridine-4-carbonitrile according to the procedure for the preparation of Example 28, part E. ¹H NMR (400 MHz, CD₃OD-d₄): δ 1.71-1.76 (1H, m), 1.93-1.97 (2H, m), 2.20-2.24 (1H, m), 2.63-2.77 (2H, m), 5.36-5.37 (1H, m), 6.01 (1H, d, J=1.6 Hz), 6.72-6.77 (2H, m), 7.19 (1H, dd, J=6.0 Hz, 8.4 Hz), 7.54 (1H, d, J=1.6 Hz), 7.69 (1H, d, J=4.8 Hz), 7.97 (1H, s), 8.49 (1H, d, J=4.8 Hz). [M+H] Calc'd for $C_{19}H_{16}FN_3O_3$, 354. Found, 354.

Example 149

2-[5-[(6-chloro-1,2,3,4-tetrahydronaphthalen-1-yl)oxy]pyrazol-1-yl]pyridine-4-carboxylic acid A. 6-chloro-1,2,3,4-tetrahydronaphthalen-1-ol

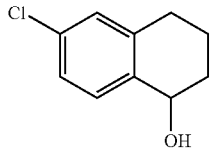 [SMILES: OC1CCCc2cc(Cl)ccc21]

The title compound was prepared from 6-chloro-3,4-dihydro-2H-naphthalen-1-one according to the procedure for the preparation of Example 146, part A. ¹H NMR (400 MHz, CDCl₃): δ 1.67 (1H, d, J=5.6 Hz), 1.75-2.01 (3H, m), 2.67-2.82 (2H, m), 4.74 (1H, t, J=4.4 Hz), 7.09 (1H, s), 7.16 (1H, dd, J=2.4 Hz, 8.4 Hz), 7.36 (1H, d, J=8.0 Hz).

B. 2-[5-[(6-chloro-1,2,3,4-tetrahydronaphthalen-1-yl)oxy]pyrazol-1-yl]pyridine-4-carbonitrile

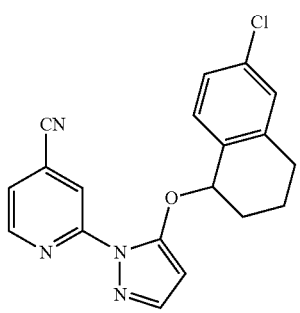 [SMILES: N#Cc1ccnc(-n2nccc2OC2CCCc3cc(Cl)ccc32)c1]

The title compound was prepared from 2-(5-hydroxy-1H-pyrazol-1-yl)pyridine-4-carbonitrile and 6-chloro-1,2,3,4- tetrahydronaphthalen-1-ol according to the procedure for the preparation of Example 39, part C. [M+H] Calc'd for $C_{19}H_{15}ClN_4O$, 351. Found, 351.

C. 2-[5-[(6-chloro-1,2,3,4-tetrahydronaphthalen-1-yl)oxy]pyrazol-1-yl]pyridine-4-carboxylic acid

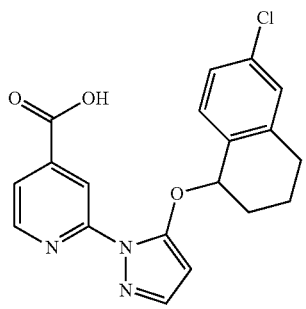

The title compound was prepared from 2-[5-[(6-chloro-1,2,3,4-tetrahydronaphthalen-1-yl)oxy]pyrazol-1-yl]pyridine-4-carbonitrile according to the procedure for the preparation of Example 28, part E. $^1$H NMR (400 MHz, CD$_3$OD-d$_4$): δ 1.80-1.87 (1H, m), 2.02-2.11 (2H, m), 2.26-2.32 (1H, m), 2.69-2.89 (2H, m), 5.43-5.45 (1H, m), 6.08 (1H, d, J=2.4 Hz), 7.12-7.13 (2H, m), 7.26-7.29 (1H, m), 7.62 (1H, d, J=2.0 Hz), 7.76 (1H, dd, J=1.2 Hz, 5.2 Hz), 8.04 (1H, s), 8.50 (1H, d, J=5.2 Hz). [M+H] Calc'd for $C_{19}H_{16}ClN_3O_3$, 370. Found, 370.

Example 150

2-[5-[(2-chloro-4-ethylphenyl)methoxy]pyrazol-1-yl]pyridine-4-carboxylic acid

A. methyl 4-bromo-2-chlorobenzoate

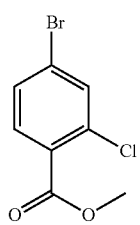

To a mixture of 4-bromo-2-chlorobenzoic acid (6.11 g, 25.94 mmol) in methanol (60 mL) cooled to 0° C. was added SOCl$_2$ (6.17 g, 51.89 mmol) drop wise. The reaction mixture was stirred at 0° C. for 15 min then at 70° C. for 3 h. It was then cooled to room temperature and removed the solvent. The residue was purified by flash column chromatograph to give 5.52 g of the title compound (85%). $^1$H NMR (400 MHz, CDCl$_3$): δ 3.92 (3H, s), 7.45 (1H, dd, J=2.0 Hz, 8.4 Hz), 7.63 (1H, d, J=2.0 Hz), 7.71 (1H, d, J=8.4 Hz).

B. methyl 2-chloro-4-ethenylbenzoate

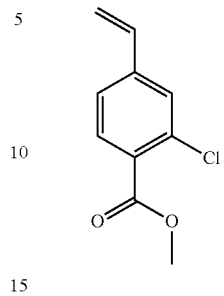

The title compound was prepared from methyl 4-bromo-2-chlorobenzoate and vinyltrifluoroborate potassium salt according to the procedure for the preparation of Example 135, part A. $^1$H NMR (400 MHz, CDCl$_3$): δ 3.92 (3H, s), 5.41 (1H, d, J=11.2 Hz), 5.85 (1H, d, J=9.2 Hz), 6.66 (1H, dd, J=11.2 Hz, 17.6 Hz), 7.32 (1H, d, J=8.0 Hz), 7.47 (1H, s), 7.81 (1H, d, J=8.0 Hz).

C. methyl 2-chloro-4-ethylbenzoate

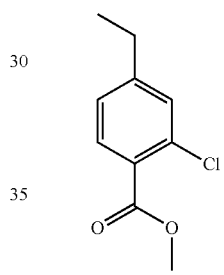

Charged methyl 2-chloro-4-ethenylbenzoate (437 mg, 2.23 mmol), BaSO$_4$/Pd (100 mg, 5%) and ethyl acetate (9 mL) to a flask, the mixture was then purged with H$_2$, and stirred at room temperature for 4 h. The reaction mixture was then filtered, concentrated to give 424 mg of the title compound (96%). $^1$H NMR (400 MHz, CDCl$_3$): δ 1.24 (3H, t, J=7.6 Hz), 2.65 (2H, q, J=7.6 Hz), 3.91 (3H, s), 7.12 (1H, dd, J=1.2 Hz, 8.4 Hz), 7.28 (1H, d, J=1.6 Hz), 7.77 (1H, d, J=8.0 Hz).

D. (2-chloro-4-ethylphenyl)methanol

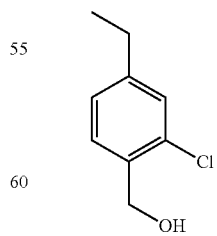

The title compound was prepared from methyl 2-chloro-4-ethylbenzoate according to the procedure for the preparation of Example 135, part C. The crude product was used for the next step without further purification.

E. 2-[5-[(2-chloro-4-ethylphenyl)methoxy]pyrazol-1-yl]pyridine-4-carbonitrile

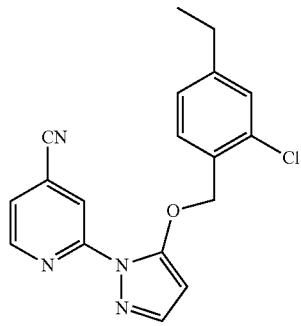 [SMILES: CCc1ccc(COc2ccnn2-c2cc(C#N)ccn2)c(Cl)c1]

The title compound was prepared from 2-(5-hydroxy-1H-pyrazol-1-yl)pyridine-4-carbonitrile and (2-chloro-4-ethylphenyl)methanol according to the procedure for the preparation of Example 39, part C. $^1$H NMR (400 MHz, CDCl$_3$): δ 1.24 (3H, t, J=7.6 Hz), 2.65 (2H, q, J=7.6 Hz), 5.30 (2H, s), 5.80 (1H, d, J=2.0 Hz), 7.12-7.14 (1H, m), 7.26 (1H, s), 7.39 (1H, dd, J=1.6 Hz, 4.8 Hz), 7.43 (1H, d, J=8.0 Hz), 7.58 (1H, d, J=2.0 Hz), 8.06 (1H, s), 8.71 (1H, d, J=4.4 Hz). [M+H] Calc'd for C$_{18}$H$_{15}$ClN$_4$O, 339. Found, 339.

F. 2-[5-[(2-chloro-4-ethylphenyl)methoxy]pyrazol-1-yl]pyridine-4-carboxylic acid

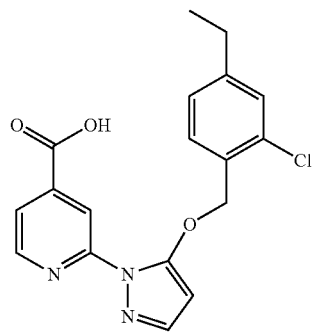 [SMILES: CCc1ccc(COc2ccnn2-c2cc(C(=O)O)ccn2)c(Cl)c1]

The title compound was prepared from 2-[5-[(2-chloro-4-ethylphenyl)methoxy]pyrazol-1-yl]pyridine-4-carbonitrile according to the procedure for the preparation of Example 28, part E. $^1$H NMR (400 MHz, DMSO-d$_6$): δ 1.17 (3H, t, J=7.6 Hz), 2.61 (2H, q, J=7.6 Hz), 5.29 (2H, s), 6.06 (1H, d, J=2.0 Hz), 7.22 (1H, d, J=2.0 Hz, 8.0 Hz), 7.34 (1H, d, J=1.2 Hz), 7.58 (1H, d, J=8.0 Hz), 7.60 (1H, d, J=2.0 Hz), 7.75 (1H, dd, J=1.2 Hz, 4.8 Hz), 8.07 (1H, s), 8.67 (1H, d, J=5.2 Hz). [M+H] Calc'd for C$_{18}$H$_{16}$ClN$_3$O$_3$, 358. Found, 358.

Example 151

2-[5-[(4-ethyl-2-fluorophenyl)methoxy]pyrazol-1-yl]pyridine-4-carboxylic acid

A. methyl 4-bromo-2-fluorobenzoate

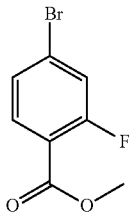

The title compound was prepared from 4-bromo-2-fluorobenzoic acid according to the procedure for the preparation of Example 150, part A. The crude product was used for the next step without further purification.

B. methyl 4-ethenyl-2-fluorobenzoate

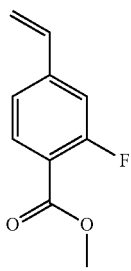

The title compound was prepared from methyl 4-bromo-2-fluorobenzoate and vinyltrifluoroborate potassium salt according to the procedure for the preparation of Example 135, part A. $^1$H NMR (300 MHz, CDCl$_3$): δ 3.92 (3H, s), 5.43 (1H, d, J=11.1 Hz), 5.86 (1H, d, J=17.4 Hz), 6.69 (1H, dd, J=11.1 Hz, 17.4 Hz), 7.15 (1H, d, J=12.0 Hz), 7.21 (1H, dd, J=0.9 Hz, 7.8 Hz), 7.89 (1H, t, J=8.1 Hz).

C. methyl 4-ethyl-2-fluorobenzoate

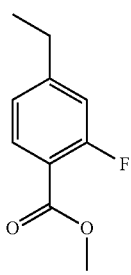

The title compound was prepared from methyl 4-ethenyl-2-fluorobenzoate according to the procedure for the preparation of Example 150, part C. $^1$H NMR (400 MHz, CDCl$_3$):

1.24 (3H, t, J=7.6 Hz), 2.68 (2H, q, J=7.6 Hz), 3.91 (3H, s), 6.96 (1H, dd, J=11.6 Hz), 7.02 (1H, d, J=1.6 Hz, 8.0 Hz), 7.82-7.86 (1H, m).

D. (4-ethyl-2-fluorophenyl)methanol

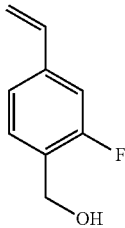

The title compound was prepared from methyl 4-ethyl-2-fluorobenzoate according to the procedure for the preparation of Example 135, part C. The crude product was used for the next step without further purification.

E. 2-[5-[(4-ethyl-2-fluorophenyl)methoxy]pyrazol-1-yl]pyridine-4-carbonitrile

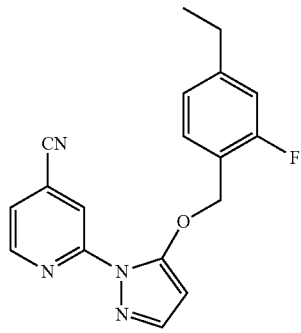 [SMILES: CCc1ccc(COc2ccnn2-c2cc(C#N)ccn2)c(F)c1]

The title compound was prepared from 2-(5-hydroxy-1H-pyrazol-1-yl)pyridine-4-carbonitrile and (4-ethyl-2-fluorophenyl)methanol according to the procedure for the preparation of Example 39, part C. $^1$H NMR (400 MHz, CDCl$_3$): δ 1.23 (3H, t, J=7.6 Hz), 2.66 (2H, q, J=7.6 Hz), 5.26 (2H, s), 5.81 (1H, d, J=2.0 Hz), 6.95 (1H, d, J=11.2 Hz), 7.00 (1H, d, J=7.6 Hz), 7.35 (1H, d, J=8.0 Hz), 7.38 (1H, dd, J=1.6 Hz, 5.2 Hz), 7.57 (1H, d, J=1.6 Hz), 8.00-8.01 (1H, m), 8.69 (1H, d, J=0.8 Hz, 5.2 Hz). [M+H] Calc'd for C$_{18}$H$_{15}$FN$_4$O, 323. Found, 323.

F. 2-[5-[(4-ethyl-2-fluorophenyl)methoxy]pyrazol-1-yl]pyridine-4-carboxylic acid

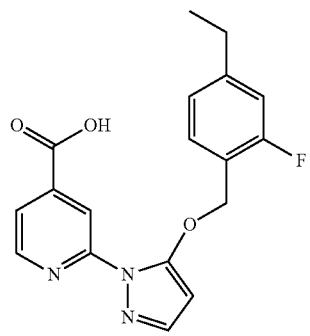 [SMILES: CCc1ccc(COc2ccnn2-c2cc(C(=O)O)ccn2)c(F)c1]

The title compound was prepared from 2-[5-[(4-ethyl-2-fluorophenyl)methoxy]pyrazol-1-yl]pyridine-4-carbonitrile according to the procedure for the preparation of Example 28, part E. $^1$H NMR (400 MHz, DMSO-d$_6$): δ 1.17 (3H, t, J=7.6 Hz), 2.61 (2H, q, J=7.6 Hz), 5.27 (2H, s), 6.06 (1H, d, J=1.6 Hz), 7.06-7.10 (2H, m), 7.47-7.51 (1H, m), 7.60 (1H, d, J=2.0 Hz), 7.74 (1H, dd, J=1.6 Hz, 5.2 Hz), 8.04 (1H, d, J=0.8 Hz), 8.65-8.67 (1H, m). [M+H] Calc'd for C$_{18}$H$_{16}$FN$_3$O$_3$, 342. Found, 342.

Example 152

2-[5-[(2-chloro-4-cyclopropylphenyl)methoxy]pyrazol-1-yl]pyridine-4-carboxylic acid A. methyl 2-chloro-4-cyclopropylbenzoate

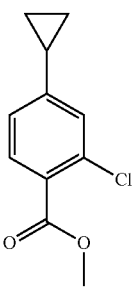

Charged methyl 4-bromo-2-chlorobenzoate (1.50 g, 6.01 mmol), cyclopropylboronic acid (931 mg, 10.82 mmol), Pd(PPh$_3$)$_4$ (347 mg, 0.30 mmol), K$_3$PO$_4$ (1.82 g, 18.04 mmol), toluene (15 mL) and water (15 mL) to a flask, the mixture was then purged with nitrogen, and heated to 110° C. overnight. It was then cooled to room temperature and filtered, the filtrate was extracted with ethylacetate twice, concentrated the organic phase and purified by flash column chromatograph to give 800 mg of the title compound (63%). $^1$H NMR (400 MHz, CDCl$_3$): δ 0.73-0.77 (2H, m), 0.98-1.07 (2H, m), 1.85-1.90 (1H, m), 3.90 (3H, s), 6.96 (1H, dd, J=1.6 Hz, 8.0 Hz), 7.11 (1H, d, J=1.6 Hz), 7.74 (1H, d, J=8.0 Hz).

B. (2-chloro-4-cyclopropylphenyl)methanol

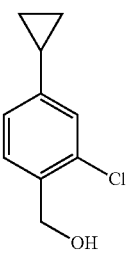 [SMILES: OCc1ccc(C2CC2)cc1Cl]

The title compound was prepared from methyl 2-chloro-4-cyclopropylbenzoate according to the procedure for the preparation of Example 135, part C. $^1$H NMR (400 MHz, CDCl$_3$): δ 0.65-0.70 (2H, m), 0.95-1.00 (2H, m), 1.83-1.90 (1H, m), 1.96 (1H, t, J=6.0 Hz), 4.72 (2H, d, J=6.0 Hz), 6.97 (1H, dd, J=1.6 Hz, 8.0 Hz), 7.06 (1H, d, J=1.6 Hz), 7.32 (1H, d, J=8.0 Hz).

C. 2-[5-[(2-chloro-4-cyclopropylphenyl)methoxy]
pyrazol-1-yl]pyridine-4-carbonitrile

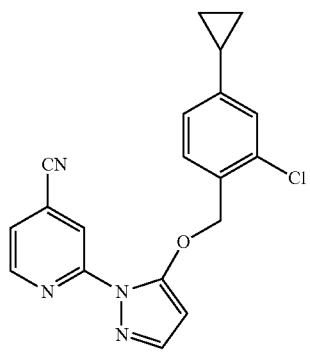 [SMILES: N#Cc1ccnc(-n2nccc2OCc2ccc(C3CC3)cc2Cl)c1]

The title compound was prepared from 2-(5-hydroxy-1H-pyrazol-1-yl)pyridine-4-carbonitrile and (2-chloro-4-cyclopropylphenyl)methanol according to the procedure for the preparation of Example 39, part C. [M+H] Calc'd for C₁₉H₁₅ClN₄O, 351. Found, 351.

D. 2-[5-[(2-chloro-4-cyclopropylphenyl)methoxy]
pyrazol-1-yl]pyridine-4-carboxylic acid

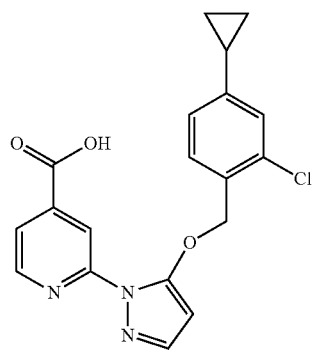 [SMILES: O=C(O)c1ccnc(-n2nccc2OCc2ccc(C3CC3)cc2Cl)c1]

The title compound was prepared from 2-[5-[(2-chloro-4-cyclopropylphenyl)methoxy]pyrazol-1-yl]pyridine-4-carbonitrile according to the procedure for the preparation of Example 28, part E. ¹H NMR (400 MHz, DMSO-d₆): δ 0.69-0.73 (2H, m), 0.94-0.99 (2H, m), 1.90-1.97 (1H, m), 5.26 (2H, s), 6.03 (1H, d, J=1.6 Hz), 7.07 (1H, d, J=8.4 Hz), 7.20 (1H, d, J=1.2 Hz), 7.52 (1H, d, J=7.6 Hz), 7.58 (1H, d, J=1.2 Hz), 7.73 (1H, d, J=4.8 Hz), 8.04 (1H, s), 8.61 (1H, d, J=5.2 Hz). [M+H] Calc'd for C₁₉H₁₆ClN₃O₃, 370. Found, 370.

Example 153

2-[5-[(4-cyclopropyl-2-fluorophenyl)methoxy]pyrazol-1-yl]pyridine-4-carboxylic acid A. methyl 4-cyclopropyl-2-fluorobenzoate

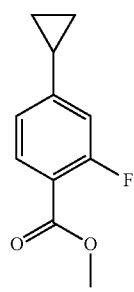

The title compound was prepared from methyl 4-bromo-2-fluorobenzoate and cyclopropylboronic acid according to the procedure for the preparation of EXAMPLE 152, part A. ¹H NMR (400 MHz, CDCl₃): δ 0.74-0.78 (2H, m), 1.04-1.09 (2H, m), 1.87-1.94 (1H, m), 3.90 (3H, s), 6.75-6.79 (1H, m), 6.86-6.89 (1H, m), 7.79-7.82 (1H, m).

B. (4-cyclopropyl-2-fluorophenyl)methanol

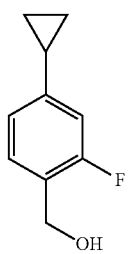 [SMILES: OCc1ccc(C2CC2)cc1F]

The title compound was prepared from methyl 4-cyclopropyl-2-fluorobenzoate according to the procedure for the preparation of Example 135, part C. ¹H NMR (400 MHz, CDCl₃): δ 0.66-0.70 (2H, m), 0.95-1.00 (2H, m), 1.77 (1H, t, J=6.0 Hz), 1.84-1.91 (1H, m), 4.69 (2H, d, J=6.0 Hz), 6.71-6.75 (1H, m), 6.85-6.87 (1H, m), 7.24-7.28 (1H, m).

C. 2-[5-[(4-cyclopropyl-2-fluorophenyl)methoxy]
pyrazol-1-yl]pyridine-4-carbonitrile

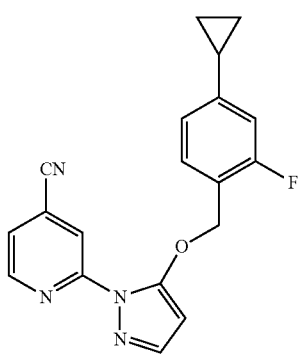 [SMILES: N#Cc1ccnc(-n2nccc2OCc2ccc(C3CC3)cc2F)c1]

The title compound was prepared from 2-(5-hydroxy-1H-pyrazol-1-yl)pyridine-4-carbonitrile and (4-cyclopropyl-2-fluorophenyl)methanol according to the procedure for the preparation of Example 39, part C. ¹H NMR (800 MHz, CDCl₃): δ 0.68-0.73 (2H, m), 0.99-1.04 (2H, m), 1.86-1.92 (1H, m), 5.24 (2H, s), 5.80 (1H, d, J=4.0 Hz), 6.78 (1H, dd, J=4.0 Hz, 23.2 Hz), 6.88 (1H, dd, J=3.2 Hz, 16.0 Hz), 7.30-7.34 (1H, m), 7.39 (1H, dd, J=1.6 Hz, 9.6 Hz), 7.57 (1H, d, J=3.2 Hz), 8.00 (1H, s), 8.69 (1H, d, J=9.6 Hz). [M+H] Calc'd for C₁₉H₁₈FN₄O, 335. Found, 335.

D. 2-[5-[(4-cyclopropyl-2-fluorophenyl)methoxy]pyrazol-1-yl]pyridine-4-carboxylic acid

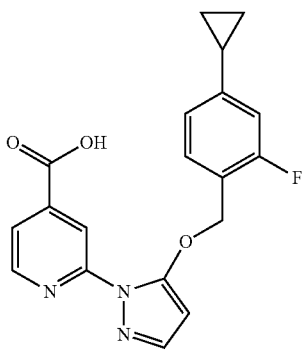 [SMILES: O=C(O)c1ccnc(-n2nccc2OCc2ccc(C3CC3)cc2F)c1]

The title compound was prepared from 2-[5-[(4-cyclopropyl-2-fluorophenyl)methoxy]pyrazol-1-yl]pyridine-4-carbonitrile according to the procedure for the preparation of Example 28, part E. $^1$H NMR (400 MHz, DMSO-$d_6$): δ 0.69-0.73 (2H, m), 0.95-0.99 (2H, m), 1.90-1.97 (1H, m), 5.24 (2H, s), 6.05 (1H, d, J=2.0 Hz), 6.91-6.96 (2H, m), 7.42-7.46 (1H, m), 7.59 (1H, d, J=2.0 Hz), 7.73 (1H, dd, J=1.6 Hz, 4.8 Hz), 8.03 (1H, s), 8.64-8.65 (1H, m). [M+H] Calc'd for $C_{19}H_{16}FN_3O_3$, 354. Found, 354.

Example 154

2-[5-[(3-chloro-4-cyclopropylphenyl)methoxy]pyrazol-1-yl]pyridine-4-carboxylic acid A. methyl 3-chloro-4-cyclopropylbenzoate

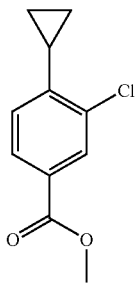

The title compound was prepared from methyl 4-bromo-3-chlorobenzoate and cyclopropylboronic acid according to the procedure for the preparation of EXAMPLE 152, part A. $^1$H NMR (400 MHz, CDCl$_3$): δ 0.73-0.77 (2H, m), 1.07-1.12 (2H, m), 2.24-2.30 (1H, m), 3.90 (3H, s), 6.93 (1H, d, J=8.0 Hz), 7.80 (1H, dd, J=1.6 Hz, 8.0 Hz), 8.01 (1H, d, J=1.6 Hz).

B. (3-chloro-4-cyclopropylphenyl)methanol

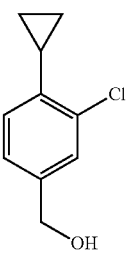 [SMILES: OCc1ccc(C2CC2)c(Cl)c1]

The title compound was prepared from methyl 3-chloro-4-cyclopropylbenzoate according to the procedure for the preparation of Example 135, part C. The crude product was used for next step without further purifications.

C. 2-[5-[(3-chloro-4-cyclopropylphenyl)methoxy]pyrazol-1-yl]pyridine-4-carbonitrile

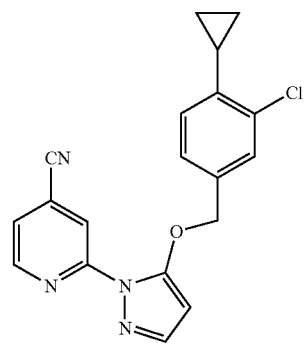 [SMILES: N#Cc1ccnc(-n2nccc2OCc2ccc(C3CC3)c(Cl)c2)c1]

The title compound was prepared from 2-(5-hydroxy-1H-pyrazol-1-yl)pyridine-4-carbonitrile and (3-chloro-4-cyclopropylphenyl)methanol according to the procedure for the preparation of Example 39, part C. $^1$H NMR (400 MHz, CDCl$_3$): δ 0.68-0.71 (2H, m), 1.01-1.06 (2H, m), 2.16-2.23 (1H, m), 5.17 (2H, s), 5.73 (1H, d, J=2.0 Hz), 6.94 (1H, d, J=8.0 Hz), 7.20 (1H, dd, J=1.6 Hz, 8.0 Hz), 7.40 (1H, dd, J=1.2 Hz, 5.2 Hz), 7.45 (1H, d, J=1.6 Hz), 7.56 (1H, d, J=1.6 Hz), 8.03 (1H, s), 8.71 (1H, d, J=4.8 Hz). [M+H] Calc'd for $C_{19}H_{15}ClN_4O$, 351. Found, 351.

D. 2-[5-[(3-chloro-4-cyclopropylphenyl)methoxy]pyrazol-1-yl]pyridine-4-carboxylic acid

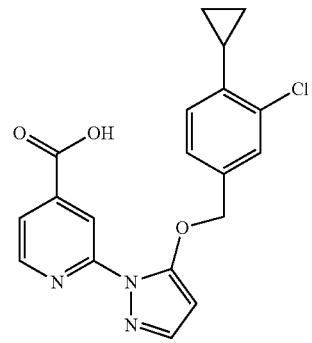 [SMILES: O=C(O)c1ccnc(-n2nccc2OCc2ccc(C3CC3)c(Cl)c2)c1]

The title compound was prepared from 2-[5-[(3-chloro-4-cyclopropylphenyl)methoxy]pyrazol-1-yl]pyridine-4-carbonitrile according to the procedure for the preparation of Example 28, part E. $^1$H NMR (400 MHz, DMSO-d$_6$): δ 0.66-0.75 (2H, m), 0.95-1.07 (2H, m), 2.09-2.16 (1H, m), 5.24 (2H, s), 6.00 (1H, s), 7.03 (1H, d, J=8.4 Hz), 7.33 (1H, d, J=8.4 Hz), 7.57 (2H, d, J=17.6 Hz), 7.76 (1H, d, J=4.0 Hz), 8.07 (1H, s), 8.68 (1H, d, J=4.8 Hz). [M+H] Calc'd for C$_{19}$H$_{16}$ClN$_3$O$_3$, 370. Found, 370.

Example 155

2-[5-[(4-cyclopropyl-3-fluorophenyl)methoxy]pyrazol-1-yl]pyridine-4-carboxylic acid A. methyl 4-cyclopropyl-3-fluorobenzoate

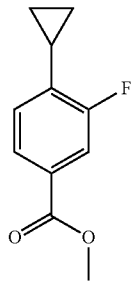

The title compound was prepared from methyl 4-bromo-3-fluorobenzoate and cyclopropylboronic acid according to the procedure for the preparation of EXAMPLE 152, part A. $^1$H NMR (400 MHz, CDCl$_3$): δ 0.77-0.81 (2H, m), 1.04-1.09 (2H, m), 2.12-2.16 (1H, m), 3.89 (3H, s), 6.88-6.92 (1H, m), 7.63-7.66 (1H, m), 7.69-7.72 (1H, m).

B. (4-cyclopropyl-3-fluorophenyl)methanol

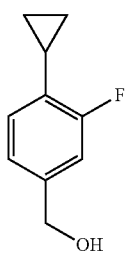

The title compound was prepared from methyl 4-cyclopropyl-3-fluorobenzoate according to the procedure for the preparation of Example 135, part C. The crude product was used for next step without further purifications.

C. 2-[5-[(4-cyclopropyl-3-fluorophenyl)methoxy]pyrazol-1-yl]pyridine-4-carbonitrile

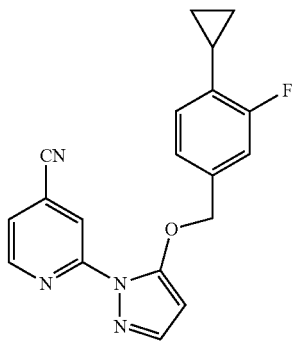 [SMILES: N#Cc1ccnc(-n2nccc2OCc2ccc(C3CC3)c(F)c2)c1]

The title compound was prepared from 2-(5-hydroxy-1H-pyrazol-1-yl)pyridine-4-carbonitrile and (4-cyclopropyl-3-fluorophenyl)methanol according to the procedure for the preparation of Example 39, part C. $^1$H NMR (400 MHz, CDCl$_3$): δ 0.71-0.75 (2H, m), 0.96-1.02 (2H, m), 2.06-2.10 (1H, m), 5.17 (2H, s), 5.72 (1H, d, J=1.6 Hz), 6.88-6.92 (1H, m), 7.07-7.10 (2H, m), 7.40 (1H, dd, J=1.6 Hz, 5.2 Hz), 7.55 (1H, d, J=2.0 Hz), 8.02 (1H, s), 8.70 (1H, d, J=5.2 Hz). [M+H] Calc'd for C$_{19}$H$_{18}$FN$_4$O, 335. Found, 335.

D. 2-[5-[(4-cyclopropyl-3-fluorophenyl)methoxy]pyrazol-1-yl]pyridine-4-carboxylic acid

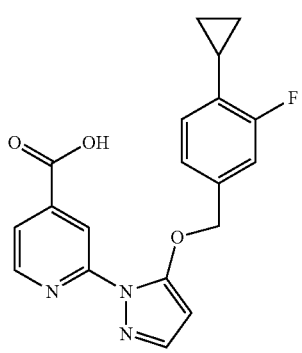 [SMILES: O=C(O)c1ccnc(-n2nccc2OCc2ccc(C3CC3)c(F)c2)c1]

The title compound was prepared from 2-[5-[(4-cyclopropyl-3-fluorophenyl)methoxy]pyrazol-1-yl]pyridine-4-carbonitrile according to the procedure for the preparation of Example 28, part E. $^1$H NMR (400 MHz, DMSO-d$_6$): δ 0.69-0.73 (2H, m), 0.94-0.99 (2H, m), 1.98-2.04 (1H, m), 5.24 (2H, s), 5.99 (1H, d, J=1.6 Hz), 6.98-7.01 (1H, m), 7.20 (1H, d, J=8.0 Hz), 7.24 (1H, dd, J=1.6 Hz, 11.6 Hz), 7.58 (1H, d, J=2.0 Hz), 7.76 (1H, dd, J=1.6 Hz, 4.8 Hz), 8.07 (1H, s), 8.68 (1H, dd, J=0.4 Hz, 4.8 Hz). [M+H] Calc'd for C$_{19}$H$_{16}$FN$_3$O$_3$, 354. Found, 354.

Example 156

2-[4-[2-[(4-fluorophenyl)methyl-methylamino]ethyl]pyrazol-1-yl]pyridine-4-carboxylic acid

A. 2-[4-[2-[tert-butyl(dimethyl)silyl]oxyethyl]pyrazol-1-yl]pyridine-4-carbonitrile

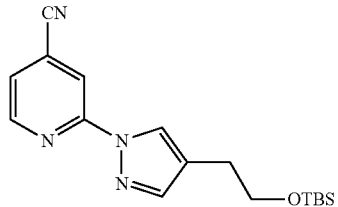 [SMILES: CC(C)(C)[Si](C)(C)OCCc1cnn(-c2cc(C#N)ccn2)c1]

A mixture of 2-chloropyridine-4-carbonitrile (1.38 g, 10 mmol), tert-butyl-dimethyl-[2-(1H-pyrazol-4-yl)ethoxy]silane (2.481 g, 11 mmol) in NMP (30 mL) was stirred for 5 hr at 150° C. Then the reaction mixture was cooled to room temperature and poured into water and extracted with ethyl acetate three times. Organic extracts collected and washed with water twice, brine and dried with anhydrous $Na_2SO_4$. It was then concentrated and purified by flash column chromatograph to give the title compound (1.2 g, 36%). [M+H] Calc'd for $C_{17}H_{24}N_4O_3Si$, 329. Found, 329.

B. 2-[4-(2-hydroxyethyl)pyrazol-1-yl]pyridine-4-carbonitrile

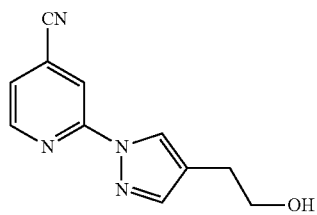 [SMILES: N#Cc1ccnc(-n2cc(CCO)cn2)c1]

To a solution of 2-[4-[2-[tert-butyl(dimethyl)silyl]oxyethyl]pyrazol-1-yl]pyridine-4-carbonitrile (1.2 g, 3.6 mmol) in THF (15 mL) at 0° C. was added 3N HCl (5 mL). The reaction mixture was then stirred for 2 hours at room temperature. Cool to 0° C., added ethyl acetate, water and acidified with $NaHCO_3$ to pH=8. The mixture was then extracted with ethylacetate, concentrated to afford the title compound (700 mg, 91%). [M+H] Calc'd for $C_{11}H_{10}N_4O$, 215. Found, 215.

C. 2-[1-(4-cyanopyridin-2-yl)pyrazol-4-yl]ethyl methanesulfonate

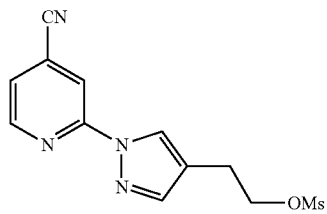 [SMILES: CS(=O)(=O)OCCc1cnn(-c2cc(C#N)ccn2)c1]

To a mixture of 2-[4-(2-hydroxyethyl)pyrazol-1-yl]pyridine-4-carbonitrile (700 mg, 3.3 mmol), $Et_3N$ (670 mg, 6.6 mmol) in DCM (15 mL) was added $MeSO_2Cl$ (410 mg, 3.6 mmoL) at 0° C., the mixture was then stirred for 2 hours at room temperature, water was added and extracted with DCM and concentrated give the title compound (830 mg, 87%). [M+H] Calc'd for $C_{12}H_{12}N_4O_3S$, 293. Found, 293.

D. 2-[4-[2-[(4-fluorophenyl)methyl-methylamino]ethyl]pyrazol-1-yl]pyridine-4-carbonitrile

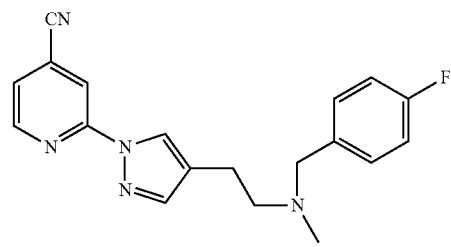 [SMILES: CN(CCc1cnn(-c2cc(C#N)ccn2)c1)Cc1ccc(F)cc1]

To a mixture of 2-[1-(4-cyanopyridin-2-yl)pyrazol-4-yl]ethyl methanesulfonate (476 mg, 1.6 mmol) and (4-flourobenzyl)-methyl-amine (444 mg, 3.2 mmol) in ACN (30 mL) at rt was added $K_2CO_3$ (4.5 g, 32 mmol) and KI (1.0 g, 6.2 mmol. The reaction mixture was heated to 80° C. and stirred overnight. Filtered, solvent removed and purified by prep-HPLC to give the title compound (270 mg, 50%). [M+H] Calc'd for $C_{19}H_{18}FN_5$, 336. Found, 336.

E. 2-[4-[2-[(4-fluorophenyl)methyl-methylamino]ethyl]pyrazol-1-yl]pyridine-4-carboxylic acid

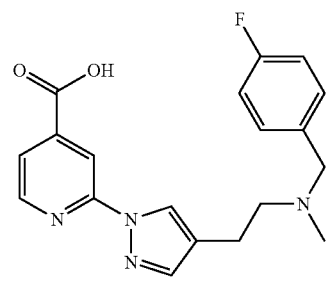 [SMILES: CN(CCc1cnn(-c2cc(C(=O)O)ccn2)c1)Cc1ccc(F)cc1]

Charged 2-[4-[2-[(4-fluorophenyl)methyl-methylamino]ethyl]pyrazol-1-yl]pyridine-4-carbonitrile (270 mg, 0.8 mmol), NaOH aqueous (5M, 0.5 mL) and ethanol (10 mL) to a flask, the mixture was then heated to reflux for half an hour, cooled in an ice-water bath, adjusted PH to 3-4, filtered, collected the solid and dried to give the title compound (226 mg, 80%). $^1$H NMR (400 MHz, DMSO-d6): 2.70 (3H, s), 3.01-3.06 (2H, m), 3.25-3.27 (1H, m), 3.31-3.39 (1H, m), 4.26-4.30 (1H, m), 4.44-4.48 (1H, m), 7.29-7.34 (2H, m), 7.64-7.68 (2H, m), 7.74-7.76 (1H, m), 7.81 (1H, s), 8.28 (1H, s), 8.61 (s, 1H), 8.64 (1H, J=5.2 Hz, d), 10.49 (1H, br). [M+H] Calc'd for $C_{19}H_{19}FN_4O_2$, 355. Found, 355.

Example 157

N-cyano-2-[4-[2-[(4-fluorophenyl)methyl-methyl-amino]ethyl]pyrazol-1-yl]pyridine-4-carboxamide

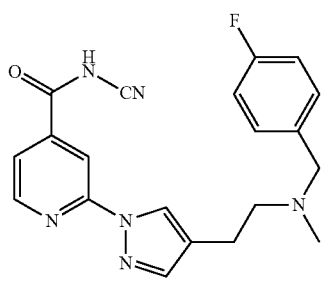 [SMILES: CN(CCc1cnn(-c2cc(C(=O)NC#N)ccn2)c1)Cc1ccc(F)cc1]

A mixture of 2-[4-[2-[(4-fluorophenyl)methyl-methyl-amino]ethyl]pyrazol-1-yl]pyridine-4-carboxylic acid (70 mg, 0.2 mmol), cyanamide (17 mg, 0.4 mmol), HATU (113 mg, 0.3 mmol) and DIEA (59 mg, 0.6 mmol) in DMF (3 mL) was stirred at room temperature for 3 hours. The mixture was concentrated and purified by prep-HPLC to give the compound (15 mg, 20%). $^1$H NMR (400 MHz, DMSO-d6): 2.67-2.74 (3H, m), 2.94-2.98 (2H, m), 3.28 (1H, m), 3.43-3.45 (1H, m), 4.26-4.30 (1H, m), 4.44-4.48 (1H, m), 7.31-7.36 (2H, m), 7.59-7.61 (2H, m), 7.70-7.71 (1H, m), 7.76 (1H, s), 8.31 (1H, s), 8.42 (1H, d, J=5.2 Hz), 8.58 (1H, s), 9.56 (1H, br). [M+H] Calc'd for $C_{20}H_{19}FN_6O$, 379. Found, 379.

Example 158

2-[3-(4-chlorophenyl)-5-hydroxypyrazol-1-yl]pyridine-4-carboxylic acid

A. 2-[3-(4-chlorophenyl)-5-hydroxypyrazol-1-yl]pyridine-4-carbonitrile

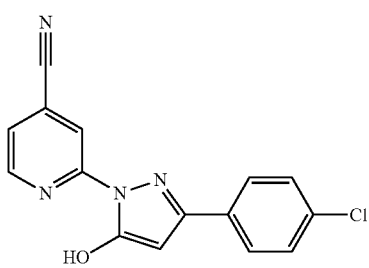 [SMILES: N#Cc1ccnc(-n2nc(-c3ccc(Cl)cc3)cc2O)c1]

To a mixture of ethyl 3-(4-chlorophenyl)-3-oxopropanoate (500 mg, 2.2 mmol) and 2-hydrazinylpyridine-4-carbonitrile (PREPARATION 2, 296 mg, 2.2 mmol) in EtOH (15 mL) was added AcOH (2 mL) at r.t. The reaction mixture was stirred at 90° C. overnight. After the reaction was completed, the mixture was concentrated, washed with PE/EA (10 mL, V/V=1/1) to give the title compound (500 mg, 76%) as a brown solid and used as crude for next step.

B. 2-[3-(4-chlorophenyl)-5-hydroxypyrazol-1-yl]pyridine-4-carboxylic acid

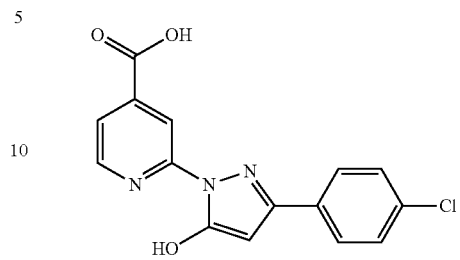

To a solution of 2-[3-(4-chlorophenyl)-5-hydroxypyrazol-1-yl]pyridine-4-carbonitrile (250 mg, 0.85 mmol) in EtOH (10 mL) and water (5 mL) was added NaOH (168 mg, 4.2 mmol) at r.t. The reaction mixture was stirred at 90° C. for 2 h. Removed EtOH, acidified with 1N HCl to pH 5, filtered, washed with ethyl acetate (5 mL) to give the title compound (200 mg, 75%) as a brown solid. $^1$H NMR (400 MHz, DMSO-d$_6$): δ 6.20 (1H, s), 7.50 (2H, d, J=8.4 Hz), 7.76 (1H, d, J=4.0 Hz), 7.91 (2H, d, J=8.4 Hz), 8.26 (1H, s), 8.65 (1H, d, J=5.2 Hz), 12.20 (1H, brs), 13.96 (1H, brs). [M+H] Calc'd for $C_{15}H_{10}ClN_3O_3$, 316. Found, 316.

Example 159

2-[3-(3-chlorophenyl)-5-hydroxypyrazol-1-yl]pyridine-4-carboxylic acid

A. 2-[3-(3-chlorophenyl)-5-hydroxypyrazol-1-yl]pyridine-4-carbonitrile

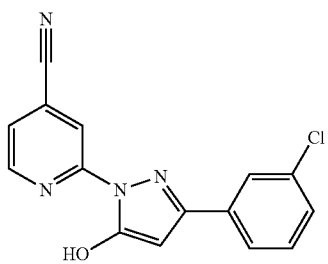 [SMILES: N#Cc1ccnc(-n2nc(-c3cccc(Cl)c3)cc2O)c1]

The title compound was prepared in 53% yield from 2-hydrazinylpyridine-4-carbonitrile (PREPARATION 2) and ethyl 3-(3-chlorophenyl)-3-oxopropanoate according to the procedure for the preparation of Example 158, part A.

B. 2-[3-(3-chlorophenyl)-5-hydroxypyrazol-1-yl]pyridine-4-carboxylic acid

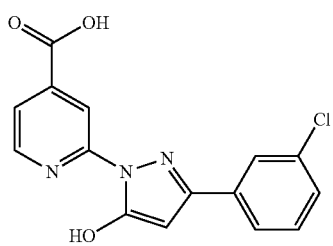 [SMILES: O=C(O)c1ccnc(-n2nc(-c3cccc(Cl)c3)cc2O)c1]

The title compound was prepared in 75% yield from 2-[3-(3-chlorophenyl)-5-hydroxypyrazol-1-yl]pyridine-4-carbonitrile according to the procedure for the preparation of Example 158, part B. $^1$H NMR (300 MHz, DMSO-d$_6$): δ 6.18 (1H, s), 7.40-7.49 (2H, m), 7.73 (1H, d, J=4.2 Hz), 7.83-7.90 (2H, m), 8.33 (1H, s), 8.57 (1H, d, J=4.8 Hz). [M+H] Calc'd for C$_{15}$H$_{10}$ClN$_3$O$_3$, 316. Found, 316.

Example 160

2-(3-cyclopentyl-5-hydroxypyrazol-1-yl)pyridine-4-carboxylic acid

A. 2-(3-cyclopentyl-5-hydroxypyrazol-1-yl)pyridine-4-carbonitrile

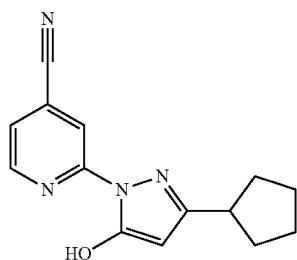 [SMILES: N#Cc1ccnc(-n2nc(C3CCCC3)cc2O)c1]

The title compound was prepared in 72% yield from 2-hydrazinylpyridine-4-carbonitrile (PREPARATION 2) and ethyl 3-cyclopentyl-3-oxopropanoate according to the procedure for the preparation of Example 158, part A.

B. 2-(3-cyclopentyl-5-hydroxypyrazol-1-yl)pyridine-4-carboxylic acid

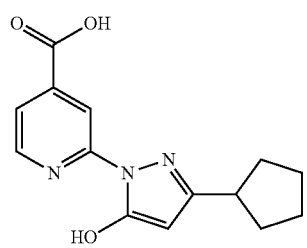 [SMILES: O=C(O)c1ccnc(-n2nc(C3CCCC3)cc2O)c1]

The title compound was prepared in 75% yield from 2-(3-cyclopentyl-5-hydroxypyrazol-1-yl)pyridine-4-carbonitrile according to the procedure for the preparation of Example 158, part B. $^1$H NMR (400 MHz, CD$_3$OD): δ 1.71-1.85 (6H, m), 2.11-2.14 (2H, m), 3.04-3.08 (1H, m), 7.73 (1H, dd, J=0.8, 5.2 Hz), 8.57 (1H, d, J=5.2 Hz), 8.82 (1H, s). [M+H] Calc'd for C$_{14}$H$_{15}$N$_3$O$_3$, 274. Found, 274.

Example 161

2-[3-[(2,6-difluorophenyl)methyl]-5-hydroxypyrazol-1-yl]pyridine-4-carboxylic acid A. methyl 4-(2,6-difluorophenyl)-3-oxobutanoate

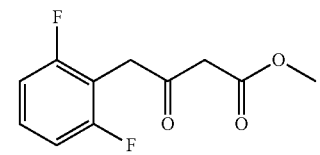 [SMILES: COC(=O)CC(=O)Cc1c(F)cccc1F]

The title compound was prepared from 2-(2,6-difluorophenyl)acetic acid and 3-methoxy-3-oxopropanoic acid potassium salt according to the procedure for the preparation of Example 170, part A. $^1$H NMR (300 MHz, CDCl$_3$): δ 3.56 (2H, s), 3.75 (3H, s), 3.92 (2H, s), 6.89-6.93 (2H, m), 7.22-7.27 (1H, m).

B. 2-[3-[(2,6-difluorophenyl)methyl]-5-hydroxypyrazol-1-yl]pyridine-4-carbonitrile

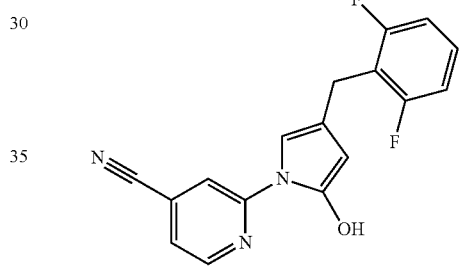

The title compound was prepared from 2-hydrazinylpyridine-4-carbonitrile (PREPARATION 2) and methyl 4-(2,6-difluorophenyl)-3-oxobutanoate according to the procedure for the preparation of Example 158, part A.

C. 2-[3-[(2,6-difluorophenyl)methyl]-5-hydroxypyrazol-1-yl]pyridine-4-carboxylic acid

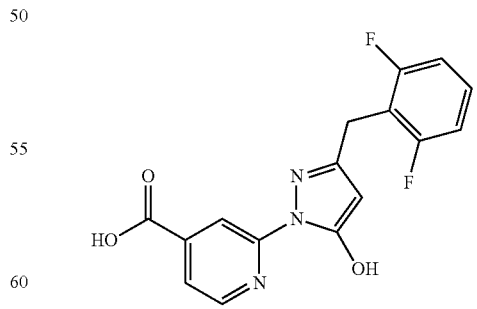

The title compound was prepared in 26% yield from 2-[3-[(2,6-difluorophenyl)methyl]-5-hydroxypyrazol-1-yl]pyridine-4-carbonitrile according to the procedure for the preparation of Example 158, part B. $^1$H NMR (300 MHz, CD$_3$OD/DMSO-d$_6$): δ 3.92 (2H, s), 7.03-7.08 (2H, m), 7.32-7.37 (1H, m), 7.65-7.67 (1H, m), 8.54 (1H, d, J=5.1 Hz). [M+H] Calc'd for $C_{16}H_{11}F_2N_3O_3$, 332. Found, 332.

Example 162

2-[5-hydroxy-3-(1-phenylethyl)pyrazol-1-yl]pyridine-4-carboxylic acid

A. ethyl 3-oxo-4-phenylpentanoate

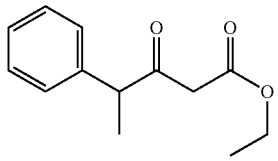 [SMILES: CCOC(=O)CC(=O)C(C)c1ccccc1]

To a solution of 2-phenylpropanoic acid (5.0 g, 33.3 mmol) in DCM (50 mL) was added (COCl)$_2$ (8.5 g, 66.7 mmol) and 2 drops of DMF in ice-bath. The reaction mixture was stirred at r.t. for 2 h. After the reaction was completed, the reaction mixture was concentrated under reduced pressure. To a solution of pyridine (6 mL) in DCM (50 mL) was added 2,2-dimethyl-1,3-dioxane-4,6-dione (5.8 g, 40.0 mmol) and the above residue in ice-bath. The reaction mixture was stirred at r.t. for 2 h. Diluted with 1N HCl (50 mL), extracted with DCM (50 mL×3), washed with brine (50 mL), dried over Na$_2$SO$_4$, filtered, concentrated to give a residue. The residue was dissolved in EtOH (50 mL) and then stirred at reflux for 3 h. Removed solvent, purified by flash column chromatography to give the title compound (3.6 g, 49%) as a yellow oil. $^1$H NMR (400 MHz, CDCl$_3$): δ 1.22 (3H, t, J=7.2 Hz), 1.41 (3H, d, J=7.2 Hz), 3.28 (1H, d, J=15.6 Hz), 3.40 (1H, d, J=15.6 Hz), 3.89-3.91 (1H, m), 4.11-4.14 (2H, m), 7.20-7.22 (2H, m), 7.27-7.36 (3H, m).

B. 2-[5-hydroxy-3-(1-phenylethyl)pyrazol-1-yl]pyridine-4-carbonitrile

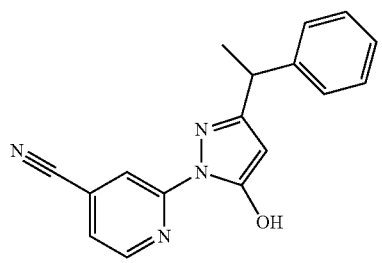 [SMILES: CC(c1ccccc1)c1cc(O)n(-c2cc(C#N)ccn2)n1]

The title compound was prepared in 40% yield from 2-hydrazinylpyridine-4-carbonitrile (PREPARATION 2) and ethyl 3-oxo-4-phenylpentanoate according to the procedure for the preparation of Example 158, part A.

C. 2-[5-hydroxy-3-(1-phenylethyl)pyrazol-1-yl]pyridine-4-carboxylic acid

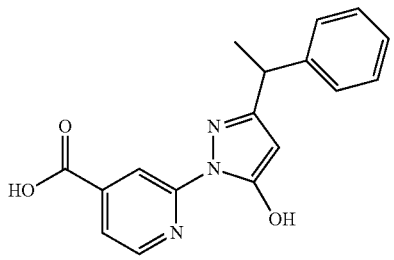 [SMILES: CC(c1ccccc1)c1cc(O)n(-c2cc(C(=O)O)ccn2)n1]

The title compound was prepared in 40% yield from 2-[5-hydroxy-3-(1-phenylethyl)pyrazol-1-yl]pyridine-4-carbonitrile according to the procedure for the preparation of Example 158, part B. $^1$H NMR (300 MHz, CD$_3$OD): δ 1.65 (3H, d, J=7.2 Hz), 4.09-4.16 (1H, m), 7.23-7.25 (1H, m), 7.29-7.36 (4H, m), 7.72 (1H, dd, J=1.2, 5.1 Hz), 8.53 (1H, d, J=5.4 Hz), 8.70 (1H, s). [M+H] Calc'd for $C_{17}H_{15}N_3O_3$, 310. Found, 310.

Example 163

2-[3-[(2-chlorophenyl)methyl]-5-hydroxypyrazol-1-yl]pyridine-4-carboxylic acid

A. ethyl 4-(2-chlorophenyl)-3-oxobutanoate

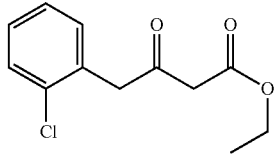 [SMILES: CCOC(=O)CC(=O)Cc1ccccc1Cl]

The title compound was prepared in 43% yield from 2-(2-chlorophenyl)acetic acid and 2,2-dimethyl-1,3-dioxane-4,6-dione according to the procedure for the preparation of Example 162, part A.

B. 2-[3-[(2-chlorophenyl)methyl]-5-hydroxypyrazol-1-yl]pyridine-4-carbonitrile

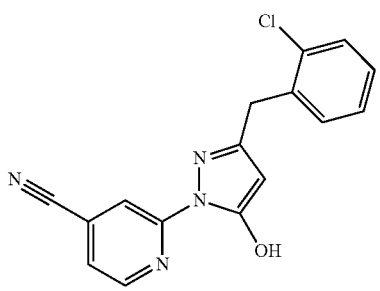 [SMILES: N#Cc1ccnc(-n2nc(Cc3ccccc3Cl)cc2O)c1]

The title compound was prepared in 39% yield from 2-hydrazinylpyridine-4-carbonitrile (PREPARATION 2)

and ethyl 4-(2-chlorophenyl)-3-oxobutanoate according to the procedure for the preparation of Example 158, part A.

C. 2-[3-[(2-chlorophenyl)methyl]-5-hydroxypyrazol-1-yl]pyridine-4-carboxylic acid

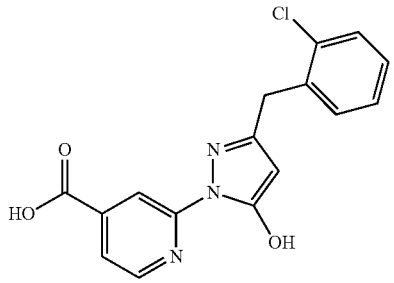 [SMILES: O=C(O)c1ccnc(-n2nc(Cc3ccccc3Cl)cc2O)c1]

The title compound was prepared in 57% yield from 2-[3-[(2-chlorophenyl)methyl]-5-hydroxypyrazol-1-yl]pyridine-4-carbonitrile according to the procedure for the preparation of Example 158, part B. $^1$H NMR (300 MHz, CD$_3$OD): δ 4.07 (2H, s), 7.25-7.29 (2H, m), 7.37-7.43 (2H, m), 7.72 (1H, dd, J=0.9, 3.9 Hz), 8.52 (1H, d, J=4.2 Hz), 8.65 (1H, brs). [M+H] Calc'd for C$_{16}$H$_{12}$ClN$_3$O$_3$, 330. Found, 330.

Example 164

2-[3-[(3-chlorophenyl)methyl]-5-hydroxypyrazol-1-yl]pyridine-4-carboxylic acid

A. ethyl 4-(3-chlorophenyl)-3-oxobutanoate

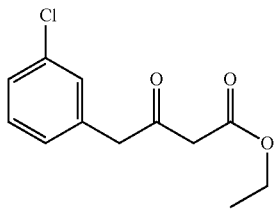 [SMILES: CCOC(=O)CC(=O)Cc1cccc(Cl)c1]

The title compound was prepared in 43% yield from 2-(3-chlorophenyl)acetic acid and 2,2-dimethyl-1,3-dioxane-4,6-dione according to the procedure for the preparation of Example 162, part A.

B. 2-[3-[(3-chlorophenyl)methyl]-5-hydroxypyrazol-1-yl]pyridine-4-carbonitrile

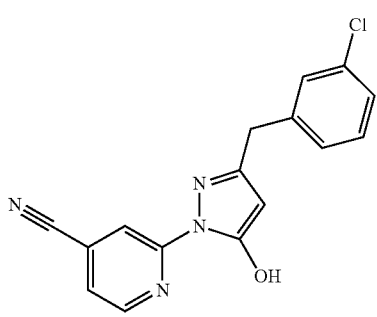 [SMILES: N#Cc1ccnc(-n2nc(Cc3cccc(Cl)c3)cc2O)c1]

The title compound was prepared in 32% yield from 2-hydrazinylpyridine-4-carbonitrile (PREPARATION 2) and ethyl 4-(3-chlorophenyl)-3-oxobutanoate according to the procedure for the preparation of Example 158, part A.

C. 2-[3-[(3-chlorophenyl)methyl]-5-hydroxypyrazol-1-yl]pyridine-4-carboxylic acid

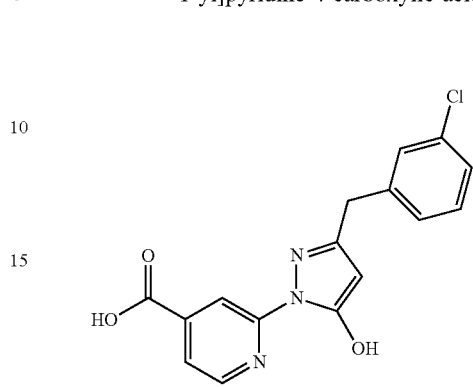

The title compound was prepared in 47% yield from 2-[3-[(3-chlorophenyl)methyl]-5-hydroxypyrazol-1-yl]pyridine-4-carbonitrile according to the procedure for the preparation of Example 158, part B. $^1$H NMR (400 MHz, CD$_3$OD): δ 3.92 (2H, s), 7.25-7.34 (4H, m), 7.73 (1H, dd, J=5.2 Hz), 8.53 (1H, d, J=5.2 Hz), 8.66 (1H, brs).
[M+H] Calc'd for C$_{16}$H$_{12}$ClN$_3$O$_3$, 330. Found, 330.

Example 165

2-[3-[(4-chlorophenyl)methyl]-5-hydroxypyrazol-1-yl]pyridine-4-carboxylic acid

A. ethyl 4-(4-chlorophenyl)-3-oxobutanoate

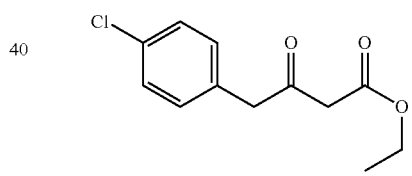

The title compound was prepared in 43% yield from 2-(4-chlorophenyl)acetic acid and 2,2-dimethyl-1,3-dioxane-4,6-dione according to the procedure for the preparation of Example 162, part A.

B. 2-[3-[(4-chlorophenyl)methyl]-5-hydroxypyrazol-1-yl]pyridine-4-carbonitrile

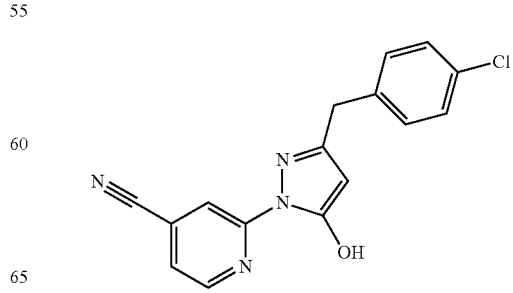

The title compound was prepared in 32% yield from 2-hydrazinylpyridine-4-carbonitrile (PREPARATION 2) and ethyl 4-(4-chlorophenyl)-3-oxobutanoate according to the procedure for the preparation of Example 158, part A.

C. 2-[3-[(4-chlorophenyl)methyl]-5-hydroxypyrazol-1-yl]pyridine-4-carboxylic acid

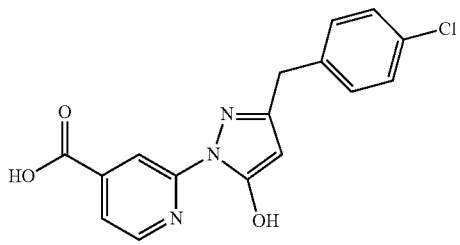 [SMILES: O=C(O)c1ccnc(-n2nc(Cc3ccc(Cl)cc3)cc2O)c1]

The title compound was prepared in 61% yield from 2-[3-[(4-chlorophenyl)methyl]-5-hydroxypyrazol-1-yl]pyridine-4-carbonitrile according to the procedure for the preparation of Example 158, part B. $^1$H NMR (400 MHz, CD$_3$OD): δ 3.91 (2H, s), 7.29-7.31 (4H, m), 7.72 (1H, dd, J=1.2, 5.2 Hz), 8.51 (1H, d, J=5.2 Hz), 8.63 (1H, brs).

[M+H] Calc'd for C$_{16}$H$_{12}$ClN$_3$O$_3$, 330. Found, 330.

Example 166

5-(1-phenylethyl)-2-[4-(1H-tetrazol-5-yl)pyridin-2-yl]pyrazol-3-ol

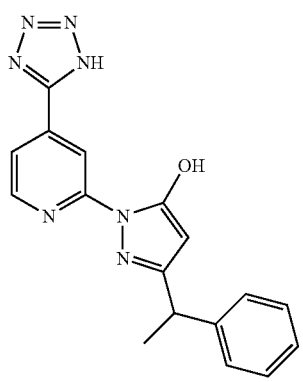 [SMILES: CC(c1ccccc1)c1cc(O)n(-c2cc(-c3nnn[nH]3)ccn2)n1]

To a suspension of 2-[5-hydroxy-3-(1-phenylethyl)pyrazol-1-yl]pyridine-4-carbonitrile (150 mg, 0.5 mmol), NH$_4$Cl (278 mg, 5.2 mmol) in DMF (5 mL) was added NaN$_3$ (338 mg, 5.2 mmol) at r.t. The reaction mixture was stirred at 110° C. for 2 h in a microwave oven. The reaction mixture was then filtered and purified by pre-HPLC to give the title compound (100 mg, 58%) as a brown solid. $^1$H NMR (400 MHz, CD$_3$OD): δ 1.64 (3H, d, J=7.2 Hz), 4.07-4.12 (1H, m), 7.17-7.19 (1H, m), 7.20-7.35 (4H, m), 7.83 (1H, dd, J=1.2, 5.2 Hz), 8.43 (1H, d, J=5.2 Hz), 8.74 (1H, s). [M+H] Calc'd for C$_{17}$H$_{15}$N$_7$O, 334. Found, 334.

Example 167

5-[(2-chlorophenyl)methyl]-2-[4-(1H-tetrazol-5-yl)pyridin-2-yl]pyrazol-3-ol

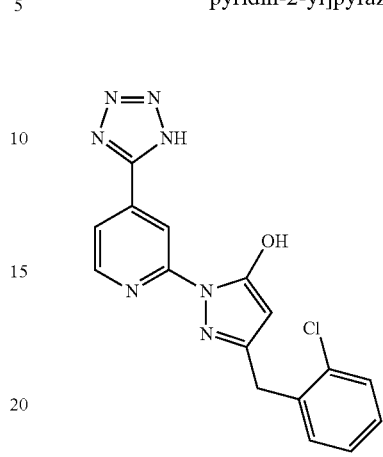

The title compound was prepared in 47% yield from 2-[3-[(2-chlorophenyl)methyl]-5-hydroxypyrazol-1-yl]pyridine-4-carbonitrile according to the procedure for the preparation of Example 166. $^1$H NMR (400 MHz, CD$_3$OD): δ 4.06 (2H, s), 7.23-7.28 (2H, m), 7.37-7.41 (2H, m), 7.85 (1H, dd, J=1.2, 5.2 Hz), 8.44 (1H, d, J=5.2 Hz), 8.70 (1H, s). [M+H] Calc'd for C$_{16}$H$_{12}$ClN$_7$O, 354. Found, 354.

Example 168

5-[(3-chlorophenyl)methyl]-2-[4-(1H-tetrazol-5-yl)pyridin-2-yl]pyrazol-3-ol

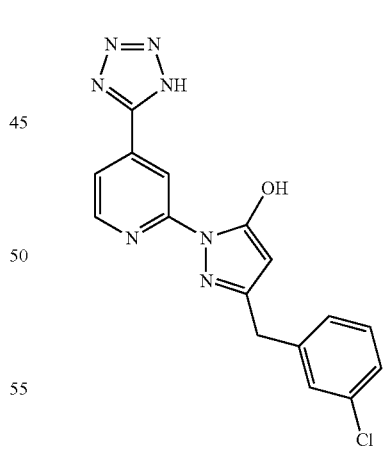

The title compound was prepared in 43% yield from 2-[3-[(3-chlorophenyl)methyl]-5-hydroxypyrazol-1-yl]pyridine-4-carbonitrile according to the procedure for the preparation of Example 166. $^1$H NMR (400 MHz, CD$_3$OD): δ 3.91 (2H, s), 7.21-7.33 (4H, m), 7.85 (1H, dd, J=1.6, 5.6 Hz), 8.47 (1H, d, J=5.2 Hz), 8.72 (1H, s). [M+H] Calc'd for C$_{16}$H$_{12}$ClN$_7$O, 354. Found, 354.

Example 169

5-[(4-chlorophenyl)methyl]-2-[4-(1H-tetrazol-5-yl)pyridin-2-yl]pyrazol-3-ol

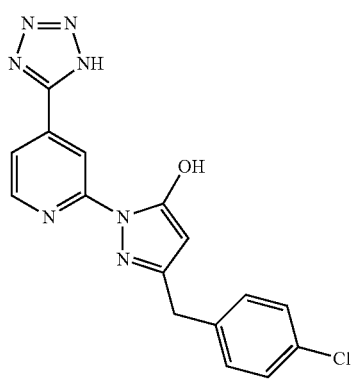 [SMILES: Oc1cc(Cc2ccc(Cl)cc2)nn1-c1cc(-c2nnn[nH]2)ccn1]

The title compound was prepared in 47% yield from 2-[3-[(4-chlorophenyl)methyl]-5-hydroxypyrazol-1-yl]pyridine-4-carbonitrile according to the procedure for the preparation of Example 166. $^1$H NMR (400 MHz, CD$_3$OD): δ 3.97 (2H, s), 7.35 (4H, s), 7.91 (1H, dd, J=1.2, 5.2 Hz), 8.62 (1H, d, J=5.2 Hz), 8.85 (1H, s). [M+H] Calc'd for C$_{16}$H$_{12}$ClN$_7$O, 354. Found, 354.

Example 170

2-[3-[2-(4-chlorophenyl)propan-2-yl]-5-hydroxy-pyrazol-1-yl]pyridine-4-carboxylic acid

A. methyl 4-(4-chlorophenyl)-4-methyl-3-oxopentanoate

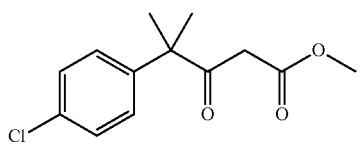 [SMILES: COC(=O)CC(=O)C(C)(C)c1ccc(Cl)cc1]

To a solution of 2-(4-chlorophenyl)-2-methylpropanoic acid (200 mg, 1.01 mmol) in THF (20 mL) was added CDI (172 mg, 1.06 mmol) at rt. The reaction mixture was stirred at rt for 2 h. Added MgCl$_2$ (105 mg, 1.11 mmol) and 3-methoxy-3-oxopropanoic acid potassium salt (173 mg, 1.11 mmol) at rt. The mixture was stirred at 60° C. overnight. Dilute with ethyl acetate (100 mL), washed with 0.5 N HCl (20 mL×2) and brine (50 mL), dried over Na$_2$SO$_4$, filtered, concentrated, purified by flash column chromatography to give the title compound (60 mg, 23%) as a yellow oil. $^1$H NMR (300 MHz, CDCl$_3$): δ 1.51 (6H, s), 3.28 (2H, s), 3.67 (3H, s), 7.20-7.30 (2H, m), 7.34-7.37 (2H, m).

B. 2-[3-[2-(4-chlorophenyl)propan-2-yl]-5-hydroxy-pyrazol-1-yl]pyridine-4-carbonitrile

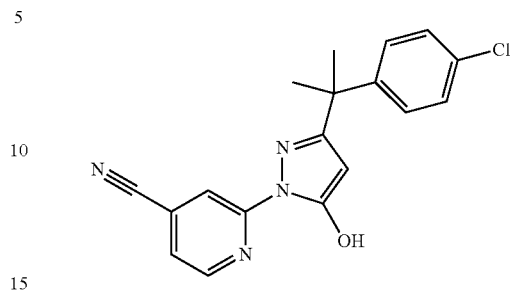

The title compound was prepared from 2-hydrazinylpyridine-4-carbonitrile (PREPARATION 2) and methyl 4-(4-chlorophenyl)-4-methyl-3-oxopentanoate according to the procedure for the preparation of Example 158, part A.

C. 2-[3-[2-(4-chlorophenyl)propan-2-yl]-5-hydroxy-pyrazol-1-yl]pyridine-4-carboxylic acid

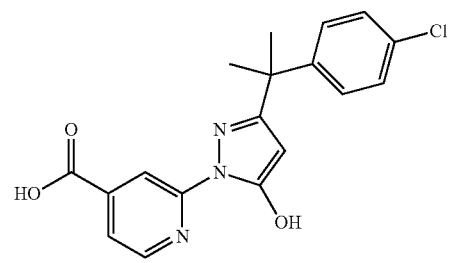 [SMILES: CC(C)(c1ccc(Cl)cc1)c1cc(O)n(-c2cc(C(=O)O)ccn2)n1]

The title compound was prepared in 40% yield from 2-[3-[2-(4-chlorophenyl)propan-2-yl]-5-hydroxypyrazol-1-yl]pyridine-4-carbonitrile according to the procedure for the preparation of Example 158, part B. $^1$H NMR (300 MHz, CD$_3$OD/DMSO-d$_6$): δ 1.58 (6H, s), 7.27-7.35 (4H, m), 7.66-7.69 (1H, m), 8.18-8.19 (1H, m), 8.53 (1H, dd, J=0.6, 5.1 Hz). [M+H] Calc'd for C$_{18}$H$_{16}$ClN$_3$O$_3$, 358. Found, 358.

Example 171

2-[3-[1-(4-chlorophenyl)cyclopropyl]-5-hydroxy-pyrazol-1-yl]pyridine-4-carboxylic acid

A. methyl 3-[1-(4-chlorophenyl)cyclopropyl]-3-oxopropanoate

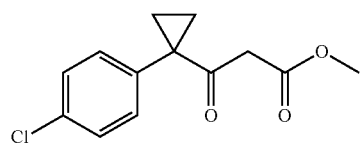 [SMILES: COC(=O)CC(=O)C1(c2ccc(Cl)cc2)CC1]

The title compound was prepared in 78% yield from 1-(4-chlorophenyl)cyclopropane-1-carboxylic acid and 3-methoxy-3-oxopropanoic acid potassium salt according to the procedure for the preparation of Example 170, part A. $^1$H NMR (300 MHz, CDCl$_3$): δ 1.22-1.26 (2H, m), 1.70-1.74 (2H, m), 3.35 (2H, s), 3.67 (3H, s), 7.29-7.34 (4H, m).

B. 2-[3-[1-(4-chlorophenyl)cyclopropyl]-5-hydroxy-pyrazol-1-yl]pyridine-4-carbonitrile

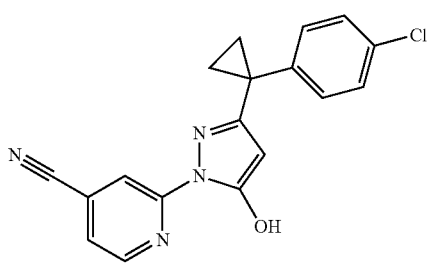 [SMILES: N#Cc1ccnc(-n2nc(C3(c4ccc(Cl)cc4)CC3)cc2O)c1]

The title compound was prepared from 2-hydrazinylpyridine-4-carbonitrile (PREPARATION 2) and methyl 3-[1-(4-chlorophenyl)cyclopropyl]-3-oxopropanoate according to the procedure for the preparation of Example 158, part A.

C. 2-[3-[1-(4-chlorophenyl)cyclopropyl]-5-hydroxy-pyrazol-1-yl]pyridine-4-carboxylic acid

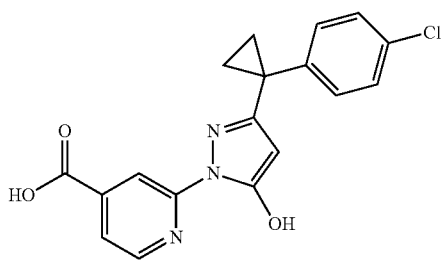 [SMILES: O=C(O)c1ccnc(-n2nc(C3(c4ccc(Cl)cc4)CC3)cc2O)c1]

The title compound was prepared in 36% yield from 2-[3-[1-(4-chlorophenyl)cyclopropyl]-5-hydroxypyrazol-1-yl]pyridine-4-carbonitrile according to the procedure for the preparation of Example 158, part B. $^1$H NMR (300 MHz, CD$_3$OD/DMSO-d$_6$): δ 1.19-1.21 (2H, m), 1.40-1.42 (2H, m), 7.29-7.36 (4H, m), 7.64-7.65 (1H, m), 8.15 (1H, brs), 8.50 (1H, d, J=5.4 Hz). [M+H] Calc'd for C$_{18}$H$_{14}$ClN$_3$O$_3$, 356. Found, 356.

Example 172

2-[3-[(3,5-dichlorophenyl)methyl]-5-hydroxypyra-zol-1-yl]pyridine-4-carboxylic acid A. methyl 4-(3,5-dichlorophenyl)-3-oxobutanoate

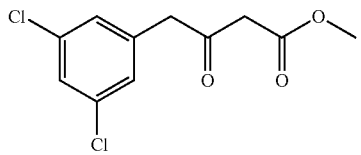 [SMILES: COC(=O)CC(=O)Cc1cc(Cl)cc(Cl)c1]

The title compound was prepared in 78% yield from 2-(3,5-dichlorophenyl)acetic acid and 3-methoxy-3-oxopropanoic acid potassium salt according to the procedure for the preparation of Example 170, part A.

B. 2-[3-[(3,5-dichlorophenyl)methyl]-5-hydroxy-pyrazol-1-yl]pyridine-4-carbonitrile

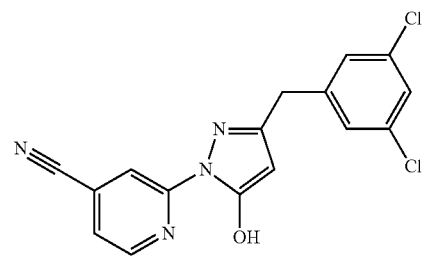 [SMILES: N#Cc1ccnc(-n2nc(Cc3cc(Cl)cc(Cl)c3)cc2O)c1]

The title compound was prepared from 2-hydrazinylpyridine-4-carbonitrile (PREPARATION 2) and methyl 4-(3,5-dichlorophenyl)-3-oxobutanoate according to the procedure for the preparation of Example 158, part A.

C. 2-[3-[(3,5-dichlorophenyl)methyl]-5-hydroxy-pyrazol-1-yl]pyridine-4-carboxylic acid

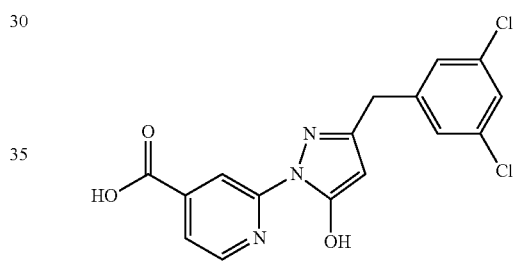

The title compound was prepared in 59% yield from 2-[3-[(3,5-dichlorophenyl)methyl]-5-hydroxypyrazol-1-yl]pyridine-4-carbonitrile according to the procedure for the preparation of Example 158, part B. $^1$H NMR (300 MHz, CD$_3$OD/DMSO-d$_6$): δ 4.06 (2H, m), 7.52-7.54 (3H, m), 7.83-7.84 (1H, m), 8.72 (1H, d, J=5.1 Hz). [M+H] Calc'd for C$_{16}$H$_{11}$Cl$_2$N$_3$O$_3$, 364. Found, 364.

Example 173

2-[3-[(4-fluoro-2-methylphenyl)methyl]-5-hydroxy-pyrazol-1-yl]pyridine-4-carboxylic acid A. methyl 4-(4-fluoro-2-methylphenyl)-3-oxobutanoate

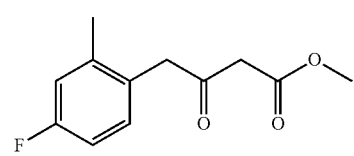 [SMILES: COC(=O)CC(=O)Cc1ccc(F)cc1C]

The title compound was prepared in 78% yield from 2-(4-fluoro-2-methylphenyl)acetic acid and 3-methoxy-3- oxopropanoic acid potassium salt according to the procedure for the preparation of Example 170, part A. $^1$H NMR (300 MHz, CDCl$_3$): δ 2.24 (3H, s), 3.47 (2H, s), 3.74 (3H, s), 3.83 (2H, s), 6.88-6.94 (2H, m), 7.07-7.12 (1H, m).

B. 2-[3-[(4-fluoro-2-methylphenyl)methyl]-5-hydroxypyrazol-1-yl]pyridine-4-carbonitrile

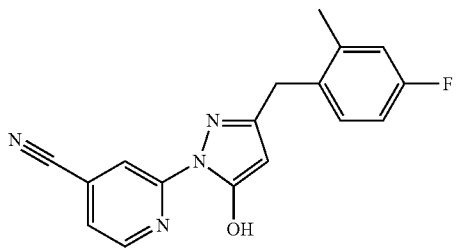 [SMILES: Cc1cc(F)ccc1Cc1cc(O)n(-c2cc(C#N)ccn2)n1]

The title compound was prepared from 2-hydrazinylpyridine-4-carbonitrile (PREPARATION 2) and methyl 4-(4-fluoro-2-methylphenyl)-3-oxobutanoate according to the procedure for the preparation of Example 158, part A.

C. 2-[3-[(4-fluoro-2-methylphenyl)methyl]-5-hydroxypyrazol-1-yl]pyridine-4-carboxylic acid

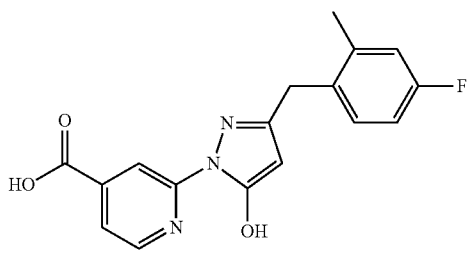 [SMILES: Cc1cc(F)ccc1Cc1cc(O)n(-c2cc(C(=O)O)ccn2)n1]

The title compound was prepared in 41% yield from 2-[3-[(4-fluoro-2-methylphenyl)methyl]-5-hydroxypyrazol-1-yl]pyridine-4-carbonitrile according to the procedure for the preparation of Example 158, part B. $^1$H NMR (300 MHz, CD$_3$OD): δ 2.34 (3H, s), 3.92 (2H, s), 6.87-6.98 (2H, m), 7.23-7.28 (1H, m), 7.75 (1H, dd, J=1.2, 5.1 Hz), 8.55 (1H, d, J=5.1 Hz), 8.72 (1H, brs). [M+H] Calc'd for C$_{17}$H$_{14}$FN$_3$O$_3$, 328. Found, 328.

Example 174

2-[3-[(2-fluoro-4-methylphenyl)methyl]-5-hydroxypyrazol-1-yl]pyridine-4-carboxylic acid A. methyl 4-(2-fluoro-4-methylphenyl)-3-oxobutanoate

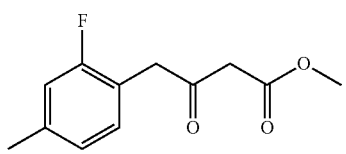

The title compound was prepared from 2-(2-fluoro-4-methylphenyl)acetic acid and 3-methoxy-3-oxopropanoic acid potassium salt according to the procedure for the preparation of Example 170, part A. $^1$H NMR (300 MHz, CDCl$_3$): δ 2.35 (3H, s), 3.52 (2H, s), 3.74 (3H, s), 3.83 (2H, s), 6.89-6.95 (2H, m), 7.05-7.08 (1H, m).

B. 2-[3-[(2-fluoro-4-methylphenyl)methyl]-5-hydroxypyrazol-1-yl]pyridine-4-carbonit

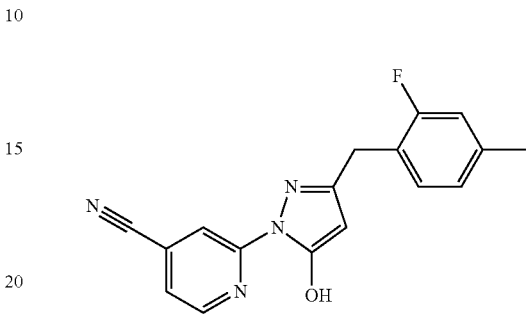

The title compound was prepared from 2-hydrazinylpyridine-4-carbonitrile (PREPARATION 2) and methyl 4-(2-fluoro-4-methylphenyl)-3-oxobutanoate according to the procedure for the preparation of Example 158, part A.

C. 2-[3-[(2-fluoro-4-methylphenyl)methyl]-5-hydroxypyrazol-1-yl]pyridine-4-carboxylic acid

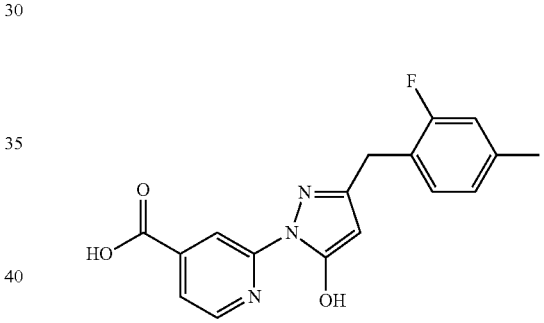

The title compound was prepared from 2-[3-[(2-fluoro-4-methylphenyl)methyl]-5-hydroxypyrazol-1-yl]pyridine-4-carbonit according to the procedure for the preparation of Example 158, part B. $^1$H NMR (300 MHz, CD$_3$OD): δ 2.33 (3H, s), 3.92 (2H, s), 6.92-6.97 (2H, m), 7.18-7.24 (1H, m), 7.73 (1H, d, J=4.8 Hz), 8.54 (1H, d, J=4.8 Hz), 8.69 (1H, brs). [M+H] Calc'd for C$_{17}$H$_{14}$FN$_3$O$_3$, 328. Found, 328.

Example 175

2-[3-[(2,4-difluorophenyl)methyl]-5-hydroxypyrazol-1-yl]pyridine-4-carboxylic acid A. methyl 4-(2,4-difluorophenyl)-3-oxobutanoate

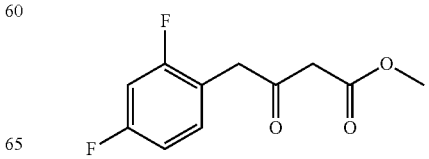

The title compound was prepared from 2-(2,4-difluorophenyl)acetic acid and 3-methoxy-3-oxopropanoic acid potassium salt according to the procedure for the preparation of Example 170, part A. $^1$H NMR (300 MHz, CDCl$_3$): δ 3.54 (2H, s), 3.76 (3H, s), 3.86 (2H, s), 6.83-6.90 (2H, m), 7.13-7.19 (1H, m).

B. 2-[3-[(2,4-difluorophenyl)methyl]-5-hydroxy-pyrazol-1-yl]pyridine-4-carbonitrile

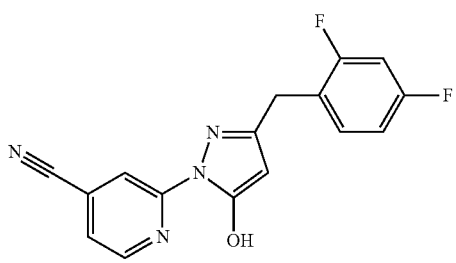 [SMILES: N#Cc1ccnc(-n2nc(Cc3ccc(F)cc3F)cc2O)c1]

The title compound was prepared from 2-hydrazinylpyridine-4-carbonitrile (PREPARATION 2) and methyl 4-(2,4-difluorophenyl)-3-oxobutanoate according to the procedure for the preparation of Example 158, part A.

C. 2-[3-[(2,4-difluorophenyl)methyl]-5-hydroxy-pyrazol-1-yl]pyridine-4-carboxylic acid

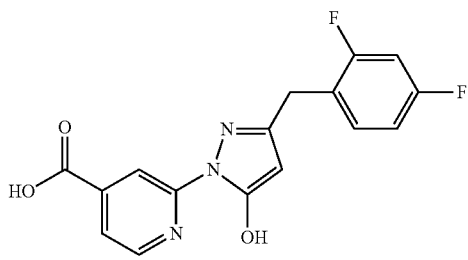 [SMILES: O=C(O)c1ccnc(-n2nc(Cc3ccc(F)cc3F)cc2O)c1]

The title compound was prepared in 20% yield from 2-[3-[(2,4-difluorophenyl)methyl]-5-hydroxypyrazol-1-yl]pyridine-4-carbonitrile according to the procedure for the preparation of Example 158, part B. $^1$H NMR (300 MHz, CD$_3$OD/DMSO-d$_6$): δ 3.88 (2H, s), 6.97-7.04 (1H, m), 7.11-7.17 (1H, m), 7.37-7.43 (1H, m), 7.65-7.66 (1H, m), 8.56 (1H, d, J=5.1 Hz). [M+H] Calc'd for C$_{16}$H$_{11}$F$_2$N$_3$O$_3$, 332. Found, 332.

II. Biological Evaluation

Example 1

In Vitro Enzyme Inhibition Assay

This assay determines the ability of a test compound to inhibit Jarid1A, Jarid1B, JMJD2C, and JMJD2A demethylase activity. Baculovirus expressed Jarid1A (GenBank Accession #NM 001042603, AA1-1090) was purchased from BPS Bioscience (Cat#50110). Baculovirus expressed Jarid1B (GenBank Accession #NM_006618, AA 2-751) was purchased from BPS Bioscience (Cat #50121) or custom made by MolecularThroughput. Baculovirus expressed JMJD2C (GenBank Accession #BC143571, AA 2-372) was purchased from BPS Bioscience (Cat#50105). Baculovirus expressed JMJD2A (GenBank Accession #NM 014663, AA 1-350) was purchased from BPS Bioscience (Cat#50123). Baculovirus expressed FBXL10 (GenBank Accession #NM 032590, AA 1-650) was purchased from BPS Bioscience (Cat#50120).

Jarid1A Assay

The enzymatic assay of Jarid1A activity is based upon Time Resolved-Fluorescence Resonance Energy Transfer (TR-FRET) detection. The ability of test compounds to inhibit the activity of Jarid1A was determined in 384-well plate format under the following reaction conditions: 1 nM Jarid1A, 300 nM H3K4me3-biotin labeled peptide (Anaspec cat #64357), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 μl of the mixture of 900 nM H3K4me3-biotin labeled peptide and 6 μM alpha-ketoglutaric acid with 2 μl of 11-point serial diluted inhibitor in 3% DMSO was added to each well of plate, followed by the addition of 2 μl of 3 nM Jarid1A to initiate the reaction. The reaction mixture was incubated at room temperature for 30 minutes, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 μl of the mixture of 900 nM H3K4me3-biotin labeled peptide and 6 μM alpha-ketoglutaric acid with 2 μl of 11-point serial diluted inhibitor in 3% DMSO was added to each well of the plate, followed by the addition of 2 μl of 2.4 nM Jarid1B to initiate the reaction. The reaction mixture was incubated at room temperature for 30 minutes, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM alpha-ketoglutaric acid with 2 μl of 11-point serial diluted inhibitor in 3% DMSO were added to each well of the plate, followed by the addition of 2 μl of 0.9 nM JMJD2C to initiate the reaction. The reaction mixture was incubated at room temperature for 30 minutes, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

JMJD2A Assay

The ability of test compounds to inhibit the activity of JMJD2A was determined in 384-well plate format under the following reaction conditions: 2 nM JMJD2A, 300 nM H3K9me3-biotin labeled peptide (Anaspec cat #64360), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM alpha-ketoglutaric acid with 2 μl of 11-point serial diluted inhibitor in 3% DMSO were added to each well of plate, followed by the addition of 2 μl of 6 nM JMJD2A to initiate the reaction. The reaction mixture was incubated at room temperature for 30 minutes, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC50).

FBXL10 Assay

The ability of test compounds to inhibit the activity of FBXL10 was determined in 384-well plate format under the following reaction conditions: 0.3 nM FBXL10, 30 nM H3K36me2-biotin labeled peptide (Anaspec cat #64442), 0.2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 5 μM ammonium iron(II) sulfate. Reaction product was determined quantitatively by AlphaScreen detection after the addition of detection reagents anti-H3K36me1 antibody, AlphaScreen® Streptavidin-coated Donor beads, and AlphaScreen® Protein A Acceptor beads in 50 mM HEPES, pH7.3, 10 mM NaCl, 0.005% Brij35, 5 mM EDTA, 2 mg/ml BSA to final 10 μg/ml beads.

The assay reaction was initiated by the following: 3 μl of the mixture of 90 nM H3K36me2-biotin labeled peptide and 0.6 μM alpha-ketoglutaric acid with 3 μl of 11-point serial diluted inhibitor in 3% DMSO were added to each well of 384 well Proxiplate (Perkin Elmer), followed by the addition of 3 μl of 0.9 nM FBXL10 to initiate the reaction. The reaction mixture was incubated at room temperature for 30 minutes, and terminated by the addition of 3 μl of 50 mM HEPES, pH7.3, 10 mM NaCl, 0.005% Brij35, 5 mM EDTA, 2 mg/ml BSA containing appropriate dilution of anti H3K36me1 antibody. Plates were incubated at room temperature for 40 minutes, followed by addition of 3 μl of 50 μg/ml AlphaScreen® Streptavidin-coated Donor beads and AlphaScreen® Protein A Acceptor beads in 50 mM HEPES, pH7.3, 10 mM NaCl, 0.005% Brij35, 5 mM EDTA, 2 mg/ml BSA. Plates were read by EnVisionMultilabel Reader in AlphaScreen mode after a minimum of 2 hour or up to overnight incubation at room temperature. The AlphaScreen signal for each well was used to determine inhibition constant ($IC_{50}$).

The ability of the compounds disclosed herein to inhibit demethylase activity was quantified and the respective $IC_{50}$ value was determined. Tables 3 provides the $IC_{50}$ values of various compounds disclosed herein.

TABLE 3

| Chemical Synthesis Example | Name | JARID1A $IC_{50}$ (μM) | JARID1B $IC_{50}$ (μM) | JMJD2C $IC_{50}$ (μM) | JMJD2A $IC_{50}$ (μM) | FBXL10 $IC_{50}$ (μM) |
|---|---|---|---|---|---|---|
| 1 | 2-(5-hydroxy-3-methyl-1H-pyrazol-1-yl)isonicotinic acid | B | A | B |  | B |
| 2 | 2-(3-cyclopropyl-5-hydroxy-1H-pyrazol-1-yl)isonicotinic acid | A | A | B | B | A |
| 3 | 2-(5-hydroxy-3,4-dimethyl-1H-pyrazol-1-yl)isonicotinic acid | B | A | B |  | B |
| 4 | 2-(5-hydroxy-3-methyl-4-phenyl-1H-pyrazol-1-yl)isonicotinic acid | C | C | C |  | B |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 5 | 2-(3-(2-fluorophenyl)-5-hydroxy-1H-pyrazol-1-yl)isonicotinic acid | C | C | C | | A |
| 6 | 2-(5-hydroxy-3-propyl-1H-pyrazol-1-yl)isonicotinic acid | B | B | B | | B |
| 7 | 2-(3-(2-chlorophenyl)-5-hydroxy-1H-pyrazol-1-yl)isonicotinic acid | C | C | D | | A |
| 8 | 2-(3-benzyl-5-hydroxy-1H-pyrazol-1-yl)isonicotinic acid | B | B | C | | A |
| 9 | 2-(5-hydroxy-3-(methoxymethyl)-1H-pyrazol-1-yl)isonicotinic acid | B | B | C | | A |
| 10 | 2-(5-hydroxy-3-(phenoxymethyl)-1H-pyrazol-1-yl)isonicotinic acid | C | B | D | | A |
| 11 | 2-(5-hydroxy-1H-pyrazol-1-yl)isonicotinic acid | A | A | B | | B |
| 12 | 2-(5-p-tolyl-1H-pyrazol-1-yl)isonicotinic acid | B | B | B | B | |
| 13 | 2-(5-m-tolyl-1H-pyrazol-1-yl)isonicotinic acid | B | B | B | | |
| 14 | 2-(5-(2,4-difluorophenyl)-1H-pyrazol-1-yl)isonicotinic acid | B | B | B | B | |
| 15 | 2-(5-(3,4-difluorophenyl)-1H-pyrazol-1-yl)isonicotinic acid | B | B | B | | |
| 16 | 2-(5-(3-fluorophenyl)-1H-pyrazol-1-yl)isonicotinic acid | B | B | B | | |
| 17 | 2-(5-(3-hydroxyphenyl)-1H-pyrazol-1-yl)isonicotinic acid | B | B | B | B | |
| 18 | 2-(5-(4-hydroxyphenyl)-1H-pyrazol-1-yl)isonicotinic acid | B | B | B | | |
| 19 | 2-(5-(4-(methylsulfonyl)phenyl)-1H-pyrazol-1-yl)isonicotinic acid | B | B | C | | |
| 20 | 2-(5-(3-methoxy-4-methylphenyl)-1H-pyrazol-1-yl)isonicotinic acid | B | B | C | | |
| 21 | 2-(5-(3-hydroxy-4-methylphenyl)-1H-pyrazol-1-yl)isonicotinic acid | A | A | B | | |
| 22 | 2-(5-(4-chloro-3-methoxyphenyl)-1H-pyrazol-1-yl)isonicotinic acid | B | B | C | | |
| 23 | 2-(5-(4-chloro-3-hydroxyphenyl)-1H-pyrazol-1-yl)isonicotinic acid | B | B | C | | |
| 24 | 2-[5-(1H-indazol-6-yl)-1H-pyrazol-1-yl]pyridine-4-carboxylic acid | B | B | C | | |
| 25 | methyl 2-[5-1H-indazol-6-yl)-1H-pyrazol-1-yl]pyridine-4-carboxylate | | | | | |
| 26 | 2-(5-phenyl-1H-pyrazol-1-yl)isonicotinic acid | C | C | C | | |
| 27 | 2-(5-(4-fluorophenyl)-1H-pyrazol-1-yl)isonicotinic acid | B | B | B | | D |
| 28 | 2-(5-(3-hydroxy-4-(methylsulfonyl)phenyl)-1H-pyrazol-1-yl)isonicotinic acid | B | B | C | | |
| 29 | 2-(3-methyl-5-p-tolyl-1H-pyrazol-1-yl)isonicotinic acid | C | C | C | | |
| 30 | 2-(3-ethyl-5-p-tolyl-1H-pyrazol-1-yl)isonicotinic acid | C | B | C | | |
| 31 | 2-(5-methyl-1H-pyrazol-1-yl)isonicotinic acid | C | C | B | | |
| 32 | 2-(5-benzyl-1H-pyrazol-1-yl)isonicotinic acid | D | D | D | | C |
| 33 | 2-(3-benzyl-1H-pyrazol-1-yl)isonicotinic acid | C | C | C | | C |
| 34 | 2-(5-phenethyl-1H-pyrazol-1-yl)isonicotinic acid | C | C | D | | |
| 35 | 2-(3-phenethyl-1H-pyrazol-1-yl)isonicotinic acid | B | B | B | B | |
| 36 | 2-(5-methyl-4-phenyl-1H-pyrazol-1-yl)isonicotinic acid | B | B | D | | |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 37 | 2-(5-methoxy-3-methyl-1H-pyrazol-1-yl)isonicotinic acid | C | C | C | | |
| 38 | 2-(5-(benzyloxy)-3-methyl-1H-pyrazol-1-yl)isonicotinic acid | B | A | B | | |
| 39 | 2-(5-(benzyloxy)-1H-pyrazol-1-yl)isonicotinic acid | A | A | A | A | |
| 40 | 2-{5-[(4-fluorobenzyl)oxy]-1H-pyrazol-1-yl}pyridine-4-carboxylic acid | A | A | A | | D |
| 41 | 2-{5-[(3-fluorobenzyl)oxy]-1H-pyrazol-1-yl}pyridine-4-carboxylic acid | A | A | A | | |
| 42 | 2-{5-[(3-methoxybenzyl)oxy]-1H-pyrazol-1-yl}pyridine-4-carboxylic acid | A | A | A | | |
| 43 | 2-{5-[(4-methoxybenzyl)oxy]-1H-pyrazol-1-yl}pyridine-4-carboxylic acid | A | A | B | | |
| 44 | 2-(5-butyl-1H-pyrazol-1-yl)isonicotinic acid | C | C | D | | |
| 45 | 2-(3-butyl-1H-pyrazol-1-yl)pyridine-4-carboxylic acid | B | B | B | | |
| 46 | 2-(5-(4-bromophenyl)-1H-pyrazol-1-yl)isonicotinic acid | B | B | C | | |
| 47 | 2-{5-[4-(dimethylamino)phenyl]-1H-pyrazol-1-yl}pyridine-4-carboxylic acid | B | B | C | | |
| 48 | 2-[3-amino-5-(4-methylphenyl)-1H-pyrazol-1-yl]pyridine-4-carboxylic acid | A | B | C | | |
| 49 | 2-[5-(1H-indazol-6-ylmethoxy)-1H-pyrazol-1-yl]pyridine-4-carboxylic acid | B | B | C | | B |
| 50 | 2-{5-[(1-methyl-1H-indazol-6-yl)methoxy]-1H-pyrazol-1-yl}pyridine-4-carboxylic acid | A | A | B | | B |
| 51 | 2-{5-[(1-methyl-1H-indazol-6-yl)methoxy]-1H-pyrazol-1-yl}pyridine-4-carboxylic acid | A | A | B | | |
| 52 | 2-{5-[(3,4-difluorobenzyl)oxy]-1H-pyrazol-1-yl}pyridine-4-carboxylic acid | A | A | B | | |
| 53 | 2-{5-[(4-chlorobenzyl)oxy]-1H-pyrazol-1-yl}pyridine-4-carboxylic acid | A | A | A | | |
| 54 | 2-(5-{[4-(trifluoromethyl)benzyl]oxy}-1H-pyrazol-1-yl)pyridine-4-carboxylic acid | A | A | B | | |
| 55 | 2-{5-[(4-methylbenzyl)oxy]-1H-pyrazol-1-yl}pyridine-4-carboxylic acid | A | A | A | | C |
| 56 | 2-{5-[(4-ethylbenzyl)oxy]-1H-pyrazol-1-yl}pyridine-4-carboxylic acid | A | A | B | | C |
| 57 | 2-{5-[(4-bromobenzyl)oxy]-1H-pyrazol-1-yl}pyridine-4-carboxylic acid | A | A | A | | |
| 58 | 2-{5-[(3-chlorobenzyl)oxy]-1H-pyrazol-1-yl}pyridine-4-carboxylic acid | A | A | A | | |
| 59 | 2-{5-[(2-fluorobenzyl)oxy]-1H-pyrazol-1-yl}pyridine-4-carboxylic acid | A | A | A | | |
| 60 | 2-[5-(pyridin-3-ylmethoxy)-1H-pyrazol-1-yl]pyridine-4-carboxylic acid | A | A | B | | |
| 61 | 2-[5-(pyridin-4-ylmethoxy)-1H-pyrazol-1-yl]pyridine-4-carboxylic acid | A | A | A | | |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 62 | methyl 2-{5-[(4-fluorobenzyl)oxy]-1H-pyrazol-1-yl}pyridine-4-carboxylate | | | | | |
| 63 | methyl 2-{5-[(3,4-difluorobenzyl)oxy]-1H-pyrazol-1-yl}pyridine-4-carboxylate | | | | | |
| 64 | methyl 2-{5-[(4-chlorobenzyl)oxy]-1H-pyrazol-1-yl}pyridine-4-carboxylate | | | | | |
| 65 | methyl 2-(5-{[4-(trifluoromethyl)benzyl]oxy}-1H-pyrazol-1-yl)pyridine-4-carboxylate | | | | | |
| 66 | methyl 2-{5-[(4-methylbenzyl)oxy]-1H-pyrazol-1-yl}pyridine-4-carboxylate | | | | | |
| 67 | methyl 2-{5-[(4-ethylbenzyl)oxy]-1H-pyrazol-1-yl}pyridine-4-carboxylate | | | | | |
| 68 | methyl 2-{5-[(4-bromobenzyl)oxy]-1H-pyrazol-1-yl}pyridine-4-carboxylate | | | | | |
| 69 | methyl 2-[5-(benzyloxy)-1H-pyrazol-1-yl]pyridine-4-carboxylate | | | | | |
| 70 | methyl 2-{5-[(3-fluorobenzyl)oxy]-1H-pyrazol-1-yl}pyridine-4-carboxylate | | | | | |
| 71 | 2-{5-[(4,4-difluorocyclohexyl)methoxy]-1H-pyrazol-1-yl}pyridine-4-carboxylic acid | A | A | B | | |
| 72 | 2-{5-[(3-bromobenzyl)oxy]-1H-pyrazol-1-yl}pyridine-4-carboxylic acid | A | A | A | | |
| 73 | 2-{5-[(3-hydroxybenzyl)oxy]-1H-pyrazol-1-yl}pyridine-4-carboxylic acid | A | A | A | | |
| 74 | 2-{5-[(4-chloro-3-fluorobenzyl)oxy]-1H-pyrazol-1-yl}pyridine-4-carboxylic acid | A | A | A | | |
| 75 | 2-{5-[(4-chloro-2-fluorobenzyl)oxy]-1H-pyrazol-1-yl}pyridine-4-carboxylic acid | A | A | A | | |
| 76 | 2-{5-[(3-chloro-4-fluorobenzyl)oxy]-1H-pyrazol-1-yl}pyridine-4-carboxylic acid | A | A | A | | |
| 77 | 2-{5-[(4-cyclopropylbenzyl)oxy]-1H-pyrazol-1-yl}pyridine-4-carboxylic acid | A | A | B | | |
| 78 | methyl 2-{5-[(4-chloro-3-fluorobenzyl)oxy]-1H-pyrazol-1-yl}pyridine-4-carboxylate | | | | | |
| 79 | methyl 2-{5-[(4-chloro-2-fluorobenzyl)oxy]-1H-pyrazol-1-yl}pyridine-4-carboxylate | | | | | |
| 80 | methyl 2-{5-[(3-chloro-4-fluorobenzyl)oxy]-1H-pyrazol-1-yl}pyridine-4-carboxylate | | | | | |
| 81 | methyl 2-{5-[(4-cyclopropylbenzyl)oxy]-1H-pyrazol-1-yl}pyridine-4-carboxylate | | | | | |

TABLE 3-continued

| Chemical Synthesis Example | Name | JARID1A IC$_{50}$ (µM) | JARID1B IC$_{50}$ (µM) | JMJD2C IC$_{50}$ (µM) | JMJD2A IC$_{50}$ (µM) | FBXL10 IC$_{50}$ (µM) |
|---|---|---|---|---|---|---|
| 82 | 2-[5-[1-(4-fluorophenyl)ethoxy]pyrazol-1-yl]pyridine-4-carboxylic acid | A | A | B | | |
| 83 | 2-[5-[(3,3-difluorocyclobutyl)methoxy]pyrazol-1-yl]pyridine-4-carboxylic acid | A | A | A | | |
| 84 | 2-[5-[(4-fluorophenyl)methoxy]-4-methylpyrazol-1-yl]pyridine-4-carboxylic acid | A | A | B | | |
| 85 | 2-[4-ethyl-5-[(4-fluorophenyl)methoxy]pyrazol-1-yl]pyridine-4-carboxylic acid | A | A | B | | |
| 86 | 2-[5-[(2,4-difluorophenyl)methoxy]pyrazol-1-yl]pyridine-4-carboxylic acid | A | A | B | | |
| 87 | 2-[5-[(3,4-dichlorophenyl)methoxy]pyrazol-1-yl]pyridine-4-carboxylic acid | A | A | B | | |
| 88 | 2-[5-[(2,4-dichlorophenyl)methoxy]pyrazol-1-yl]pyridine-4-carboxylic acid | A | A | B | | |
| 89 | 2-[5-[(4-chloro-2-methylphenyl)methoxy]pyrazol-1-yl]pyridine-4-carboxylic acid | A | A | B | | B |
| 90 | 2-[5-[(4-chloro-2-methoxyphenyl)methoxy]pyrazol-1-yl]pyridine-4-carboxylic acid | A | A | A | | |
| 91 | 2-[5-[[4-chloro-3-(trifluoromethyl)phenyl]methoxy]pyrazol-1-yl]pyridine-4-carboxylic acid | A | A | B | | |
| 92 | 2-[5-[(3-chloro-4-methylphenyl)methoxy]pyrazol-1-yl]pyridine-4-carboxylic acid | A | A | A | | C |
| 93 | 2-[5-[(3-fluoro-4-methylphenyl)methoxy]pyrazol-1-yl]pyridine-4-carboxylic acid | A | A | A | | |
| 94 | 2-[5-[(2,3-difluoro-4-methylphenyl)methoxy]pyrazol-1-yl]pyridine-4-carboxylic acid | A | A | A | | |
| 95 | 2-[5-[(3-chloro-4-ethylphenyl)methoxy]pyrazol-1-yl]pyridine-4-carboxylic acid | A | A | B | | |
| 96 | 2-[5-[(4-ethyl-3-fluorophenyl)methoxy]pyrazol-1-yl]pyridine-4-carboxylic acid | A | A | B | | |
| 97 | 2-[5-[(3-cyanophenyl)methoxy]pyrazol-1-yl]pyridine-4-carboxylic acid | A | A | A | | |
| 98 | methyl 2-[5-[(4-cyanophenyl)methoxy]pyrazol-1-yl]pyridine-4-carboxylate | | | | | |
| 99 | 2-[5-[(4-cyanophenyl)methoxy]pyrazol-1-yl]pyridine-4-carboxylic acid | A | A | A | | C |
| 100 | methyl 2-[5-[(3-chloro-4-methylphenyl)methoxy]pyrazol-1-yl]pyridine-4-carboxylate | | | | | |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 101 | methyl 2-[5-[(3-fluoro-4-methylphenyl)methoxy]pyrazol-1-yl]pyridine-4-carboxylate | | | | | |
| 102 | methyl 2-[5-[(3-chloro-4-ethylphenyl)methoxy]pyrazol-1-yl]pyridine-4-carboxylate | | | | | |
| 103 | methyl 2-[5-[(2,3-difluoro-4-methylphenyl)methoxy]pyrazol-1-yl]pyridine-4-carboxylate | | | | | |
| 104 | methyl 2-[5-[(4-ethyl-3-fluorophenyl)methoxy]pyrazol-1-yl]pyridine-4-carboxylate | | | | | |
| 105 | 2-[5-[(4-chloro-2-phenylmethoxyphenyl)methoxy]pyrazol-1-yl]pyridine-4-carboxylic acid | A | A | B | | B |
| 106 | 2-[5-[[4-chloro-2-(cyclopropylmethoxy)phenyl]methoxy]pyrazol-1-yl]pyridine-4-carboxylic acid | A | A | B | | C |
| 107 | 2-[5-[(4-chloro-2-propoxyphenyl)methoxy]pyrazol-1-yl]pyridine-4-carboxylic acid | | | | | |
| 108 | 2-[5-[[4-chloro-2-(2,2,2-trifluoroethoxy)phenyl]methoxy]pyrazol-1-yl]pyridine-4-carboxylic acid | A | A | B | | C |
| 109 | 2-[5-[(4-fluorophenyl)methoxy]-4-(2-hydroxyethyl)pyrazol-1-yl]pyridine-4-carboxylic acid | A | A | C | | |
| 110 | 2-[4-[2-(dimethylamino)ethyl]-5-[(4-fluorophenyl)methoxy]pyrazol-1-yl]pyridine-4-carboxylic acid | A | A | B | | |
| 111 | 2-[5-[(2-butoxy-4-chlorophenyl)methoxy]pyrazol-1-yl]pyridine-4-carboxylic acid | B | B | C | C | C |
| 112 | 2-[5-[[4-chloro-2-(2-methylpropoxy)phenyl]methoxy]pyrazol-1-yl]pyridine-4-carboxylic acid | B | B | C | C | C |
| 113 | 2-[5-[(4-chloro-2-propan-2-yloxyphenyl)methoxy]pyrazol-1-yl]pyridine-4-carboxylic acid | B | B | C | | |
| 114 | 2-[5-[(2-butan-2-yloxy-4-chlorophenyl)methoxy]pyrazol-1-yl]pyridine-4-carboxylic acid | B | B | C | | |
| 115 | 2-[5-[(4-chloro-2-ethoxyphenyl)methoxy]pyrazol-1-yl]pyridine-4-carboxylic acid | A | A | B | | |
| 116 | 2-[5-[[4-chloro-2-(2-methoxyethoxy)phenyl]methoxy]pyrazol-1-yl]pyridine-4-carboxylic acid | A | A | B | | |
| 117 | 2-[5-[[4-chloro-2-[(4-fluorophenyl)methoxy]phenyl]methoxy]pyrazol-1-yl]pyridine-4-carboxylic acid | B | B | C | C | C |
| 118 | 2-[5-[[4-fluoro-2-[(4-fluorophenyl)methoxy]phenyl]methoxy]pyrazol-1-yl]pyridine-4-carboxylic acid | A | A | B | B | C |
| 119 | 2-[5-[[4-fluoro-2-[(E)-2-(4-fluorophenyl)ethenyl]phenyl]methoxy]pyrazol-1-yl]pyridine-4-carboxylic acid | B | B | C | | |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 120 | 2-[5-[[4-chloro-2-[(E)-2-(4-fluorophenyl)ethenyl]phenyl]methoxy]pyrazol-1-yl]pyridine-4-carboxylic acid | B | B | C | | |
| 121 | 2-[5-[[4-fluoro-2-[2-(4-fluorophenyl)ethyl]phenyl]methoxy]pyrazol-1-yl]pyridine-4-carboxylic acid | B | B | C | | |
| 122 | 2-[5-[[4-chloro-2-[2-(4-fluorophenyl)ethyl]phenyl]methoxy]pyrazol-1-yl]pyridine-4-carboxylic acid | B | B | C | | |
| 123 | 2-[5-(2,3-dihydro-1-benzofuran-7-ylmethoxy)pyrazol-1-yl]pyridine-4-carboxylic acid | A | A | B | | |
| 124 | 2-[5-[(2,2-dimethyl-3H-1-benzofuran-7-yl)methoxy]pyrazol-1-yl]pyridine-4-carboxylic acid | B | A | B | | |
| 125 | 2-[5-[(4-cyano-2-methylphenyl)methoxy]pyrazol-1-yl]pyridine-4-carboxylic acid | A | A | B | | |
| 126 | 2-[5-[(4-cyano-2-ethylphenyl)methoxy]pyrazol-1-yl]pyridine-4-carboxylic acid | A | A | B | | |
| 127 | 2-[5-[(4-chloro-2-ethylphenyl)methoxy]pyrazol-1-yl]pyridine-4-carboxylic acid | B | B | C | | |
| 128 | 2-[5-[(4-fluoro-2-methylphenyl)methoxy]pyrazol-1-yl]pyridine-4-carboxylic acid | A | A | B | | |
| 129 | 2-[5-[(2-ethyl-4-fluorophenyl)methoxy]pyrazol-1-yl]pyridine-4-carboxylic acid | A | A | B | | |
| 130 | 2-[5-[(2-chloro-4-methylphenyl)methoxy]pyrazol-1-yl]pyridine-4-carboxylic acid | B | B | C | B | C |
| 131 | 2-[5-[(2-fluoro-4-methylphenyl)methoxy]pyrazol-1-yl]pyridine-4-carboxylic acid | A | A | B | | |
| 132 | 2-[5-[(2,4-dimethylphenyl)methoxy]pyrazol-1-yl]pyridine-4-carboxylic acid | A | A | B | B | C |
| 133 | 2-[5-[(2-methoxy-4-methylphenyl)methoxy]pyrazol-1-yl]pyridine-4-carboxylic acid | A | A | B | B | C |
| 134 | 2-[5-[(2-cyano-4-methylphenyl)methoxy]pyrazol-1-yl]pyridine-4-carboxylic acid | A | A | B | | |
| 135 | 2-[5-[(2-ethyl-4-methylphenyl)methoxy]pyrazol-1-yl]pyridine-4-carboxylic acid | B | B | C | | |
| 136 | 2-[5-[[4-chloro-2-(1-phenylethoxy)phenyl]methoxy]pyrazol-1-yl]pyridine-4-carboxylic acid | B | B | C | | |
| 137 | 2-[5-[[4-fluoro-2-(1-phenylethoxy)phenyl]methoxy]pyrazol-1-yl]pyridine-4-carboxylic acid | B | B | C | | |
| 138 | 2-[5-[[4-chloro-3-[(4-fluorophenyl)methoxy]phenyl]methoxy]pyrazol-1-yl]pyridine-4-carboxylic acid | A | A | B | | |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 139 | 2-[5-[[4-fluoro-3-[(4-fluorophenyl)methoxy]phenyl]methoxy]pyrazol-1-yl]pyridine-4-carboxylic acid | A | A | B | | |
| 140 | 2-[5-[[4-chloro-3-(cyclopropylmethoxy)phenyl]methoxy]pyrazol-1-yl]pyridine-4-carboxylic acid | B | B | B | B | C |
| 141 | 2-[5-[[4-chloro-3-(2,2,2-trifluoroethoxy)phenyl]methoxy]pyrazol-1-yl]pyridine-4-carboxylic acid | A | A | B | | |
| 142 | 2-[5-[(4-bromo-2-methylphenyl)methoxy]pyrazol-1-yl]pyridine-4-carboxylic acid | B | B | B | | |
| 143 | 2-[5-[(4-bromo-2-methoxyphenyl)methoxy]pyrazol-1-yl]pyridine-4-carboxylic acid | A | A | B | | |
| 144 | 2-[5-[(4-iodo-2-methylphenyl)methoxy]pyrazol-1-yl]pyridine-4-carboxylic acid | A | A | B | | |
| 145 | 2-[5-[(4-iodo-2-methoxyphenyl)methoxy]pyrazol-1-yl]pyridine-4-carboxylic acid | A | A | B | | |
| 146 | 2-[5-[(5-fluoro-2,3-dihydro-1H-inden-1-yl)oxy]pyrazol-1-yl]pyridine-4-carboxylic acid | B | B | B | | |
| 147 | 2-[5-[(5-chloro-2,3-dihydro-1H-inden-1-yl)oxy]pyrazol-1-yl]pyridine-4-carboxylic acid | B | B | C | | |
| 148 | 2-[5-[(6-fluoro-1,2,3,4-tetrahydronaphthalen-1-yl)oxy]pyrazol-1-yl]pyridine-4-carboxylic acid | B | B | C | | |
| 149 | 2-[5-[(6-chloro-1,2,3,4-tetrahydronaphthalen-1-yl)oxy]pyrazol-1-yl]pyridine-4-carboxylic acid | B | A | C | | |
| 150 | 2-[5-[(2-chloro-4-ethylphenyl)methoxy]pyrazol-1-yl]pyridine-4-carboxylic acid | B | B | C | | |
| 151 | 2-[5-[(4-ethyl-2-fluorophenyl)methoxy]pyrazol-1-yl]pyridine-4-carboxylic acid | B | A | C | | |
| 152 | 2-[5-[(2-chloro-4-cyclopropylphenyl)methoxy]pyrazol-1-yl]pyridine-4-carboxylic acid | B | B | C | | |
| 153 | 2-[5-[(4-cyclopropyl-2-fluorophenyl)methoxy]pyrazol-1-yl]pyridine-4-carboxylic acid | B | B | C | | |
| 154 | 2-[5-[(3-chloro-4-cyclopropylphenyl)methoxy]pyrazol-1-yl]pyridine-4-carboxylic acid | B | B | C | | |
| 155 | 2-[5-[(4-cyclopropyl-3-fluorophenyl)methoxy]pyrazol-1-yl]pyridine-4-carboxylic acid | B | A | C | | |
| 156 | 2-[4-[2-[(4-fluorophenyl)methyl-methylamino]ethyl]pyrazol-1-yl]pyridine-4-carboxylic acid | A | A | A | | D |
| 157 | N-cyano-2-[4-[2-[(4-fluorophenyl)methyl-methylamino]ethyl]pyrazol-1-yl]pyridine-4-carboxamide | A | A | A | | |

TABLE 3-continued

| Chemical Synthesis Example | Name | JARID1A IC$_{50}$ (μM) | JARID1B IC$_{50}$ (μM) | JMJD2C IC$_{50}$ (μM) | JMJD2A IC$_{50}$ (μM) | FBXL10 IC$_{50}$ (μM) |
|---|---|---|---|---|---|---|
| 158 | 2-(3-(4-chlorophenyl)-5-hydroxypyrazol-1-yl]pyridine-4-carboxylic acid | C | C | C | C | A |
| 159 | 2-(3-(3-chlorophenyl)-5-hydroxypyrazol-1-yl]pyridine-4-carboxylic acid | C | C | C | D | A |
| 160 | 2-(3-cyclopentyl-5-hydroxypyrazol-1-yl)pyridine-4-carboxylic acid | C | B | C | D | A |
| 161 | 2-[3-[(2,6-difluorophenyl)methyl]-5-hydroxypyrazol-1-yl]pyridine-4-carboxylic acid | | | C | | A |
| 162 | 2-[5-hydroxy-3-(1-phenylethyl)pyrazol-1-yl]pyridine-4-carboxylic acid | | C | C | D | A |
| 163 | 2-[3-[(2-chlorophenyl)methyl]-5-hydroxypyrazol-1-yl]pyridine-4-carboxylic acid | | C | C | D | A |
| 164 | 2-[3-[(3-chlorophenyl)methyl]-5-hydroxypyrazol-1-yl]pyridine-4-carboxylic acid | | C | C | D | A |
| 165 | 2-[3-[(4-chlorophenyl)methyl]-5-hydroxypyrazol-1-yl]pyridine-4-carboxylic acid | | B | C | D | A |
| 166 | 5-(1-phenylethyl)-2-[4-(1H-tetrazol-5-yl)pyridin-2-yl]pyrazol-3-ol | | | C | | A |
| 167 | 5-[(2-chlorophenyl)methyl]-2-[4-(1H-tetrazol-5-yl)pyridin-2-yl]pyrazol-3-ol | | | C | | A |
| 168 | 5-[(3-chlorophenyl)methyl]-2-[4-(1H-tetrazol-5-yl)pyridin-2-yl]pyrazol-3-ol | | | C | | A |
| 169 | 5-[(4-chlorophenyl)methyl]-2-[4-(1H-tetrazol-5-yl)pyridin-2-yl]pyrazol-3-ol | | C | C | D | A |
| 170 | 2-[3-[2-(4-chlorophenyl)propan-2-yl]-5-hydroxypyrazol-1-yl]pyridine-4-carboxylic acid | | | C | | A |
| 171 | 2-[3-[1-(4-chlorophenyl)cyclopropyl]-5-hydroxypyrazol-1-yl]pyridine-4-carboxylic acid | | | C | | A |
| 172 | 2-[3-[(3,5-dichlorophenyl)methyl]-5-hydroxypyrazol-1-yl]pyridine-4-carboxylic acid | | | C | | B |
| 173 | 2-(3-[(4-fluoro-2-methylphenyl)methyl]-5-hydroxypyrazol-1-yl]pyridine-4-carboxylic acid | | | C | | A |
| 174 | 2-(3-[(2-fluoro-4-methylphenyl)methyl]-5-hydroxypyrazol-1-yl]pyridine-4-carboxylic acid | | | C | | A |
| 175 | 2-(3-[(2,4-difluorophenyl)methyl]-5-hydroxypyrazol-1-yl]pyridine-4-carboxylic acid | | | C | | A |

Note:
Biochemical assay IC$_{50}$ data are designated within the following ranges:

A: ≤0.10 μM

B: >0.10 μM to ≤1.0 μM

C: >1.0 μM to ≤10 μM

D: >10 μM

Example 2

In Vitro Cell-Based Assay

An assay to measure the degree of cellular inhibition of KDM5A and 5B was developed. This quantitative immuno-blotting assay measures the amount tri-methylated histone H3 at amino acid Lysine number 4, a specific substrate and product of the direct enzymatic activity of the histone demethylases KDM5A and KDM5B from extracts of the ZR-75-1 breast cancer cell line. Upon analysis a correlation was observed between the inhibition of these enzymes in a biochemical assay and the degree of inhibition of these enzymes within cancer cell lines.

Assay Principle

This assay is a fluorometric immunoassay for the quantification of tri-methyl H3K4 extracted from cells treated with test compound and is used as a measure of the cellular inhibition of KDM5A/B.

Assay Method

ZR-75-1 (PTEN null, ER+) breast cancer cells numbering 50,000 (ATCC) were seeded into each well of a 96-well tissue culture treated plate and then exposed to an 11 point dilution of test compound with final concentration ranges of test compound ranging from 2000 uM to 10 nM. Cells were left in the presence of test compound for 72 hours. Extracts were prepared containing all of the cellular histone material using detergent based lysis and sonication methods. These lysates were subsequently normalized for total protein content using a colorimetric bicinchonic acid assay (MicroBCA Pierce/Thermo Scientific). Normalized cell extracts were then subjected to typical immuno-blotting procedures using NuPage reagents (Life Technologies). Electrophoretically separated histones were then transferred and immobilized using polyvinylidene difluoride membrane (Immobilon-FL Millipore). The amount of tri-methylated lysine 4 of histone H3 was detected using an antibody specific to the tri-methylated state (Cell Signaling Technologies) and quantified on an infrared imager using a densitometry software package (Odyssey CLx, Image Studio, Li-Cor). This background subtracted densitometry value was reported as a ration of the GAPDH amount for that sample and then calculated as a percent of the DMSO treated sample. The software package XL-fit (IDBS) was then used to calculate a relative $IC_{50}$ value for the dilution series of a given test compound according to the equation:

$$\text{fit} = (D + ((V\max*(x\char`\^n))/((x\char`\^n) + (Km\char`\^n))))$$

Table 4 provides the cellular $IC_{50}$ values of various compounds disclosed herein.

TABLE 4

| Example | Cellular $IC_{50}$ (µM) |
|---|---|
| 39 | C |
| 40 | B |
| 41 | D |
| 50 | D |
| 52 | B |
| 53 | B |
| 55 | B |
| 56 | B |
| 57 | B |
| 58 | B |
| 62 | C |
| 63 | B |
| 64 | B |
| 71 | C |

TABLE 4-continued

| Example | Cellular $IC_{50}$ (µM) |
|---|---|
| 72 | C |
| 74 | C |
| 75 | C |
| 76 | C |
| 86 | C |
| 87 | B |
| 89 | A |
| 90 | B |
| 92 | B |
| 93 | B |
| 94 | C |
| 98 | C |
| 99 | B |
| 115 | B |
| 117 | C |
| 118 | C |
| 121 | C |
| 124 | D |
| 125 | C |
| 126 | D |
| 127 | C |
| 128 | B |
| 129 | C |
| 130 | C |
| 131 | C |
| 132 | B |
| 133 | B |
| 134 | C |
| 136 | C |
| 137 | C |
| 138 | C |
| 139 | B |
| 140 | C |
| 141 | C |
| 142 | C |
| 144 | C |
| 145 | C |
| 151 | C |

Note:
Cellular assay $IC_{50}$ data are designated within the following ranges:
A: ≤0.10 µM
B: >0.10 µM to ≤1.0 µM
C: >1.0 µM to ≤10 µM
D: >10 µM

Example 3

In Vivo Xenograph Study

Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1 \times 10^7$ cells/mL. MCF-7 cells are subcutaneously injected (100 µL/animal) on the right flank 2-3 days post pellet implantation and tumor volume (length× width²/2) is monitored bi-weekly. When tumors reach an average volume of ~200 mm³ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1

Oral Tablet

A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.
We claim:
1. A compound, or a pharmaceutically acceptable salt thereof, selected from:
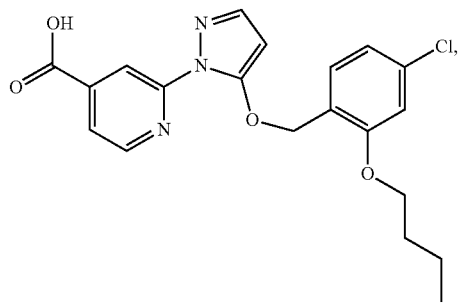
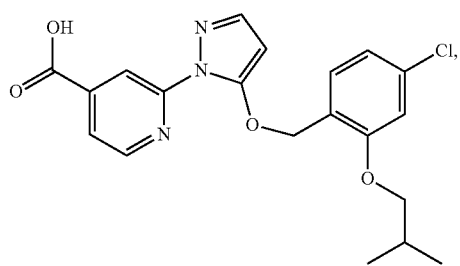
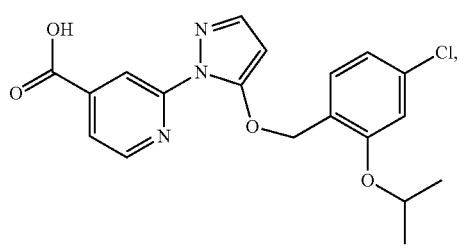
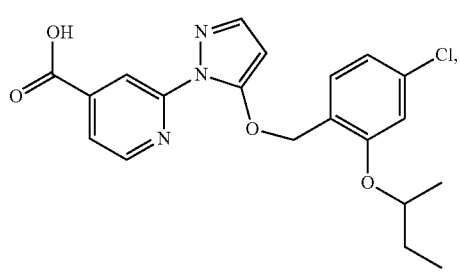
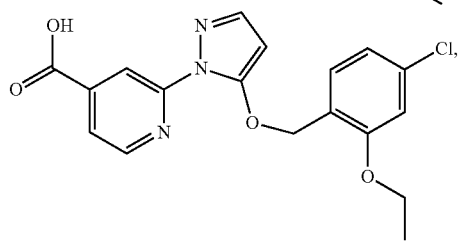
-continued
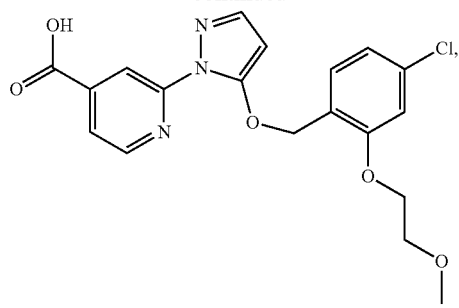
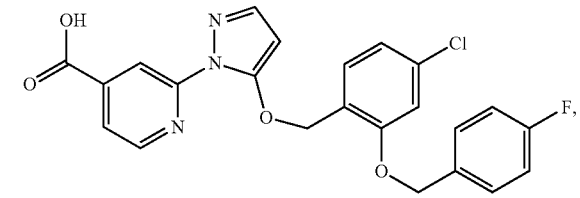
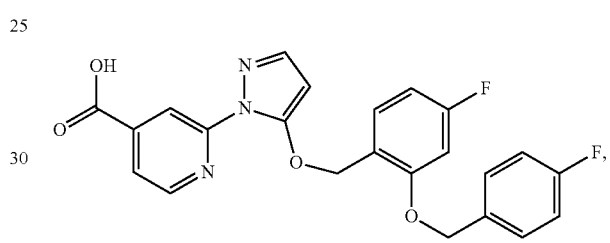
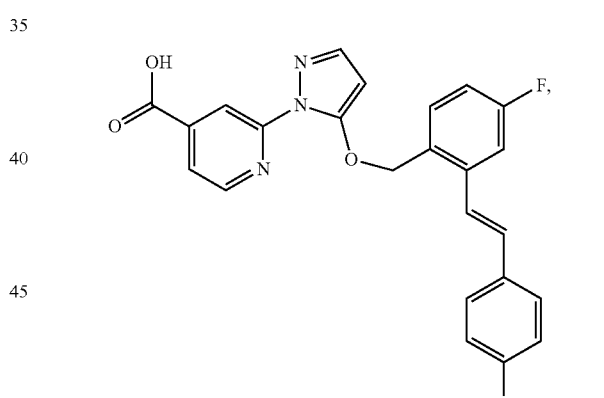
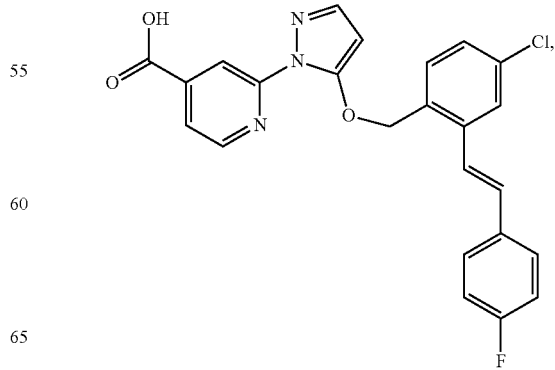

349
-continued
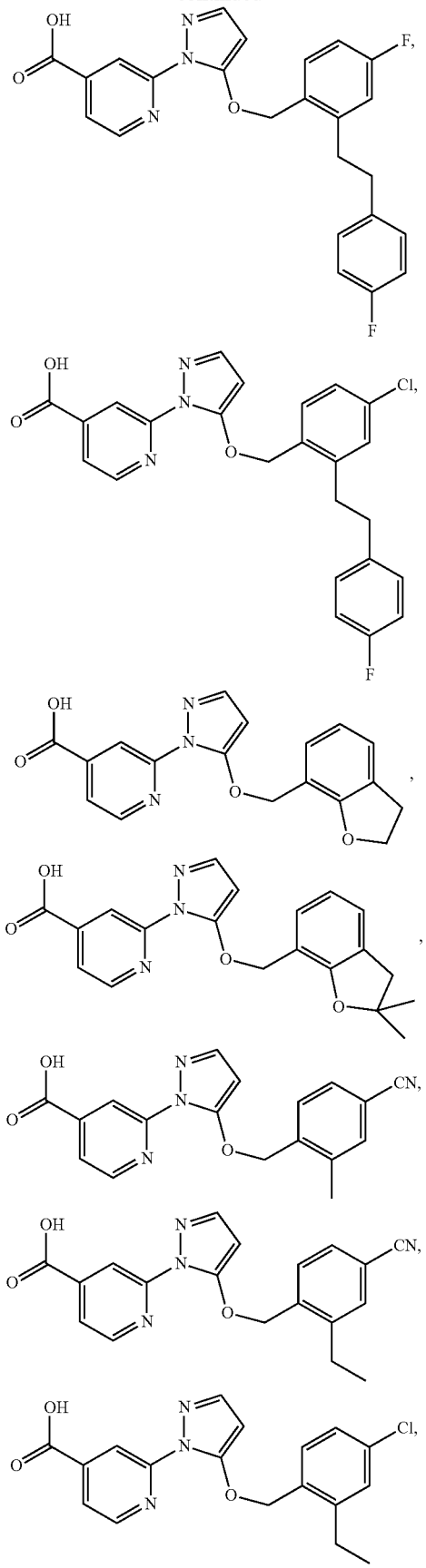
350
-continued
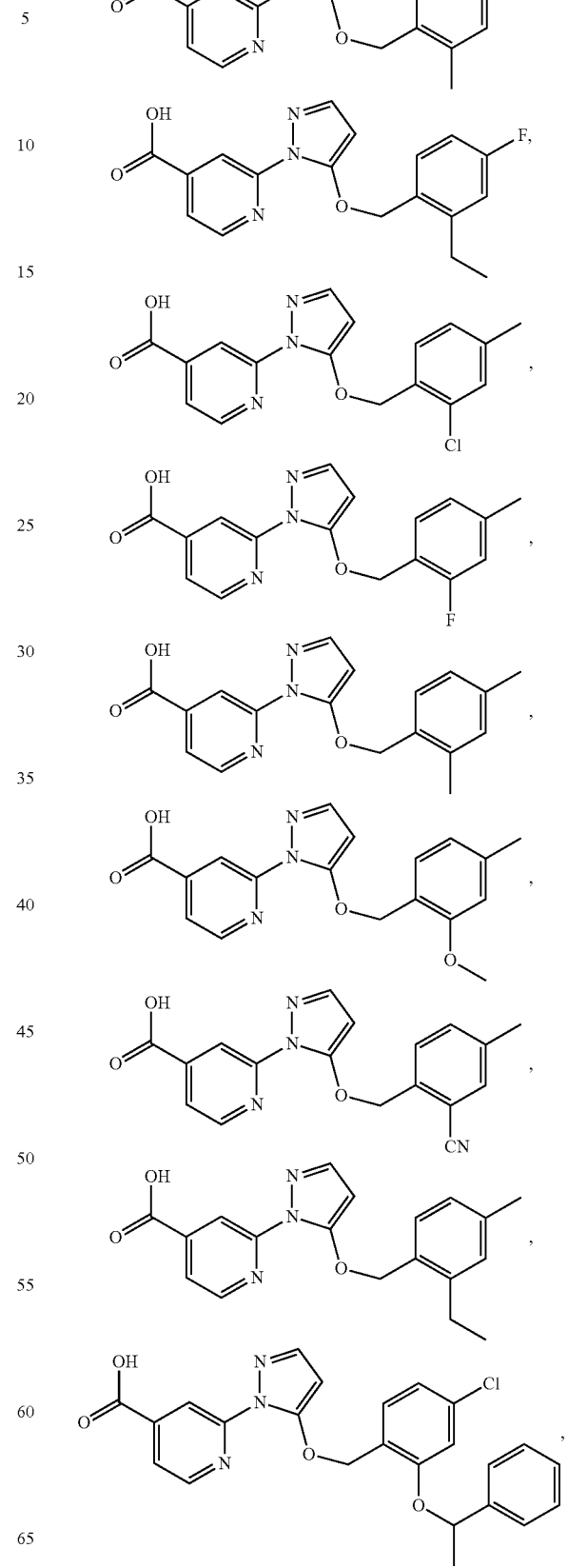

351
-continued
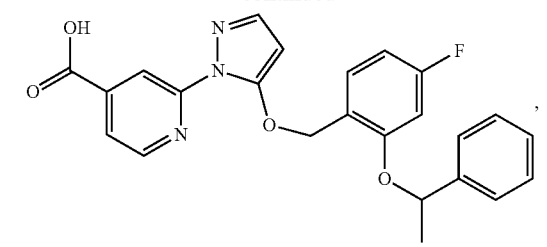
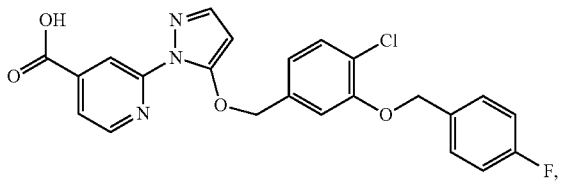
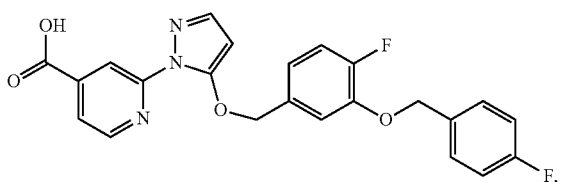
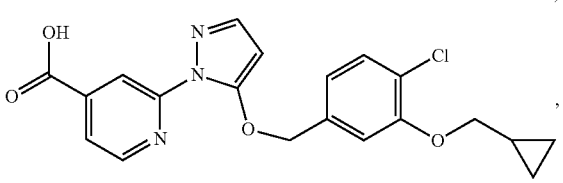
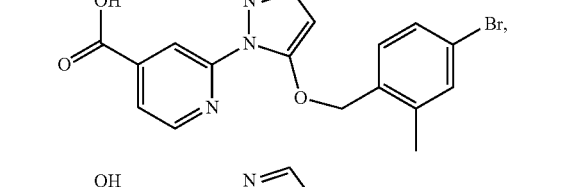
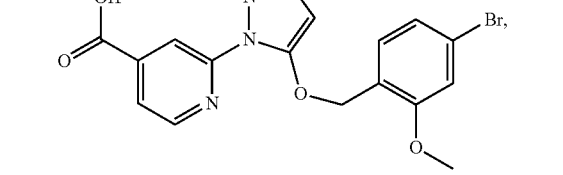
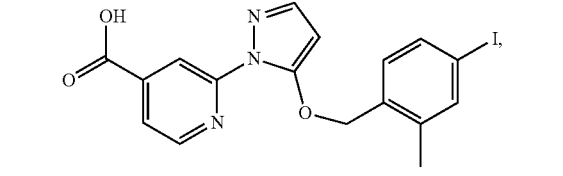
352
-continued
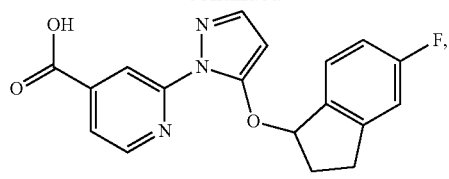
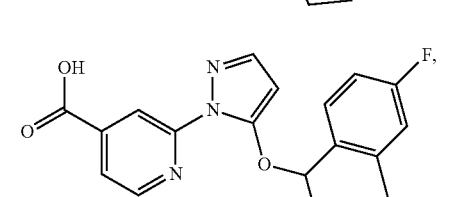
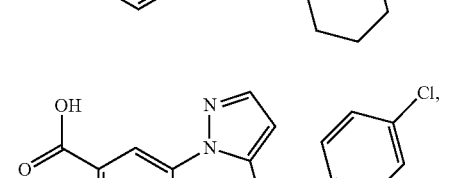
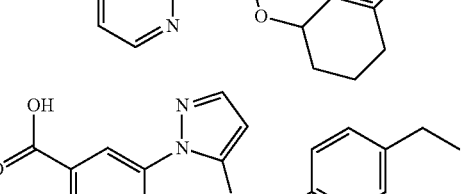
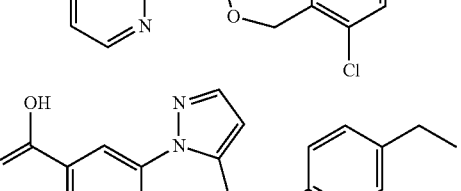
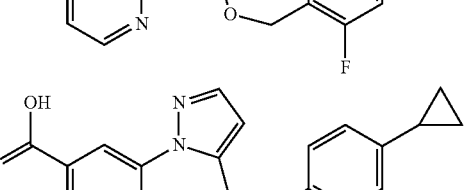
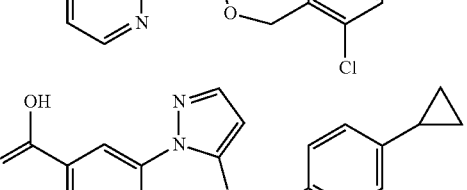
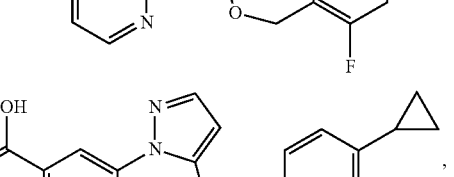
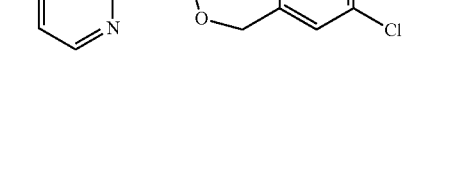, or -continued
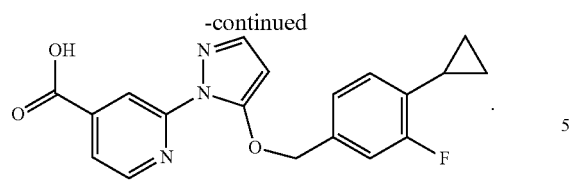
5
2. A pharmaceutical composition comprising a pharmaceutically acceptable carrier and a compound claim 1 or a pharmaceutically acceptable salt thereof.
* * * * *